(12) United States Patent
Zhong

(10) Patent No.: US 12,365,670 B2
(45) Date of Patent: *Jul. 22, 2025

(54) GLP-IR AGONISTS AND USES THEREOF

(71) Applicant: QILU REGOR THERAPEUTICS INC., Shanghai (CN)

(72) Inventor: Wenge Zhong, Thousand Oaks, CA (US)

(73) Assignee: QILU REGOR THERAPEUTICS INC., Shanghai (CN)

(*) Notice: Subject to any disclaimer, the term of this patent is extended or adjusted under 35 U.S.C. 154(b) by 1064 days.

This patent is subject to a terminal disclaimer.

(21) Appl. No.: 17/296,078

(22) PCT Filed: Nov. 19, 2019

(86) PCT No.: PCT/CN2019/119373
§ 371 (c)(1),
(2) Date: May 21, 2021

(87) PCT Pub. No.: WO2020/103815
PCT Pub. Date: May 28, 2020

(65) Prior Publication Data
US 2022/0024901 A1 Jan. 27, 2022

(30) Foreign Application Priority Data
Nov. 22, 2018 (WO) ............. PCT/CN2018/117047

(51) Int. Cl.
*C07D 405/14* (2006.01)
*A61K 31/4427* (2006.01)
(Continued)

(52) U.S. Cl.
CPC ......... *C07D 405/14* (2013.01); *C07D 471/04* (2013.01); *C07D 471/08* (2013.01); *C07D 498/04* (2013.01)

(58) Field of Classification Search
CPC .. C07D 405/14; C07D 471/04; C07D 471/08; C07D 498/04; C07D 401/14;
(Continued)

(56) References Cited

U.S. PATENT DOCUMENTS 10,208,019 B2    2/2019  Aspnes et al.
10,844,049 B2 *  11/2020 Zhong .................. C07D 471/08
(Continued)

FOREIGN PATENT DOCUMENTS

CN     113493447 A    10/2021
JP     2011-513431 A   4/2011
(Continued)

OTHER PUBLICATIONS

Brown, ed., Bioisosteres in Medicinal Chemistry, Wiley-VCH Verlag Gmbh & Co., pp. 7, 9, 17-19, and 131 (Year: 2012).*
(Continued)

*Primary Examiner* — Jeffrey S Lundgren
*Assistant Examiner* — Alexander K. Showalter
(74) *Attorney, Agent, or Firm* — McCarter & English, LLP; Yu Lu; Wei Song

(57) ABSTRACT

Provided are compounds of Formula (I) and pharmaceutical compositions thereof, for use in, e.g. treating type 2 diabetes mellitus, pre-diabetes, obesity, non-alcoholic fatty liver disease, non-alcoholic steatohepatitis, and cardiovascular disease.

25 Claims, 12 Drawing Sheets

(51) Int. Cl.
| | |
|---|---|
| *A61K 31/497* | (2006.01) |
| *A61K 31/506* | (2006.01) |
| *A61K 31/5383* | (2006.01) |
| *A61P 1/16* | (2006.01) |
| *A61P 3/10* | (2006.01) |
| *A61P 9/00* | (2006.01) |
| *C07D 401/04* | (2006.01) |
| *C07D 401/14* | (2006.01) |
| *C07D 405/04* | (2006.01) |
| *C07D 413/14* | (2006.01) |
| *C07D 471/04* | (2006.01) |
| *C07D 471/08* | (2006.01) |
| *C07D 487/04* | (2006.01) |
| *C07D 498/04* | (2006.01) |

(58) Field of Classification Search
CPC .. C07D 413/14; C07D 401/04; C07D 405/04; C07D 487/04; A61P 1/16; A61P 3/10; A61P 9/00; A61K 31/4427; A61K 31/497; A61K 31/506; A61K 31/5383
See application file for complete search history.

(56) References Cited

U.S. PATENT DOCUMENTS

| | | | |
|---|---|---|---|
| 10,954,221 B2 | 3/2021 | Zhong et al. | |
| 11,591,321 B2 | 2/2023 | Zhong et al. | |
| 2004/0127504 A1 | 7/2004 | Cowart et al. | |
| 2013/0123237 A1 | 5/2013 | Anand et al. | |
| 2020/0071306 A1 | 3/2020 | Esler et al. | |
| 2020/0407347 A1 | 12/2020 | Coates et al. | |
| 2021/0179594 A1 | 6/2021 | Zhong et al. | |
| 2023/0203023 A1* | 6/2023 | Jiang | C07D 405/14 514/333 |
| 2023/0278991 A1 | 9/2023 | Zhong et al. | |

FOREIGN PATENT DOCUMENTS

| | | |
|---|---|---|
| WO | 2004/099192 A2 | 11/2004 |
| WO | 2006/030925 A1 | 3/2006 |
| WO | 2006/055708 A2 | 5/2006 |
| WO | 2007/082264 A2 | 7/2007 |
| WO | 2011/079315 A1 | 6/2011 |
| WO | 2011/143365 A1 | 11/2011 |
| WO | 2011/156655 A2 | 12/2011 |
| WO | 2012/129562 A2 | 9/2012 |
| WO | 2013/090454 A2 | 6/2013 |
| WO | 2016/109559 A2 | 7/2016 |
| WO | 2017/161028 A1 | 9/2017 |
| WO | WO-2018109607 A1 * | 6/2018 ......... A61K 31/4545 |
| WO | 2019/239319 A1 | 12/2019 |
| WO | 2019/239371 A1 | 12/2019 |
| WO | 2020/033413 A2 | 2/2020 |
| WO | 2020/103815 A1 | 5/2020 |
| WO | 2020/207474 A1 | 10/2020 |
| WO | 2020/263695 A1 | 12/2020 |
| WO | 2021/018023 A1 | 2/2021 |
| WO | 2021/081207 A1 | 4/2021 |
| WO | 2021/112538 A1 | 6/2021 |
| WO | 2021/116874 A1 | 6/2021 |
| WO | 2021/154796 A1 | 8/2021 |
| WO | 2021/155841 A1 | 8/2021 |
| WO | 2021/160127 A1 | 8/2021 |
| WO | 2021/191812 A1 | 9/2021 |
| WO | 2021/196949 A1 | 10/2021 |
| WO | 2021/196951 A1 | 10/2021 |
| WO | 2021/197464 A1 | 10/2021 |

OTHER PUBLICATIONS

U.S. Appl. No. 16/950,393, filed Nov. 17, 2020, 2021-019594, Allowed.
Teno et al., Novel type of plasmin inhibitors: providing insight into P4 moiety and alternative scaffold to pyrrolopyrimidine. Bioorg Med Chem. Jul. 1, 2015;23(13):3696-704.
U.S. Appl. No. 16/874,908, filed May 15, 2020, U.S. Pat. No. 10,844,049, Issued.
U.S. Appl. No. 16/902,807, filed Jun. 16, 2020, U.S. Pat. No. 10,954,221, Issued.
U.S. Appl. No. 16/950,393, filed Nov. 17, 2020, 2021-0179594, Published.
U.S. Appl. No. 16/950,393, filed Nov. 17, 2020, U.S. Pat. No. 11,591,321, Issued.
U.S. Appl. No. 18/113,859, filed Feb. 24, 2023, 2023-0278991, Published.
Gejl et al., In Alzheimer's disease, 6-month treatment with GLP-1 analog prevents decline of brain glucose metabolism: randomized, placebo-controlled, double-blind clinical trial. Front Aging Neurosci. May 2016;8(Article 108):1-10.
Ishoy et al., GLP-1 receptor agonist treatment in schizophrenia patients with obesity. Schizophr Bull. 2017;43(Suppl 1):S167.
Nylander et al., Liraglutide in polycystic ovary syndrome: a randomized trial, investigating effects on thrombogenic potential. Endocr Connect. Feb. 2017;6(2):89-99.
Prasad-Reddy et al., A clinical review of GLP-1 receptor agonists: efficacy and safety in diabetes and beyond. Drugs Context. Jul. 2015;4:212283. 19 pages.
Suchankova et al., The glucagon-like peptide-1 receptor as a potential treatment target in alcohol use disorder: evidence from human genetic association studies and a mouse model of alcohol dependence. Transl Psychiatry. Jun. 2015;5(6):e583. 11 pages.
International Search Report and Written Opinion for Application No. PCT/CN2018/117047, dated Aug. 21, 2019, 14 pages.
International Search Report and Written Opinion for Application No. PCT/CN2019/082381, dated Jan. 9, 2020, 18 pages.
International Search Report and Written Opinion for Application No. PCT/CN2019/119373, dated Feb. 5, 2020, 16 pages.
International Search Report and Written Opinion for Application No. PCT/CN2020/084203, dated Jul. 9, 2020, 14 pages.

* cited by examiner

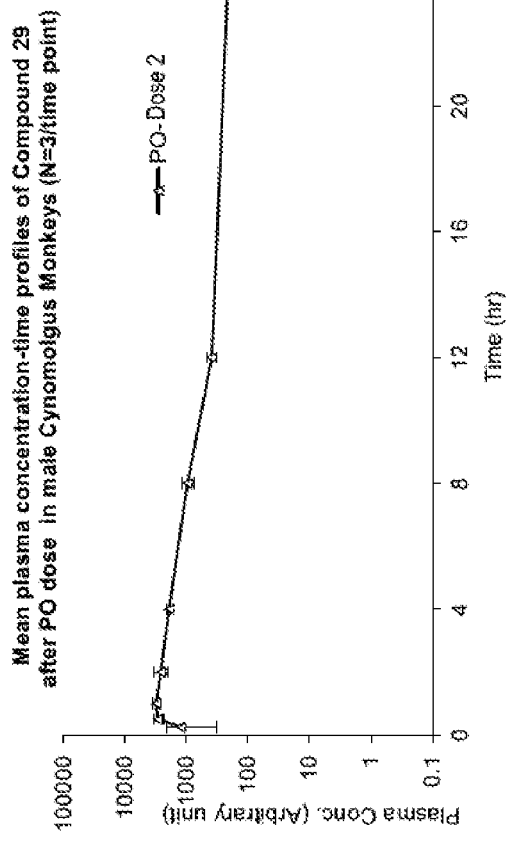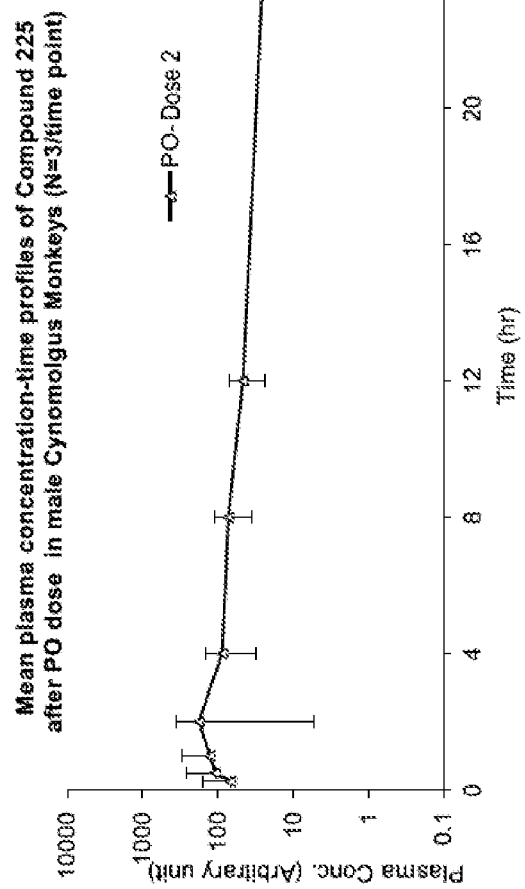

GLP-IR AGONISTS AND USES THEREOF

CROSS REFERENCE TO RELATED APPLICATION

This application a U.S. national stage filing, under 35 U.S.C. § 371 (c), of International Application No. PCT/CN2019/119373, filed on Nov. 19, 2019, which claims the benefit of priority to International Patent Application Number PCT/CN2018/117047, filed on Nov. 22, 2018. The entire contents of each of the aforementioned applications are incorporated herein by in their entirety.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2.

Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp et al., *Use of Antidiabetic Drugs in the U.S.*, 2003-2012, *Diabetes Care* 37:1367-1374, 2014). These may be grouped into six major classes, each acting through a different primary mechanism.

Insulin secretogogues, including sulphonyl-ureas (e.g., glipizide, glimepiride, glyburide), meglitinides (e.g., nateglidine, repaglinide), dipeptidyl peptidase IV (DPP-IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity.

Biguanides (e.g., metformin) are thought to act primarily by decreasing hepatic glucose production. Biguanides often cause gastrointestinal disturbances and lactic acidosis, further limiting their use.

Inhibitors of alpha-glucosidase (e.g., acarbose) decrease intestinal glucose absorption. These agents often cause gastrointestinal disturbances.

Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia.

Insulin is used in more severe cases, either alone or in combination with the above agents, and frequent use may also lead to weight gain and carries a risk of hypoglycemia.

Sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining 0-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects.

There is therefore a need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al., *Biodrugs*. 17(2): 93-102, 2013).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll et al., *Diabetes*. 50:609-613, 2001).

Hoist (*Physiol. Rev.* 87:1409, 2007) and Meier (*Nat. Rev. Endocrinol.* 8:728, 2012) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need for an easily-administered prevention and/or treatment for cardiometabolic and associated diseases.

SUMMARY OF THE INVENTION

In a first embodiment, the invention provides a compound represented by structural formula (I):

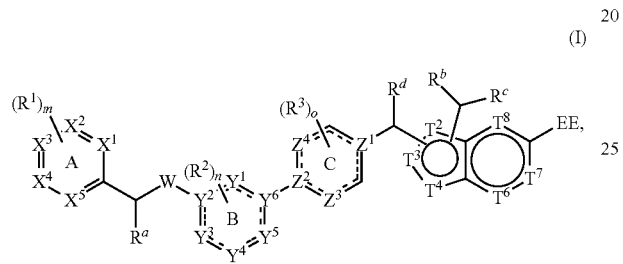

(I)

or a pharmaceutically acceptable salt, stereoisomer, solvate, or hydrate thereof, wherein:

======= indicates a single bond or a double bond;

$X^1$, $X^2$, $X^3$, $X^4$, and $X^5$ are each independently selected from N and CH; wherein no more than three of $X^1$, $X^2$, $X^3$, $X^4$, and $X^5$ are N and wherein ring A does not contain 3 nitrogen ring atoms at 3 contiguous positions;

W is selected from O, S, $CR^5R^6$, and $NR^5$;

$Y^1$, $Y^3$, $Y^4$, and $Y^5$ are each independently selected from N, NH, CH, and $CH_2$;

$Y^2$ and $Y^6$ are each independently selected from N, C, or CH;

wherein there is no more than 3 nitrogen ring atoms in ring B and wherein ring B does not contain 3 nitrogen ring atoms at 3 contiguous positions;

$Z^1$ and $Z^2$ are each independently selected from N, C, and CH; wherein at least one of $Z^1$ and $Z^2$ is N; $Z^3$ and $Z^4$ are each independently selected from a bond, CH, $CH_2$, CH=CH, $CH_2CH_2$, $CH_2CH$, and $CHCH_2$; wherein ring C contains no more than two double bonds;

provided that when ring B is

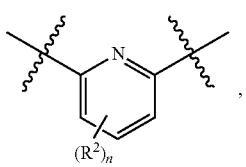

then (1) W is not O, and/or (2) ring C is not

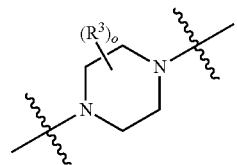

and/or (3) ring C is not

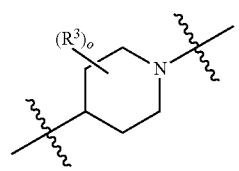

wherein $Z^1$ is N, and/or (4) ring A is not phenyl;

wherein:

$T^2$, $T^3$, and $T^4$ are each independently selected from N, $NR^4$, O, S, C, and $CR^4$; $T^6$, $T^7$, and T are each independently selected from N and $CR^4$;

wherein no more than 4 of $T^2$, $T^3$, $T^4$, $T^6$, $T^7$, and $T^8$ are selected from N, O, and S;

EE is —COOH or a carboxylic group surrogate, optionally, the carboxylic group surrogate is:

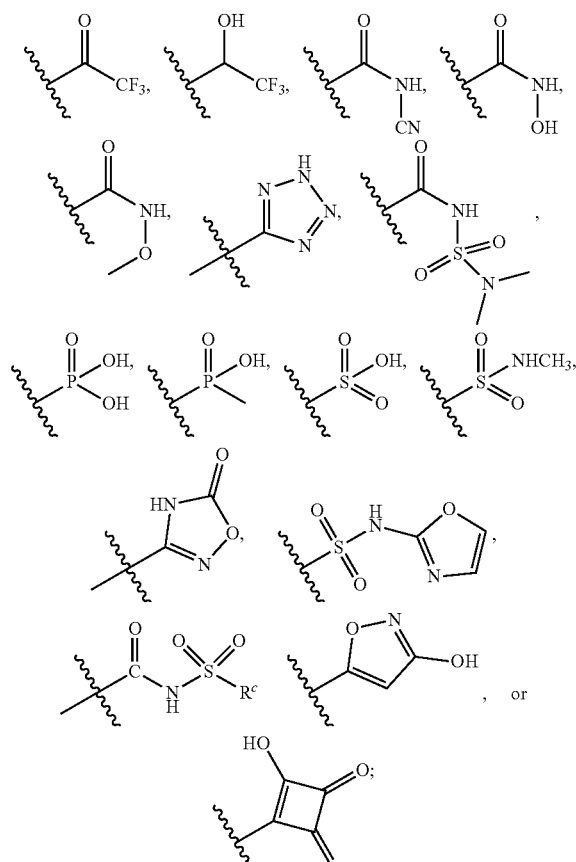

$R^a$ is selected from hydrogen, deuterium, halogen, —CN, $C_1$-$C_6$ alkyl, $C_1$-$C_6$ alkoxy, $NR^5R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^a$ is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^a$ or in the group represented by $R^a$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

$R^b$ is selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by R is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^b$ or in the group represented by $R^b$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

$R^c$ is selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by R is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^c$ or in the group represented by $R^c$ is optionally substituted with one or more groups selected from halogen, oxo, CN, and $NR^{5'}R^{6'}$;

$R^d$ is selected from hydrogen, deuterium, halogen, —CN, $C_1$-$C_6$ alkyl, $C_1$-$C_6$ alkoxy, $NR^5R^6$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^d$ is optionally substituted with one or more groups selected from halogen, oxo, CN, and saturated or partially saturated $C_3$-$C_6$ cycloalkyl; and wherein the aryl, heteroaryl, saturated or partially saturated cycloalkyl, or saturated or partially saturated heterocyclyl represented by $R^d$ or in the group represented by $R^d$ is optionally substituted with one or more groups selected from halogen, oxo, CN, and $N^{5'}R^{6'}$;

each $R^1$ is independently selected from halogen, —CN, OH, $C_1$-$C_6$ alkyl, $C_1$-$C_6$ alkoxy, $C_1$-$C_6$ alkenyl, $C_1$-$C_6$ alkynyl, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl, $C_1$-$C_6$ alkoxy, $C_1$-$C_6$ alkenyl, or $C_1$-$C_6$ alkynyl represented by $R^1$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^1$ or in the group represented by $R^1$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^2$ is independently selected from halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^2$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^2$ or in the group represented by $R^2$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^3$ is independently selected from halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^3$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^3$ or in the group represented by $R^3$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^4$ is H, deuterium, halogen, OH, —CN, $C_1$-$C_6$ alkyl, $C_1$-$C_6$ alkoxy, or $NR^{5'}R^{6'}$, wherein the $C_1$-$C_6$ alkyl and $C_1$-$C_6$ alkoxy represented by $R^4$ is optionally substituted with one or more groups selected from halogen, oxo, CN, $CF_3$, and saturated or partially saturated $C_3$-$C_6$ cycloalkyl (optionally substituted with one or more groups selected from halogen, oxo, CN, $CF_3$, OH, $OCH_3$, $OCH_2CH_3$);

$R^5$ and $R^6$ are each independently selected from hydrogen, deuterium, halogen, CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl, $C_1$-$C_6$ alkoxy, $C_1$-$C_6$ alkenyl, or $C_1$-$C_6$ alkynyl represented by $R^5$ or $R^6$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^5$ or $R^6$ or in the group represented by $R^5$ or $R^6$ is optionally substituted with one or more groups selected from halogen, oxo, CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$.

$R^{5'}$ and $R^{6'}$ are each independently selected from hydrogen, deuterium, and $C_1$-$C_6$ alkyl;

wherein optionally two $R^1$; two $R^2$; two $R^3$; two $R^4$; $R^1$ and $R^2$; $R^2$ and $R^3$; $R^a$ and $R^1$; $R^a$ and $R^2$; $R^1$ and any of $R^5$, $R^{5'}$ (in the group represented by W), or $R^6$; $R^a$ and any of $R^5$, $R^{5'}$ (in the group represented by W), or $R^6$; $R^2$ and any of $R^5$, $R^{5'}$ (in the group represented by W), or $R^6$; $R^5$ and $R^6$; any of two groups selected from $R^c$, $R^d$, $R^e$, and $R^f$; or $R^4$ and any one of $R^c$, $R^d$, $R^e$, and $R^f$; taken together with their respective intervening carbon or hetero atom(s), form phenyl, 5-6 membered heteroaryl, 4-8 membered saturated or partially saturated cycloalkyl or 4-8 membered saturated or partially saturated heterocyclyl, each of which is optionally substituted with one or more groups selected from halogen, —CN, —OH, $CF_3$, $C_1$-$C_6$ alkyl, $C_1$-$C_6$ alkoxy, —$NH_2$, —$NHC_1$-$C_6$ alkyl, —$N(C_1$-$C_6$ alkyl)$_2$, oxo, and saturated or partially saturated $C_3$-$C_6$ cycloalkyl, wherein the $C_1$-$C_6$ alkyl and $C_1$-$C_6$ alkoxy is optionally substituted with one or more groups selected from halogen, oxo, CN, $CF_3$, OH, $OCH_3$, $OCH_2CH_3$, and saturated or partially saturated $C_3$-$C_6$ cycloalkyl, wherein the cycloalkyl is optionally substituted with one or more groups selected from halogen, oxo, CN, $CF_3$, OH, $OCH_3$, $OCH_2CH_3$;

m is an integer selected from 0, 1, 2, 3, and 4,
n is an integer selected from 0, 1, 2, 3, 4, and 5, and
is an integer selected from 0, 1, 2, 3, 4, and 5.

In a second embodiment, the invention provides a compound according to the first embodiment, wherein the compound is represented by the structural formula (II-A):

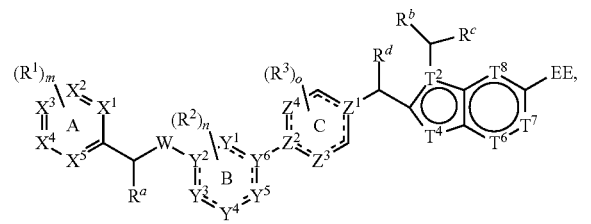

(II-A)

or a pharmaceutically acceptable salt, stereoisomer, solvate, or hydrate thereof, wherein $R^d$ is H, F, $CH_3$, or $CF_3$, wherein the remainder of the variables are as defined in the first embodiment.

In a third embodiment the invention provides a compound according to the first or second embodiment, wherein the compound is represented by structural formula (III-A):

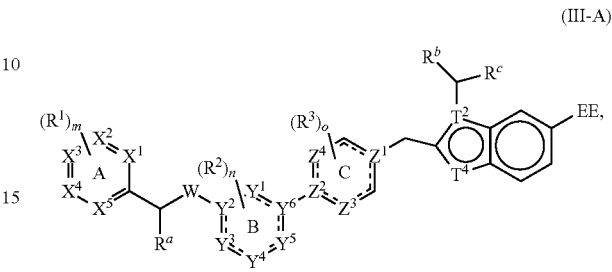

(III-A)

or a pharmaceutically acceptable salt, stereoisomer, solvate, or hydrate thereof, wherein $T^2$ is N, and $T^4$ is N or $CR^4$, wherein $R^4$ is H, halogen, OH, CN, $C_1$-$C_3$ alkyl, $C_1$-$C_3$ haloalkyl, or $C_1$-$C_3$ alkoxy; or $T^2$ is C, and $T^4$ is $NR^4$, wherein $R^4$ is H, $C_1$-$C_3$ alkyl, $C_1$-$C_3$ haloalkyl, wherein the remainder of the variables are as defined in the first or second embodiment.

In a fourth embodiment the invention provides a compound according to the first, second, or third embodiments, wherein the compound is represented by structural formula (IV-A):

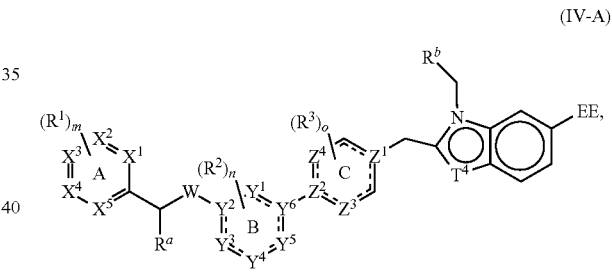

(IV-A)

or a pharmaceutically acceptable salt, stereoisomer, solvate, or hydrate thereof, wherein $T^4$ is N or CH; and $R^a$ is H, $CH_3$, or $CF_3$; or $R^a$, $R^1$ and $X^5$, taken together with their respective intervening carbons, form 5-7 membered cycloalkenyl or 5-7 membered partially saturated monoheterocyclyl, wherein the remainder of the variables are as defined in the first, second, or third embodiment.

In a fifth embodiment, the invention provides a compound according to the first, second, third or fourth embodiments, wherein $R^b$ is

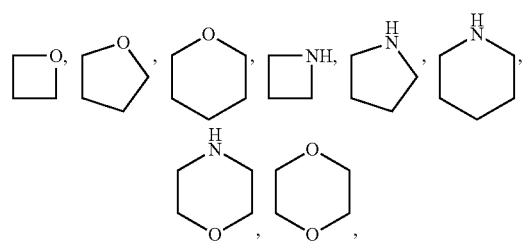

wherein R<sup>b</sup> is optionally substituted with 1 or 2 groups selected from oxo, CN, F, Cl, $C_1$-$C_3$ alkyl, and $C_1$-$C_3$ alkoxy, wherein the $C_1$-$C_3$ alkyl or $C_1$-$C_3$ alkoxy in the group represented by R<sup>b</sup> is optionally substituted with 1 or 2 groups selected from F, OH, and $OCH_3$, wherein the remainder of the variables are as defined in the first, second, third or fourth embodiment.

In a sixth embodiment, the invention provides a compound according to first, second, third or fourth embodiments, wherein R is

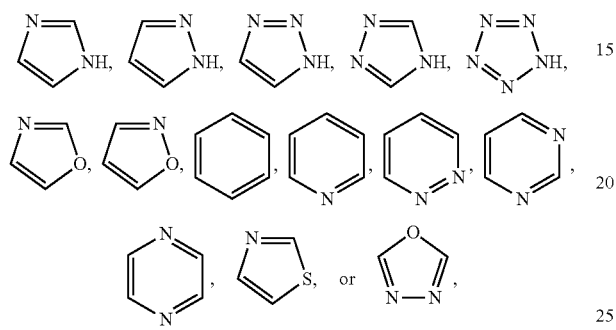

wherein R<sup>b</sup> is optionally substituted with 1 or 2 groups selected from halogen, OH, $NR^{5'}R^{6'}$, $C_1$-$C_3$ alkyl, and $C_1$-$C_3$ alkoxy, wherein the $C_1$-$C_3$ alkyl or $C_1$-$C_3$ alkoxy in the group represented by R is optionally substituted with 1 or 2 groups selected from F, OH, and $OCH_3$, wherein the remainder of the variables are as defined in the first, second, third or fourth embodiment.

In a seventh embodiment, the invention provides a compound according to the fourth embodiment, wherein

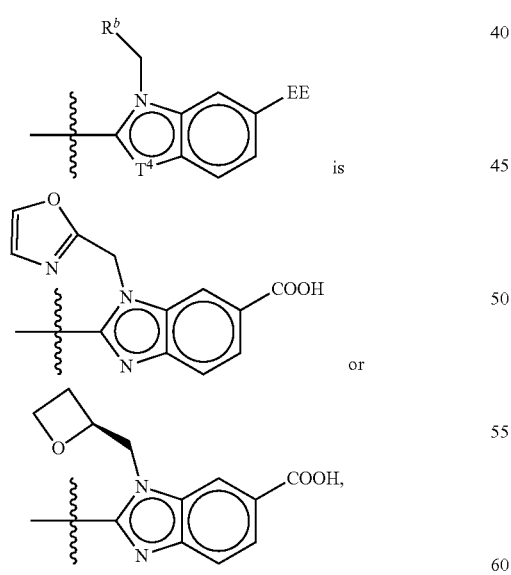

wherein the remainder of the variables are as defined in the first, second, third or fourth embodiment.

In an eighth embodiment, the invention provides a compound according to first, second, third, fourth, fifth, sixth, or seventh embodiments, wherein is

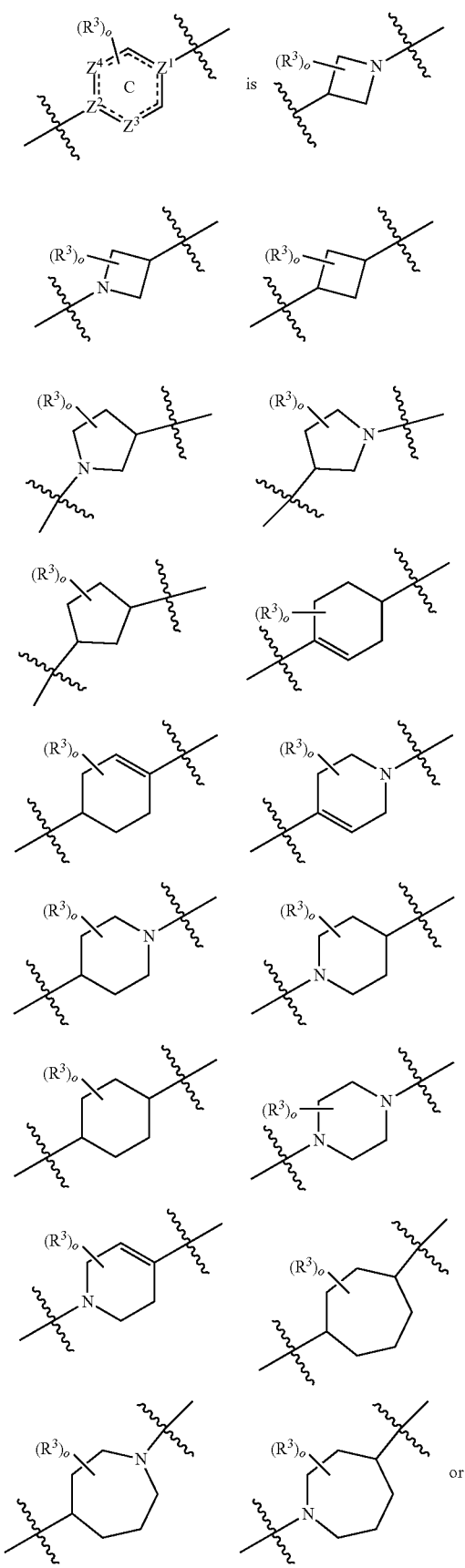

-continued

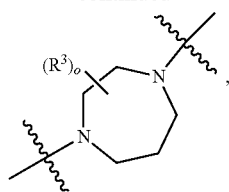

wherein R³ is halogen, CN, OH, oxo, $C_1$-$C_4$ alkyl, $C_1$-$C_4$ haloalkyl, $C_1$-$C_4$ alkoxy, or $NR^{5'}R^{6'}$; and o is an integer selected from 0, 1, 2, and 3, wherein the remainder of the variables are as defined in the first, second, third, fourth, fifth, sixth, or seventh embodiment.

In a ninth embodiment, the invention provides a compound according to first, second, third, fourth, fifth, sixth, seventh, or eighth embodiment, wherein

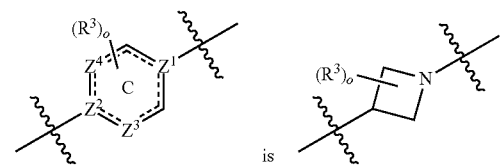 is

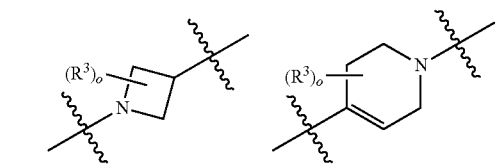

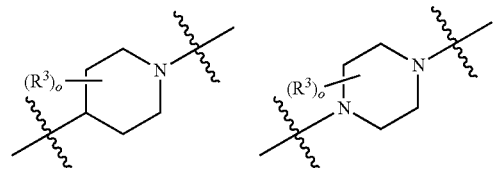

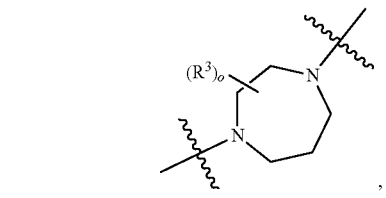

, wherein the remainder of the variables are as defined in the first, second, third, fourth, fifth, sixth, seventh, or eighth embodiment.

In a tenth embodiment, the invention provides a compound according to first, second, third, fourth, fifth, sixth, seventh, eighth, or ninth embodiment, wherein

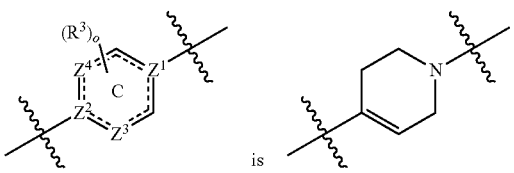 is

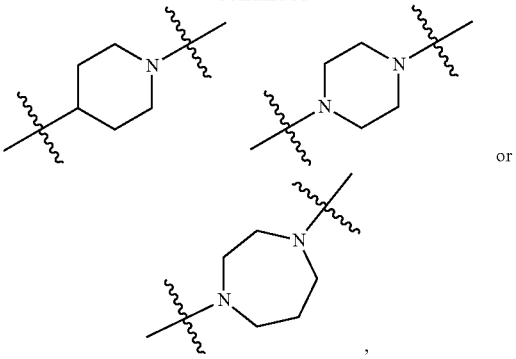

, each of which is optionally substituted with 1 or 2 groups selected from halogen, CN, and oxo; or two R³ groups taken together with ring C, form bridged ($C_5$-$C_8$)heterocyclene or bridged ($C_5$-$C_8$)cycloalkylene, wherein the remainder of the variables are as defined in the first, second, third, fourth, fifth, sixth, seventh, eighth, or ninth embodiment.

In an eleventh embodiment, the invention provides a compound according to first, second, third, fourth, fifth, sixth, seventh, eighth, or ninth embodiment, wherein

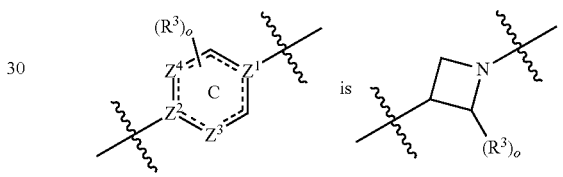 is

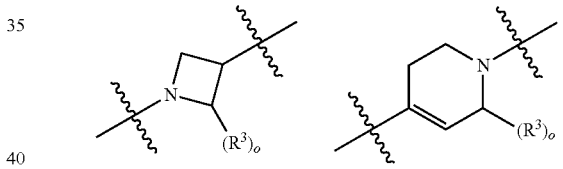

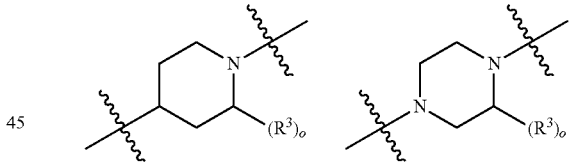

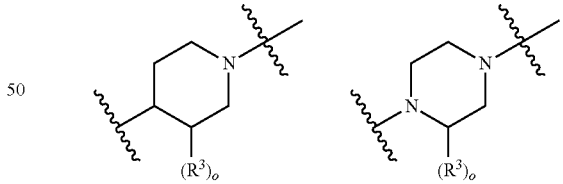

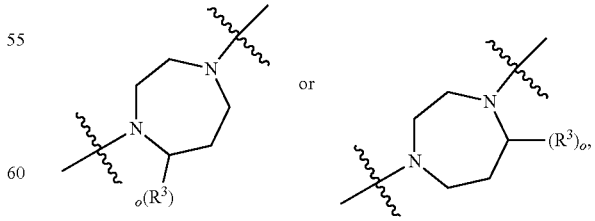

wherein R³ is halogen, CN, oxo, $CH_3$, $CF_3$, $CH_2CH_3$, or $CH_2CF_3$; and o is 0 or 1, wherein the remainder of the variables are as defined in the first, second, third, fourth, fifth, sixth, seventh, eighth, or ninth embodiment.

In a twelfth embodiment, the invention provides a compound according to first, second, third, fourth, fifth, sixth, seventh, eighth, ninth, tenth, or eleventh embodiment, wherein

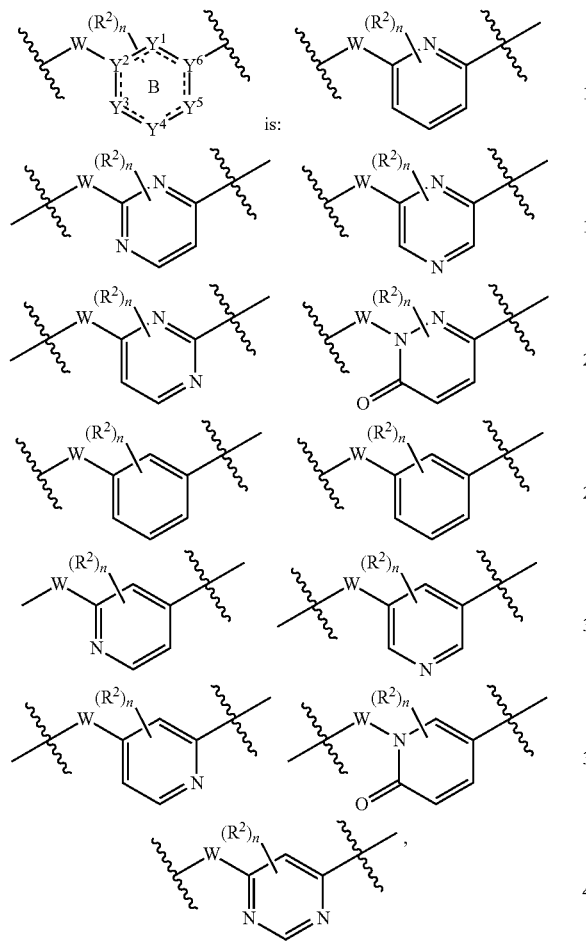

is:

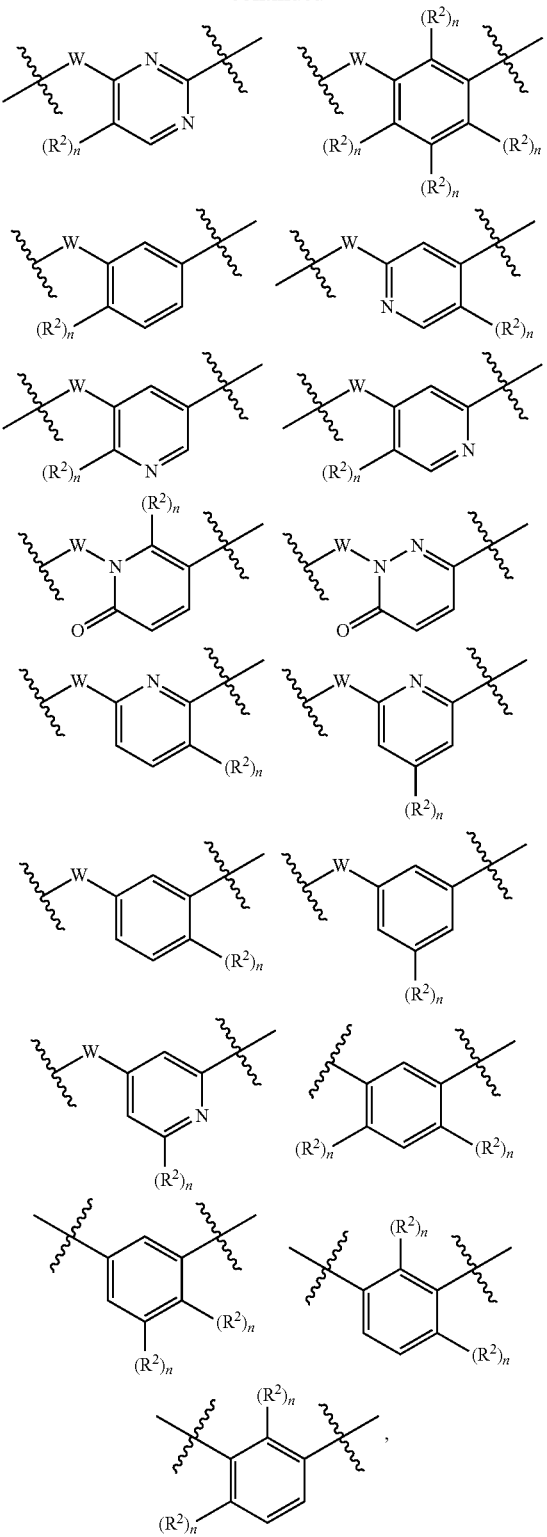

wherein each $R^2$ is independently selected from halogen, —CN, OH, oxo, $C_1$-$C_2$ alkyl, $C_1$-$C_2$ haloalkyl, and $C_1$-$C_2$ alkoxy; and n is an integer selected from 0, 1, 2, and 3, wherein the remainder of the variables are as defined in the first, second, third, fourth, fifth, sixth, seventh, eighth, ninth, tenth, or eleventh embodiment.

In a thirteenth embodiment, the invention provides a compound according to first, second, third, fourth, fifth, sixth, seventh, eighth, ninth, tenth, eleventh, or twelfth embodiment, wherein

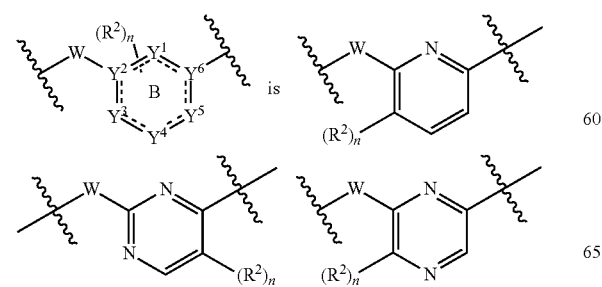

is wherein $R^2$ is halogen, —CN, OH, oxo, $C_1$-$C_2$ alkyl, $C_1$-$C_2$ haloalkyl, or $C_1$-$C_2$ alkoxy, n is 0 or 1, and no more than two $R^2$ are attached to ring B, wherein the remainder of the variables are as defined in the first, second, third, fourth, fifth, sixth, seventh, eighth, ninth, tenth, eleventh, or twelfth embodiment.

In a fourteenth embodiment, the invention provides a compound according to the twelfth embodiment, wherein two $R^2$ groups together with ring B form a bicyclic structure:

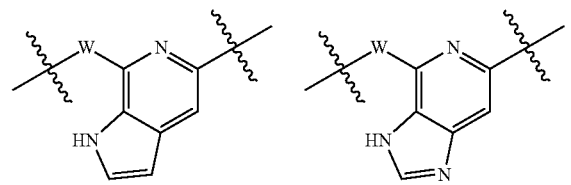

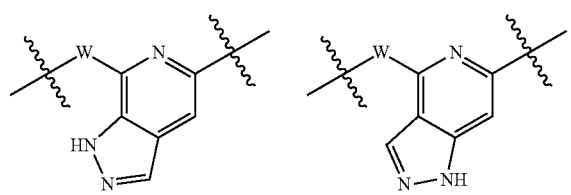

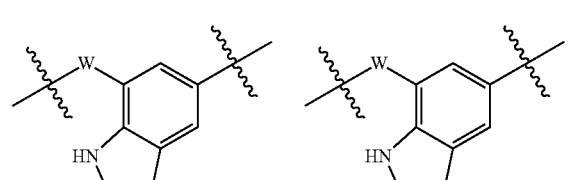

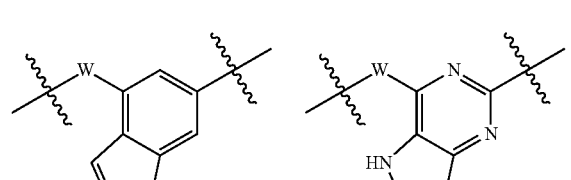

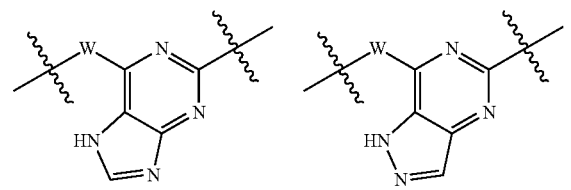

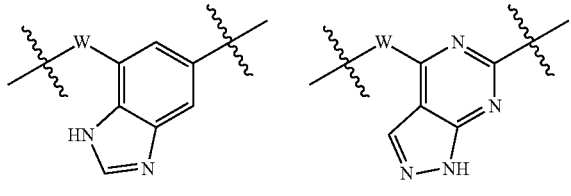

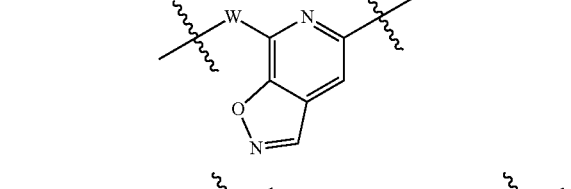

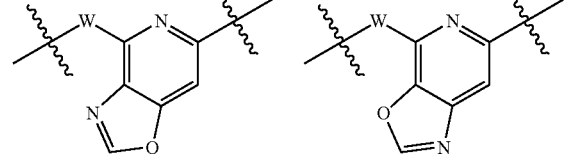

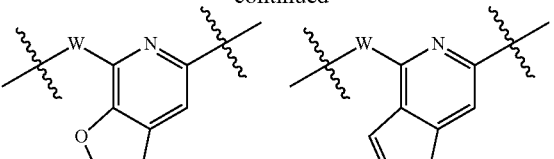

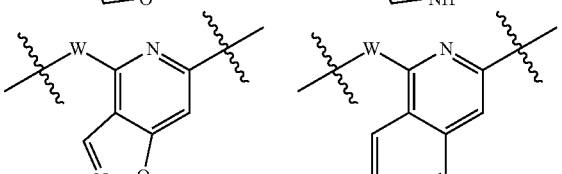

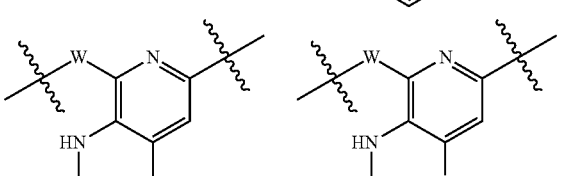

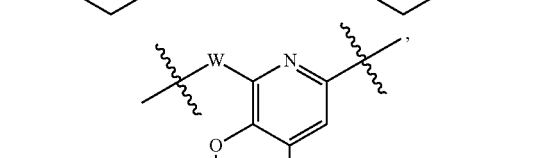

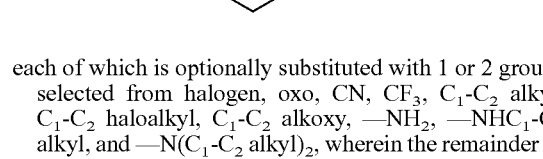

each of which is optionally substituted with 1 or 2 groups selected from halogen, oxo, CN, $CF_3$, $C_1$-$C_2$ alkyl, $C_1$-$C_2$ haloalkyl, $C_1$-$C_2$ alkoxy, —$NH_2$, —$NHC_1$-$C_2$ alkyl, and —$N(C_1$-$C_2$ alkyl$)_2$, wherein the remainder of the variables are as defined in the first, second, third, fourth, fifth, sixth, seventh, eighth, ninth, tenth, eleventh, or twelfth embodiment.

In a fifteenth embodiment, the invention provides a compound according to the fourteenth embodiment, wherein two $R^2$ groups together with ring B form a bicyclic structure:

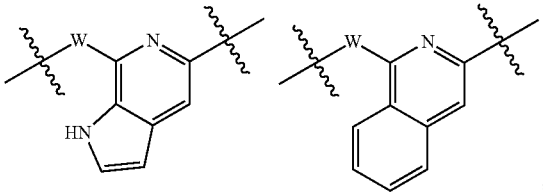

each of which is optionally substituted with halogen, wherein the remainder of the variables are as defined in the first, second, third, fourth, fifth, sixth, seventh, eighth, ninth, tenth, eleventh, or twelfth embodiment.

In a sixteenth embodiment, the invention provides a compound according to the twelfth embodiment, wherein W and ring B form a bicyclic structure:

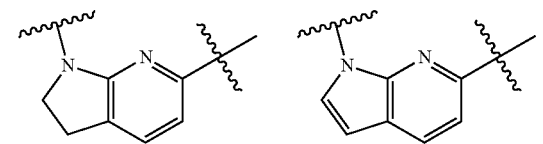

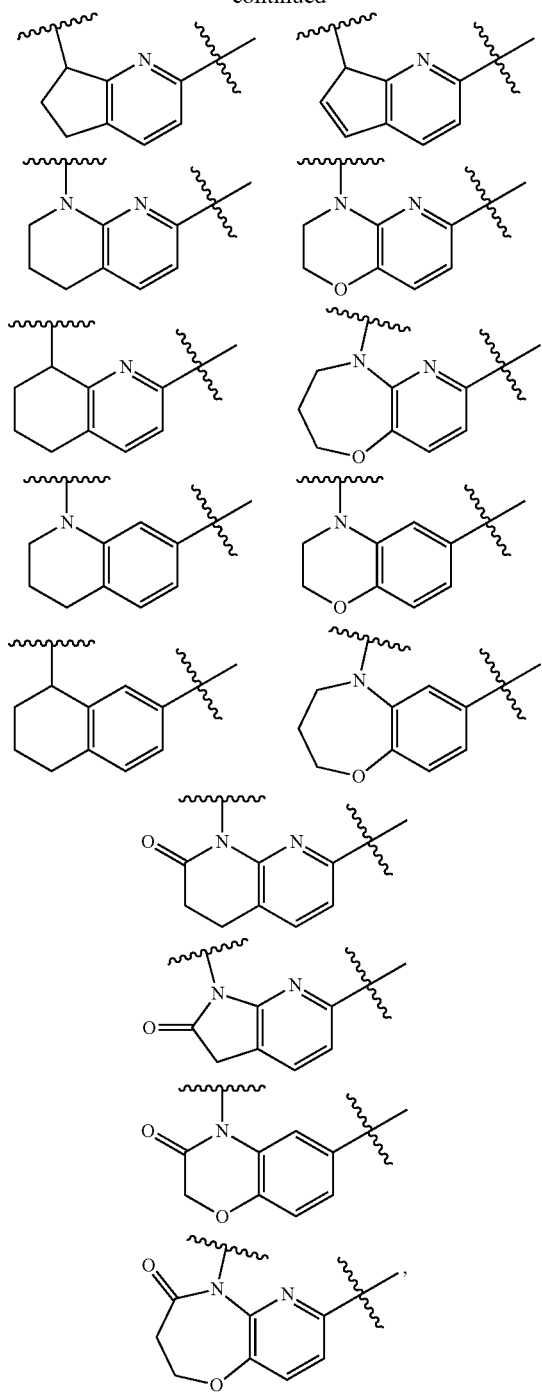

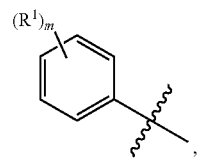

each R¹ is independently selected from halogen, OH, CN, CF₃, $C_1$-$C_2$ alkyl, $C_1$-$C_2$ haloalkyl, $C_1$-$C_2$ alkoxy, —NH₂, —NHC₁-C₂ alkyl, —N(C₁-C₂ alkyl)₂, and $C_2$-$C_4$alkynyl optionally substituted with cyclopropane; and m is an integer selected from 0, 1, 2, and 3, wherein the remainder of the variables are as defined in the first, second, third, fourth, fifth, sixth, seventh, eighth, ninth, tenth, eleventh, twelfth, thirteenth, fourteenth, fifteenth, or sixteenth embodiment.

In an eighteenth embodiment, the invention provides a compound according to the first, second, third, fourth, fifth, sixth, seventh, eighth, ninth, tenth, eleventh, twelfth, thirteenth, fourteenth, fifteenth, sixteenth, or seventeenth embodiment, wherein ring A is

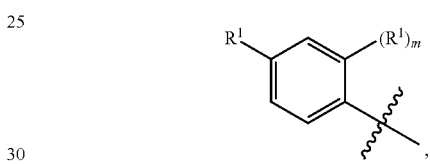

and m is 0 or 1, and R¹ is halogen, CN, CH₃, CF₃, OH, or $C_2$-$C_4$alkynyl optionally substituted with cyclopropane; preferably ring A is

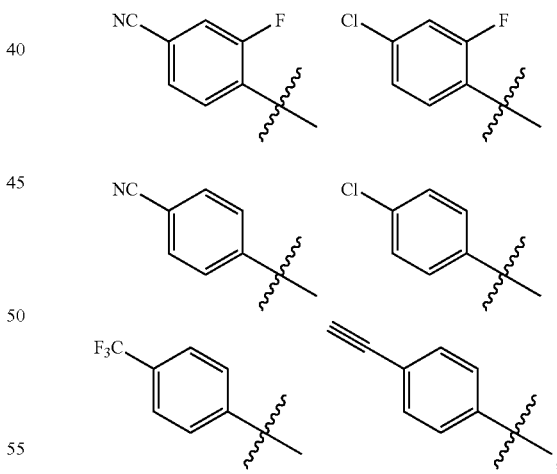

wherein the remainder of the variables are as defined in the first, second, third, fourth, fifth, sixth, seventh, eighth, ninth, tenth, eleventh, twelfth, thirteenth, fourteenth, fifteenth, sixteenth, or seventeenth embodiment.

each of which is optionally substituted with 1 or 2 groups selected from halogen, oxo, CN, CF₃, —NH₂, —NHC₁-C₂ alkyl, and —N(C₁-C₂ alkyl)₂, wherein the remainder of the variables are as defined in the first, second, third, fourth, fifth, sixth, seventh, eighth, ninth, tenth, eleventh, or twelfth embodiment.

In a seventeenth embodiment, the invention provides a compound according to the first, second, third, fourth, fifth, sixth, seventh, eighth, ninth, tenth, eleventh, twelfth, thirteenth, fourteenth, fifteenth, or sixteenth embodiment, wherein ring A is In a nineteenth embodiment, the invention provides a compound according to the first, second, third, fourth, fifth, sixth, seventh, eighth, ninth, tenth, eleventh, twelfth, thirteenth, fourteenth, fifteenth, or sixteenth embodiment, wherein ring A is

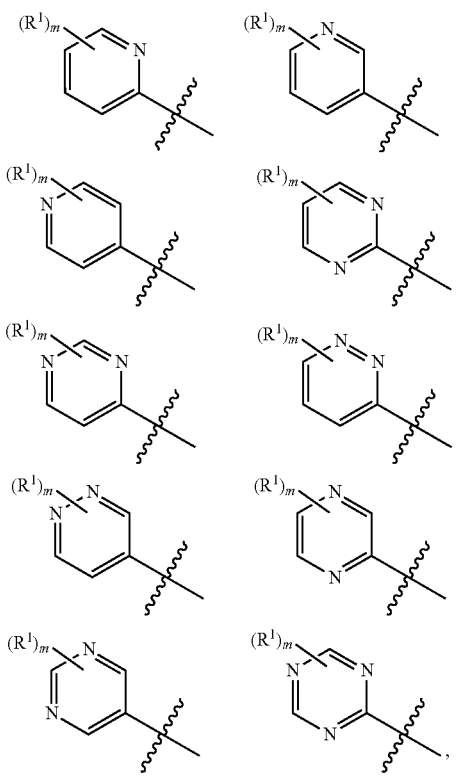

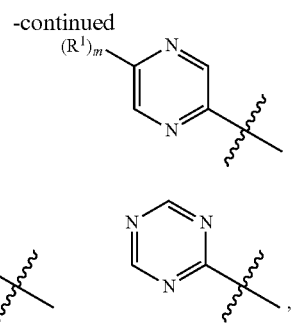

each R¹ is independently selected from halogen, OH, CN, CF₃, C₁-C₂ alkyl, C₁-C₂ haloalkyl, C₁-C₂ alkoxy, —NH₂, —NHC₁-C₂ alkyl, —N(C₁-C₂ alkyl)₂, and C₂-C₄alkynyl optionally substituted with cyclopropane; and m is an integer selected from 0, 1, and 2, wherein the remainder of the variables are as defined in the first, second, third, fourth, fifth, sixth, seventh, eighth, ninth, tenth, eleventh, twelfth, thirteenth, fourteenth, fifteenth, or sixteenth embodiment.

In a twentieth embodiment, the invention provides a compound according to the nineteenth embodiment, wherein ring A is

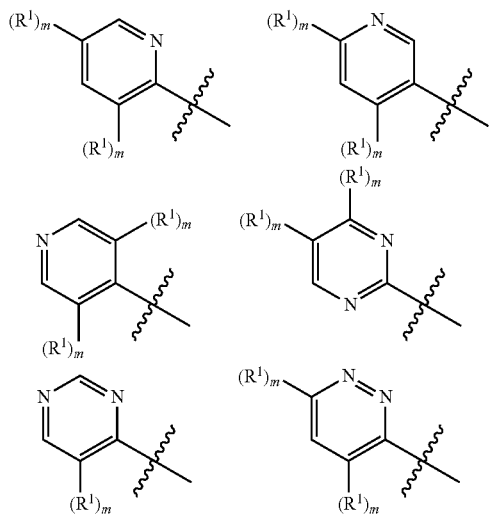

each of which is optionally substituted with halogen, OH, CN, C≡CH, CH₃, or CF₃, m is 0 or 1, wherein the remainder of the variables are as defined in the first, second, third, fourth, fifth, sixth, seventh, eighth, ninth, tenth, eleventh, twelfth, thirteenth, fourteenth, fifteenth, sixteenth, or nineteenth embodiment.

In a twenty-first embodiment, the invention provides a compound according to any one of the first through fifteenth and the seventeenth through twentieth embodiments, wherein W is O, NH or CH₂, wherein the remainder of the variables are as defined in the first, second, third, fourth, fifth, sixth, seventh, eighth, ninth, tenth, eleventh, twelfth, thirteenth, fourteenth, fifteenth, seventeenth, eighteenth, nineteenth or twentieth embodiment.

In a twenty-second embodiment, the invention provides a compound according to any one of the first through twentieth embodiments, wherein R¹ is selected from halogen, CN, CH₃, CF₃, and C≡CH, wherein the remainder of the variables are as defined in the first, second, third, fourth, fifth, sixth, seventh, eighth, ninth, tenth, eleventh, twelfth, thirteenth, fourteenth, fifteenth, seventeenth, eighteenth, nineteenth, twentieth, or twenty-first embodiment.

In a twenty-third embodiment, the invention provides a compound according to the first embodiment, wherein the compound is represented by the structural formula (I'):

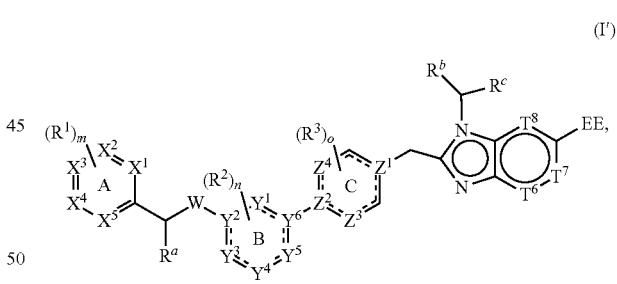

(I')

or a pharmaceutically acceptable salt, stereoisomer, solvate, or hydrate thereof, wherein ------ indicates a single bond or a double bond;

X¹, X², X³, X⁴, and X⁵ are each independently selected from N and CH; wherein no more than three of X¹, X², X³, X⁴, and X⁵ are N and ring A does not contain 3 nitrogen ring atoms at 3 contiguous positions;

W is selected from O, CR⁵R⁶', and NR⁵;

Y¹, Y³, Y⁴, and Y⁵ are each independently selected from N, NH, CH, and CH₂;

Y² and Y⁶ are each independently selected from N, C, or CH;

wherein there is no more than 3 nitrogen ring atoms in ring B and wherein ring B does not contain 3 nitrogen ring atoms at 3 contiguous positions;

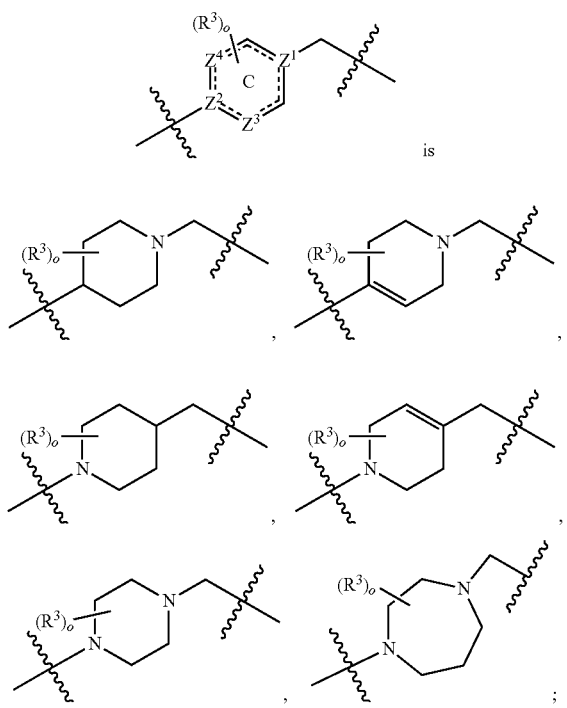

is

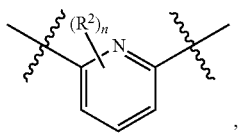

provided that when ring B

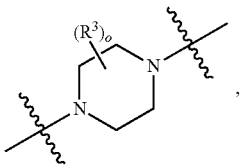

then (1) W is not 0, and/or (2) ring C is not

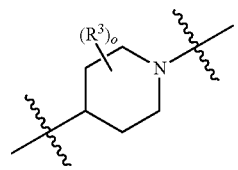

and/or (3) ring C is not

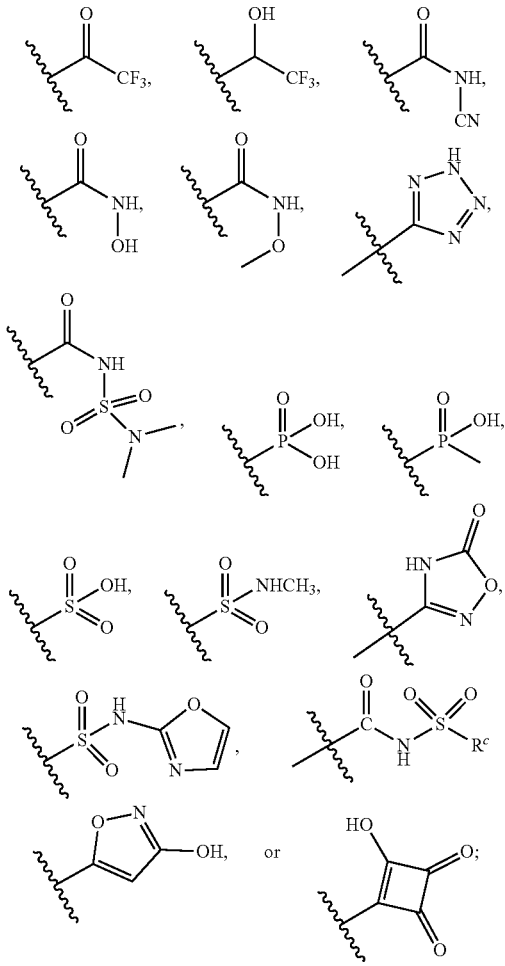

wherein $Z^1$ is N, and/or (4) ring A is not phenyl;

$T^6$, $T^7$, and T are each independently selected from N and $CR^4$; and no more than 2 of $T^6$, $T^7$, and $T^8$ are selected from N;

EE is —COOH, $R^a$ is selected from hydrogen, halogen, $C_1$-$C_6$ alkyl, $C_1$-$C_6$ alkoxy, $NR^5R^{6'}$, wherein the $C_1$-$C_6$ alkyl or $C_1$-$C_6$ alkoxy represented by $R^a$ is optionally substituted with one or more groups selected from halogen, oxo, CN, and OH;

$R^b$ is 5-6 membered heteroaryl or 4-7 membered saturated or partially saturated heterocyclyl, wherein the heteroaryl or saturated or partially saturated heterocyclyl represented by R is optionally substituted with one or more groups selected from halogen, $C_1$-$C_3$ alkyl, $C_1$-$C_3$ haloalkyl, $C_1$-$C_3$ hydroxyalkyl, $C_1$-$C_3$ alkoxy, and $C_1$-$C_3$ haloalkoxy;

$R^c$ is hydrogen, $C_1$-$C_6$ alkyl, or $C_1$-$C_6$ haloalkyl;

each $R^1$ is independently halogen, —CN, OH, $C_1$-$C_6$ alkyl, $C_1$-$C_6$ alkoxy, $C_2$-$C_6$ alkenyl, $C_2$-$C_6$ alkynyl, $NR^5R^6$, phenyl, 5-6 membered heteroaryl, 4-6 membered saturated or partially saturated cycloalkyl and 3-7 membered saturated or partially saturated heterocyclyl, wherein the $C_1$-$C_6$ alkyl, $C_1$-$C_6$ alkoxy, $C_2$-$C_6$ alkenyl, or $C_2$-$C_6$ alkynyl represented by $R^1$ is optionally substituted with one or more groups selected from halogen, CN, OH, and $C_3$-$C_6$ cycloalkyl; and wherein the aryl, heteroaryl, saturated or partially saturated cycloalkyl, or saturated or partially saturated heterocyclyl represented by $R^1$ or in the group represented by $R^1$ is optionally substituted with one or more groups selected from halogen, oxo, CN, OH, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_1$-$C_3$ hydroxyalkoxy, and $NR^{5'}R^{6'}$;

each $R^2$ is independently selected from halogen, oxo, $C_1$-$C_6$ alkyl, $C_1$-$C_6$ haloalkyl, $C_1$-$C_6$ alkoxy, $C_1$-$C_6$ haloalkoxy, and $NR^{5'}R^{6'}$;

each $R^3$ is independently halogen, —CN, oxo, $C_1$-$C_6$ alkyl, $C_1$-$C_6$ haloalkyl, $C_1$-$C_6$ alkoxy, or $C_1$-$C_6$ haloalkoxy; and/or two $R^3$ taken together with Ring C, form 6-10 membered bridged heterocyclyl optionally substituted with one or more groups selected from halogen, $C_1$-$C_6$ alkyl, $C_1$-$C_6$ haloalkyl, $C_1$-$C_6$ alkoxy, or $C_1$-$C_6$ haloalkoxy;

each $R^4$ is independently H, halogen, or $C_1$-$C_6$ alkyl optionally substituted with one or more groups selected from halogen;

$R^{5'}$ and $R^{6'}$ are each independently hydrogen or $C_1$-$C_6$ alkyl;

wherein optionally two $R^1$; two $R^2$; two $R^3$; $R^a$ and $R^1$; $R^a$ and $R^2$; $R^1$ and $R^{5'}$; $R^2$ and $R^{5'}$; taken together with their respective intervening carbon or hetero atom(s), form phenyl, 5-6 membered heteroaryl, 4-6 membered saturated or partially saturated cycloalkyl or 4-7 membered saturated or partially saturated heterocyclyl, each of which is optionally substituted with one or more groups selected from halogen, —CN, —OH, $C_1$-$C_6$ alkyl, $C_1$-$C_6$ haloalkyl, $C_1$-$C_6$ alkoxy, $C_1$-$C_6$ haloalkoxy, and $NR^{5'}R^{6'}$;

m is 0, 1, 2, 3, or 4;

n is 0, 1, 2, 3, or 4; and is 0, 1, 2, 3, or 4, wherein the remainder of the variables are as defined in the first embodiment.

In a twenty-fourth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, or twenty-third (e.g., twenty-third) embodiment, or a pharmaceutically acceptable salt, stereoisomer, solvate, or hydrate thereof, wherein

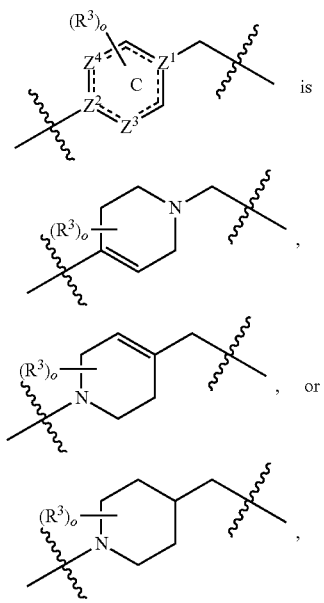

wherein $R^3$ is independently halogen, $C_1$-$C_4$ alkyl, or $C_1$-$C_4$ haloalkyl; and o is 0, 1, or 2.

In a twenty-fifth embodiment, the invention provides a compound according to first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, or twenty-fourth (e.g., twenty-third or twenty-fourth) embodiment, or a pharmaceutically acceptable salt, stereoisomer, solvate, or hydrate thereof, wherein

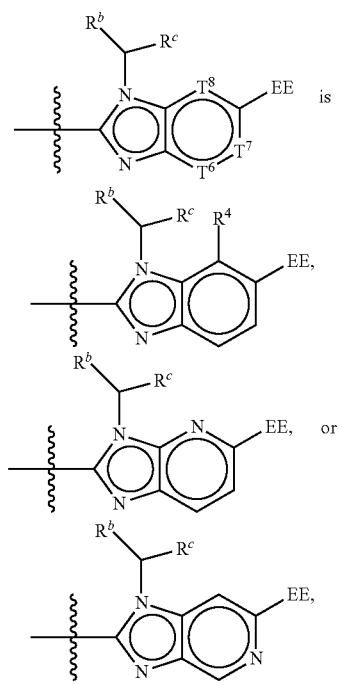

wherein $R^4$ is H or halogen, preferably, H or F.

In a twenty-sixth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, or twenty-fifth (e.g., twenty-third, twenty-fourth or twenty-fifth) embodiment, or a pharmaceutically acceptable salt, stereoisomer, solvate, or hydrate thereof, wherein EE is —COOH, —C(O)NHOH, —C(O)NHSO$_2$CH$_3$, —C(O)NHSO$_2$CF$_3$,

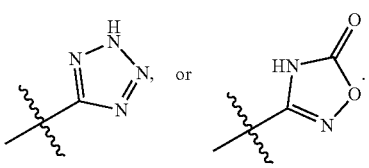 [SMILES: *c1nn[nH]n1 ; *c1noc(=O)[nH]1]

In a twenty-seventh embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, or twenty-sixth (e.g., twenty-third, twenty-fourth, twenty-fifth, or twenty-sixth) embodiment, or a pharmaceutically acceptable salt, stereoisomer, solvate, or hydrate thereof, wherein $R^b$ is

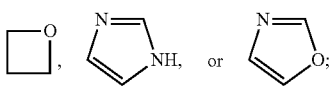

each of which is optionally substituted with one or more groups selected from $C_1$-$C_3$ alkyl; and $R^c$ is H or $C_1$-$C_3$ alkyl.

In a twenty-eighth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, or twenty-seventh (e.g., twenty-third, twenty-fourth, twenty-fifth, twenty-sixth, or twenty-seventh) embodiment, or a pharmaceutically acceptable salt, stereoisomer, solvate, or hydrate thereof, wherein

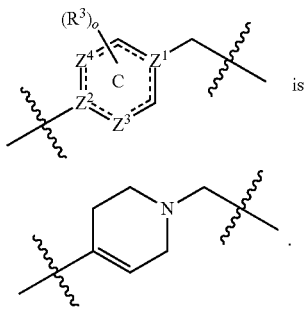

In a twenty-ninth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, or twenty-eighth (e.g., twenty-third, twenty-fourth, twenty-fifth, twenty-sixth, twenty-seventh, or twenty-eighth) embodiment, or a pharmaceutically acceptable salt, stereoisomer, solvate, or hydrate thereof, wherein

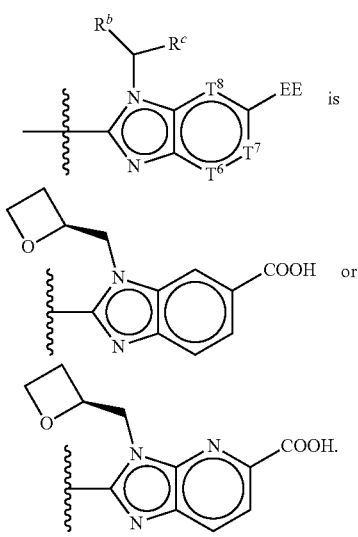

In a thirtieth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth (e.g., twenty-third, twenty-fourth, twenty-fifth, twenty-sixth, twenty-seventh, twenty-eighth, or twenty-ninth) embodiment, or a pharmaceutically acceptable salt, stereoisomer, solvate, or hydrate thereof, wherein W is O, NH or $CH_2$, and $R^a$ is H.

In a thirty-first embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, or thirtieth (e.g., twenty-third, twenty-fourth, twenty-fifth, twenty-sixth, twenty-seventh, twenty-eighth, twenty-ninth, or thirtieth) embodiment, or a pharmaceutically acceptable salt, stereoisomer, solvate, or hydrate thereof, wherein

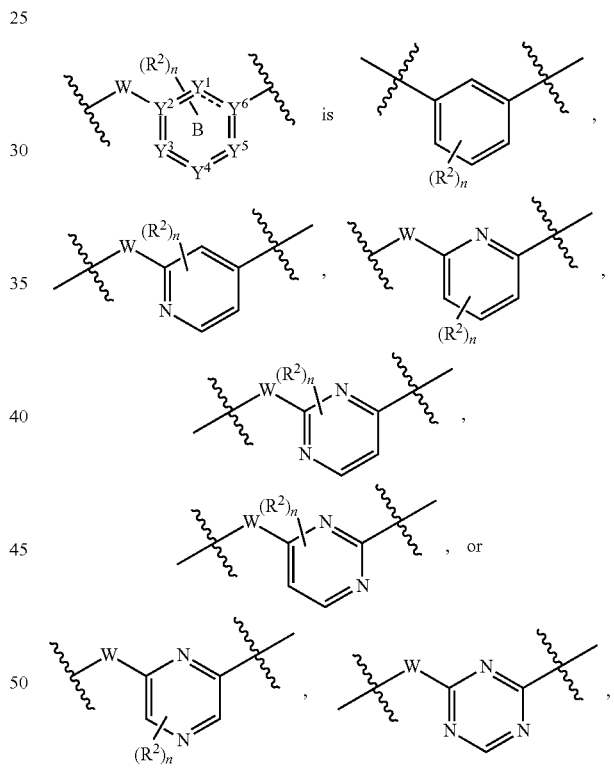

wherein $R^2$ is halogen; n is 0, 1, or 2.

In a thirty-second embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first (e.g., twenty-third, twenty-fourth, twenty-fifth, twenty-sixth, twenty-seventh, twenty-eighth, twenty-ninth, thirtieth, or thirty-first) embodiment, or a pharmaceutically acceptable salt, stereoisomer, solvate, or hydrate thereof, wherein

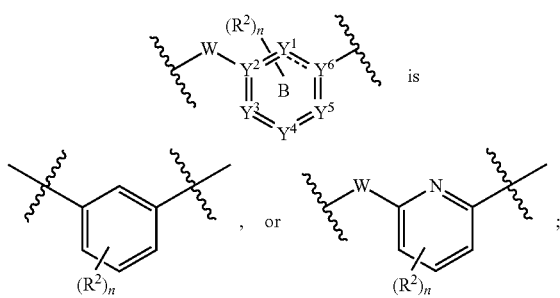

is $R^2$ is F; and n is 0, 1, or 2.

In a thirty-third embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, or thirty-second (e.g., twenty-third, twenty-fourth, twenty-fifth, twenty-sixth, twenty-seventh, twenty-eighth, twenty-ninth, thirtieth, thirty-first, or thirty-second) embodiment, or a pharmaceutically acceptable salt, stereoisomer, solvate, or hydrate thereof, wherein ring A is

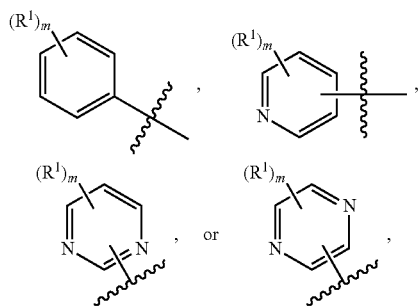

each $R^1$ is independently selected from halogen, CN, $C_1$-$C_4$ alkyl, $C_1$-$C_4$ haloalkyl, $C_1$-$C_4$ alkoxy, $C_1$-$C_4$ haloalkoxy, $C_2$-$C_4$ alkynyl optionally substituted with cyclopropyl, 5-6 membered heteroaryl (wherein the hetero ring atom is nitrogen) optionally substituted with $C_1$-$C_4$ alkyl; and/or two $R^1$, taken together with and their respective intervening carbon atoms, form 4-7 membered heterocyclyl (wherein the hetero ring atom is nitrogen and/or oxygen) optionally substituted with $C_1$-$C_4$ alkyl; and m is 0, 1, 2, or 3.

In a thirty-fourth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, or thirty-third (e.g., twenty-third, twenty-fourth, twenty-fifth, twenty-sixth, twenty-seventh, twenty-eighth, twenty-ninth, thirtieth, thirty-first, thirty-second or thirty-third) embodiment, or a pharmaceutically acceptable salt, stereoisomer, solvate, or hydrate thereof, wherein W is O.

In a thirty-fifth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, or thirty-fourth (e.g., twenty-third, twenty-fourth, twenty-fifth, twenty-sixth, twenty-seventh, twenty-eighth, twenty-ninth, thirtieth, thirty-first, thirty-second, thirty-third, or thirty-fourth) embodiment, or a pharmaceutically acceptable salt, stereoisomer, solvate, or hydrate thereof, wherein ring A is

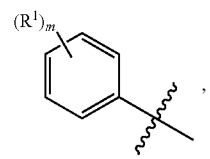

each $R^1$ is independently selected from halogen, CN, $C_1$-$C_4$ alkyl, $C_1$-$C_4$ haloalkyl, $C_1$-$C_4$ alkoxy, imidazolyl, triazolyl, pyridyl, and $C_2$-$C_4$ alkynyl optionally substituted with cyclopropyl; and m is 0, 1, or 2.

In a thirty-sixth embodiment, the invention provides a compound according to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth (e.g., twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth) embodiment, or a pharmaceutically acceptable salt, stereoisomer, solvate, or hydrate thereof, wherein $R^1$ is selected from halogen and CN.

In a thirty-seventh embodiment, the compound, or a pharmaceutically acceptable salt, stereoisomer, solvate, or hydrate thereof, is selected from the compounds disclosed in examples and Table 1.

In one embodiment, the invention provides a pharmaceutical composition comprising the compound according to any one of the first through thirty-seventh embodiments, and a pharmaceutically acceptable excipient.

In another aspect, the invention provides a method of treating cardiometabolic and associated diseases comprising administering to a subject in need of such treatment a therapeutically effective amount of any one of the compound according to any one of the first through twenty-second embodiments, wherein the disease is T1D, T2DM, prediabetes, idiopathic T1D (Type 1b), LADA (latent autoimmune diabetes in adults), EOD (early-onset T2DM), YOAD (youth-onset atypical diabetes), MODY (maturity onset diabetes of the young), malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), excessive sugar craving, dyslipidemia, hyperinsulinemia, NAFLD (including related diseases such as steatosis, NASH, fibrosis, cirrhosis, and hepatocellular carcinoma), NASH, fibrosis, cirrhosis, hepatocellular carcinoma, cardiovascular disease, atherosclerosis (including coronary artery disease), coronary artery disease, peripheral vascular disease, hypertension, endothelial dysfunction, impaired vascular compliance, congestive heart failure, myocardial infarction (e.g., necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome Crohn's disease, colitis, irritable bowel syndrome, prevention or treatment of Polycystic Ovary Syndrome and treatment of addiction (e.g., alcohol and/or drug abuse).

In a further aspect, the invention includes use of a therapeutically effective amount of the compound according to any one of the first through twenty-second embodiments in the manufacture of a medicament for treating a subject in need of with cardiometabolic and associated diseases, wherein the disease is T1D, T2DM, pre-diabetes, idiopathic T1D (Type 1b), LADA (latent autoimmune diabetes in adults), EOD (early-onset T2DM), YOAD (youth-onset atypical diabetes), MODY (maturity onset diabetes of the young), malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), excessive sugar craving, dyslipidemia, hyperinsulinemia, NAFLD (including related diseases such as steatosis, NASH, fibrosis, cirrhosis, and hepatocellular carcinoma), NASH, fibrosis, cirrhosis, hepatocellular carcinoma, cardiovascular disease, atherosclerosis (including coronary artery disease), coronary artery disease, peripheral vascular disease, hypertension, endothelial dysfunction, impaired vascular compliance, congestive heart failure, myocardial infarction (e.g., necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome Crohn's disease, colitis, irritable bowel syndrome, prevention or treatment of Polycystic Ovary Syndrome and treatment of addiction (e.g., alcohol and/or drug abuse).

It should be understood that any embodiment of the invention, including those described only in the Examples or claims, or only in one section of the specification, can be combined with one or more additional embodiments of the invention, to the extent that such combinations are not expressly disclaimed or are improper.

BRIEF DESCRIPTION OF THE DRAWINGS

FIG. 1A compares Compounds 1, 10, 11, 19, and 35 to GLP-1 (7-37). The two panels of FIG. 1B compare Compounds 225, 237, & 239 (left panel) and 236 & 238 (right panel) to GLP-1 (7-37).

FIGS. 8A-8F show favorable pharmacokinetic (PK) property of the subject compounds, as compared to a control compound ("Compound 418"), in the form of substantially constant mean plasma concentration—time profiles for Compounds 19 (Dose 1) (FIG. 8A), 28 (Dose 1) (FIG. 8B), 29 (Dose 2) (FIG. 8C), 225 (Dose 2) (FIG. 8D), Compounds 19 (Dose 2) (FIG. 8E), and Compounds 418 (Dose 2) (FIG. 8F), respectively.

DETAILED DESCRIPTION OF THE INVENTION

1. Overview

Figure 1A:
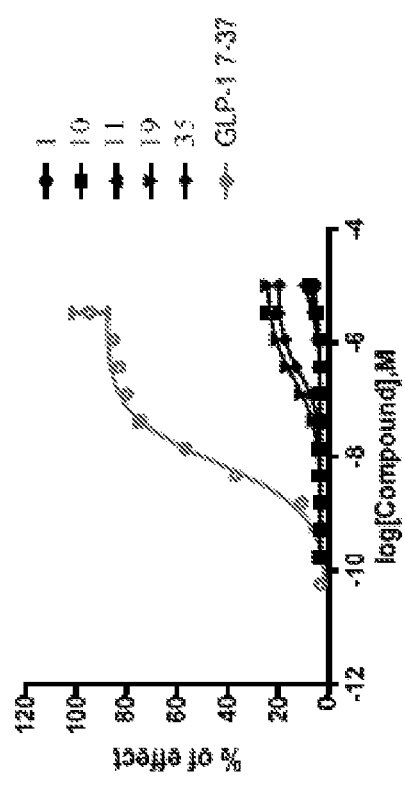
FIGS. 1A and 1B show dose-response curves for the GLP-1R/β-Arrestin recruitment assay using certain compounds of the invention and GLP-1 (7-37) as control. The vertical axis represents relative effects of the test compounds normalized to percentage of effect by the natural ligand GLP-1 (7-37).

In one aspect, the invention provides a compound of any one of the formulae described above (e.g., Formulae I, II-A, III-A, and IV-A).

In another aspect, the invention provides a pharmaceutical composition comprising a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, in a mixture with at least one pharmaceutically acceptable excipient.

In another aspect, the invention provides a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for use as a medicament.

In another aspect, the invention provides a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for use in the prevention and/or treatment of cardiometabolic and associated diseases discussed herein, including T2DM, pre-diabetes, NASH, and cardiovascular disease.

In another aspect, the invention provides a method of treating a disease for which an agonist of GLP-1R is indicated, in a subject in need of such prevention and/or treatment, comprising administering to the subject a therapeutically effective amount of a compound of any one of the formulae described above (e.g., Formulae I, II-A, III-A, and IV-A), or a pharmaceutically acceptable salt, stereoisomer, solvate, or hydrate thereof, as defined in any one of the embodiments described herein.

In another aspect, the invention provides a use of a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for the manufacture of a medicament for treating a disease or condition for which an agonist of the GLP-1R is indicated.

In another aspect, the invention provides a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for use in the treatment of a disease or condition for which an agonist of GLP-1R is indicated.

In another aspect, the invention provides a pharmaceutical composition for the treatment of a disease or condition for which an agonist of the GLP-1R is indicated, comprising a compound of any one of the formulae described above (e.g., Formulae I, II-A, III-A, and IV-A), or a pharmaceutically acceptable salt, stereoisomer, solvate, or hydrate thereof, as defined in any one of the embodiments described herein.

Every Example or pharmaceutically acceptable salt thereof may be claimed individually or grouped together in any combination with any number of each and every embodiment described herein.

The invention also provides a pharmaceutical composition comprising a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for use in the treatment and/or prevention of cardiometabolic and associated diseases discussed herein, including T2DM, pre-diabetes, NASH, and cardiovascular disease.

In another aspect, the invention provides a compound of any one of the formulae described above (e.g., Formulae I, II-A, III-A, and IV-A), or a pharmaceutically acceptable salt, stereoisomer, solvate, or hydrate thereof, as defined in any one of the embodiments described herein, for use in the treatment and/or treatment for cardiometabolic and associated diseases including diabetes (T1D and/or T2DM, including pre-diabetes), idiopathic T1D (Type 1b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

In certain embodiments, the disease or disorder is obesity, eating disorders, weight gain from use of other agents, excessive sugar craving, and dyslipidemia.

In certain embodiments, the disease or disorder is obesity.

In certain embodiments, the disease or disorder is prediabetes.

In certain embodiments, the disease or disorder is T2DM.

In certain embodiments, the disease or disorder is NASH.

In certain embodiments, the disease or disorder is NAFLD.

In certain embodiments, the disease or disorder is a cardiovascular disease, such as hypertension.

In another aspect, the invention provides a method of enhancing or stimulating GLP-1R-mediated cAMP signaling with reduced β-arrestin/arrestin-2 recruitment, comprising administering a compound of any one of the formulae described above (e.g., Formulae I, II-A, III-A, and IV-A), or a pharmaceutically acceptable salt, stereoisomer, solvate, or hydrate thereof, as defined in any one of the embodiments described herein. This is partly based on the surprising finding that the compounds of the invention, while being full agonists of GLP-1R-mediated cAMP signaling, are partial agonists of 3-arrestin recruitment to activated GLP-1R, compared to the natural GLP-1R ligand GLP-1, in that maximal β-arrestin recruitment to activated GLP-1R by the compounds of the invention is lower than maximal β-arrestin recruitment by GLP-1. Such partial and/or biased agonists of GLP-1R for cAMP signaling may provide a more sustained cAMP signaling activity for better efficacy and lowered side effects.

Thus, the method of the invention may be advantageously used for the treatment of any of the diseases or conditions described herein, such as type II diabetes (T2D) and related diseases.

In certain embodiments, the treatment elicits a glycemic benefit without concomitant increase, or at least reduced increase, in a GI side effect such as nausea, vomiting, or diarrhea. In certain embodiments, the treatment has greater tolerability compared to a control treatment that has normal or enhanced β-arrestin recruitment (such as β-arrestin recruitment by GLP-1).

2. Definitions

The term "alkyl," as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl and hexyl.

The term "alkylene" as used herein, means a straight or branched chain divalent hydrocarbon group of formula —$C_nH_{2n}$—. Non-limiting examples include ethylene, and propylene.

The term "cycloalkyl," as used herein, means a cyclic, hydrocarbon group containing at least three carbon atoms (e.g., $C_3$, $C_4$, $C_5$, $C_6$, $C_7$, $C_8$, or $C_{3-8}$ or $C_{3-6}$). The cycloalkyl may be (fully) saturated or partially saturated (i.e., not aromatic, for example, cycloalkenyl or cycloalknyl), and may contain one or more carbon-carbon double bond(s).

A fully saturated cycloalkyl has the formula $C_nH_{(2n-1)}$. Non-limiting examples include cyclopropyl, cyclobutyl, cyclopentyl and cyclohexyl.

The term "halogen," as used herein, refers to fluoride, chloride, bromide, or iodide.

The term "heterocycloalkyl" or "heterocyclyl" as used herein, refers to a (fully saturated or partially saturated, for example, heterocycloalkenyl) 3-12 membered cycloalkyl group, such as those defined above, in which one or more (e.g., one to four) of the ring carbon atom(s) has been replaced with a group selected from —O—, —S—, or —N—, wherein the nitrogen may provide a point of attachment or may be substituted as provided within each embodiment. Where nitrogen provides a point of attachment, a structural drawing of a heterocycloalkyl would have a hydrogen on said nitrogen.

Generally, the cycloalkyl or the heterocycloalkyl/heterocyclyl may be unsubstituted, or be substituted with one or more substituents as valency allows, wherein the substituents can be independently selected from a number of groups such as oxo, —CN, halogen, alkyl and alkoxyl, optionally, the alkyl substitution may be further substituted.

The term "heteroaryl," as used herein, refers to a monocyclic or multicyclic aromatic hydrocarbon in which at least one of the ring carbon atoms (typically 1 to 4, more typically 1 or 2) has been replaced with a heteroatom independently selected from oxygen, nitrogen and sulfur. As such, "5-14 membered heteroaryl" includes monocyclic, bicyclic or tricyclic ring systems. Preferably, the heteroaryl is based on a $C_{5-8}$ aryl with one or more of its ring carbon atoms replaced by the heteroatom. An heteroaryl group may be attached through a ring carbon atom or, where valency permits, through a ring nitrogen atom. Generally, the heteroaryl may be unsubstituted, or be substituted with one or more substituents as valency allows with the substituents being independently selected from halogen, OH, alkyl, alkoxyl, and amino (e.g., $NH_2$, NHalkyl, N(alkyl)$_2$), optionally, the alkyl may be further substituted.

Certain abbreviations used herein include: Room temperature: RT; Methanol: MeOH.; Ethanol: EtOH; Isopropanol: iPrOH; Ethyl acetate: EtOAc; Tetrahydrofuran: THF; Toluene: $PhCH_3$; Cesium carbonate: $Cs_2CO_3$; Lithium bis (trimethylsilyl)amide: LiHMDS; Sodium t-butoxide: NaOtBu; Potassium t-butoxide: KotBu; Lithium diisopropylamide: LDA; Triethylamine: $Et_3N$; N,N-diisopropylethyl amine: DIPEA; Potassium carbonate: $K_2CO_3$; Dimethyl formamide: DMF; Dimethyl acetamide: DMAc; Dimethyl sulfoxide: DMSO; N-Methyl-2-pyrrolidinone: NMP; Sodium hydride: NaH; Trifluoroacetic acid: TFA; Trifluoroacetic anhydride: TFAA; Acetic anhydride: $Ac_2O$; Dichloromethane: DCM; 1,2-Dichloroethane: DCE; Hydrochloric acid: HCl; 1,8-Diazabicyclo[5.4.0]undec-7-ene: DBU; Borane-dimethylsulfide complex: $BH_3$-DMS; Borane-tetrahydrofuran complex: $BH_3$-THF; Lithium aluminum hydride: LAH; Acetic acid: AcOH; Acetonitrile: MeCN; p-Toluenesulfonic acid: pTSA; Dibenzylidine acetone: DBA; 2,2'-Bis(diphenylphosphino)-1,1'-binaphthalene: BINAP; 1,1'-Ferrocenediyl-bis(diphenylphosphine): dppf, 1,3-Bis(diphenylphosphino)propane: DPPP; 3-Chloroperbenzoic acid: m-CPBA; Tert-Butyl methyl ether: MTBE; Methanesulfonyl: Ms; N-Methylpyrrolidinone: NMP; Thin layer chromatography: TLC; Supercritical fluid chromatography: SFC; 4-(Dimethylamino)pyridine: DMAP; Tert-Butyloxycarbonyl: Boc; 1-[Bis(dimethylamino)methylene]-1H-1,2,3-triazolo[4,5-b]pyridinium 3-oxid hexafluorophosphate: HATU; Petroleum ether: PE; 2-(1H-Benzotriazole-1-yl)-1,1,3,3-tetramethyluronium hexafluorophosphate:

HBTU; and 2-Amino-2-(hydroxymethyl)propane-1,3-diol: tris; tris(dibenzylideneacetone)dipalladium: $Pd_2(dba)_3$ $^1$H Nuclear magnetic resonance (NMR) spectra were in all cases consistent with the proposed structures. Characteristic chemical shifts (δ) are given in parts-per-million relative to the residual proton signal in the deuterated solvent ($CHCl_3$ at 7.27 ppm; $CD_2HOD$ at 3.31 ppm; MeCN at 1.94 ppm; DMSO at 2.50 ppm) and are reported using conventional abbreviations for designation of major peaks: e.g. s, singlet; d, doublet; t, triplet; q, quartet; m, multiplet; br, broad. $^1$H NMR spectra were obtained with field strengths of 400 or 600 MHz if not stated.

As used herein, a wavy line denotes a point of attachment of a substituent to another group.

Pharmaceutically Acceptable Salts

Pharmaceutically acceptable salts of the compounds of any one of the formulae described above include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002). Incorporated herein by reference.

Pharmaceutically acceptable salts of compounds of any one of the formulae described above may be prepared by one or more of three methods:
(i) by reacting the compound of any one of the formulae described above with the desired acid or base;
(ii) by removing an acid- or base-labile protecting group from a suitable precursor of the compound of any one of the formulae described above or by ring-opening a suitable cyclic precursor, for example, a lactone or lactam, using the desired acid or base; or
(iii) by converting one salt of the compound of any one of the formulae described above to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of any one of the formulae described above, and pharmaceutically acceptable salts thereof, may exist in unsolvated and solvated forms.

Solvates and Hydrates

The term "solvate" is used herein to describe a molecular complex comprising the compound of any one of the formulae described above, or a pharmaceutically acceptable salt thereof, and one or more pharmaceutically acceptable solvent molecules, for example, ethanol.

The term "hydrate" is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Stereoisomers and Other Variations

The compounds of any one of the formulae described above may exhibit one or more kinds of isomerism (e.g. optical, geometric or tautomeric isomerism). The compounds of any one of the formulae described above may also be isotopically labelled. Such variation is implicit to the compounds of any one of the formulae described above defined as they are by reference to their structural features and therefore within the scope of the invention.

Compounds of any one of the formulae described above containing one or more asymmetric carbon atoms can exist as two or more stereoisomers. Where a compound of any one of the formulae described above contains an alkenyl or alkenylene group, geometric cis/trans (or Z/E) isomers are possible. Where structural isomers are interconvertible via a low energy barrier, tautomeric isomerism ("tautomerism") can occur. This can take the form of proton tautomerism in compounds of any one of the formulae described above containing, for example, an imino, keto, or oxime group, or so-called valence tautomerism in compounds which contain an aromatic moiety. It follows that a single compound may exhibit more than one type of isomerism.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The pharmaceutically acceptable salts of compounds of any one of the formulae described above may also contain a counterion which is optically active (e.g. d-lactate or l-lysine) or racemic (e.g. dl-tartrate or dl-arginine).

Cis trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of any one of the formulae described above contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of any one of the formulae described above (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub-and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). Columns can be obtained from Chiral Technologies, Inc, West Chester, Pa., USA, a subsidiary of Daicel® Chemical Industries, Ltd., Tokyo, Japan.

It must be emphasized that the compounds of any one of the formulae described above have been drawn herein in a single tautomeric form, all possible tautomeric forms are included within the scope of the invention.

The present invention also includes all pharmaceutically acceptable isotopically-labeled compounds of any one of the formulae described above wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of any one of the formulae described above, for example those incorporating a radioactive isotope, are useful in drug and/or substrate tissue distribution studies. The radioactive isotopes tritium, i.e., $^3$H, and carbon-14, i.e., $^4$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of any one of the formulae described above can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g., $D_2O$, $d_6$-acetone, $d_6$-DMSO.

Prodrugs

One way of carrying out the invention is to administer a compound of any one of the formulae described above in the form of a prodrug. Thus, certain derivatives of a compound of any one of the formulae described above which may have little or no pharmacological activity themselves can, when administered into or onto the body, be converted into a compound of any one of the formulae described above having the desired activity, for example by hydrolytic cleavage, particularly hydrolytic cleavage promoted by an esterase or peptidase enzyme. Such derivatives are referred to as "prodrugs." Further information on the use of prodrugs may be found in *Pro-drugs as Novel Delivery Systems*, Vol. 14, *ACS Symposium Series* (T. Higuchi and W. Stella) and *Bioreversible Carriers in Drug Design*, Pergamon Press, 1987 (Ed. E. B. Roche, American Pharmaceutical Association). Reference can also be made to *Nature Reviews Drug Discovery*, 7:355, 2008, and *Current Opinion in Drug Discovery and Development*, 10:550, 2007.

Prodrugs in accordance with the invention can, for example, be produced by replacing appropriate functionalities present in the compounds of any one of the formulae described above with certain moieties known to those skilled in the art as "pro-moieties" as described, for example, in *Design of Prodrugs* by H. Bundgaard (Elsevier, 1985) and Y. M. Choi-Sledeski and C. G. Wermuth, *Designing Prodrugs and Bioprecursors* in Practice of Medicinal Chemistry, (Fourth Edition), Chapter 28, 657-696 (Elsevier, 2015).

Thus, a prodrug in accordance with the invention is (a) an ester or amide derivative of a carboxylic acid in a compound of any one of the formulae described above; (b) an ester, carbonate, carbamate, phosphate or ether derivative of a hydroxyl group in a compound of any one of the formulae described above; (c) an amide, imine, carbamate or amine derivative of an amino group in a compound form any one of the formulae described above; (d) an oxime or imine derivative of a carbonyl group in a compound of any one of the formulae described above; or (e) a methyl, primary alcohol or aldehyde group that can be metabolically oxidized to a carboxylic acid in a compound of any one of the formulae described above.

Some specific examples of prodrugs in accordance with the invention include:

(i) where the compound of any one of the formulae described above contains a carboxylic acid functionality (—COOH), an ester thereof, such as a compound wherein the hydrogen of the carboxylic acid functionality of the compound of any one of the formulae described above is replaced by $C_1$-$C_8$ alkyl (e.g. ethyl) or ($C_1$-$C_8$ alkyl)C(=O)OCH$_2$— (e.g. $^t$BuC(=O)OCH$_2$—);

(ii) where the compound of any one of the formulae described above contains an alcohol functionality (—OH), an ester thereof, such as a compound wherein the hydrogen of the alcohol functionality of the compound of any one of the formulae described above is replaced by —CO($C_1$-$C_8$ alkyl) (e.g. methylcarbonyl) or the alcohol is esterified with an amino acid;

(iii) where the compound of any one of the formulae described above contains an alcohol functionality (—OH), an ether thereof, such as a compound wherein the hydrogen of the alcohol functionality of the compound of any one of the formulae described above is replaced by ($C_1$-$C_8$ alkyl)C(=O)OCH$_2$— or —CH$_2$OP (=O)(OH)$_2$;

(iv) where the compound of any one of the formulae described above contains an alcohol functionality (—OH), a phosphate thereof, such as a compound wherein the hydrogen of the alcohol functionality of the compound of any one of the formulae described above is replaced by —P(=O)(OH)$_2$ or —P(=O)(ONa)$_2$ or —P(=O)(O$^-$)$_2$Ca$^{2+}$;

(v) where the compound of any one of the formulae described above contains a primary or secondary amino functionality (—NH$_2$ or —NHR where R≠H), an amide thereof, for example, a compound wherein, as the case may be, one or both hydrogens of the amino functionality of the compound of any one of the formulae described above is/are replaced by ($C_1$-$C_{10}$)alkanoyl, —COCH$_2$NH$_2$ or the amino group is derivatised with an amino acid;

(vi) where the compound of any one of the formulae described above contains a primary or secondary amino functionality (—NH$_2$ or —NHR where R≠H), an amine thereof, for example, a compound wherein, as the case may be, one or both hydrogens of the amino functionality of the compound of any one of the formulae described above is/are replaced by —CH$_2$OP(=O) (OH)$_2$;

(vii) where the carboxylic acid group within compound of any one of the formulae described above is replaced by a methyl group, a —CH$_2$OH group or an aldehyde group.

Certain compounds of any one of the formulae described above may themselves act as prodrugs of other compounds of any one of the formulae described above. It is also possible for two compounds of any one of the formulae described above to be joined together in the form of a prodrug. In certain circumstances, a prodrug of a compound of any one of the formulae described above may be created by internally linking two functional groups in a compound of any one of the formulae described above, for instance by forming a lactone.

References to compounds of any one of the formulae described above are taken to include the compounds themselves and prodrugs thereof. The invention includes such compounds of any one of the formulae described above as well as pharmaceutically acceptable salts of such compounds and pharmaceutically acceptable solvates of said compounds and salts.

3. Administration and Dosing

Typically, a compound of the invention is administered in an amount effective to treat a condition as described herein. The compounds of the invention can be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, or topically.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the invention is typically from about 0.001 to about 100 mg/kg (i.e., mg compound of the invention per kg body weight) for the treatment of the indicated conditions discussed herein. In another embodiment, total daily dose of the compound of the invention is from about 0.01 to about 30 mg/kg, and in another embodiment, from about 0.03 to about 10 mg/kg, and in yet another embodiment, from about 0.1 to about 3 mg/kg. It is not uncommon that the administration of the compounds of the invention will be repeated a plurality of times in a day (typically no greater than 4 times). Multiple doses per day typically may be used to increase the total daily dose, if desired. In certain embodiments, the patient is a human, such as a human with one of the treatable disease indications or disorders described elsewhere herein.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects or patients according to the invention include mammalian subjects, including human, or non-human mammals such as primates, rodents (mice, rats, hamsters, rabbits etc). In one embodiment, humans are suitable subjects. Human subjects may be of either gender and at any stage of development. In certain embodiments, the human is a child less than 18 years old, 15 years old or around 14 years old, 12 years old, 10 years old, or less than 5 years old.

4. Pharmaceutical Compositions

In another embodiment, the invention comprises pharmaceutical compositions. Such pharmaceutical compositions comprise a compound of the invention presented with a pharmaceutically acceptable carrier. Other pharmacologically active substances can also be present.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of any one of the formulae described above are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form.

"Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form.

"Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, *J. Pharm. Sci.,* 88:955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures.

The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman et al., Eds., *Pharmaceutical Dosage Forms*, Marcel Decker, New York, N.Y., 1980; and Kibbe et al., Eds., *Handbook of Pharmaceutical Excipients* (3$^{rd}$ Ed.), American Pharmaceutical Association, Washington, 1999.

5. Co-Administration

The compounds of the invention can be used alone, or in combination with other therapeutic agents. The invention provides any of the uses, methods or compositions as defined herein wherein the compound of any embodiment of any one of the formulae described above herein, or pharmaceutically acceptable salt thereof, or pharmaceutically acceptable solvate of said compound or salt, is used in combination with one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering compounds of the present invention in combination with one or more other pharmaceutical agents, wherein the one or more other pharmaceutical agents may be selected from the agents discussed herein.

In one embodiment, the compounds of this invention are administered with an anti-diabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this invention are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this invention are administered with an agent to treat NASH including but not limited to PF-05221304, an FXR agonist (e.g., obeticholic acid), a PPAR a/S agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, $20^{th}$ Ed., Mack Publishing (2000).

Sustained-release preparations may be used. Suitable examples of sustained-release preparations include semipermeable matrices of solid hydrophobic polymers containing the compound of any one of the formulae described above, which matrices are in the form of shaped articles, e.g., films, or microcapsules. Examples of sustained-release matrices include polyesters, hydrogels (for example, poly (2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(–)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™ Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 m, particularly 0.1 and 0.5 m, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

6. Kits

Another aspect of the invention provides kits comprising the compound of any one of the formulae described above or pharmaceutical compositions comprising the compound of any one of the formulae described above of the invention. A kit may include, in addition to the compound of any one of the formulae described above, of the invention or pharmaceutical composition thereof, diagnostic or therapeutic agents. A kit may also include instructions for use in a diagnostic or therapeutic method. In some embodiments, the kit includes the compound of any one of the formulae described above, or a pharmaceutical composition thereof and a diagnostic agent. In other embodiments, the kit includes the compound of any one of the formulae described above, or a pharmaceutical composition thereof.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

7. Preparation

The compounds of any one of the formulae described above, may be prepared by the general and specific methods described below, using the common general knowledge of one skilled in the art of synthetic organic chemistry. Such common general knowledge can be found in standard reference books such as *Comprehensive Organic Chemistry*, Ed. Barton and Ollis, Elsevier; *Comprehensive Organic Transformations: A Guide to Functional Group Preparations*, Larock, John Wiley and Sons; and *Compendium of Organic Synthetic Methods*, Vol. I-XII (published by Wiley-Interscience). The starting materials used herein are commercially available or may be prepared by routine methods known in the art.

In the preparation of the compounds of any one of the formulae described above, it is noted that some of the preparation methods described herein may require protection of remote functionality (e.g., primary amine, secondary amine, carboxyl in any one of the formulae described above precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines, and lower alkyl or benzyl esters for carboxylic acids) which are generally not chemically reactive under the reaction conditions described and can typically be removed without chemically altering other functionality in the any one of the formulae described above compounds.

The Schemes described below are intended to provide a general description of the methodology employed in the preparation of the compounds of the present invention. Some of the compounds of the present invention may contain single or multiple chiral centers with the stereochemical designation (R) or (S). It will be apparent to one skilled in the art that all of the synthetic transformations can be conducted in a similar manner whether the materials are enantioenriched or racemic. Moreover, the resolution to the desired optically active material may take place at any desired point in the sequence using well known methods such as described herein and in the chemistry literature.

Amine compounds prepared via methods described herein can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds. Standard ester hydrolysis can be performed to provide acids. If $Pg^2$ is t-butyl, standard acidic deprotection methods such as TFA/DCM, HCl/1,4-dioxane, HCl/EtOAc or other suitable conditions may be used to deliver acids.

EXAMPLES

Activation of a G protein-coupled receptor (GPCR) GLP-1R by its natural ligand GLP-1 causes recruitment of multiple intracellular proteins, each of which can activate distinct signaling pathways, most prominently the activation of downstream G proteins (which can be measured by cAMP production), the recruitment of β-Arrestin, and/or the subsequent internalization of the GPCR (i.e., GLP-1R)-β-Arrestin complex. Unlike the natural ligand GLP-1, certain GLP-1R agonists are so-called "biased agonists," in that they preferentially stimulate subsets among the natural signaling pathways, such as the G protein activation/cAMP production pathway, as compared to the recruitment of β-Arrestin, and/or the subsequent internalization of the GPCR (i.e., GLP-1R)-β-Arrestin complex. The assays below provide means to measure the various downstream signaling pathways upon activation by the subject compounds.

Biological Example 1: GLP-1R/β-Arrestin Assay and Internalization Assay for Demonstrating Small Molecule Compound-Mediated GLP-1R/β-Arrestin Interaction Activation GLP1 plays an important physiological role in maintaining blood glucose homeostasis. GLP-1R is known to be expressed in pancreatic beta cells. GLP-1 mediates its effects via a Gas-coupled pathway. Activated GLP-1R stimulates the adenylyl cyclase pathway thus increases the intracellular concentration of cAMP, which results in increased insulin synthesis and release of insulin. Consequently GLP-1R has been suggested as a potential target for the treatment of diabetes.

GLP-1R activation following agonist/ligand binding also leads to β-arrestin recruitment to the GLP-1 receptor, which blocks GLP-1R signaling by, for example, occluding the binding site on GLP-1R for heterotrimeric G-protein to prevent its activation (desensitization), and by linking the GLP-1R to elements of the internalization machinery, such as clathrin and clathrin adaptor AP2, which promotes receptor internalization via coated pits and subsequent transport to internal compartments endosomes. Subsequently, the receptor could be either directed to degradation compartments (lysosomes) or recycled back to the plasma membrane where it can again signal. The strength of arrestin-receptor interaction is believed to play a role in this choice: tighter complexes tend to increase the probability of receptor degradation (Class B), whereas more transient complexes favor recycling (Class A), although this "rule" is far from being absolute.

GLP-1R agonist activity with respect to β-arrestin recruitment can be determined with a cell-based functional assay using PathHunter eXpress GLP1R CHO-K1 β-Arrestin GPCR Assay kit (DiscoverX Cat #93-0300E2CPOM).

The PathHunter β-Arrestin GPCR assay technology utilizes a β-galactosidase (D-gal) enzyme that is split into two fragments, the smaller Enzyme Donor (ED) and the larger Enzyme Acceptor (EA). These fragments can be fused to two proteins that may interact with each other, such as EA-β-Arrestin and ED-GLP-1R. The fusions can be stably expressed in a test cell line, such as the PathHunter CHO-K1 GLP1R β-Arrestin cells described below.

Independently, these fragment fusions have no β-gal activity; however, in solution or in a living cell, they can be brought together and complement to form an active β-gal enzyme due to the interaction between the fused proteins, thus generating a chemiluminescent signal in the presence of a suitable R-gal substrate.

In this experiment, PathHunter CHO-K1 GLP1R β-Arrestin cells from the assay kit were plated at a density of 1000 or 2000 cells/20 l/well in a 384-well white/clear bottom plates (Greiner Cat #781098). Frozen cells were quickly thawed and 10 mL of cell plating medium (provided by the kit) was added to thawed cells. Cells were stored in a 37° C. incubator under 5% $CO_2$ and kept for approximately 48 hours until ready to run the assay.

Reference and test compounds were dissolved in 100% DMSO. 5×concentration of an agonist was prepared in serum free DMEM (Thermo Cat #11965). 5 μL of this solution was added to 20 μL cell medium in assay plate for a final top concentration of 10 μM. Plates were then incubated at 37° C. under 5% $CO_2$ for 90 min.

Following 90 min incubation, detection reagents were made up by combining 1 part Galacton Star Substrate with 5 parts Emerald II™ Solution, and 19 parts of PathHunter Cell Assay Buffer, respectively. 12.5 μL detection reagent was added to each well. The plates were then incubated at room temperature in dark for 60 min. Plates were then read on Envision for 0.1 sec/well.

$EC_{50}$ determinations were made from agonist dose-response curves analyzed with a curve fitting program using a 4-parameter logistic dose response equation.

The effect of a small molecule compound, such as one of the instant invention, on the GLP-1R/β-Arrestin interaction activation, or β-Arrestin recruitment, can be demonstrated and measured using the assay and commercial reagents described herein below.

Preparations
Reagents and Consumables:

| Reagent | Vendor | Catalog No. |
|---|---|---|
| PathHunter eXpress GLP1R CHO-K1 β-Arrestin GPCR Assay kit | Discover X | 93-0300E2CP0M |
| 384 well white/clear bottom plates | Greiner | 781098 |

Instruments:

| Instrument | Vendor | Internal Code |
|---|---|---|
| EnVision | PerkinElmer | HD-4HYSG2330 |

Media and Solutions

Prepare detection Working Solution by combining 1 part Galacton Star® Substrate with 5 parts Emerald II™ Solution, and 19 parts of PathHunter Cell Assay Buffer, respectively.

Once prepared, the working solution is stable for at least 24 hours at room temperature with no impact on assay performance. Sufficient reagents are provided in each kit to perform the indicated number of assays.

Procedures
1. Plating Cells

Cells were plated at a density of 1000 or 2000 cells/20 μL/well. Frozen cells were quickly thawed and added to 10 mL of cell plating medium. Cells were stored in a 37° C. incubator under 5% $CO_2$ and left for approximately 48 hours until ready to run the assay.

2. Compound Preparation
   1) Reference agonist compound GLP1 (7-37): dissolved with DMSO to make 1 mM stock solutions, aliquoted and stored at −80° C.
   2) Test compounds (such as the compounds of the invention) came solubilized in 100% DMSO. Prepare 10× concentration of an agonist in serum free DMEM, and add all solutions into the compound plate. 2.5 μL of this solution was added to 20 μL cell medium in assay plate for a final top concentration of 10 μM. Plates were incubated at 37° C. under 5% $CO_2$ for 30 min. An additional 2.5 μL of Buffer was added to the entire plate for agonist mode and incubated at 37° C. for another 90 min.

3. Detection Reagents

Following 90 min incubation, detection reagents were made up as described. 12.5 μL was added to all wells. The plates were then incubated at room temperature in dark for 60 min. Plates were then read on Envision for 0.1 sec/well.

4. β-Arrestin Assay Data Processing

Data analysis: GraphPad Prism 6 was used for establishment of progression curve. $EC_{50}$s or $IC_{50}$s were determined by 4-parameter logistic dose response equation.

Figure 1B:
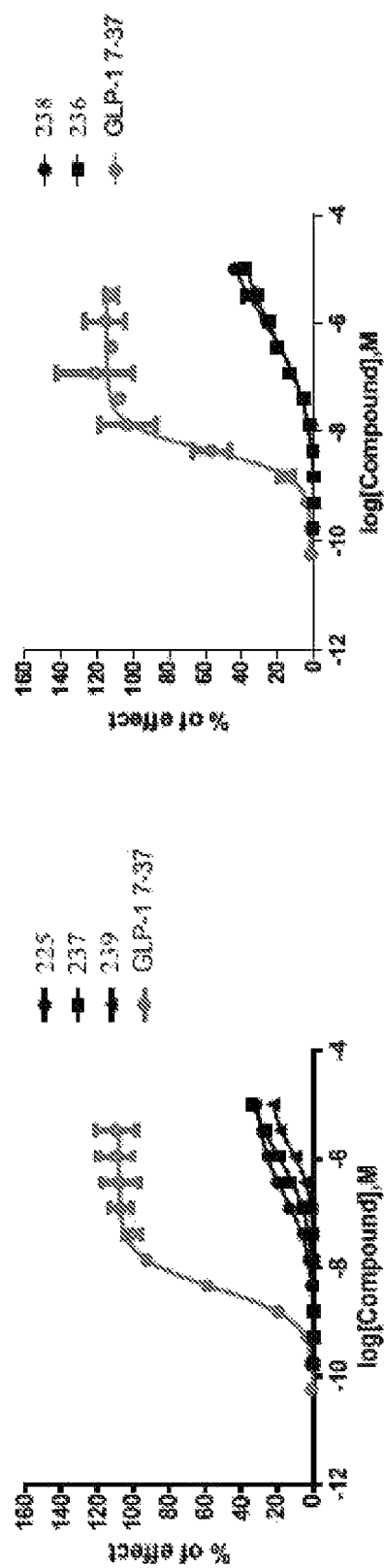

The β-Arrestin recruitment dose-response curves for selected compounds of the invention, as compared to GLP-1 (7-37) as a control, were shown in FIGS. 1A and 1B. The tested compounds include Compounds 1, 10, 11, 19, and 35 in FIG. 1A, and Compounds 225 & 236-239 in FIG. 1B.

Using this assay system, β-Arrestin recruitment was also measured for selected compounds of the invention, and the results are compiled in the table below.

β-Arrestin Recruitment as Measured by PathHunter CHO-K1-Based Assay

| Compound No. | $B_{max}$ (POC)* |
|---|---|
| 1 | 2.80 (n = 1) |
| 10 | 4.48 (n = 1) |
| 11 | 7.16 (n = 1) |
| 12 | 9.66 (n = 1) |
| 18 | 26.2 ± 1.55 (n = 2) |
| 19 | 26.0 ± 2.78 (n = 2) |
| 21 | 19.0 ± 0.982 (n = 2) |
| 22 | 10.9 ± 0.0317 (n = 2) |
| 23 | 18.2 ± 1.51 (n = 2) |
| 28 | 28.5 ± 6.36 (n = 3) |
| 29 | 36.6 ± 7.77 (n = 3) |
| 34 | 20.2 ± 1.89 (n = 2) |
| 35 | 19.9 ± 4.44 (n = 4) |
| 221 | 35.6 ± 5.38 (n = 2) |
| 222 | 31.1 ± 4.67 (n = 2) |
| 224 | 33.4 ± 3.78 (n = 2) |
| 225 | 32.5 ± 3.55 (n = 3) |
| 236 | 40.3 ± 4.10 (n = 3) |
| 237 | 37.9 ± 4.66 (n = 3) |
| 238 | 55.8 ± 14.1 (n = 3) |
| 239 | 25.6 ± 5.31 (n = 2) |
| 242 | 22.5 ± 4.32 (n = 2) |
| 245 | 38.0 ± 6.42 (n = 2) |

*This value stands for averaged $B_{max}$ where applicable (POC, or Percentage of Control).

Note that in these tested compounds of the invention, with few exceptions, the partial maximum relative effect $B_{max}$ (at the highest concentration tested in the assays) for the tested compounds generally fall within about 10% to about 40% of the $B_{max}$ for the natural ligand GLP-1 (7-37). See $B_{max}$ values in the table above.

A similar assay can also be used to assess the extent of signal attenuation due to GLP-1R internalization (the β-Arrestin Internalization Assay). In this assay, activated GLP1R Internalization cells were engineered to co-express an untagged GLP1R, Enzyme Acceptor (EA) tagged β-Arrestin, and a ProLink™ (PK) tag localized to the endosomes. Activation of the GLP1R induces β-Arrestin recruitment, which leads to internalization of the Receptor/Arrestin-EA complex in PK-tagged endosomes. This forces complementation of the two β-galactosidase enzyme fragments (EA and PK) to form a functional enzyme that hydrolyzes substrate to generate a chemiluminescent signal. These cells have been modified to prevent long term propagation and expansion using a proprietary compound that has no apparent effect on assay performance.

Specifically, PathHunter engineered U2OS cells from the assay kit (Cat #93-0724E3CP0L) were plated at a density of 2000 cells/20 μL/well in a 384-well white/clear bottom plates (Greiner Cat #781098). Frozen cells were quickly thawed and 10 mL of cell plating medium (provided by the kit) was added to thawed cells. Cells were stored in a 37° C. incubator and kept for approximately 48 hours until ready for the assay.

Reference and test compounds were dissolved in 100% DMSO. 5× concentration of an agonist was prepared in serum free DMEM (Thermo Cat #11965). 5 μL of this solution was added to 20 μL cell medium in assay plate for a final top concentration of 10 μM. Plates were incubated at 37° C. for 180 min.

Following 180 min incubation, detection reagents were made up by combining 1 part Galacton Star Substrate with 5 parts Emerald II™ Solution, and 19 parts of PathHunter Cell Assay Buffer, respectively. 12.5 μL detection reagent was added to each well. The plates were then incubated at room temperature for 60 min. Plates were then read on Envision for 0.1 sec/well.

$EC_{50}$ determinations were made from agonist dose-response curves analyzed with a curve fitting program using a 4-parameter logistic dose response equation.

Figure 2A:
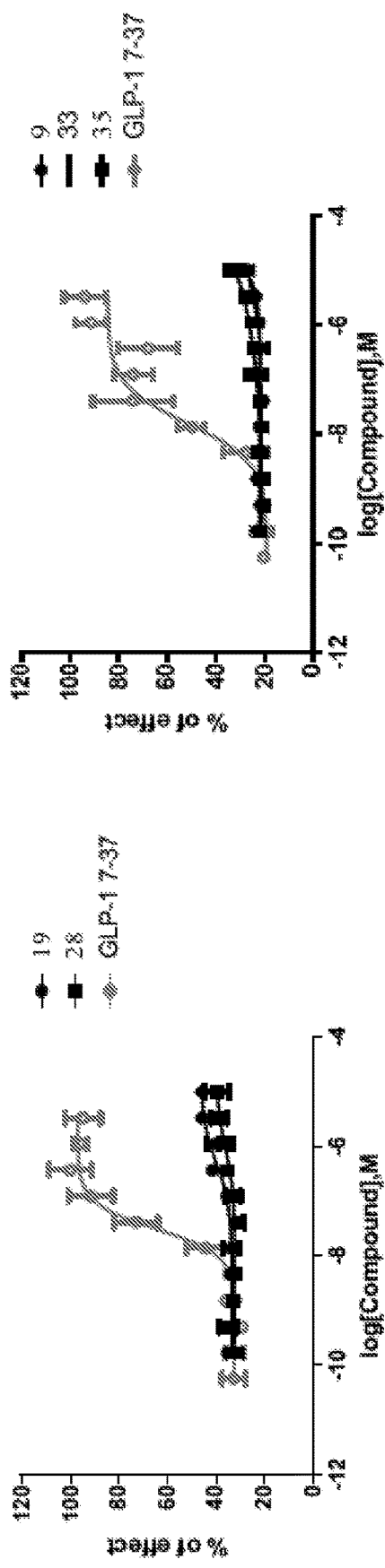
FIGS. 2A and 2B show dose-response curves for the GLP-1R/β-Arrestin internalization assay using certain compounds of the invention and GLP-1 (7-37) as control. The vertical axis represents relative effects of the test compounds normalized to percentage of effect by the natural ligand GLP-1 (7-37). The two panels in FIG. 2A compare Compounds 19 & 28 (left panel), and Compounds 9, 33, & 35 (right panel), respectively, to GLP-1 (7-37). The three panels in FIG. 2B compare Compounds 221, 222, & 225 (left panel), 224 & 239 (middle panel), and 236 (right panel), respectively, to GLP-1 (7-37).
Figure 2B:

The GLP-1R internalization dose-response curves for selected compounds of the invention, as compared to GLP-1 (7-37) as a control, were shown in FIGS. 2A-2B. The tested compounds include Compounds 19 & 28 (left panel), and Compounds 9, 33, & 35 (right panel) in FIG. 2A, and Compounds 221, 222, & 225 (left panel), 224 & 239 (middle panel), and 236 (right panel) in FIG. 2B.

Using this assay system, β-Arrestin-mediatd GLP1R internalization was also measured for other selected compounds of the invention, and the results are compiled in the table below.

β-Arrestin-Mediated GLP1R Internalization As Measured by PathHunter Assay

| Compound No. | $B_{max}$ (POC)* |
|---|---|
| 9 | 27.03 (n = 1) |
| 18 | 21.3 ± 3.47 (n = 3) |
| 19 | 20.1 (n = 1) |
| 21 | 6.64 ± 1.55 (n = 2) |
| 22 | 7.40 ± 6.97 (n = 2) |
| 23 | 8.92 ± 3.70 (n = 2) |
| 28 | 17.6 ± 6.62 (n = 3) |
| 29 | 25.9 ± 1.24 (n = 3) |
| 34 | 8.88 ± 3.19 (n = 2) |
| 35 | 14.3 ± 9.21 (n = 3) |
| 45 | 19.1 (n = 1) |
| 46 | 27.4 (n = 1) |
| 47 | 22.8 (n = 1) |
| 105 | 24.2 (n = 1) |
| 221 | 30.0 ± 6.40 (n = 2) |
| 222 | 31.4 ± 2.62 (n = 2) |
| 224 | 22.5 ± 1.41 (n = 2) |
| 225 | 24.0 ± 6.70 (n = 2) |
| 236 | 30.0 (n = 1) |
| 237 | 17.7 ± 1.20 (n = 2) |
| 238 | 52.8 ± 1.14 (n = 2) |
| 239 | 14.1 ± 1.57 (n = 2) |
| 242 | 15.4 (n = 1) |
| 245 | 27.7 (n = 1) |

*This value stands for averaged $B_{max}$ where applicable (POC, or Percentage of Control).

Again, note that in each case, with few exceptions, the partial maximum relative effect $B_{max}$, (at the highest concentration tested in the assays) for the tested compounds generally fall within about 10% to about 35% of the $B_{max}$ for the natural ligand GLP-1 (7-37).

Biological Example 2: NanoBit GLP1R/β-Arrestin Interaction Assay for Demonstrating Small Molecule Compounds-Mediated GLP1R and β-Arrestin Interaction Activation GLP-1R-mediated interaction with β-Arrestin by agonist activity is determined with a cell-based functional assay, utilizing a NanoLuc® Binary Technology (NanoBiT) (Promega N2015) designed to detect GLP-1R and β-Arrestin interaction in a living cell. The method is a two-subunit system based on NanoLuc® luciferase that can be used for intracellular detection of protein: protein interactions (PPIs). The two subunits are known as the Large BiT (LgBiT; 17.6 kDa) and the Small BiT (SmBiT; 11 amino acids). These two subunits are fused to two proteins of interest, respectively. When both are expressed, the PPI brings the subunits into close proximity to form a functional enzyme that generates a bright, luminescent signal.

More specifically, the human GLP-1R coding sequence (NCBI Reference Sequence NM_002062) and β-Arrestin2 coding sequence (NCBI Reference Sequence NM_004313.3) were subcloned into transient expression vectors provided in the NanoBiT kit, such that GLP-1R-LgBiT and SmBiT-β-Arrestin2 fusions were generated. A total of 8 combinations were selected using HEK293T-based transfection with activation by the natural ligand GLP-1$_{7-37}$. The combination showed the highest assay window (GLP-1R-LgBiT and SmBiT-β-Arrestin2) was selected for testing the compounds of the invention.

The NanoBit assay was performed as briefly described herein: HEK293T cells (7.5 k cells/well) were seeded in 96-well culture plate (Corning Cat #3917) in DMEM (Thermo Cat #11965) with 10% FBS (Biosera Cat #FB-10581) that was heat inactivated, and 25 mM glucose. After 48 hours, cells were transfected with the GLP-1R-LgBiT and SmBiT-β-Arrestin2 constructs using Lipofectamine2000 (Thermo Cat #11668019) following the manufacturer's assay protocol. Briefly, plasmids encoding the GLP-1R-LgBiT and SmBiT-β-Arrestin2 fusions, and transfection reagent were diluted with Opti-MEM (Thermo Cat #31985-070). Then about 50 ng of GLP-1R-LgBiT and 50 ng of SmBiT-β-Arrestin2 plasmid constructs were mixed, and the resulting plasmids mixture was added into diluted transfection reagent. The ratio of plasmid (μg): Lipofectamine2000 (μl) was 1:10. The mixtures were then added into cells after 5 minutes' incubation at room temperature. About 48 hours after transfection, medium was replaced by 65 μL/well fresh Opti-MEM.

Nano-Glo® Live Cell Substrate was then diluted with Nano-Glo® LCS Dilution Buffer at 1:24 ratio. About 25 μL of Nano-Glo® Live Cell Reagent was added into each well. Varying concentrations of each subject compound to be tested (in DMSO) were diluted in Opti-MEM with 0.1% BSA (Sigma Cat #A7409) to make 10× stocks. About 10 μL compound stocks were added into each well using pipette. Luminescence was measured immediately by EnVision for 40, 60, or 120 repeats, with 0.25 seconds per well.

$EC_{50}$ determinations were made from agonist dose-response curves analyzed with a curve fitting program using a 4-parameter logistic dose response equation.

The effect of a small molecule compound, such as one of the instant invention, on the GLP-1R/β-Arrestin interaction activation, or β-Arrestin recruitment, can be demonstrated and measured using the assay and commercial reagents described herein or equivalents thereof. The reagents and detailed experimental protocols used in this example are further described below.

Preparations
Reagents and Consumables:

| Reagent | Vendor | Catalog No. |
| --- | --- | --- |
| NanoBiT® Protein: Protein Interaction System | Promega | N2015 |
| Opti-MEM™ I Reduced Serum Medium | Thermo Fisher | 31985-070 |
| Lipofectamine™ 2000 Transfection Reagent | Thermo Fisher | 11668019 |
| Human GLP-1-(7-36)-amide | MCE | HY-P0054A |
| 96 well plates, white | Corning | 3917 |
| DMEM | Thermo Fisher | 11965 |
| Fetal Bovine Serum | Biosera | FB-10581/500 |
| DMSO | Sigma | D2650 |

Instruments:

| Instrument | Vendor | Internal Code |
| --- | --- | --- |
| EnVision | PerkinElmer | HD-4HYSG2330 |

Preparation of the Nano-Glo® Live Cell Reagent:
1. Equilibrate Nano-Glo® LCS Dilution Buffer to ambient temperature if using for the first time.
2. Remove the Nano-Glo® Live Cell Substrate from storage and mix.
3. Prepare the desired amount of reconstituted Nano-Glo® Live Cell Reagent by combining 1 volume of Nano-Glo® Live Cell Substrate with 24 volumes of Nano-Glo® LCS Dilution Buffer (a 25-fold dilution), creating a 4× stock to mix with cell culture medium.

Procedures
Compound Preparation:
GLP-1 (7-36) is dissolved in 100% DMSO and the stock concentration is 1 mM. A typical plate layout for GLP-1 is shown below.

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | | | | | | | | | | | | |
| B | GLP-1 | HPE | 1.00E−05 | 2.50E−06 | 6.25E−07 | 1.56E−07 | 3.91E−08 | 9.77E−09 | 2.44E−09 | 6.10E−10 | ZPE | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

HPE: 10 μM GLP-1 (7-36)
ZPE: 0.1% DMSO

For test compounds, dilute 1 mM stock to 100 M using Opti-MEM containing 1% BSA, final top concentration is 10 μM, ¼ log (4-fold) dilution, 8-dilution points, duplicate samples for each dilution. The layout is similar to GLP-1 above (not shown).

Assay Procedure:
Cell Culture and Transfection:
1. Seed 7.5 k cells/well 293T cells in 96 well culture plate (Corning #3917) in the DMEM with 10% FBS (heat inactivated and 25 mM glucose).
2. After 48 hours, performance transfection according to protocol of Lipofectamine2000.
3. 50 ng Lg-Bit and 50 ng Sm-Bit/well, the ratio of plasmid (g): Lipofectamine2000 (L) is 1:10.
4. 48 hours later after transfection, medium was replaced by fresh 65 μL Opti-MEM/well.

Activation and Luminescence Measurement:
5. Prepare Nano-Glo® Live Cell Reagent, diluted Nano-Glo® Live Cell Substrate with Nano-Glo® LCS Dilution Buffer in 1:24 ratio.
6. Add 25 μL Nano-Glo® Live Cell Reagent into each well.
7. Add 10 μL 10% DMSO or 10×GLP-1 solutions or test compounds into each well.

8. Immediately measure luminescence for 40, 60, or 120 repeats, with 0.25 second/well.

Figure 3:
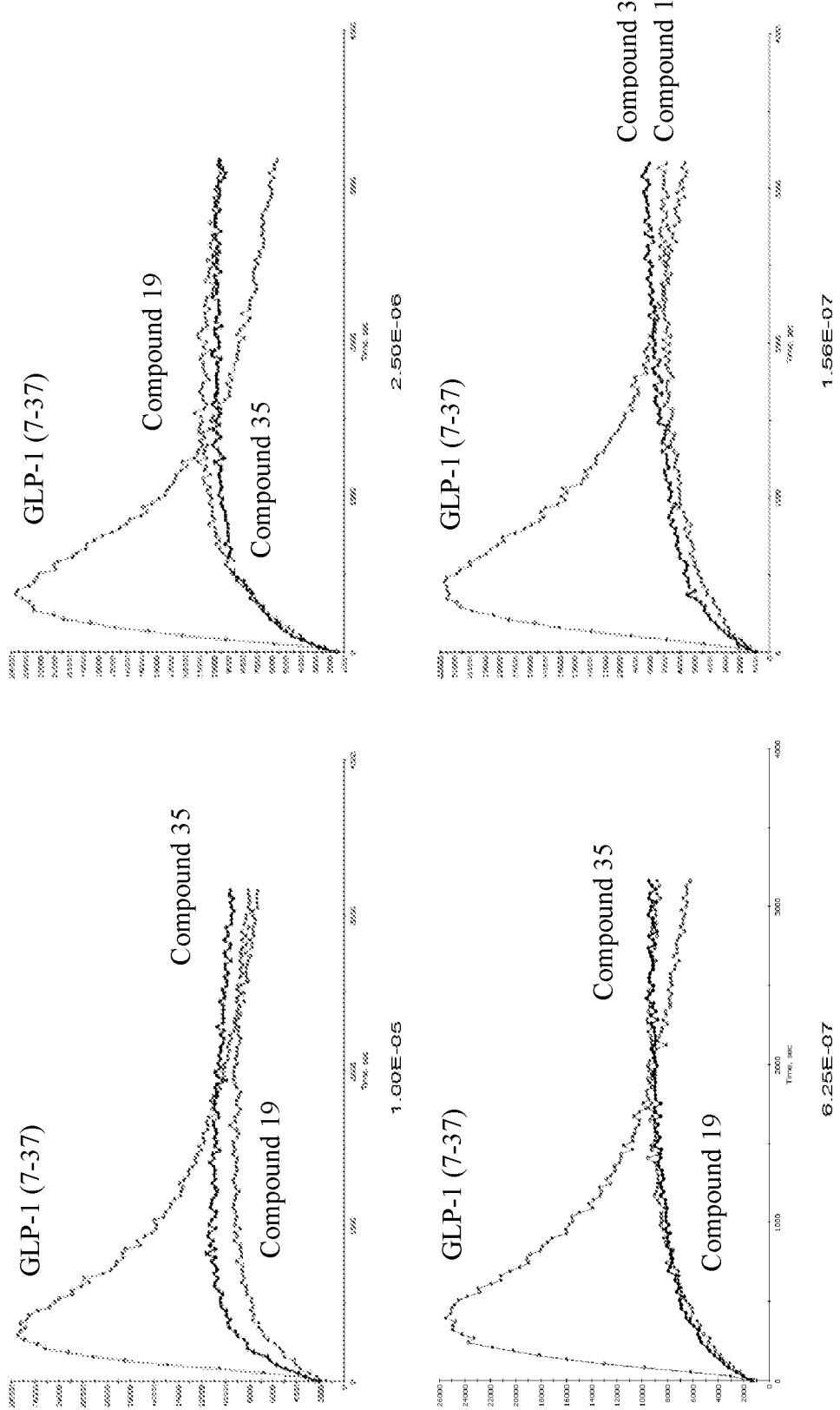
FIGS. 3 and 4 show time-course responses of GLP-1R and β-arrestin2 interaction as measured by the NanoBit Assay, in the presence of indicated different concentrations (serial 4-fold dilutions) of GLP-1 (7-37) peptide (natural agonist of GLP-1R), as well as two representative compounds of the instant application (i.e., Compounds 19 and 35). The black curves are for Compound 35. It is apparent that the compounds of the invention behaved differently from the natural peptide agonist GLP-1.
Figure 4:
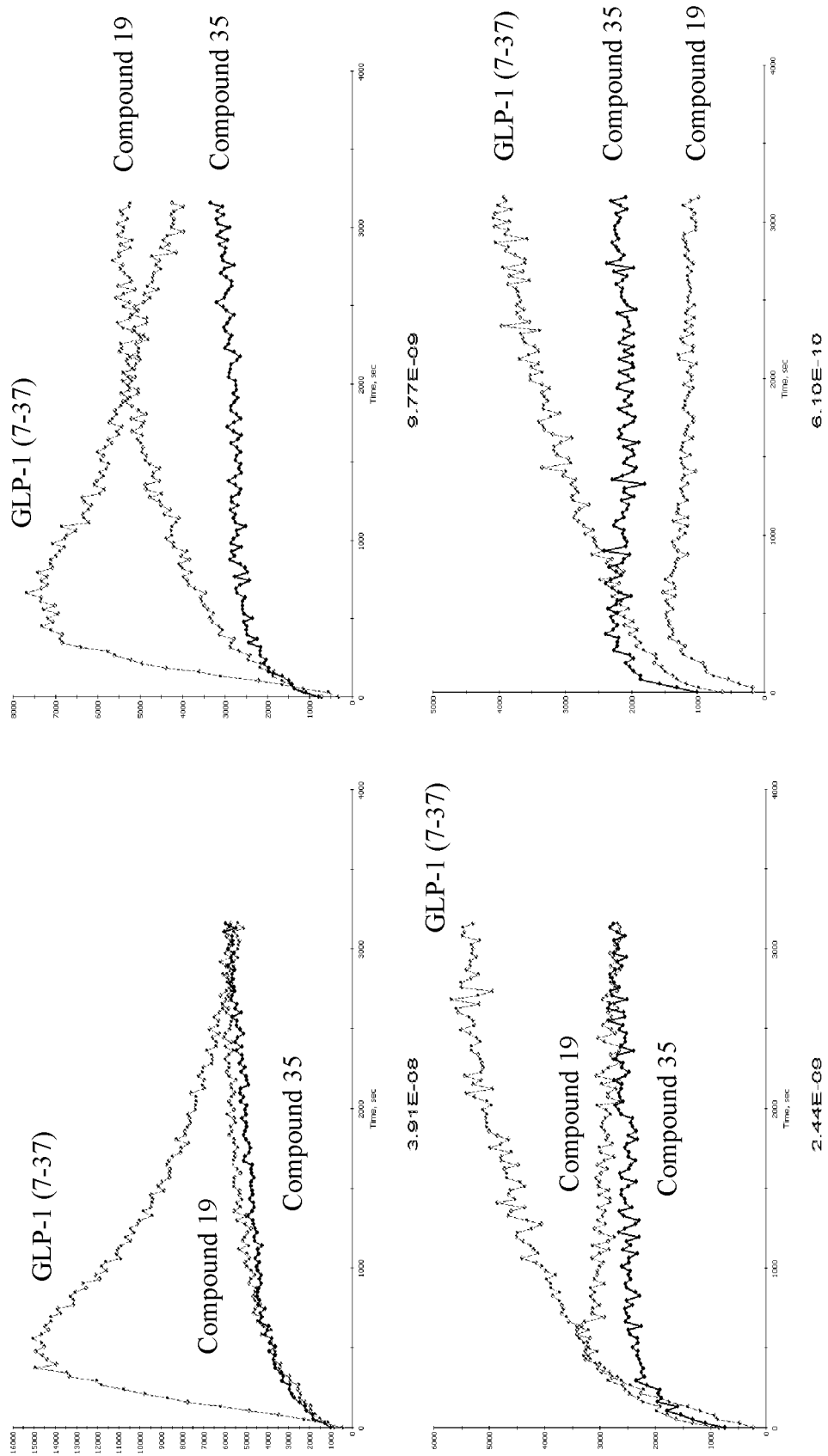

As shown in FIGS. 3 and 4, tested Compounds 19 and 35 clearly behaved differently from the natural agonist GLP-1 (7-37).

Figure 5A:
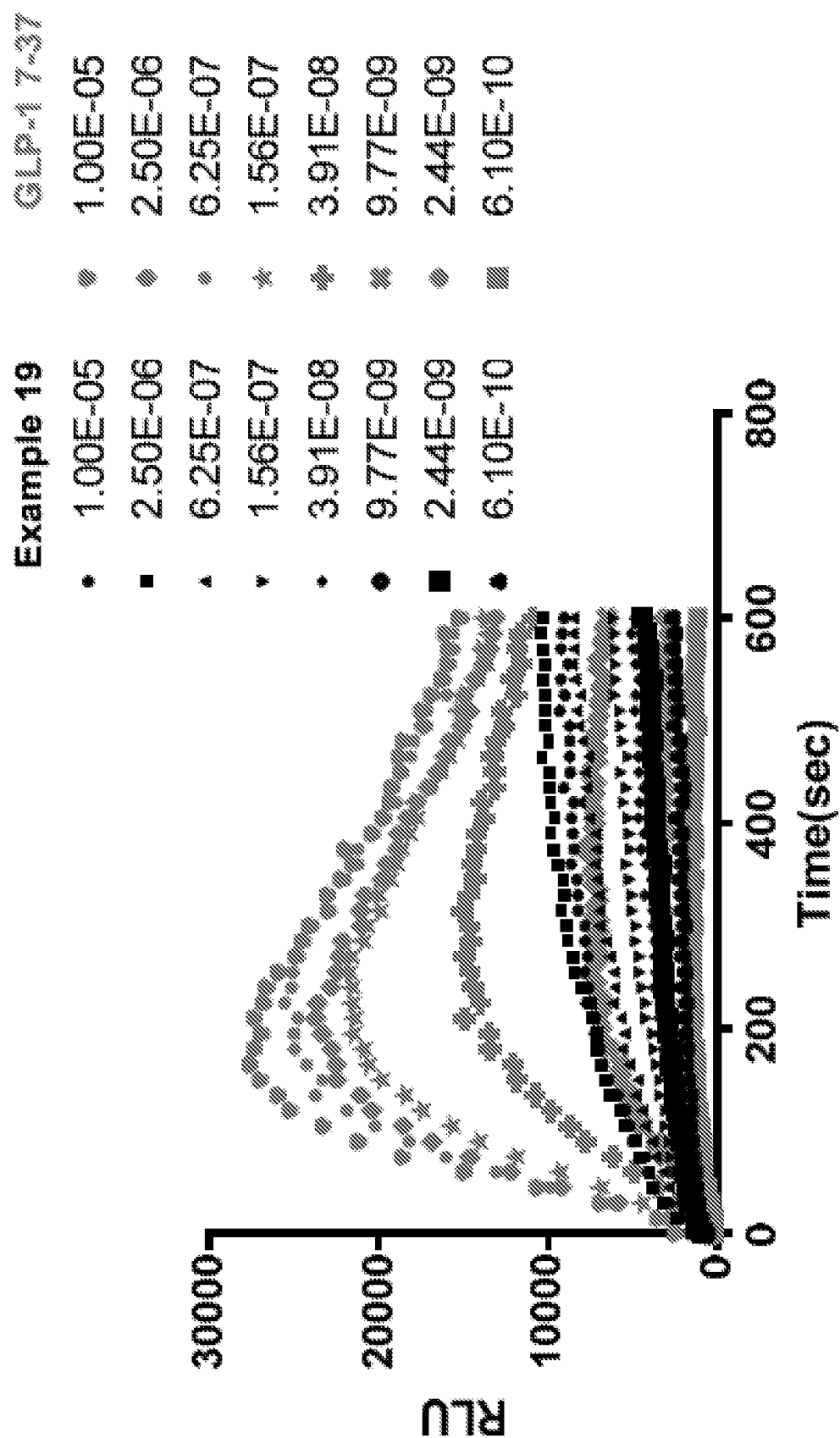
FIGS. 5A-5C show NanoBit assay time-course responses for both GLP-1 (7-37) and Compound 19, 10, or 35, respectively, at different compound concentrations.
Figure 5B:
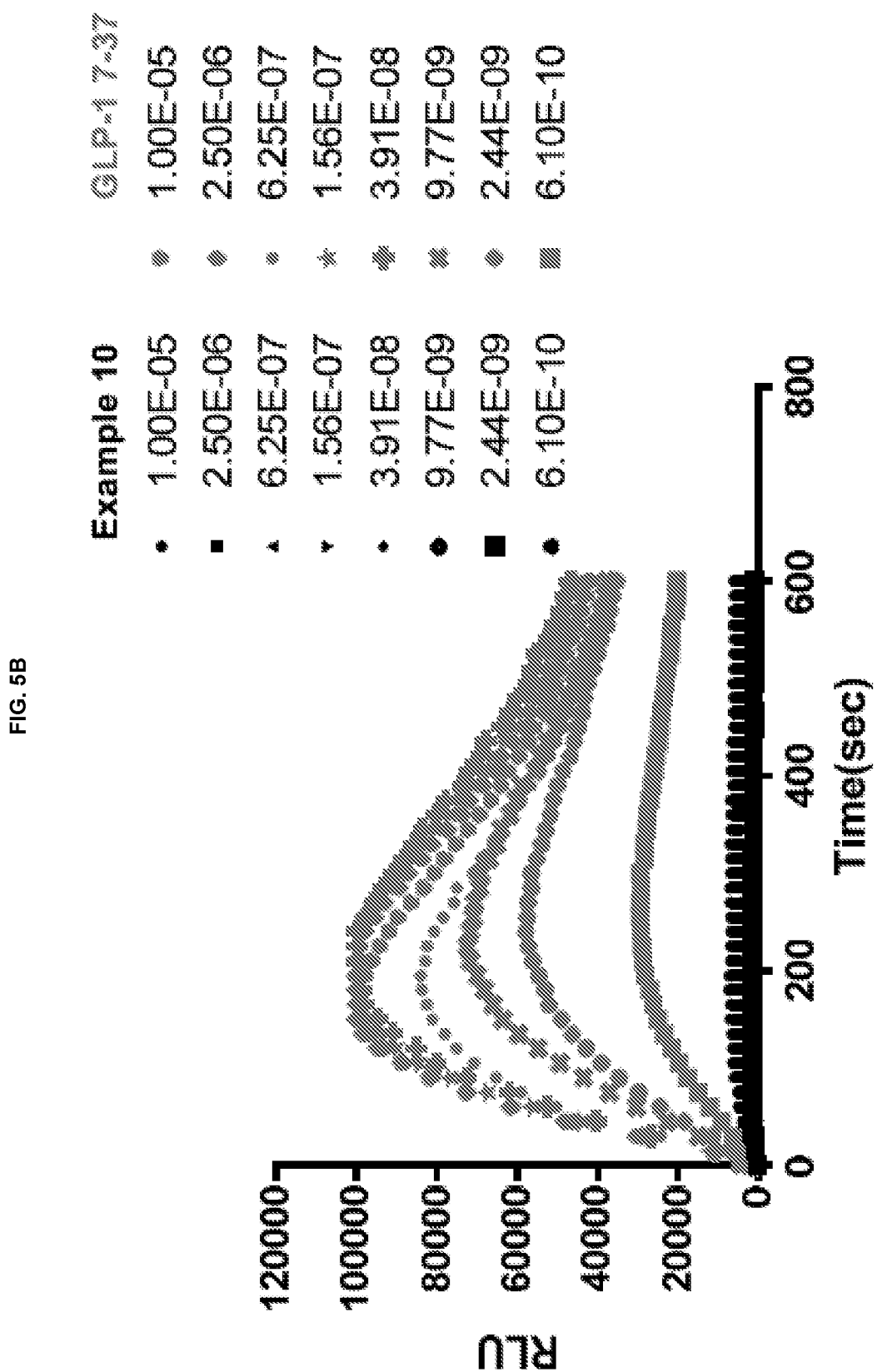
Figure 5C:
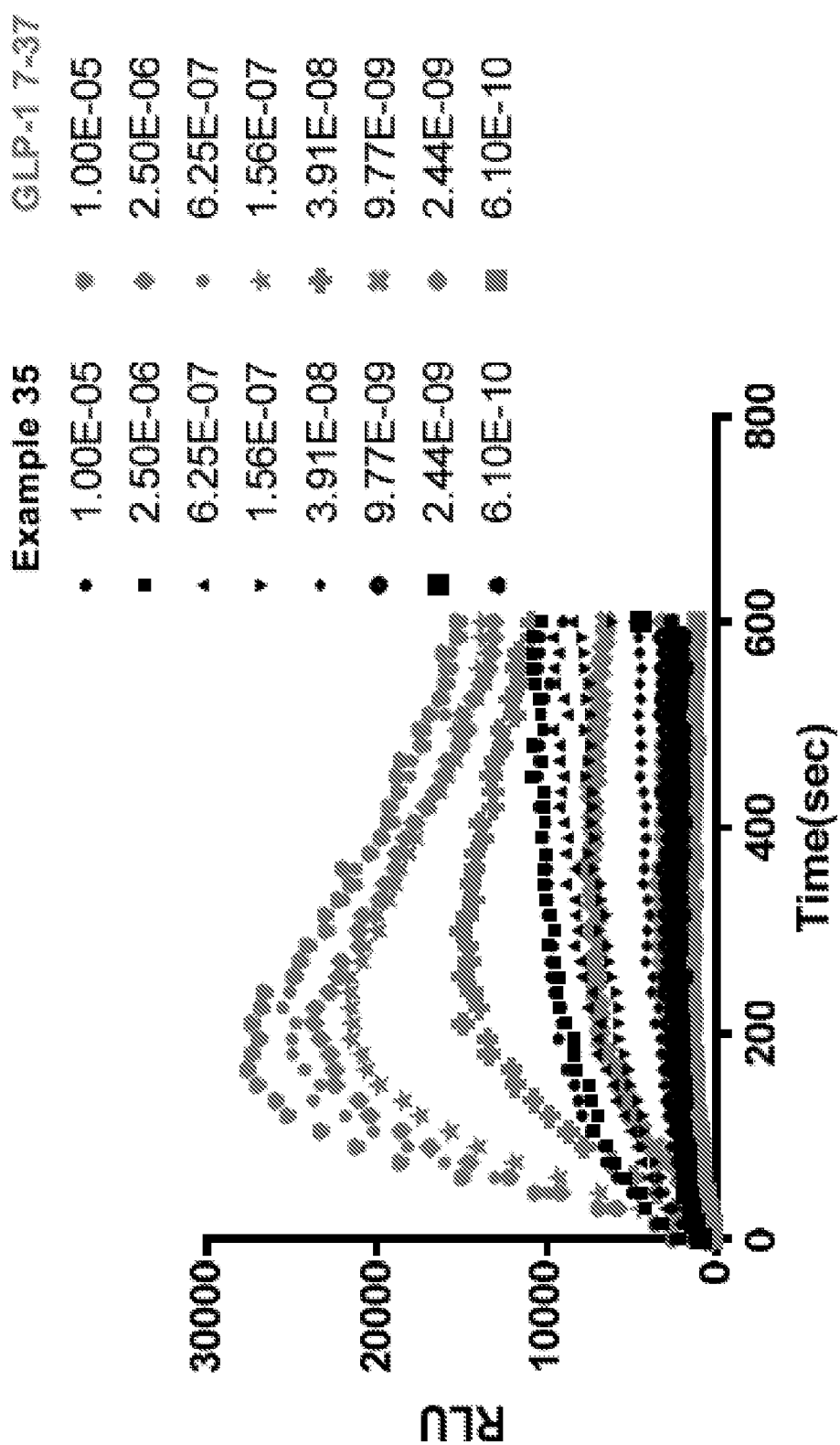

FIGS. 5A-5C show NanoBit assay time-course responses for both GLP-1 (7-37) and Compound 19, 10, or 35, respectively, at different compound concentrations.

Figure 6:
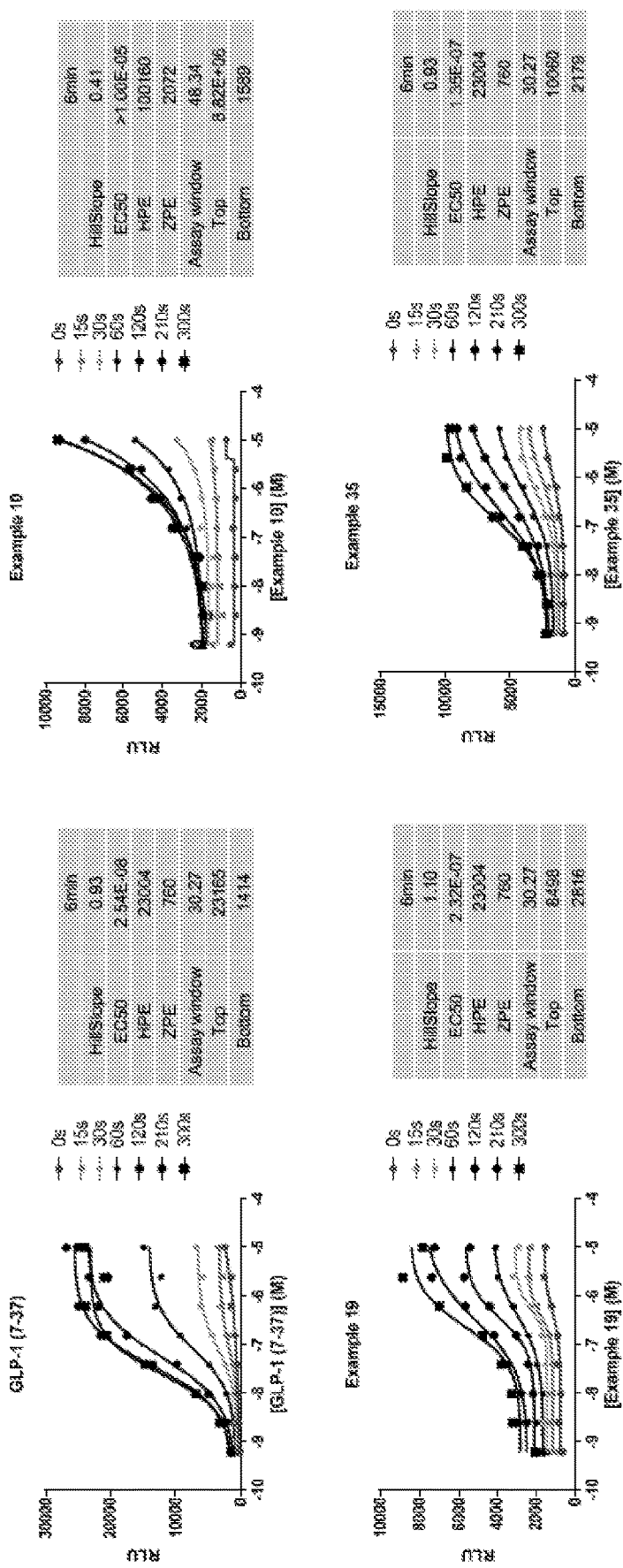
FIG. 6 shows dose-response curves of GLP-1R and β-arrestin2 interaction as measured by the NanoBit Assay, in the presence of indicated different time points (i.e., 0, 15, 30, 60, 120, 210, and 300 sec) of GLP-1 peptide (natural agonist of GLP-1R), as well as three representative compounds of the instant application (i.e., Compounds 10, 19 and 35). Arbitrarily, t=6 min (300 s) was chosen for dose response $EC_{50}$ determination. Alternatively, data analysis/report can be done to obtain $EC_{50}$ values when compounds reach maximal signals at about 450-500 sec (~ 8 min).

$EC_{50}$ values were also measured based on dose response curves. As shown in FIG. 6, the arbitrarily t=6 min time point was chosen for dose response $EC_{50}$ determination, for Compounds 10, 19, and 35. The results were shown in FIG. 6.

Figure 7A:
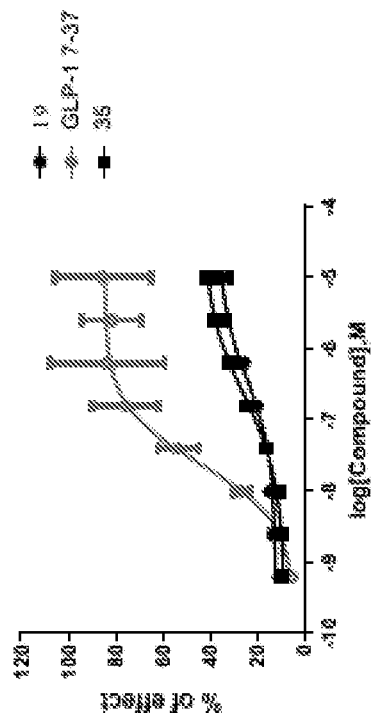
FIGS. 7A-7B show dose-response curves for the GLP-1R/β-Arrestin NanoBit assay using certain compounds of the invention and GLP-1 (7-37) as control. The vertical axis represents relative effects of the test compounds normalized to percentage of effect by the natural ligand GLP-1 (7-37). The two panels in FIG. 7A compare Compounds 19 & 35 to GLP-1 (7-37) at 3 min. and 5 min. readouts, respectively. The two panels in FIG. 7B compare Compound 10 to GLP-1 (7-37) at 3 min. and 5 min. readouts, respectively.
Figure 7A:
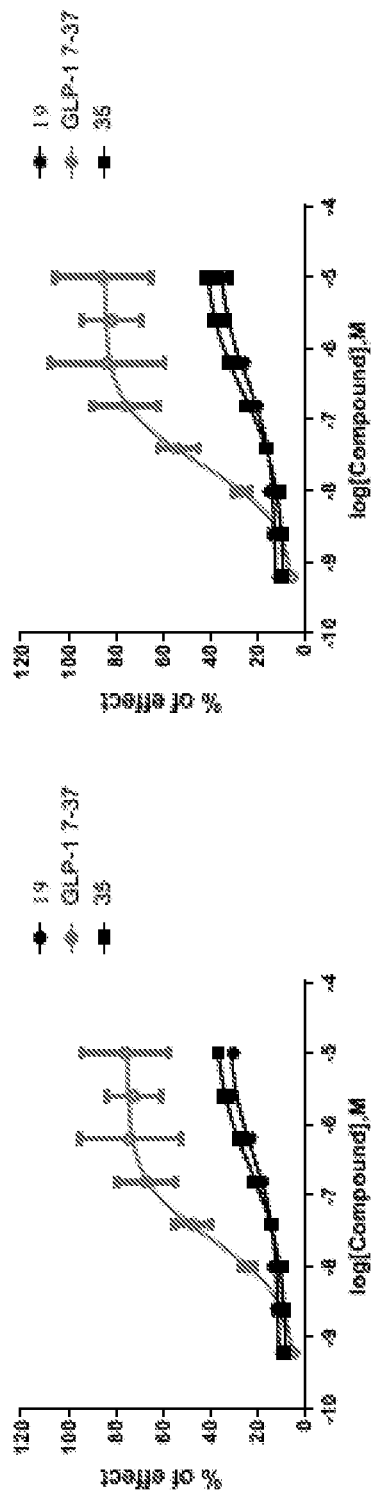
Figure 7B:
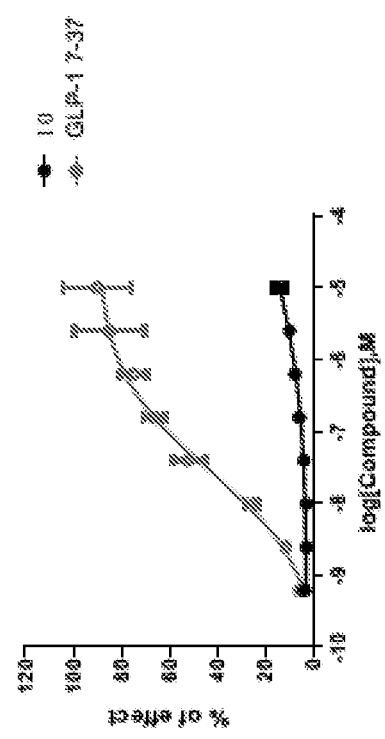
Figure 7B:
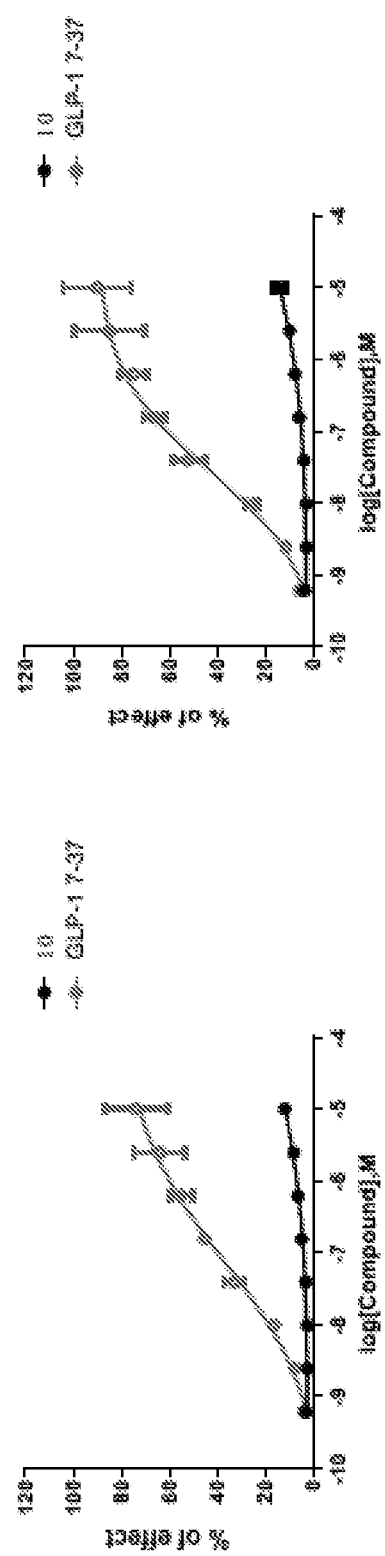

Also see FIGS. 7A-7B showing dose-response curves at 3-minute (180-second) and 5-minute (300-second) readouts for the GLP-1R/β-Arrestin NanoBit assay, using Compounds 19 and 35 (FIG. 7A) and Compound 10 (FIG. 7B), with GLP-1 (7-37) as control. In each of these figures, the maximum relative effects for the tested compounds $B_{max}$, for the highest concentrations tested, are generally no more than 40% (usually about 20-40%) of that of GLP-1 (7-37).

As an alternative, data analysis/report to obtain $EC_{50}$ values can also be done when compounds reach maximal signals—such as at 450-500 sec (~8 min).

Biological Example 3: GLP1R cAMP Assay for Demonstrating Small Molecule Compounds-Mediated GLP-1R Activation HEK293/GLP-1R/CRE/Luc, Clone 4—cAMP Assay GLP-1R-mediated agonist activity was determined with a cell-based functional assay utilizing an HTRF (Homogeneous Time-Resolved Fluorescence) cAMP detection kit (cAMP Dynamic 2 Assay Kit; CisBio cat #62AM4PEC) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e., energy transfer) is inversely proportional to the concentration of cAMP in either standard or experimental sample.

The human GLP-1R coding sequence (NCBI Reference Sequence NM_002062) was subcloned into pcDNA3.1+/Hygro vector (Invitrogen) and transfected into HEK293/CRE/Luc parental cell line. A cell line stably expressing the receptor was isolated. Saturation binding analyses (filtration assay procedure) using $^{125}I$-GLP-$1_{7\text{-}36}$ (Perkin Elmer) shows that plasma membranes derived from this cell line express a high GLP-1R density ($K_d$: <1 nM, $B_{max}$: >800 fmol/mg protein).

Varying concentrations of each compound to be tested (in DMSO) were diluted in DMSO to obtain 200× compound working solution first and then 50 nl compounds were added to a white 384-well assay plate (Greiner 784075) with ECHO. The final DMSO concentration was 0.5%. The compound concentration range may be adjusted at any time.

Cells were removed from cryopreservation, re-suspended in 5 mL of Dulbecco's Phosphate Buffered Saline (DPBS-Sigma Cat #D8537) and centrifuged at 900 g for 5 min at 22° C. The cell pellet was then re-suspended in 1 mL of assay buffer [DPBS with 500 M IBMX (Sigma #15879) and 0.1% BSA (Sigma # A1933). IBMX and BSA were freshly added on the day of assay]. A 10 μL sample of the cell suspension was counted on an Invitrogen Countess II to determine cell viability and cell count per mL. The remaining cell suspension was then adjusted with assay buffer to deliver 1000 viable cells per well using a Matrix Combi Multidrop reagent dispenser. 10 μL cell suspensions were added to each well of the assay plate which already contains compound. The plate was sealed and incubated at 37° C. with 5% $CO_2$ for 30 minutes.

Following the 30 minute incubation, 5 μL of labeled d2 cAMP and 5 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-$1_{7\text{-}37}$ (10 nM) included on each plate. $EC_{50}$ determinations were made from agonist dose-response curves analyzed with a curve fitting program using a 4-parameter logistic dose response equation.

This assay demonstrates that the compounds of the invention activates GLP-1R signaling through the cAMP pathway, thus behave as GLP-1R agonists. The representative commercial reagents/kits that can be (were) used in such assays are described below.

Preparations

Reagents and Consumables:

| Reagent | Vendor | Catalog No. |
| --- | --- | --- |
| HEK/GLP1R/CRE/Luc cell line | HDB | |
| DMEM | Gibco | 12100 |
| Exendin (9-39) | MCE | HY-P0264 |
| Human GLP-1-(7-37)-amide | MCE | HY-P0055 |
| 384 well plates, white | Greiner | 784075 |
| cAMP dynamic 2 | Cisbio | 62AM4PEC |
| Fetal Bovine Serum | Biosera | FB-10581/500 |
| IBMX | Sigma | I5879 |
| BSA | Sigma | A1933-5G |
| DPBS | Sigma | D8537 |

Instruments:

| Instrument | Vendor | Internal Code |
| --- | --- | --- |
| EnVision | PerkinElmer | HD-4HYSG2330 |

Media and Solutions:
1) Assay Buffer
   DPBS with 500 μM IBMX and 0.1% BSA. IBMX and BSA were freshly added on the day of assay.
2) cAMP-d2 Working Solution Preparation
   a) The lyophilisate was reconstituted with an appropriate amount of distilled water according to manufacturer's instructions to make working stock which can be aliquoted and frozen (−20° C.).
   b) The working stock solution was diluted 1:20 in the conjugate and lysis buffer before use.
3) Anti-cAMP Antibody-Cryptate Working Solution Preparation
   c) The lyophilisate was reconstituted with appropriate amount of distilled water according to manufacturer's instruction to make working stock which can be aliquoted and frozen (−20° C.).
   d) The working stock solution was diluted 1:20 in the conjugate and lysis buffer before use.

Procedures
Procedures for Cell Suspension Preparation
1. Frozen cells were thawed very briefly in a 37° C. water bath under sterile conditions until just before ice completely melt (for about 1 minute) with a continuous agitation. Caution was taken because a longer incubation could result in cell death.
2. DMSO was removed from the media by carefully transferring thawed cells to a sterile 15/50 mL tube, filling a tube with 10-50 mL of complete media pre-warmed to 37° C., and allowing the cells to sit 5 min before centrifuging at 900 rpm for 5 minutes for cell collection.
3. The cells were resuspended with assay buffer.
4. For stable GLP1-R assay, the optimized cell density is 1000 cells/well. Caution was taken because cell density optimization was crucial and needed to be optimized in different labotatories. The level of cAMP produced by the cells must fall within the linear range of the standard curve.

Procedures for Compound Preparation
1) Reference agonist compound GLP1 (7-37) was dissolved with DMSO to make a 1 mM stock solution, which was then aliquoted and stored at −80° C.
2) Reference antagonist compound Exendin (9-39) was dissolved with DMSO to make a 2 mM stock solution, which was then aliquoted and stored at −80° C.
3) Test compounds were dissolved with DMSO to make stock solutions, aliquoted and stored at −80° C. Serial dilutions of compound solutions were made using DMSO to obtain a 200× compound working solution first and then 50 nL of the working solution to 384-well plate with ECHO. The final DMSO concentration is 0.5%. The compound concentration range may be adjusted at any time.
4) IBMX: 500 mM stock solution dissolved in DMSO, aliquot and stored at −20° C.

Procedures for Agonist Assay
1) Compound preparation: compound addition plates were prepared in advance of the assay. 200× compound working solutions were prepared according to procedures described above.
2) Cell preparation: cell suspensions were prepared according to procedures described above before running the assay.
3) Compound addition: 50 nL/well of 200× compound working solutions were added to low-volume 384 white assay plate with Echo.
4) Cell addition: 10 μL cell suspensions were added to each well of the assay plate which already contained the compound working solution. The plate was sealed and incubated at 37° C. with 5% $CO_2$ for 30 minutes.
5) 5 μL of a cAMP-d2 working solution was added to each well of the assay plate.
6) 5 μL of an anti-cAMP antibody-cryptate working solution was added to each well of the assay plate. The plate was covered with a lid. Incubate at room temperature for 1 hours.
7) The fluorescence was read at 665 and 615 nm with an EnVision plate reader with TRF LASER using the specified settings and the data was saved.

Procedures for Antagonist Blocking Assay
1) Compound preparation: prepare compound addition plates in advance of assay. Prepare 200× concentration of compound working solutions according to procedures described above.
2) Cell preparation: cell suspensions are prepared according to procedures described above before running the assay.
3) Compound addition: add 50 nL/well of working concentration of 200× compound to low-volume 384 white assay plate.
4) Cell addition: Add 5 μL of 2× cell suspensions to each well of the assay plate which already contains compound.
5) Exendin (9-39) Antagonist addition: Add 5 μL of 2× Exendin (9-39) to each well of the assay plate which already contains compound and cells. The final concentration of Exendin (9-39) is IC80. Seal the plate and incubate at 37° C. with 5% CO2 for 30 minutes.
6) Add 54 cAMP-d2 working solution to each well of the assay plate.
7) Add 54 Anti-cAMP antibody-cryptate working solution to each well of the assay plate. Cover the plate with lid. Incubate at room temperature for 1-4 hours.
8) Read the fluorescence at 665 and 615 nm with EnVision plate reader with TRF LASER using the specified settings and save data.

Setting up EnVision for HTRF cAMP Measurements
Required Filters and Mirrors
  Excitation: TRF LASER
  Emission #1: 665 nm (CWL 665 nm BW 7.5 nm)
  Emission #2: 615 nm (CWL 615 nm BW 8.5 nm)
  Dichroic mirror: DELFIA/LANCE Dual Enh D400/D630
Required Settings:
  Delay: 50 μs
  Window Time: 300 μs (also called "integration time")
  Number of sequence windows: 1
  Cycle: Default 2000 μs (also called "time between flashes")
  Time between flashes: 2000 μs
  number of flashes: 20
  number of flashes for 2nd detector: 10
  measurement height (mm): 6.5
  Z height: Must be optimized (use optimization Wizard, optimize on a well with maximum FRET)
  Excitation and Emissions are done on the top of the well cAMP Assay Data Processing
  Data analysis: GraphPad Prism 5 or IDBS XLfit software is used for establishment of progression curve. EC50s or IC50s were determined by 4-parameter logistic dose response equation.
Representative Plate Layout

|   | 1 | 2 | 3 | 4 | 5 | 6 | 7 | 8 | 9 | 10 | 11 | 12 | 13 | 8 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A |   | Compound1 |   |   |   |   |   |   |   |   |   |   |   |   | Compound1 |   |   |   |   |   |   |   |   |   |
| B |   | Compound2 |   |   |   |   |   |   |   |   |   |   |   |   | Compound2 |   |   |   |   |   |   |   |   |   |
| C |   | Compound3 |   |   |   |   |   |   |   |   |   |   |   |   | Compound3 |   |   |   |   |   |   |   |   |   |
| D |   | Compound4 |   |   |   |   |   |   |   |   |   |   |   |   | Compound4 |   |   |   |   |   |   |   |   |   |
| E |   | Compound5 |   |   |   |   |   |   |   |   |   |   |   |   | Compound5 |   |   |   |   |   |   |   |   |   |
| F |   | Compound6 |   |   |   |   |   |   |   |   |   |   |   |   | Compound6 |   |   |   |   |   |   |   |   |   |

| | 1 | 2 | 3 | 4 | 5 | 6 | 7 | 8 | 9 | 10 | 11 | 12 | 13 | | 8 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|---|
| G | Compound7 | | | | | | | | | | | | | | Compound7 | | | | | | | | | | |
| H | Compound8 | | | | | | | | | | | | | | Compound8 | | | | | | | | | | |
| I | Compound9 | | | | | | | | | | | | | | Compound9 | | | | | | | | | | |
| J | Compound10 | | | | | | | | | | | | | | Compound10 | | | | | | | | | | |
| K | Compound11 | | | | | | | | | | | | | | Compound11 | | | | | | | | | | |
| L | Compound12 | | | | | | | | | | | | | | Compound12 | | | | | | | | | | |
| M | Compound13 | | | | | | | | | | | | | | Compound13 | | | | | | | | | | |
| N | Compound14 | | | | | | | | | | | | | | Compound14 | | | | | | | | | | |
| O | Compound15 | | | | | | | | | | | | | | Compound15 | | | | | | | | | | |
| P | GLP-1(7-37) | | | | | | | | | | | | | | GLP-1(7-37) | | | | | | | | | | |

HPE GLP-1 2 uM 100% DMSO
ZPE: 100% DMSO
Working plate Compound starting concentration: 2 mM
Final compound concentration: 10 uM 0.5% DMSO
Compound starting well: A2 A13
Compound dilution fold: 3 fold 11 point
Working plate volume: 50 nl/well Using the assay substantially as described above, dose-response curve for each compound tested below were obtained, and their respective $EC_{50}$ values calculated and tabulated. Here, $EC_{50}$ value for each compound is defined as the compound concentration that yielded 50% of the maximum cAMP level achieved with the same compound.

Two different cell types were used for this assay. In one assay, each compound was tested in HEK293T cells. The results are shown below in Table 1. In another assay, selected compounds were also tested in CHO cells that have been stably transfected to express human GLP-1R. The results are shown below in Table 2.

TABLE 1

Compound $EC_{50}$ Values in HEK293T Cells

| Compound # | $EC_{50}$<br>A = ≤0.015 μM<br>B = ≤0.15 μM<br>C = ≤1 μM<br>D = >1 μM |
|---|---|
| Compound 1 | A |
| Compound 2 | D |
| Compound 3 | D |
| Compound 4 | D |
| Compound 5 | D |
| Compound 6 | D |
| Compound 7 | D |
| Compound 8 | D |
| Compound 9 | A |
| Compound 10 | B |
| Compound 11 | A |
| Compound 12 | A |
| Compound 13 | B |
| Compound 14 | D |
| Compound 15 | B |
| Compound 16 | B |
| Compound 17 | D |
| Compound 18 | A |
| Compound 19 | A |
| Compound 20 | C |
| Compound 21 | A |
| Compound 22 | B |
| Compound 23 | A |
| Compound 24 | B |
| Compound 25 | B |
| Compound 26 | D |
| Compound 27 | D |
| Compound 28 | A |
| Compound 29 | A |
| Compound 30 | B |
| Compound 31 | C |

TABLE 1-continued

Compound $EC_{50}$ Values in HEK293T Cells

| Compound # | $EC_{50}$<br>A = ≤0.015 μM<br>B = ≤0.15 μM<br>C = ≤1 μM<br>D = >1 μM |
|---|---|
| Compound 32 | C |
| Compound 33 | A |
| Compound 34 | A |
| Compound 35 | A |
| Compound 36 | C |
| Compound 37 | D |
| Compound 38 | C |
| Compound 39 | B |
| Compound 40 | C |
| Compound 41 | A |
| Compound 42 | A |
| Compound 43 | A |
| Compound 44 | A |
| Compound 45 | A |
| Compound 46 | A |
| Compound 47 | A |
| Compound 48 | B |
| Compound 49 | D |
| Compound 50 | D |
| Compound 51 | D |
| Compound 52 | D |
| Compound 53 | D |
| Compound 54 | D |
| Compound 55 | A |
| Compound 56 | D |
| Compound 57 | C |
| Compound 58 | D |
| Compound 59 | D |
| Compound 60 | C |
| Compound 61 | C |
| Compound 62 | B |
| Compound 63 | C |
| Compound 64 | B |
| Compound 66 | D |
| Compound 67 | B |
| Compound 68 | A |
| Compound 69 | C |
| Compound 70 | A |
| Compound 71 | D |
| Compound 72 | A |
| Compound 73 | B |
| Compound 103 | B |
| Compound 104 | C |
| Compound 105 | A |
| Compound 106 | A |
| Compound 107 | A |
| Compound 108 | A |

TABLE 1-continued

Compound EC$_{50}$ Values in HEK293T Cells

| Compound # | EC$_{50}$<br>A = ≤0.015 μM<br>B = ≤0.15 μM<br>C = ≤1 μM<br>D = >1 μM |
|---|---|
| Compound 109 | C |
| Compound 110 | A |
| Compound 111 | A |
| Compound 112 | C |
| Compound 113 | B |
| Compound 114 | A |
| Compound 115 | A |
| Compound 116 | A |
| Compound 117 | A |
| Compound 118 | A |
| Compound 119 | A |
| Compound 120 | A |
| Compound 121 | B |
| Compound 122 | B |
| Compound 123 | A |
| Compound 124 | C |
| Compound 125 | B |
| Compound 126 | A |
| Compound 127 | B |
| Compound 128 | B |
| Compound 129 | A |
| Compound 130 | C |
| Compound 131 | A |
| Compound 132 | C |
| Compound 133 | A |
| Compound 134 | A |
| Compound 135 | B |
| Compound 136 | A |
| Compound 137 | C |
| Compound 138 | C |
| Compound 139 | B |
| Compound 140 | B |
| Compound 141 | A |
| Compound 142 | B |
| Compound 143 | A |
| Compound 144 | A |
| Compound 145 | A |
| Compound 146 | A |
| Compound 147 | C |
| Compound 148 | A |
| Compound 149 | A |
| Compound 150 | C |
| Compound 151 | A |
| Compound 152 | A |
| Compound 153 | A |
| Compound 154 | A |
| Compound 155 | A |
| Compound 156 | B |
| Compound 157 | A |
| Compound 158 | B |
| Compound 159 | B |
| Compound 160 | B |
| Compound 161 | B |
| Compound 162 | B |
| Compound 163 | A |
| Compound 164 | B |
| Compound 165 | C |
| Compound 166 | B |
| Compound 167 | B |
| Compound 168 | A |
| Compound 169 | A |
| Compound 170 | A |
| Compound 171 | A |
| Compound 172 | A |
| Compound 173 | C |
| Compound 174 | A |
| Compound 175 | A |
| Compound 176 | A |
| Compound 177 | A |
| Compound 178 | A |
| Compound 179 | A |
| Compound 180 | A |
| Compound 181 | A |
| Compound 182 | A |
| Compound 183 | B |
| Compound 184 | A |
| Compound 185 | A |
| Compound 186 | B |
| Compound 187 | A |
| Compound 188 | B |
| Compound 189 | B |
| Compound 190 | B |
| Compound 191 | B |
| Compound 192 | B |
| Compound 193 | B |
| Compound 194 | B |
| Compound 195 | A |
| Compound 196 | B |
| Compound 197 | C |
| Compound 198 | C |
| Compound 199 | B |
| Compound 200 | A |
| Compound 201 | A |
| Compound 202 | B |
| Compound 203 | B |
| Compound 204 | A |
| Compound 205 | B |
| Compound 206 | A |
| Compound 208 | B |
| Compound 208 | B |
| Compound 209 | A |
| Compound 210 | A |
| Compound 211 | A |
| Compound 212 | A |
| Compound 213 | A |
| Compound 214 | B |
| Compound 215 | B |
| Compound 216 | A |
| Compound 217 | A |
| Compound 218 | B |
| Compound 219 | C |
| Compound 220 | A |
| Compound 221 | A |
| Compound 222 | A |
| Compound 223 | A |
| Compound 224 | A |
| Compound 225 | A |
| Compound 226 | A |
| Compound 227 | A |
| Compound 228 | A |
| Compound 229 | A |
| Compound 230 | B |
| Compound 231 | B |
| Compound 232 | B |
| Compound 233 | B |
| Compound 234 | B |
| Compound 235 | C |
| Compound 236 | A |
| Compound 237 | A |
| Compound 238 | A |
| Compound 239 | A |
| Compound 240 | B |
| Compound 241 | B |
| Compound 242 | A |
| Compound 243 | B |
| Compound 244 | A |
| Compound 245 | A |

TABLE 2

Compound EC$_{50}$ Values in CHO Cells Stably Expressing GLP-1R

| Compound # | CHO cAMP stable EC$_{50}$<br>A = ≤0.015 µM<br>B = ≤0.15 µM<br>C = ≤1 µM<br>D = >1 µM |
|---|---|
| Compound 18 | B |
| Compound 19 | A |
| Compound 21 | C |
| Compound 22 | C |
| Compound 23 | C |
| Compound 28 | B |
| Compound 29 | B |
| Compound 34 | B |
| Compound 35 | B |
| Compound 221 | A |
| Compound 222 | A |
| Compound 224 | B |
| Compound 225 | A |
| Compound 227 | B |
| Compound 228 | B |
| Compound 236 | B |
| Compound 237 | B |
| Compound 238 | B |
| Compound 239 | B |
| Compound 245 | A |

The data shows that, similar to GLP-1(7-37), many tested compounds have nanomolar or sub-nanomolar (<10 nM) EC$_{50}$ values in the cAMP assay. This, coupled with the fact that many tested compounds also have B$_{max}$ values reaching substantially the same level of that for GLP-1(7-37), suggests that many of the tested compounds of the invention are full agonists of the GLP-1R signaling leading to cAMP production.

In contrast, as shown in Examples 1 and 2 above, the compounds of the invention generally have B$_{max}$ approaching about 20-40% of that of GLP-1 (7-37) in the β-Arrestin recruitment assay and GLP-1R internalization assay, and the NanoBit time course profiles are different between the compounds of the invention and those of GLP-1(7-37).

Biological Example 4: Monkey Oral Pharmacokinetic (PK) Studies

This example demonstrates that compounds of the invention possess superior pharmacokinetic property (e.g., oral PK property), such that at the tested single oral dose, plasma concentrations of the test compounds decreased very graduallly over the course of 24 hours.

Test Articles

The following exemplary compounds of the invention were tested in this study: Compound 19, Compound 28, Compound 29, Compound 225, and Compound 418 as the control compound:

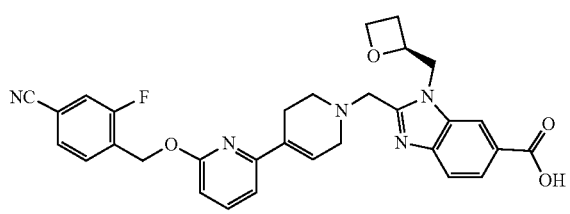

Compound 19

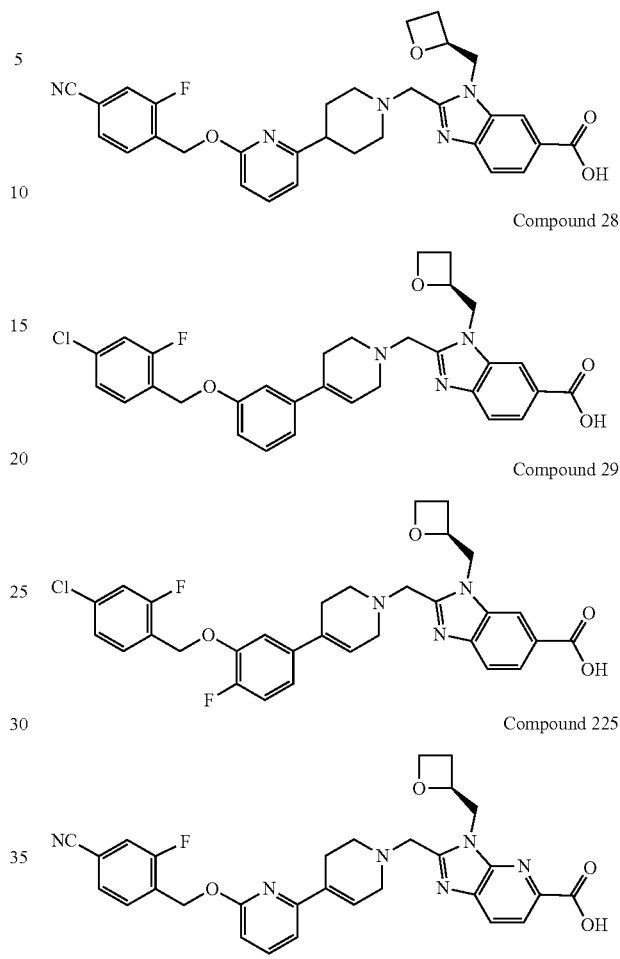

Compound 418

Compound 28

Compound 29

Compound 225

Dose Formulation Preparation

Accurate amounts of the test compounds, i.e., Compound 19, Compound 28, Compounds 29, Compound 225, or Compound 418 (Control Compound) were weighed into a mortar, and grinded until no obvious granules were left. Appropriate volumes of vehicles (e.g., 2% Tween 80 (v:v) and 0.5% MC (w:v) in saline or 0.5% MC (w:v) in water were then added into the mortar containing the ground compounds, and the mixture was then grinded with a pestle until a homogeneous paste was formed. Additional appropriate volumes of vehicles were added into the mortar containing each compound, and the mixture was grinded further with the pestle until a homogeneous suspension was obtained.

The suspension was then transferred into a glass bottle. The mortar and the pestle were rinsed with the vehicle until no compound was left in the mortar or on the pestle.

The rest of the vehicle was added to make up the final dosing volume of about 1 mg/mL or 2 mg/mL (i.e., final dosing volume of about 5 mL/kg), and the homogenous suspension was continuously stirred prior to and during the dosing.

Test Animals

Non-nave Cynomolgus male monkeys (n=3/test article; sourced from Hainan Jingang Biotech Co., Ltd., Nayang Xintan, Fucheng Town, Qiongshan District, Haikou City, Hainan Province, China); or non-naïve aged, obese, and diabetic male *Macaca fascicularis* monkeys (n=3/test article, Source: Kunming Biomed International Colony) were used in pre-clinical in vivo studies. All non-nave Cynomolgus male monkeys were approximately 3 to 5 years old, weighed about 2.5-5 kg, and were within ±20% of the average body weight. All non-nave aged, obese, and diabetic male *Macaca fascicularis* monkeys were approximately 12 to 20 years old, weighed about >8-12 kg.

Study Design
Group Designation and Oral Dose Plan

| Dose (mg/kg) | Number of animals | Gender | Dose volume (mL/kg) |
|---|---|---|---|
| Dose 1 | 3 | M | 5 |
| Dose 2 | 3 | M | 5 |

All animals were fasted overnight before dosing, and the food were supplied approximately 4 hours post dose (with free access to water all the time).

Sample Collection

Animals were restrained at designated time points for blood sampling. Approximately 500 μL of blood samples was taken via cephalic or saphenous vein into EDTA-K2 tubes. Blood samples were put on wet ice before centrifugation.

Collection Intervals

For oral administration (PO) of either Dose 1 or Dose 2: blood samples were collected at pre-dose, and at 15 min, 30 min, 1 hr, 2 hr, 4 hr, (6 hr for compounds 19 and 28 with cynomolgus monkeys only), 8 hr, 12 hr, and 24 hr post dose (i.e., 9 or 10 total time points for each compound at each dose).

Sample Procedure

The blood samples were centrifuged at approximately 2,000-4,000 rpm for about 10-15 minutes at 2-8° C., and each resulting plasma portion was then transferred into an individual tube.

Sample Storage Conditions

All plasma samples were stored in −70° C. freezer until analysis (transfer samples were stored on dry ice). The remaining samples were stored at −20° C. freezer, and can be stored for at most 1-2 years after issuance of the final reports.

Bioanalytical Analysis

LC-MS/MS methods were developed, and bioanalysis for the test articles in monkey plasma was performed according to the developed LC-MS/MS methods.

Sample Preparation

Undiluted plasma samples: An aliquot of 20-50 μL plasma sample was mixed with 200 μL of ACN or MeOH containing one of the internal standards (IS, e.g., Diclofenac or Terfenadine) The mixture was then vortexed for about 1-5 min, and centrifuged at about 4,000-5,800 rpm for about 10-15 min. An aliquot of 1 μL supernatant was used for LC-MS/MS analysis.

Plasma samples with 10-fold dilution: An aliquot of 2 μL plasma sample was first mixed with 18 μL of blank plasma, then 200 μL of ACN containing 100 ng/mL IS (e.g. Diclofenac) was added to the mixture. The mixture was then vortexed for about 10 min, and was centrifuged at about 5,800 rpm for about 10 min. An aliquot of 1 μL supernatant was used for LC-MS/MS analysis.

LC/MS MS Method

MS conditions: Positive ion, ESI, MRM detection with parent and daughter ions, internal standard Diclofenac.

Compound ID: Compounds 19, 28, 29, 225 or 418 (control)

HPLC conditions

Method 1:
  Mobile Phase A: $H_2O$-0.025% FA-1 mM $NH_4OAC$
  Mobile Phase B: MeOH-0.025% FA-1 mM $NH_4OAC$

| Time (min) | Mobile Phase B (%) |
|---|---|
| 0.20 | 10 |
| 0.50 | 65 |
| 1.00 | 90 |
| 1.50 | 90 |
| 1.51 | 10 |
| 2.00 | stop |

Column: Xbridge BEH C18 (2.1×50 mm, 2.5 μm)
Flow rate: 0.60 mL/min
Column temperature: 60° C.
Retention time: approximately between 1.0 to 1.4 min for the analyte(s)
Diclofenac: approximately around 1.4 min Method 2:
  Mobile Phase A: 0.05% FA-5 mM $NH_4OAC$
  Mobile Phase B: 1% FA-Acetonitrile

| Time (min) | Mobile Phase B (%) |
|---|---|
| 0.40 | 15 |
| 1.20 | 95 |
| 1.60 | 95 |
| 1.61 | 15 |
| 2.50 | 15 |

Column: Kinetex 2.6μ C18 100A column (30 mm*3.0 mm)
Flow rate: 0.70 mL/min
Column temperature: Room Temperature
Retention time: approximately 1.7 min for the analyte(s)
Terfenadine; approximately 1.2 min Pharmacokinetics (PK) Parameters Pharmacokinetics parameters, including area under the curve ($AUC_{0-t}$), maximum plasma concentration ($C_{max}$), time to reach maximum plasma concentration ($T_{max}$), oral bioavailability (F %), etc., were calculated using Phoenix software (Version 6.4) and non-compartment model.

The results of the pharmacokinetics studies are presented in Table 3 and FIGS. 8A-8F.

Figure 8A:
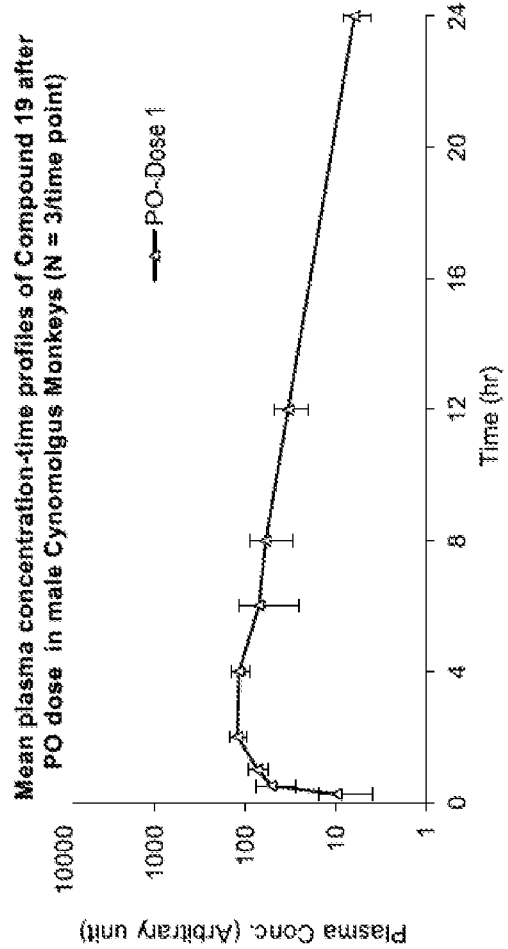
Figure 8B:
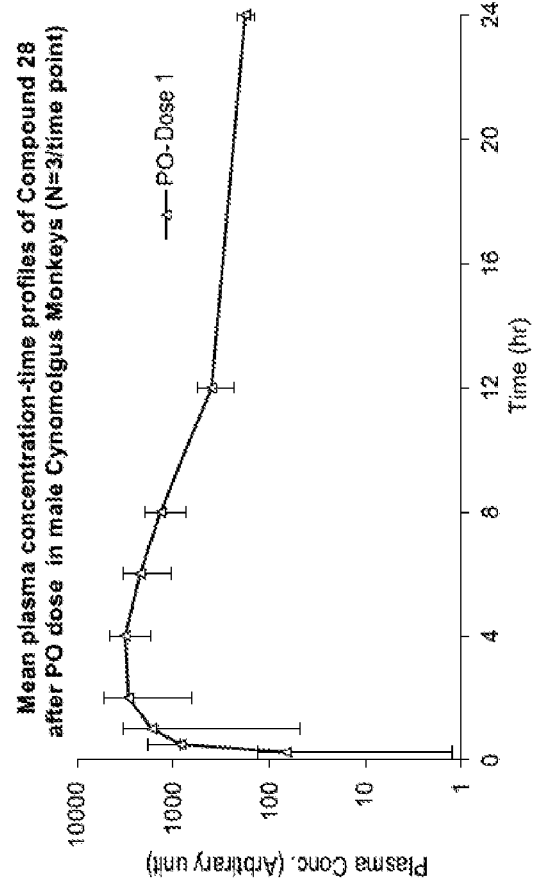
Figure 8E:
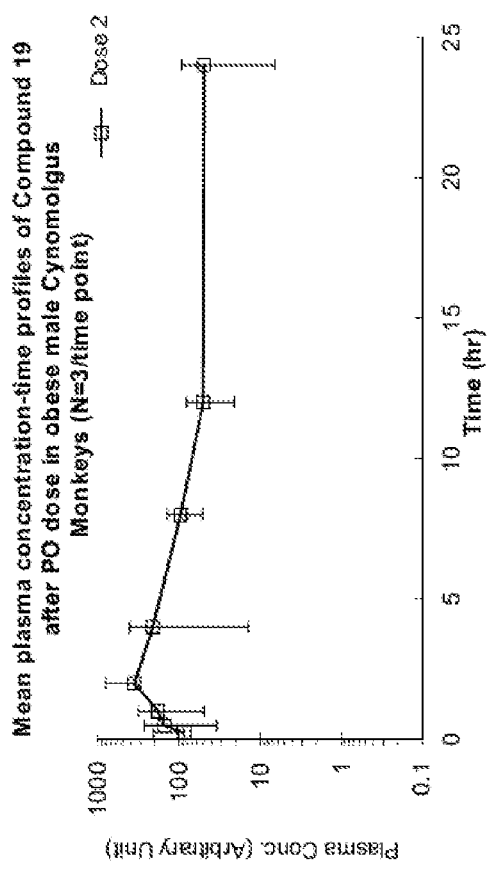
Figure 8F:
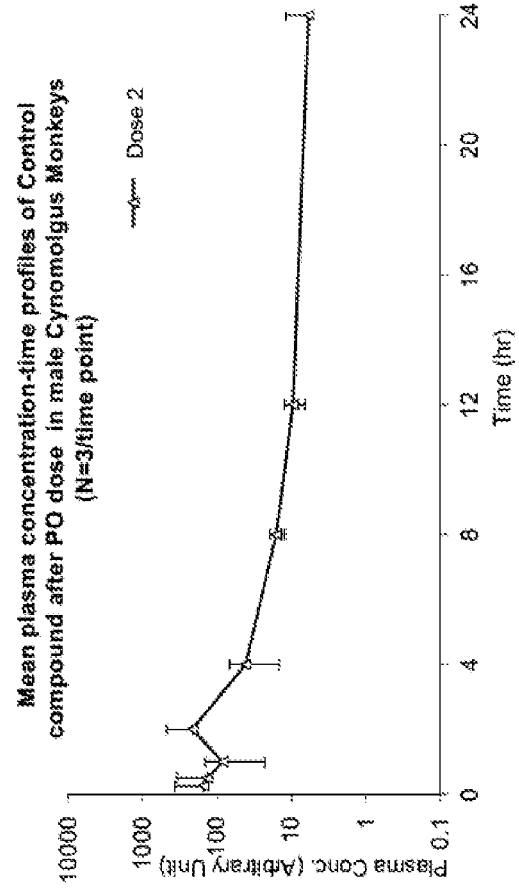

As is apparent in FIG. 8F, the comparator/control compound (Compound 418), while having reasonable PK profile after dosing with the same oral dose used in some compounds of the invention (i.e., Dose 2), has a relatively precipitous drop of about 10-fold in plasma concentration over a period of about 24 hours post oral dosing.

In contrast, as illustrated in FIGS. 8A-8E, the plasma concentrations of PO-administered Compounds 19, 28, 29, and 225 at the same dose level (i.e., Dose 2) were surprisingly sustained at a more constant level over the entire course of about 24 hours after oral dosing, with relatively minimal reduction in plasma concentration. Similar data has also been obtained (data not shown) or is expected for other compounds of the invention. Collectively, these data suggest that the compounds of the invention have a prolonged or sustained bioavailability, at least over the course of about 1 day (24 hours) following the administration of a single oral dose.

Indeed, preliminary data (not shown here) indicated that certain compounds of the invention, when administered to obese and diabetic male *Macaca fascicularis* monkeys at selected doses similar to the ones used here appeared to be efficacious in the monkeys in terms of increasing insulin secretion, reducing blood glucose level, etc.

TABLE 3

In vivo Monkey PK Profiles

| Compound No. | Oral dose (Arbitrary unit) | $C_{max}$ (Arbitrary unit) | $T_{max}$ (hr) | $AUC_{0-24\,h}$ (Arbitrary units) | F % |
|---|---|---|---|---|---|
| Compound 19 | Dose 1 | 125 | 2.7 | 1130 | 10.8 |
| Compound 28 | Dose 1 | 3910 | 3.3 | 24900 | 56.1 |
| Compound 29 | Dose 2 | 3380 | 1.2 | 21800 | 41.0 |
| Compound 225 | Dose 2 | 184 | 4.0 | 1500 | 9.93 |
| Compound 19[a] | Dose 2 | 413 | 8.8 | 2470 | 15.5 |
| Compound 418[b] | Dose 2 | 232 | 1.7 | 774 | 8.17 |

[a]Non-naïve aged, obese, and diabetic male *Macaca fascicularis* monkeys
[b]Compound 418 is the control compound.

Biological Example 5: Comparative Data

The following eight pairs of compounds were evaluated to compare their cAMP assay $EC_{50}$ values (see Biological Example 3 above) in HEK293T and CHO cells. The results in Table 4 generally show that compounds having a non-saturated ring C (with reference to Formula (I)) have $EC_{50}$ values that are superior (i.e., lower) to their corresponding counterparts having a saturated ring C. As $EC_{50}$ values are indicative of the drug concentration that produces half-maximal cAMP stimulation/response, lower $EC_{50}$ values indicate that a lower drug concentration is required to achieve half-maximal cAMP stimulation/response.

TABLE 4

Comparative $EC_{50}$ Values in HEK293T Cells and CHO cells

| Compound & Comparator Structures | HEK293T cells $EC_{50}$ (μM) | CHO cells $EC_{50}$ (μM) |
|---|---|---|
| 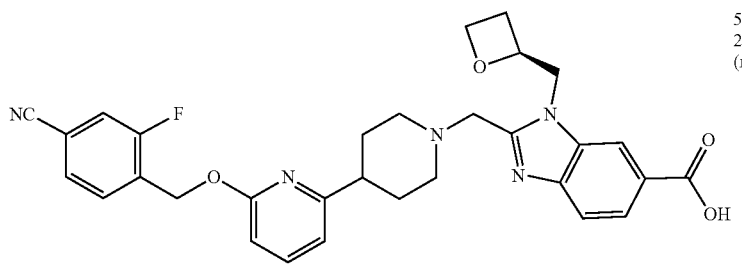 (Compound A or Compound 418) | 5.44E−04 ± 2.30E−04 (n = 3) | 1.53E−02 ± 0.464E−02 (n = 6) |
| 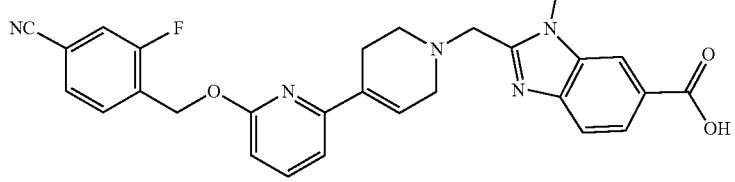 (Compound 19) | 2.19E−04 ± 0.898E−04 (n = 16) | 0.225E−02 ± 0.0590E−02 (n = 6) |
| 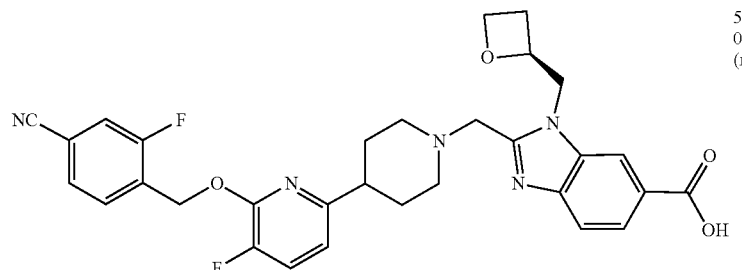 (Compound B) | 5.65E−03 ± 0.386E−03 (n = 2) | 463E−03 ± 93.1E−03 (n = 5) |

TABLE 4-continued
Comparative EC$_{50}$ Values in HEK293T Cells and CHO cells
| Compound & Comparator Structures | HEK293T cells EC$_{50}$ (μM) | CHO cells EC$_{50}$ (μM) |
|---|---|---|
| 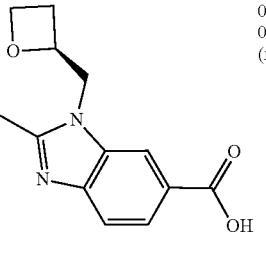 (Compound 222) | 0.517E−03 ± 0.337E−03 (n = 2) | 6.05E−03 ± 2.64E−03 (n = 5) |
| 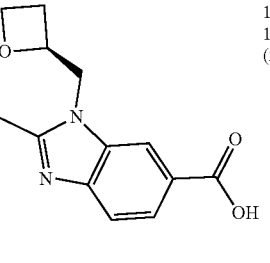 (Compound C) | 1.98E−03 ± 1.30E−03 (n = 2) | 9.58E−02 ± 1.49E−02 (n = 5) |
| 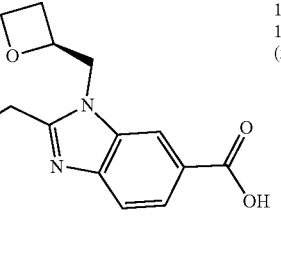 (Compound 35) | 1.80E−03 ± 1.18E−03 (n = 6) | 7.37E−02 ± 1.47E−02 (n = 5) |
| 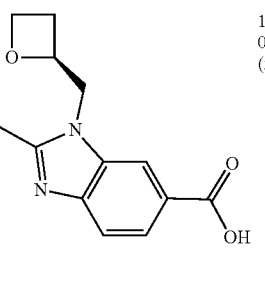 (Compound D) | 1.05E−02 ± 0.439E−02 (n = 2) | 0.289 ± 0.0530 (n = 5) |

TABLE 4-continued
Comparative EC$_{50}$ Values in HEK293T Cells and CHO cells
| Compound & Comparator Structures | HEK293T cells EC$_{50}$ (μM) | CHO cells EC$_{50}$ (μM) |
|---|---|---|
| 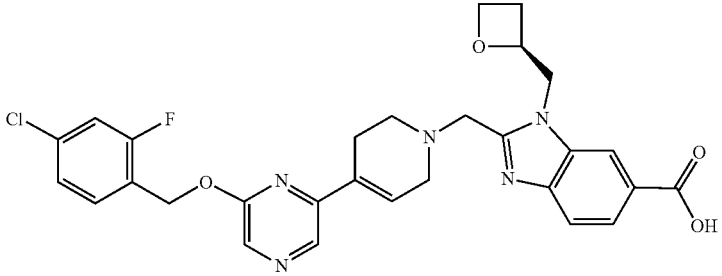 [SMILES: O=C(O)c1ccc2nc(CN3CC=C(c4cncc(OCc5ccc(Cl)cc5F)n4)CC3)n(C[C@@H]3CCO3)c2c1] (Compound 34) | 0.294E−02 ± 0.0798E−02 (n = 2) | 0.136 ± 0.0326 (n = 5) |
| 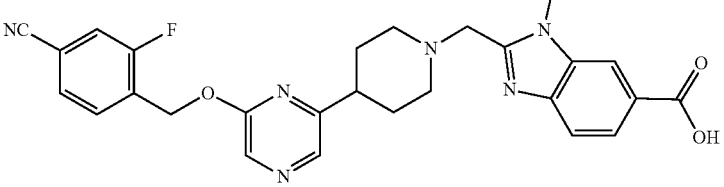 (Compound E) | 1.59E−02 ± 0.768E−02 (n = 2) | 0.924 ± 0.230 (n = 4) |
| 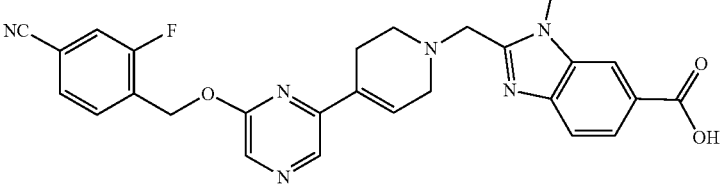 (Compound 23) | 0.985E−02 ± 0.866E−02 (n = 2) | 0.260 ± 0.0380 (n = 5) |
| 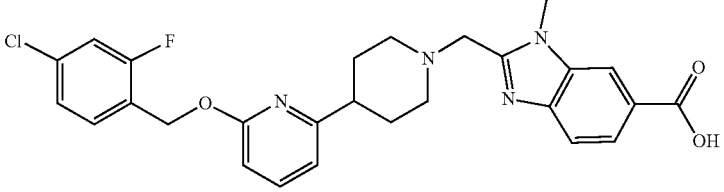 (Compound F) | 4.12E−04 ± 3.73E−04 (n = 2) | 7.65E−03 (n = 1) |

TABLE 4-continued

Comparative EC$_{50}$ Values in HEK293T Cells and CHO cells

| Compound & Comparator Structures | HEK293T cells EC$_{50}$ (μM) | CHO cells EC$_{50}$ (μM) |
|---|---|---|
| (Compound 221) | 3.93E−04 ± 0.698E−04 (n = 2) | 3.28E−03 (n = 1) |
| (Compound G) | 8.58E−03 ± 1.10E−03 (n = 2) | 0.105 ± 0.0327 (n = 3) |
| (Compound 28) | 3.94E−03 ± 0.971E−03 (n = 13) | 0.0426 ± 0.0115 (n = 8) |
| (Compound H) | 3.00E−04 ± 0.327E−04 (n = 2) | 3.50E−03 ± 0.700E−03 (n = 3) |

TABLE 4-continued
Comparative EC$_{50}$ Values in HEK293T Cells and CHO cells
| Compound & Comparator Structures | HEK293T cells EC$_{50}$ (μM) | CHO cells EC$_{50}$ (μM) |
|---|---|---|
| 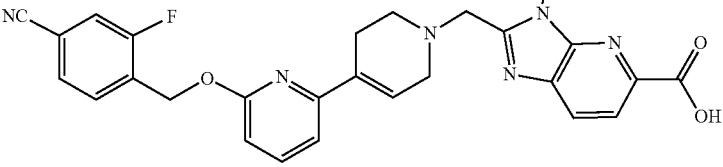<br>(Compound 225) | 1.68E−04 ± 0.488E−04 (n = 4) | 3.86E−03 ± 1.27E−03 (n = 6) |
Example 6 Compound Synthesis
(S)-2-((4-(6-(4-chloro-2-fluorobenzylamino)pyridin-2-yl)piperazin-1-yl)methyl)-1-(oxetan-2-ylmethyl)-1h-benzo[d]imidazole-6-carboxylic acid (Compound 1)
Compound 1
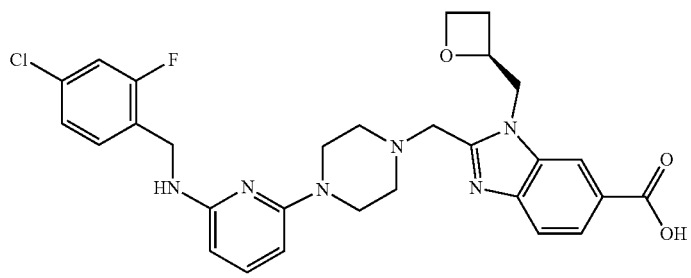
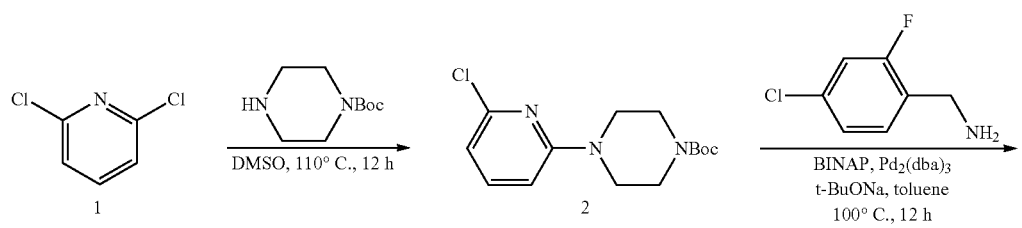
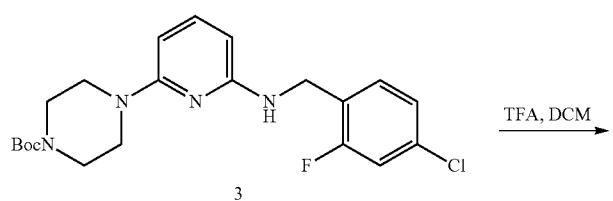

-continued

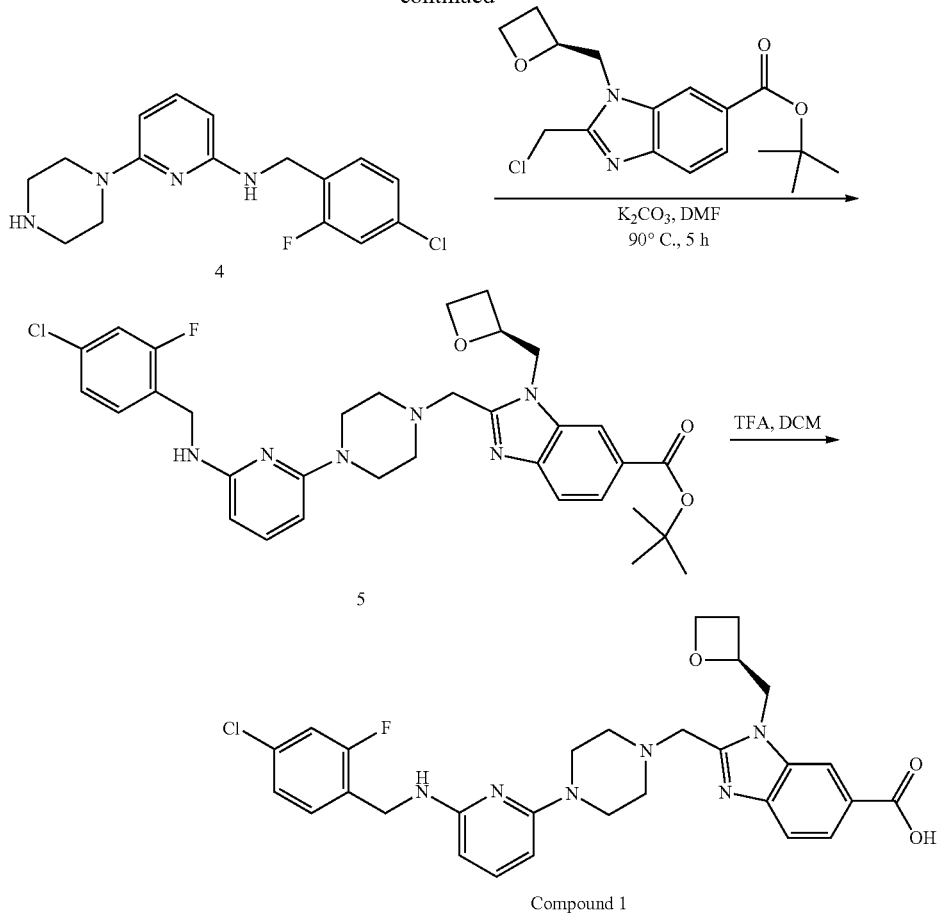

Compound 1

Step 1

To the solution of 2,6-dichloropyridine (10.0 g, 67.6 mmol) in DMSO (100 mL) was added tert-butyl piperazine-1-carboxylate (15.1 g, 81.1 mmol). The mixture was stirred at 110° C. overnight. The mixture was diluted with water, extracted with EA (30 mL×3), washed with saturated brine, dried over $Na_2SO_4$, filtered and concentrated. The crude product was recrystallized from petroleum ether (200 mL) to give tert-butyl 4-(6-chloropyridin-2-yl) piperazine-1-carboxylate (9.5 g, yield 48%) as a white solid. LCMS: [M+H]$^+$=298.1; Retention time (0.01% TFA)=1.78 min.

Step 2

To the solution of (4-chloro-2-fluorophenyl)methanamine (176 mg, 1.1 mmol) in toluene (8 mL) was added tert-butyl 4-(6-chloropyridin-2-yl)piperazine-1-carboxylate (297 mg, 1 mmol), $Pd_2(dba)_3$ (46 mg, 0.05 mmol), BINAP (62 mg, 0.1 mmol) and t-BuONa (288 mg, 3 mmol) under $N_2$. The reaction mixture was stirred at 90° C. for 12 h. 50 mL of ice water was added to quench the reaction. The solution was extracted with EA (50 mL×3), washed with brine and dried over $Na_2SO_4$. After evaporation of solvent, the crude product was purified by column chromatography (PE/EA=2/1) to give tert-butyl 4-(6-(4-chloro-2-fluorobenzylamino) pyridin-2-yl) piperazine-1-carboxylate (320 mg, 76%) as a yellow oil. LCMS: [M+H]$^+$=420.8; Retention time (0.01% TFA)=1.75 min.

Step 3

To the solution of tert-butyl 4-(6-(4-chloro-2-fluorobenzylamino) pyridin-2-yl) piperazine-1-carboxylate (320 mg, 0.8 mmol) in DCM (10 mL) was added TFA (10 mL) at 0° C. The reaction mixture was stirred at 0° C. for 2 h. 10 mL of ice water was added to quench the reaction. Aq. $NaHCO_3$ was added to adjust the pH to 9, then the solution was extracted with EA (40 mL×3), washed with brine and dried over $Na_2SO_4$. After evaporation of solvent, the crude product was purified by column chromatography (PE/EA=2/1) to give N-(4-chloro-2-fluorobenzyl)-6-(piperazin-1-yl) pyridin-2-amine (120 mg, 43%) as yellow oil. LCMS: [M+H]= 321.0; Retention time (10 mM $NH_4HCO_3$)=1.72 min.

Step 4

To the solution of N-(4-chloro-2-fluorobenzyl)-6-(piperazin-1-yppyridin-2-amine (120 mg, 0.4 mmol) in DMF (6 mL) was added (S)-tert-butyl 2-(chloromethyl)-1-(oxetan-2-ylmethyl)-1H-benzo[d]imidazole-6-carboxylate (100 mg, 0.3 mmol, the synthesis is disclosed in international application WO/2018/109607, which is incorporated herein by reference); The values of the optical rotation, $[\alpha]_{25.0° C. 589 nm}$=−25.02 (c=0.1, MeOH)) and $K_2CO_3$ (415 mg, 1.1 mmol). The reaction mixture was stirred at 60° C. for 12 h. 60 mL of ice water was added to quench the reaction. The solution was extracted with EA (30 mL×3), washed with brine and dried over $Na_2SO_4$. After evaporation of solvent, the crude was purified with column chromatography (PE/EA=2/1) to give (S)-tert-butyl-2-((4-(6-(4-chloro-2-fluorobenzylamino) pyridin-2-yl) piperazin-1-yl) methyl)-1-(oxetan-2-ylmethyl)-1H-benzo[d]imidazole-6-carboxylate (140 mg, 60%) as a yellow solid. LCMS: [M+H]=620.7; Retention time (0.01% TFA)=1.77 min.

Step 5

To the solution of (S)-tert-butyl-2-((4-(6-(4-chloro-2-fluorobenzylamino)pyridin-2-yl)piperazin-1-yl)methyl)-1-(oxetan-2-ylmethyl)-1H-benzo[d]imidazole-6-carboxylate (120 mg, 0.1 mmol) in DCM (6 mL) was added TFA (3 mL) at 0° C. The reaction mixture was stirred at 0° C. for 6 h. After evaporation of solvent, the crude was purified with HPLC to give (S)-2-((4-(6-(4-chloro-2-fluorobenzylamino) pyridin-2-yl) piperazin-1-yl) methyl)-1-(oxetan-2-ylmethyl)-1H-benzo[d]imidazole-6-carboxylic acid (60 mg, 73%) as a yellow solid. LCMS: [M+H]=566.0; Retention time (10 mM NH$_4$HCO$_3$)=1.48 min.

$^1$H NMR (400 MHz, DMSO-d6) δ 8.27 (d, J=0.8 Hz, 1H), 7.82-7.80 (m, 1H), 7.64 (d, J=8.4 Hz, 1H), 7.38-7.34 (m, 2H), 7.23-7.15 (m, 2H), 6.83 (t, J=6.4 Hz, 1H), 5.90-5.82 (m, 2H), 5.11-5.08 (m, 1H), 4.79 (dd, J=7.2, 15.2 Hz, 1H), 4.64 (dd, J=2.4, 15.2 Hz, 1H), 4.51-4.46 (m, 1H), 4.41-4.35 (m, 3H), 3.97-3.75 (m, 2H), 2.71-2.67 (m, 1H), 2.48-2.40 (m, 8H).

(S)-2-((4-(6-((4-chloro-2-fluorobenzyl)(methyl)amino)pyridin-2-yl)piperazin-1-yl)methyl)-1-(oxetan-2-ylmethyl)-1 h-benzo[d]imidazole-6-carboxylic acid (Compound 2)

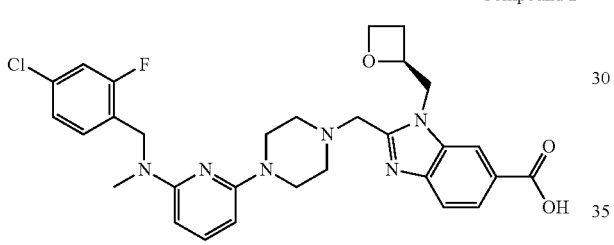

Compound 2

Prepared in analogous manner as for Compound 1
LCMS: [M+4]$^+$=579; Retention time (0.01% TFA)=1.70 min.

$^1$H NMR (400 MHz, DMSO-d6) δ 8.30 (s, 1H), 7.99-7.97 (m, 1H), 7.66 (d, J=8.4 Hz, 1H), 7.35-7.32 (m, 1H), 7.17-7.08 (m, 3H), 6.01 (dd, J=8.0, 26.4 Hz, 1H), 5.27 (dd, J=4.8, 7.2 Hz, 1H), 4.91-4.89 (m, 1H), 4.88-4.86 (m, 1H), 4.79 (s, 2H), 4.73 (dd, J=2.4, 15.2 Hz, 1H), 4.65-4.63 (m, 1H), 4.49-4.46 (m, 1H), 4.04-3.89 (m, 2H), 3.46-3.44 (m, 4H), 3.04 (s, 3H), 2.82-2.77 (m, 1H), 2.59-2.53 (m, 5H).

(S)-2-((4-(8-(4-chloro-2-fluorobenzyl)-5,6,7,8-tetrahydro-1,8-naphthyridin-2yl)piperazin-1-yl)methyl)-1-(oxetan-2-ylmethyl)-1 h-benzo[d]imidazole-6-carboxylic acid (Compound 3)

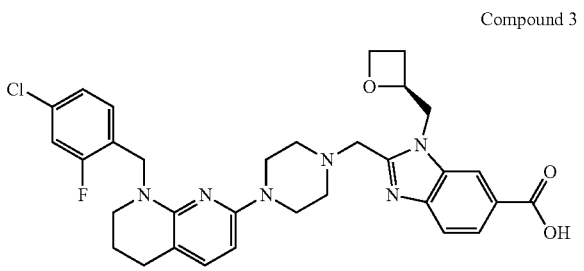 [SMILES: O=C(O)c1ccc2nc(CN3CCN(c4ccc5c(n4)N(Cc4ccc(Cl)cc4F)CCC5)CC3)n(C[C@@H]3CCO3)c2c1]

Compound 3

Prepared in analogous manner as for Compound 5

LCMS: [M+4]$^+$=605.2; Retention time (0.01% TFA)=1.45 min.

$^1$H NMR (400 MHz, DMSO-d6) δ 8.29-8.25 (brs, 1H), 7.80 (dd, J=8.4, 1.4 Hz, 1H), 7.64 (d, J=8.5 Hz, 1H), 7.37 (dd, J=10.1, 1.7 Hz, 1H), 7.26-7.19 (m, 2H), 7.01 (d, J=8.0 Hz, 1H), 5.90 (d, J=8.0 Hz, 1H), 5.12-5.04 (m, 1H), 4.77 (dd, J=15.2, 7.3 Hz, 1H), 4.71 (s, 2H), 4.66-4.59 (m, 1H), 4.52-4.44 (m, 1H), 4.40-4.32 (m, 1H), 3.93 (d, J=13.5 Hz, 1H), 3.75 (d, J=13.5 Hz, 1H), 3.28-3.20 (brs, 4H), 2.72-2.64 (m, 1H), 2.59 (t, J=6.0 Hz, 2H), 2.49-2.31 (m, 7H), 1.89-1.80 (m, 2H).

(S)-2-((4-(4-(4-chloro-2-fluorobenzyl)-3,4-dihydro-2H-pyrido[3,2-b][1,4]oxazin-6-yl)piperazin-1-yl)methyl)-1-(oxetan-2-ylmethyl)-1H-benzo[d]imidazole-6-carboxylic acid (Compound 4)

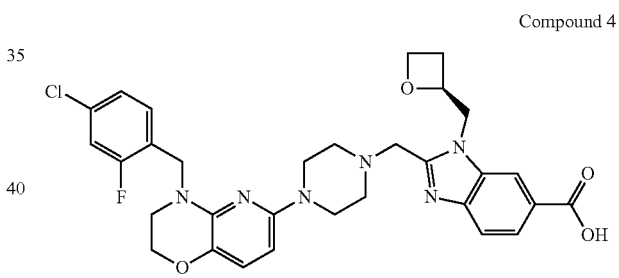

Compound 4

Prepared in analogous manner as for Compound 5

LCMS: [M+H]+=607.6; Retention time (10 mmol NH$_4$HCO$_3$)=1.63 min.

$^1$H NMR (400 MHz, DMSO-d6) δ 8.29-8.25 (brs, 1H), 7.80 (dd, J=8.4, 1.3 Hz, 1H), 7.64 (d, J=8.4 Hz, 1H), 7.40 (dd, J=10.0, 2.0 Hz, 1H), 7.32 (t, J=8.2 Hz, 1H), 7.23 (dd, J=8.3, 1.9 Hz, 1H), 6.85 (d, J=8.3 Hz, 1H), 5.90 (d, J=8.4 Hz, 1H), 5.13-5.05 (m, 1H), 4.78 (dd, J=15.2, 7.3 Hz, 1H), 4.71 (s, 2H), 4.63 (dd, J=12.8 Hz, 1H), 4.51-4.45 (m, 1H), 4.40-4.34 (m, 1H), 4.12-4.07 (m, 2H), 3.95 (d, J=13.5 Hz, 1H), 3.76 (d, J=13.5 Hz, 1H), 3.25-3.15 (brs, 6H), 2.72-2.64 (m, 1H), 2.57-2.52 (m, 1H), 2.50-2.33 (m, 4H).

2-((4-(4-(4-chloro-2-fluorobenzyl)-3,4-dihydro-2 h-pyrido[3,2-b][1,4]oxazin-6-yl)piperazin-1-yl) methyl)-1-((1-methyl-1 h-imidazol-2-yl)methyl)-1 h-benzo[d] imidazole-6-carboxylic acid (Compound 5)
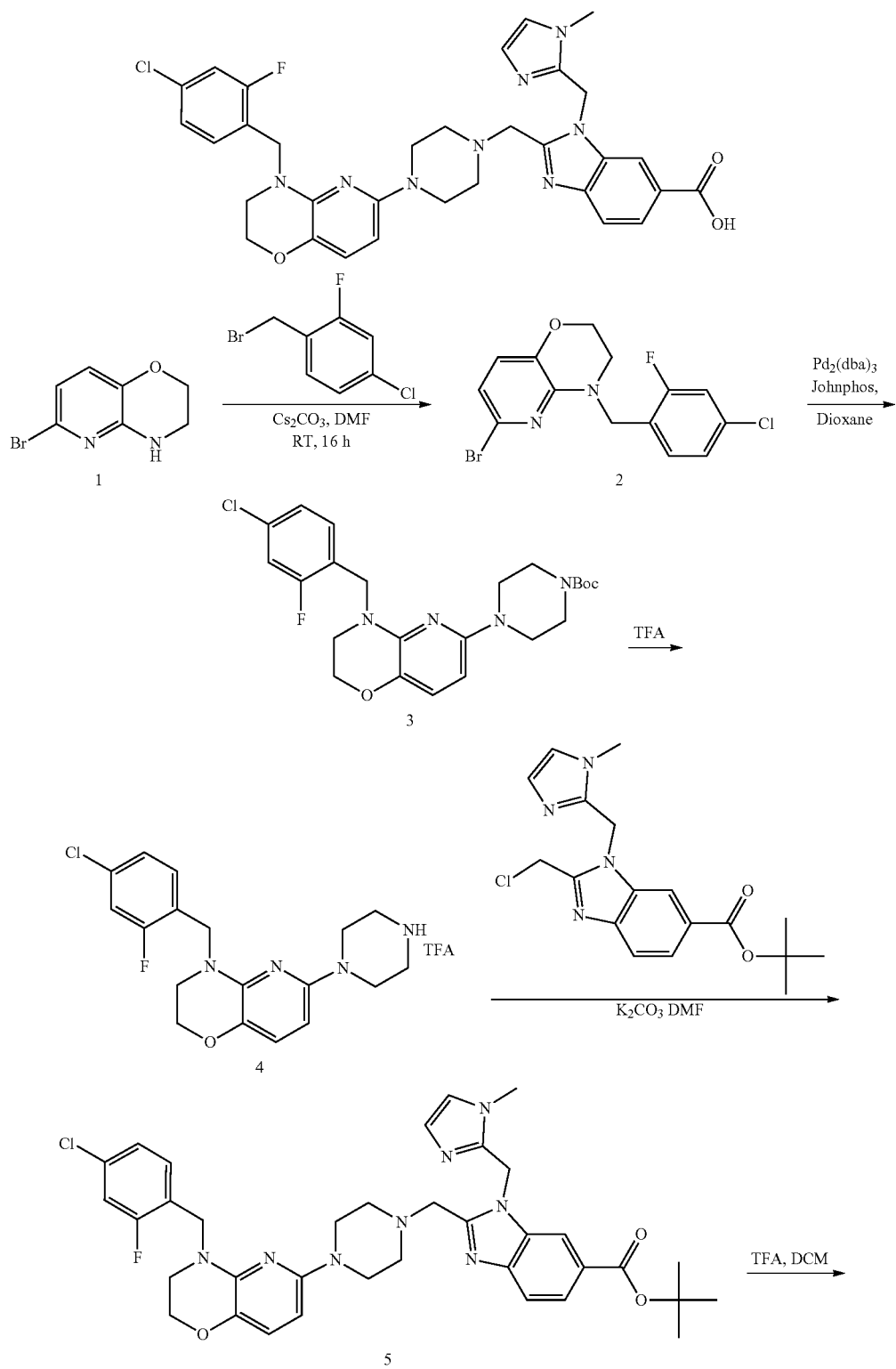

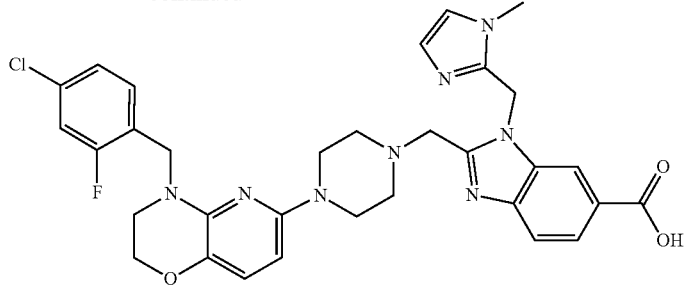

Compound 5

Step 1

To a solution of 6-bromo-3,4-dihydro-2 h-pyrido[3,2-b][1,4]oxazine (0.5 g, 2.3 mmol) in DMF (10 mL) were added 1-(bromomethyl)-4-chloro-2-fluorobenzene (0.6 g, 2.5 mmol) and $Cs_2CO_3$ (2.3 g, 6.9 mmol). The mixture was stirred at 25° C. for 16 h. The solution was diluted with water (20 mL) and extracted with ethyl acetate (20 mL×3). The combined organics were washed with brine (20 mL×3), dried over $Na_2SO_4$ and concentrated to give crude product, which was purified by chromatography column on silica gel (eluting with PE:EA=10:1) to give 6-bromo-4-(4-chloro-2-fluorobenzyl)-3,4-dihydro-2 h-pyrido[3,2-b][1,4]oxazine (0.72 g, 72.7% yield) as yellow solid.

LCMS: $[M+H]^+$=356.8; Retention time (10 mM $NH_4HCO_3$)=1.91 min.

Step 2

To a solution of 6-bromo-4-(4-chloro-2-fluorobenzyl)-3,4-dihydro-2 h-pyrido[3,2-b][1,4]oxazine (200 mg, 0.56 mmol) in 1,4-Dioxane (5 mL) were added tert-butyl piperazine-1-carboxylate (135 mg, 0.73 mmol), JohnPhos (16 mg, 0.06 mmol), $Pd_2(dba)_3$ (26 mg) and $Cs_2CO_3$ (292 mg, 0.90 mmol, 1.6 eq). The mixture was stirred at 100° C. for 16 h under nitrogen. The reaction was cooled to RT, then diluted with water (50 mL) and extracted with ethyl acetate (50 mL×3). The combined organics were washed with brine (20 mL×3), dried over $Na_2SO_4$ and concentrated in vacuum to give crude product. The crude product was purified by chromatography column on silica gel (eluting with PE:EA=5:1) to give the tert-butyl 4-(4-(4-chloro-2-fluorobenzyl)-3,4-dihydro-2 h-pyrido[3,2-b][1,4]oxazin-6-yl)piperazine-1-carboxylate (0.1 g, 0.22 mmol, 37.9% yield) as yellow solid. LCMS: $[M+H]^+$=462.7; Retention time (0.01% TFA)=2.13 min.

Step 3

A solution of tert-butyl 4-(4-(4-chloro-2-fluorobenzyl)-3,4-dihydro-2 h-pyrido[3,2-b][1,4]oxazin-6-yl)piperazine-1-carboxylate (0.1 g, 0.22 mmol, 1.0 eq) in TFA (1 mL) and DCM (5 mL) was stirred at 25° C. for 2 h. The mixture was diluted with saturated aq. $NaHCO_3$ until pH was adjusted to 7, and extracted with DCM (50 mL×3). The combined organics were washed with brine (20 mL×3), dried over $Na_2SO_4$ and concentrated in vacuum to give 4-(4-chloro-2-fluorobenzyl)-6-(piperazin-1-yl)-3,4-dihydro-2 h-pyrido[3,2-b][1,4]oxazine (65 mg, 70% yield) as yellow solid. LCMS: $[M+H]^+$=362.8; Retention time (0.01% TFA)=1.45 min.

Step 4

A mixture of 4-(4-chloro-2-fluorobenzyl)-6-(piperazin-1-yl)-3,4-dihydro-2 h-pyrido[3,2-b][1,4]oxazine (40 mg, 0.1 mmol), tert-butyl 2-(chloromethyl)-1-((1-methyl-1 h-imidazol-2-yl)methyl)-1 h-benzo[d]imidazole-6-carboxylate (32 mg, 0.13 mmol, the synthesis is disclosed in in international application WO/2018/109607) and $K_2CO_3$ (132.6 mg, 0.96 mmol) in DMF (5 mL) were heated to 60° C., stirred for 3 h under $N_2$ atmosphere. LCMS showed the reaction was completed. The mixture was extracted with EA (10 mL×2), the organic layer was dried in $Na_2SO_4$, the filtrate was concentrated to give the crude product, which was purified by biotage flash (eluting with EA:PE=1:10) to give the desired product tert-butyl 2-((4-(4-(4-chloro-2-fluorobenzyl)-3,4-dihydro-2 h-pyrido[3,2-b][1,4]oxazin-6-yl)piperazin-1-yl)methyl)-1-((1-methyl-1 h-imidazol-2-yl)methyl)-1 h-benzo[d]imidazole-6-carboxylate (23 mg, 0.03 mmol, 30% yield) as white solid. LCMS: $[M+H]^+$=687.0; Retention time (0.01% TFA)=1.85 min.

Step 5

A solution of tert-butyl 2-((4-(4-(4-chloro-2-fluorobenzyl)-3,4-dihydro-2 h-pyrido[3,2-b][1,4]oxazin-6-yl)piperazin-1-yl)methyl)-1-((1-methyl-1 h-imidazol-2-yl)methyl)-1 h-benzo[d]imidazole-6-carboxylate (23 mg, 0.03 mmol) in DCE (3 mL) and TFA (1 mL) was stirred for 1 h. LCMS showed the reaction was completed. The solvent was removed in vacuum and the residue was purified by Prep-HPLC to give the desired product (6 mg, 35% yield). LCMS: $[M+H]^+$=631.2; Retention time (0.01% TFA)=1.31 min.

$^1$H NMR (400 MHz, MeOD) δ 8.20-8.17 (brs, 1H), 8.04 (dd, J=8.5 Hz, 1H), 7.84-7.80 (m, 1H), 7.30-7.25 (m, 2H), 7.19-7.12 (m, 2H), 7.03 (d, J=1.2 Hz, 1H), 6.95-6.90 (m, 1H), 6.01 (d, J=8.3 Hz, 1H), 5.93 (s, 2H), 4.75 (s, 2H), 4.30 (s, 2H), 4.14-4.20 (m, 2H), 3.93 (s, 3H), 3.53-3.46 (m, 2H), 3.29-3.20 (brs, 4H), 2.94-2.86 (m, 4H).

(S)-2-((4-(1-(4-chloro-2-fluorophenethyl)-6-oxo-1,6-dihydropyridazin-3-yl)piperazin-1-yl)methyl)-1-(oxetan-2-ylmethyl)-1 h-benzo[d]imidazole-6-carboxylic acid (Compound 6)
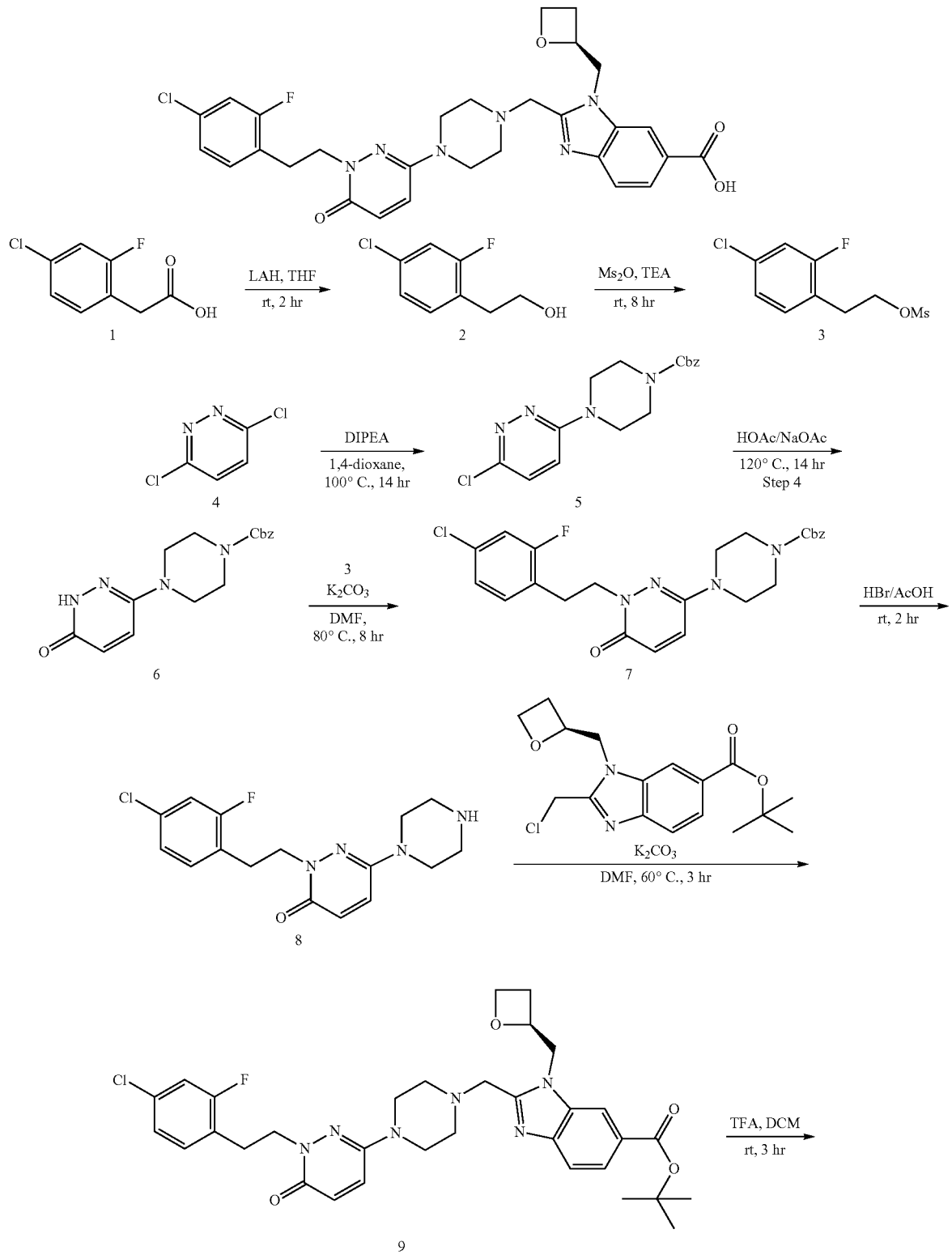

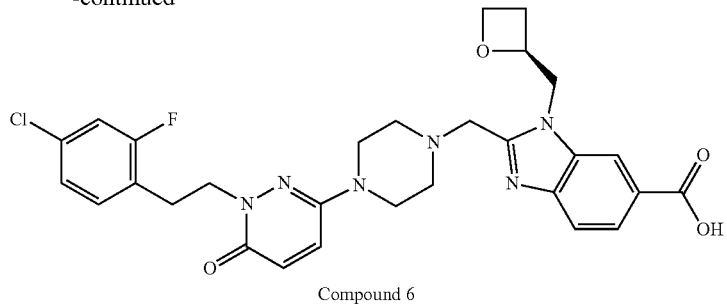

Compound 6

Step 1

To a solution of 2-(4-chloro-2-fluorophenyl) acetic acid (1.8 g, 9.6 mmol) in THF (20 mL) was added LAH (19 mL, 19.1 mmol). The mixture was stirred at RT for 3 h. The reaction was diluted with water (50 mL) and extracted with ethyl acetate (50 mL×3), The combined organics were washed with brine (50 mL×3), dried over $Na_2SO_4$ and concentrated in vacuum to give crude product 2-(4-chloro-2-fluorophenyl)ethanol (1.5 g, 89% yield) as a yellow oil. LCMS: [M−18+H]=157.0, Retention time (0.01% TFA)=1.61 min.

Step 2

To a solution of 2-(4-chloro-2-fluorophenyl) ethanol (1.5 g, 8.6 mmol) in DCM (30 mL) were added methanesulfonic anhydride (2.2 g, 12.9 mmol) and TEA (3.6 mL, 25.8 mmol). The mixture was stirred at RT for 8 h. The reaction was diluted with water (50 mL) and extracted with ethyl acetate (50 mL×3). The combined organics were washed with brine (50 mL×3), dried over $Na_2SO_4$ and concentrated in vacuum to give crude product, which was purified by column chromatography on silica gel (PE:EA=10:1) to give 4-chloro-2-fluorophenethyl methanesulfonate (1.2 g, 55% yield) as yellow oil.

LCMS: [M+Na]=275.0, Retention time (0.01% TFA)=1.79 min.

Step 3

To a solution of 3,6-dichloropyridazine (1.0 g, 6.7 mmol) in 1,4-dioxane (20 mL) were added benzyl piperazine-1-carboxylate (1.6 g, 7.4 mmol) and DIPEA (3.6 mL, 20.1 mmol). The mixture was stirred at 100° C. for 16 h. The reaction mixture was diluted with water (50 mL) and extracted with ethyl acetate (50 mL×3), The combined organics were washed with brine (50 mL×3), dried over $Na_2SO_4$ and concentrated in vacuum to give the desired product benzyl 4-(6-chloropyridazin-3-yl)piperazine-1-carboxylate (1.2 g, 55% yield) as yellow solid. LCMS: [M+H]⁺= 332.1, Retention time (0.01% TFA)=1.61 min.

Step 4

To a solution of benzyl 4-(6-chloropyridazin-3-yl) piperazine-1-carboxylate (1.0 g, 3.0 mmol) in HOAc (75 mL) was added NaOAc (0.25 g, 3.05 mmol). The mixture was stirred at 120° C. for 16 h. The reaction was concentrated in vacuum, diluted with $NaHCO_3$ (1 N, 30 mL) and extracted with ethyl acetate (50 mL×3), The combined organics were washed with brine (50 mL×3), dried over $Na_2SO_4$ and concentrated in vacuum to give benzyl 4-(6-oxo-1,6-dihydropyridazin-3-yl)piperazine-1-carboxylate (900 mg, 95% yield) as yellow solid. LCMS: [M+H]⁺=314.1, Retention time (0.01% TFA)=1.46 min.

Step 5

To a solution of 4-chloro-2-fluorophenethyl methanesulfonate (80 mg, 0.32 mmol) in DMF (10 mL) was added benzyl 4-(6-oxo-1,6-dihydropyridazin-3-yl)piperazine-1-carboxylate (100 mg, 0.32 mmol) and $K_2CO_3$ (132 mg, 1.0 mmol). The mixture was stirred at 80° C. for 3 h. The reaction was diluted with water (50 mL) and extracted with ethyl acetate (50 mL×3). The combined organics were washed with brine (50 mL×3), dried over $Na_2SO_4$ and concentrated in vacuum to give crude product, which was purified by Prep-TLC (DCM:MeOH=10:1) to give benzyl 4-(1-(4-chloro-2-fluorophenethyl)-6-oxo-1,6-dihydropyridazin-3-yl) piperazine-1-carboxylate (100 mg, 67% yield) as brown oil. LCMS: [M+H]⁺=471.1, Retention time (0.01% TFA)=1.89 min.

Step 6

To a solution of benzyl 4-(1-(4-chloro-2-fluorophenethyl)-6-oxo-1,6-dihydropyridazin-3-yl)piperazine-1-carboxylate (400 mg, 0.9 mmol, 1.0 eq) in AcOH (10 mL), was added HBr/AcOH (33%) (3 mL, 12.37 mmol). The mixture was stirred at RT for 1 h. The reaction was diluted with $NaHCO_3$ (100 mL) and extracted with ethyl acetate (50 mL×3). The combined organics were washed with brine (50 mL×3), dried over $Na_2SO_4$ and concentrated in vacuum to give crude product, which was purified by Prep-HPLC ($NH_4HCO_3$) to give 2-(4-chloro-2-fluorophenethyl)-6-(piperazin-1-yl)pyridazin-3(2H)-one (60 mg, 21% yield) as brown solid. LCMS: [M+H]⁺=336.7, Retention time (0.01% TFA)=1.41 min.

Step 7

To a solution of 2-(4-chloro-2-fluorophenethyl)-6-(piperazin-1-yl)pyridazin-3(2H)-one (60 mg, 0.18 mmol, 1.0 eq) in 1,4-dioxane (10 mL) was added (S)-tert-butyl 2-(chloromethyl)-1-(oxetan-2-ylmethyl)-1 h-benzo[d]imidazole-6-carboxylate (60 mg, 0.179 mmol) and DIPEA (69 mg, 0.54 mmol). The mixture was stirred at 80° C. for 3 h. The reaction was diluted with water (50 mL) and extracted with ethyl acetate (50 mL×3), the combined organics were washed with brine (50 mL×3), dried over $Na_2SO_4$ and concentrated in vacuum to give crude product, which was purified by Prep-TLC (DCM:MeOH=10:1) to give (S)-tert-butyl 2-((4-(1-(4-chloro-2-fluorophenethyl)-6-oxo-1,6-dihydropyridazin-3-yl)piperazin-1-yl)methyl)-1-(oxetan-2-ylmethyl)-1 h-benzo[d]imidazole-6-carboxylate (80 mg, 70% yield) as yellow solid. LCMS: [M+H]⁺=637.2, Retention time (0.01% TFA)=1.76 min.

Step 8

To a solution of (S)-tert-butyl 2-((4-(1-(4-chloro-2-fluorophenethyl)-6-oxo-1,6-dihydropyridazin-3-yl)piperazin-1-yl)methyl)-1-(oxetan-2-ylmethyl)-1 h-benzo[d]imidazole-6-carboxylate (80 mg, 0.13 mmol) in DCM (8 mL) was added TFA (1 mL). The mixture was stirred at RT for 3 h. The reaction was concentrated in vacuum to give crude product, which was purified by Prep-HPLC to give (S)-2-((4-(1-(4-chloro-2-fluorophenethyl)-6-oxo-1,6-dihydropyridazin-3-yl)piperazin-1-yl)methyl)-1-(oxetan-2-ylmethyl)-1 h-benzo[d]imidazole-6-carboxylic acid (22.8 mg, 32% yield) as white solid. LCMS: [M+H]+=581.2, Retention time (0.01% TFA)=1.35 min.

$^1$H NMR (400 MHz, MeOD) δ 8.37-8.36 (brs, 1H), 8.00 (d, J=8.5 Hz, 1H), 7.70 (d, J=8.5 Hz, 1H), 7.42 (d, J=10.0 Hz, 1H), 7.11 (ddt, J=10.1, 8.1, 5.1 Hz, 3H), 6.84 (d, J=9.9 Hz, 1H), 5.27 (td, J=7.2, 4.9 Hz, 1H), 4.88 (d, J=7.1 Hz, 1H), 4.74 (dd, J=15.4, 2.5 Hz, 1H), 4.66 (dd, J=13.8, 7.9 Hz, 1H), 4.48 (dt, J=9.1, 5.9 Hz, 1H), 4.29 (t, J=6.6 Hz, 2H), 4.06 (d, J=13.7 Hz, 1H), 3.95 (d, J=13.7 Hz, 1H), 3.20 (t, J=4.7 Hz, 4H), 3.11 (t, J=6.5 Hz, 2H), 2.88-2.77 (m, 1H), 2.67-2.48 (m, 5H).

(S)-2-((4-(1-(4-chloro-2-fluorobenzyl)-6-oxo-1,6-dihydropyridazin-3-yl)piperazin-1-yl)methyl)-1-(oxetan-2-ylmethyl)-1 h-benzo[d]imidazole-6-carboxylic acid (Compound 7)

Compound 7

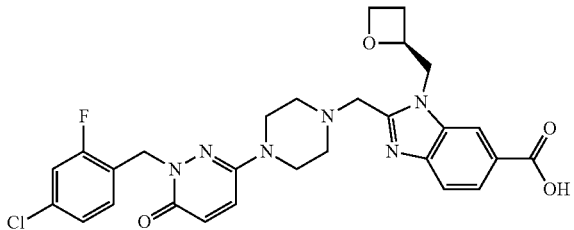

Prepared in analogous manner as for Compound 6
LCMS: [M+H]+=567.2, Retention time (0.01% TFA)= 1.28 min.
$^1$H NMR (400 MHz, MeOD) δ 8.23-8.22 (brs, 1H), 7.87 (dd, J=8.5, 1.4 Hz, 1H), 7.57 (d, J=8.5 Hz, 1H), 7.38 (d, J=10.0 Hz, 1H), 7.18 (t, J=8.1 Hz, 1H), 7.08 (ddd, J=10.2, 9.1, 1.8 Hz, 2H), 6.80 (d, J=10.0 Hz, 1H), 5.21-5.11 (m, 3H), 4.77-4.73 (m, 1H), 4.61 (dd, J=15.4, 2.6 Hz, 1H), 4.55-4.47 (m, 1H), 4.35 (dt, J=9.1, 5.9 Hz, 1H), 3.93 (d, J=13.7 Hz, 1H), 3.82 (d, J=13.7 Hz, 1H), 3.22-3.21 (brs, 4H), 2.69 (dt, J=14.1, 8.2 Hz, 1H), 2.57-2.47 (m, 4H), 2.44-2.36 (m, 1H).

(S)-2-((4-(1-(4-chloro-2-fluorophenethyl)-2-oxo-1,2-dihydropyridin-3-yl)piperazin-1-yl)methyl)-1-(oxetan-2-ylmethyl)-1h-benzo[d]imidazole-6-carboxylic acid (Compound 8)

Compound 8

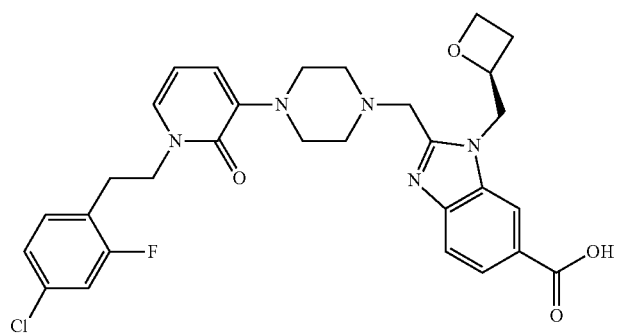

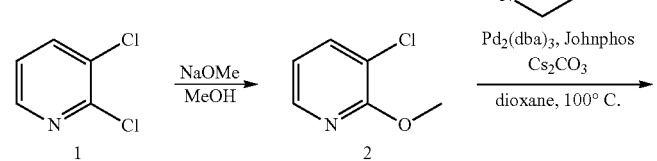

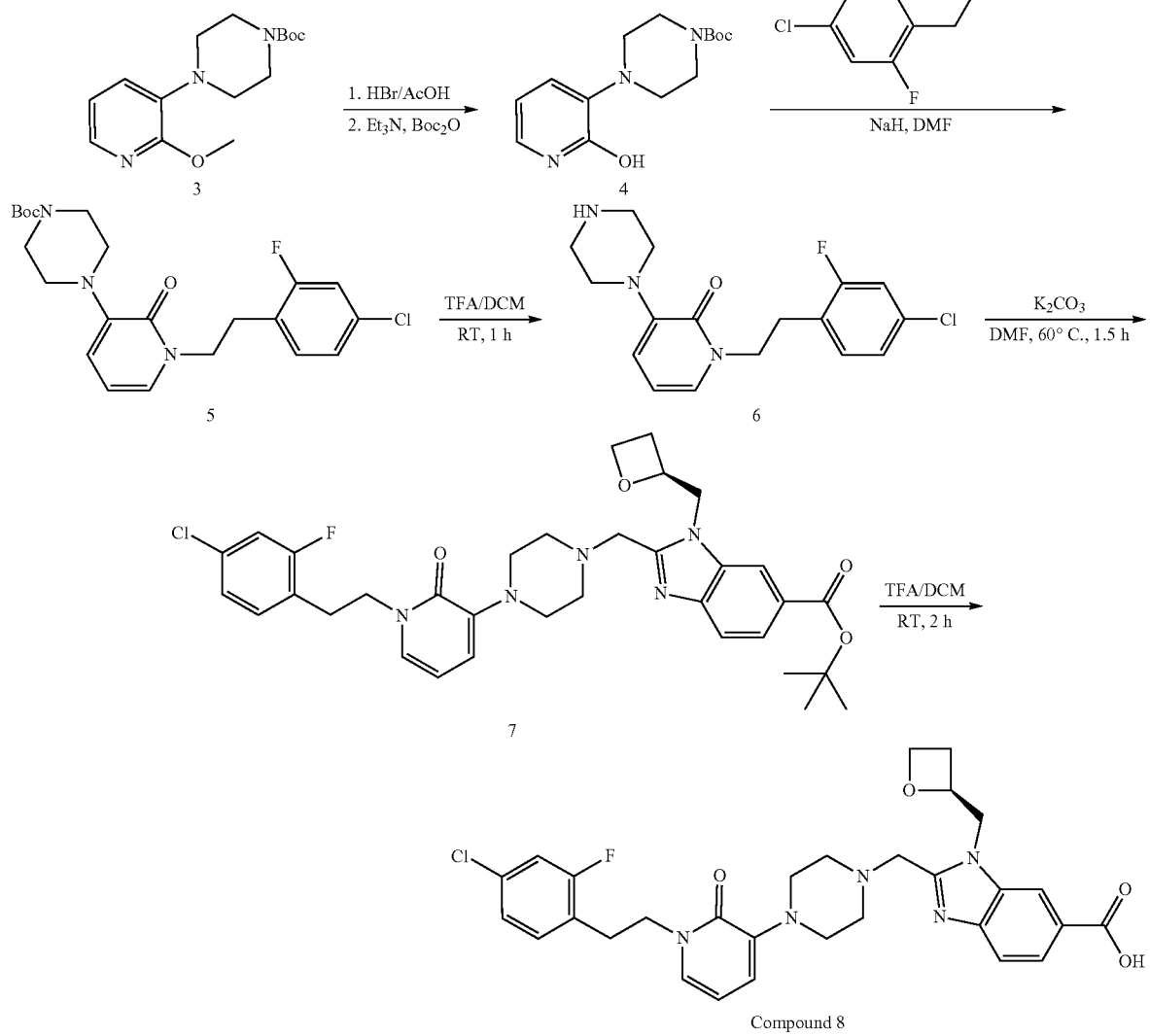

Compound 8

Step 1

To a solution of 2,3-dichloropyridine (5.0 g, 34 mmol) in MeOH (50 mL) was added NaOMe (54 mL, 1 N in MeOH). The resulting mixture was refluxed for 5 h. LCMS showed the reaction completed. The mixture was poured into ice water and was adjusted to pH 5~6 by HCl (1 N in water), extracted with EA (50 mL×3). The combined organic layers were collected and concentrated to give the desired product 3-chloro-2-methoxypyridine (4 g, yield 81%) as yellow oil, which was used in the next step without further purification.

Step 2

A mixture of 3-chloro-2-methoxypyridine (500 mg, 3.49 mmol), tert-butyl piperazine-1-carboxylate (845 mg, 4.53 mmol), Johnphos (208 mg, 0.69 mmol), Pd$_2$(dba)$_3$ (320 mg) and Cs$_2$CO$_3$ (3.45 g, 10.47 mmol) in dioxane (20 mL) was stirred at 100° C. for 16 h. LCMS showed the reaction was completed. The mixture was diluted with EA (50 mL), filtered through a pad of celite, the filtrate was concentrated to give the crude product, which was purified by biotage flash (EA/PE=1/30) to give the desired product tert-butyl 4-(2-methoxypyridin-3-yl)piperazine-1-carboxylate (1 g, yield 96%). LCMS: [M+H]$^+$=294.0, Retention time=1.62 min.

Step 3

A solution of tert-butyl 4-(2-methoxypyridin-3-yl)piperazine-1-carboxylate (1 g, 3.41 mmol) in HBr (40% in AcOH, 10 mL) was refluxed over night. After cooled to RT, the solid was collected. The solid was dissolved in DCM (15 mL), then Et$_3$N (3.1 mL, 4eq) and di-tert-butyl dicarbonate (2.43 g, 2eq) were added in sequence, and the resulting mixture was stirred at RT for 2 h. LCMS showed the reaction was completed. The solution was concentrated and purified by silica gel column chromatography (EA/PE=1/4) to give the desired product tert-butyl 4-(2-hydroxypyridin-3-yl)piperazine-1-carboxylate (600 mg, yield 63.5%) as white solid. LCMS: [M+H]$^+$=280.0, Retention time=1.27 min.

Step 4

To a solution of tert-butyl 4-(2-hydroxypyridin-3-yl)piperazine-1-carboxylate (400 mg, 1.43 mmol) in DMF (5 mL) was added NaH (68 mg, 60% in oil, 1.2 eq) and the resulting mixture was stirred at RT for 1 h. Then 4-chloro-2-fluorophenethyl methanesulfonate (722 mg) was added at once. The reaction solution was stirred at RT overnight. LCMS showed the reaction was completed. The reaction mixture was filtered and purified by prep-HPLC to give the desired product tert-butyl 4-(1-(4-chloro-2-fluorophenethyl)-2-oxo-1,2-dihydropyridin-3-yl)piperazine-1-carboxylate (17 mg, yield 2.7%) as white solid. LCMS: [M+H]$^+$=435.9, Retention time=1.75 min.

Step 5

To a solution of tert-butyl 4-(1-(4-chloro-2-fluorophenethyl)-2-oxo-1,2-dihydropyridin-3-yl) piperazine-1-carboxylate (17 mg, 0.039 mmol) in DCM (1.5 mL) was added TFA (0.5 mL). The mixture was stirred at RT for 1 h. LCMS showed the reaction was completed. The solution was poured into sat·NaHCO$_3$ and extracted with DCM (20 mL×3), the combined organic layers were dried by Na$_2$SO$_4$, filtered and concentrated in vacuo to give the desired product 1-(4-chloro-2-fluorophenethyl)-3-(piperazin-1-yl)pyridin-2(1H)-one (12 mg, yield 92.3%) as brown oil. LCMS: [M+H]$^+$=336.0, Retention time=1.31 min.

Step 6

A mixture of 1-(4-chloro-2-fluorophenethyl)-3-(piperazin-1-yl)pyridin-2(1H)-one (12 mg, 0.035 mmol), tert-butyl (S)-2-(chloromethyl)-1-(oxetan-2-ylmethyl)-1H-benzo[d]imidazole-6-carboxylate (15 mg, 0.041 mmol) and K$_2$CO$_3$ (27 mg, 0.020 mmol) in CH$_3$CN (3 mL) was warmed to 60° C. and stirred for 2 h under N$_2$. LCMS showed the reaction was completed. The solution was poured into water and extracted with DCM (20 mL×3), the combined organic layers were dried over Na$_2$SO$_4$, filtered and concentrated in vacuo to give the desired product (S)-tert-butyl 2-((4-(1-(4-chloro-2-fluorophenethyl)-2-oxo-1,2-dihydropyridin-3-yl)piperazin-1-yl)methyl)-1-(oxetan-2-ylmethyl)-1H-benzo[d]imidazole-6-carboxylate (20 mg, yield 90%) which was used in the next step directly without further purification.

LCMS: [M+H]$^+$=636.0, Retention time=1.79 min.

Step 7

To a solution of (S)-tert-butyl 2-((4-(1-(4-chloro-2-fluorophenethyl)-2-oxo-1,2-dihydropyridin-3-yl)piperazin-1-yl)methyl)-1-(oxetan-2-ylmethyl)-1H-benzo[d]imidazole-6-carboxylate (20 mg, 0.03 mmol) in DCM (1.5 mL) was added TFA (0.5 mL). The mixture was stirred at RT for 2 h. LCMS showed the reaction was completed. The solution was poured into saturated aq. NaHCO$_3$ and extracted with DCM (20 mL×3), the combined organic layers were dried by Na$_2$SO$_4$, filtered and concentrated. The crude product was purified by prep-HPLC to give the desired product (S)-2-((4-(1-(4-chloro-2-fluorophenethyl)-2-oxo-1,2-dihydropyridin-3-yl)piperazin-1-yl)methyl)-1-(oxetan-2-ylmethyl)-1 h-benzo[d]imidazole-6-carboxylic acid (3.3 mg, yield 18%) as white solid. LCMS: [M+H]$^+$=579.8, Retention time (0.01% TFA)=1.21 min.

$^1$H NMR (400 MHz, DMSO-d6) δ 8.25-8.29 (brs, 1H), 7.80 (dd, J=7.4, 1.4 Hz, 1H), 7.64 (d, J=8.4 Hz, 1H), 7.35 (dd, J=7.2, 1.6 Hz, 1H), 7.26 (t, =8.4 Hz, 1H), 7.20 (dd, J=6.4, 1.4 Hz, 1H), 7.10 (d, J=5.2 Hz, 1H), 6.65 (d, J=6.0 Hz, 1H), 6.06 (t, J=8.0 Hz, 1 h), 5.08-5.10 (m, 1H), 4.62-4.78 (m, 2H), 4.36-4.49 (m, 2H), 4.06-4.10 (m, 2H), 3.98 (d, J=13.6 Hz, 1H), 3.80 (d, J=13.2 Hz, 1H), 2.95-3.00 (m, 6H), 2.57-2.67 (m, 4H), 2.39-2.44 (m, 2H).

(S)-2-((4-(2-((4-chloro-2-fluorobenzyl)oxy)pyrimidin-4-yl)piperazin-1-yl)methyl)-1-(oxetan-2-ylmethyl)-1H-benzo[d]imidazole-6-carboxylic acid
(Compound 9)

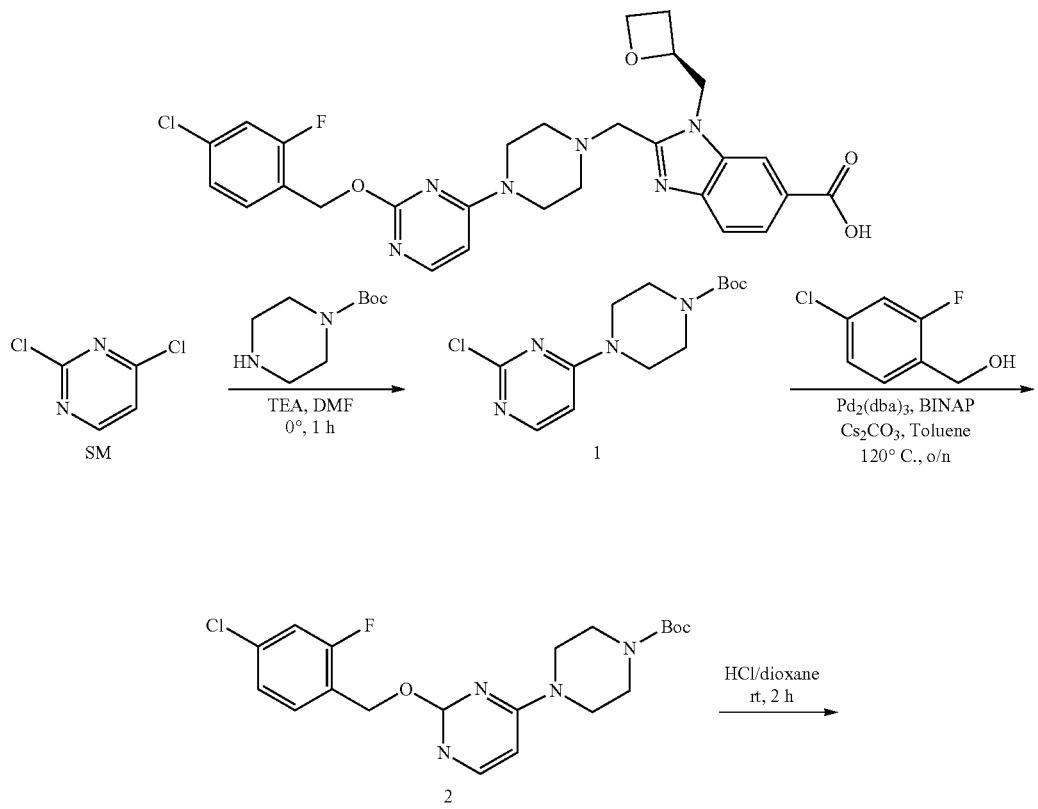

Compound 9

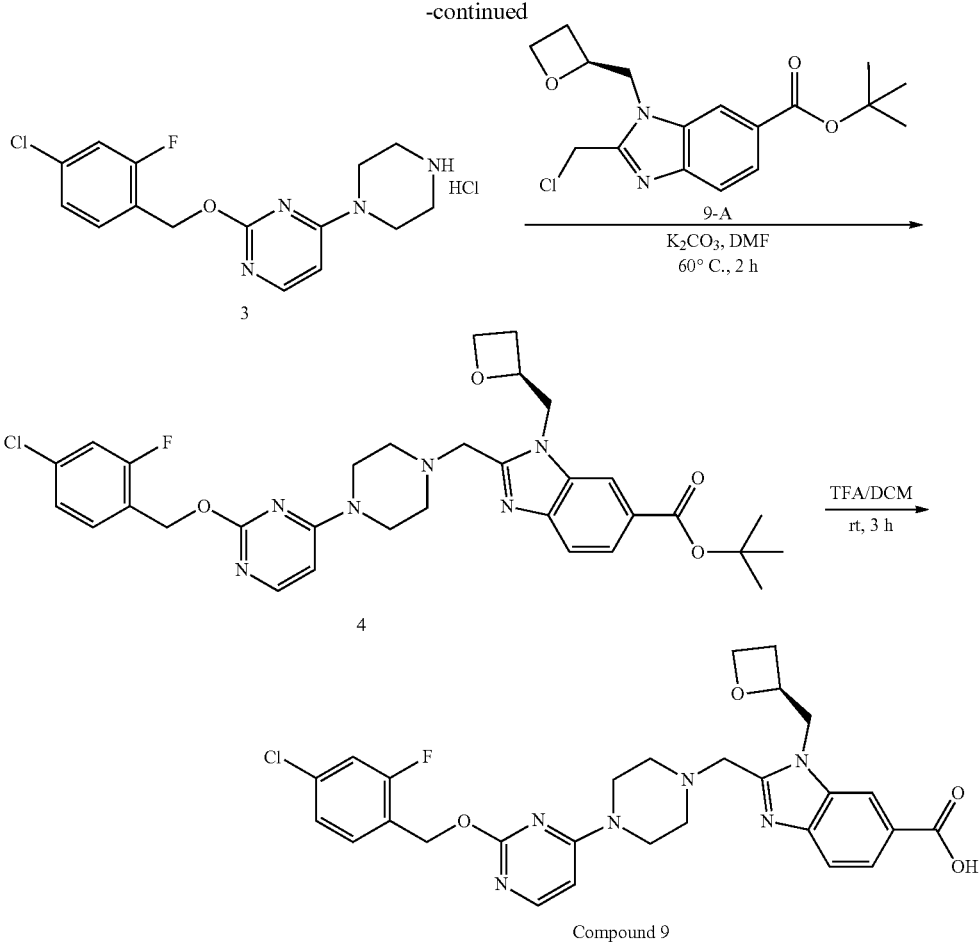

Compound 9

Step 1

A solution of 2,4-dichloropyrimidine (1 g, 6.76 mmol), tert-butyl piperazine-1-carboxylate (1.38 g, 7.43 mmol) and TEA (1.02 g, 10.14 mmol) in DMF (10 mL) was stirred at ice-bath for 1 h. Then the reaction was stirred at rt for 18 h. The mixture was diluted with water (40 mL), extracted with EA (80 mL×3). The organic layer was combined and dried in $Na_2SO_4$, filtered and concentrated. The crude product was purified by flash column chromatography on silica gel (PE:EA/0%-26%) to give tert-butyl 4-(2-chloropyrimidin-4-yl) piperazine-1-carboxylate (1.98 g, 98%) as a white solid. LCMS: $[M+H]^+$=299.1, Retention time (10 mM $NH_4HCO_3$)=1.70 min.

Step 2

To a solution of tert-butyl 4-(2-chloropyrimidin-4-yl) piperazine-1-carboxylate (1 g, 3.36 mmol), (4-chloro-2-fluorophenyl)methanol (662 g, 3.69 mmol) in Toluene (30 mL) was added $Cs_2CO_3$ (2.18 g, 6.71 mmol), BINAP (230 mg, 0.336 mmol) and $Pa_2(dba)_3$ (172 mg, 0.168 mmol) under $N_2$ at 120° C. for 18 h. The mixture was filtered and concentrated, purified by flash chromatography on silica gel (PE:EA/0%~28%) to give tert-butyl 4-(2-(4-chloro-2-fluorobenzyloxy) pyrimidin-4-yl) piperazine-1-carboxylate (910 mg, 80%) as a pale brown solid. LCMS: $[M+H]^+$=423.2, Retention time (0.01% TFA)=1.50 min.

Step 3

A solution of tert-butyl 4-(2-(4-chloro-2-fluorobenzyloxy) pyrimidin-4-yl) piperazine-1-carboxylate (905 mg, 2.14 mmol) in HCl/dioxane (10 mL) was stirred at room temperature for 3 h. The reaction was filtered to give 2-(4-chloro-2-fluorobenzyloxy)-4-(piperazin-1-yl) pyrimidine hydrochloric acid salt (745 mg, 97% yield) as off-white solid. LCMS: $[M+H]^+$=323.0, Retention time (10 mM $NH_4HCO_3$)=1.55 min.

Step 4

To a solution of 2-(4-chloro-2-fluorobenzyloxy)-4-(piperazin-1-yl) pyrimidine hydrochloric acid salt (37 mg, 0.107 mmol), (S)-tert-butyl 2-(chloromethyl)-3-(oxetan-2-ylmethyl)-3H-benzo[d]imidazole-5-carboxylate (30 mg, 0.0893 mmol) and $K_2CO_3$ (19 mg, 0.134 mmol) in DMF (3 mL) was stirred at 60° C. for 2 h. The mixture was diluted with water (5 mL), and extracted with EA (30 mL×3), the organic layer was dried in $Na_2SO_4$, filtered and concentrated, purified by prep-TLC (PE:EA/1:5) to give (S)-tert-butyl 2-((4-(2-(4-chloro-2-fluorobenzyloxy) pyrimidin-4-yl) piperazin-1-yl) methyl)-3-(oxetan-2-ylmethyl)-3H-benzo[d]imidazole-5-carboxylate (43 mg, 81%) as a colorless oil. LCMS: $[M+H]^+$= 623.0, Retention time (10 mM $NH_4HCO_3$)=2.04 min.

Step 5

To a solution of (S)-tert-butyl 2-((4-(2-(4-chloro-2-fluorobenzyloxy) pyrimidin-4-yl) piperazin-1-yl) methyl)-3-(oxetan-2-ylmethyl)-3H-benzo[d]imidazole-5-carboxylate (47 mg, 0.08 mmol) in DCM (4 mL) was added TFA (0.8 mL) at rt. The mixture was stirred at for 1 h. The reaction was evaporated, dissolved in ACN (4 mL), adjusted to pH=7~8 with Sat. aqueous $NaHCO_3$. The reaction was evaporated, dissolved in THF (1 mL), purified by prep-HPLC ($NH_4HCO_3$) to give (S)-2-((4-(2-((4-chloro-2-fluorobenzyl)oxy)pyrimidin-4-yl)piperazin-1-yl)methyl)-1-(oxetan-2-ylmethyl)-1H-benzo[d]imidazole-6-carboxylic acid (15.6 mg, 36%) as white solid. LCMS: $[M+H]^+$=567.0, Retention time (10 mM $NH_4HCO_3$)=1.37 min.

¹H NMR (400 MHz, CDCl₃) δ 8.21-8.20 (brs, 2H), 8.06 (d, J=6.4 Hz, 2H), 7.83 (d, J=8.4 Hz, 1H), 7.47 (t, J=7.6 Hz, 1H), 7.11 (dd, J=8.4 Hz, 2H), 6.18 (d, J=6.0 Hz, 1H), 5.37 (s, 2H), 5.23-5.22 (brs, 1H), 4.72-4.70 (m, 1H), 4.66-4.60 (m, 1H), 4.38-4.34 (m, 1H), 4.12 (d, J=9.2 Hz, 2H), 3.66 (s, 4H), 2.77-2.70 (m, 1H), 2.61 (s, 4H), 2.49-2.40 (m, 2H).

(S)-2-((4-(2-((4-cyano-2-fluorobenzyl)oxy)pyrimidin-4-yl)piperazin-1-yl)methyl)-1-(oxetan-2-ylmethyl)-1H-benzo[d]imidazole-6-carboxylic acid (Compound 10)

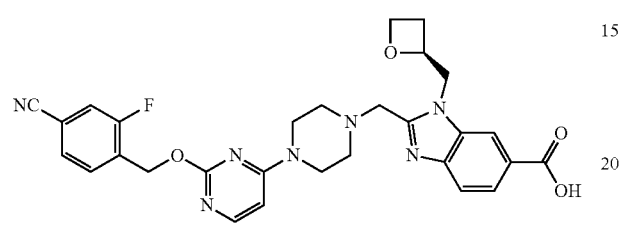

Compound 10

Prepared in analogous manner as for Compound 9
LCMS: [M+H]⁺=558.0, Retention time (10 mM NH₄HCO₃)=1.26 min.
¹H NMR (400 MHz, CDCl₃) δ 8.21-8.20 (brs, 2H), 8.07 (t, J=9.6 Hz, 2H), 7.83 (d, J=8.4 Hz, 1H), 7.68 (t, J=7.6 Hz, 1H), 7.44 (d, J=8 Hz, 1H), 7.35 (d, J=9.2 Hz, 1H), 6.19 (d, J=6.0 Hz, 1H), 5.45 (s, 2H), 5.25-5.23 (m, 1H), 4.69-4.68 (brs, 2H), 4.66-4.60 (m, 1H), 4.39-4.34 (m, 1H), 4.10 (dd, J=13.2 11.2 Hz, 2H), 3.64 (s, 4H), 2.77-2.72 (m, 1H), 2.57 (s, 4H), 2.49-2.40 (m, 2H).

(S)-2-((4-(6-(4-chloro-2-fluorobenzyloxy)pyrazin-2-yl)piperazin-1-yl)methyl)-1-(oxetan-2-ylmethyl)-1h-benzo[d]imidazole-6-carboxylic acid (Compound 11)

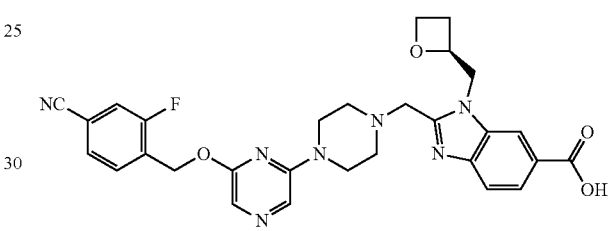

Compound 11

Prepared in analogous manner as for Compound 9
LCMS: [M+H]⁺=566.9; Retention time (10 mM NH₄HCO₃)=1.90 min.
¹H NMR (400 MHz, DMSO-d6) δ 8.28 (s, 1H), 7.87-7.76 (m, 2H), 7.65 (d, J=8.4 Hz, 1H), 7.59-7.43 (m, 3H), 7.31 (dd, J=8.3, 1.7 Hz, 1H), 5.34 (s, 2H), 5.10 (d, J=7.0 Hz, 1H), 4.80 (dd, J=15.3, 7.2 Hz, 1H), 4.66 (d, J=12.7 Hz, 1H), 4.49 (dd, J=13.6, 7.7 Hz, 1H), 4.38 (dt, J=9.0, 5.9 Hz, 1H), 3.99 (d, J=13.6 Hz, 1H), 3.82 (d, J=13.6 Hz, 1H), 3.54-3.53 (brs, 4H), 2.74-2.61 (m, 1H), 2.61-2.53 (m, 4H), 2.50-2.42 (m, 1H).

(S)-2-((4-(6-(4-cyano-2-fluorobenzyloxy)pyrazin-2-yl)piperazin-1-yl)methyl)-1-(oxetan-2-ylmethyl)-1h-benzo[d]imidazole-6-carboxylic acid (Compound 12)

Compound 12

Prepared in analogous manner as for Compound 9
LCMS: [M+H]⁺=558.2; Retention time (10 mM NH₄HCO₃)=1.18 min.
¹H NMR (400 MHz, DMSO-d6) δ 8.28 (s, 1H), 7.90 (d, J=10.4 Hz, 1H), 7.85-7.78 (m, 2H), 7.73-7.71 (m, 2H), 7.65 (d, J=8.4 Hz, 1H), 7.55 (s, 1H), 5.43 (s, 2H), 5.14-5.03 (m, 1H), 4.80 (dd, J=15.2, 7.3 Hz, 1H), 4.65 (d, J=12.7 Hz, 1H), 4.49 (dd, J=13.5, 7.8 Hz, 1H), 4.38 (dt, J=9.0, 5.9 Hz, 1H), 3.98 (d, J=13.6 Hz, 1H), 3.81 (d, J=13.6 Hz, 1H), 3.51-3.50 (brs, 4H), 2.78-2.63 (m, 1H), 2.59-2.51 (m, 4H), 2.44-2.35 (m, 1H).

(S)-2-((4-(1-(4-chloro-2-fluorobenzyl)-1h-pyrrolo[2,3-b]pyridin-6-yl)piperazin-1-yl)methyl)-1-(oxetan-2-ylmethyl)-1h-benzo[d]imidazole-6-carboxylic acid (Compound 13)

Compound 13

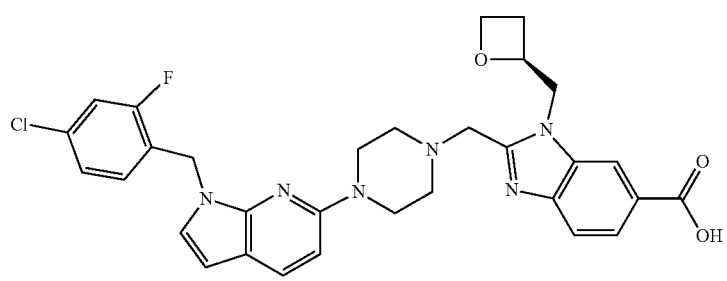

-continued
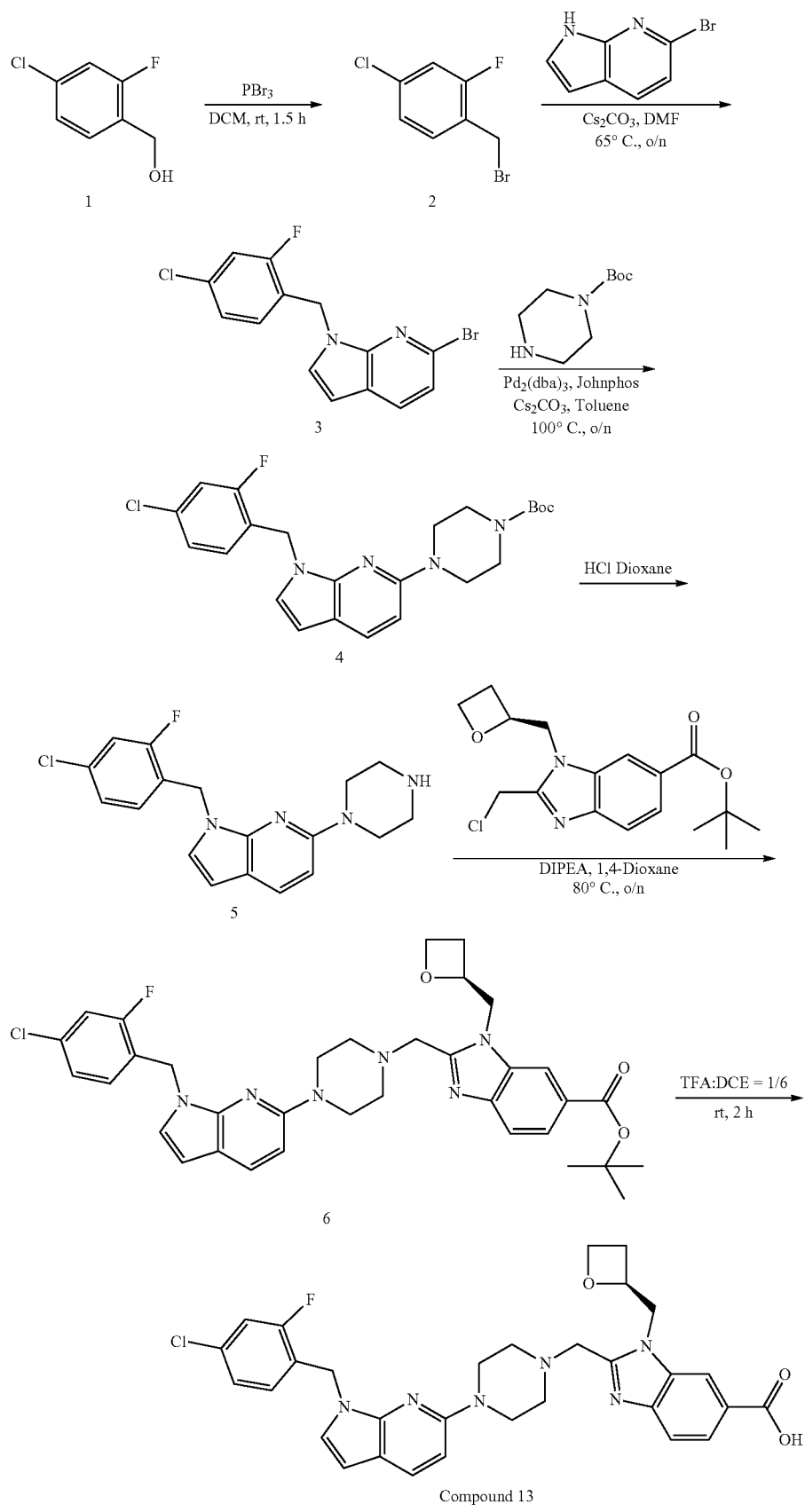
Compound 13

Step 1

To a solution of (4-chloro-2-fluorophenyl) methanol (3.0 g, 18.69 mmol) in DCM (40 mL) was added PBr$_3$ (1.2 mL, 13.1 mmol) at 0° C. The mixture was stirred at RT for 1.5 h. TLC show the reaction was completed. The reaction was quenched by water (20 mL) at 0° C., extracted with DCM (50 mL×3), The combined organics were washed with saturated NaHCO$_3$ and brine (20 mL×3), dried over Na$_2$SO$_4$ and concentrated in vacuum to give the desired product (3.0 g, 73% yield) as yellow oil.

Step 2

To a solution of 1-(bromomethyl)-4-chloro-2-fluorobenzene (1.0 g, 5.08 mmol) in DMF (80 mL) was added Cs$_2$CO$_3$ (5.0 g, 15.3 mmol) and 6-bromo-1 h-pyrrolo[2,3-b]pyridine (1.4 g, 6.1 mmol). The mixture was stirred at 65° C. for overnight. TLC showed the reaction was completed. The reaction was quenched by water (30 mL), extracted with ethyl acetate (50 mL×3), The combined organics were washed with brine (30 mL×3), dried over Na$_2$SO$_4$ and concentrated in vacuum to give crude product, which was purified by silica gel column (PE:EA=20:1) to obtain the desired product (1.0 g, 59% yield) as yellow solid.

Step 3

To a solution of 6-bromo-1-(4-chloro-2-fluorobenzyl)-1 h-pyrrolo[2,3-b]pyridine (1 g, 2.94 mmol, 1.0 eq) in toluene (50 mL) was added tert-butyl piperazine-1-carboxylate (657 mg, 3.53 mmol), Cs$_2$CO$_3$ (2.9 g, 8.9 mmol), Pd$_2$(dba)$_3$ (269 mg, 0.29 mmol) and Johnphos (175 mg, 0.59 mmol). The mixture was stirred at 100° C. for overnight. The reaction mixture was worked up by adding saturated aq. NH$_4$Cl, and extracted with ethyl acetate (100 mL×3). The combined organics were washed with brine (50 mL×3), dried over Na$_2$SO$_4$ and concentrated in vacuum to give crude product, which was purified by silica gel column (PE:EA=20:1) to obtain the desired product (100 mg, 8% yield) as yellow solid. LCMS: [M+H]$^+$=444.1; Retention time (0.01% TFA)= 2.33 min.

Step 4

The solution of tert-butyl 4-(1-(4-chloro-2-fluorobenzyl)-1 h-pyrrolo[2,3-b]pyridin-6-yl)piperazine-1-carboxylate (100 mg, 0.23 mmol) in HCl/dioxane (4 N, 10 mL) was stirred at 25° C. for 0.5 h. The mixture was concentrated to obtain the desired product (60 mg, 80% yield) as white solid. LCMS: [M+H]$^+$=344.7; Retention time (0.01% TFA)=1.49 min.

Step 5

To a solution of 1-(4-chloro-2-fluorobenzyl)-6-(piperazin-1-yl)-1 h-pyrrolo[2,3-b]pyridine (34 mg, 0.01 mmol, 1.1 eq) in 1,4-dioxane (3 mL) was added DIPEA (1 mL, 1 mmol) and tert-butyl (S)-2-(chloromethyl)-1-(oxetan-2-ylmethyl)-1 h-benzo[d]imidazole-6-carboxylate (30 mg, 0.09 mmol), The mixture was stirred at 80° C. overnight. The reaction was purified by Prep-TLC (PE:EA=1:1, R$_f$=0.25), and then purified by Prep-HPLC to obtain the desired product (20 mg, 30% yield) as yellow solid.

LCMS: [M+H]$^+$=645.2; Retention time (10 mM NH$_4$HCO$_3$)=2.00 min.

Step 6

A solution of tert-butyl (S)-2-((4-(1-(4-chloro-2-fluorobenzyl)-1 h-pyrrolo[2,3-b]pyridin-6-yl)piperazin-1-yl) methyl)-1-(oxetan-2-ylmethyl)-1 h-benzo[d]imidazole-6-carboxylate (20 mg, 0.03 mmol) in TFA (1 mL) and DCE (6 mL) was stirred at RT for 2 h. The mixture was neutralized to pH~7 by aqueous ammonia (0.1 mL), and purified by Prep-HPLC to obtain the desired product (14.1 mg, 79.9% yield) as white solid. LCMS: [M+H]$^+$=589.0; Retention time (10 mM NH$_4$HCO$_3$)=1.56 min.

$^1$H NMR (400 MHz, DMSO-d6) δ 8.27 (s, 1H), 7.81 (dd, J=8.4, 1.4 Hz, 1H), 7.73 (d, J=8.7 Hz, 1H), 7.65 (d, J=8.5 Hz, 1H), 7.43 (dd, J=10.0, 1.7 Hz, 1H), 7.24-7.16 (m, 3H), 6.66 (d, J=8.7 Hz, 1H), 6.30 (d, J=3.5 Hz, 1H), 5.33 (s, 2H), 5.10 (dt, J=7.3, 5.0 Hz, 1H), 4.81 (dd, J=15.2, 7.3 Hz, 1H), 4.66 (dd, J=15.2, 2.5 Hz, 1H), 4.49 (dd, J=13.5, 7.9 Hz, 1H), 4.38 (dt, J=9.0, 5.9 Hz, 1H), 3.99 (d, J=13.5 Hz, 1H), 3.81 (d, J=13.4 Hz, 1H), 3.48-3.47 (brs, 4H), 2.77-2.65 (m, 1H), 2.63-2.52 (m, 4H), 2.50-2.43 (m, 1H).

(S)-2-((4-(1-(4-chloro-2-fluorobenzyl)-1 h-indol-6-yl)piperazin-1-yl)methyl)-1-(oxetan-2-ylmethyl)-1 h-benzo[d]imidazole-6-carboxylic acid (Compound 14)

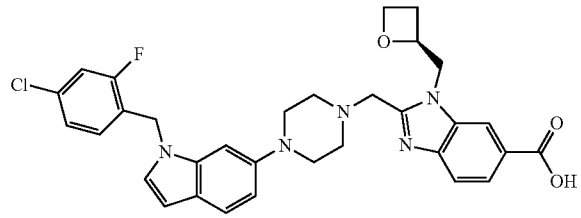

Compound 14

Prepared in analogous manner as for Compound 13

LCMS: [M+H]$^+$=588.2; Retention time (10 mM NH$_4$HCO$_3$)=1.34 min.

$^1$H NMR (400 MHz, DMSO-d6) δ 8.26 (s, 1H), 7.81 (dd, J=8.4, 1.5 Hz, 1H), 7.64 (d, J=8.4 Hz, 1H), 7.45 (dd, J=10.1, 2.0 Hz, 1H), 7.38 (d, J=8.7 Hz, 1H), 7.26-7.18 (m, 2H), 6.97 (dd, J=21.0, 12.8 Hz, 2H), 6.79 (dd, J=8.7, 2.0 Hz, 1H), 6.35 (d, J=3.1 Hz, 1H), 5.39 (s, 2H), 5.15-5.05 (m, 1H), 4.80 (dd, J=15.2, 7.3 Hz, 1H), 4.70-4.61 (m, 1H), 4.48 (dd, J=13.3, 8.1 Hz, 1H), 4.38 (dt, J=9.2, 6.0 Hz, 1H), 4.00 (d, J=13.5 Hz, 1H), 3.82 (d, J=13.4 Hz, 1H), 3.08-3.07 (brs, 5H), 2.75-2.54 (m, 5H).

(S)-2-((4-(6-(4-chloro-2-fluorobenzyloxy)pyridin-2-yl)-1,4-diazepan-1-yl)methyl)-1-(oxetan-2-ylmethyl)-1 h-benzo[d]imidazole-6-carboxylic acid (Compound 15)

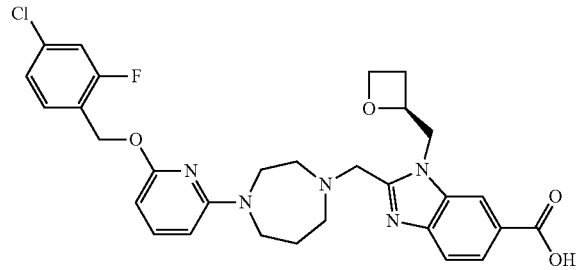

Compound 15

Prepared in analogous manner as for Compound 9

LCMS: [M+H]$^+$=579.8, Retention time (0.01% TFA)= 1.41 min.

$^1$H NMR (400 MHz, DMSO-d6) δ 12.76 (s, 1H), 8.22-8.25 (brs, 1H), 7.79 (d, J=8.8 Hz, 1H), 7.63 (d, J=8.8 Hz, 1H), 7.40-7.45 (m, 1H), 7.25 (dd, J=6.4, 1.6 Hz, 1H), 6.16

(d, J=8 Hz, 1H), 6.01 (d, J=7.6 Hz, 1H), 5.25 (s, 2H), 4.30-4.97 (m, 5H), 3.85-4.05 (m, 2H), 3.53-3.72 (m, 4H), 2.55-2.80 (m, 5H), 2.23-2.35 (m, 1H), 1.65-1.79 (m, 2H).

2-((5-(6-((4-chloro-2-fluorobenzyl)oxy)pyridin-2-yl)-2,5-diazabicyclo[2.2.1]heptan-2-yl)methyl)-1-(((S)-oxetan-2-yl)methyl)-1 h-benzo[d]imidazole-6-carboxylic acid (Compound 16)

Compound 16

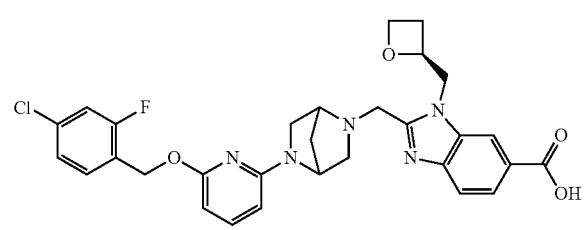

Prepared in analogous manner as for Compound 9
LCMS: [M+H]$^+$=578.2; Retention time (0.01% TFA)= 1.36 min.
$^1$H NMR (400 MHz, MeOD) δ 8.32-8.24 (brs, 1H), 7.99 (dd, J=8.5, 1.3 Hz, 1H), 7.71 (d, J=8.5 Hz, 1H), 7.44 (t, J=7.9 Hz, 2H), 7.17-7.09 (m, 2H), 6.10 (d, J=7.8 Hz, 1H), 6.05 (d, J=7.9 Hz, 1H), 5.42 (d, J=13.0 Hz, 1H), 5.28 (d, J=13.0 Hz, 1H), 5.22-5.15 (m, 1H), 4.78-4.62 (m, 3H), 4.58-4.51 (m, 1H), 4.51-4.37 (m, 2H), 4.32-4.25 (m, 1H), 4.10 (s, 1H), 3.65 (d, J=10.6 Hz, 1H), 3.52 (dd, J=10.6, 1.8 Hz, 1H), 3.19 (dd, J=10.4, 1.6 Hz, 1H), 2.99 (d, J=10.2 Hz, 1H), 2.78-2.64 (m, 1H), 2.49-2.36 (m, 1H), 2.19 (d, J=10.4 Hz, 1H), 2.07 (d, J=10.5 Hz, 1H).

2-((5-(6-((4-chloro-2-fluorobenzyl)oxy)pyridin-2-yl)-2,5-diazabicyclo[2.2.2]octan-2-yl)methyl)-1-(((S)-oxetan-2-yl)methyl)-1 h-benzo[d]imidazole-6-carboxylic acid (Compound 17)

Compound 17

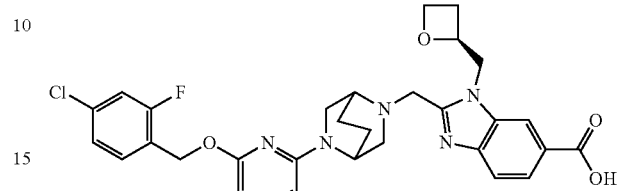

Prepared in analogous manner as for Compound 9
LCMS: [M+H]$^+$=591.6; Retention time (0.01% TFA)= 1.74 min.
$^1$H NMR (400 MHz, MeOD) δ 8.36-8.33 (brs, 1H), 8.05-8.00 (m, 1H), 7.77 (dd, J=8.5, 2.9 Hz, 1H), 7.53-7.43 (m, 2H), 7.21-7.14 (m, 2H), 6.13 (dd, J=12.4, 5.2 Hz, 2H), 5.40-5.31 (m, 2H), 5.25-5.16 (m, 1H), 4.86-4.61 (m, 5H), 4.61-4.52 (m, 1H), 4.40-4.31 (m, 1H), 3.98 (d, J=11.9 Hz, 1H), 3.80-3.68 (brs, 2H), 3.59-3.39 (m, 3H), 2.81-2.70 (m, 1H), 2.54-2.45 (m, 1H), 2.05-1.93 (m, 3H).

(S)-2-((4-(2-((4-chloro-2-fluorobenzyl)oxy)pyrimidin-4-yl)piperidin-1-yl)methyl)-1-(oxetan-2-ylmethyl)-1H-benzo[d]imidazole-6-carboxylic acid (Compound 18)

Compound 18

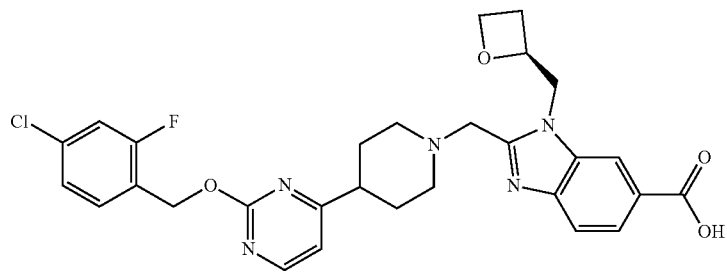

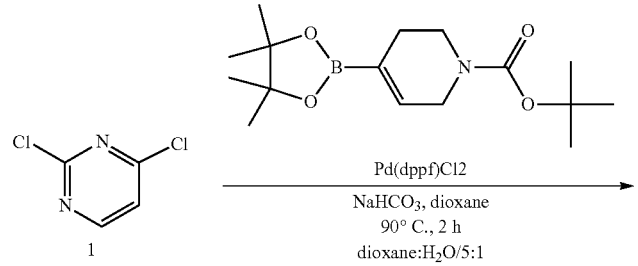

-continued
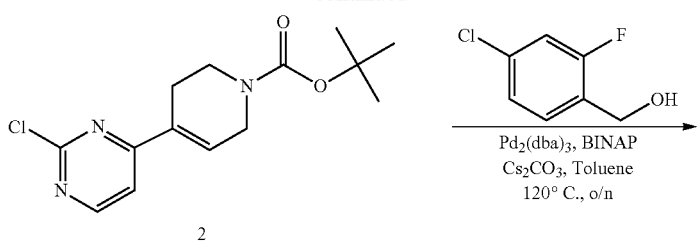
2
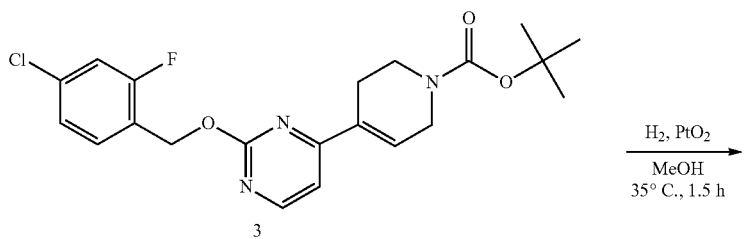
3
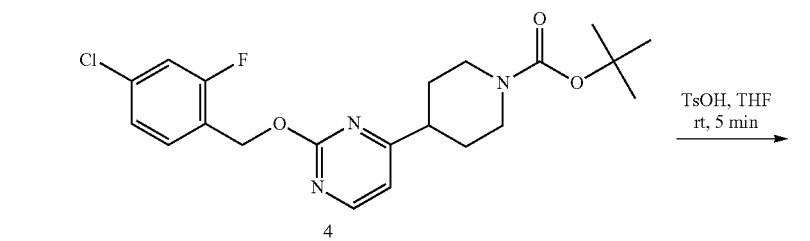
4
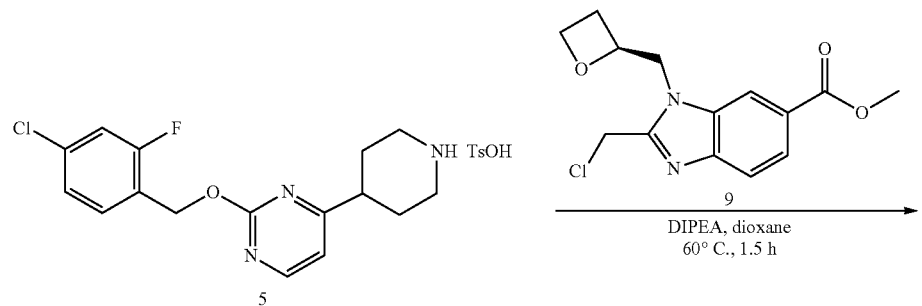
5
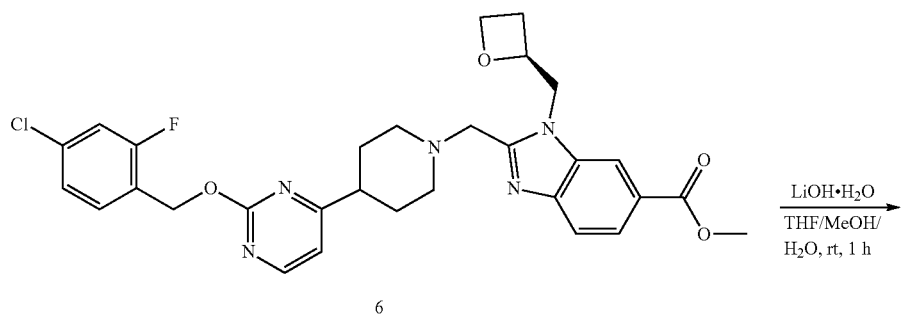
6
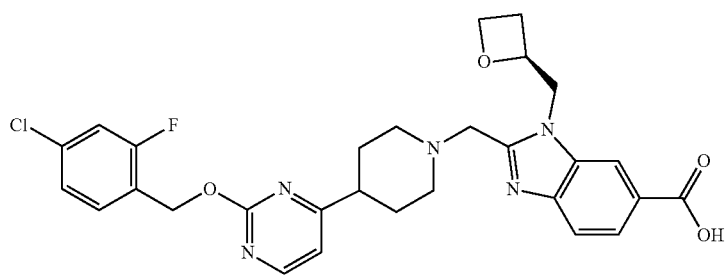
Compound 18

Step 1

To a solution of 2,4-dichloropyrimidine (5 g, 34.01 mmol, 1.0 eq) and tert-butyl 4-(4,4,5,5-tetramethyl-1,3,2-dioxaborolan-2-yl)-5,6-dihydropyridine-1(2H)-carboxylate (11.56 g, 37.4 mmol, 1.1 eq) in dioxane (60 mL) and water (12 mL) was added NaHCO$_3$ (4.29 g, 51.0 mmol, 1.5 eq) and Pd(dppf)Cl$_2$ (497 mg, 3.4 mmol, 0.04 eq). The mixture was stirred under N$_2$ at 90° C. for 2 h. The mixture was filtered and concentrated. The crude product was purified by chromatography on silica gel (PE:EA=10:1) to give tert-butyl 4-(2-chloropyrimidin-4-yl)-5,6-dihydropyridine-1(2H)-carboxylate (7 g, 70%) as pale yellow oil. LCMS: [M+H]$^+$=296.0, Retention time (10 mM NH$_4$HCO$_3$)=1.83 min.

Step 2

To a mixture of tert-butyl 4-(2-chloropyrimidin-4-yl)-5,6-dihydropyridine-1(2H)-carboxylate (4.0 g, 13.56 mmol), (4-chloro-2-fluorophenyl)methanol (2.6 g, 16.27 mmol), BINAP (844 mg, 1.36 mmol) and Cs$_2$CO$_3$ (8.81 g, 27.12 mmol) in toluene (80 mL) was added Pa$_2$(dba)$_3$ (622 mg, 0.68 mmol), the reaction was stirred at 120° C. for 18 h. The mixture was filtered with and concentrated, purified by flash chromatography on silica gel (PE:EA=0%~25%) to give tert-butyl 4-(2-(4-chloro-2-fluorobenzyloxy) pyrimidin-4-yl)-5,6-dihydropyridine-1(2H)-carboxylate (2.7 g, 47%) as pale yellowish oil. LCMS: [M+H]$^+$=420.0, Retention time (10 mM NH$_4$HCO$_3$)=2.22 min.

Step 3

To a solution of tert-butyl 4-(2-((4-chloro-2-fluorobenzyl)oxy)pyrimidin-4-yl)-5,6-dihydropyridine-1(2H)-carboxylate (200 mg, 0.477 mmol, 1.0 eq) in MeOH (8 mL) was added PtO$_2$ (20 mg), the reaction was stirred at RT for 1.5 h. The mixture was filtered and concentrated, purified by Prep-HPLC to give tert-butyl 4-(2-(4-chloro-2-fluorobenzyloxy) pyrimidin-4-yl) piperidine-1-carboxylate (100 mg, 50%) as colorless oil. LCMS: [M+H]$^+$=422.0, Retention time (10 mM NH$_4$HCO$_3$)=2.15 min.

Step 4

To a solution of tert-butyl 4-(2-(4-chloro-2-fluorobenzyloxy) pyrimidin-4-yl) piperidine-1-carboxylate (90 mg, 0.021 mmol) in THF (5 mL) was added p-TsOH (203 mg, 1.07 mmol), the reaction was stirred at RT for 15 min. The mixture was concentrated to give 2-(4-chloro-2-fluorobenzyloxy)-4-(piperidin-4-yl) pyrimidine 4-methylbenzenesulfonic acid salt (96 mg, crude) as yellow solid. The crude was directly used next step without further purification. LCMS: [M+H]$^+$=321.8, Retention time (0.01% TFA)=1.42 min.

Step 5

To a solution of 2-(4-chloro-2-fluorobenzyloxy)-4-(piperidin-4-yl) pyrimidine 4-methylbenzenesulfonic acid salt (96 mg, 0.16 mmol), (S)-methyl 2-(chloromethyl)-3-(oxetan-2-ylmethyl)-3H-benzo[d]imidazole-5-carboxylate (40 mg, 0.14 mmol) and DIPEA (53 mg, 0.41 mmol) in dioxane (12 mL) was stirred at 60° C. for 1.5 h. The mixture was evaporated, diluted with EA (60 mL), washed with water (20 mL×2), dried in Na$_2$SO$_4$, filtered and concentrated. The crude product was purified by Prep-HPLC to give (S)-methyl 2-((4-(2-(4-chloro-2-fluorobenzyloxy) pyrimidin-4-yl) piperidin-1-yl) methyl)-3-(oxetan-2-ylmethyl)-3H-benzo[d]imidazole-5-carboxylate (20 mg, 26%) as pale white solid. LCMS: [M+H]$^+$=580.0, Retention time (10 mM NH$_4$HCO$_3$)=1.96 min.

Step 6

To a solution of (S)-methyl 2-((4-(2-(4-chloro-2-fluorobenzyloxy) pyrimidin-4-yl) piperidin-1-yl) methyl)-3-(oxetan-2-ylmethyl)-3H-benzo[d]imidazole-5-carboxylate (20 mg, 0.0345 mmol) in THF (2 mL), MeOH (2 mL) and H$_2$O (1 mL) was added LiOH·H$_2$O (8 mg, 0.17 mmol). The reaction was stirred at RT for 2 h. The mixture was evaporated, diluted with water (0.5 mL), adjusted to pH=6 with aq. HCl (1 N), the solution was concentrated and purified by Prep-HPLC to give (S)-2-((4-(2-(4-chloro-2-fluorobenzyloxy) pyrimidin-4-yl) piperidin-1-yl) methyl)-3-(oxetan-2-ylmethyl)-3H-benzo[d]imidazole-5-carboxylic acid (9.3 mg, 47%) as white solid. LCMS: [M+H]$^+$=566.0, Retention time (10 mM NH$_4$HCO$_3$)=1.48 min.

$^1$H NMR (400 MHz, DMSO-d6) δ 8.51 (d, J=5.2 Hz, 1H), 8.25-8.24 (brs, 2H), 7.81 (d, J=8.4 Hz, 1H), 7.63-7.55 (m, 2H), 7.51 (dd, J=1.6, 1.6 Hz, 1H), 7.33 (dd, J=1.6, 8.4 Hz, 1H), 7.10 (d, J=5.2 Hz, 1H), 5.39 (s, 2H), 5.09 (dd, J=5.2, 1.6 Hz 1H), 4.82 (dd, J=6.8, 6.8 Hz 1H), 4.67-4.63 (m, 1H), 4.50 (dd, J=7.2, 7.2 Hz 1H), 4.39 (dd, J=6, 5.6 Hz, 1H), 3.96 (d, J=13.2 Hz, 1H), 3.80 (d, J=13.6 Hz, 1H), 3.00 (d, J=10.8 Hz, 1H), 2.87 (d, J=11.2 Hz, 1H), 2.72-2.61 (m, 2H), 2.44 (dd, J=8.4, 1.2 Hz, 1H), 2.26-2.14 (m, 2H), 1.85-1.76 (m, 2H), 1.72-1.64 (m, 2H).

(S)-2-((4-(6-(4-cyano-2-fluorobenzyloxy)pyridin-2-yl)-5,6-dihydropyridin-1(2H)-yl)methyl)-1-(oxetan-2-ylmethyl)-1 h-benzo[d]imidazole-6-carboxylic acid (Compound 19)

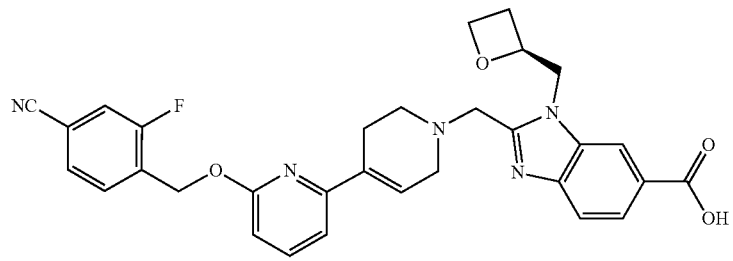

Compound 19

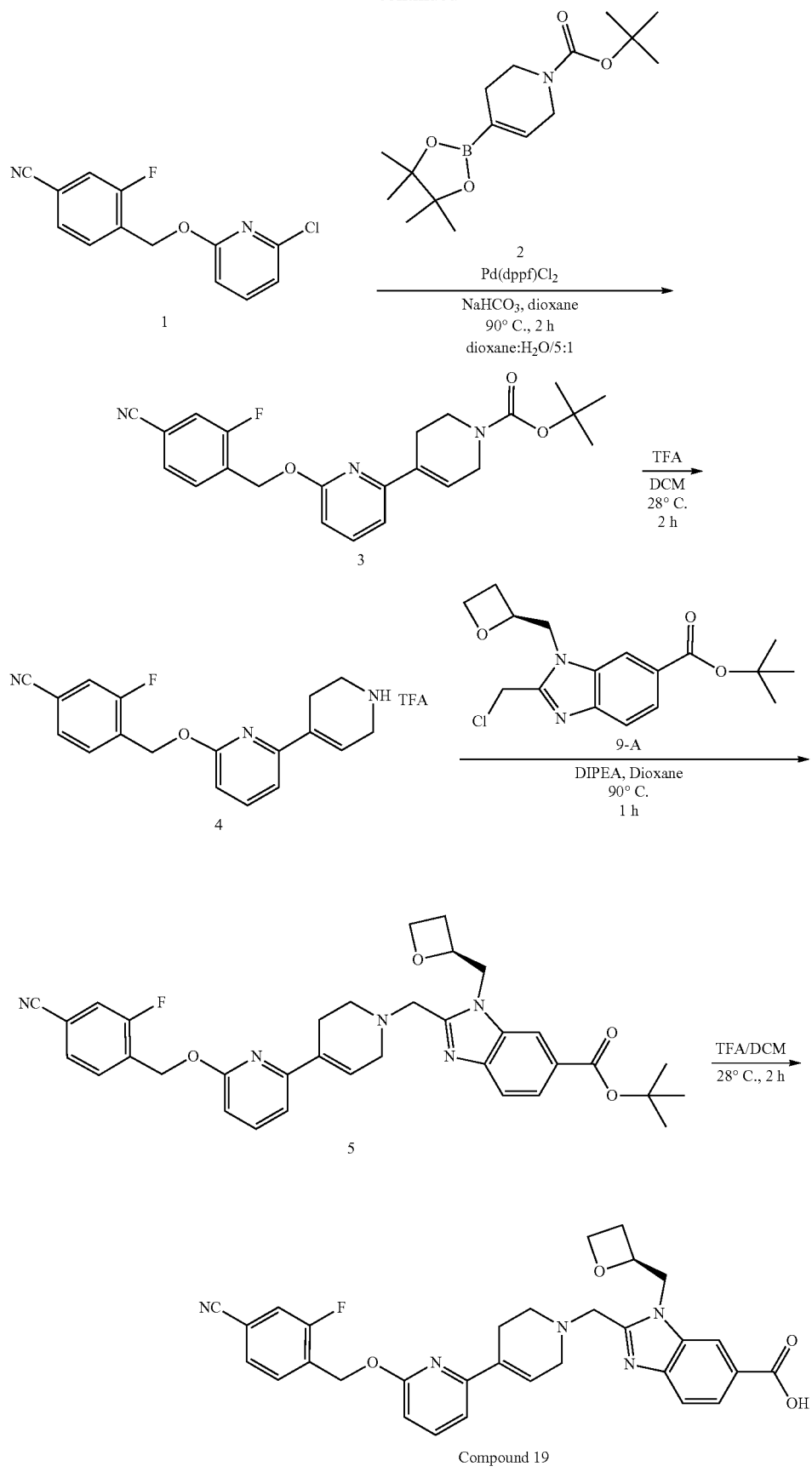

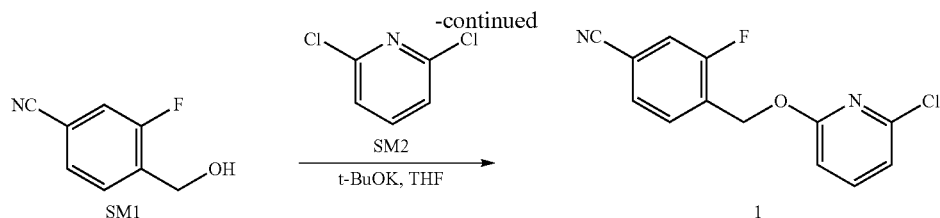

Step 1

To a stirred suspension of t-BuOK (31.3 g, 279.7 mmol) in THF (500 mL) was added 3-fluoro-4-(hydroxymethyl)benzonitrile (28.1 g, 186.5 mmol) portion wise between 10-15° C. The mixture was stirred at 15° C. for 45 min and 2,6-dichloropyridine (23.0 g, 155.4 mmol) was added in several portions to the reaction mixture at 15° C. and the mixture was stirred at 15° C. for 18 h. The mixture was poured into aq. NH₄Cl (1000 mL). EtOAc (1000 mL) was added and the mixture was stirred for 15 min. The mixture was filtered through a pad of Celite. The organic layer was separated and the aq. layer extracted with EtOAc (2×600 mL). The combined organic layers were washed with brine (500 mL). dried over Na₂SO₄, filtered and concentrated under reduced pressure. The crude product was purified by column chromatography on silica gel (PE/EtOAc=10/1) to obtain 4-((6-chloropyridin-2-yloxy)methyl)-3-fluorobenzonitrile (26.0 g, 64% yield) as light yellow solid.

¹H NMR (400 MHz, CDCl3) δ 7.67-7.63 (t, J=7.6 Hz, 1H), 7.59-7.55 (t, J=7.6 Hz, 1H), 7.49-7.46 (dd, J1=8.0 Hz, J2=1.2 Hz, 1H), 7.40-7.37 (dd, J1=9.2 Hz, J2=1.2 Hz, 1H), 6.97-6.95 (d, J=7.6 Hz, 1H), 6.75-6.73 (d, J=8.4 Hz, 1H), 5.48 (s, 2H).

Step 1a

A mixture of 4-[(6-chloro-2-pyridyl)oxymethyl]-3-fluoro-benzonitrile (1 g, 3.81 mmol), tert-butyl 4-(4,4,5,5-tetramethyl-1,3,2-dioxaborolan-2-yl)-3,6-dihydro-2H-pyridine-1-carboxylate (1.29 g, 4.19 mmol), Pd(dppf)Cl₂ (278.3 mg, 0.38 mmol) and NaHCO₃ (479.69 mg, 5.71 mmol) in dioxane (20 mL) and H₂O (4 g, 222.22 mmol) was stirred for 2 h at 90° C. under N₂, until the reaction was complete as indicated by LCMS. The reaction mixture was filtered through a pad of Celite with EtOAc, and the combined organics were concentrated in vacuo, purified by silica gel chromatography (Hexanes/EtOAc=0~11%) to give the desired product tert-butyl 4-[6-[(4-cyano-2-fluoro-phenyl)methoxy]-2-pyridyl]-3,6-dihydro-2H-pyridine-1-carboxylate (1.5 g, 3.63 mmol, 95.4% yield) as pale yellow liquid. LCMS: [M+H]⁺=410.1; Retention time (10 mM NH₄HCO₃)= 2.22 min.

Step 2

To a solution of tert-butyl 4-[6-[(4-cyano-2-fluoro-phenyl)methoxy]-2-pyridyl]-3,6-dihydro-2H-pyridine-1-carboxylate (1.5 g, 3.66 mmol) in DCM (20 mL) was added slowly TFA (7.40 g, 64.90 mmol, 5 mL).

The reaction was stirred at 28° C. for 2 h. After completion of the reaction as determined by LCMS, reaction mixture was concentrated in vacuo to afford 3-fluoro-4-[[6-(1,2,3,6-tetrahydropyridin-4-yl)-2-pyridyl]oxymethyl]benzonitrile (1.8 g, 3.94 mmol) TFA salt as a pale yellowish liquid. The crude product was used directly next step without further purification. LCMS: [M+H]⁺=310.1; Retention time (0.01% TFA)=1.42 min.

Step 3

A mixture of 3-fluoro-4-[[6-(1,2,3,6-tetrahydropyridin-4-yl)-2-pyridyl]oxymethyl]benzonitrile (340 mg, 0.80 mmol), tert-butyl 2-(chloromethyl)-3-[[(2S)-oxetan-2-yl]methyl]benzimidazole-5-carboxylate (225 mg, 670 mmol) and DIPEA (216.42 mg, 1.67 mmol) in Dioxane (10 mL) was stirred for 1 h at 90° C., until the reaction was complete as indicated by LCMS, the reaction mixture was concentrated in vacuo, purified by silica gel chromatography (Hexanes/EtOAc=20:1) to give the desired product tert-butyl 2-[[4-[6-[(4-cyano-2-fluoro-phenyl)methoxy]-2-pyridyl]-3,6-dihydro-2H-pyridin-1-yl]methyl]-3-[[(2S)-oxetan-2-yl]methyl]benzimidazole-5-carboxylate (366 mg, 0.31 mmol) as pale brown solid. LCMS: [M+H]⁺=610.0; Retention time (10 mM NH₄H CO₃)=1.87 min.

Step 4

To a solution of tert-butyl 2-[[4-[6-[(4-cyano-2-fluorophenyl)methoxy]-2-pyridyl]-3,6-dihydro-2H-pyridin-1-yl]methyl]-3-[[(2S)-oxetan-2-yl]methyl]benzimidazole-5-carboxylate (180 mg, 0.30 mmol) in DCM (6 mL) was added slowly TFA (2.96 g, 25.96 mmol, 2 mL) in DCM (2 mL) at 28° C. and stirred for 1 h. After completion of the reaction as judged by LCMS, reaction mixture was concentrated in vacuo, the crude product was purified by Prep-HPLC (10 mM NH₄HCO₃) to afford (S)-2-((4-(6-(4-cyano-2-fluorobenzyloxy)pyridin-2-yl)-5,6-dihydropyridin-1(2H)-yl)methyl)-1-(oxetan-2-ylmethyl)-1 h-benzo[d]imidazole-6-carboxylic acid (54 mg, 33% yield) as a white solid. LCMS: [M+H]⁺=554.2; Retention time (10 mM NH₄HCO₃)=1.42 min.

¹H NMR (400 MHz, DMSO-d6) δ 12.73-12.72 (brs, 1H), 8.27-8.26 (brs, 1H), 7.90 (d, J=10.3 Hz, 1H), 7.81 (dd, J=8.5, 1.5 Hz, 1H), 7.69 (dt, J=13.2, 8.0 Hz, 4H), 7.10 (d, J=7.5 Hz, 1H), 6.85-6.61 (m, 2H), 5.49 (s, 2H), 5.15-5.02 (m, 1H), 4.80 (dd, J=15.2, 7.3 Hz, 1H), 4.71-4.60 (m, 1H), 4.40 (ddt, J=11.9, 8.9, 6.0 Hz, 2H), 4.07 (d, J=13.5 Hz, 1H), 3.91 (d, J=13.5 Hz, 1H), 3.28-3.17 (m, 2H), 2.73 (d, J=2.5 Hz, 2H), 2.70-2.60 (m, 1H), 2.43-2.42 (m, 2H), 2.44-2.34 (m, 1H).

(S)-2-((4-(1-(4-chloro-2-fluorophenethyl)-6-oxo-1,6-dihydropyridazin-3-yl)-5,6-dihydropyridin-1(2H)-yl)methyl)-1-(oxetan-2-ylmethyl)-1 h-benzo[d]imidazole-6-carboxylic acid (Compound 20)

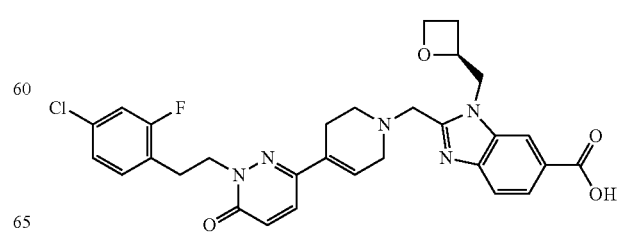

Compound 20

Prepared in analogous manner as for Compound 26
LCMS: [M+H]⁺=578.2, Retention time (0.01% TFA)= 1.34 min.
¹H NMR (400 MHz, MeOD) δ 8.35 (d, J=0.8 Hz, 1H), 8.00 (dd, J=8.5, 1.4 Hz, 1H), 7.74 (dd, J=23.2, 9.2 Hz, 2H), 7.10 (ddt, J=10.1, 8.1, 5.0 Hz, 3H), 6.90 (d, J=9.8 Hz, 1H), 6.41-6.40 (brs, 1H), 5.23 (tt, J=7.2, 3.6 Hz, 1H), 4.90-4.81 (m, 1H), 4.72 (dd, J=15.4, 2.5 Hz, 1H), 4.64 (dd, J=13.9, 7.9 Hz, 1H), 4.52-4.45 (m, 1H), 4.42 (t, J=6.6 Hz, 2H), 4.17 (d, J=13.8 Hz, 1H), 4.06 (d, J=13.7 Hz, 1H), 3.29-3.28 (brs, 2H), 3.14 (t, J=6.5 Hz, 2H), 2.86-2.71 (m, 3H), 2.56-2.47 (m, 1H), 2.36-2.35 (brs, 2H).

(S)-2-((4-(6-(4-chloro-2-fluorobenzyloxy)pyrazin-2-yl)piperidin-1-yl)methyl)-1-(oxetan-2-ylmethyl)-1 h-benzo[d]imidazole-6-carboxylic acid (Compound 21)

Compound 21

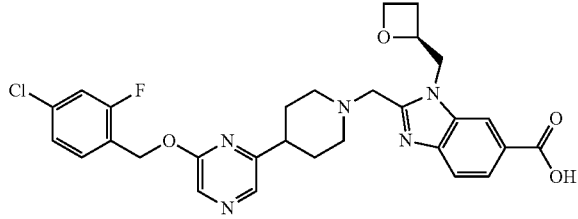

Prepared in analogous manner as for Compound 18
LCMS: [M+H]⁺=566.0; Retention time (10 mM NH₄HCO₃)=1.45 min.
¹H NMR (400 MHz, DMSO-d6) δ 8.28 (s, 1H), 8.18 (d, J=3.4 Hz, 2H), 7.80 (dd, J=8.4, 1.4 Hz, 1H), 7.67-7.54 (m, 2H), 7.49 (dd, J=10.0, 2.0 Hz, 1H), 7.32 (dd, J=8.2, 1.7 Hz, 1H), 5.41 (s, 2H), 5.13 (d, J=7.0 Hz, 1H), 4.81 (dd, J=15.2, 7.3 Hz, 1H), 4.67 (dd, J=15.1, 2.5 Hz, 1H), 4.51-4.31 (m, 2H), 3.97 (d, J=13.5 Hz, 1H), 3.79 (d, J=13.5 Hz, 1H), 3.02 (d, J=11.0 Hz, 1H), 2.87 (d, J=11.3 Hz, 1H), 2.74-2.68 (m, 2H), 2.46-2.38 (m, 1H), 2.33-2.11 (m, 2H), 1.81-1.72 (m, 4H).

(S)-2-((4-(6-(4-cyano-2-fluorobenzyloxy)pyrazin-2-yl)piperidin-1-yl)methyl)-1-(oxetan-2-ylmethyl)-1 h-benzo[d]imidazole-6-carboxylic acid (Compound 22)

Compound 22

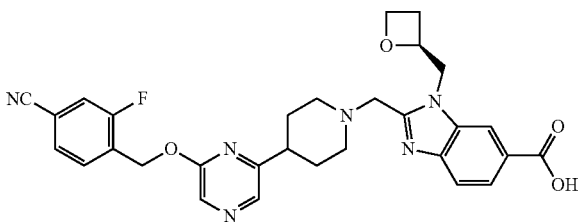

Prepared in analogous manner as for Compound 18
LCMS: [M+H]⁺=557.1; Retention time (10 mM NH₄HCO₃)=1.35 min.
¹H NMR (400 MHz, DMSO-d6) δ 8.28 (d, J=0.9 Hz, 1H), 8.23 (s, 1H), 8.19 (s, 1H), 7.92 (d, J=9.4 Hz, 1H), 7.80 (dd, J=8.4, 1.5 Hz, 1H), 7.78-7.70 (m, 2H), 7.64 (d, J=8.4 Hz, 1H), 5.51 (s, 2H), 5.16-5.04 (m, 1H), 4.81 (dd, J=15.1, 7.2 Hz, 1H), 4.67 (dd, J=15.1, 2.5 Hz, 1H), 4.49 (dd, J=13.6, 7.8 Hz, 1H), 4.39 (dt, J=9.0, 5.9 Hz, 1H), 3.96 (d, J=13.5 Hz, 1H), 3.79 (d, J=13.5 Hz, 1H), 3.00 (d, J=11.0 Hz, 1H), 2.86 (d, J=11.0 Hz, 1H), 2.79-2.63 (m, 2H), 2.48-2.37 (m, 1H), 2.25-2.16 (m, 2H), 1.83-1.60 (m, 4H).

(S)-2-((4-(6-(4-cyano-2-fluorobenzyloxy)pyrazin-2-yl)-5,6-dihydropyridin-1(2H)-yl)methyl)-1-(oxetan-2-ylmethyl)-1 h-benzo[d]imidazole-6-carboxylic acid (Compound 23)

Compound 23

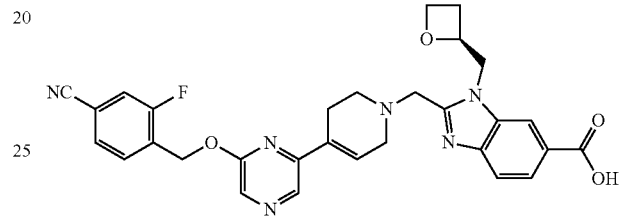

Prepared in analogous manner as for Compound 19
LCMS: [M+H]⁺=555.0; Retention time (10 mM NH₄HCO₃)=1.35 min.
¹H NMR (400 MHz, DMSO-d6) δ 8.39 (s, 1H), 8.29-8.18 (m, 2H), 7.91 (dd, J=10.0, 1.1 Hz, 1H), 7.81 (dd, J=8.4, 1.5 Hz, 1H), 7.78-7.69 (m, 2H), 7.65 (d, J=8.5 Hz, 1H), 6.83 (s, 1H), 5.53 (s, 2H), 5.10-4.98 (m, 1H), 4.79 (dd, J=15.2, 7.2 Hz, 1H), 4.64 (dd, J=15.2, 2.7 Hz, 1H), 4.46 (dd, J=13.6, 7.7 Hz, 1H), 4.36 (dt, J=9.0, 5.9 Hz, 1H), 4.08 (d, J=13.6 Hz, 1H), 3.93 (d, J=13.5 Hz, 1H), 3.28-3.25 (m, 2H), 2.78-2.75 (m, 2H), 2.68-2.63 (m, 1H), 2.53-2.51 (m, 2H), 2.42-2.39 (m, 1H).

(S)-2-((4-(1-(4-chloro-2-fluorobenzyl)-1H-pyrrolo[2,3-b]pyridin-6-yl)piperidin-1-yl)methyl)-1-(oxetan-2-ylmethyl)-1H-benzo[d]imidazole-6-carboxylic acid (Compound 24)

Compound 24

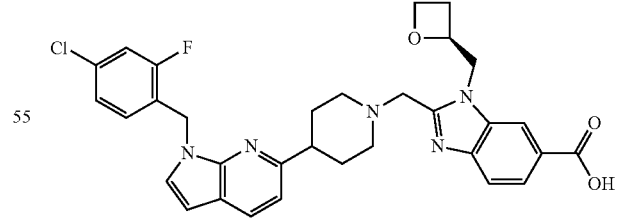

Prepared in analogous manner as for Compound 26
LCMS: [M+H]⁺=588.0; Retention time (10 mM NH₄HCO₃)=1.41 min.
¹H NMR (400 MHz, DMSO-d6) δ 8.29-8.25 (brs, 1H), 7.88 (d, J=8.0 Hz, 1H), 7.80 (dd, J=8.5, 1.4 Hz, 1H), 7.63 (d, J=8.5 Hz, 1H), 7.49 (d, J=3.5 Hz, 1H), 7.45 (dd, J=9.9, 1.9 Hz, 1H), 7.22 (dd, J=8.3, 1.8 Hz, 1H), 7.15 (t, J=8.2 Hz, 1H), 7.02 (d, J=8.1 Hz, 1H), 6.45 (d, J=3.5 Hz, 1H), 5.48 (s, 2H), 5.16-5.08 (m, 1H), 4.81 (dd, J=15.1, 7.4 Hz, 1H), 4.67 (dd, J=12.6 Hz, 1H), 4.52-4.35 (m, 2H), 3.97 (d, J=13.4 Hz, 1H), 3.78 (d, J=13.5 Hz, 1H), 3.02 (d, J=11.6 Hz, 1H), 2.86 (d, J=10.9 Hz, 1H), 2.78-2.67 (m, 2H), 2.47-2.41 (m, 1H), 2.34-2.17 (m, 2H), 1.88-1.73 (m, 4H).

(S)-2-((4-(1-(4-chloro-2-fluorobenzyl)-1 h-pyrrolo[2,3-b]pyridin-6-yl)-5,6-dihydropyridin-1(2H)-yl)methyl)-1-(oxetan-2-ylmethyl)-1 h-benzo[d]imidazole-6-carboxylic acid (Compound 25)

Compound 25

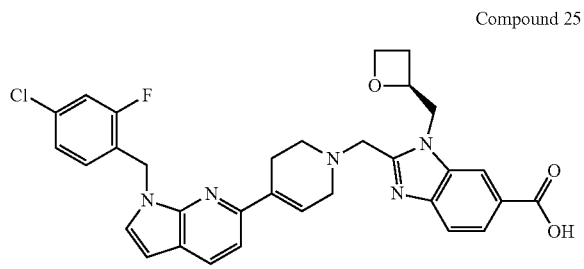 [SMILES: O=C(O)c1ccc2nc(CN3CC=C(c4ccc5ccn(Cc6ccc(Cl)cc6F)c5n4)CC3)n(C[C@@H]3CCO3)c2c1]

Prepared in analogous manner as for Compound 26

LCMS: [M+H]⁺=586.2; Retention time (10 mM NH₄HCO₃)=1.39 min.

¹H NMR (400 MHz, DMSO-d6) δ 8.34 (d, J=0.8 Hz, 1H), 8.01-7.99 (m, 1H), 7.87 (d, J=8.4 Hz, 1H), 7.70 (d, J=8.4 Hz, 1H), 7.37-7.32 (m, 2H), 7.22-7.07 (m, 3H), 6.62 (brs, 1H), 6.47 (d, J=3.6 Hz, 1H), 5.51 (brs, 2H), 5.27-5.24 (m, 1H), 4.88 (d, J=7.2 Hz, 1H), 4.73 (dd, J=4.8, 15.2 Hz, 1H), 4.63-4.60 (m, 1H), 4.50-4.45 (m, 1H), 4.15 (dd, J=13.6, 49.2 Hz, 2H), 3.36-3.33 (m, 2H), 2.94-2.91 (m, 2H), 2.82-2.74 (m, 3H), 2.54-2.47 (m, 1H).

(S)-2-((4-(1-(4-chloro-2-fluorobenzyl)-1 h-indol-6-yl)piperidin-1-yl)methyl)-1-(oxetan-2-ylmethyl)-1 h-benzo[d]imidazole-6-carboxylic acid (Compound 26)

Compound 26

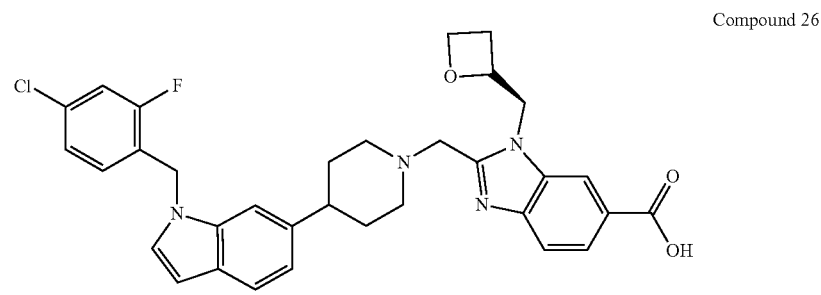

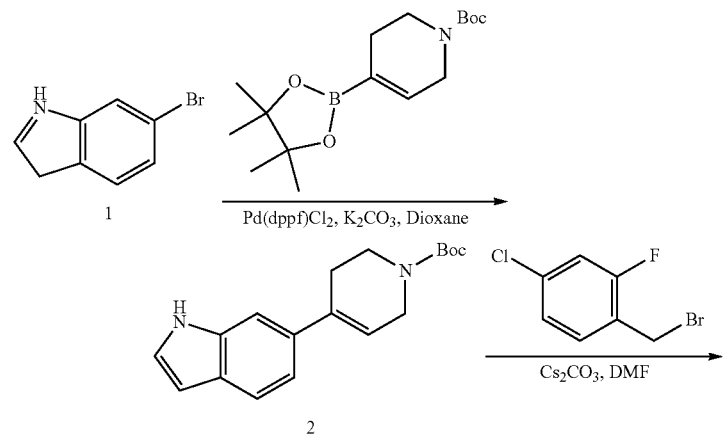

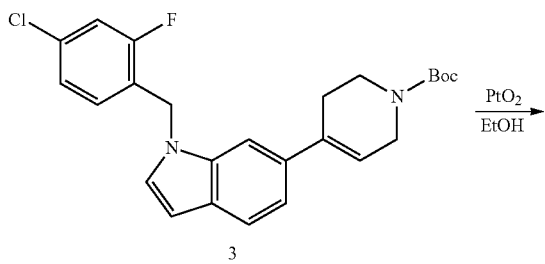

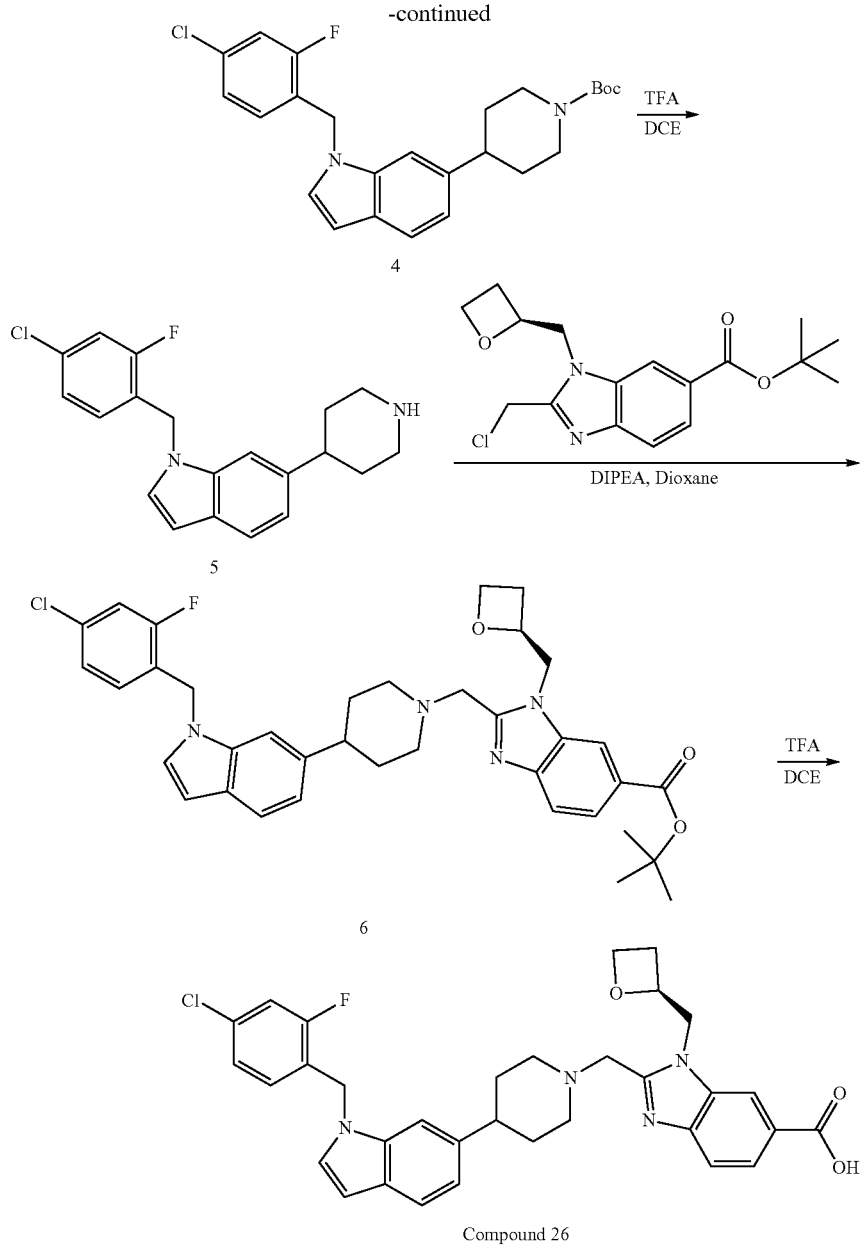

Compound 26

Step 1

To a solution of tert-butyl 4-(4,4,5,5-tetramethyl-1,3,2-dioxaborolan-2-yl)-5,6-dihydropyridine-1(2H)-carboxylate (618.4 mg, 2 mmol) in dioxane (30 mL)/H$_2$O (5 mL) was added 6-bromo-1H-indole (392 mg, 2 mmol), Pd(dppf)Cl$_2$ (100 mg, 10%) and K$_2$CO$_3$ (0.83 g, 6 mmol). The reaction mixture was purged with N$_2$ for three times, heated to 80° C. for 2 h. The mixture was cooled to RT, quenched with H$_2$O (10 mL), extracted by EtOAc (30 mL×3). The combined organics were dried over Na$_2$SO$_4$, concentrated to give tert-butyl 4-(1 h-indol-6-yl)-5,6-dihydropyridine-1(2H)-carboxylate (730 mg, 100% yield) as yellow oil. LCMS: [M−55]$^+$=243.0; Retention time (10 mM NH$_4$HCO$_3$)=1.97 min.

Step 2

To a mixture of 1-(bromomethyl)-4-chloro-2-fluorobenzene (0.55 g, 2.45 mmol) in DMF (20 mL) was added tert-butyl 4-(1 h-indol-6-yl)-5,6-dihydropyridine-1(2H)-carboxylate (0.73 g, 2.45 mmol) and Cs$_2$CO$_3$ (2.4 g, 7.34 mmol). The reaction mixture was stirred at RT for 2 h. The mixture was cooled to RT, quenched with H$_2$O (10 mL), extracted by EtOAc (30 mL×3). The combined organic layer was dried over Na$_2$SO$_4$, concentrated and purified by silica gel column chromatography (PE:EA=30:1) to give tert-butyl 4-(1-(4-chloro-2-fluorobenzyl)-1 h-indol-6-yl)-5,6-dihydropyridine-1(2H)-carboxylate (730 mg, 68% yield) as yellow oil. LCMS: [M+H]$^+$=441.0; purity=62.0% (254 nm); Retention time (10 mM NH$_4$HCO$_3$)=2.45 min.

Step 3

To a mixture of tert-butyl 4-(1-(4-chloro-2-fluorobenzyl)-1 h-indol-6-yl)-5,6-dihydropyridine-1(2H)-carboxylate (200 mg, 0.45 mmol) in EtOH (20 mL) was added PtO$_2$ (20 mg, 10%). The reaction mixture was purged with H$_2$ for three times, and stirred at RT overnight. The mixture was filtered and evaporated to dryness to give tert-butyl 4-(1-(4-chloro-2-fluorobenzyl)-1 h-indol-6-yl) piperidine-1-carboxylate (200 mg, 100% yield) as yellow oil. LCMS: [M−55]=387.0; Retention time (10 mM NH₄HCO₃)=2.42 min.

Step 4

To a mixture of tert-butyl 4-(1-(4-chloro-2-fluorobenzyl)-1 h-indol-6-yl) piperidine-1-carboxylate (200 mg, 0.45 mmol, 1.0 eq) in DCE (15 mL) was added TFA (3 mL, excess). The reaction mixture was stirred at RT for 1 h. The mixture was evaporated to dryness to give 1-(4-chloro-2-fluorobenzyl)-6-(piperidin-4-yl)-1 h-indole (150 mg, 97% yield) as light yellow solid. LCMS: [M+H]⁺=343.0; purity=64.3% (254 nm); Retention time (10 mM NH₄HCO₃)= 2.01 min.

Step 5

To a mixture of (S)-tert-butyl 2-(chloromethyl)-1-(oxetan-2-ylmethyl)-1 h-benzo[d]imidazole-6-carboxylate (80 mg, 0.24 mmol) in Dioxane (20 mL) was added 1-(4-chloro-2-fluorobenzyl)-6-(piperidin-4-yl)-1H-indole (110 mg, 0.32 mmol), DIPEA (125 mg, 0.97 mmol) and NaI (10 mg, 0.067 mmol). The reaction mixture was heated to 80° C. for 2 h. The mixture was evaporated to dryness, the residue was purified by Prep-HPLC to give (S)-tert-butyl 2-((4-(1-(4-chloro-2-fluorobenzyl)-1 h-indol-6-yl)piperidin-1-yl) methyl)-1-(oxetan-2-ylmethyl)-1 h-benzo[d]imidazole-6-carboxylate (11 mg, 9% yield) as white solid. LCMS: [M+H]⁺=643.0; Retention time (10 mM NH₄HCO₃)=2.44 min.

Step 6

To a mixture of (S)-tert-butyl 2-((4-(1-(4-chloro-2-fluorobenzyl)-1 h-indol-6-yl)piperidin-1-yl)methyl)-1-(oxetan-2-ylmethyl)-1 h-benzo[d]imidazole-6-carboxylate (11 mg, 0.017 mmol) in DCE (15 mL) was added TFA (3 mL). The reaction mixture was stirred at RT for 1 h. The mixture was evaporated to dryness. The residue was dissolved in DMF and purified by Prep-HPLC to give (S)-2-((4-(1-(4-chloro-2-fluorobenzyl)-1 h-indol-6-yl)piperidin-1-yl)methyl)-1-(oxetan-2-ylmethyl)-1 h-benzo[d]imidazole-6-carboxylic acid (1.8 mg, 18% yield) as white solid. LCMS: [M+H]⁺= 587.0; Retention time (10 mM NH₄HCO₃)=1.60 min.

¹H NMR (400 MHz, DMSO-d6) δ 8.26 (s, 1H), 7.81-7.78 (t, J=8.0 Hz, 1H), 7.64-7.61 (d, J=8.4 Hz, 1H), 7.48-7.44 (m, 2H), 7.37-7.36 (d, J=2.8 Hz, 1H), 7.32 (s, 1H), 7.23-7.20 (t, J=8.4 Hz, 1H), 7.02-6.97 (t, J=8.8 Hz, 1H), 6.95-6.92 (d, J=8.4 Hz, 1H), 6.43-6.42 (d, J=3.2 Hz, 1H), 5.45 (s, 2H), 5.10-5.09 (d, J=1.6 Hz, 1H), 4.80-4.78 (d, J=7.6 Hz, 1H), 4.69 (s, 1H), 4.51-4.49 (d, J=5.2 Hz, 1H), 4.39-4.37 (t, J=2.8 Hz, 1H), 3.97-3.93 (d, J=13.6 Hz, 1H), 3.80-3.76 (d, J=13.6 Hz, 1H), 3.02-2.85 (m, 6H), 2.68-2.67 (d, J=2.0 Hz, 1H), 2.22-1.64 (m, 4H).

(S)-2-((4-(1-(4-chloro-2-fluorobenzyl)-1 h-indol-6-yl)-5,6-dihydropyridin-1(2H)-yl)methyl)-1-(oxetan-2-ylmethyl)-1 h-benzo[d]imidazole-6-carboxylic acid (Compound 27)

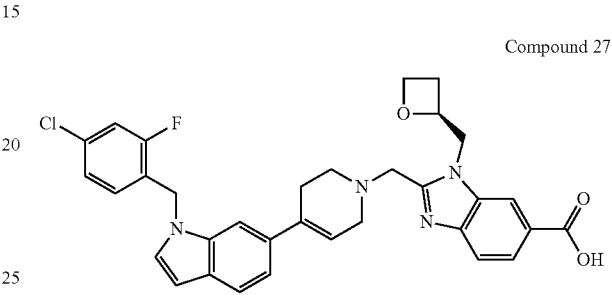

Compound 27

Prepared in analogous manner as for Compound 26

LCMS: [M+H]⁺=585.0; Retention time (10 mM NH₄HCO₃)=1.60 min.

¹H NMR (400 MHz, CDCl₃) δ 8.00-7.97 (d, J=8.8 Hz, 1H), 7.74 (s, 2H), 7.64-7.61 (d, J=8.0 Hz, 1H), 7.18-7.13 (m, 3H), 7.03-7.02 (d, J=5.6 Hz, 2H), 6.77-6.73 (t, J=8.4 Hz, 1H), 6.57-6.56 (d, J=2.8 Hz, 1H), 6.09 (s, 1H), 5.38-5.30 (m, 4H), 5.16-5.13 (d, J=10.8 Hz, 1H), 4.61-4.56 (m, 1H), 4.35 (s, 1H), 2.70-2.68 (d, J=7.2 Hz, 1H), 2.27-2.23 (t, J=8.0 Hz, 2H), 2.05-2.02 (t, J=6.0 Hz, 4H), 1.69-1.60 (m, 4H).

(S)-2-((4-(3-((4-chloro-2-fluorobenzyl)oxy)phenyl)-3,6-dihydropyridin-1(2H)-yl)methyl)-1-(oxetan-2-ylmethyl)-1 h-benzo[d]imidazole-6-carboxylic acid (Compound 28)

Compound 28

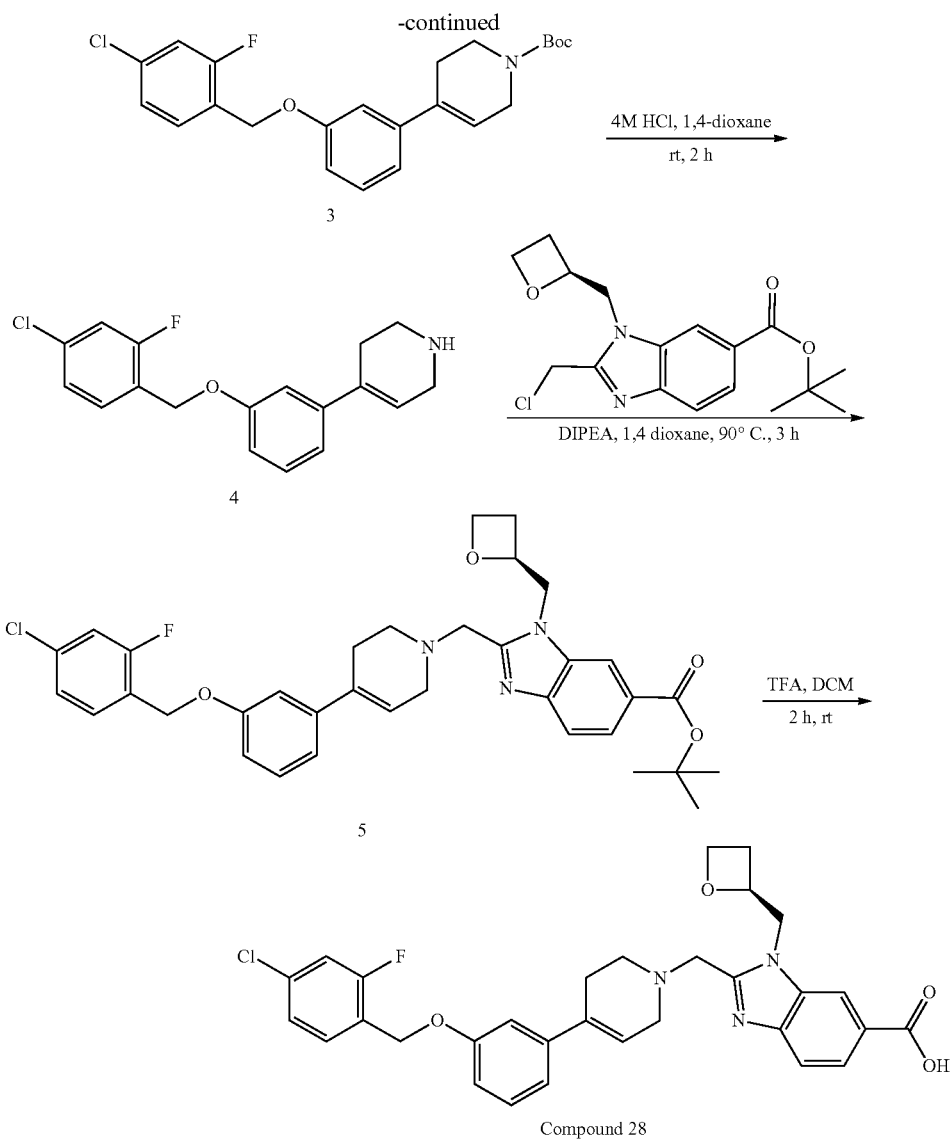

Compound 28

Step 1

To a solution of 3-bromophenol (1.0 g, 5.8 mmol) in 1,4-dioxane (50 mL) was added tert-butyl 4-(4,4,5,5-tetramethyl-1,3,2-dioxaborolan-2-yl)-3,6-dihydropyridine-1(2H)-carboxylate (1.9 g, 6.4 mmol), and $Cs_2CO_3$ (3.8 g, 11.6 mmol) and $Pd(dppf)Cl_2$ (416 mg, 0.58 mmol). The mixture was stirred under nitrogen at 90° C. for 8 h. The mixture was filtered though Celite to give a solution, diluted with water (150 mL) and extracted with ethyl acetate (150 mL×3), the combine organic was washed with brine (150 mL×3), dried and concentrated in vacuo to give crude product. The crude product was purified by Pre-TLC (PE:EA=2:1) to give tert-butyl 4-(3-hydroxyphenyl)-3,6-dihydropyridine-1(2H)-carboxylate (1.51 g, 94% yield) as a white solid. LCMS: $[M+H]^+$=221, Retention time (10 mM $NH_4HCO_3$)=1.81 min.

Step 2

To a solution of tert-butyl 4-(3-hydroxyphenyl)-3,6-dihydropyridine-1(2H)-carboxylate (275 mg, 1.0 mmol) in 1,4-dioxane (10 mL) was added 1-(bromomethyl)-4-chloro-2-fluorobenzene (223 mg, 1.0 mmol) and $Pd_2(dba)_3$ (91.5 mg, 0.1 mmol) and BINAP (62.2 mg, 0.1 mmol). The mixture was stirred under nitrogen at 100° C. for 8 h. The reaction was cooled to rt and the reaction was diluted with water (150 mL), extracted with ethyl acetate (150 mL×3), The combine organic was washed with brine (150 mL×3), dried and concentrated in vacuo to give crude product. Then the crude product was purified by Pre-TLC (PE:EA=3:1) to give tert-butyl 4-(3-((4-chloro-2-fluorobenzyl)oxy)phenyl)-3,6-dihydropyridine-1(2H)-carboxylate (241 mg, 57.8% yield) as a yellow oil. LCMS: $[M+H]^+$=363, Retention time (10 mM $NH_4HCO_3$)=2.04 min.

Step 3

To a solution of tert-butyl 4-(3-((4-chloro-2-fluorobenzyl)oxy)phenyl)-3,6-dihydropyridine-1(2H)-carboxylate (322 mg, 0.77 mmol) in DCM (10 mL) was added HCl/1,4dioxane (1.2 mL). The mixture was stirred at rt for 2 h. The reaction was diluted with water (50 mL) and extracted with ethyl acetate (50 mL×3), The combine organic was washed with brine (50 mL×3), dried and concentrated in vacuo to give crude product, which was purified by Pre-TLC (PE:EA=5:1) to give 4-(3-((4-chloro-2-fluorobenzyl)oxy)phenyl)-1,2,3,6-tetrahydropyridine (198 mg) as a yellow oil. LCMS: [M+H]⁺=318, Retention time (10 mM NH₄HCO₃)= 1.61 min.

Step 4

To a solution of 4-(3-((4-chloro-2-fluorobenzyl)oxy)phenyl)-1,2,3,6-tetrahydropyridine (90 mg, 0.28 mmol) in 1,4-dioxane (10 mL) was added tert-butyl (S)-2-(chloromethyl)-1-(oxetan-2-ylmethyl)-1H-benzo[d]imidazole-6-carboxylate (85 mg, 0.28 mmol) and added DIPEA (0.3 mL, 1.4 mol). The mixture was stirred at 90° C. for 3 h. The reaction was diluted with water (100 mL) and extracted with ethyl acetate (100 mL×3), the combined organic layers were washed with brine (100 mL×3), dried and concentrated in vacuo to give crude product, which was purified by pre-TLC to give tert-butyl (S)-2-((4-(3-((4-chloro-2-fluorobenzyl)oxy)phenyl)-3,6-dihydropyridin-1(2H)-yl)methyl)-1-(oxetan-2-ylmethyl)-1H-benzo[d]imidazole-6-carboxylate (80 mg, 46% yield) as a yellow solid.

LCMS: [M+H]⁺=618, Retention time (10 mM NH₄HCO₃)=2.36 min.

Step 5

To a solution of tert-butyl (S)-2-((4-(3-((4-chloro-2-fluorobenzyl)oxy)phenyl)-3,6-dihydropyridin-1(2H)-yl)methyl)-1-(oxetan-2-ylmethyl)-1H-benzo[d]imidazole-6-carboxylate (80 mg, 0.13 mmol) in DCM (12 mL) was added TFA (2 mL, 26.93 mmol). The mixture was stirred at rt for 3 h. The reaction was concentrated in vacuo to give crude product, which was purified by Pre-HPLC (NH₄HCO₃) to give (S)-2-((4-(3-((4-chloro-2-fluorobenzyl)oxy)phenyl)-3,6-dihydropyridin-1(2H)-yl)methyl)-1-(oxetan-2-ylmethyl)-1H-benzo[d]imidazole-6-carboxylic acid (18.5 mg, 25% yield) as white solid. LCMS: [M+H]⁺=562.0, Retention time (10 mM NH₄HCO₃)=1.40 min.

¹H NMR (400 MHz, MeOD) δ 8.21-8.20 (brs, 1H), 7.97 (dd, J=8.5, 1.4 Hz, 1H), 7.62 (d, J=8.5 Hz, 1H), 7.54 (t, J=8.2 Hz, 1H), 7.25 (ddd, J=6.3, 5.6, 2.0 Hz, 3H), 7.11-7.02 (m, 2H), 6.89 (dd, J=7.3, 1.9 Hz, 1H), 6.13-6.12 (brs, 1H), 5.28 (dd, J=9.4, 5.0 Hz, 1H), 5.13 (s, 2H), 4.92 (d, J=7.1 Hz, 1H), 4.77-4.71 (m, 1H), 4.63 (dd, J=13.4, 8.2 Hz, 1H), 4.53-4.46 (m, 1H), 4.14 (d, J=13.6 Hz, 1H), 4.03 (d, J=13.6 Hz, 1H), 3.25 (d, J=2.4 Hz, 2H), 2.80 (ddd, J=22.5, 12.9, 7.2 Hz, 3H), 2.62-2.48 (m, 3H).

(S)-2-((4-(3-((4-chloro-2-fluorobenzyl)oxy)-4-fluorophenyl)-3,6-dihydropyridin-1(2H)-yl)methyl)-1-(oxetan-2-ylmethyl)-1 h-benzo[d]imidazole-6-carboxylic acid (Compound 29)

Compound 29

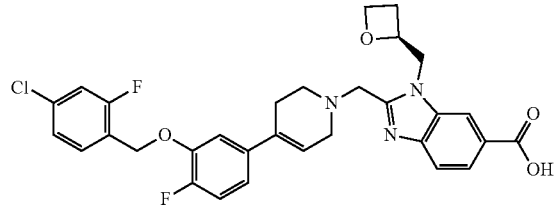

Prepared in analogous manner as for Compound 28
LCMS: [M+H]⁺=580.0, Retention time (10 mM NH₄HCO₃)=1.59 min.

¹H NMR (400 MHz, DMSO-d6) δ 8.26-8.25 (brs, 1H), 7.82 (d, J=7.3 Hz, 1H), 7.69-7.58 (m, 2H), 7.52 (dd, J=9.9, 2.0 Hz, 1H), 7.38-7.30 (m, 2H), 7.17 (dd, J=11.2, 8.6 Hz, 1H), 7.02-7.01 (brs, 1H), 6.16-6.15 (brs, 1H), 5.24 (s, 2H), 5.06 (d, J=4.4 Hz, 1H), 4.79 (dd, J=14.8, 6.9 Hz, 1H), 4.65 (d, J=12.4 Hz, 1H), 4.47 (dd, J=13.2, 7.9 Hz, 1H), 4.39-4.29 (m, 1H), 4.06 (d, J=13.6 Hz, 1H), 3.91 (d, J=13.6 Hz, 1H), 3.19-3.18 (brs, 2H), 2.75-2.74 (brs, 2H), 2.66 (d, J=11.8 Hz, 1H), 2.48-2.45 (m, 2H), 2.41 (d, J=8.4 Hz, 1H).

(S)-2-((4-((4-chloro-2-fluorobenzyl)oxy)-3,6'-dihydro-[2,4'-bipyridin]-1'(2'H)-yl)methyl)-1-(oxetan-2-ylmethyl)-1 h-benzo[d]imidazole-6-carboxylic acid (Compound 30)

Compound 30

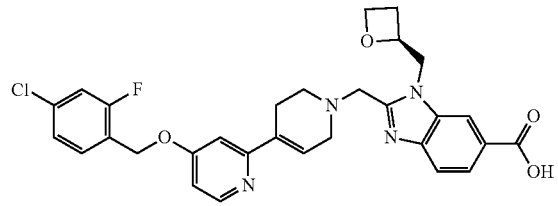

Prepared in analogous manner as for Compound 28
LCMS: [M+H]⁺=563.2, Retention time (10 mM NH₄HCO₃)= 1.29 min.

¹H NMR (400 MHz, MeOD) δ 8.33 (d, J=6.2 Hz, 2H), 8.00 (d, J=8.5 Hz, 1H), 7.70 (d, J=8.4 Hz, 1H), 7.55 (t, J=8.1 Hz, 1H), 7.29 (t, J=8.3 Hz, 2H), 7.15 (d, J=2.2 Hz, 1H), 6.96 (dd, J=5.8, 2.3 Hz, 1H), 6.59-6.58 (brs, 1H), 5.25 (s, 3H), 4.96 (m, 1H), 4.74 (d, J=12.7 Hz, 1H), 4.64 (d, J=5.9 Hz, 1H), 4.48 (dd, J=15.0, 5.9 Hz, 1H), 4.19 (d, J=13.9 Hz, 1H), 4.06 (d, J=13.7 Hz, 1H), 3.31-3.28 (m, 2H), 2.88-2.87 (brs, 2H), 2.78 (m, 1H), 2.67-2.66 (brs, 2H), 2.53 (m, 1H).

(S)-2-((2'-((4-chloro-2-fluorobenzyl)oxy)-3,6-dihydro-[4,4'-bipyridin]-1(2H)-yl)methyl)-1-(oxetan-2-ylmethyl)-1H-benzo[d]imidazole-6-carboxylic acid (Compound 31)

Compound 31

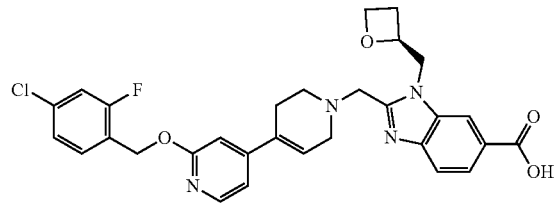

Prepared in analogous manner as for Compound 28
LCMS: [M+H]⁺=563.0; Retention time (10 mM NH₄HCO₃)= 1.54 min.

¹H NMR (400 MHz, DMSO-d6) δ 8.25 (d, J=1.0 Hz, 1H), 8.09 (d, J=5.5 Hz, 1H), 7.81 (dd, J=8.4, 1.5 Hz, 1H), 7.64 (d, J=8.4 Hz, 1H), 7.56 (t, J=8.2 Hz, 1H), 7.47 (dd, J=10.0, 2.0 Hz, 1H), 7.31 (dd, J=8.2, 1.7 Hz, 1H), 7.11 (dd, J=5.5, 1.5 Hz, 1H), 6.86-6.81 (brs, 1H), 6.51-6.45 (m, 1H), 5.37 (s, 2H), 5.05 (dt, J=6.8, 4.4 Hz, 1H), 4.77 (dd, J=15.3, 7.2 Hz, 1H), 4.63 (dd, J=15.2, 2.8 Hz, 1H), 4.50-4.42 (m, 1H), 4.38-4.32 (m, 1H), 4.05 (d, J=13.6 Hz, 1H), 3.91 (d, J=13.5 Hz, 1H), 3.23-3.17 (m, 2H), 2.78-2.70 (m, 2H), 2.69-2.62 (m, 1H), 2.46-2.41 (m, 3H).

(S)-2-((5-((4-chloro-2-fluorobenzyl)oxy)-3,6'-di-hydro-[3,4'-bipyridin]-1'(2'H)-yl)methyl)-1-(oxetan-2-ylmethyl)-1h-benzo[d]imidazole-6-carboxylic acid (Compound 32)

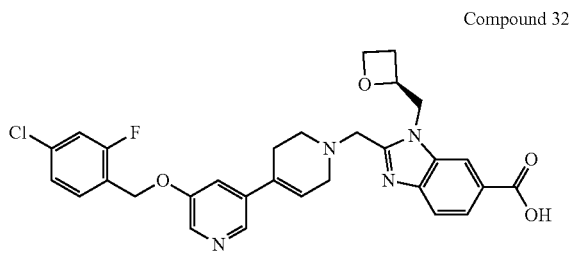 [SMILES: O=C(O)c1ccc2nc(CN3CC=C(c4cncc(OCc5ccc(Cl)cc5F)c4)CC3)n(C[C@@H]3CCO3)c2c1]

Compound 32

Prepared in analogous manner as for Compound 28

LCMS: [M+H]⁺=563.2; Retention time (10 mM $NH_4HCO_3$)=1.26 min.

¹H NMR (400 MHz, DMSO-d6) δ 8.30 (d, J=1.7 Hz, 1H), 8.25 (dd, J=8.9, 1.9 Hz, 2H), 7.81 (dd, J=8.4, 1.5 Hz, 1H), 7.68-7.59 (m, 2H), 7.53-7.48 (m, 2H), 7.35 (dd, J=8.2, 1.8 Hz, 1H), 6.35-6.27 (brs, 1H), 5.24 (s, 2H), 5.10-5.03 (m, 1H), 4.80 (dd, J=15.3, 7.2 Hz, 1H), 4.65 (dd, J=15.2, 2.7 Hz, 1H), 4.51-4.43 (m, 1H), 4.39-4.32 (m, 1H), 4.07 (d, J=13.6 Hz, 1H), 3.92 (d, J=13.5 Hz, 1H), 3.23-3.15 (m, 2H), 2.80-2.71 (m, 2H), 2.70-2.63 (m, 1H), 2.47-2.30 (m, 3H).

(S)-2-((4-(4-(4-chloro-2-fluorobenzyloxy)pyrimidin-2-yl)-5,6-dihydropyridin-1(2H)-yl)methyl)-1-(oxetan-2-ylmethyl)-1h-benzo[d]imidazole-6-carboxylic acid (Compound 33)

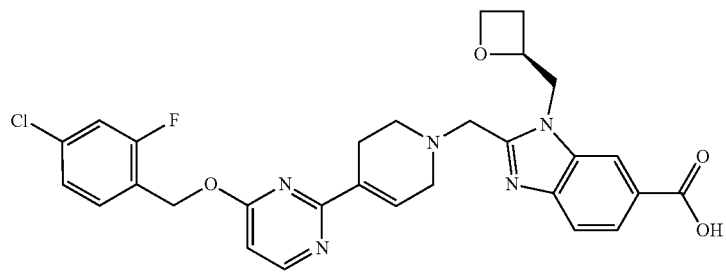

Compound 33

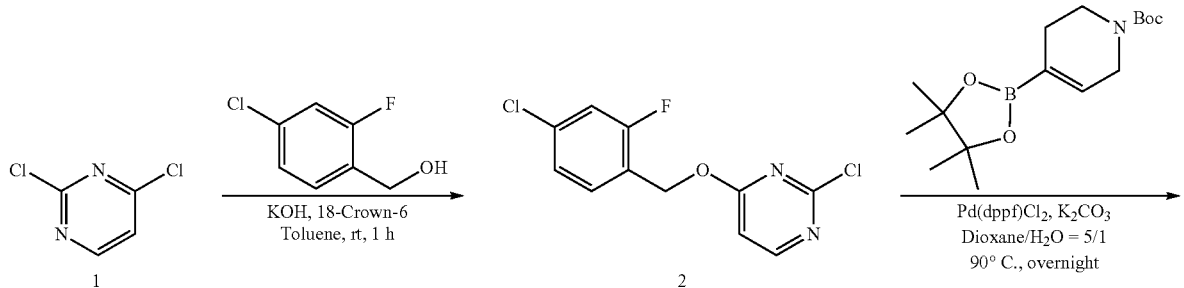

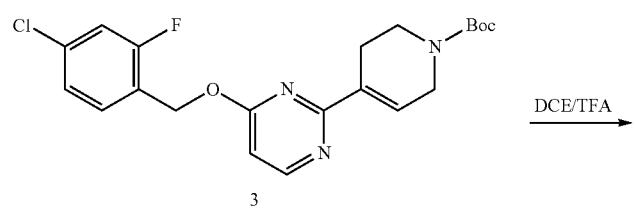

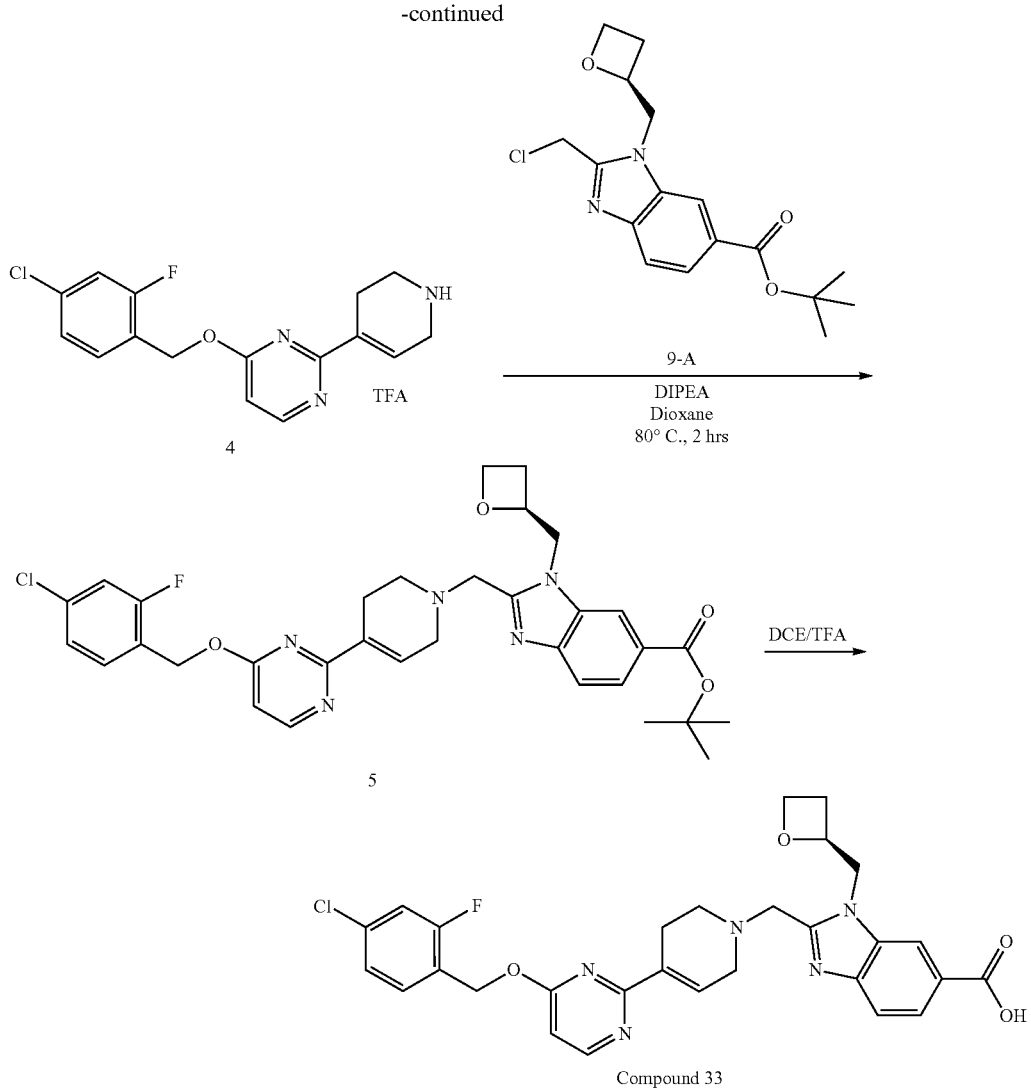

Step 1

To a solution of 2,4-dichloropyrimidine (1.0 g, 6.8 mmol) in toluene (20 mL) were added (4-chloro-2-fluorophenyl)methanol (1.2 g, 7.48 mmol), KOH (419 mg, 7.48 mol) and 18-crown-6 (90 mg, 0.34 mmol), and the resulting solution was stirred at rt for 1 h. The reaction mixture was diluted with EtOAc (100 mL), washed with water (50 mL×3), dried over Na$_2$SO$_4$, filtered and concentrated, and purified by flash column chromatography on silica gel (PE:EA=0%~28%) to give 2-chloro-4-(4-chloro-2-fluorobenzyloxy) pyrimidine (3.6 g, 95%) as a white solid. LCMS: [M+H]$^+$=272.8, Retention time (0.01% TFA)=2.01 min.

Step 2

To a mixture of tert-butyl 4-(4,4,5,5-tetramethyl-1,3,2-dioxaborolan-2-yl)-5,6-dihydropyridine-1(2H)-carboxylate (3.17 g, 10.25 mmol) in Dioxane (100 mL) and H$_2$O (20 mL) was added 2-chloro-4-(4-chloro-2-fluorobenzyloxy)pyrimidine (2.8 g, 10.25 mmol) and Pd(dppf)Cl$_2$ (500 mg, 1.03 mmol) and K$_2$CO$_3$ (4.24 g, 30.76 mmol). The reaction mixture was heated to 90° C. overnight. The mixture was evaporated to dryness, extracted by EtOAc/H$_2$O, the organic layer was evaporated and the residue was purified by silica gel column chromatography (PE/EA=50/1) to give the crude product, then purified by prep-HPLC to give tert-butyl 4-(4-(4-chloro-2-fluorobenzyloxy)pyrimidin-2-yl)-5,6-dihydropyridine-1(2H)-carboxylate (364 mg, 8.5% yield) as an white solid. LCMS: [M+H]$^+$=420.0, Retention time (0.01% TFA)=2.31 min.

Step 3

To a mixture of tert-butyl 4-(4-(4-chloro-2-fluorobenzyloxy)pyrimidin-2-yl)-5,6-dihydropyridine-1(2H)-carboxylate (200 mg, 0.476 mmol) in 1,2-dichloroethane (15 mL) was added TFA (3 mL). The reaction mixture was stirred at rt for 1 h. The mixture was evaporated to dryness to give 4-(4-chloro-2-fluorobenzyloxy)-2-(1,2,3,6-tetrahydropyridin-4-yl)pyrimidine (270 mg, 100% yield) as a light yellow solid. LCMS: [M+H]$^+$=320.0, Retention time (0.01% TFA)=1.74 min.

Step 4

To a mixture of (S)-tert-butyl 2-(chloromethyl)-1-(oxetan-2-ylmethyl)-1H-benzo[d]imidazole-6-carboxylate (140 mg, 0.41 mmol) in Dioxane (20 mL) was added 4-(4-chloro-2-fluorobenzyloxy)-2-(1,2,3,6-tetrahydropyridin-4-yl)pyrimidine (180 mg, 0.41 mmol) and DIPEA (215 mg, 1.66 mmol) and NaI (10 mg). The reaction mixture was heated to 80° C. for 2 h. The mixture was evaporated to dryness, the residue was extracted by EtOAc/H₂O, after removal of solvent to give (S)-tert-butyl 2-((4-(4-(4-chloro-2-fluorobenzyloxy)pyrimidin-2-yl)-5,6-dihydropyridin-1(2H)-yl)methyl)-1-(oxetan-2-ylmethyl)-1H-benzo[d]imidazole-6-carboxylate (86 mg, 58% yield) as an light yellow solid. LCMS: [M+H]⁺=620.0, Retention time (0.01% TFA)= 2.28 min.

Step 5

To a mixture of (S)-tert-butyl 2-((4-(4-(4-chloro-2-fluorobenzyloxy)pyrimidin-2-yl)-5,6-dihydropyridin-1(2H)-yl)methyl)-1-(oxetan-2-ylmethyl)-1H-benzo[d]imidazole-6-carboxylate (86 mg, 0.134 mmol) in 1,2-dichloroethane (15 mL) was added TFA (3 mL). The reaction mixture was stirred at rt for 1 h. The mixture was evaporated to dryness. The residue was dissolved in DMF and purified by prep-HPLC to give (S)-2-((4-(4-(4-chloro-2-fluorobenzyloxy)pyrimidin-2-yl)-5,6-dihydropyridin-1(2H)-yl)methyl)-1-(oxetan-2-ylmethyl)-1H-benzo[d]imidazole-6-carboxylic acid (28 mg, 36% yield) as an white solid.

LCMS: [M+H]⁺=564.0, Retention time (10 mM NH₄HCO₃)=1.48 min.

¹H NMR (400 MHz, DMSO-d6) δ 8.51-8.49 (d, J=5.6 Hz, 1H), 8.26-8.25 (d, J=1.2 Hz, 1H), 7.83-7.80 (dd, J1=8.4 Hz, J2=1.6 Hz, 1H), 7.66-7.64 (d, J=8.0 Hz, 1H), 7.60-7.56 (t, J=8.4 Hz, 1H), 7.50-7.47 (dd, J1=10.0 Hz, J2=2.0 Hz, 1H), 7.33-7.30 (dd, J1=8.4 Hz, J2=2.0 Hz, 1H), 7.17 (s, 1H), 6.82-6.80 (d, J=5.6 Hz, 1H), 5.48 (s, 2H), 5.08-5.05 (dd, J1=7.2 Hz, J2=2.4 Hz, 1H), 4.83-4.77 (dd, J1=15.2 Hz, J2=7.2 Hz, 1H), 4.67-4.62 (dd, J1=15.2 Hz, J2=2.8 Hz, 1H), 4.48-4.44 (m, 1H), 4.39-4.33 (m, 1H), 4.11-4.07 (d, J=13.6 Hz, 1H), 3.95-3.91 (d, J=13.6 Hz, 1H), 3.30-3.26 (m, 2H), 2.76-2.72 (d, J=7.6 Hz, 2H), 2.67-2.63 (m, 1H), 2.59 (s, 2H), 2.44-2.37 (m, 2H).

(S)-2-((4-(6-(4-chloro-2-fluorobenzyloxy)pyrazin-2-yl)-5,6-dihydropyridin-1(2H)-yl)methyl)-1-(oxetan-2-ylmethyl)-1 h-benzo[d]imidazole-6-carboxylic acid (Compound 34)

Compound 34

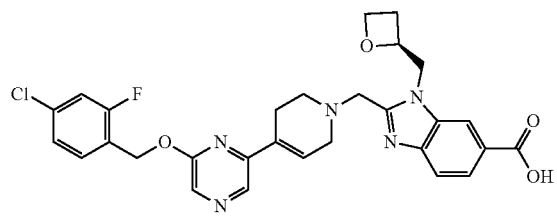

Prepared in analogous manner as for Compound 19
LCMS: [M+H]⁺=564.0; Retention time (10 mM NH₄HCO₃)= 1.51 min.

¹H NMR (400 MHz, DMSO-d6) δ 8.37 (s, 1H), 8.25 (s, 1H), 8.21 (s, 1H), 7.81 (dd, J=8.4, 1.4 Hz, 1H), 7.67-7.56 (m, 2H), 7.50 (dd, J=10.0, 2.0 Hz, 1H), 7.32 (dd, J=8.2, 1.6 Hz, 1H), 6.86-6.85 (brs, 1H), 5.44 (s, 2H), 5.06 (dd, J=14.2, 7.0 Hz, 1H), 4.79 (dd, J=15.2, 7.3 Hz, 1H), 4.69-4.60 (m, 1H), 4.47 (dd, J=13.7, 7.5 Hz, 1H), 4.36 (dt, J=9.0, 5.9 Hz, 1H), 4.08 (d, J=13.6 Hz, 1H), 3.93 (d, J=13.5 Hz, 1H), 3.29-3.21 (m, 2H), 2.79-2.75 (m, 2H), 2.68-2.64 (m, 2H), 2.56-2.55 (brs, 2H), 2.45-2.30 (m, 1H).

(S)-2-((4-(2-((4-chloro-2-fluorobenzyl)oxy)pyrimidin-4-yl)-3,6-dihydropyridin-1(2H)-yl)methyl)-1-(oxetan-2-ylmethyl)-1H-benzo[d]imidazole-6-carboxylic acid (Compound 35)

Compound 35

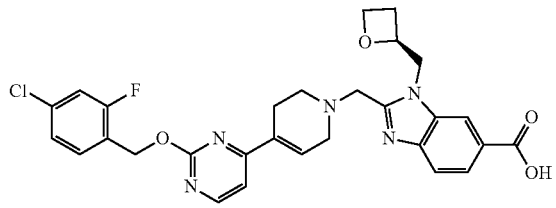

Prepared in analogous manner as for Compound 18

LCMS: [M+H]⁺=564.0, Retention time (10 mM NH₄HCO₃)=1.46 min.

¹H NMR (400 MHz, CDCl₃) δ 8.46 (d, J=5.2 Hz 1H), 8.15-8.14 (brs, 1H), 8.02 (d, J=8.4 Hz, 1H), 7.81 (d, J=8.4 Hz, 1H), 7.48 (dd, J=4.4 8 Hz, 1H), 7.13 (m, 1H), 6.89 (d, J=5.2 Hz, 1H), 6.92-6.91 (brs, 1H), 5.46 (s, 2H), 5.19-5.17 (m, 1H), 4.81-4.74 (m, 1H), 4.72-4.65 (m, 1H), 4.64 (dd, J=8.8 8 Hz, 1H), 4.39-4.36 (m, 1H), 4.35-4.13 (m, 2H), 3.46-3.19 (m, 2H), 3.01-2.84 (m, 1H), 2.74-2.66 (m, 3H), 2.48-2.40 (m, 2H).

(S)-2-((4-(1-((4-chloro-2-fluorobenzyl)oxy)isoquinolin-3-yl)piperazin-1-yl)methyl)-1-(oxetan-2-ylmethyl)-1 h-benzo[d]imidazole-6-carboxylic acid (Compound 36)

Compound 36

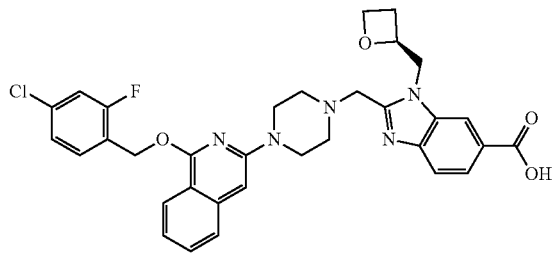

Prepared in analogous manner as for Compound 9

LCMS: [M+H]⁺=616.0; Retention time (10 mM NH₄HCO₃)=1.69 min.

¹H NMR (400 MHz, DMSO-d6) δ 8.29 (s, 1H), 7.94 (d, J=8.3 Hz, 1H), 7.82 (dd, J=8.5, 1.5 Hz, 1H), 7.69-7.63 (m, 2H), 7.62-7.57 (m, 1H), 7.54-7.48 (m, 2H), 7.32 (dd, J=8.2, 1.8 Hz, 1H), 7.20 (m, 1H), 6.52 (s, 1H), 5.55 (s, 2H), 5.17-5.08 (m, 1H), 4.82 (m, 1H), 4.67 (m, 1H), 4.49 (m, 1H), 4.39 (m, 1H), 4.01 (m, 1H), 3.83 (m, 1H), 3.49 (m, 4H), 2.76-2.68 (m, 1H), 2.60 (m, 4H), 2.47-2.40 (m, 1H).

131

(S)-2-((4-(4-(3-chlorophenethyl)-3,4-dihydro-2 h-pyrido[3,2-b][1,4]oxazin-6-yl)-5,6-dihydropyridin-1(2H)-yl)methyl)-1-(oxetan-2-ylmethyl)-1 h-benzo[d]imidazole-6-carboxylic acid (Compound 37)

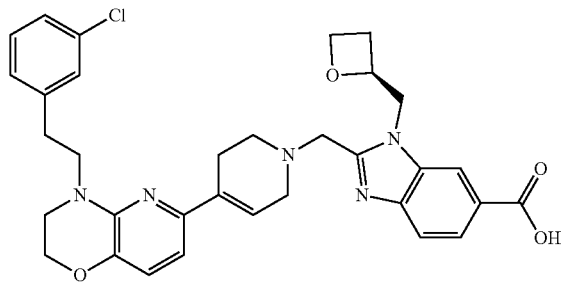

Compound 37

Prepared in analogous manner as for Compound 26
LCMS: [M+H]⁺=600.2; Retention time (0.01% TFA)=1.55 min.

¹H NMR (400 MHz, MeOD) δ 8.31-8.30 (brs, 1H), 7.99 (dd, J=8.5, 1.4 Hz, 1H), 7.69 (d, J=8.5 Hz, 1H), 7.28-7.27 (brs, 1H), 7.26-7.21 (m, 1H), 7.18-7.15 (m, 2H), 6.86 (d, J=8.0 Hz, 1H), 6.65 (d, J=8.0 Hz, 1H), 6.53-6.52 (brs, 1H), 5.27 (d, J=5.0 Hz, 1H), 4.87 (d, J=9.7 Hz, 1H), 4.74 (dd, J=15.4, 2.6 Hz, 1H), 4.63 (dd, J=13.9, 7.8 Hz, 3H), 4.48 (dt, J=9.2, 6.0 Hz, 1H), 4.19 (d, J=13.6 Hz, 1H), 4.14-4.09 (m, 2H), 4.07 (d, J=13.7 Hz, 1H), 3.88-3.78 (m, 2H), 3.45-3.38 (m, 2H), 2.95 (d, J=7.4 Hz, 2H), 2.88 (d, J=5.5 Hz, 2H), 2.83-2.76 (m, 1H), 2.67-2.66 (brs, 2H), 2.56-2.49 (m, 1H).

132

(S)-2-((4-(4-(4-chloro-2-fluorobenzyl)-3-oxo-3,4-dihydro-2 h-pyrido[3,2-b][1,4]oxazin-6-yl)-5,6-dihydropyridin-1(2H)-yl)methyl)-1-(oxetan-2-ylmethyl)-1 h-benzo[d]imidazole-6-carboxylic acid (Compound 38)

Prepared in analogous manner as for Compound 26
LCMS: [M+H]⁺=618.2, Retention time (0.01% TFA)=1.44 min.

¹H NMR (400 MHz, DMSO-d6) δ 8.25 (s, 1H), 7.81 (dd, J=8.4, 1.4 Hz, 1H), 7.65 (d, J=8.5 Hz, 1H), 7.47-7.35 (m, 2H), 7.30-7.12 (m, 3H), 6.48 (s, 1H), 5.24 (s, 2H), 5.08-4.98 (m, 1H), 4.87 (s, 2H), 4.77 (dd, J=15.4, 7.3 Hz, 1H), 4.62 (d, J=12.6 Hz, 1H), 4.45 (dd, J=13.7, 7.7 Hz, 1H), 4.35 (dt, J=9.0, 6.0 Hz, 1H), 4.04 (d, J=13.6 Hz, 1H), 3.88 (d, J=13.4 Hz, 1H), 3.16 (d, J=6.6 Hz, 2H), 2.70 (dd. J=13.3, 8.5 Hz, 2H), 2.64-2.57 (m, 1H), 2.40 (s, 3H).

(S)-2-((6-(6-chloro-3,4-dihydroisoquinolin-2(1H)-yl)-3,6'-dihydro-[2,4'-bipyridin]-1'(2'H)-yl)methyl)-1-(oxetan-2-ylmethyl)-1 h-benzo[d]imidazole-6-carboxylic acid (Compound 39)

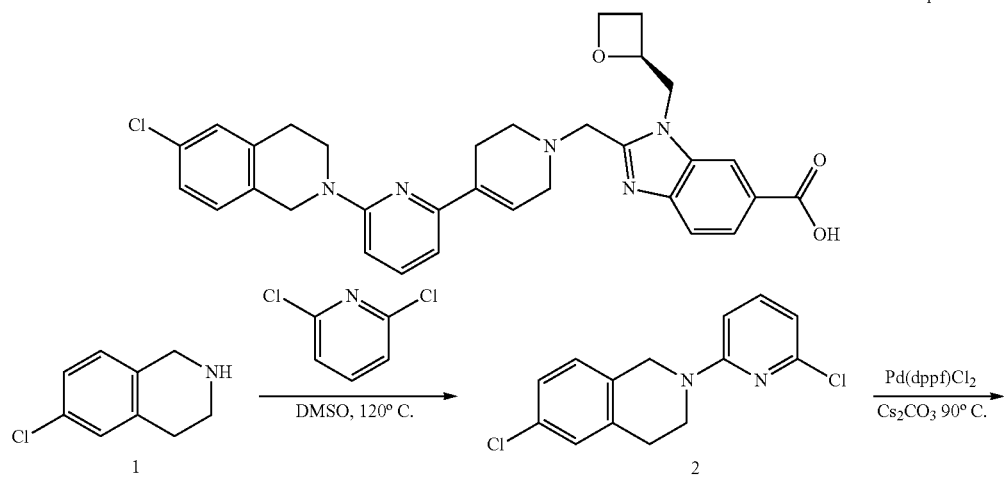

Compound 39

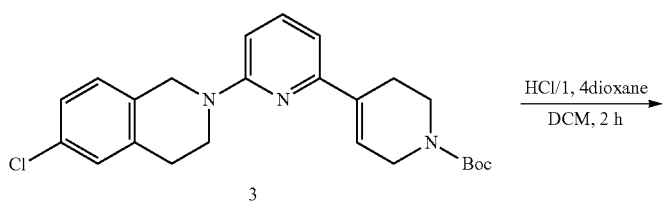

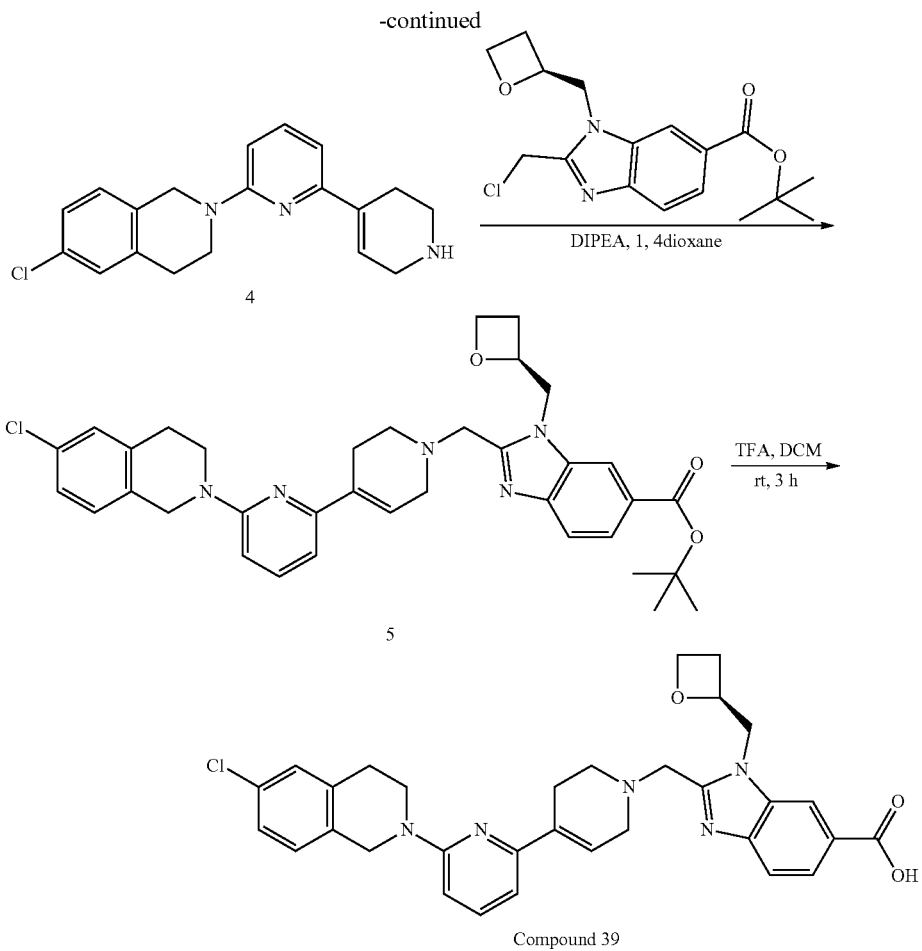

Compound 39

Step 1

To a solution of 6-chloro-1,2,3,4-tetrahydroisoquinoline (500 mg, 30 mmol, 1.0 eq) in DMSO (30 mL) was added 2,6-dichloropyridine (480 mg, 33 mmol), the mixture was stirred at 120° C. for 8 h. The reaction was cooled to rt and concentrated in vacuo to give crude product, the crude product was purified by prep-TLC (PE:EA=5:1) to give 6-chloro-2-(6-chloropyridin-2-yl)-1,2,3,4-tetrahydroisoquinoline (620 mg, 73% yield) as a white solid. LCMS: [M+H]$^+$=279, Retention time (0.01% TFA)=2.23 min.

Step 2

To a solution of 6-chloro-2-(6-chloropyridin-2-yl)-1,2,3,4-tetrahydroisoquinoline (310 mg, 1.11 mmol) in 1,4-dioxane (30 mL) was added tert-butyl 4-(4,4,5,5-tetramethyl-1,3,2-dioxaborolan-2-yl)-3,6-dihydropyridine-1(2H)-carboxylate (413 mg, 1.11 mmol) and Pd(dppf)Cl$_2$ (79 mg, 0.111 mmol) and Cs$_2$CO$_3$ (1.08 g, 3.33 mmol). The mixture was stirred under nitrogen at 90° C. for 8 h. The reaction was diluted with water (100 mL) and extracted with ethyl acetate (100 mL×3), The combine organic was washed with brine (100 mL×3), dried and concentrated in vacuo to give crude product. It was purified by filtration with PE to give tert-butyl 6-(6-chloro-3,4-dihydroisoquinolin-2(1H)-yl)-3',6'-dihydro-[2,4'-bipyridine]-1'(2'H)-carboxylate (157 mg, 54% yield) as a yellow solid.

LCMS: [M+H]$^+$=426, Retention time (0.01% TFA)=2.58 min.

Step 3

To a solution of tert-butyl 6-(6-chloro-3,4-dihydroisoquinolin-2(1H)-yl)-3',6'-dihydro-[2,4'-bipyridine]-1'(2'H)-carboxylate (157 mg, 0.37 mmol) in DCM (16 mL) and added HCl/1,4dioxane (2 mL), the reaction was stirred at rt for 2 h. The reaction was diluted with water (50 mL) and extracted with ethyl acetate (50 mL×3), The combine organic was washed with brine (50 mL×3), dried and concentrated in vacuo to give crude product, which was purified by prep-TLC (PE:EA=5:1) to give 6-chloro-2-(1',2',3',6'-tetrahydro-[2,4'-bipyridin]-6-yl)-1,2,3,4-tetrahydroisoquinoline (65 mg, 54% yield) as a yellow oil. LCMS: [M+H]$^+$=326, Retention time (0.01% TFA)=1.46 min.

Step 4

To a solution of 6-chloro-2-(1',2',3',6'-tetrahydro-[2,4'-bipyridin]-6-yl)-1,2,3,4-tetrahydroisoquinoline (65 mg, 0.2 mmol) in 1,4-dioxane (10 mL) was added tert-butyl-(S)-2-(chloromethyl)-1-(oxetan-2-ylmethyl)-1H-benzo[d]imidazole-6-carboxylate (66 mg, 0.2 mmol) and added DIPEA (0.1 mL, 1 mol).

The mixture was stirred at 90° C. for 3 h. The reaction was diluted with water (50 mL) and extracted with ethyl acetate (50 mL×3), The combine organic was washed with brine (50 mL×3), dried and concentrated in vacuo to give crude product, which was purified by prep-TLC (PE:PA=3:1) to give tert-butyl (R)-2-((6-(6-chloro-3,4-dihydroisoquinolin-2 (1H)-yl)-3',6'-dihydro-[2,4'-bipyridin]-1'(2'H)-yl)methyl)-1-(oxetan-2-ylmethyl)-1H-benzo[d]imidazole-6-carboxylate (45 mg, 47% yield) as a yellow solid. LCMS: [M+H]$^+$=626, Retention time (0.01% TFA)=2.13 min.

Step 5

To a solution of tert-butyl (S)-2-((6-(6-chloro-3,4-dihydroisoquinolin-2(1H)-yl)-3',6'-dihydro-[2,4'-bipyridin]-1'(2'H)-yl)methyl)-1-(oxetan-2-ylmethyl)-1H-benzo[d]imidazole-6-carboxylate (45 mg, 0.072 mmol) in DCM (8 mL) was added TFA (2 mL, 26.93 mmol). The mixture was stirred at rt for 3 h. The reaction was concentrated in vacuo to give crude product, which was purified by prep-HPLC to give(S)-2-((6-(6-chloro-3,4-dihydroisoquinolin-2(1H)-yl)-3',6'-dihydro-[2,4'-bipyridin]-1'(2'H)-yl)methyl)-1-(oxetan-2-ylmethyl)-1H-benzo[d]imidazole-6-carboxylic acid (5.4 mg, 13% yield) as yellow solid. LCMS: [M+H]$^+$=570.2, Retention time (0.01% TFA)=1.59 min.

$^1$H NMR (400 MHz, MeOD) δ 8.35-8.34 (brs, 1H), 8.00 (d, J=8.4 Hz, 1H), 7.71 (d, J=8.7 Hz, 1H), 7.53 (t, J=7.9 Hz, 1H), 7.21 (t, J=6.9 Hz, 3H), 6.81 (d, J=7.6 Hz, 1H), 6.72 (d, J=8.5 Hz, 1H), 6.67-6.66 (brs, 1H), 5.26-5.25 (m, 1H), 4.89-4.88 (brs, 1H), 4.74 (d, J=17.9 Hz, 1H), 4.69 (s, 2H), 4.64 (d, J=5.9 Hz, 1H), 4.48 (d, J=9.3 Hz, 1H), 4.21 (d, J=13.6 Hz, 1H), 4.09 (d, J=13.6 Hz, 1H), 3.88 (t, J=6.0 Hz, 2H), 3.31-3.25 (m, 2H), 2.97-2.88 (m, 4H), 2.78-2.77 (brs, 1H), 2.71-2.70 (brs, 2H), 2.53-2.52 (brs, 1H).

(S)-2-((4-(3-(4-chloro-2-fluorobenzyloxy)-2-fluorophenyl)-5,6-dihydropyridin-1(2H)-yl)methyl)-1-(oxetan-2-ylmethyl)-1h-benzo[d]imidazole-6-carboxylic acid (Compound 40)

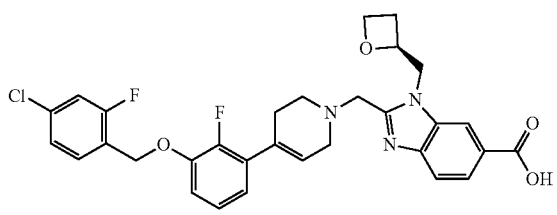

Compound 40

Prepared in analogous manner as for 28

LCMS: [M+H]$^+$=580.1; Retention time (10 mM NH$_4$HCO$_3$)=1.41 min.

$^1$H NMR (400 MHz, DMSO-d6) δ 8.25 (s, 1H), 7.81 (d, J=8.5 Hz, 1H), 7.68-7.55 (m, 2H), 7.51 (dd, J=10.0, 1.8 Hz, 1H), 7.35 (d, J=8.1 Hz, 1H), 7.17 (t, J=7.6 Hz, 1H), 7.08 (t, J=8.0 Hz, 1H), 6.91 (t, J=6.7 Hz, 1H), 5.94-5.93 (brs, 1H), 5.18 (s, 2H), 5.07 (d, J=4.7 Hz, 1H), 4.78 (dd, J=14.9, 7.2 Hz, 1H), 4.65 (d, J=13.9 Hz, 1H), 4.47 (dd, J=14.0, 7.4 Hz, 1H), 4.36 (dd, J=14.7, 5.8 Hz, 1H), 4.06 (d, J=13.6 Hz, 1H), 3.90 (d, J=13.6 Hz, 1H), 3.24-3.08 (m, 2H), 2.74-2.62 (m, 3H), 2.46-2.38 (m, 3H).

(S)-2-((4-(3-(4-chloro-2-fluorobenzyloxy)-4,5-difluorophenyl)-5,6-dihydropyridin-1(2H)-yl)methyl)-1-(oxetan-2-ylmethyl)-1 h-benzo[d]imidazole-6-carboxylic acid (Compound 41)

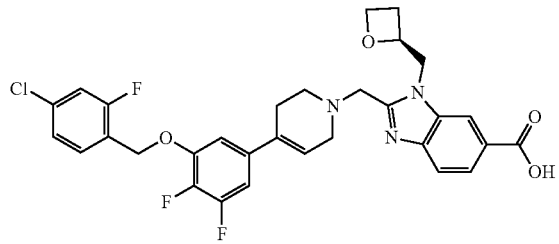

Compound 41

Prepared in analogous manner as for Compound 28

LCMS: [M+H]$^+$=598.0; Retention time (10 mM NH$_4$HCO$_3$)= 1.64 min.

$^1$H NMR (400 MHz, DMSO-d6) δ 8.24 (s, 1H), 7.81 (dd, J=8.4, 1.4 Hz, 1H), 7.62 (dd, J=14.9, 8.2 Hz, 2H), 7.53 (dd, J=10.0, 1.9 Hz, 1H), 7.36 (dd, J=8.2, 1.7 Hz, 1H), 7.19 (d, J=6.8 Hz, 1H), 7.10 (dd, J=11.8, 6.7 Hz, 1H), 6.26 (s, 1H), 5.29 (s, 2H), 5.11-5.00 (m, 1H), 4.79 (dd, J=15.2, 7.2 Hz, 1H), 4.64 (d, J=12.7 Hz, 1H), 4.47 (dd, J=13.6, 7.7 Hz, 1H), 4.36 (dt, J=9.0, 6.0 Hz, 1H), 4.06 (d, J=13.5 Hz, 1H), 3.91 (d, J=13.5 Hz, 1H), 3.25-3.10 (m, 2H), 2.79-2.58 (m, 3H), 2.47-2.31 (m, 3H).

(S)-2-((4-(3-((4-chloro-2-fluorobenzyl)oxy)-5-fluorophenyl)-3,6-dihydropyridin-1(2H)-yl)methyl)-1-(oxetan-2-ylmethyl)-1 h-benzo[d]imidazole-6-carboxylic acid (Compound 42)

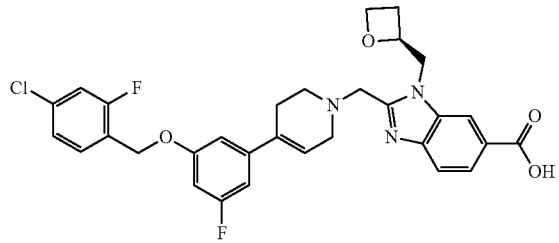

Compound 42

Prepared in analogous manner as for Compound 28

LCMS: [M+H]$^+$=580.2; Retention time (10 mM NH$_4$HCO$_3$)=1.41 min.

$^1$H NMR (400 MHz, CD$_3$OD) δ 8.32 (s, 1H), 7.99 (dd, J=8.5, 1.4 Hz, 1H), 7.69 (d, J=8.5 Hz, 1H), 7.53 (t, J=8.2 Hz, 1H), 7.29-7.24 (m, 2H), 6.89 (s, 1H), 6.81 (d, J=10.1 Hz, 1H), 6.69 (d, J=10.5 Hz, 1H), 6.19 (s, 1H), 5.28-5.21 (m, 1H), 5.13-5.12 (brs, 2H), 4.88 (d, J=7.1 Hz, 1H), 4.73 (dd, J=15.3, 2.5 Hz, 1H), 4.64 (dd, J=13.9, 7.8 Hz, 1H), 4.47 (dt, J=9.0, 5.9 Hz, 1H), 4.16 (d, J=13.6 Hz, 1H), 4.05 (d, J=13.7 Hz, 1H), 3.22 (dd, J=31.9, 14.1 Hz, 2H), 2.90-2.81 (m, 2H), 2.81-2.72 (m, 1H), 2.46-2.60 (m, 3H).

(S)-2-((4-(5-((4-chloro-2-fluorobenzyl)oxy)-2-fluorophenyl)-3,6-dihydropyridin-1(2H)-yl)methyl)-1-(oxetan-2-ylmethyl)-1H-benzo[d]imidazole-6-carboxylic acid (Compound 43)

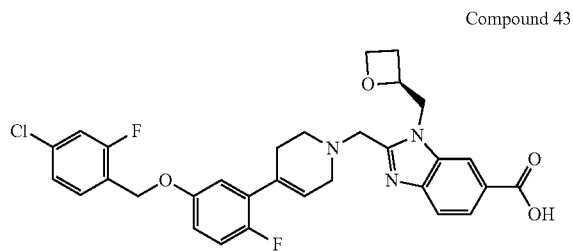 [SMILES: O=C(O)c1ccc2nc(CN3CC=C(c4cc(OCc5ccc(Cl)cc5F)ccc4F)CC3)n(C[C@@H]3CCO3)c2c1]

Compound 43

Prepared in analogous manner as for Compound 28

LCMS: [M+H]$^+$=580.0, Retention time (10 mM NH$_4$HCO$_3$)=1.61 min.

$^1$H NMR (400 MHz, DMSO-d6) δ 8.26-8.25 (brs, 1H), 7.82 (dd, J=1.6 6.8 Hz, 1H), 7.66 (d, J=8.4 Hz, 1H), 7.60 (dd, J=8 8.4 Hz, 1H), 7.51 (dd, J=2 8 Hz, 1H), 7.34 (dd, J=1.6 6.4 Hz, 1H), 7.13 (dd, J=9.2 1.6 Hz, 1H), 6.97-6.91 (m, 2H), 5.99-5.98 (brs, 1H), 5.10 (s, 2H), 5.08 (dd, J=2 4.8 Hz, 1H), 4.82 (dd, J=7.2 8 Hz, 1H), 4.67 (dd, J=2.4 12.8 Hz, 1H), 4.48 (dd, J=5.6 8 Hz, 1H), 4.38-4.35 (m, 1H), 4.07 (d, J=13.2 Hz, 1H), 3.92 (d, J=13.6 Hz, 1H), 3.19 (dd, J=2 3.6 Hz, 2H), 2.75-2.723 (m, 2H), 2.69-2.65 (m, 1H), 2.44-2.38 (m, 3H).

(S)-2-((6-((4-chlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 44)

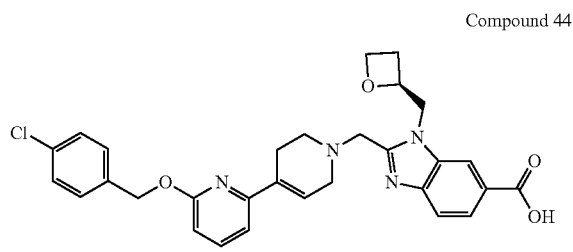 [SMILES: O=C(O)c1ccc2nc(CN3CC=C(c4cccc(OCc5ccc(Cl)cc5)n4)CC3)n(C[C@@H]3CCO3)c2c1]

Compound 44

Prepared in analogous manner as for Compound 19

LCMS: [M+H]$^+$=545.0; Retention time (10 mM NH4HCO3)=1.55 min.

$^1$H NMR (400 MHz, DMSO-d6) δ 8.28-8.25 (brs, 1H), 7.81 (dd, J=8.4, 1.5 Hz, 1H), 7.71-7.64 (m, 2H), 7.47 (d, J=8.5 Hz, 2H), 7.42 (d, J=8.5 Hz, 2H), 7.07 (d, J=7.4 Hz, 1H), 6.73 (d, J=8.1 Hz, 2H), 5.36 (s, 2H), 5.10-5.03 (m, 1H), 4.80 (dd, J=15.2, 7.3 Hz, 1H), 4.65 (dd, J=15.2, 2.5 Hz, 1H), 4.50-4.43 (m, 1H), 4.40-4.33 (m, 1H), 4.07 (d, J=13.5 Hz, 1H), 3.91 (d, J=13.5 Hz, 1H), 3.33-3.26 (m, 1H), 3.26-3.12 (m, 2H), 2.78-2.69 (m, 2H), 2.69-2.61 (m, 1H), 2.49-2.31 (m, 2H).

(S)-1-(oxetan-2-ylmethyl)-2-((4-(6-((6-(trifluoromethyl)pyridin-3-yl)methoxy)pyridin-2-yl)-5,6-dihydropyridin-1(2H)-yl)methyl)-1h-benzo[d]imidazole-6-carboxylic acid (Compound 45)

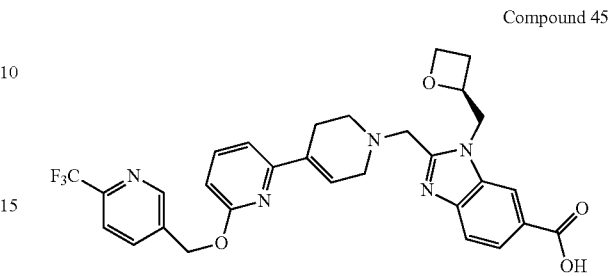

Compound 45

Prepared in analogous manner as for Compound 19

LCMS: [M+H]$^+$=580.0, Retention time (10 mM NH$_4$HCO$_3$)=1.48 min.

$^1$H NMR (400 MHz, DMSO-d6) δ 8.86 (s, 1H), 8.26 (s, 1H), 8.14-8.12 (d, J=8.0 Hz, 1H), 7.92-7.89 (d, J=8.0 Hz, 1H), 7.83-7.80 (dd, J1=8.4 Hz, J2=1.6 Hz, 1H), 7.72-7.64 (m, 2H), 7.10-7.08 (d, J=7.2 Hz, 1H), 6.79-6.77 (d, J=8.0 Hz, 1H), 6.73 (s, 1H), 5.53 (s, 2H), 5.07-5.04 (q, 1H), 4.82-4.76 (m, 1H), 4.66-4.62 (t, J=2.0 Hz, 1H), 4.48-4.43 (m, 1H), 4.38-4.32 (m, 1H), 4.08-4.05 (d, J=13.2 Hz, 1H), 3.93-3.89 (d, J=13.2 Hz, 1H), 3.28-3.21 (t, J=18.4 Hz, 4H), 2.74 (s, 2H), 2.67-2.62 (m, 1H), 2.41-2.36 (m, 1H).

(S)-1-(oxetan-2-ylmethyl)-2-((6-((4-(trifluoromethyl)benzyl)oxy)-3',6'-dihydro-[2,4'-bipyridin]-1'(2'H)-yl)methyl)-1h-benzo[d]imidazole-6-carboxylic acid (Compound 46)

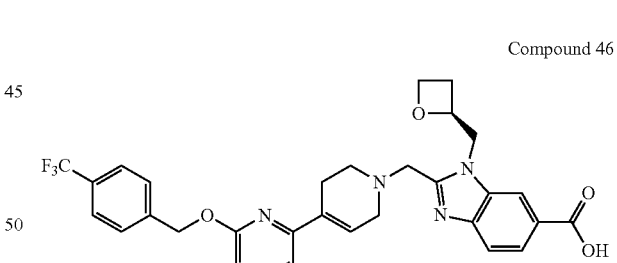

Compound 46

Prepared in analogous manner as for Compound 19

LCMS: [M+H]$^+$=579.0, Retention time (10 mM NH$_4$HCO$_3$)= 1.60 min.

$^1$H NMR (400 MHz, DMSO-d6) δ 8.28-8.24 (brs, 1H), 7.81 (dd, J=8.4, 1.4 Hz, 1H), 7.69 (dt, J=14.1, 8.2 Hz, 6H), 7.08 (d, J=7.4 Hz, 1H), 6.77 (d, J=8.1 Hz, 1H), 6.75-6.70 (brs, 1H), 5.48 (s, 2H), 5.10-5.02 (m, 1H), 4.80 (dd, J=15.2, 7.3 Hz, 1H), 4.68-4.58 (m, 1H), 4.49-4.43 (m, 1H), 4.39-4.33 (m, 1H), 4.07 (d, J=13.5 Hz, 1H), 3.91 (d, J=13.5 Hz, 1H), 3.25-3.16 (m, 2H), 2.77-2.68 (m, 2H), 2.68-2.60 (m, 1H), 2.48-2.31 (m, 3H).

(S)-2-((4-(6-(4-chloro-2-fluorobenzyloxy)pyridin-2-yl)-5,6-dihydropyridin-1(2H)-yl)methyl)-N-(methylsulfonyl)-1-(oxetan-2-ylmethyl)-1 h-benzo[d]imidazole-6-carboxamide (Compound 47)

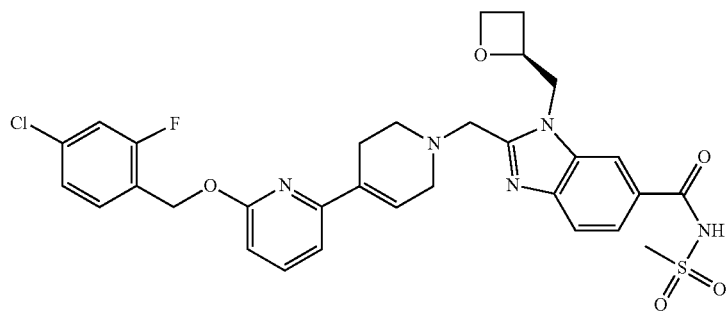

Compound 47

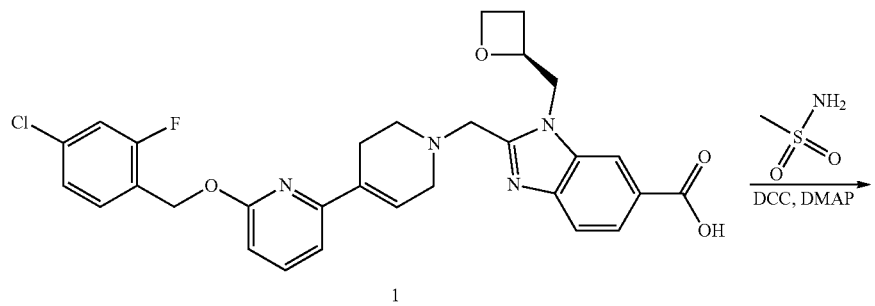

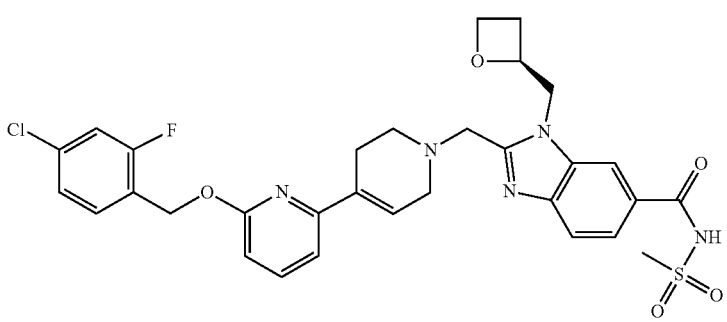

Compound 47

Step 1

DCC (88 mg, 0.426 mmol) in DCM (3 mL) was added to a solution of (S)-2-((4-(6-(4-chloro-2-fluorobenzyloxy)pyridin-2-yl)-5,6-dihydropyridin-1(2H)-yl)methyl)-1-(oxetan-2-ylmethyl)-1H-benzo[d]imidazole-6-carboxylic acid (80 mg, 0.142 mmol), DMAP (52 mg, 0.426 mmol) and methanesulfonamide (41 mg, 0.426 mmol) in DCM (7 mL). The mixture was stirred at 20° C. for 8 h. The reaction was diluted with water (50 mL) and extracted with DCM (50 mL×3), The combine organic was washed with brine (25 mL×3), dried and concentrated in vacuo to give crude product, which was purified by prep-HPLC (NH$_4$HCO$_3$) to give (S)-2-((4-(6-(4-chloro-2-fluorobenzyloxy)pyridin-2-yl)-5,6-dihydropyridin-1(2H)-yl)methyl)-N-(methylsulfonyl)-1-(oxetan-2-ylmethyl)-1H-benzo[d]imidazole-6-carboxamide (27.3 mg, 30% yield) as a white solid. LCMS: [M+H]$^+$=640.0, Retention time (10 mM NH$_4$HCO$_3$)=1.61 min.

$^1$H NMR (400 MHz, DMSO-d6) δ 12.06-12.05 (brs, 1H), 8.25-8.24 (brs, 1H), 7.83 (dd, J=8.5, 1.4 Hz, 1H), 7.73-7.61 (m, 2H), 7.56 (t, J=8.2 Hz, 1H), 7.48 (dd, J=10.0, 2.0 Hz, 1H), 7.30 (dd, J=8.2, 1.8 Hz, 1H), 7.09 (d, J=7.4 Hz, 1H), 6.74 (t, J=6.0 Hz, 2H), 5.40 (s, 2H), 5.18-5.04 (m, 1H), 4.79 (dd, J=15.1, 7.4 Hz, 1H), 4.63 (dd, J=15.1, 3.0 Hz, 1H), 4.48 (dd, J=13.7, 7.6 Hz, 1H), 4.39 (dt, J=9.0, 6.0 Hz, 1H), 4.13 (d, J=13.7 Hz, 1H), 3.95 (d, J=13.6 Hz, 1H), 3.28 (d, J=9.7 Hz, 2H), 3.23 (s, 3H), 2.79-2.78 (brs, 2H), 2.69 (dd, J=12.6, 4.8 Hz, 1H), 2.54-2.53 (brs, 2H), 2.44-2.38 (m, 1H).

(S)-2-((4-(7-((4-chloro-2-fluorobenzyl)oxy)-1h-pyrrolo[2,3-c]pyridin-5-yl)-3,6-dihydropyridin-1(2H)-yl)methyl)-1-(oxetan-2-ylmethyl)-1h-benzo[d]imidazole-6-carboxylic acid (Compound 48)
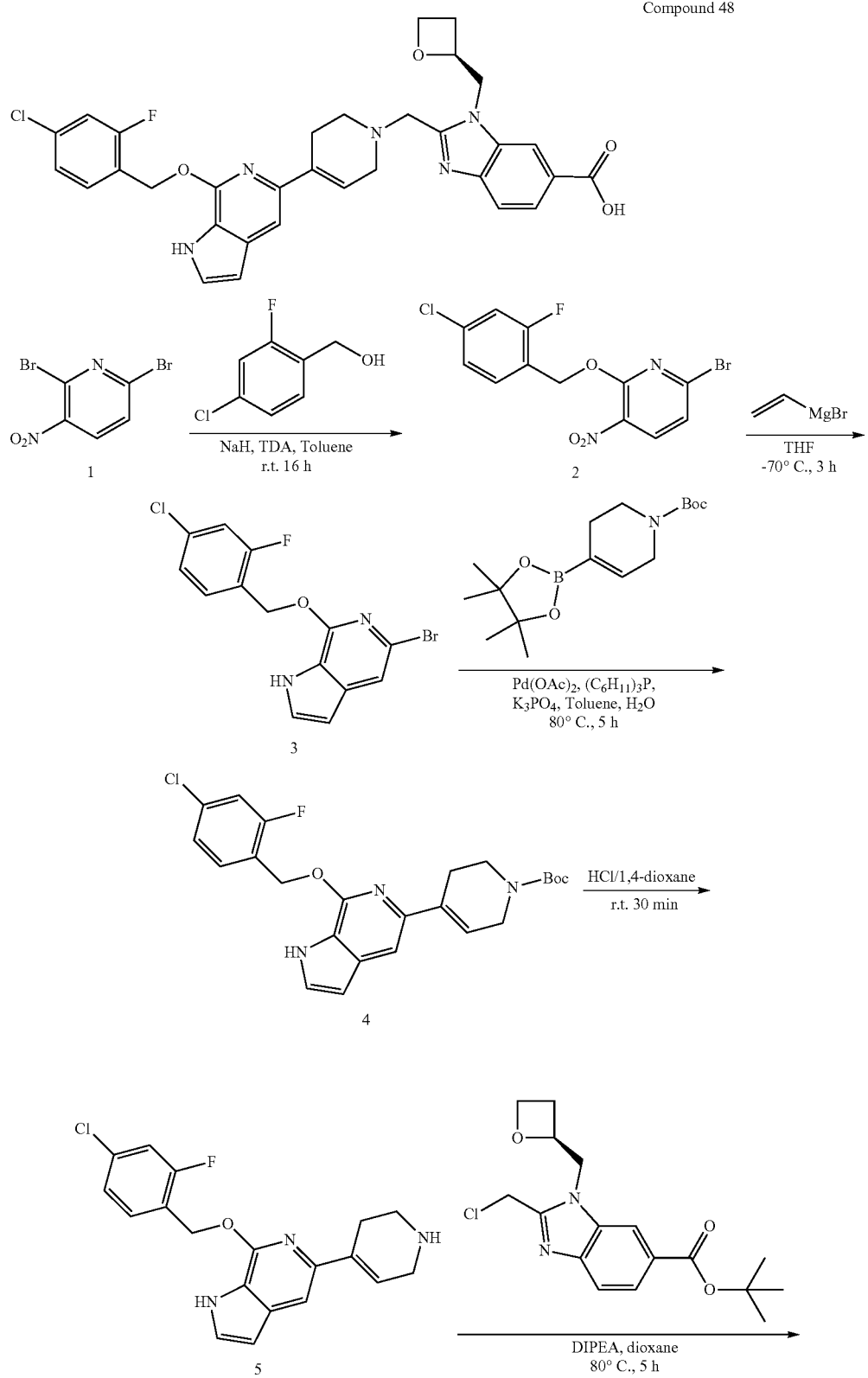

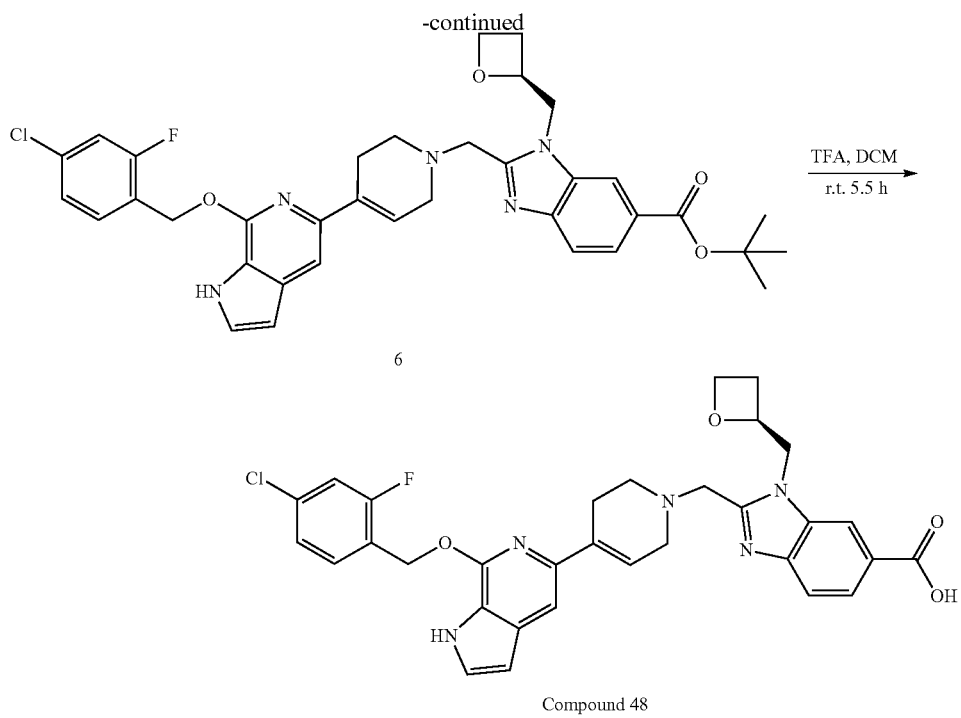

Compound 48

Step 1

To the solution of (4-chloro-2-fluorophenyl) methanol (1.2 g, 7.47 mmol) in toluene (15 mL) was added NaH (350 mg, 8.75 mmol) at 0° C. Then a solution of 2,6-dibromo-3-nitropyridine (2.0 g, 7.09 mmol) in 5 toluene (15 mL) was added into the above mixture followed by TDA (200 mg, 0.7 mmol) at 0° C. The reaction mixture was allowed to warm to RT. The reaction mixture was stirred at RT for 16 h, quenched with water (20 mL) and extracted with EA (50 mL×2). The organic phase was washed by sat. NH$_4$Cl. The solvent was evaporated to give a residue, which was purified by chromatography (PE:EA=10:1) to give the desired product (1.6 g, 62% yield) as pale yellow solid. LCMS: [M+Na]= 382.9; Retention time (0.01% TFA)=2.02 min.

Step 2

To the solution of 6-bromo-2-((4-chloro-2-fluorobenzyl)oxy)-3-nitropyridine (1.0 g, 2.77 mmol) in THF was added vinylmagnesium bromide (1 N in THF, 8.5 mL, 8.30 mmol) at −70° C. The reaction mixture was stirred at −70° C. for 3 h. The reaction was quenched with aq. NH$_4$Cl (50 mL) and extracted with EA (50 mL×3). The combined organic phase was washed by sat. NH$_4$Cl. The organic phase was dried by Na$_2$SO$_4$, evaporated and the residue was purified by flash chromatography (PE:EA=10:1) to give the desired product (300 mg, 31% yield) as pale yellow solid. LCMS: [M+H]$^+$= 354.6; Retention time (0.01% TFA)=2.17 min.

Step 3

The mixture of 5-bromo-7-((4-chloro-2-fluorobenzyl)oxy)-1 h-pyrrolo[2,3-c]pyridine (100 mg, 0.32 mmol), tert-butyl 4-(4,4,5,5-tetramethyl-1,3,2-dioxaborolan-2-yl)-3,6-dihydropyridine-1(2H)-carboxylate (120 mg, 0.39 mmol), Pd(OAc)$_2$ (4 mg, 0.06 mmol), K$_3$PO$_4$ (220 mg, 1.04 mmol), tricyclohexyl phosphane (9 mg, 0.03 mmol), toluene (3 mL) and water (0.3 mL) was stirred at 80° C. for 5 h. The reaction mixture was cooled to RT, filtered and the filtrate was evaporated. The crude product was purified by chromatography (PE:EA=10:1) to give the expected product (50 mg, 39% yield) as pale yellow solid. LCMS: [M+H]$^+$=457.7; Retention time (0.01% TFA)=2.25 min.

Step 4

The solution of tert-butyl 4-(7-((4-chloro-2-fluorobenzyl)oxy)-1 h-pyrrolo[2,3-c]pyridin-5-yl)-3,6-dihydropyridine-1(2H)-carboxylate (50 mg, 0.11 mmol) in HCl/Dioxane (4 N, 5 mL) was stirred at RT for 30 min. LCMS showed the reaction was completed. The solvent was evaporated to give the expected product (40 mg, 59% yield) as pale yellow solid. LCMS: [M+H]$^+$=357.7; Retention time (0.01% TFA)= 1.52 min.

Step 5

The solution of 7-((4-chloro-2-fluorobenzyl)oxy)-5-(1,2,3,6-tetrahydropyridin-4-yl)-1 h-pyrrolo[2,3-c]pyridine (40 mg, 0.11 mmol), tert-butyl (S)-2-(chloromethyl)-1-(oxetan-2-ylmethyl)-1 h-benzo[d]imidazole-6-carboxylate (40 mg, 0.12 mmol) and DIPEA (150 mg, 1.16 mmol) in dioxane (5 mL) was stirred at 80° C. for 5 h. The solvent was evaporated. The residue was purified by Prep-TLC (PE:EA=1:1) to give the expected product (10 mg, 13% yield) as pale yellow solid. LCMS: [M+H]$^+$=657.8; Retention time (0.01% TFA)=1.92 min.

Step 6

To the solution of tert-butyl (S)-2-((4-(7-((4-chloro-2-fluorobenzyl)oxy)-1 h-pyrrolo[2,3-c]pyridin-5-yl)-3,6-dihydropyridin-1(2H)-yl)methyl)-1-(oxetan-2-ylmethyl)-1 h-benzo[d]imidazole-6-carboxylate (10 mg, 0.11 mmol) in DCM (4 mL) was added TFA (1 mL). The reaction mixture was stirred at RT for 5.5 h. DCM and excess TFA were evaporated and a pale yellow solution in DMF was obtained. The DMF solution was purified by prep-HPLC to give the expected product (1.3 mg, 14% yield) as white solid.

LCMS: [M+H]$^+$=602.0; Retention time (10 mM NH$_4$HCO$_3$)=1.48 min.

$^1$H NMR (400 MHz, DMSO-d6) δ 11.78-11.71 (brs, 1H), 8.27-8.21 (brs, 1H), 7.82 (dd, J=8.3 Hz, 1H), 7.70 (t, J=8.2 Hz, 1H), 7.63 (d, J=8.3 Hz, 1H), 7.52-7.47 (m, 1H), 7.39 (t, J=2.7 Hz, 1H), 7.33 (dd, J=8.2 Hz, 1H), 7.21-7.19 (m, 1H), 6.69-6.65 (m, 1H), 6.47-6.41 (m, 1H), 5.59 (s, 2H), 5.12-5.04 (m, 1H), 4.84-4.76 (m, 1H), 4.66 (d, J=15.2 Hz, 1H), 4.50-4.43 (m, 1H), 4.41-4.33 (m, 1H), 4.07 (d, J=13.1 Hz, 1H), 3.91 (d, J=13.6 Hz, 1H), 3.25-3.21 (m, 2H), 2.78-2.71 (m, 2H), 2.69-2.64 (m, 1H), 2.58-2.53 (m, 2H), 2.46-2.41 (m, 1H).

(S)-2-((4-(6-(4-chloro-2-fluorobenzyloxy)pyridin-2-yl)piperazin-1-yl)methyl)-1-(oxetan-2-ylmethyl)-1h-indole-6-carboxylic acid (Compound 49)
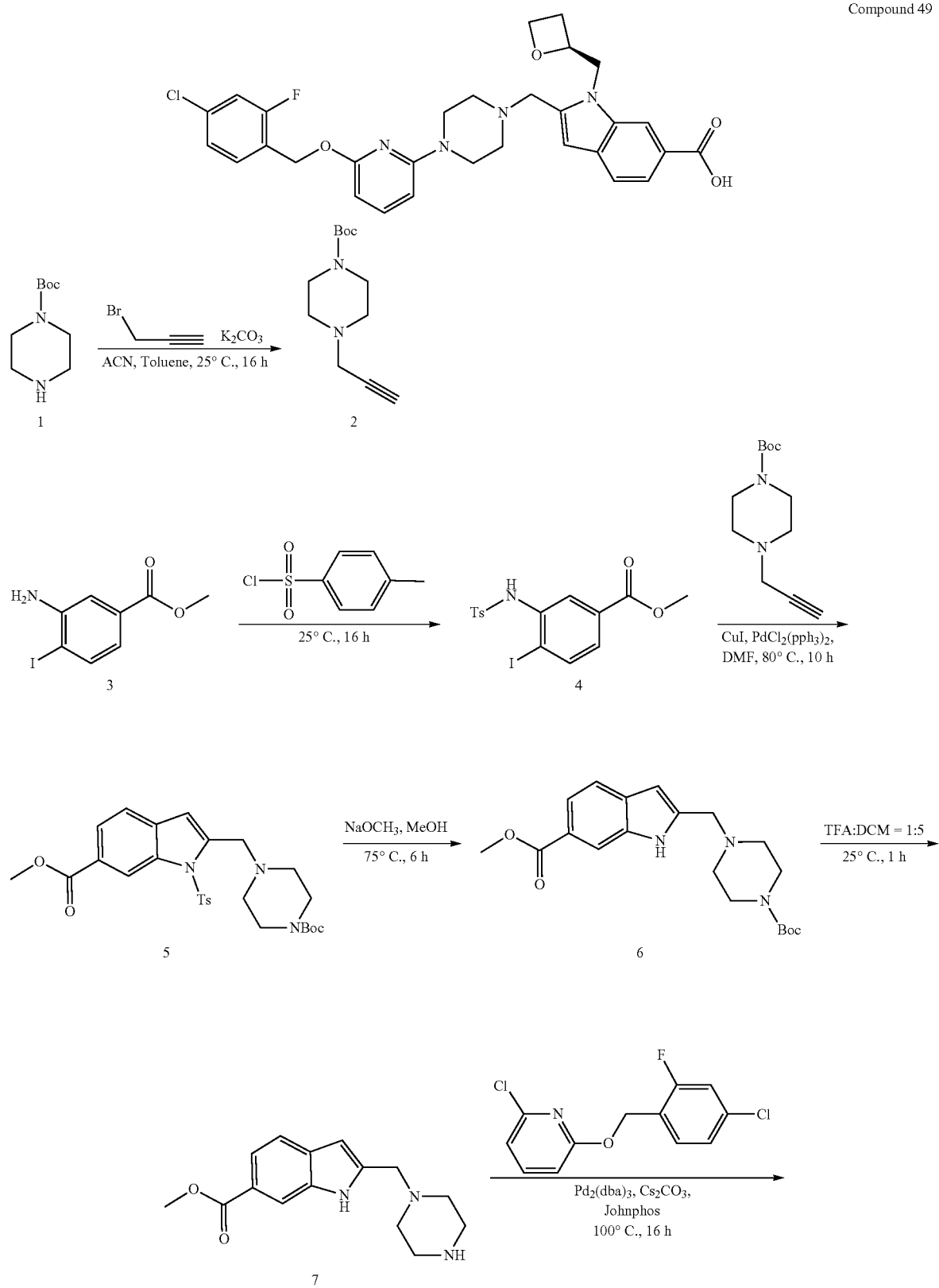

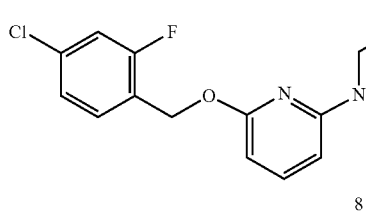 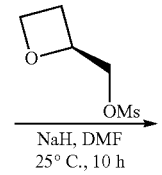

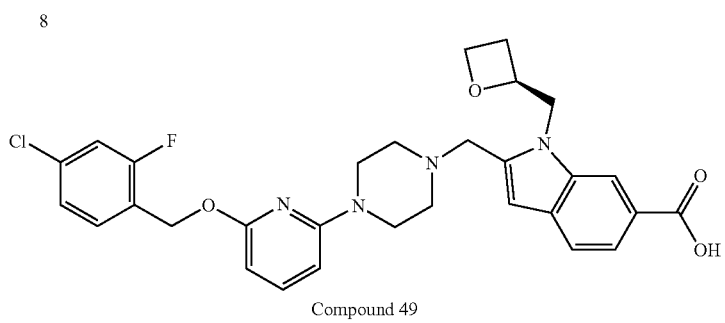

Compound 49

Step 1

To a solution of tert-butyl piperazine-1-carboxylate (5.0 g, 26.8 mmol, 1.0 eq) in ACN (30 mL) was added K$_2$CO$_3$ (7.42 g, 53.6 mmol, 2.0 eq), the mixture was cooled to 0° C., then 3-bromoprop-1-yne (3.2 mL, 37.52 mmol, 1.4 eq) in toluene (0.8 mL) was added dropwise during 10 min to the stirred reaction at 0° C. The mixture was stirred at 25° C. for 16 h. The mixture was filtered and the filtrate was evaporated, the crude product was purified by chromatography column on silica gel (eluting with 0% ethyl acetate to 50% ethyl acetate in petroleum) to give tert-butyl 4-(prop-2-ynyl)piperazine-1-carboxylate (1.9 g, 8.5 mmol, 32% yield) as brown oil. LCMS: [M+H]$^+$=225.1; Retention time (10 mM NH$_4$HCO$_3$)= 1.43 min.

Step 2

To a solution of methyl 3-amino-4-iodobenzoate (2.0 g, 7.2 mmol) in Pyridine (30 mL) was added 4-methylbenzene-1-sulfonyl chloride (2.1 g, 10.8 mmol). The mixture was stirred at 25° C. for 16 h. Then the reaction mixture was acidified with aq. HCl (2 N, 30 mL), extracted with ethyl acetate (100 mL×3) and washed with brine (200 mL). The combined organics were dried over Na$_2$SO$_4$ and concentrated in vacuo to give crude product, the crude product was purified by chromatography column on silica gel (eluting with 0% ethyl acetate to 50% ethyl acetate in petroleum) to give methyl 4-iodo-3-(4-methylphenylsulfonamido)benzoate (1.64 g, 3.8 mmol, 78% yield) as yellow solid. LCMS: [M+H]$^+$=453.5; Retention time (0.01% TFA)=1.94 min.

Step 3

To a solution of methyl 4-iodo-3-(4-methylphenylsulfonamido)benzoate (1.0 g, 2.3 mmol) in DMF (10 mL) was added tert-butyl 4-(prop-2-ynyl)piperazine-1-carboxylate (0.78 g, 3.5 mmol), triethylamine (1.0 mL, 6.9 mmol), CuI (35 mg, 0.2 mmol, 0.08 eq) and PdCl$_2$(PPh$_3$)$_2$ (81 mg, 0.1 mmol). The mixture was stirred at 80° C. for 10 h. The reaction was cooled to RT, diluted with water (50 mL) and extracted with ethyl acetate (50 mL×3). The combined organics were washed with brine (50 mL×3), dried over Na$_2$SO$_4$ and concentrated in vacuo to give crude product, the crude product was purified by chromatography column on silica gel (eluting with 0% methanol to 50% methanol in dichloromethane) to give methyl 2-((4-(tert-butoxycarbonyl)piperazin-1-yl)methyl)-1-tosyl-1 h-indole-6-carboxylate (0.89 g, 1.69 mmol, 74% yield) as white solid.

LCMS: [M+H]$^+$=527.7; Retention time (0.01% TFA)= 1.69 min.

Step 4

To a solution of methyl 2-((4-(tert-butoxycarbonyl)piperazin-1-yl)methyl)-1-tosyl-1 h-indole-6-carboxylate (890 mg, 1.7 mmol) in methanol (10 mL) was added sodium methoxide (666 mg, 12.2 mmol), the mixture was stirred and refluxed at 75° C. for 6 h. The reaction was cooled to RT, diluted with water (50 mL) and extracted with DCM (50 mL×3). The combined organics were washed with brine (50 mL×3), dried over Na$_2$SO$_4$ and concentrated in vacuo to give methyl 2-((4-(tert-butoxycarbonyl)piperazin-1-yl)methyl)-1 h-indole-6-carboxylate (500 mg, 65% yield) as brown oil.

LCMS: [M+H]$^+$=373.8; Retention time (0.01% TFA)= 1.46 min.

Step 5

To a solution of methyl 2-((4-(tert-butoxycarbonyl)piperazin-1-yl)methyl)-1 h-indole-6-carboxylate (500 mg, 1.34 mmol) in TFA (1 mL) and DCM (5 mL), the mixture was stirred at 25° C. for 1 h. The mixture was diluted with saturated aq. NaHCO$_3$ until pH was adjusted to 7, and extracted with DCM (50 mL×3).

The combined organics were washed with brine (20 mL×3), dried over Na$_2$SO$_4$ and concentrated in vacuo to give methyl 2-(piperazin-1-ylmethyl)-1 h-indole-6-carboxylate (0.31 g, 70% yield) as yellow oil.

LCMS: [M+H]$^+$=273.9; Retention time (0.01% TFA)= 1.06 min.

Step 6

To a solution of methyl 2-(piperazin-1-ylmethyl)-1 h-indole-6-carboxylate (310 mg, 1.13 mmol) in 1,4-dioxane (5 mL) was added 2-chloro-6-(4-chloro-2-fluorobenzyloxy) pyridine (370 mg, 2.26 mmol), JohnPhos (70 mg, 0.23 mmol), Pd$_2$(dba)$_3$ (110 mg, 0.11 mmol) and Cs$_2$CO$_3$ (590 mg, 1.81 mmol). The mixture was stirred at 100° C. for 16 h. The reaction was cooled to RT then diluted with water (50 mL) and extracted with ethyl acetate (50 mL×3). The combined organics were washed with brine (20 mL×3), dried over Na$_2$SO$_4$ and concentrated in vacuo to give crude product. The crude product was purified by chromatography column on silica gel (eluting with 0% ethyl acetate to 20% ethyl acetate in petroleum) to give methyl 2-((4-(6-(4-chloro-2-fluorobenzyloxy)pyridin-2-yl)piperazin-1-yl)methyl)-1 h-indole-6-carboxylate (54 mg, 9.4% yield) as a yellow oil. LCMS: [M+H]$^+$=509.2; Retention time (10 mM NH$_4$HCO$_3$)=2.35 min.

Step 7

A solution of methyl 2-((4-(6-(4-chloro-2-fluorobenzyloxy)pyridin-2-yl)piperazin-1-yl)methyl)-1 h-indole-6-carboxylate (54 mg, 0.11 mmol) in DMF (5 mL) was cooled to 0° C., then NaH (5.2 mg, 0.22 mmol) was added, the reaction was stirred at 25° C. for 1 h. Then (S)-oxetan-2-ylmethyl methanesulfonate (44 mg, 0.35 mmol) was added to a stirred reaction. The mixture was allowed warm to 55° C. and stirred for 10 h. Then, the crude product was purified by Prep-HPLC followed by SFC to give (S)-2-((4-(6-(4-chloro-2-fluorobenzyloxy)pyridin-2-yl)piperazin-1-yl)methyl)-1-(oxetan-2-ylmethyl)-1h-indole-6-carboxylic acid (2.3 mg, 4% yield) as white solid. LCMS: [M+H]$^+$=565.0; Retention time (10 mM NH$_4$HCO$_3$)=1.71 min. $^1$H NMR (400 MHz, DMSO-d6) δ 8.14-8.05 (brs, 1H), 7.63 (d, J=8.3 Hz, 1H), 7.53-7.42 (m, 4H), 7.29 (dd, J=8.3, 1.8 Hz, 1H), 6.44 (s, 1H), 6.32 (d, J=8.1 Hz, 1H), 6.08 (d, J=7.8 Hz, 1H), 5.30 (s, 2H), 5.09-5.00 (m, 1H), 4.68 (dd, J=15.2, 6.9 Hz, 1H), 4.57-4.44 (m, 2H), 4.39-4.33 (m, 1H), 3.83 (d, J=13.7 Hz, 1H), 3.65 (d, J=13.6 Hz, 1H), 3.46-3.43 (m, 2H), 2.70-2.61 (m, 1H), 2.48-2.42 (m, 5H).

2-((4-(6-(4-chloro-2-fluorobenzyloxy)pyridin-2-yl)piperazin-1-yl)methyl)-1-methyl-1 h-indole-6-carboxylic acid (Compound 50)

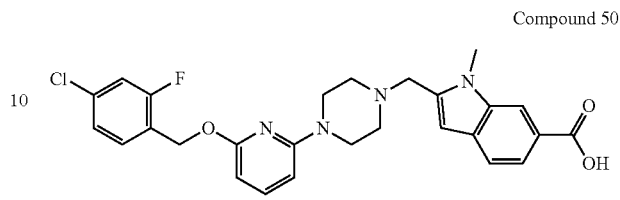

Compound 50

Prepared in analogous manner as for Compound 49

LCMS: [M+H]$^+$=509.0; Retention time (10 mM NH4HCO3)=1.71 min.

$^1$H NMR (400 MHz, DMSO-d6) δ 8.06-8.00 (brs, 1H), 7.63 (d, J=8.4 Hz, 1H), 7.51-7.43 (m, 4H), 7.31-7.27 (m, 1H), 6.42 (s, 1H), 6.32 (d, J=8.2 Hz, 1H), 6.08 (d, J=7.8 Hz, 1H), 5.30 (s, 2H), 3.84 (s, 3H), 3.70 (s, 2H), 3.46-3.41 (m, 4H), 2.49-2.46 (m, 4H).

(S)-2-((4-(3-(4-chloro-2-fluorobenzyloxy)-2-oxopyridin-1(2H)-yl)-5,6-dihydropyridin-1(2H)-yl)methyl)-1-(oxetan-2-ylmethyl)-1 h-benzo[d]imidazole-6-carboxylic acid (Compound 51)

Compound 51

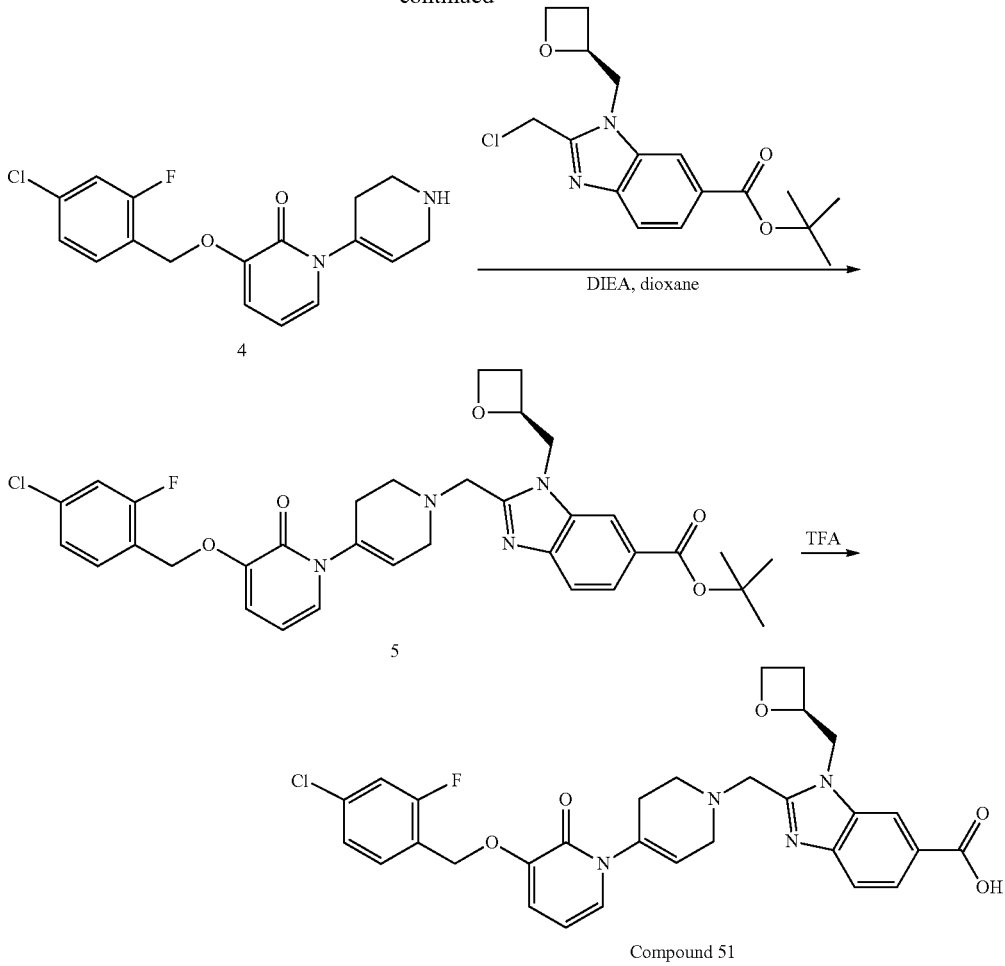

Compound 51

Step 1

To the solution of 3-hydroxypyridin-2(1H)-one (433 mg, 3.9 mmol) in MeOH (15 mL) was added NaOH (1 N, 3.9 mL) at 0° C. A solution of 1-(bromomethyl)-4-chloro-2-fluorobenzene (669 mg, 3.0 mmol) in MeOH (5 mL) was added dropwise to this mixture. The reaction mixture was stirred at RT for 6 h. Ice water (80 mL) was added to quench the reaction. The solution was extracted with EA (30 mL×3), washed with brine and dried in $Na_2SO_4$ and evaporated to give the crude product (700 mg, 92% yield), which was used in the next step without further purification. LCMS: $[M+H]^+$= 253.8; Retention time (0.01% TFA)=1.47 min.

Step 2

To the solution of 3-(4-chloro-2-fluorobenzyloxy)pyridin-2(1H)-one (800 mg, 3.16 mmol) in DMF (10 mL) and DCM (10 mL) was added tert-butyl 4-(4,4,5,5-tetramethyl-1,3,2-dioxaborolan-2-yl)-5,6-dihydropyridine-1(2H)-carboxylate (1.95 g, 6.32 mmol), Cu(OAc)$_2$ (862 mg, 4.74 mmol), TEA (957 mg, 9.48 mmol) and 4 Å sieves. The reaction mixture was stirred at RT for 36 h. 50 mL of ice water was added to quench the reaction. The solution was extracted with EA, washed with brine and dried in $Na_2SO_4$, concentrated and the crude was purified with column chromatography (PE:EA=2:1) to give tert-butyl 4-(3-(4-chloro-2-fluorobenzyloxy)-2-oxopyridin-1(2H)-yl)-5,6-dihydropyridine-1(2H)-carboxylate (275 mg, 20% yield) as yellow oil.

LCMS: $[M+H]^+$=435.1; Retention time (10 mM $NH_4HCO_3$)=1.68 min.

Step 3

To the solution of tert-butyl 4-(3-(4-chloro-2-fluorobenzyloxy)-2-oxopyridin-1(2H)-yl)-5,6-dihydropyridine-1(2H)-carboxylate (60 mg, 0.14 mmol) in DCM (2 mL) was added TFA (2 mL) at 0° C. The reaction mixture was stirred at 0° C. for 2 h. After evaporation of solvent, the crude was dissolved in dioxane (4 mL), then (S)-tert-butyl 2-(chloromethyl)-1-(oxetan-2-ylmethyl)-1 h-benzo[d]imidazole-6-carboxylate (50 mg, 0.15 mmol) and DIEA (90 mg, 0.7 mmol) were added. The reaction mixture was stirred at 90° C. for 6 h. Ice water (60 mL) was added to quench the reaction. The solution was extracted with EA (30 mL×3), washed with brine and dried in $Na_2SO_4$, concentrated and the crude product was purified with column chromatography (PE: EA=1:1) to give (S)-tert-butyl 2-((4-(3-(4-chloro-2-fluorobenzyloxy)-2-oxopyridin-1(2H)-yl)-5,6-dihydropyridin-1(2H)-yl)methyl)-1-(oxetan-2-ylmethyl)-1 h-benzo[d]imidazole-6-carboxylate (30 mg, 34% yield) as yellow solid.

LCMS: $[M+H]^+$=635.2; Retention time (0.01% TFA)= 1.77 min.

Step 4

To the solution of (S)-tert-butyl 2-((4-(3-(4-chloro-2-fluorobenzyloxy)-2-oxopyridin-1(2H)-yl)-5,6-dihydropyridin-1(2H)-yl)methyl)-1-(oxetan-2-ylmethyl)-1 h-benzo[d]imidazole-6-carboxylate (30 mg, 0.05 mmol) in DCM (2 mL) was added TFA (2 mL) at 0° C. The reaction mixture was stirred at 0° C. for 6 h. After evaporation of solvent, the crude was purified with HPLC to give (S)-2-((4-(3-(4-chloro-2-fluorobenzyloxy)-2-oxopyridin-1(2H)-yl)-5,6-dihydropyridin-1(2H)-yl)methyl)-1-(oxetan-2-ylmethyl)-1 h-benzo[d]imidazole-6-carboxylic acid (3.2 mg, 11% yield) as yellow solid. LCMS: [M+H]$^+$=578.6; Retention time (0.01% TFA)=1.48 min.
(S)-2-((4-(3-(4-chloro-2-fluorophenethyl)-2-oxo-2,3-dihydro-1 h-benzo[d]imidazol-1-yl)piperidin-1-yl)methyl)-1-(oxetan-2-ylmethyl)-1 h-benzo[d]imidazole-6-carboxylic acid (Compound 52)
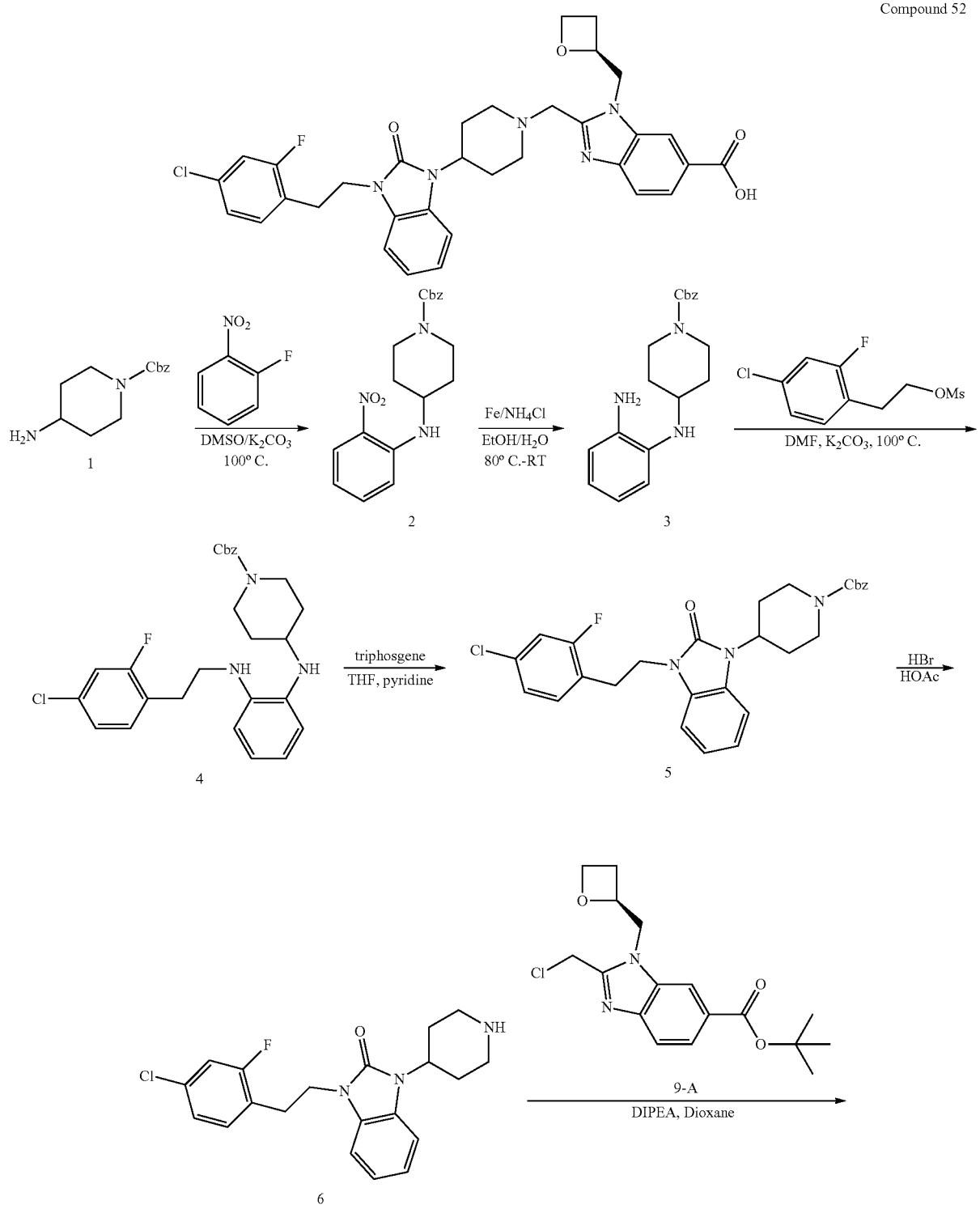

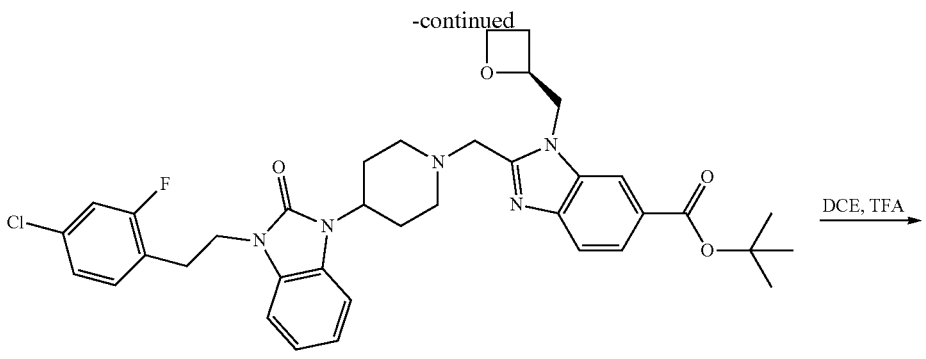

7

DCE, TFA →

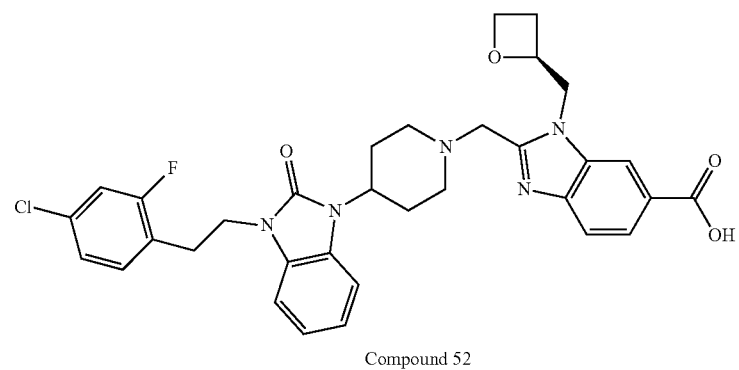 [SMILES: O=C(O)c1ccc2nc(CN3CCC(n4c(=O)n(CCc5ccc(Cl)cc5F)c5ccccc54)CC3)n(C[C@@H]3CCO3)c2c1]

Compound 52

Step 1

To a mixture of 1-fluoro-2-nitrobenzene (1.76 g, 12.5 mmol) in DMSO (15 mL) was added benzyl 4-aminopiperidine-1-carboxylate (2 g, 8.5 mmol) and $K_2CO_3$ (1.32 g, 9.6 mmol). The reaction mixture was heated to 100° C. overnight. The mixture was poured into ice-water, extracted by EtOAc (50 mL×3), combined the organic layer, washed by brine, dried over $Na_2SO_4$, after removal of solvent, the residue was purified by flash column to give benzyl 4-(2-nitrophenylamino)piperidine-1-carboxylate (3 g, 98% yield) as an yellow oil.

Step 2

To a mixture of benzyl 4-(2-nitrophenylamino)piperidine-1-carboxylate (0.7 g, 2 mmol, 1.0 eq) in EtOH (20 mL) and $H_2O$ (10 mL) was added Fe (1.12 g, 20 mmol, 10 eq) and $NH_4Cl$ (1.07 g, 20 mmol). The reaction mixture was heated to 80° C. for 15 min, then cooled to RT and stirred overnight. The mixture was diluted with EtOAc (50 mL), filtered by celite, extracted by EtOAc (50 mL×3). The combined organics were washed by brine, dried over $Na_2SO_4$, filtered and concentrated to give benzyl 4-(2-aminophenylamino)piperidine-1-carboxylate (0.7 g, 100% yield) as dark brown oil.

Step 3

To a mixture of benzyl 4-(2-aminophenylamino)piperidine-1-carboxylate (0.7 g, 2.15 mmol) in DMF (10 mL) was added 4-chloro-2-fluorophenethyl methanesulfonate (0.82 g, 3.23 mmol), $K_2CO_3$ (1.19 g, 8.6 mmol) and NaI (30 mg, 0.2 mmol). The reaction mixture was heated to 100° C. overnight. The mixture was cooled and treated with water (20 mL), extracted by EtOAc (30 mL×3). The combined organics was washed by brine, dried over $Na_2SO_4$, after removal of solvent, the residue was purified by silica gel column chromatography (PE:EA=20:1) to give benzyl 4-(2-(4-chloro-2-fluorophenethylamino) phenylamino) piperidine-1-carboxylate (0.2 g, 20% yield) as dark brown oil.

Step 4

To a mixture of benzyl 4-(2-(4-chloro-2-fluorophenethylamino)phenylamino)piperidine-1-carboxylate (0.2 g, 0.42 mmol) in THF (5 mL) was added Pyridine (0.33 g, 4.15 mmol) and triphosgene (0.12 g, 0.415 mmol). The reaction mixture was heated to 50° C. overnight. The mixture was cooled and treated with water (20 mL), extracted by EtOAc (30 mL×3). The combined organics was washed by brine, dried over $Na_2SO_4$, after removal of solvent, the residue was purified by Prep-TLC (PE:EA=20:1) to give benzyl 4-(3-(4-chloro-2-fluorophenethyl)-2-oxo-2,3-dihydro-1 h-benzo[d]imidazol-1-yl)piperidine-1-carboxylate (0.1 g, 48% yield) as yellow oil. LCMS: $[M+H]^+$=508.0; Retention time (0.01% TFA)=2.13 min.

Step 5

To a mixture of benzyl 4-(3-(4-chloro-2-fluorophenethyl)-2-oxo-2,3-dihydro-1 h-benzo[d]imidazol-1-yl)piperidine-1-carboxylate (200 mg, 0.4 mmol) in HOAc (1 mL) was added HBr/HOAc (40%, 3 mL).

The reaction mixture was stirred at RT for 1 h. The mixture was diluted with $H_2O$ and adjusted to pH=7 by saturated aq. $NaHCO_3$, extracted by EtOAc (30 mL×3), The combined organics was washed by brine, dried over $Na_2SO_4$, after removal of solvent, to give 1-(4-chloro-2-fluorophenethyl)-3-(piperidin-4-yl)-1 h-benzo[d]imidazol-2(3H)-one (140 mg, 95% yield) as yellow oil. LCMS: $[M+H]^+$=373.5; Retention time (0.01% TFA)=1.25 min.

Step 6

To a mixture of (S)-tert-butyl 2-(chloromethyl)-1-(oxetan-2-ylmethyl)-1 h-benzo[d]imidazole-6-carboxylate (105 mg, 0.312 mmol) in Dioxane (20 mL) was added 1-(4-chloro-2-fluorophenethyl)-3-(piperidin-4-yl)-1 h-benzo[d]imidazol-2(3H)-one (140 mg, 0.37 mmol), DIPEA (161 mg, 1.25 mmol) and NaI (10 mg, 0.1 eq). The reaction mixture was heated to 80° C. for 2 h. The mixture was quenched with $H_2O$, extracted by EtOAc (30 mL×3), The combined organics was washed by brine, dried over Na₂SO₄, after removal of solvent, the residue was purified by Prep-HPLC to give (S)-tert-butyl 2-((4-(3-(4-chloro-2-fluorophenethyl)-2-oxo-2,3-dihydro-1 h-benzo[d]imidazol-1-yl)piperidin-1-yl)methyl)-1-(oxetan-2-ylmethyl)-1 h-benzo[d]imidazole-6-carboxylate (45 mg, 22% yield) as white solid. LCMS: [M+H]⁺=674.1; purity=100% (254 nm); Retention time (0.01% TFA)=2.21 min.

Step 7

To a mixture of (S)-tert-butyl 2-((4-(3-(4-chloro-2-fluorophenethyl)-2-oxo-2,3-dihydro-1 h-benzo[d]imidazol-1-yl)piperidin-1-yl)methyl)-1-(oxetan-2-ylmethyl)-1 h-benzo[d]imidazole-6-carboxylate (45 mg, 66.7 mmol) in DCE (8 mL) was added TFA (1 mL, excess). The reaction mixture was stirred at RT for 1 h. The mixture was evaporated to dryness. The residue was dissolved in DMF and purified by Prep-HPLC to give (S)-2-((4-(3-(4-chloro-2-fluorophenethyl)-2-oxo-2,3-dihydro-1 h-benzo[d]imidazol-1-yl)piperidin-1-yl)methyl)-1-(oxetan-2-ylmethyl)-1 h-benzo[d]imidazole-6-carboxylic acid (22.4 mg, 55% yield) as white solid. LCMS: [M+H]⁺=618.0; Retention time (10 mM NH₄HCO₃)=1.54 min.

¹H NMR (400 MHz, DMSO-d6) δ 8.28 (s, 1H), 7.81-7.78 (dd, J1=8.4 Hz, J2=1.6 Hz, 1H), 7.64-7.62 (d, J=8.0 Hz, 1H), 7.30-7.27 (dd, J1=10.0 Hz, J2=2.0 Hz, 1H), 7.25-7.18 (m, 2H), 7.15-7.12 (dd, J1=8.4 Hz, J2=2.0 Hz, 1H), 7.09-7.07 (m, 1H), 7.04-6.98 (m, 2H), 5.14-5.10 (m, 1H), 4.84-4.79 (m, 1H), 4.70-4.66 (m, 1H), 4.55-4.50 (m, 1H), 4.43-4.38 (m, 1H), 4.17-4.12 (m, 1H), 4.05-4.01 (t, J=6.8 Hz, 2H), 3.99-3.94 (m, 1H), 3.84-3.80 (d, J=13.2 Hz, 1H), 3.03-2.89 (m, 5H), 2.80-2.73 (m, 1H), 2.36-2.21 (m, 5H), 1.64-1.58 (m, 2H).

(S)-2-((4-(1-(4-chloro-2-fluorophenethyl)-2-oxo-1,4-dihydroquinazolin-3(2H)-yl)piperidin-1-yl)methyl)-1-(oxetan-2-ylmethyl)-1H-benzo[d]imidazole-6-carboxylic acid (Compound 53)

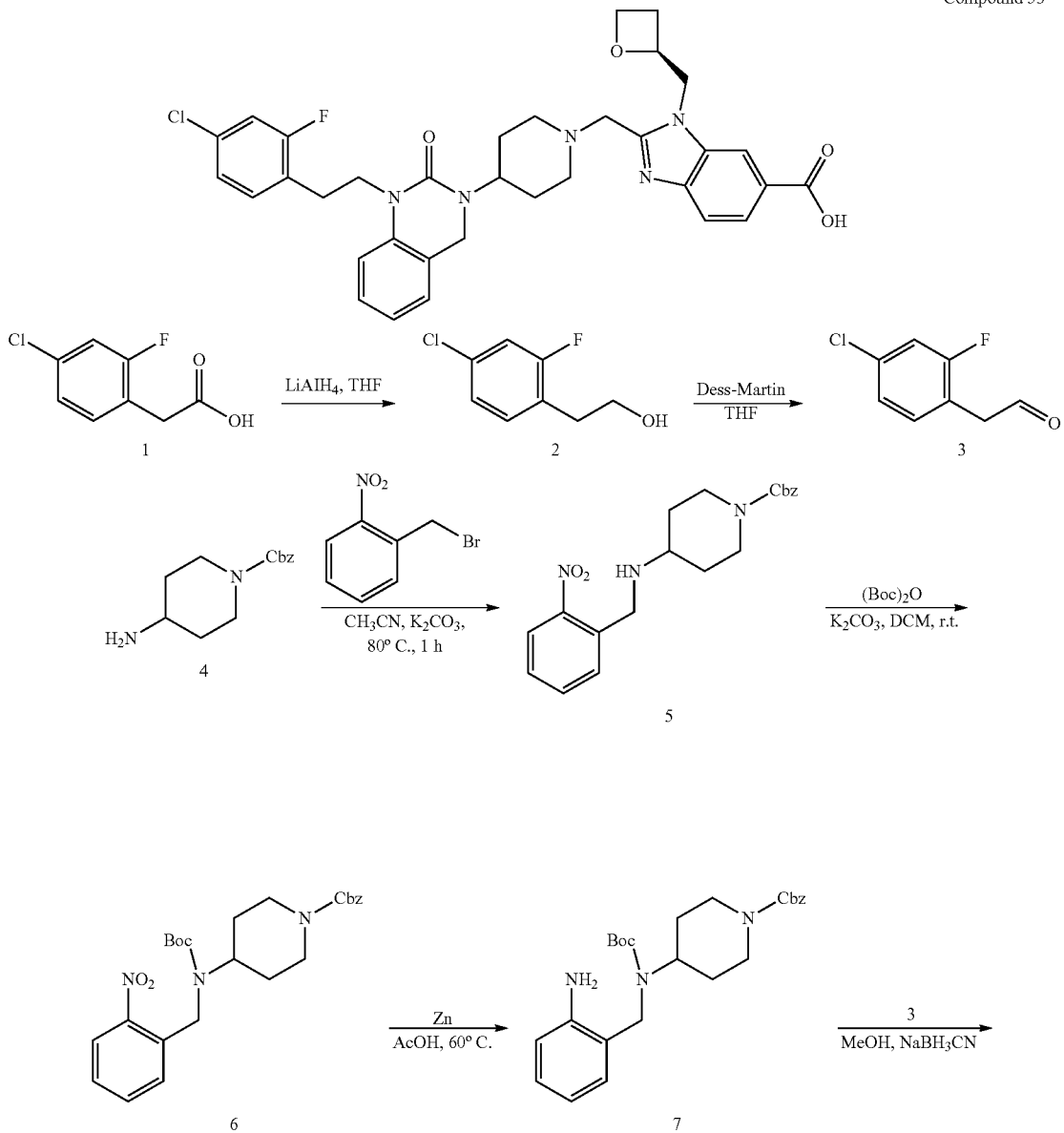

-continued
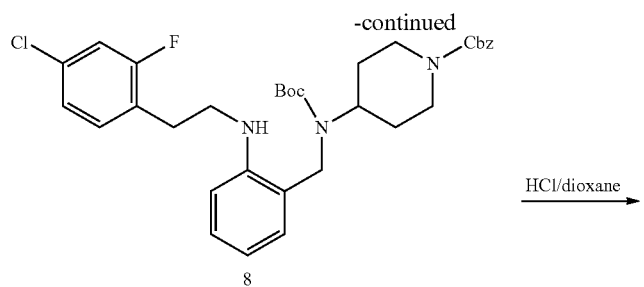
8
HCl/dioxane →
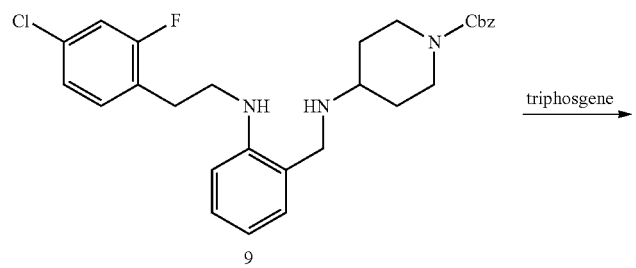
9
triphosgene →
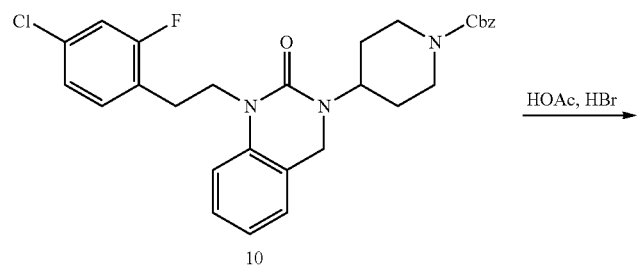
10
HOAc, HBr →
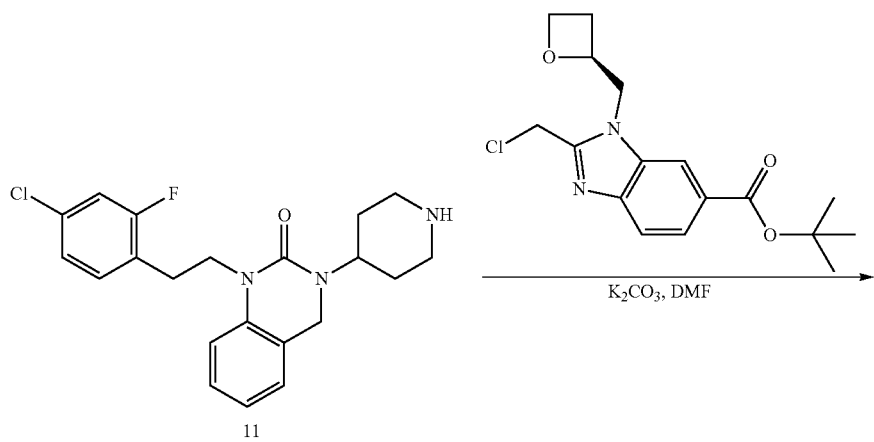
11
K₂CO₃, DMF →
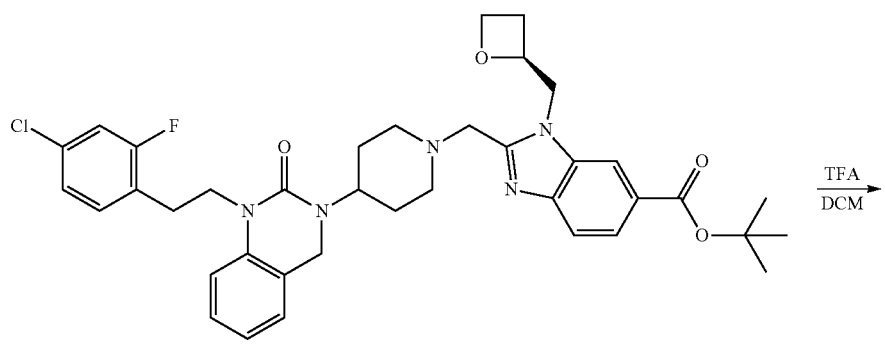
12
TFA/DCM →

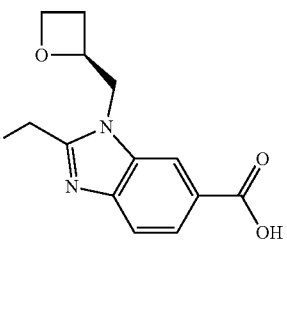

Compound 53

Step 1

To a solution of 2-(4-chloro-2-fluorophenyl) acetic acid (500 mg, 2.65 mmol) in THF (4 mL) was added LiAlH$_4$ (152 mg, 4 mmol) at 0° C. The mixture was stirred at 0° C. for 1 h. LCMS showed the reaction worked well. The mixture was quenched with water at 0° C., extracted with EA (50 mL×3), concentrated to give the crude product (400 mg, 86.5% yield) as yellow oil. LCMS: [M−18+H]=157.0; Retention time (0.01% TFA)=1.47 min.

Step 2

To a solution of 2-(4-chloro-2-fluorophenyl) ethanol (400 mg, 2.29 mmol) in THF (5 mL) was added Dess-Martin periodiane (974 mg, 3 mmol). The mixture was stirred at RT for 3 h. LCMS showed the reaction worked well. The mixture was filtered and concentrated to give the crude product (250 mg, 63% yield) as yellow oil. Retention time (0.01% TFA)=2.19 min.

Step 3

To a solution of benzyl 4-aminopiperidine-1-carboxylate (1.2 g, 5.12 mmol) in MeCN (30 mL) was added 1-(bromomethyl)-2-nitrobenzene (1 g, 5.12 mmol) and K$_2$CO$_3$ (1.93 g, 15.3 mmol). The mixture was stirred at 80° C. for 4 h. LCMS showed the reaction worked well. The mixture was filtered and concentrated, purified by silica-gel column (PE:EA=10:1) to afford the desired product (1.5 g, 87% yield) as white oil.

LCMS: [M+H]$^+$=370.2; Purity 96.5% (254 nm); Retention time (0.01% TFA)=1.68 min.

Step 4

To a solution of benzyl 4-(2-nitrobenzylamino)piperidine-1-carboxylate (1.5 g, 4.06 mmol) in DCM (20 mL) was added di-tert-butyl dicarbonate (1.75 g, 8.12 mmol) and K$_2$CO$_3$ (1.66 g, 12.18 mmol). The mixture was stirred at RT for 16 h. LCMS showed worked well. The mixture was filtered and concentrated, purified by silica-gel column (PE: EA=1:1) to give the desires product (1.7 g, 89% yield) as white oil.

LCMS: [M−100+H]=370.1; Purity 93% (254 nm); Retention time (0.01% TFA)=1.88 min.

Step 5

To a solution of benzyl 4-(tert-butoxycarbonyl(2-nitrobenzyl)amino)piperidine-1-carboxylate (1.7 g, 3.62 mmol) in AcOH (16 mL) and H$_2$O (2 mL) was added Zn (460 mg, 7.24 mmol). The mixture was stirred at 60° C. for 16 h. LCMS showed the reaction worked well. The mixture was filtered and concentrated, purified by silica-gel column PE:EA=2:1 to afford the product (1.45 g, 91% yield) as white oil. LCMS: [M+H]$^+$=440.3; Purity 98% (254 nm); Retention time (0.01% TFA)=1.77 min.

Step 6

To a solution of benzyl 4-((2-aminobenzyl)(tert-butoxycarbonyl)amino)piperidine-1-carboxylate (250 mg, 0.57 mmol) in MeOH (5 mL) was added 2-(4-chloro-2-fluorophenyl)acetaldehyde (638 mg, 3.7 mmol). The mixture was stirred at RT for 2 h. Then NaBH$_3$CN (91 mg, 1.4 mmol) was added. The mixture was continued to stir for 3 h. LCMS showed the reaction worked well. The mixture was quenched with water, extracted with EA ((30 mL×3), the combined organics was washed by brine, dried over Na$_2$SO$_4$, filtered and concentrated to give the crude material, which was purified by Prep-HPLC to give the product (100 mg) as white solid. LCMS: [M+H]$^+$=596.2; purity 100% (254 nm); Retention time (0.01% TFA)=2.62 min.

Step 7

To a 50 mL round bottom flask with benzyl 4-(tert-butoxycarbonyl(2-(4-chloro-2-fluorophenethylamino)benzyl)amino)piperidine-1-carboxylate (200 mg, 0.33 mmol) was added HCl/dioxane (4 N, 5 mL). The mixture was stirred at RT for 2 h. LCMS showed the reaction worked well. The mixture was concentrated to give the crude product (150 mg, 90% yield). LCMS: [M+H]$^+$=496.3; Retention time (0.01% TFA)=2.05 min.

Step 8

To a solution of benzyl 4-(2-(4-chloro-2-fluorophenethylamino)benzylamino) piperidine-1-carboxylate (150 mg, 0.30 mmol) in THF (4 mL) was added triphosgene (177 mg, 0.60 mmol) and TEA (2 mL). The mixture was stirred at RT for 2 h. LCMS showed the reaction worked well. The mixture was concentrated to give the crude product (140 mg, 88% yield) as yellow solid. LCMS: [M+H]$^+$=522.2; Retention time (0.01% TFA)=2.23 min.

Step 9

To a solution of benzyl 4-(1-(4-chloro-2-fluorophenethyl)-2-oxo-1,2-dihydroquinazolin-3(4H)-yl)piperidine-1-carboxylate (140 mg, 0.27 mmol) in THF (4 mL) was added HBr (1 mL) and AcOH (3 mL). The mixture was stirred at RT for 3 h. LCMS showed the reaction worked well. The mixture was concentrated to give the crude product (90 mg, 88% yield) as yellow solid. LCMS: [M+H]$^+$=388.1; Retention time (0.01% TFA)=1.47 min.

Step 10

To a solution of 1-(4-chloro-2-fluorophenethyl)-3-(piperidin-4-yl)-3,4-dihydroquinazolin-2(1H)-one (90 mg, 0.23 mmol) in 1,4-dioxane (5 mL) was added (S)-tert-butyl 2-(chloromethyl)-3-(oxetan-2-ylmethyl)-3H-benzo[d]imidazole-5-carboxylate (84 mg, 0.25 mmol) and DIPEA (262 mg, 0.69 mmol). The mixture was stirred at 90° C. for 30 min. LCMS showed the reaction worked well. The mixture was concentrated to give the crude material. The crude material was purified by Prep-HPLC to give the desired product (20 mg, 13% yield) as white solid. LCMS: [M+H]$^+$=388.2; Retention time (0.01% TFA)=1.96 min.

Step 11

To a solution of (S)-tert-butyl 2-((4-(1-(4-chloro-2-fluorophenethyl)-2-oxo-1,2-dihydroquinazolin-3(4H)-yl)piperidin-1-yl)methyl)-3-(oxetan-2-ylmethyl)-3H-benzo[d]imidazole-5-carboxylate (20 mg, 0.03 mmol) in DCM (2 mL) was added TFA (0.3 mL). The mixture was stirred at RT for 2 h. LCMS showed the reaction worked well. The mixture was concentrated to give the crude material. The crude material was purified by Prep-HPLC to give the desired product (4.5 mg, 25% yield) as white solid. LCMS: [M+H]$^+$=631.2; purity 95.9% (254 nm); Retention time (0.01% TFA)=1.54 min.

(S)-2-((4-(7-(4-chloro-2-fluorophenyl)-1-oxo-3,4-dihydroisoquinolin-2(1H)-yl)piperidin-1-yl)methyl)-1-(oxetan-2-ylmethyl)-1h-benzo[d]imidazole-6-carboxylic acid (Compound 54)

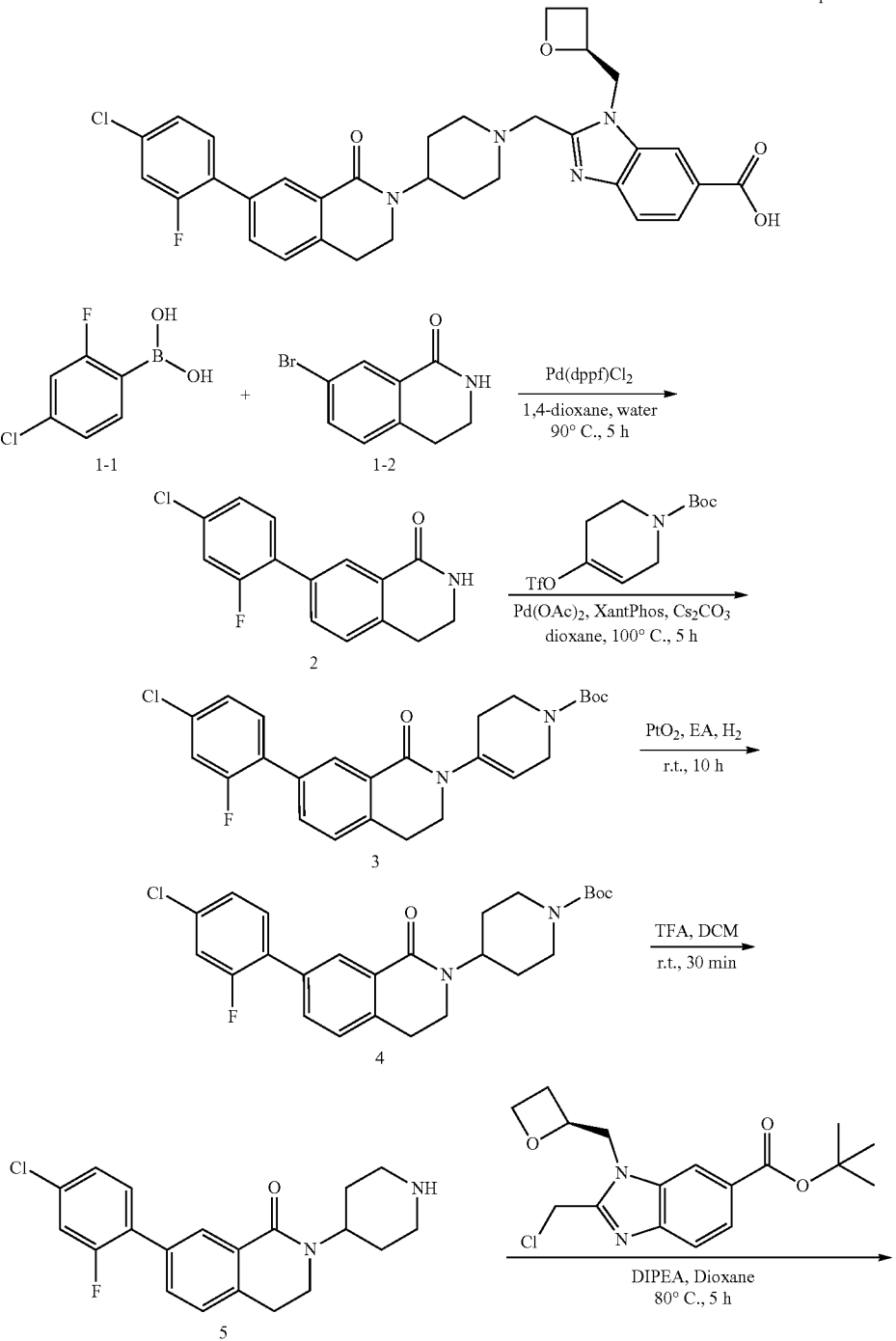

-continued

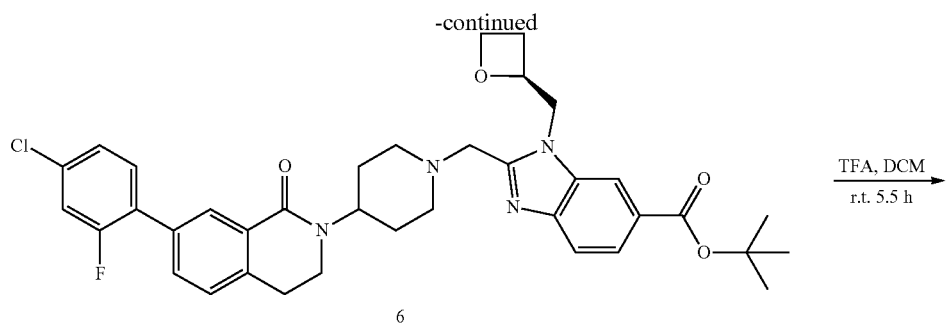

6

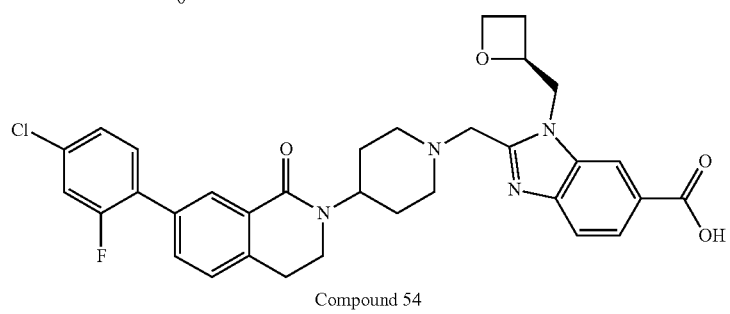

Compound 54

Step 1

To the solution of 7-bromo-3,4-dihydroisoquinolin-1(2H)-one (436 mg, 2.50 mmol) and (4-chloro-2-fluorophenyl)boronic acid (678 mg, 3.00 mmol) in 1,4-dioxane (15 mL) were added Pd(dppf)Cl$_2$ (183 mg, 0.25 mmol), Cs$_2$CO$_3$ (1.83 g, 5.62 mmol) and water (3 mL) at RT. The reaction mixture was stirred at 80° C. for 5 h. Then the reaction mixture was cooled to RT, filtered and the filtrate was evaporated. The crude product was purified by chromatography (PE:EA=3:2) to give the desired product (350 mg, 51% yield) as pale yellow solid. LCMS: [M+H]$^+$=275.8; Retention time (0.01% TFA)=1.77 min.

Step 2

To the solution of 7-(4-chloro-2-fluorophenyl)-3,4-dihydroisoquinolin-1(2H)-one (100 mg, 0.36 mmol) and tert-butyl 4-(((trifluoromethyl)sulfonyl)oxy)-3,6-dihydropyridine-1(2H)-carboxylate (180 mg, 0.54 mmol) in 1,4-dioxane (5 mL) were added Pd(OAc)$_2$ (8 mg, 0.04 mmol), Cs$_2$CO$_3$ (150 mg, 0.46 mmol), and XantPhos (25 mg, 0.04 mmol) at RT. The reaction mixture was stirred at 80° C. for 5 h and was cooled to RT. The reaction mixture was filtered and the filtrate was evaporated. The crude product was purified by chromatography (PE:EA=3:2) to give the expected product (50 mg, 31% yield) as a pale yellow solid. LCMS: [M+Na]=478.6; Retention time (0.01% TFA)=2.19 min.

Step 3

To the solution of tert-butyl 4-(7-(4-chloro-2-fluorophenyl)-1-oxo-3,4-dihydro-isoquinolin-2(1H)-yl)-3,6-dihydropyridine-1(2H)-carboxylate (80 mg, 0.18 mmol) in EA (5 mL) was added PtO$_2$ (5 mg, 0.02 mmol). The reaction mixture was stirred at RT under hydrogen atmosphere for 10 h. The reaction mixture was filtered and the filtrate was evaporated. The residue was purified by chromatography (PE:EA=3:2) to give the expected product (50 mg, 10% yield) as pale yellow solid. LCMS: [M+H]$^+$=458.1; Retention time (0.01% TFA)=2.06 min.

Step 4

To the solution of tert-butyl 4-(7-(4-chloro-2-fluorophenyl)-1-oxo-3,4-dihydro isoquinolin-2(1H)-yl)piperidine-1-carboxylate (50 mg, 0.07 mmol) in DCM (5 mL) was added TFA (1.0 mL). The reaction mixture was stirred at RT for 30 min. The LCMS of the mixture showed that the reaction was completed.

The mixture was evaporated to give the expected product (25 mg, 100% yield) as pale yellow solid, and the product was used for next step without further purification. LCMS: [M+H]$^+$=359.1; Retention time (0.01% TFA)=1.45 min.

Step 5

To the solution of 7-(4-chloro-2-fluorophenyl)-2-(piperidin-4-yl)-3,4-dihydroisoquinolin-1(2H)-one (25 mg, 0.07 mmol) in dioxane (5 mL) were added tert-butyl (S)-2-(chloromethyl)-1-(oxetan-2-ylmethyl)-1 h-benzo[d]imidazole-6-carboxylate (25 mg, 0.07 mmol) and DIPEA (150 mg, 1.16 mmol) at RT. The reaction mixture was stirred at 80° C. for 5 h. The solvent was evaporated. The residue was purified by prep-HPLC to give the expected product (10 mg, 22% yield) as pale yellow solid.

LCMS: [M+H]$^+$=658.9; Retention time (10 mM NH$_4$HCO$_3$)=1.95 min.

Step 6

To the solution of tert-butyl (S)-2-((4-(7-(4-chloro-2-fluorophenyl)-1-oxo-3,4-dihydro isoquinolin-2(1H)-yl)piperidin-1-yl)methyl)-1-(oxetan-2-ylmethyl)-1 h-benzo[d]imidazole-6-carboxylate (10 mg, 0.11 mmol) in DCM (4 mL), was added TFA (1 mL). The reaction mixture was stirred at RT for 5.5 h. The mixture was concentrated and purified by Prep-HPLC to give the expected product (5.7 mg, 14% yield) as a white solid. LCMS: [M+H]$^+$=603.0; Retention time (10 mM NH$_4$HCO$_3$)=1.52 min.

$^1$H NMR (400 MHz, DMSO-d6) δ 8.27 (s, 1H), 8.00 (s, 1H), 7.80 (m, 1H), 7.69-7.62 (m, 2H), 7.62-7.55 (m, 2H), 7.45-7.39 (m, 2H), 5.09 (m, 1H), 4.81 (m, 1H), 4.66 (m, 1H), 4.57-4.44 (m, 2H), 4.39 (m, 1H), 3.95 (m, 1H), 3.80 (m, 1H), 3.75 (m, 1H), 3.49 (m, 2H), 3.08 (m, 1H), 3.02 (m, 1H), 2.96 (m, 2H), 2.88 (m, 1H), 2.81-2.65 (m, 2H), 2.44 (m, 2H), 2.26 (m, 2H).

(S)-2-((4-(6-((4-chloro-2-fluorobenzyl)oxy)pyridin-2-yl)-3-oxopiperazin-1-yl)methyl)-1-(oxetan-2-ylmethyl)-1H-benzo[d]imidazole-6-carboxylic acid
(Compound 55)
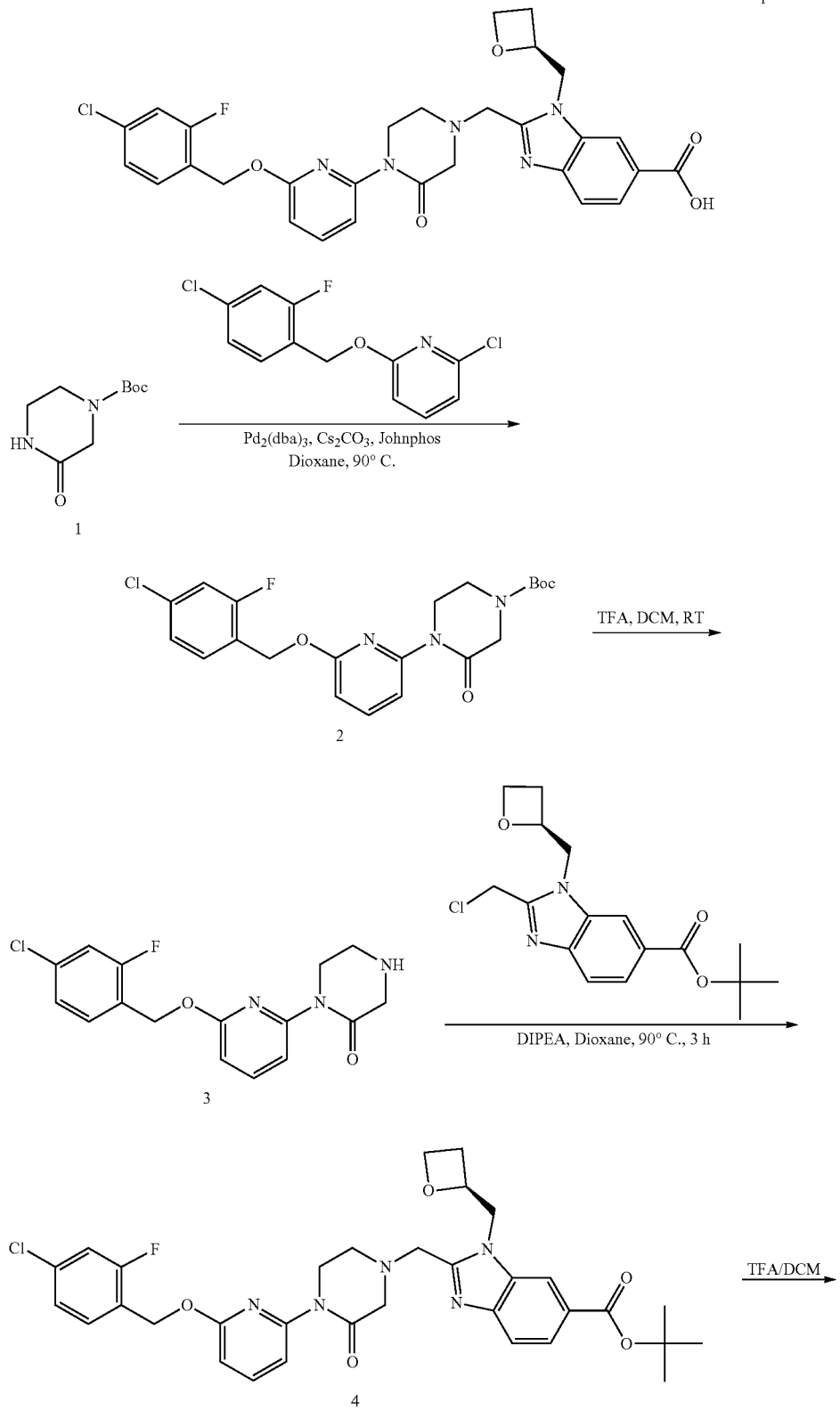

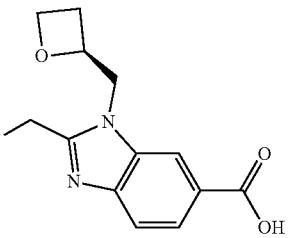
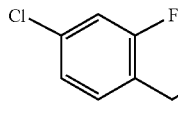

Compound 55

Step 1

To a solution of tert-butyl 3-oxopiperazine-1-carboxylate (200 mg, 1.01 mmol) in 1,4-Dioxane (5 mL) was added 2-chloro-6-(4-chloro-2-fluorobenzyloxy)pyridine (182 mg, 0.67 mmol), JohnPhos (40 mg, 0.13 mmol), $Pd_2(dba)_3$ (31 mg, 0.03 mmol) and $Cs_2CO_3$ (349 mg, 1.07 mmol). The mixture was stirred at 90° C. for 12 h. The reaction was cooled to RT, diluted with water (50 mL), and extracted with ethyl acetate (50 mL×3). The combined organic was washed with brine (20 mL×3), dried over $Na_2SO_4$ and concentrated in vacuo to give crude product, which was purified by chromatography column on silica gel (PE/EA=4/1) to give tert-butyl 4-(6-(4-chloro-2-fluorobenzyloxy)pyridin-2-yl)-3-oxopiperazine-1-carboxylate (70 mg, 16% yield) as yellow oil. LCMS: [M+H]⁺=462.7; Retention time (10 mM $NH_4HCO_3$)=2.22 min.

Step 2

To the solution of tert-butyl 4-(6-(4-chloro-2-fluorobenzyloxy) pyridin-2-yl)-3-oxopiperazine-1-carboxylate (70 mg, 0.16 mmol) in DCM (5 mL) was added TFA (1 mL), the mixture was stirred at 25° C. for 1 h. The mixture was diluted with saturated aq. $NaHCO_3$ until pH was adjusted to 7, extracted with DCM (50 mL×3). The combined organic was washed with brine (20 mL×3), dried over $Na_2SO_4$ and concentrated in vacuo to give 1-(6-(4-chloro-2-fluorobenzyloxy) pyridin-2-yl) piperazin-2-one (40 mg, 0.12 mmol) as yellow oil. LCMS: [M+H]⁺=335.7; Retention time (0.01% TFA)=1.40 min.

Step 3

To a solution of 1-(6-(4-chloro-2-fluorobenzyloxy)pyridin-2-yl)piperazin-2-one (40 mg, 0.12 mmol) in 1,4-Dioxane (5 mL) was added (S)-tert-butyl 2-(chloromethyl)-3-(oxetan-2-ylmethyl)-3H-benzo[d]imidazole-5-carboxylate (40 mg, 0.12 mmol) and DIPEA (46 mg, 0.36 mmol). The mixture was stirred at 90° C. for 3 h. The reaction was cooled to RT, diluted with water (50 mL) and extracted with DCM (50 mL×3). The combine organic was washed with brine (50 mL×3), dried over $Na_2SO_4$ and concentrated in vacuo to give crude product, which was purified by chromatography column on silica gel (PE/EA=3/1) to give (S)-tert-butyl 2-((4-(6-(4-chloro-2-fluorobenzyloxy)pyridin-2-yl)-3-oxopiperazin-1-yl)methyl)-3-(oxetan-2-ylmethyl)-3H-benzo[d]imidazole-5-carboxylate (35 mg, 0.06 mmol, 46.1% yield) as yellow oil. LCMS: [M+H]⁺=635.7; Retention time (0.01% TFA)=1.91 min.

Step 4

To a solution of (S)-tert-butyl 2-((4-(6-(4-chloro-2-fluorobenzyloxy)pyridin-2-yl)-3-oxopiperazin-1-yl)methyl)-3-(oxetan-2-ylmethyl)-3H-benzo[d]imidazole-5-carboxylate (35 mg, 0.06 mmol) in DCM (5 mL) was added TFA (1 mL). The mixture was stirred at 25° C. for 4 h. Then the mixture was diluted with water (50 mL), extracted with DCM (50 mL×3). The combined organic layer was dried over $Na_2SO_4$ and concentrated in vacuo to give crude product, which was purified by prep-HPLC to give (S)-2-((4-(6-(4-chloro-2-fluorobenzyloxy)pyridin-2-yl)-3-oxopiperazin-1-yl) methyl)-3-(oxetan-2-ylmethyl)-3H-benzo[d]imidazole-5-carboxylic acid (11.9 mg, 37.2% yield) as white solid.

LCMS: [M+H]⁺=580.0; Retention time (10 mM $NH_4HCO_3$)=1.43 min.

¹H NMR (400 MHz, DMSO-d6) δ 8.29-8.25 (d, J=0.9 Hz, 1H), 7.82 (dd, J=8.4, 1.5 Hz, 1H), 7.75 (t, J=8.0 Hz, 1H), 7.67 (d, J=8.5 Hz, 1H), 7.58-7.53 (m, 2H), 7.48 (dd, J=10.0, 2.0 Hz, 1H), 7.31 (dd, J=8.2, 1.8 Hz, 1H), 6.69 (d, J=7.9 Hz, 1H), 5.35 (s, 2H), 5.10-5.04 (m, 1H), 4.80 (dd, J=15.3, 7.3 Hz, 1H), 4.65 (dd, J=15.2, 2.5 Hz, 1H), 4.47 (dd, J=13.6, 7.7 Hz, 1H), 4.36 (dt, J=9.0, 5.9 Hz, 1H), 4.08 (d, J=13.7 Hz, 1H), 3.95 (d, J=13.7 Hz, 1H), 3.86 (t, J=5.5 Hz, 2H), 3.42 (d, J=16.5 Hz, 2H), 2.93 (t, J=5.3 Hz, 2H), 2.71-2.64 (m, 1H), 2.45-2.35 (m, 1H).

(S)-2-((4-(6-((4-chloro-2-fluorobenzyl)oxy)pyridin-2-yl)-3-oxo-1,4-diazepan-1-yl)methyl)-1-(oxetan-2-ylmethyl)-1H-benzo[d]imidazole-6-carboxylic acid (Compound 56

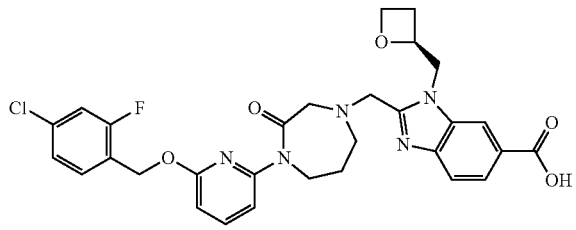

Compound 56

Prepared in analogous manner as for Compound 55

LCMS: [M+H]⁺=594.0; Retention time (10 mM $NH_4HCO_3$)=1.47 min.

¹H NMR (400 MHz, DMSO-d6) δ 8.23 (s, 1H), 7.80 (d, J=8.4 Hz, 1H), 7.74 (t, J=8.0 Hz, 1H), 7.62 (d, J=8.4 Hz, 1H), 7.56 (t, J=8.2 Hz, 1H), 7.50 (dd, J=10.0, 1.9 Hz, 1H), 7.32 (dd, J=13.6, 4.8 Hz, 2H), 6.69 (d, J=8.0 Hz, 1H), 5.37 (s, 2H), 5.02 (d, J=4.8 Hz, 1H), 4.74 (dd, J=15.2, 7.2 Hz, 1H), 4.58 (d, J=12.8 Hz, 1H), 4.44 (dd, J=13.8, 7.4 Hz, 1H), 4.35 (dd, J=14.9, 6.0 Hz, 1H), 4.15 (d, J=13.9 Hz, 1H), 4.04 (d, J=13.9 Hz, 3H), 3.77 (d, J=7.4 Hz, 2H), 2.90 (s, 2H), 2.68-2.56 (m, 1H), 2.40-2.32 (m, 1H), 1.85 (s, 2H).

((S)-2-((4-(6-((4-chloro-2-fluorobenzyl)oxy)pyridin-2-yl)-5-oxo-1,4-diazepan-1-yl)methyl)-1-(oxetan-2-ylmethyl)-1H-benzo[d]imidazole-6-carboxylic acid (Compound 57)

Compound 57

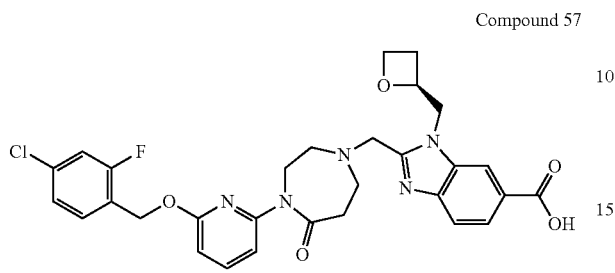

Prepared in analogous manner as for Compound 55

LCMS: [M+H]⁺=594.0; Retention time (10 mM NH₄HCO₃)=1.40 min.

¹H NMR (400 MHz, DMSO-d6) δ 8.29-8.25 (brs, 1H), 7.80 (dd, J=8.4, 1.5 Hz, 1H), 7.72 (t, J=8.0 Hz, 1H), 7.64 (d, J=8.4 Hz, 1H), 7.50-7.43 (m, 2H), 7.38 (d, J=7.8 Hz, 1H), 7.29 (dd, J=8.2, 1.8 Hz, 1H), 6.65 (d, J=8.0 Hz, 1H), 5.32-5.23 (m, 2H), 5.09-5.02 (m, 1H), 4.77 (dd, J=15.3, 7.4 Hz, 1H), 4.61 (dd, J=15.2, 2.4 Hz, 1H), 4.49-4.43 (m, 1H), 4.39-4.32 (m, 1H), 4.18-4.08 (m, 2H), 4.04 (d, J=13.8 Hz, 1H), 3.90 (d, J=13.7 Hz, 1H), 2.85-2.81 (m, 2H), 2.80-2.71 (m, 4H), 2.70-2.64 (m, 1H), 2.41-2.32 (m, 1H).

(S)-2-((4-(4-((4-chloro-2-fluorobenzyl)oxy)-3H-imidazo[4,5-c]pyridin-6-yl)-3,6-dihydropyridin-1(2H)-yl)methyl)-1-(oxetan-2-ylmethyl)-1H-benzo[d]imidazole-6-carboxylic acid (Compound 58)

Compound 58

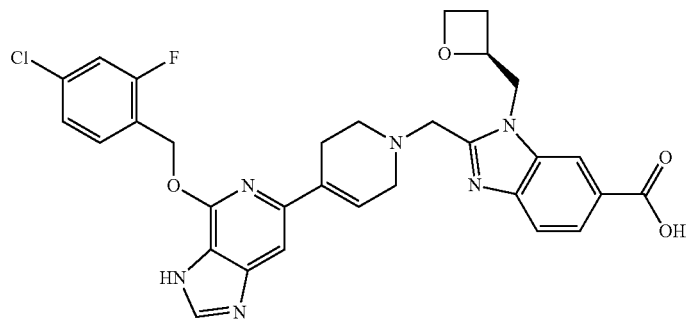

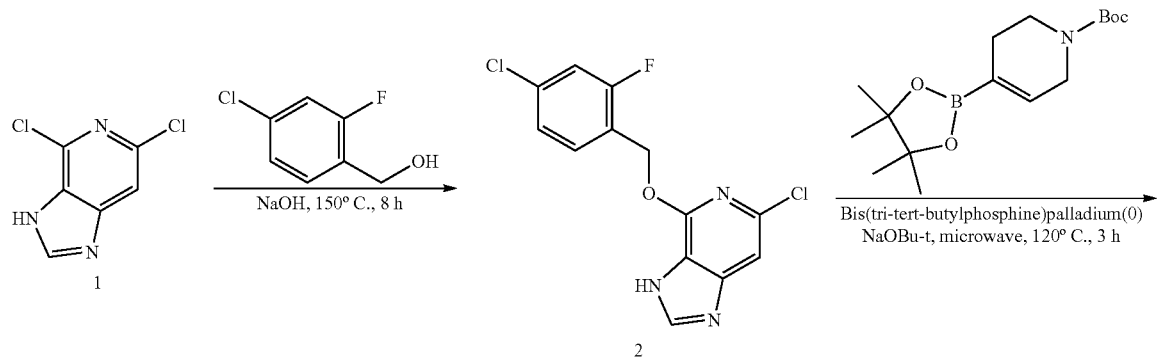

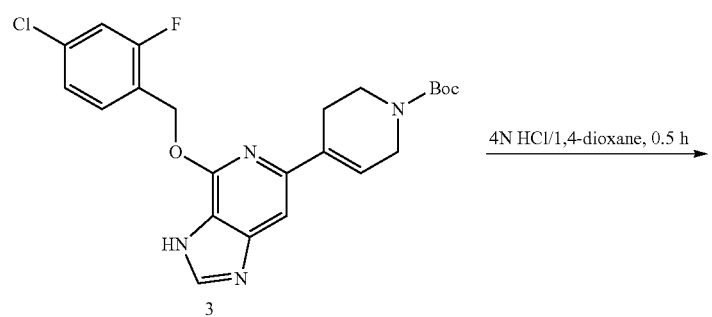

-continued

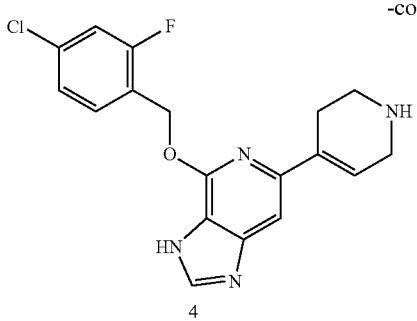 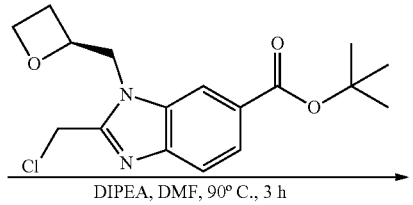

DIPEA, DMF, 90° C., 3 h

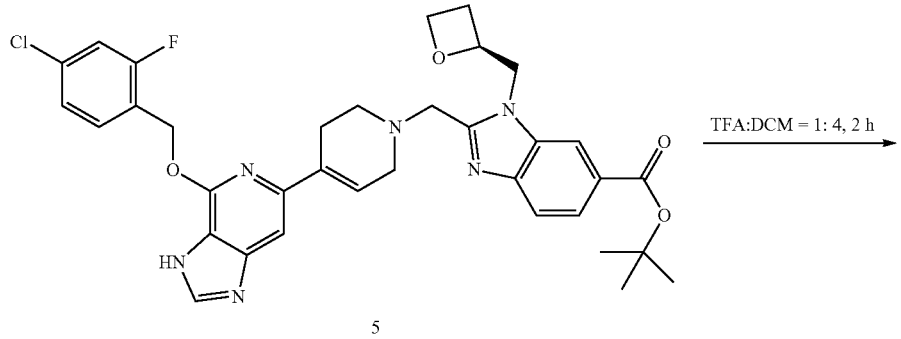

TFA:DCM = 1: 4, 2 h

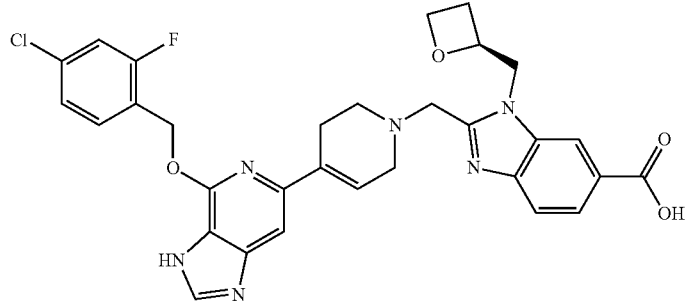

Compound 58

Step 1

To the mixture of 4,6-dichloro-3H-imidazo[4,5-c]pyridine (500 mg, 2.67 mmol) and NaOH (642 mg, 8.02 mmol) in DMF (10 mL) was added (4-chloro-2-fluorophenyl)methanol (1.3 g, 16.04 mmol) and the mixture was stirred at 150° C. for 8 h. The mixture was diluted with water and TFA was added to adjust the PH to 7, extracted with DCM (20 mL×3). The combined organics were washed with brine (10 mL×3), dried over Na$_2$SO$_4$ and concentrated in vacuo to give crude product, which was purified by silica gel column (PE:EA=1:5) to obtain the desired product (400 mg, 40% yield).

LCMS: [M+H]$^+$=312.0, 314.0, Retention time (10 mM NH$_4$HCO$_3$)=1.58 min.

Step 2

The mixture of 6-chloro-4-((4-chloro-2-fluorobenzyl)oxy)-3H-imidazo[4,5-c]pyridine (200 mg, 0.64 mmol) and tert-butyl 4-(4,4,5,5-tetramethyl-1,3,2-dioxaborolan-2-yl)-3,6-dihydropyridine-1(2H)-carboxylate (238 mg, 0.72 mmol), Bis(tri-tert-butylphosphine)palladium(0) (33 mg, 0.064 mmol) and t-BuONa (185 mg, 1.92 mmol) in DMF (4 mL) and H$_2$O (1 mL) was stirred at 120° C. for 3 h under microwave. The mixture was concentrated to yield a residue which was purified by prep-HPLC to obtain the desired product (60 mg, 20% yield). LCMS: [M+H]$^+$=459.2, Retention time (0.01% TFA)=1.90 min.

Step 3

The solution of tert-butyl 4-(4-((4-chloro-2-fluorobenzyl)oxy)-3H-imidazo[4,5-c]pyridin-6-yl)-3,6-dihydropyridine-1(2H)-carboxylate (60 mg, 0.13 mmol) in HCl/dioxane (4 N, 1 mL) was stirred at 25° C. for 0.5 h. The reaction was concentrated to yield a residue (45 mg, Crude), which was used in the next step without further purification.

LCMS: [M+H]$^+$=358.9, Retention time (10 mM NH$_4$HCO$_3$)=1.28 min.

Step 4

To a solution of 4-((4-chloro-2-fluorobenzyl)oxy)-6-(1,2,3,6-tetrahydropyridin-4-yl)-3H-imidazo[4,5-c]pyridine (45 mg, 0.125 mmol, 1.0 eq) in DMF (3 mL) was added tert-butyl (S)-2-(chloromethyl)-1-(oxetan-2-ylmethyl)-1H-benzo[d]imidazole-6-carboxylate (40 mg, 0.119 mmol, 0.950 eq) and DIPEA (161 mg, 1.25 mmol, 10 eq). The reaction mixture was purified by TLC (PE:EA=1:1, R$_f$=0.25) to obtain the desired product (40 mg, 0.06 mmol, 40% yield). LCMS: [M+H]$^+$=659.7, Retention time (10 mM NH$_4$HCO$_3$)=1.77 min.

Step 5

A solution of tert-butyl (S)-2-((4-(4-((4-chloro-2-fluorobenzyl)oxy)-3H-imidazo[4,5-c]pyridin-6-yl)-3,6-dihydropyridin-1(2H)-yl)methyl)-1-(oxetan-2-ylmethyl)-1H-benzo[d]imidazole-6-carboxylate (40 mg, 0.06 mmol) in TFA (1 mL) and DCM (4 mL) was stirred at 20° C. for 2 h. The mixture was neutralized to PH=7 by aq. ammonia solution (0.1 mL), and purified by prep-HPLC to obtain the desired product (S)-2-((4-(4-((4-chloro-2-fluorobenzyl)oxy)-3H-imidazo[4,5-c]pyridin-6-yl)-3,6-dihydropyridin-1(2H)-yl)methyl)-1-(oxetan-2-ylmethyl)-1H-benzo[d]imidazole-6-carboxylic acid (10.6 mg, 29% yield) as white solid. LCMS: [M+H]$^+$=603.2, Retention time (10 mM NH$_4$HCO$_3$)=1.24 min.

$^1$H NMR (400 MHz, CD$_3$OD) δ 8.34 (s, 1H), 8.20 (s, 1H), 8.00 (dd, J=8.5, 1.4 Hz, 1H), 7.70 (d, J=8.5 Hz, 1H), 7.61 (t, J=7.9 Hz, 1H), 7.29 (dd, J=8.0, 1.5 Hz, 1H), 7.23 (d, J=7.8 Hz, 2H), 6.24 (s, 1H), 5.60-5.58 (brs, 2H), 5.34-5.18 (m, 1H), 4.88 (d, J=7.3 Hz, 1H), 4.74 (dd, J=15.4, 2.5 Hz, 1H), 4.70-4.56 (m, 2H), 4.47 (dt, J=9.2, 5.9 Hz, 1H), 4.18 (d, J=13.7 Hz, 1H), 4.06 (d, J=13.7 Hz, 1H), 3.27 (d, J=21.8 Hz, 2H), 2.88 (d, J=5.7 Hz, 2H), 2.79 (dt, J=22.0, 7.9 Hz, 1H), 2.60-2.58 (brs, 2H), 2.51 (dd, J=19.2, 8.3 Hz, 1H).

(S)-2-((4-(5-(4-chloro-2-fluorobenzyl)-2,3,4,5-tetrahydropyrido[3,2-b][1,4]oxazepin-7-yl)-3,6-dihydropyridin-1(2H)-yl)methyl)-1-(oxetan-2-ylmethyl)-1H-benzo[d]imidazole-6-carboxylic acid
(Compound 59)

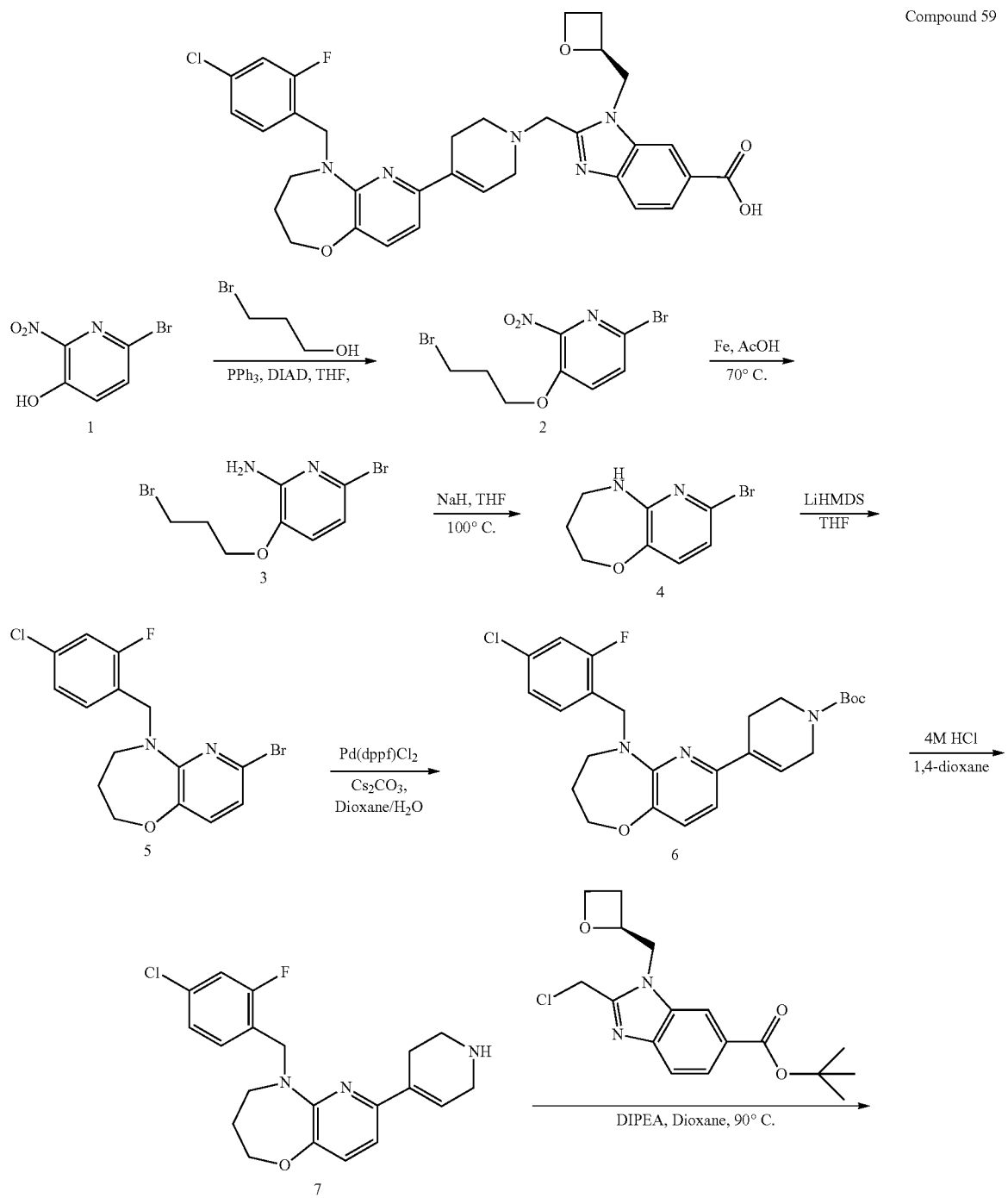

Compound 59

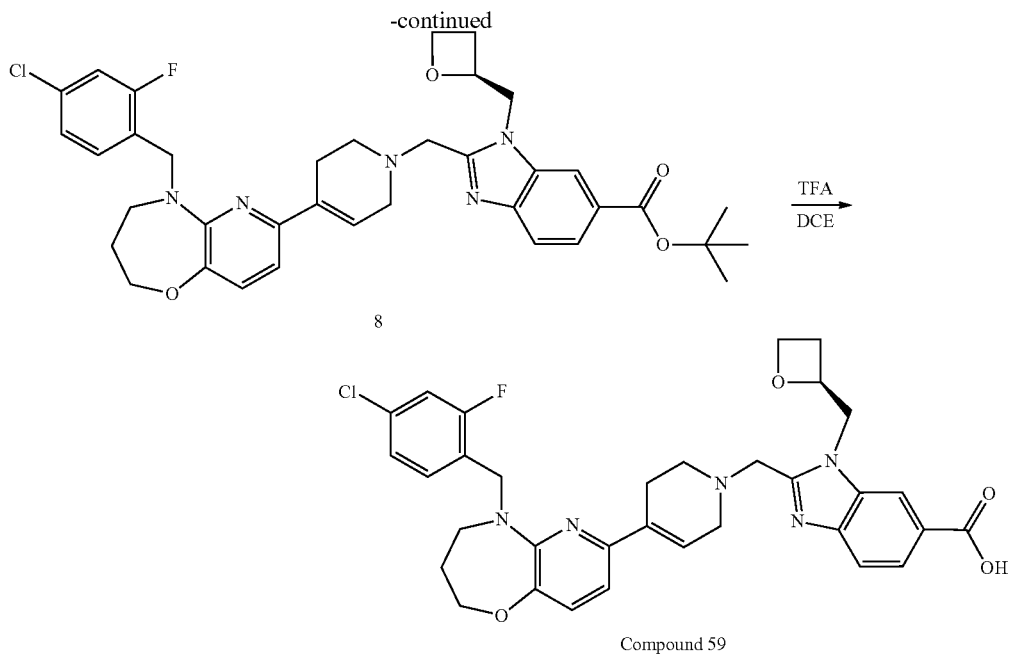

Compound 59

Step 1

To a solution of 3-bromopropan-1-ol (1.5 g, 10.8 mmol), 6-bromo-2-nitropyridin-3-ol (2.6 g, 11.9 mmol) and PPh$_3$ (4.3 g, 16.2 mmol) in THF (50 mL) was added DIAD (3.3 g, 16.2 mmol) at 0° C. The mixture was stirred at 25° C. for 24 hours. Water (80 mL) was added and extracted with ethyl acetate (75 mL×3).

The combined organic layer was washed with brine (70 mL×3), dried over Na$_2$SO$_4$ and was concentrated in vacuo to give crude product. The crude product was purified by column chromatography on silica gel (PE/EA=8/1) to give 6-bromo-3-(3-bromopropoxy)-2-nitropyridine (2.95 g, 80.4% yield) as a yellow solid. LCMS: [M+H]$^+$=340.9, Retention time (0.01% TFA)=1.85 min.

Step 2

To a solution of 6-bromo-3-(3-bromopropoxy)-2-nitropyridine (2.5 g, 7.35 mmol) in AcOH (80 mL) was added Fe (3.29 g, 58.8 mmol). The mixture was stirred at 70° C. for 2 h. The reaction solution was concentrated in vacuo to give crude product. Water (100 mL) was added and extracted with ethyl acetate (70 mL×3). The combined organic layer was washed with brine (100 mL×2), dried over Na$_2$SO$_4$ and was concentrated in vacuo to give crude product. The crude product was purified by column chromatography on silica gel (PE/EA=4/1) to 6-bromo-3-(3-bromopropoxy)pyridin-2-amine (1.2 g, 52.6% yield) as a yellow solid. LCMS: [M+H]$^+$=310.9, Retention time (0.01% TFA)=1.75 min.

Step 3

To a solution of 6-bromo-3-(3-bromopropoxy) pyridin-2-amine (0.4 g, 1.29 mmol) in THF (50 mL) was added NaH (0.103 g, 2.58 mmol) at 0° C. The mixture was heated to 100° C. and stirred for 24 h. Water (60 mL) was added and extracted with ethyl acetate (40 mL×3). The combined organic layer was washed with brine (50 mL×2), dried over Na$_2$SO$_4$ and was concentrated in vacuo to give crude product. The crude product was purified by column chromatography on silica gel (PE/EA=5/1) to give 7-bromo-2,3,4,5-tetrahydropyrido[3,2-b][1,4]oxazepine (160 mg, 53% yield) as a yellow solid. LCMS: [M+H]$^+$=229.0, Retention time (10 mM NH$_4$HCO$_3$)=2.17 min.

Step 4

7-bromo-2,3,4,5-tetrahydropyrido[3,2-b][1,4]oxazepine (110 mg, 0.48 mmol) was solved in THF (6 mL) and was cooled to and −50° C. LiHMDS (0.48 mL, 0.96 mmol) was added dropwise to the reaction mixture and the mixture was stirred for 20 min. A solution of 1-(bromomethyl)-4-chloro-2-fluorobenzene (160 mg, 0.72 mmol) in THF (1 mL) was added to the reaction mixture at −50° C. The mixture was warmed to 25° C. and stirred for 3 h. Water (25 mL) was added and extracted with ethyl acetate (20 mL×3). The combined organic layer was washed with brine (30 mL×2), dried over Na$_2$SO$_4$ and was concentrated in vacuo to give crude product. The crude product was purified by column chromatography on silica gel (PE/EA=5/1) to give 7-bromo-5-(4-chloro-2-fluorobenzyl)-2,3,4,5-tetrahydropyrido[3,2-b][1,4]oxazepine (72 mg, 40% yield) as a yellow solid. LCMS: [M+H]$^+$=370.9, Retention time (10 mM NH$_4$HCO$_3$)= 2.33 min.

Step 5

To a solution of 7-bromo-5-(4-chloro-2-fluorobenzyl)-2,3,4,5-tetrahydropyrido[3,2-b][1,4]oxazepine (70 mg, 0.19 mmol), tert-butyl 4-(4,4,5,5-tetramethyl-1,3,2-dioxaborolan-2-yl)-3,6-dihydropyridine-1(2H)-carboxylate (87 mg, 0.28 mmol), Cs$_2$CO$_3$ (122 mg, 0.38 mmol) in dioxane (5 mL) and H$_2$O (1.3 mL) was added Pd(dppf)Cl$_2$ (14 mg, 0.019 mmol, 0.1 eq) at 25° C. The reaction mixture was stirred for 3 h at 90° C. under N$_2$. Water (15 mL) was added and extracted with ethyl acetate (20 mL×3). The combined organic layer was washed with brine (30 mL×2), dried over Na$_2$SO$_4$ and was concentrated in vacuo to give crude product. The crude product was purified by column chromatography on silica gel (PE/EA=1/1) to give tert-butyl 4-(5-(4-chloro-2-fluorobenzyl)-2,3,4,5-tetrahydropyrido[3,2-b][1,4]oxazepin-7-yl)-3,6-dihydropyridine-1(2H)-carboxylate (61 mg, 56% yield) as a yellow solid. LCMS: [M+H]$^+$=474.0, Retention time (10 mM NH$_4$HCO$_3$)=4.10 min.

Step 6

Tert-butyl 4-(5-(4-chloro-2-fluorobenzyl)-2,3,4,5-tetrahydropyrido[3,2-b][1,4]oxazepin-7-yl)-3,6-dihydropyridine-1(2H)-carboxylate (45 mg, 0.095 mmol) was dissolved in DCM (3 mL). The reaction mixture was added HCl/dioxane (1 mL, 4 N) and was stirred at 25° C. for 2 h. The mixture was diluted with DCM (10 mL) and DIPEA (1 mL) was added to the above reaction mixture. The solution was concentrated to give the desired product 5-(4-chloro-2-fluorobenzyl)-7-(1,2,3,6-tetrahydropyridin-4-yl)-2,3,4,5-tetrahydropyrido[3,2-b][1,4]oxazepine (40 mg, crude), which was used for the next step directly.

LCMS: [M+H]$^+$=374.0, Retention time (10 mM NH$_4$HCO$_3$)=1.65 min.

Step 7

A mixture of 5-(4-chloro-2-fluorobenzyl)-7-(1,2,3,6-tetrahydropyridin-4-yl)-2,3,4,5-tetrahydropyrido[3,2-b][1,4]oxazepine (35 mg, 0.094 mmol), tert-butyl (S)-2-(chloromethyl)-1-(oxetan-2-ylmethyl)-1H-benzo[d]imidazole-6-carboxylate (38 mg, 0.113 mmol), DIPEA (121 mg, 0.94 mmol) in DMF (3 mL) was stirred at 60° C. for 3 h. MeOH (1 mL) was added to the reaction solution. The solution was purified by prep-HPLC to give tert-butyl (S)-2-((4-(5-(4-chloro-2-fluorobenzyl)-2,3,4,5-tetrahydropyrido[3,2-b][1,4]oxazepin-7-yl)-3,6-dihydropyridin-1(2H)-yl)methyl)-1-(oxetan-2-ylmethyl)-1H-benzo[d]imidazole-6-carboxylate (12 mg, 19% yield) as a yellow solid. LCMS: [M+H]$^+$=674.0, Retention time (10 mM NH$_4$HCO$_3$)=2.48 min.

Step 8

Tert-butyl(S)-2-((4-(5-(4-chloro-2-fluorobenzyl)-2,3,4,5-tetrahydropyrido[3,2-b][1,4] oxazepin-7-yl)-3,6-dihydropyridin-1(2H)-yl)methyl)-1-(oxetan-2-ylmethyl)-1H-benzo[d] imidazole-6-carboxylate (12 mg, 0.018 mmol, 1.0 eq) was solved in TFA (0.5 mL) and DCE (4 mL). The reaction mixture was stirred at 25° C. for 8 h. The reaction solution was concentrated in vacuo to give crude product. The crude product was purified by prep-HPLC to give (S)-2-((4-(5-(4-chloro-2-fluorobenzyl)-2,3,4,5-tetrahydropyrido[3,2-b][1,4] oxazepin-7-yl)-5,6-dihydropyridin-1(2H)-yl)methyl)-1-(oxetan-2-ylmethyl)-1H-benzo[d]imidazole-6-carboxylic acid (2.1 mg, 19% yield) as a yellow solid.

LCMS: [M+H]$^+$=618.2, Retention time (10 mM NH$_4$HCO$_3$)=1.44 min.

$^1$H NMR (400 MHz, DMSO) δ 8.24 (s, 1H), 7.80 (d, J=8.4 Hz, 1H), 7.64 (d, J=8.5 Hz, 1H), 7.39 (dd, J=10.1, 2.0 Hz, 1H), 7.33 (t, J=8.3 Hz, 1H), 7.21 (d, J=8.0 Hz, 1H), 7.06 (d, J=8.0 Hz, 1H), 6.74 (d, J=8.0 Hz, 1H), 6.38 (s, 1H), 5.03 (d, J=7.0 Hz, 1H), 4.76 (d, J=14.3 Hz, 3H), 4.62 (d, J=12.7 Hz, 1H), 4.47-4.32 (m, 1H), 4.15 (t, J=6.2 Hz, 2H), 3.94 (dd, J=65.8, 13.5 Hz, 1H), 3.51 (s, 2H), 3.13 (s, 2H), 2.66 (d, J=9.8 Hz, 4H), 2.35 (d, J=11.4 Hz, 4H), 1.99-1.91 (m, 3H).

2-((6-(((6-chloro-1,2,3,4-tetrahydronaphthalen-1-yl)oxy)-3',6'-dihydro-[2,4'-bipyridin]-1'(2'H)-yl)methyl)-1-(((S)-oxetan-2-yl)methyl)-1H-benzo[d]imidazole-6-carboxylic acid (Compound 60)

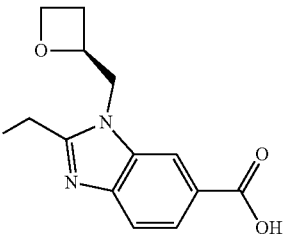

Compound 60

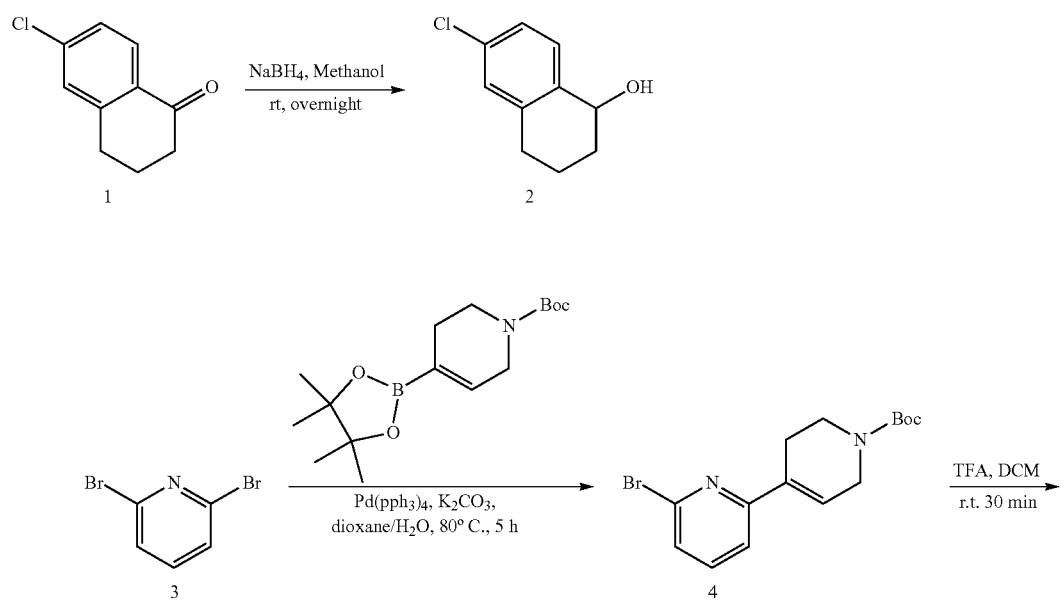

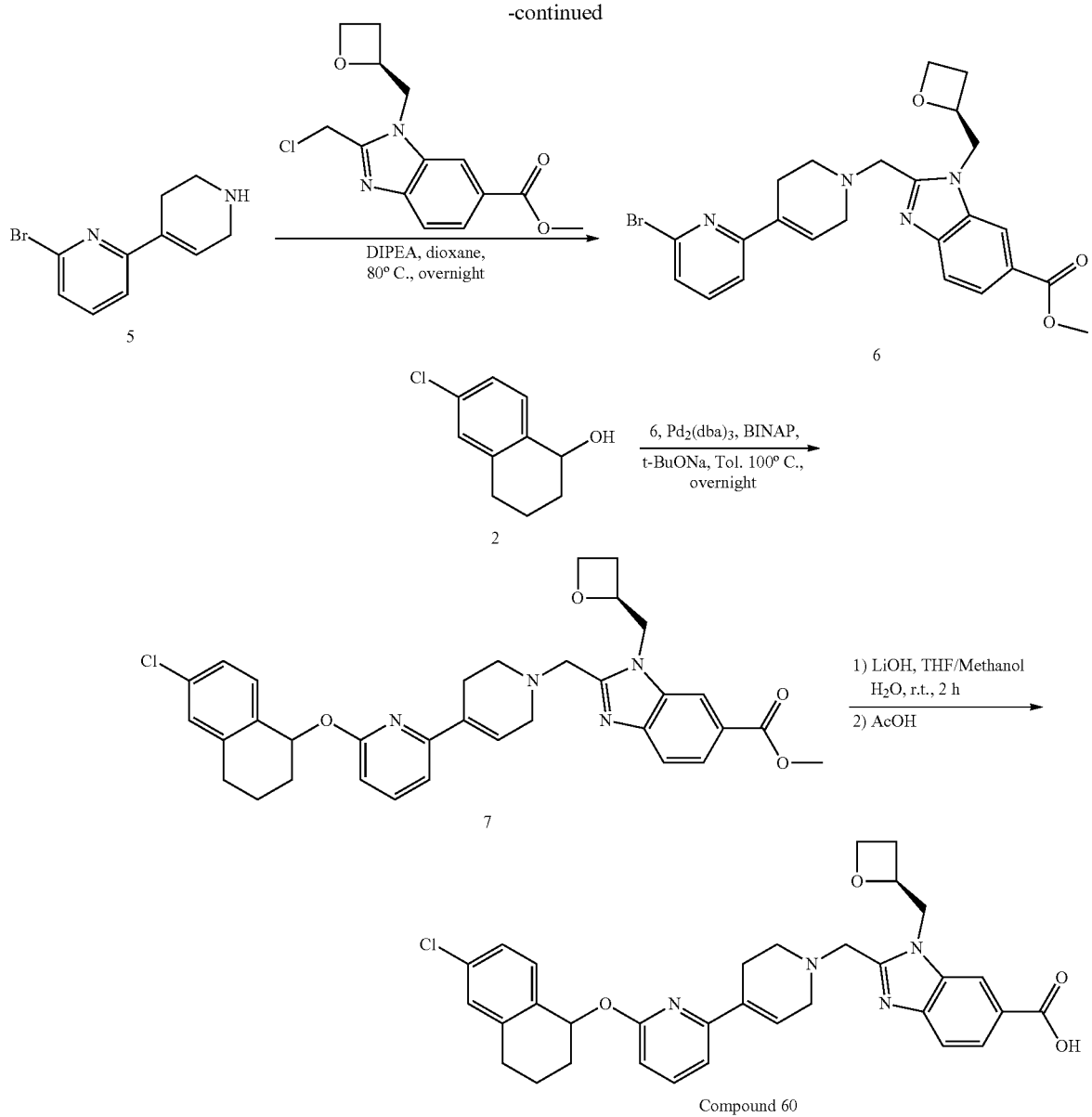

Step 1

To the solution of 6-chloro-3,4-dihydronaphthalen-1(2H)-one (500 mg, 2.768 mmol) in methanol (5 mL) was added NaBH₄ (126 mg, 3.330 mmol) at 0° C. The reaction mixture was stirred at RT overnight. Methanol was evaporated and a white solid was obtained. Sat. NH₄Cl (50 mL) and EA (100 mL) were added and the aqueous phase was extracted by EA (50 mL×2). The combined organic phase was dried by Na₂SO₄. The solvent was evaporated to give the crude product 6-chloro-1,2,3,4-tetrahydronaphthalen-1-ol (520 mg, yield 100%) as a pale yellow liquid. The crude product was used for next step without further purification. LCMS: [M+Na]=183.7; Retention time (0.01% TFA)=1.73 min.

Step 2

To the solution of 2,6-dibromopyridine (1 g, 4.221 mmol) in dioxane (25 mL) and H₂O (5 mL) were added tert-butyl 4-(4,4,5,5-tetramethyl-1,3,2-dioxaborolan-2-yl)-5,6-dihydropyridine-1(2H)-carboxylate (1.56 g, 5.045 mmol), Pd(PPh₃)₄ (500 mg, 0.422 mmol) and K₂CO₃ (1.46 g, 10.552 mmol) under N₂. The reaction mixture was stirred at 80° C. for 5 h. The reaction mixture was cooled to RT and EA (100 mL) was added. The reaction mixture was filtered and the mixture was extracted with EA (50 mL×2). The combined organic phase was washed by sat. NaCl. The organic phase was dried by Na₂SO₄. The crude product was purified by chromatography (PE/EA=10/1) to give the desired compound tert-butyl 6-bromo-5',6'-dihydro-[2,4'-bipyridine]-1'(2'H)-carboxylate (530 mg, yield 37%) as a pale yellow liquid.

LCMS: [M+Na]=361.0; Retention time (0.01% TFA)=2.15 min.

Step 3

To the solution of tert-butyl 6-bromo-5',6'-dihydro-[2,4'-bipyridine]-1'(2'H)-carboxylate (150 mg, 0.442 mmol) in DCM (5 mL) was added TFA (1 mL). The reaction mixture was stirred at RT for 30 min. DCM was evaporated to give the crude product 6-bromo-1',2',3',6'-tetrahydro-2,4'-bipyridine (90 mg, yield 85%) as a pale yellow liquid. The crude product was used for next step without further purification.

LCMS: [M+H]⁺=239.7; Retention time (0.01% TFA)=1.13 min.

Step 4

To the solution of 6-bromo-1',2',3',6'-tetrahydro-2,4'-bipyridine (90 mg, 0.376 mmol) in dioxane (5 mL) were added (S)-methyl 2-(chloromethyl)-1-(oxetan-2-ylmethyl)-1H-benzo[d]imidazole-6-carboxylate (100 mg, 0.339 mmol; The values of the optical rotation, $[\alpha]_{25.1° C. 589 nm}$=–30.06 (c=0.1, MeOH)) and DIPEA (700 mg, 5.416 mmol) at RT. The reaction mixture was stirred at 80° C. overnight. The solvent was evaporated. The residue was purified by prep-HPLC to give the expected product (150 mg, yield 80%) as a pale yellow solid. LCMS: [M+H]⁺=499.7; Retention time (0.01% TFA)=1.49 min.

Step 5

To the solution of (S)-methyl 2-(chloromethyl)-1-(oxetan-2-ylmethyl)-1H-benzo[d]imidazole-6-carboxylate (10 mg, 0.020 mmol), 6-chloro-1,2,3,4-tetrahydronaphthalen-1-ol (5 mg, 0.027 mmol) in toluene (5 mL) were added Pd₂(dba)₃ (2 mg, 0.002 mmol), BINAP (2 mg, 0.003 mmol) and t-BuONa (5 mg, 0.052 mmol) under N₂. The reaction mixture was heated to 100° C. The reaction mixture was stirred at 100° C. overnight. The solvent was evaporated. The residue was purified by prep-HPLC to give the expected product methyl 2-((6-(((6-chloro-1,2,3,4-tetrahydronaphthalen-1-yl)oxy)-5', 6'-dihydro-[2,4'-bipyridin]-1'(2'H)-yl)methyl)-1-((S)-oxetan-2-ylmethyl)-1H-benzo[d]imidazole-6-carboxylate (7.5 mg, yield 63%) as a yellow solid. LCMS: [M+H]⁺=599.2, Retention time (10 mm NH₄HCO₃)=2.05 min.

Step 6

To the solution of methyl 2-((6-(((6-chloro-1,2,3,4-tetrahydronaphthalen-1-yl)oxy)-5',6'-dihydro-[2,4'-bipyridin]-1'(2'H)-yl)methyl)-1-((S)-oxetan-2-ylmethyl)-1H-benzo[d]imidazole-6-carboxylate (7.5 mg, 0.013 mmol) in THF (0.5 mL) was added methanol (0.5 mL), H₂O (0.5 mL) and LiOH (7.5 mg, 0.407 mmol). The reaction mixture was stirred at RT for 2 h. The solvents were evaporated. The residue was purified by prep-HPLC to give the expected product 2-((6-((6-chloro-1,2,3,4-tetrahydronaphthalen-1-yl)oxy)-5',6'-dihydro-[2,4'-bipyridin]-1'(2'H)-yl)methyl)-1-((S)-oxetan-2-ylmethyl)-1H-benzo[d]imidazole-6-carboxylic acid (1.3 mg, yield 19%) as a white solid.

LCMS: [M+H]⁺=585.0, Retention time (10 mm NH₄HCO₃)=1.49 min.

2-((4-(6-(7-chlorochroman-4-ylamino)pyridin-2-yl)-5,6-dihydropyridin-1(2H)-yl)methyl)-1-((S)-oxetan-2-ylmethyl)-1H-benzo[d]imidazole-6-carboxylic acid (Compound 61)

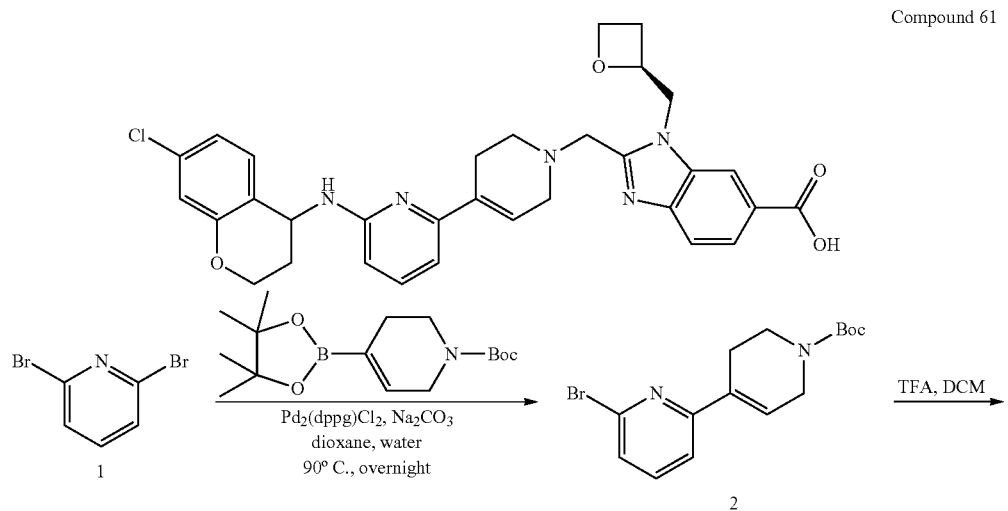

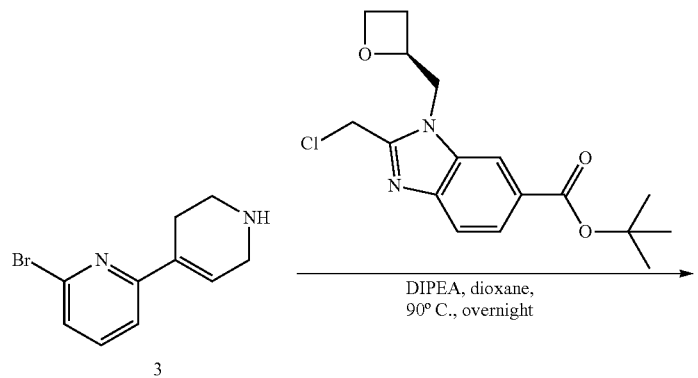

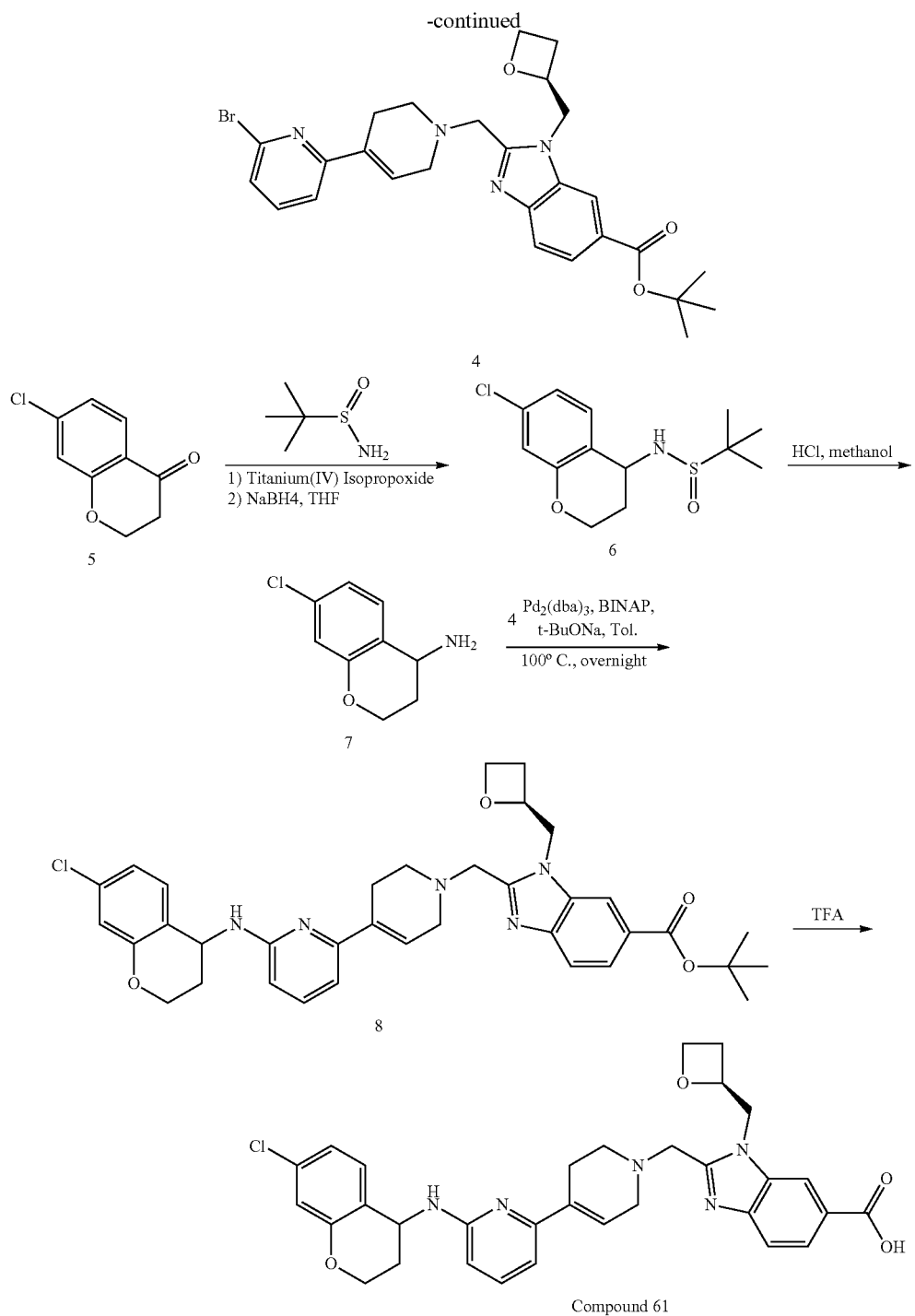

Compound 61

Step 1

To the solution of 2,6-dibromopyridine (2.37 g, 10 mmol) in dioxane (60 mL) and water (12 mL) was added tert-butyl 4-(4,4,5,5-tetramethyl-1,3,2-dioxaborolan-2-yl)-5,6-dihydropyridine-1(2H)-carboxylate (3.70 g, 12 mmol), Pd(dppf)Cl$_2$ (146 mg, 0.2 mmol) and Na$_2$CO$_3$ (2.12 g, 20 mmol) under N$_2$. The reaction mixture was stirred at 90° C. for 12 h. 80 mL of ice water was added to quench the reaction. The solution was extracted with EA (80 mL×3), washed with brine and dried in Na$_2$SO$_4$. After evaporation of solvent, the crude was purified with column chromatography (PE/EA=5/1) to give tert-butyl 4-(6-bromopyridin-2-yl)-5,6-dihydropyridine-1(2H)-carboxylate (1.8 g, 53%) as a yellow oil.

LCMS (M−55)+=283.0; Retention time (10 mm NH$_4$HCO$_3$)=1.84 min.

Step 2

To the solution of tert-butyl 4-(6-bromopyridin-2-yl)-5,6-dihydropyridine-1(2H)-carboxylate (1.69 g, 5 mmol) in DCM (10 mL) was added TFA (10 mL) at 0° C. The reaction mixture was stirred at 0° C. for 1 h. After evaporation of solvent, the crude was used in the next run without further purification.

LCMS: [M+H]⁺=322; Retention time (0.01% TFA)=1.59 min.

Step 3

To the solution of 2-bromo-6-(1,2,3,6-tetrahydropyridin-4-yl)pyridine (238 mg, 1 mmol) in dioxane (10 mL) was added (S)-tert-butyl 2-(chloromethyl)-1-(oxetan-2-ylmethyl)-1H-benzo[d]imidazole-6-carboxylate (370 mg, 1.1 mmol) and DIEA (388 mg, 3.0 mmol). The reaction mixture was stirred at 90° C. for 6 h. 60 mL of ice water was added to quench the reaction. The solution was extracted with EA (40 mL×3), washed with brine and dried in Na₂SO₄. After evaporation of solvent, the crude was purified with column chromatography (PE/EA=1/1) to give (S)-tert-butyl 2-((4-(6-bromopyridin-2-yl)-5,6-dihydropyridin-1(2H)-yl)methyl)-1-(oxetan-2-ylmethyl)-1H-benzo[d]imidazole-6-carboxylate (323 mg, 60%) as a yellow solid. LCMS: [M+H]⁺=539.2; Retention time (0.01% TFA)=1.72 min.

Step 4

To the solution of 7-chlorochroman-4-one (546 mg, 3 mmol) in DCM (10 mL) was added 2-methylpropane-2-sulfinamide (472 mg, 3.9 mmol) and Titanium tetraisopropanolate (3.3 g, 12 mmol). The mixture was heated at 70° C. overnight. The reaction mixture was cooled to 0° C. and sodium borohydride (228 mg, 6 mmol) was added. The mixture was stirred at RT for 2 h. NH₄Cl solution was added to quench the reaction. The solution was extracted with EA (50 mL×3), washed with brine and dried in Na₂SO₄. After evaporation of solvent, the crude was purified with column chromatography (PE/EA=2/1) to give N-(7-chlorochroman-4-yl)-2-methylpropane-2-sulfinamide (400 mg, 46%) as a yellow solid. LCMS: [M+H]⁺=288; Retention time (0.01% TFA)=1.77 min.

Step 5

To the solution of N-(7-chlorochroman-4-yl)-2-methylpropane-2-sulfinamide (400 mg, 1.39 mmol) in methanol (5 mL) was added HCl in dioxane (5 mL, 4 N) at 0° C. The reaction mixture was stirred at 0° C. for 1 h. After evaporation of solvent, the crude was used in the next run without further purification.

LCMS: [M-NH₂]⁺=167.0; Retention time (0.01% TFA)=1.13 min.

Step 6

To the solution of 7-chlorochroman-4-amine (30 mg, 0.16 mmol) in toluene (5 mL) was added (S)-tert-butyl 2-((4-(6-bromopyridin-2-yl)-5,6-dihydropyridin-1(2H)-yl)methyl)-1-(oxetan-2-ylmethyl)-1H-benzo[d]imidazole-6-carboxylate (45 mg, 0.08 mmol), Pd₂(dba)₃ (18 mg, 0.02 mmol), BINAP (25 mg, 0.04 mmol), and t-BuONa (46 mg, 0.48 mmol) under N₂. The reaction mixture was stirred at 100° C. for 12 h. 20 mL of ice water was added to quench the reaction. The solution was extracted with EA (40 mL×3), washed with brine and dried in Na₂SO₄. After evaporation of solvent, the crude was purified with HPLC to give tert-butyl 2-((4-(6-(7-chlorochroman-4-ylamino)pyridin-2-yl)-5,6-dihydropyridin-1(2H)-yl)methyl)-1-((S)-oxetan-2-ylmethyl)-1H-benzo[d]imidazole-6-carboxylate (30 mg, 29%) as a yellow oil.

LCMS: [M+H]⁺=642.3; Retention time (0.01% TFA)=1.85 min.

Step 7

To the solution of tert-butyl 2-((4-(6-(7-chlorochroman-4-ylamino)pyridin-2-yl)-5,6-dihydropyridin-1(2H)-yl)methyl)-1-((S)-oxetan-2-ylmethyl)-1H-benzo[d]imidazole-6-carboxylate (30 mg, 0.05 mmol) in DCM (2 mL) was added TFA (2 mL) at 0° C. The reaction mixture was stirred at 0° C. for 2 h. After evaporation of solvent, the crude was purified with HPLC to give 2-((4-(6-(7-chlorochroman-4-ylamino) pyridin-2-yl)-5,6-dihydropyridin-1(2H)-yl)methyl)-1-((S)-oxetan-2-ylmethyl)-1H-benzo[d]imidazole-6-carboxylic acid (6 mg, 21%) as a yellow solid. LCMS: [M+H]⁺=586.2; Retention time (0.01% TFA)=1.48 min.

¹H NMR (400 MHz, MeOD) δ 8.31 (s, 1H), 7.99 (d, J=8.8 Hz, 1H), 7.68 (d, J=8.4 Hz, 1H), 7.39-7.35 (m, 1H), 7.25 (d, J=8.4 Hz, 1H), 6.85-6.82 (m, 1H), 6.79 (d, J=2.0 Hz, 1H), 6.69 (d, J=7.2 Hz, 1H), 6.65-6.64 (brs, 1H), 6.40 (d, J=8.0 Hz, 1H), 5.28-5.24 (m, 2H), 4.90-4.86 (m, 2H), 4.72 (d, J=15.2 Hz, 1H), 4.65-4.60 (m, 1H), 4.50-4.45 (m, 1H), 4.28-4.25 (m, 2H), 4.20-4.04 (m, 2H), 3.32-3.29 (m, 2H), 2.87-2.84 (m, 2H), 2.80-2.73 (m, 1H), 2.66 (bs, 2H), 2.56-2.47 (m, 1H), 2.14 (dd, J=5.2 Hz, 10.4 Hz, 2H).

(S)-3-(2-((4-(6-(4-chloro-2-fluorobenzyloxy)pyridin-2-yl)-5,6-dihydropyridin-1(2H)-yl)methyl)-1-(oxetan-2-ylmethyl)-1H-benzo[d]imidazol-6-yl)-1,2,4-oxadiazol-5(4H)-one (Compound 62)

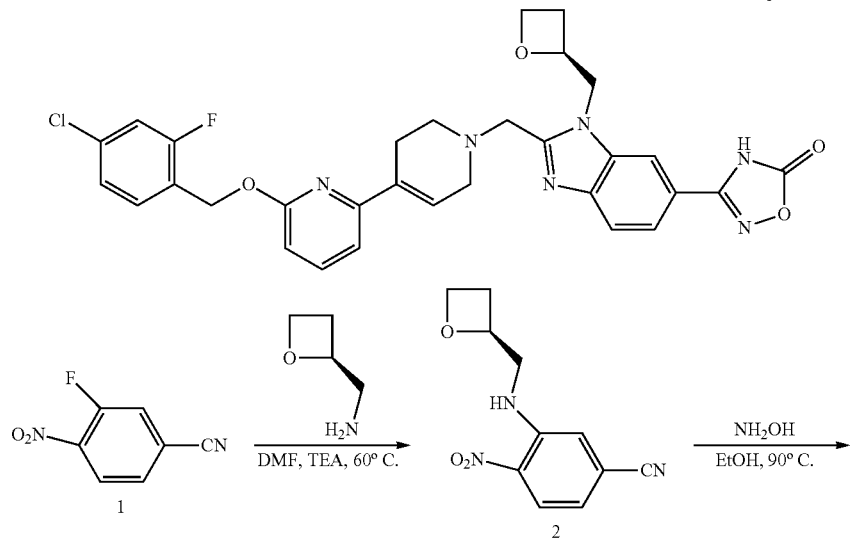

Compound 62

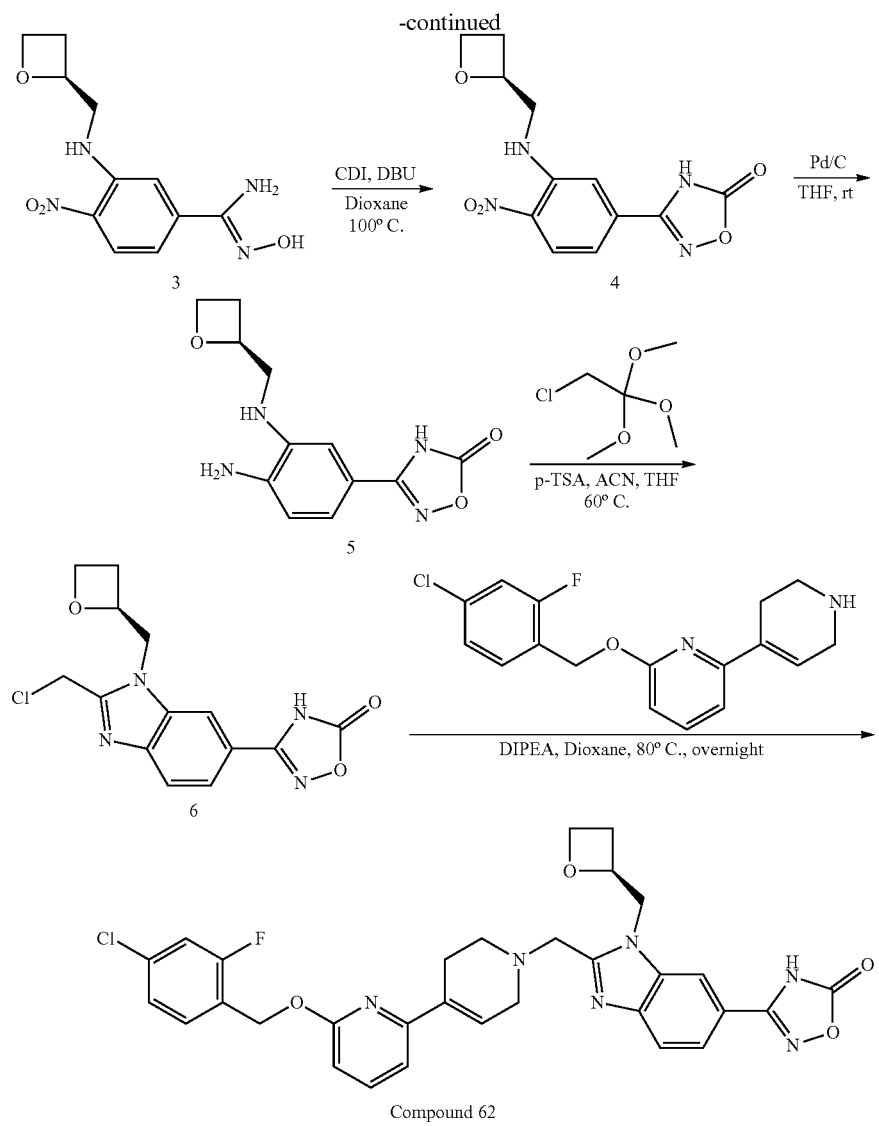

Compound 62

Step 1

A solution of 3-fluoro-4-nitrobenzonitrile (3.0 g, 18.1 mmol), (S)-oxetan-2-ylmethanamine (1.6 g, 18.4 mmol) and TEA (7.5 ml, 54.3 mmol, 3 eq) in DMF (50 mL) was stirred at 60° C. for 3 h. The reaction was diluted with water (50 mL) and extracted with ethyl acetate (50 mL×3), The combine organic was washed with brine (50 mL×3), dried over $Na_2SO_4$, filtered and concentrated in vacuo to give the crude product, which was purified by column chromatography on silica gel (PE:EA=3:1) to give (S)-4-nitro-3-(oxetan-2-ylmethylamino)benzonitrile (2.0 g, 47.6% yield) as a yellow solid. LCMS: [M+H]$^+$=234.0, Retention time (10 mM $NH_4HCO_3$)=1.59 min.

Step 2

To a mixture of (S)-4-nitro-3-(oxetan-2-ylmethylamino)benzonitrile (470 mg, 2 mmol) in EtOH (15 mL) was added $NH_2OH$ (0.238 mL, 4 mmol). The reaction mixture was heated to 90° C. for 18 h. The mixture was evaporated to dryness to give (S,Z)—N'-hydroxy-4-nitro-3-(oxetan-2-ylmethylamino)benzimidamide (450 mg, 84% yield) as a yellow solid.

LCMS: [M+H]$^+$=267.1; Retention time (10 mM $NH_4HCO_3$)=1.28 min.

Step 3

To a mixture of (S,Z)—N'-hydroxy-4-nitro-3-(oxetan-2-ylmethylamino)benzimidamide (250 mg, 0.939 mmol, 1.0 eq) in dioxane (50 mL) was added DBU (157.2 mg, 1.033 mmol) followed by CDI (182.7 mg, 1.13 mmol). The reaction mixture was heated to 100° C. for 18 h. The mixture was evaporated to dryness and purified by prep-HPLC to give crude (S)-3-(4-nitro-3-(oxetan-2-ylmethylamino) phenyl)-1,2,4-oxadiazol-5(4H)-one (260 mg, 95% yield) as light yellow solid. LCMS: [M+H]$^+$=292.2; Retention time (10 mM $NH_4HCO_3$)=1.18 min.

Step 4

To a mixture of (S)-3-(4-nitro-3-(oxetan-2-ylmethylamino) phenyl)-1,2,4-oxadiazol-5(4H)-one (150 mg, 0.513 mmol, 1.0 eq) in THF (15 mL) was added Pd/C (15 mg, 10%, w/w). The reaction mixture was stirred at RT under hydrogen for 18 h. The mixture was filtered by celite and evaporated to dryness to give (S)-3-(4-amino-3-(oxetan-2-ylmethylamino)phenyl)-1,2,4-oxadiazol-5(4H)-one (120 mg, 89% yield) as a white solid. LCMS: [M+H]$^+$=263.1; Retention time (10 mM $NH_4HCO_3$)=0.35 min.

Step 5

To a solution of (S)-3-(4-amino-3-(oxetan-2-ylmethylamino) phenyl)-1,2,4-oxadiazol-5(4H)-one (120 mg, 0.457 mmol) in MeCN (20 mL) was added 2-chloro-1,1,1-trimethoxyethane (112 mg, 0.723 mmol) and p-TSA (12 mg, 1 mmol). The reaction mixture was stirred at 60° C. for overnight. The mixture was evaporated to dryness to give (S)-3-(2-(chloromethyl)-1-(oxetan-2-ylmethyl)-1H-benzo[d]imidazol-6-yl)-1,2,4-oxadiazol-5(4H)-one (150 mg, 100% yield) as a white solid, which was used in the next step without further purification. LCMS: [M+H]$^+$=321.1; Retention time (10 mM NH$_4$HCO$_3$)=0.35 min.

Step 6

To a solution of 2-(4-chloro-2-fluorobenzyloxy)-6-(1,2,3,6-tetrahydropyridin-4-yl)pyridine (150 mg, 0.47 mmol) in dioxane (20 mL) was added (S)-3-(2-(chloromethyl)-1-(oxetan-2-ylmethyl)-1H-benzo[d]imidazol-6-yl)-1,2,4-oxadiazol-5(4H)-one (150 mg, 0.47 mmol), DIPEA (523 mg, 4.05 mmol) and NaI (15 mg, 0.1 eq). The reaction mixture was heated at 80° C. for 2 h. The mixture was evaporated to dryness, the residue was extracted by EtOAc/H$_2$O (1:1), concentrated and the residue was dissolved in DMF and purified by prep-HPLC to give (S)-3-(2-((4-(6-(4-chloro-2-fluorobenzyloxy)pyridin-2-yl)-5,6-dihydropyridin-1(2H)-yl)methyl)-1-(oxetan-2-ylmethyl)-1H-benzo[d]imidazol-6-yl)-1,2,4-oxadiazol-5(4H)-one (16 mg, 5.7% yield) as light brown solid. LCMS: [M+H]$^+$=603.0, Retention time (10 mM NH$_4$HCO$_3$)=1.65 min.

$^1$H NMR (400 MHz, DMSO-d6) δ 8.12 (s, 1H), 7.76-7.74 (d, J=8.4 Hz, 1H), 7.71-7.67 (t, J=7.6 Hz, 1H), 7.65-7.63 (dd, J1=8.4 Hz, J2=1.2 Hz, 1H), 7.58-7.53 (t, J=8.0 Hz, 1H), 7.49-7.46 (dd, J1=10.0 Hz, J2=2.0 Hz, 1H), 7.32-7.29 (dd, J1=8.0 Hz, J2=1.6 Hz, 1H), 7.10-7.08 (d, J=7.6 Hz, 1H), 6.75-6.72 (t, J=3.2 Hz, 2H), 5.39 (s, 2H), 5.10-5.08 (m, 1H), 4.80-4.74 (m, 1H), 4.65-4.60 (dd, J1=14.8 Hz, J2=2.8 Hz, 1H), 4.50-4.38 (m, 2H), 4.10-4.06 (d, J=13.6 Hz, 1H), 3.95-3.91 (d, J=13.2 Hz, 1H), 3.26-3.23 (m, 3H), 2.75 (s, 2H), 2.71-2.64 (m, 1H), 2.46-2.39 (m, 2H).

(S)-2-((4-(3-(4-chloro-2-fluorobenzyloxy)-2,4-difluorophenyl)-5,6-dihydropyridin-1(2H)-yl)methyl)-1-(oxetan-2-ylmethyl)-1H-benzo[d]imidazole-6-carboxylic acid (Compound 63)

Compound 63

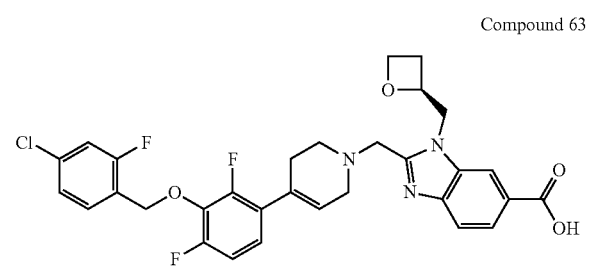 [SMILES: O=C(O)c1ccc2nc(CN3CC=C(c4ccc(F)c(OCc5ccc(Cl)cc5F)c4F)CC3)n(C[C@@H]3CCO3)c2c1]

Prepared in analogous manner as for Compound 28

LCMS: [M+H]$^+$=598.0; Retention time (10 mM NH$_4$HCO$_3$)=1.63 min.

$^1$H NMR (400 MHz, DMSO) δ 8.25 (s, 1H), 7.81 (d, J=8.4 Hz, 1H), 7.64 (d, J=8.4 Hz, 1H), 7.58-7.45 (m, 2H), 7.32 (d, J=8.2 Hz, 1H), 7.09 (d, J=8.2 Hz, 2H), 5.93 (brs, 1H), 5.17 (s, 2H), 5.07 (d, J=4.5 Hz, 1H), 4.79 (dd, J=15.2, 6.9 Hz, 1H), 4.65 (d, J=13.1 Hz, 1H), 4.48 (dd, J=13.9, 7.5 Hz, 1H), 4.36 (dd, J=14.7, 6.0 Hz, 1H), 4.05 (d, J=13.5 Hz, 1H), 3.90 (d, J=13.5 Hz, 1H), 3.22-3.16 (m, 2H), 2.80-2.61 (m, 3H), 2.46-2.40 (m, 3H).

(S)-2-((4-(3-((4-chloro-2-fluorobenzyl)oxy)-4-methylphenyl)-3,6-dihydropyridin-1(2H)-yl)methyl)-1-(oxetan-2-ylmethyl)-1H-benzo[d]imidazole-6-carboxylic acid (Compound 64)

Compound 64

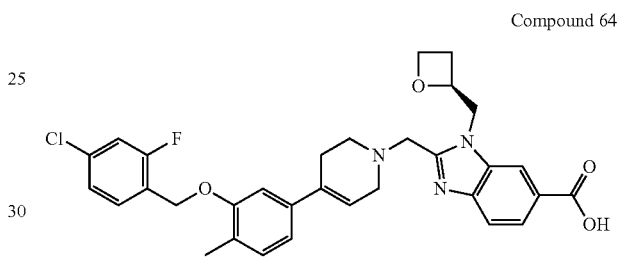

Prepared in analogous manner as for Compound 28

LCMS: [M+H]$^+$=576.0, Retention time (10 mM NH$_4$HCO$_3$)=1.65 min.

$^1$H NMR (400 MHz, DMSO) δ 8.17 (s, 1H), 7.80 (d, J=8.3 Hz, 1H), 7.63-7.48 (m, 3H), 7.35 (d, J=8.2 Hz, 1H), 7.10 (d, J=7.1 Hz, 2H), 6.93 (d, J=7.6 Hz, 1H), 6.15 (s, 1H), 5.18 (s, 2H), 5.06 (d, J=7.2 Hz, 1H), 4.76 (dd, J=15.2, 7.1 Hz, 1H), 4.63 (d, J=12.6 Hz, 1H), 4.47 (dd, J=13.6, 7.7 Hz, 1H), 4.36 (dt, J=12.2, 6.0 Hz, 1H), 4.04 (d, J=13.4 Hz, 1H), 3.89 (d, J=13.4 Hz, 1H), 3.15 (d, J=24.0 Hz, 4H), 2.71 (d, J=26.0 Hz, 2H), 2.42 (d, J=9.2 Hz, 2H), 2.13 (s, 3H).

(S)-2-((4-(6-((4-chloro-2-fluorobenzyl)oxy)pyridin-2-yl)-4-cyanopiperidin-1-yl)methyl)-1-(oxetan-2-ylmethyl)-1H-benzo[d]imidazole-6-carboxylic acid (Compound 66)

Compound 66

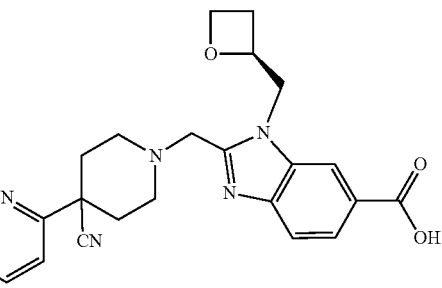

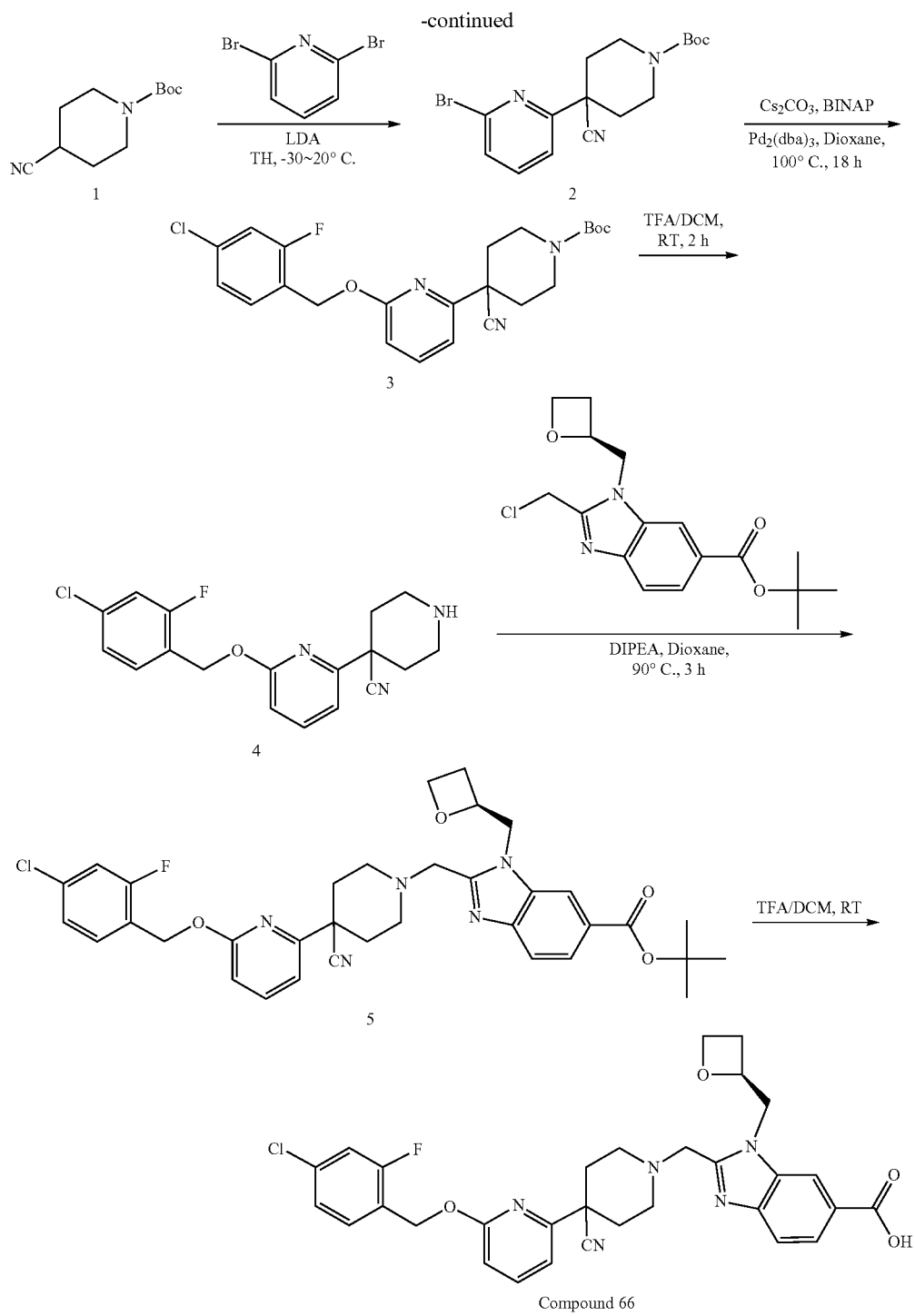

Compound 66

Step 1

A solution of tert-butyl 4-cyanopiperidine-1-carboxylate (1.0 g, 4.76 mmol) in THF (10 mL) was cooled to −30° C. under nitrogen, then LDA (2.5 mL, 2 N) was added slowly, the reaction was stirred at −30° C. for 0.5 h. Then 2,6-dibromopyridine (1.13 g, 4.76 mmol) was added to the stirred reaction. The mixture was stirred at 25° C. and stirred for 3 h. The mixture was diluted with HCl (1N) to pH 7, extracted with DCM (50 mL×3). The combined organics were washed with brine (20 mL×3), dried over $Na_2SO_4$ and concentrated in vacuo to give tert-butyl 4-(6-bromopyridin-2-yl)-4-cyanopiperidine-1-carboxylate (1.0 g, 2.73 mmol, 57.5% yield) as brown solid. LCMS: $[M-100]^+$=266.1; Retention time (0.01% TFA)=1.91 min.

Step 2

To a solution of tert-butyl 4-(6-bromopyridin-2-yl)-4-cyanopiperidine-1-carboxylate (500 mg, 1.37 mmol) in 1,4-Dioxane (10 mL) was added (4-chloro-2-fluorophenyl)methanol (264 mg, 1.64 mmol), BINAP (85 mg, 0.14 mmol), $Pd_2(dba)_3$ (63 mg, 0.07 mmol) and $Cs_2CO_3$ (1.33 g, 4.11 mmol). The mixture was stirred at 100° C. for 16 h. The reaction was cooled to RT, diluted with water (50 mL) and extracted with ethyl acetate (50 mL×3). The combined organics were washed with brine (20 mL×3), dried over $Na_2SO_4$ and concentrated in vacuo to give crude product, which was purified by chromatography column on silica gel (PE/EA=2/1) to give tert-butyl 4-(6-(4-chloro-2-fluorobenzyloxy)pyridin-2-yl)-4-cyanopiperidine-1-carboxylate (239 mg, 0.54 mmol, 30.7% yield) as white solid. LCMS [M−55]$^+$=389.9; Retention time (10 mM $NH_4HCO_3$)=1.97 min.

Step 3

To a solution of tert-butyl 4-(6-(4-chloro-2-fluorobenzyloxy) pyridin-2-yl)-4-cyanopiperidine-1-carboxylate (239 mg, 0.54 mmoll) DCM (5 mL) was added TFA (1 mL), the mixture was stirred at 25° C. for 1 h. The mixture was diluted with saturated aq. $NaHCO_3$ to pH 7, extracted with DCM (50 mL×3).

The combined organics were washed with brine (20 mL×3), dried over $Na_2SO_4$ and concentrated in vacuo to give 4-(6-(4-chloro-2-fluorobenzyloxy)pyridin-2-yl)piperidine-4-carbonitrile (150 mg, 0.43 mmol, 81% yield) as yellow oil. LCMS: [M+H]$^+$=346.1; Retention time (0.01% TFA)=1.60 min.

Step 4

To a solution of 4-(6-(4-chloro-2-fluorobenzyloxy)pyridin-2-yl)piperidine-4-carbonitrile (40 mg, 0.12 mmoll) in 1,4-Dioxane (5 mL) was added (S)-tert-butyl 2-(chloromethyl)-3-(oxetan-2-ylmethyl)-3H-benzo[d]imidazole-5-carboxylate (39 mg, 0.12 mmol) and DIPEA (45 mg, 0.36 mmol), the mixture was stirred at 90° C. for 3 h. The reaction was cooled to RT, then diluted with water (50 mL) and extracted with DCM (50 mL×3). The combined organics were washed with brine (50 mL×3), dried over $Na_2SO_4$ and concentrated in vacuo to give crude product, which was purified by chromatography column on silica gel (PE/EA=3/1) to give (S)-tert-butyl 2-((4-(6-(4-chloro-2-fluorobenzyloxy)pyridin-2-yl)-4-cyanopiperidin-1-yl)methyl)-3-(oxetan-2-ylmethyl)-3H-benzo[d]imidazole-5-carboxylate (40 mg, 0.06 mmol, 32.9% yield) as yellow oil.

LCMS: [M+H]$^+$=646.2; Retention time (0.01% TFA)=1.97 min.

Step 5

To a solution of (S)-tert-butyl 2-((4-(6-(4-chloro-2-fluorobenzyloxy)pyridin-2-yl)-4-cyanopiperidin-1-yl)methyl)-3-(oxetan-2-ylmethyl)-3H-benzo[d]imidazole-5-carboxylate (40 mg, 0.06 mmol) in DCM (5 mL) was added TFA (1 mL), the mixture was stirred at 25° C. for 4 h. Then the mixture was diluted with water (50 mL), extracted with DCM (50 mL×3). The combined organic layer was dried over $Na_2SO_4$ and concentrated in vacuo to give crude product, which was purified by prep-HPLC to give (S)-2-((4-(6-(4-chloro-2-fluorobenzyloxy)pyridin-2-yl)-4-cyanopiperidin-1-yl)methyl)-3-(oxetan-2-ylmethyl)-3H-benzo[d]imidazole-5-carboxylic acid (13.5 mg, 37% yield) as white solid.

LCMS: [M+H]$^+$=590.0; Retention time (10 mM $NH4HCO3$)=1.55 min.

$^1$H NMR (400 MHz, DMSO): δ 8.27 (d, J=0.9 Hz, 1H), 7.84-7.78 (m, 2H), 7.65 (d, J=8.4 Hz, 1H), 7.60 (t, J=8.2 Hz, 1H), 7.47 (dd, J=10.0, 1.9 Hz, 1H), 7.29 (dd, J=8.2, 1.8 Hz, 1H), 7.22 (d, J=7.4 Hz, 1H), 6.88 (d, J=8.3 Hz, 1H), 5.41 (s, 2H), 5.12-5.05 (m, 1H), 4.78 (dd, J=15.3, 7.1 Hz, 1H), 4.65 (dd, J=15.2, 2.5 Hz, 1H), 4.49-4.42 (m, 1H), 4.36 (dt, J=9.0, 5.9 Hz, 1H), 4.02 (d, J=13.6 Hz, 1H), 3.87 (d, J=13.6 Hz, 1H), 3.09-3.03 (m, 1H), 2.98-2.91 (m, 1H), 2.73-2.65 (m, 1H), 2.49-2.37 (m, 3H), 2.19-2.06 (m, 4H).

(S)-2-((4-(6-(4-chloro-2-fluorobenzyloxy)pyridin-2-yl)-4-fluoropiperidin-1-yl)methyl)-1-(oxetan-2-ylmethyl)-1H-benzo[d]imidazole-6-carboxylic acid
(Compound 67)

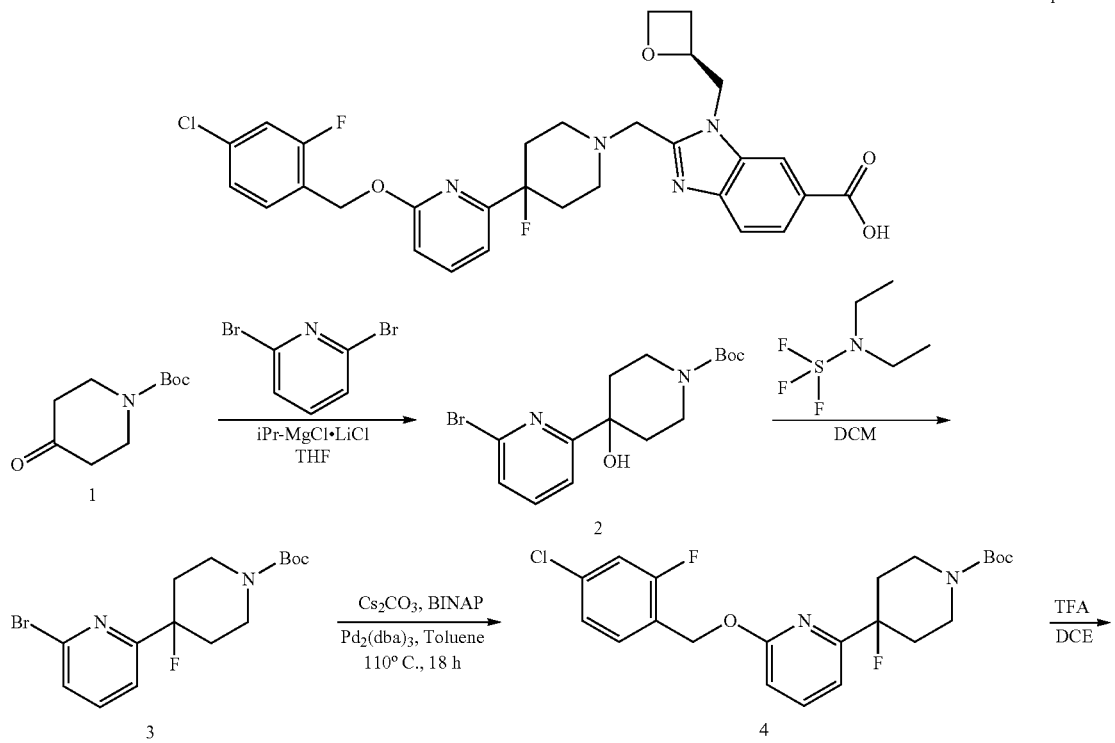

Compound 67

-continued

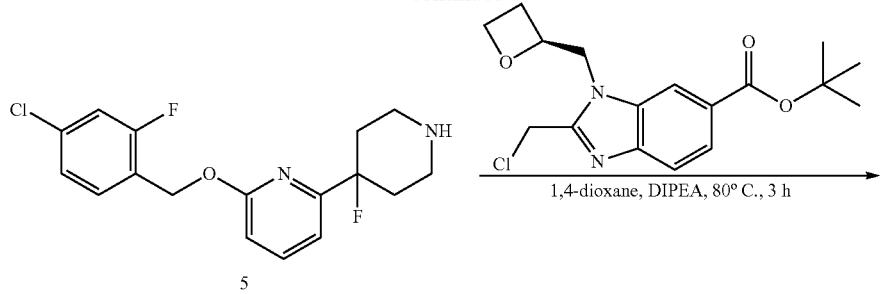

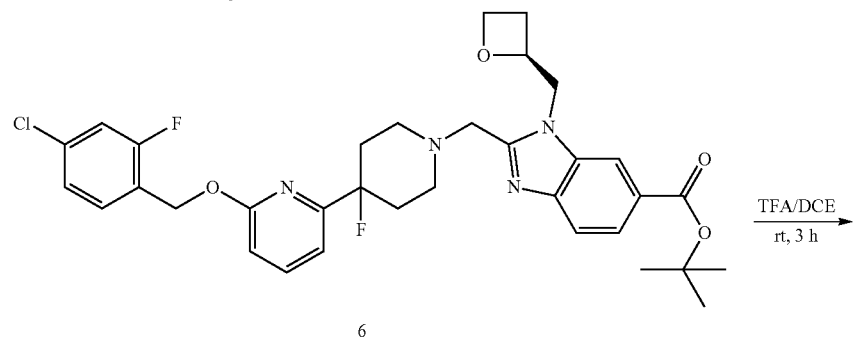

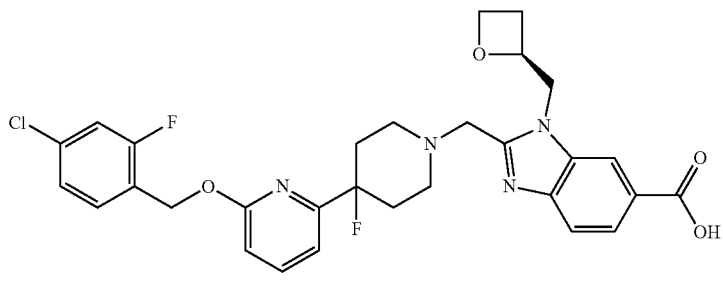

Compound 67

Step 1

To a solution of 2,6-dibromopyridine (1.18 g, 5 mmol) in anhydrous THF (20 mL) was added iPr-MgCl·LiCl (3.85 mL, 5 mmol) under $N_2$. The mixture was stirred at RT for 2 h. Then tert-butyl 4-oxopiperidine-1-carboxylate (1.0 g, 5 mmol) was added to the mixture. The reaction mixture was stirred at RT for 18 h. The mixture was quenched with 20 mL saturated $NH_4Cl$, extracted by EtOAc (20 mL×3), dried over $Na_2SO_4$, after removal of solvent, the residue was purified by prep-HPLC to give tert-butyl 4-(6-bromopyridin-2-yl)-4-hydroxypiperidine-1-carboxylate (280 mg, 16% yield) as a light yellow oil.

LCMS: [M−55]=301.0, Retention time (10 mM $NH_4HCO_3$)=1.84 min.

Step 2

A mixture of tert-butyl 4-(6-bromopyridin-2-yl)-4-hydroxypiperidine-1-carboxylate (120 mg, 0.336 mmol) in DCM (20 mL) was cooled to −78° C. under $N_2$, then DAST (0.25 mL, 1.86 mmol) was added in the mixture. The reaction mixture was stirred at RT for 4 h. The mixture was quenched by ice water and extracted by EtOAc (20 mL×3), dried over$Na_2SO_4$, after removal of solvent to give tert-butyl 4-(6-bromopyridin-2-yl)-4-fluoropiperidine-1-carboxylate (118 mg, 97% yield) as a light yellow oil.

LCMS: [M−55]=303.0, Retention time (10 mM $NH_4HCO_3$)=2.08 min.

Step 3

To a stirred suspension of tert-butyl 4-(6-bromopyridin-2-yl)-4-fluoropiperidine-1-carboxylate (118 mg, 0.328 mmol) and (4-chloro-2-fluorophenyl)methanol (58 mg, 0.361 mmol) in toluene (20 mL) was added $Cs_2CO_3$ (214 mg, 0.67 mmol), BINAP (20 mg, 0.0328 mmol) and $Pd_2(dba)_3$ (30 mg, 0.0328 mmol) under $N_2$ at 15° C. The reaction mixture was degassed and refilled with $N_2$ three times. The resulting mixture was heated to 120° C. under $N_2$ for 18 h. The mixture was cooled to RT, extracted by EtOAc (30 mL×2) and the combined organic layers were concentrated under reduced pressure. The crude product was purified by column chromatography on silica gel (PE/EA=100/1) to give crude product tert-butyl 4-(6-(4-chloro-2-fluorobenzyloxy)pyridin-2-yl)-4-fluoropiperidine-1-carboxylate (200 mg, 100% crude yield) as a light yellow oil.

LCMS: [M−55]=383.0, Retention time (10 mM $NH_4HCO_3$)=2.47 min.

Step 4

To a mixture of tert-butyl 4-(6-(4-chloro-2-fluorobenzyloxy) pyridin-2-yl)-4-fluoropiperidine-1-carboxylate (200 mg, 0.456 mmoll) in DCE (15 mL) was added TFA (3 mL). The reaction mixture was stirred at RT for 1 h. The mixture was evaporated to dryness to give 2-(4-chloro-2-fluorobenzyloxy)-6-(4-fluoropiperidin-4-yl) pyridine (190 mg, 100% yield) as a yellow solid. LCMS: [M+H]$^+$=339.0, Retention time (10 mM $NH_4HCO_3$)=1.82 min.

Step 5

To a mixture of (S)-tert-butyl 2-(chloromethyl)-1-(oxetan-2-ylmethyl)-1H-benzo[d]imidazole-6-carboxylate (60 mg, 0.18 mmol) in dioxane (20 mL) was added 2-(4-chloro-2-fluorobenzyloxy)-6-(4-fluoropiperidin-4-yl)pyridine (60 mg, 0.177 mmol), DIPEA (91.5 mg, 0.71 mmol) and NaI (12 mg, 0.1 eq). The reaction mixture was heated to 80° C. for 2 h. The mixture was evaporated to dryness, the residue was quenched with water and extracted by EtOAc (20 mL×3), after removal of solvent to give crude (S)-tert-butyl 2-((4-(6-(4-chloro-2-fluorobenzyloxy)pyridin-2-yl)-4-fluoropiperidin-1-yl)methyl)-1-(oxetan-2-ylmethyl)-1H-benzo[d]imidazole-6-carboxylate (100 mg, 88% crude yield) as a light yellow oil.

LCMS: [M+H]$^+$=639.0, Retention time (10 mM NH$_4$HCO$_3$)=2.43 min.

Step 6

To a mixture of (S)-tert-butyl 2-((4-(6-(4-chloro-2-fluorobenzyloxy)pyridin-2-yl)-4-fluoropiperidin-1-yl)methyl)-1-(oxetan-2-ylmethyl)-1H-benzo[d]imidazole-6-carboxylate (100 mg, 0.16 mmol) in DCE (15 mL) was added TFA (3 mL). The reaction mixture was stirred at RT for 1 h. The mixture was evaporated to dryness. The residue was dissolved in DMF and purified by prep-HPLC to give (S)-2-((4-(6-(4-chloro-2-fluorobenzyloxy)pyridin-2-yl)-4-fluoropiperidin-1-yl)methyl)-1-(oxetan-2-ylmethyl)-1H-benzo[d]imidazole-6-carboxylic acid (19.4 mg, 21% yield) as a white solid.

LCMS: [M+H]$^+$=583.0, Retention time (10 mM NH$_4$HCO$_3$)=1.59 min.

$^1$H NMR (400 MHz, DMSO-d6) δ 8.28-8.27 (d, J=0.4 Hz, 1H), 7.82-7.76 (m, 2H), 7.65-7.62 (d, J=8.0 Hz, 1H), 7.58-7.54 (t, J=8.4 Hz, 1H), 7.48-7.45 (dd, J$_1$=10.0 Hz, J$_2$=2.0 Hz, 1H), 7.31-7.28 (dd, J$_1$=8.4 Hz, J2=2.0 Hz, 1H), 7.16-7.14 (d, J=6.8 Hz, 1H), 6.84-6.81 (d, J=8.4 Hz, 1H), 5.39 (s, 2H), 5.15-5.12 (m, 1H), 4.84-4.78 (m, 1H), 4.71-4.66 (m, 1H), 4.48-4.35 (m, 2H), 4.02-3.98 (d, J=13.6 Hz, 1H), 3.85-3.82 (d, J=13.2 Hz, 1H), 2.91-2.88 (d, J=10.0 Hz, 1H), 2.77-2.68 (m, 2H), 2.46-2.39 (m, 3H), 2.28-2.12 (m, 2H), 1.86-1.76 (m, 2H).

(S)-2-((6-((4-ethynyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 68)

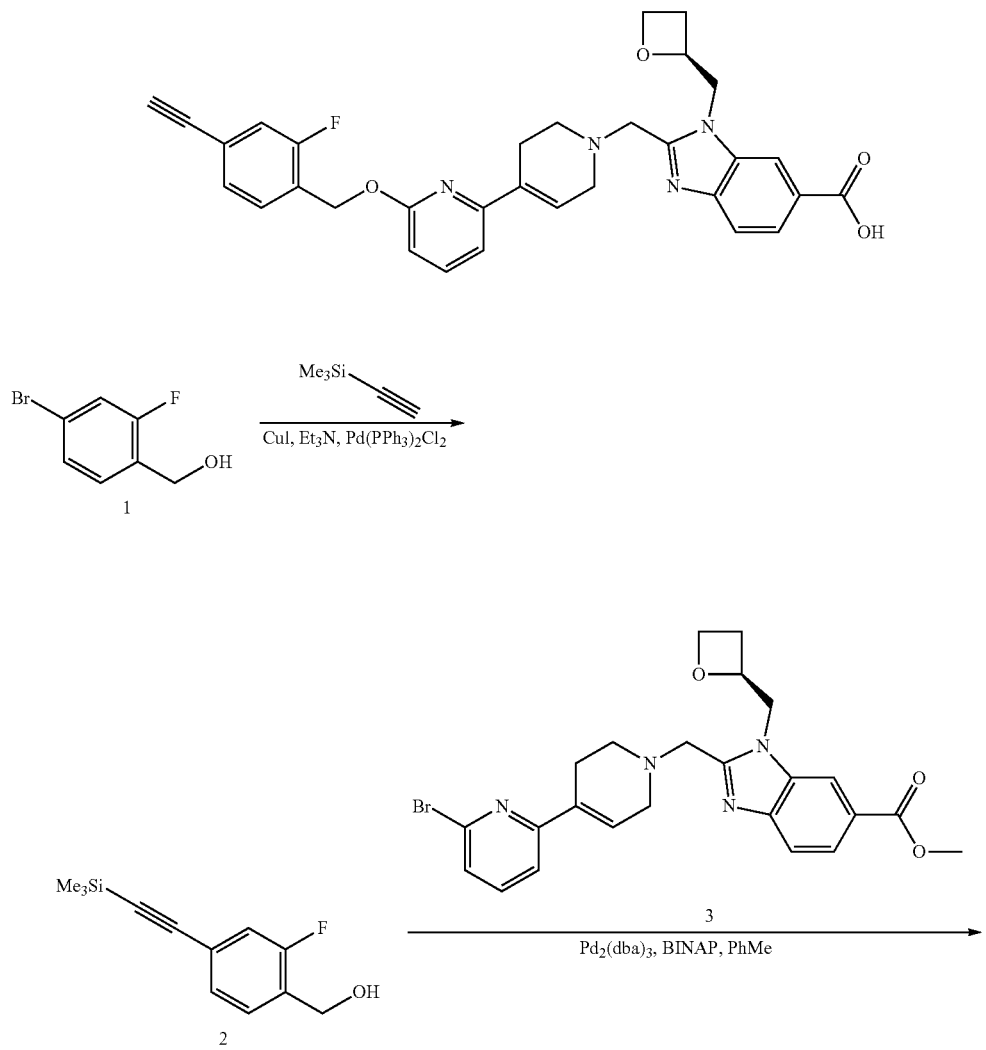

Compound 68

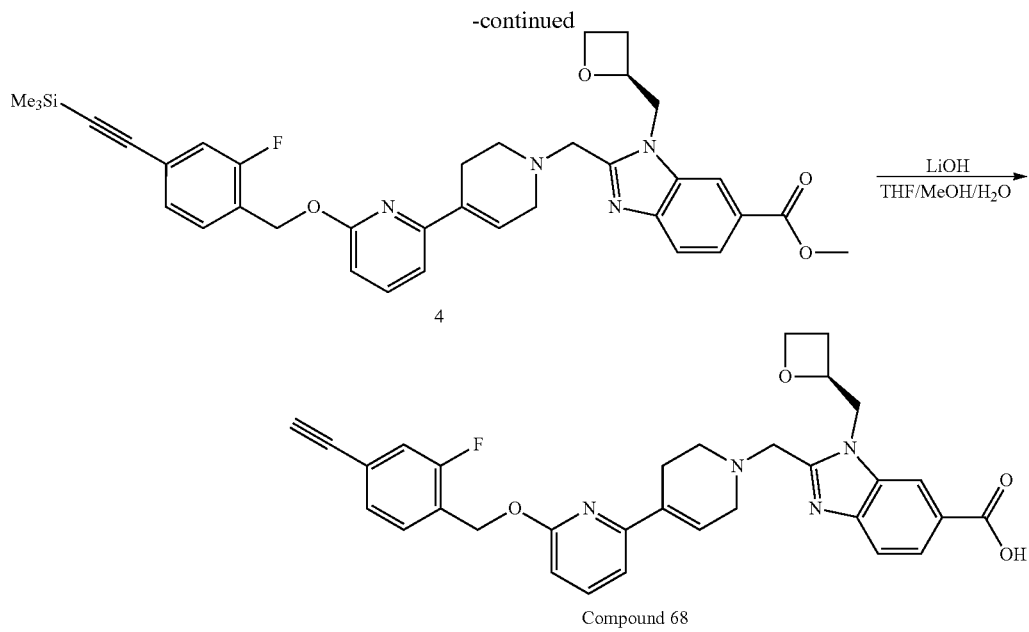

Compound 68

Step 1

To a solution of (4-bromo-2-fluorophenyl)methanol (500 mg, 2.44 mmol) in dioxane (6 mL), CuI (23 mg, 0.12 mmol) and DIPEA (630 mg, 4.88 mmol) was added Pd(PPh$_3$)$_2$Cl$_2$ (86 mg, 0.12 mmol). Finally, ethynyltrimethylsilane (287 mg, 2.93 mmol) was added into the reaction mixture and stirred for 12 h at 90° C. under N$_2$. Water (30 mL) was added into the reaction solution and extracted with ethyl acetate (25 mL×3). The combined organic layer was washed with brine (30 mL×2), dried over Na$_2$SO$_4$ and concentrated in vacuo to give crude product. The crude product was purified by column chromatography on silica gel (PE/EA=5/1) to give (2-fluoro-4-((trimethylsilyl)ethynyl)phenyl)methanol (0.2 g, 37% yield) as a yellow solid.

Step 2

To a solution of methyl (S)-2-((6-bromo-3',6'-dihydro-[2,4'-bipyridin]-1'(2'H)-yl)methyl)-1-(oxetan-2-ylmethyl)-1H-benzo[d]imidazole-6-carboxylate (30 mg, 0.060 mmol) in toluene (4.0 mL), BINAP (9.4 mg, 0.015 mmol), t-BuONa (11 mg, 0.11 mmol) was added Pd$_2$(dba)$_3$ (5.7 mg, 0.006 mmol). (2-fluoro-4-((trimethylsilyl)ethynyl)phenyl)methanol (20 mg, 0.09 mmol) was added into the reaction mixture and was stirred for 12 h at 90° C. under N$_2$. Water (10 mL) was added into the reaction solution and extracted with ethyl acetate (15 mL×3). The combined organic layer was washed with brine (20 mL×2), dried over Na$_2$SO$_4$ and concentrated in vacuo to give crude product. The crude product was purified by column chromatography on silica gel (PE/EA=1/5) to give methyl (S)-2-((6-((2-fluoro-4-((trimethylsilyl)ethynyl)benzyl)oxy)-3',6'-dihydro-[2,4'-bipyridin]-1'(2'H)-yl)methyl)-1-(oxetan-2-ylmethyl)-1H-benzo[d]imidazole-6-carboxylate (10 mg, 26% yield) as a yellow solid. LCMS: [M+H]$^+$=639.0, Retention time (10 mM NH$_4$HCO$_3$)=2.53 min.

Step 3

To a solution of Methyl (S)-2-((6-((2-fluoro-4-((trimethylsilyl)ethynyl)benzyl)oxy)-3',6'-dihydro-[2,4'-bipyridin]-1'(2'H)-yl)methyl)-1-(oxetan-2-ylmethyl)-1H-benzo[d]imidazole-6-carboxylate (10 mg, 0.016 mmol) in MeOH (0.5 mL), THF (0.5 mL) and H$_2$O (0.5 mL) was added LiOH·H$_2$O (3.8 mg, 0.16 mmol). The reaction mixture was stirred at 25° C. for 12 h, adjusted to pH 7-8 with AcOH, purified by prep-HPLC to give (S)-2-((6-((4-ethynyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (2.2 mg, 25% yield) as a yellow solid. LCMS: [M+H]$^+$=553.0, Retention time (10 mM NH$_4$HCO$_3$)=1.57 min. $^1$H NMR (400 MHz, DMSO) δ 8.26 (s, 1H), 7.81 (d, J=8.5 Hz, 1H), 7.73-7.63 (m, 2H), 7.52 (t, J=7.8 Hz, 1H), 7.38 (d, J=11.6 Hz, 1H), 7.32 (d, J=7.8 Hz, 1H), 7.09 (d, J=7.4 Hz, 1H), 6.74 (d, J=8.1 Hz, 2H), 5.42 (s, 2H), 5.06 (d, J=4.5 Hz, 1H), 4.80 (dd, J=15.2, 7.3 Hz, 1H), 4.65 (d, J=13.0 Hz, 1H), 4.46 (dd, J=13.6, 7.8 Hz, 1H), 4.41-4.31 (m, 2H), 4.07 (d, J=13.4 Hz, 1H), 3.91 (d, J=13.6 Hz, 1H), 3.31-3.12 (m, 3H), 2.74 (s, 2H), 2.64 (d, J=7.8 Hz, 1H), 2.40 (dd, J=25.8, 17.3 Hz, 2H).

2-((6-((7-chlorochroman-4-yl)oxy)-5',6'-dihydro-[2,4'-bipyridin]-1'(2'H)-yl)methyl)-1-((S)-oxetan-2-ylmethyl)-1H-benzo[d]imidazole-6-carboxylic acid (Compound 69)

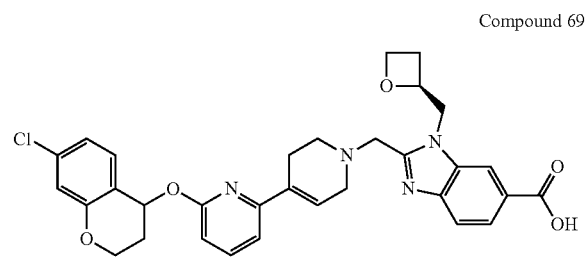 [SMILES: O=C(O)c1ccc2nc(CN3CC=C(c4cccc(OC5CCOc6cc(Cl)ccc65)n4)CC3)n(C[C@@H]3CCO3)c2c1]

Compound 69

Prepared in analogous manner as for Compound 19
LCMS: [M+H]$^+$=587.3; Retention time (10 mM NH$_4$HCO$_3$)=1.74 min.
$^1$H NMR (400 MHz, MeOD) δ 8.34 (s, 1H), 8.01-7.98 (m, 1H), 7.70 (d, J=8.4 Hz, 1H), 7.66-7.62 (m, 1H), 7.32 (d, J=8.4 Hz, 1H), 7.09 (d, J=7.2 Hz, 1H), 6.87-6.85 (m, 2H), 6.80-6.78 (brs, 1H), 6.62 (d, J=8.0 Hz, 1H), 6.35-6.33 (m, 1H), 5.29-5.24 (m, 1H), 4.92-4.88 (m, 2H), 4.77-4.72 (m, 1H), 4.65-4.61 (m, 1H), 4.51-4.45 (m, 1H), 4.33-4.30 (m, 2H), 4.22-4.06 (m, 2H), 3.39-3.33 (m, 2H), 2.91-2.88 (m, 2H), 2.81-2.72 (m, 3H), 2.57-2.48 (m, 1H), 2.29-2.25 (m, 2H).

2-((6-(1-(4-chloro-2-fluorophenyl)ethoxy)-3,6'-dihydro-[2,4'-bipyridin]-1'(2'H)-yl)methyl)-1-(((S)-oxetan-2-yl)methyl)-1H-benzo[d]imidazole-6-carboxylic acid (Compound 70)

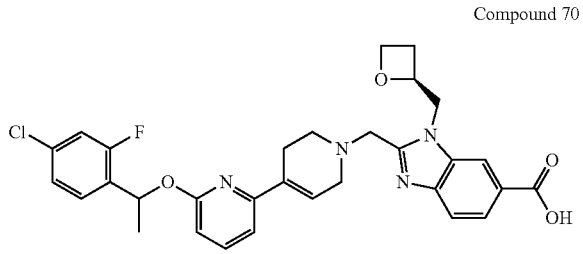 [SMILES: CC(Oc1cccc(C2=CCN(Cc3nc4ccc(C(=O)O)cc4n3C[C@@H]3CCO3)CC2)n1)c1ccc(Cl)cc1F]

Compound 70

Prepared in analogous manner as for Compound 19

LCMS: [M+H]$^+$=577.0, purity=100% (254 nm), Retention time (10 mM NH$_4$HCO$_3$)=1.63 min. 1H NMR (400 MHz, MeOD) δ 8.35-8.29 (brs, 1H), 8.00 (d, J=8.3 Hz, 1H), 7.70 (d, J=8.4 Hz, 1H), 7.60 (t, J=7.9 Hz, 1H), 7.42 (t, J=7.8 Hz, 1H), 7.18-7.10 (m, 2H), 7.01 (d, J=7.5 Hz, 1H), 6.69 (d, J=8.2 Hz, 1H), 6.40-6.30 (m, 1H), 5.27-5.20 (m, 1H), 4.83-4.86 (m, 1H), 4.73-4.63 (m, 3H), 4.50-4.41 (m, 1H), 4.16 (dd, J=13.8, 3.3 Hz, 1H), 4.04 (dd, J=13.7, 6.6 Hz, 1H), 3.27-3.21 (m, 2H), 2.84-2.71 (m, 3H), 2.64-2.44 (m, 3H), 1.61 (d, J=6.6 Hz, 3H).

(S)-2-((4-(6-(4-chloro-2-fluorobenzyloxy)pyridin-2-yl)-5,6-dihydropyridin-1(2H)-yl)methyl)-1-(oxetan-2-ylmethyl)-1H-benzo[d]imidazole-6-carbonitrile (Compound 71)

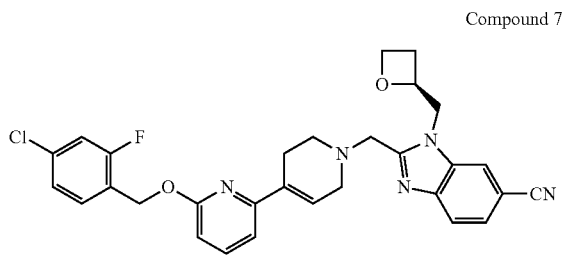

Compound 71

Prepared in analogous manner as for Compound 19

LCMS: [M+H]$^+$=544.0, purity=100% (254 nm), Retention time (10 mM NH$_4$HCO$_3$)=2.17 min.
$^1$H NMR (400 MHz, MeOD) δ 8.16-8.15 (brs, 1H), 7.80 (d, J=8.4 Hz, 1H), 7.66-7.58 (m, 2H), 7.50 (t, J=8.0 Hz, 1H), 7.29-7.16 (m, 2H), 7.07 (d, J=7.4 Hz, 1H), 6.77-6.66 (m, 2H), 5.44 (s, 2H), 5.23 (dt, J=7.2, 5.2 Hz, 1H), 4.92-4.83 (m, 1H), 4.71 (dd, J=15.3, 2.3 Hz, 1H), 4.64 (dd, J=13.9, 7.9 Hz, 1H), 4.49 (dt, J=9.2, 6.0 Hz, 1H), 4.18 (d, J=13.8 Hz, 1H), 4.03 (d, J=13.8 Hz, 1H), 3.27 (dt, J=17.4, 8.7 Hz, 2H), 2.88-2.81 (m, 2H), 2.81-2.71 (m, 1H), 2.64-2.63 (brs, 2H), 2.51 (dq, J=11.5, 7.3 Hz, 1H).

2-((6-((4-chloro-2-fluorobenzyl)oxy)-3,6'-dihydro-[2,4'-bipyridin]-1'(2'H)-yl)methyl)-1-(oxazol-2-ylmethyl)-1H-benzo[d]imidazole-6-carboxyli acid (Compound 72)

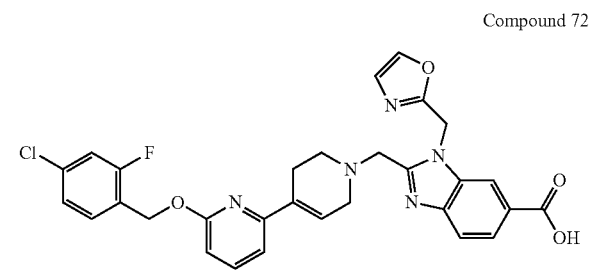 [SMILES: O=C(O)c1ccc2nc(CN3CC=C(c4cccc(OCc5ccc(Cl)cc5F)n4)CC3)n(Cc3ncco3)c2c1]

Compound 72

Prepared in analogous manner as for Compound 19

LCMS: [M+H]$^+$=574.0; Retention time (10 mM NH$_4$HCO$_3$)=1.63 min.

$^1$H NMR (400 MHz, DMSO) δ 8.17-8.16 (brs, 1H), 7.97-7.96 (brs, 1H), 7.83-7.82 (brs, 1H), 7.67-7.66 (brs, 2H), 7.52 (d, J=25.1 Hz, 2H), 7.32-7.31 (brs, 1H), 7.06 (d, J=15.4 Hz, 2H), 6.68 (d, J=22.8 Hz, 2H), 5.90 (s, 2H), 5.39 (s, 2H), 3.99 (s, 2H), 3.19-3.18 (brs, 2H), 2.66-2.65 (brs, 2H), 2.36-2.35 (brs, 2H).

(S)-2-((6-(benzyloxy)-5,6'-dihydro-[2,4'-bipyridin]-1'(2'H)-yl)methyl)-1-(oxetan-2-ylmethyl)-1H-benzo[d]imidazole-6-carboxylic acid (Compound 73)

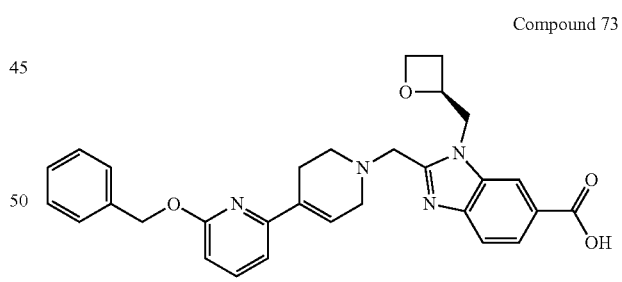

Compound 73

Prepared in analogous manner as for Compound 19

LCMS: [M+H]$^+$=511.2; Retention time (10 mM NH$_4$HCO$_3$)=1.52 min.

$^1$H NMR (400 MHz, DMSO) δ 8.36-8.34 (brs, 1H), 8.03 (dd, J=1.2, 8 Hz, 1H), 7.77 (d, J=8.4 Hz, 1H), 7.66 (t, J=7.6 Hz, 1H), 7.28-7.45 (m, 5H), 7.11 (d, J=7.6 Hz, 1H), 6.73-6.76 (m, 2H), 5.41 (s, 2H), 5.22-5.25 (m, 1H), 4.82-4.88 (m, 1H), 4.43-4.73 (m, 5H), 3.67-3.80 (m, 2H), 3.21-3.32 (m, 2H), 2.51-2.83 (m, 4H).

(S)-2-((4-(7-((4-chloro-2-fluorobenzyl)oxy)-1H-pyrazolo[3,4-c]pyridin-5-yl)-3,6-dihydropyridin-1(2H)-yl)methyl)-1-(oxetan-2-ylmethyl)-1H-benzo[d]imidazole-6-carboxylic acid (Compound 103)
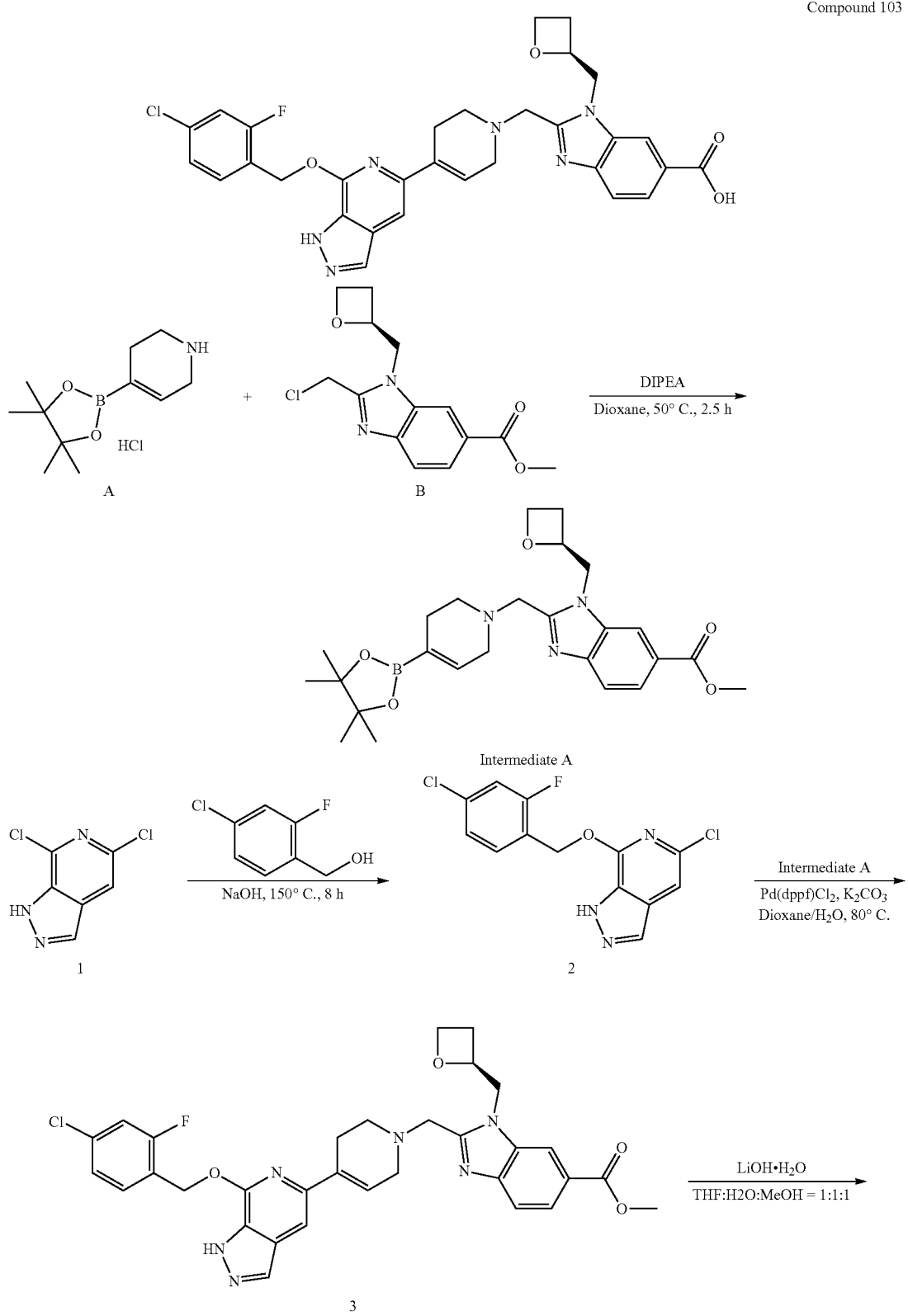

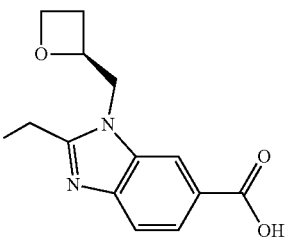

Compound 103

Step 1

To the solution of methyl (S)-2-(chloromethyl)-1-(oxetan-2-ylmethyl)-1H-benzo[d]imidazole-6-carboxylate (200 mg, 0.68 mmol, 1.0 eq) in 1,4-dioxane (10 mL) was added 4-(4,4,5,5-tetramethyl-1,3,2-dioxaborolan-2-yl)-1,2,3,6-tetrahydropyridine (200 mg, 0.68 mmol, 1.0 eq) and DIPEA (298 mg, 2.38 mmol, 3.5 eq), and then the mixture was stirred at 50° C. for 2.5 h. The reaction was quenched by water (15 mL), extracted with DCM (30 mL×3), The combine organic was washed with brine (10 mL×3), dried and concentrated in vacuo to give crude product (methyl (S)-1-(oxetan-2-ylmethyl)-2-((4-(4,4,5,5-tetramethyl-1,3,2-dioxaborolan-2-yl)-3,6-dihydropyridin-1(2H)-yl)methyl)-1H-benzo[d]imidazole-6-carboxylate, 280 mg) as a yellow solid, which was used in the next step without further purification.

LCMS: [M+H]$^+$=468.2; Retention time (10 mM NH$_4$HCO$_3$)=1.66 min.

Step 2

To a solution of 5,7-dichloro-1H-pyrazolo[3,4-c] pyridine (200 mg, 1.07 mmol, 1.0 eq) in (4-chloro-2-fluorophenyl) methanol (5 mL) was added NaOH (256 mg, 6.42 mmol, 6 eq). The mixture was stirred at 150° C. for 8 h. The reaction was purified by pre-HPLC to yield the product (5-chloro-7-((4-chloro-2-fluorobenzyl)oxy)-1H-pyrazolo[3,4-c]pyridine, 80 mg, 0.25 mmol). LCMS: [M+H]$^+$=311.8; Retention time (10 mM NH$_4$HCO$_3$)=1.73 min.

Step 3

The solution of 5-chloro-7-((4-chloro-2-fluorobenzyl)oxy)-1H-pyrazolo[3,4-c]pyridine (50 mg, 0.1 mmol, 1.0 eq) and methyl (S)-1-(oxetan-2-ylmethyl)-2-((4-(4,4,5,5-tetramethyl-1,3,2-dioxaborolan-2-yl)-3,6-dihydropyridin-1(2H)-yl)methyl)-1H-benzo[d]imidazole-6-carboxylate (56 mg, 0.12 mmol), Pd(dppf)Cl$_2$ (15 mg, 0.01 mmol) and K$_2$CO$_3$ (69 mg, 0.5 mmol) in 1,4-dioxane, (4 mL) and H$_2$O (1 mL) was stirred at 80° C. for 16 h. The reaction was purified by pre-HPLC to yield the product (methyl (S)-2-((4-(7-((4-chloro-2-fluorobenzyl)oxy)-1H-pyrazolo[3,4-c]pyridin-5-yl)-3,6-dihydropyridin-1(2H)-yl)methyl)-1-(oxetan-2-ylmethyl)-1H-benzo-[d]imidazole-6-carboxylate, 30 mg, 0.05 mmol). LCMS: [M+H]$^+$=617.3; Retention time (0.01% TFA)=1.54 min.

Step 4

A solution of methyl (S)-2-((4-(7-((4-chloro-2-fluorobenzyl)oxy)-1H-pyrazolo[3,4-c]pyridin-5-yl)-3,6-dihydropyridin-1(2H)-yl)methyl)-1-(oxetan-2-ylmethyl)-1H-benzo[d]imidazole-6-carboxylate (30 mg, 0.05 mmol), LiOH·H$_2$O (20 mg, 0.2 mmol) dihydropyridin-1(2H)-yl)methyl)-1-(oxetan-2-ylmethyl)-1H-benzo[d]imidazole-6-carboxylic acid, 1.3 mg, 0.002 mmol). LCMS: [M+H]$^+$=603.0; Retention time (10 mM NH$_4$HCO$_3$)=1.31 min.

$^1$H NMR (400 MHz, CD$_3$OD) δ 8.21 (s, 1H), 7.94-7.85 (m, 2H), 7.58 (d, J=8.5 Hz, 1H), 7.51 (d, J=7.9 Hz, 1H), 7.20 (s, 1H), 7.18-7.09 (m, 2H), 6.70 (s, 1H), 5.56 (brs, 2H), 5.19-5.11 (m, 1H), 4.82 (d, J=2.3 Hz, 1H), 4.63 (dd, J=15.4, 2.5 Hz, 1H), 4.52 (dd, J=13.9, 7.9 Hz, 2H), 4.36 (dt, J=9.2, 6.0 Hz, 1H), 4.08 (t, J=10.9 Hz, 1H), 3.97 (d, J=13.8 Hz, 1H), 3.24 (d, J=5.3 Hz, 1H), 2.80 (t, J=5.5 Hz, 2H), 2.66 (dt, J=14.4, 8.1 Hz, 1H), 2.58 (brs, 2H), 2.46-2.35 (m, 1H).

2-((6-(((6-chloro-1,2,3,4-tetrahydronaphthalen-1-yl)amino)-3,6'-dihydro-[2,4'-bipyridin]-1'(2'H)-yl)methyl)-1-(((S)-oxetan-2-yl)methyl)-1H-benzo[d]imidazole-6-carboxylic acid (Compound 104)

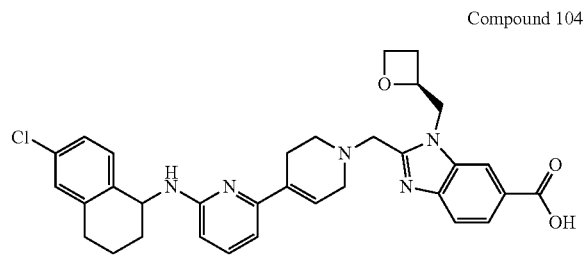 [SMILES: O=C(O)c1ccc2nc(CN3CC=C(c4cccc(NC5CCCc6cc(Cl)ccc65)n4)CC3)n(C[C@@H]3CCO3)c2c1]

Compound 104

Prepared in analogous manner as for Compound 61

LCMS: [M+H]$^+$=584.1; Retention time (10 mM NH$_4$HCO$_3$)=1.62 min.

$^1$H NMR (400 MHz, MeOD) δ 8.33-8.32 (brs, 1H), 7.99 (d, J=8.4 Hz, 1H), 7.69 (d, J=8.5 Hz, 1H), 7.42-7.25 (m, 2H), 7.14-7.04 (m, 2H), 6.68 (d, J=7.3 Hz, 1H), 6.61-6.60 (brs, 1H), 6.40 (d, J=8.3 Hz, 1H), 5.26 (d, J=6.9 Hz, 2H), 4.88 (d, J=7.1 Hz, 1H), 4.73 (d, J=13.0 Hz, 1H), 4.66-4.58 (m, 1H), 4.48 (dt, J=8.9, 5.9 Hz, 1H), 4.20 (d, J=13.6 Hz, 1H), 4.07 (d, J=14.0 Hz, 1H), 3.32-3.29 (m, 2H), 2.88-2.87 (brs, 2H), 2.78 (t, J=17.9 Hz, 3H), 2.65-2.64 (brs, 2H), 2.57-2.48 (m, 1H), 2.05-1.77 (m, 4H).

(S)-2-((4-(6-(4-chloro-2-fluorobenzyloxy)pyridin-2-yl)-5,6-dihydropyridin-1(2H)-yl)methyl)-1-(oxetan-2-ylmethyl)-6-(1H-tetrazol-5-yl)-1H-benzo[d]imidazole (Compound 105)

Compound 105

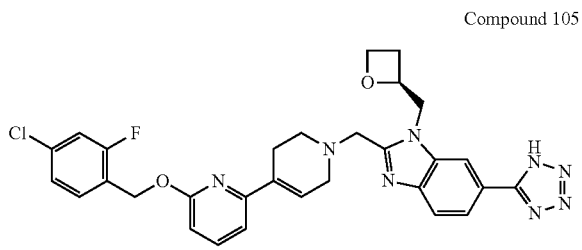 [SMILES: Fc1cc(Cl)ccc1COc1cccc(C2=CCN(Cc3nc4ccc(-c5nnn[nH]5)cc4n3C[C@@H]3CCO3)CC2)n1]

Prepared in analogous manner as for Compound 19

LCMS: [M+H]$^+$=587.0; Retention time (10 mM NH$_4$HCO$_3$)=1.64 min.

$^1$H NMR (400 MHz, DMSO) δ 8.35 (d, J=15.7 Hz, 1H), 7.87 (dd, J=8.4, 1.5 Hz, 1H), 7.78 (d, J=8.4 Hz, 1H), 7.68 (d, J=7.9 Hz, 1H), 7.56 (t, J=8.2 Hz, 1H), 7.48 (dd, J=10.0, 2.0 Hz, 1H), 7.30 (dd, J=8.2, 1.8 Hz, 1H), 7.09 (d, J=7.5 Hz, 1H), 6.79-6.70 (m, 2H), 5.40 (s, 2H), 5.18-5.07 (m, 1H), 4.81 (dd, J=15.2, 7.3 Hz, 1H), 4.67 (dd, J=15.2, 2.9 Hz, 1H), 4.48 (dd, J=14.3, 7.1 Hz, 1H), 4.41 (dt, J=9.0, 6.0 Hz, 1H), 4.10 (d, J=13.5 Hz, 1H), 3.95 (d, J=13.5 Hz, 1H), 3.27 (d, J=9.5 Hz, 2H), 2.78-2.77 (brs, 2H), 2.71-2.63 (m, 1H), 2.53-2.52 (brs, 2H), 2.48-2.41 (m, 1H).

(S)-2-((4-(6-((4-chloro-2-fluorobenzyl)oxy)pyridin-2-yl)-2-oxopiperazin-1-yl)methyl)-1-(oxetan-2-ylmethyl)-1H-benzo[d]imidazole-6-carboxylic acid (Compound 106)

Compound 106

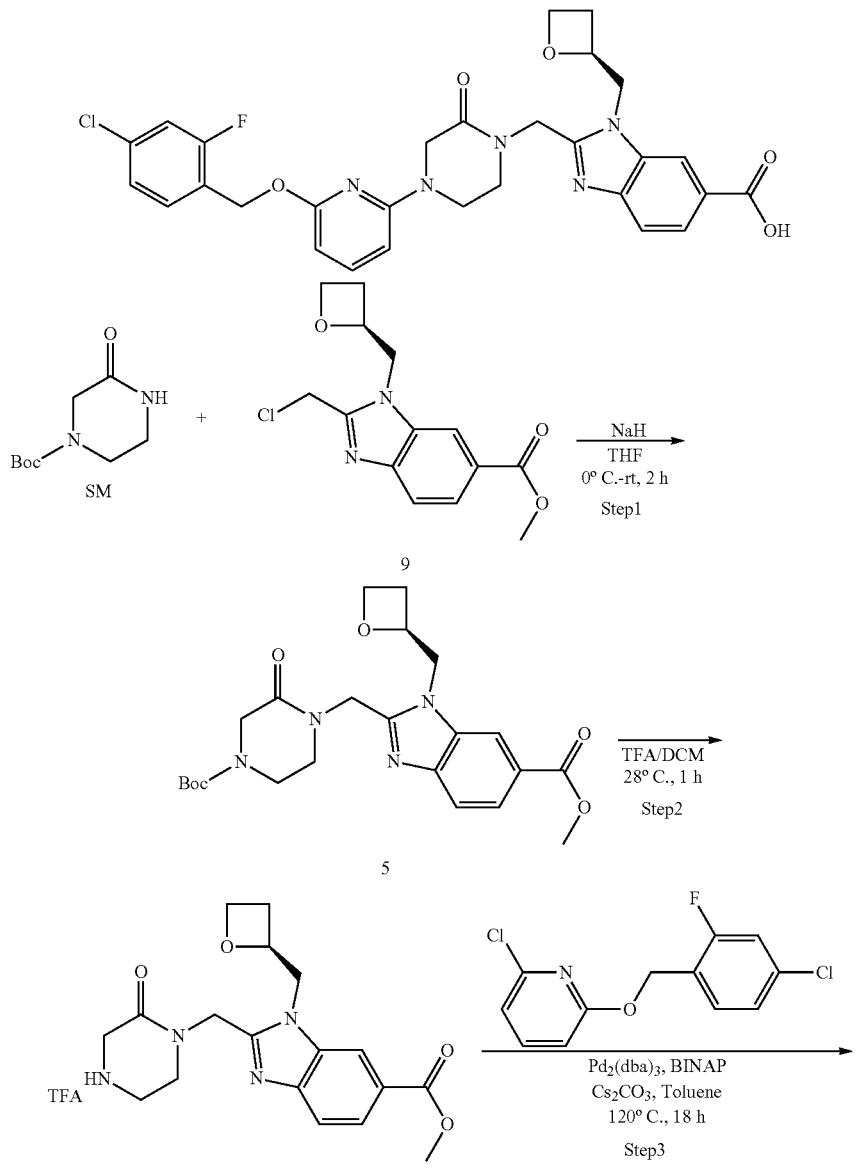

-continued

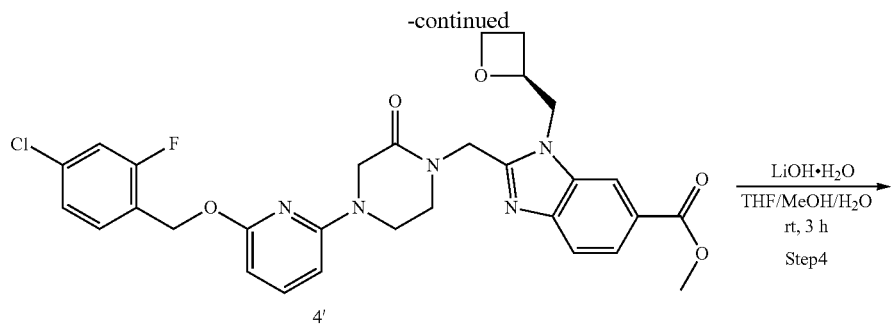

4'

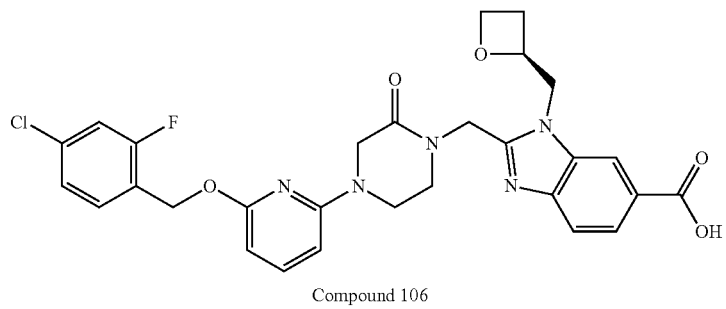

Compound 106

Step 1

A solution of tert-butyl 3-oxopiperazine-1-carboxylate (50 mg, 0.25 mmol) in THF (5 mL) was added drop-wise to a solution of NaH (50 mg, 1.25 mmol) in THF (10 mL) at ice-bath for 30 min, then a solution of (S)-methyl 2-(chloromethyl)-3-(oxetan-2-ylmethyl)-3H-benzo[d]imidazole-5-carboxylate (73 mg, 0.25 mmol) in THF (5 mL) was added drop-wise at ice-bath for 30 min, and then the reaction was warmed to rt, stirred at rt for 2 h. The mixture was diluted with water at ice-bath, and extracted with EA (2×10 mL), the organic layer was dried in $Na_2SO_4$, filtered with Buchner funnel and concentrated, purified by Pre-TLC (PE:EA=1:3) to give (S)-methyl 2-((4-(tert-butoxycarbonyl)-2-oxopiperazin-1-yl) methyl)-3-(oxetan-2-ylmethyl)-3H-benzo[d] imidazole-5-carboxylate (73 mg, 42%) as a pale white solid.

LCMS: $[M+H]^+$=459.0, Retention time (10 mM $NH_4HCO_3$)=1.55 min.

Step 2

A solution of (S)-methyl 2-((4-(tert-butoxycarbonyl)-2-oxopiperazin-1-yl)methyl)-3-(oxetan-2-ylmethyl)-3H-benzo[d]imidazole-5-carboxylate (73 mg, 0.16 mmol) in DCM (12 mL) was added drop-wise TFA (3 mL) at ice-bath. Then the reaction was stirred at 28° C. for 4 h. The mixture was concentrated to give (S)-methyl 3-(oxetan-2-ylmethyl)-2-((2-oxopiperazin-1-yl) methyl)-3H-benzo[d]imidazole-5-carboxylate (87 mg, 116%, TF salt) as a pale yellowish oil. The crude was used directly next step without further purification.

LCMS: $[M+H]^+$=359.1, Retention time (0.01% TFA)=1.02 min.

Step 3

A solution of (S)-methyl 3-(oxetan-2-ylmethyl)-2-((2-oxopiperazin-1-yl) methyl)-3H-benzo[d]imidazole-5-carboxylate (87 mg, 0.16 mmol, TF salt), 2-chloro-6-(4-chloro-2-fluorobenzyloxy) pyridine (48 mg, 0.18 mmol), BINAP (10 mg, 0.016 mmol6), $Pa_2(dba)_3$ (8 mg, 0.008 mmol) and $Cs_2CO_3$ (103 mg, 0.32 mmol) in toluene (20 mL) was stirred at 120° C. for 18 h. The mixture was filtered with Buchner funnel and concentrated, purified by Pre-HPLC ($NH_4HCO_3$) to give (S)-methyl 2-((4-(6-(4-chloro-2-fluorobenzyloxy) pyridin-2-yl)-2-oxopiperazin-1-yl) methyl)-3-(oxetan-2-ylmethyl)-3H-benzo [d]imidazole-5-carboxylate (30 mg, 31%) as a pale yellowish solid.

LCMS: $[M+H]^+$=593.9, Retention time (10 mM $NH_4HCO_3$)=1.76 min.

Step 4

To a solution of (S)-methyl 2-((4-(6-(4-chloro-2-fluorobenzyloxy) pyridin-2-yl)-2-oxopiperazin-1-yl) methyl)-3-(oxetan-2-ylmethyl)-3H-benzo [d] imidazole-5-carboxylate (30 mg, 0.05 mmol) and LiOH·$H_2O$ (17 mg, 0.40 mmol) in THF: MeOH: $H_2O$ (1:1:1, 3 mL) was stirred at rt for 2 h. The mixture was evaporated, adjusted pH=6 with 1 N of HCl aqueous, extracted with EA (3×10 mL), dried in $Na_2SO_4$, filtered and concentrated. The crude product was dissolved in THF (3 mL), purified by Pre-HPLC ($NH_4HCO_3$) to give (S)-2-((4-(6-((4-chloro-2-fluorobenzyl)oxy)pyridin-2-yl)-2-oxopiperazin-1-yl)methyl)-1-(oxetan-2-ylmethyl)-1H-benzo[d]imidazole-6-carboxylic acid (5.4 mg, 28%) as a white solid. LCMS: $[M+H]^+$=580.0, Retention time (10 mM $NH_4HCO_3$)=1.51 min.

$^1$H NMR (400 MHz, DMSO) δ 8.23 (brs, 1H), 7.82 (dd, J=1.6, 6.8 Hz, 1H), 7.65 (d, J=8.4 Hz, 1H), 7.55 (dd, J=8, 9.2 Hz, 1H), 7.47 (dd, J=2.4, 7.6 Hz, 1H), 7.29 (dd, J=2.4, 6 Hz, 1H), 6.38 (d, J=8.4 Hz, 1H), 6.15 (d, J=7.6 Hz, 1H), 5.33 (s, 2H), 5.08 (d, J=15.6 Hz, 1H), 5.01 (qd, J=2, 4.8 Hz, 1H), 4.90 (d, J=16 Hz, 1H), 4.77 (dd, J=7.6, 8.4 Hz, 1H), 4.60 (dd, J=2.4, 12.8 Hz, 1H), 4.47-4.42 (m, 1H), 4.35-4.30 (m, 1H), 4.13 (s, 2H), 3.81 (q, J=5.2 Hz, 2H), 3.95 (q, J=5.2 Hz, 2H), 2.68-2.66 (m, 1H), 2.37-2.28 (m, 1H).

(S)-2-((6-((2-fluoro-4-(prop-1-yn-1-yl)benzyl)oxy)-3,6'-dihydro-[2,4'-bipyridin]-1'(2'H)-yl)methyl)-1-(oxetan-2-ylmethyl)-1H-benzo[d]imidazole-6-carboxylic acid (Compound 107)

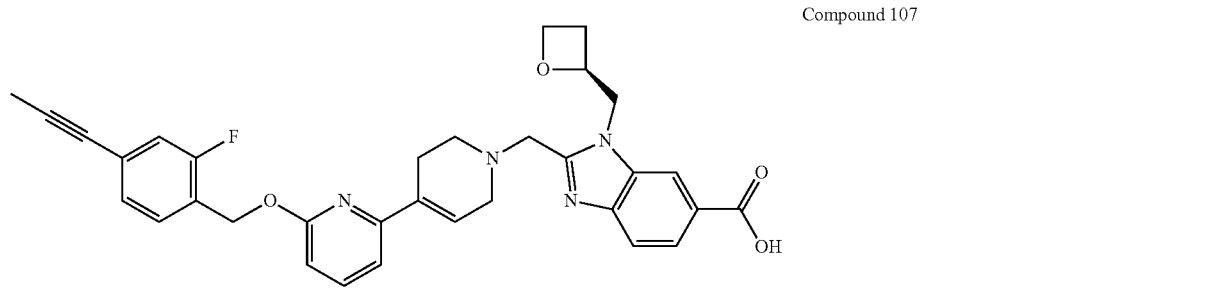 [SMILES: CC#Cc1ccc(COc2cccc(C3=CCN(Cc4nc5ccc(C(=O)O)cc5n4C[C@@H]4CCO4)CC3)n2)c(F)c1]

Compound 107

Prepared in analogous manner as for Compound 19
LCMS: [M+H]$^+$=567.0; Retention time (10 mM NH$_4$HCO$_3$)=1.63 min.
$^1$H NMR (400 MHz, MeOD) δ 8.34 (s, 1H), 8.00 (d, J=8.6 Hz, 1H), 7.70 (d, J=8.5 Hz, 1H), 7.66-7.60 (m, 1H), 7.42 (t, J=7.8 Hz, 1H), 7.17-7.04 (m, 3H), 6.73 (s, 1H), 6.69 (d, J=8.2 Hz, 1H), 5.44 (s, 2H), 5.26 (d, J=5.0 Hz, 1H), 4.77-4.70 (m, 1H), 4.67-4.60 (m, 1H), 4.52-4.44 (m, 2H), 4.19 (d, J=13.7 Hz, 1H), 4.07 (d, J=13.7 Hz, 1H), 3.29-3.23 (m, 2H), 2.88 (s, 3H), 2.76 (d, J=6.0 Hz, 2H), 2.66 (s, 2H), 2.56-2.45 (m, 2H), 2.04 (d, J=8.9 Hz, 3H), 1.33 (d, J=18.2 Hz, 1H).

(S)-2-((6-((4-(cyclopropylethynyl)-2-fluorobenzyl)oxy)-3,6'-dihydro-[2,4'-bipyridin]-1'(2'H)-yl)methyl)-1-(oxetan-2-ylmethyl)-1H-benzo[d]imidazole-6-carboxylic acid (Compound 108)

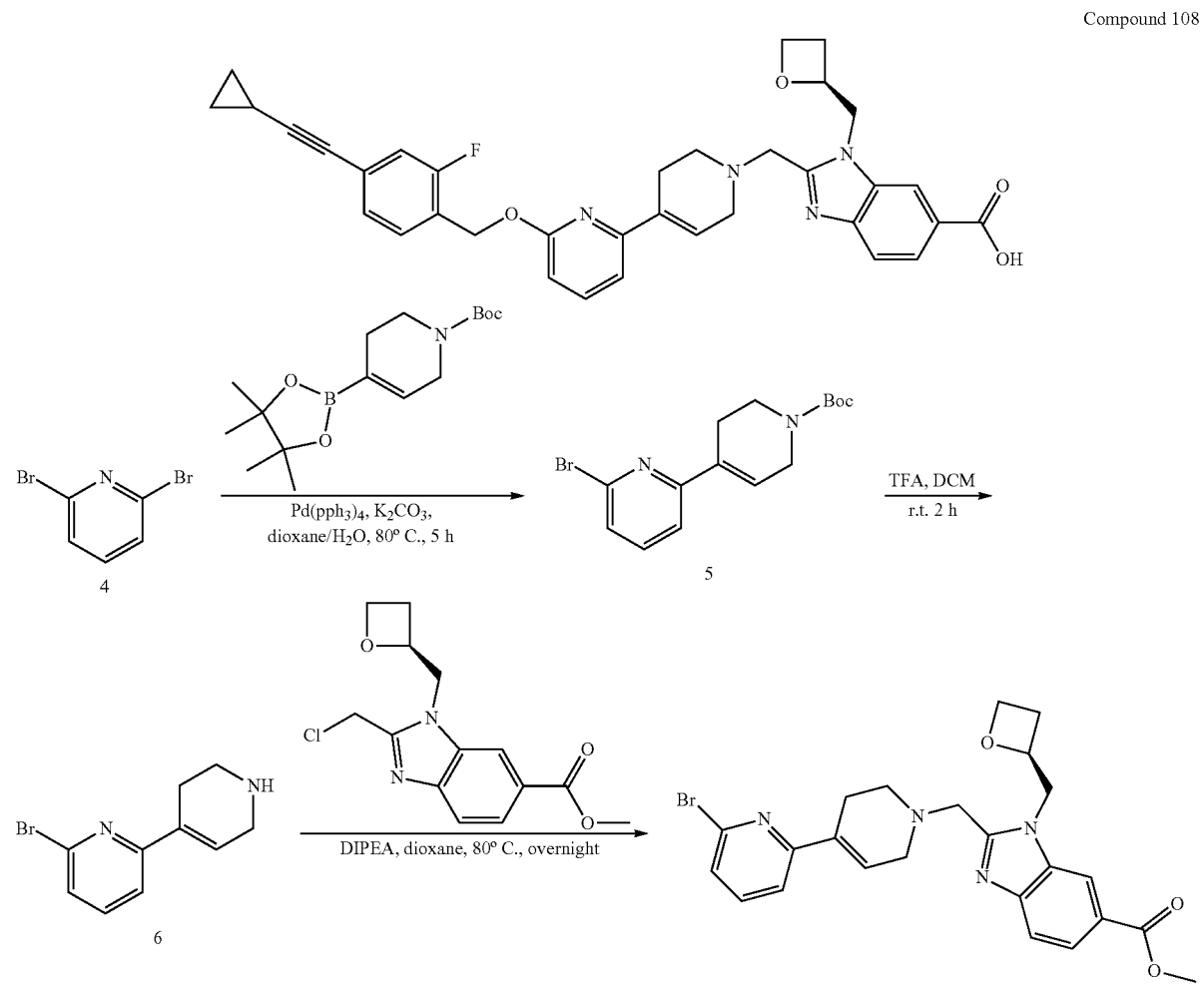

Compound 108

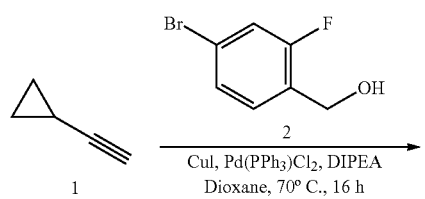
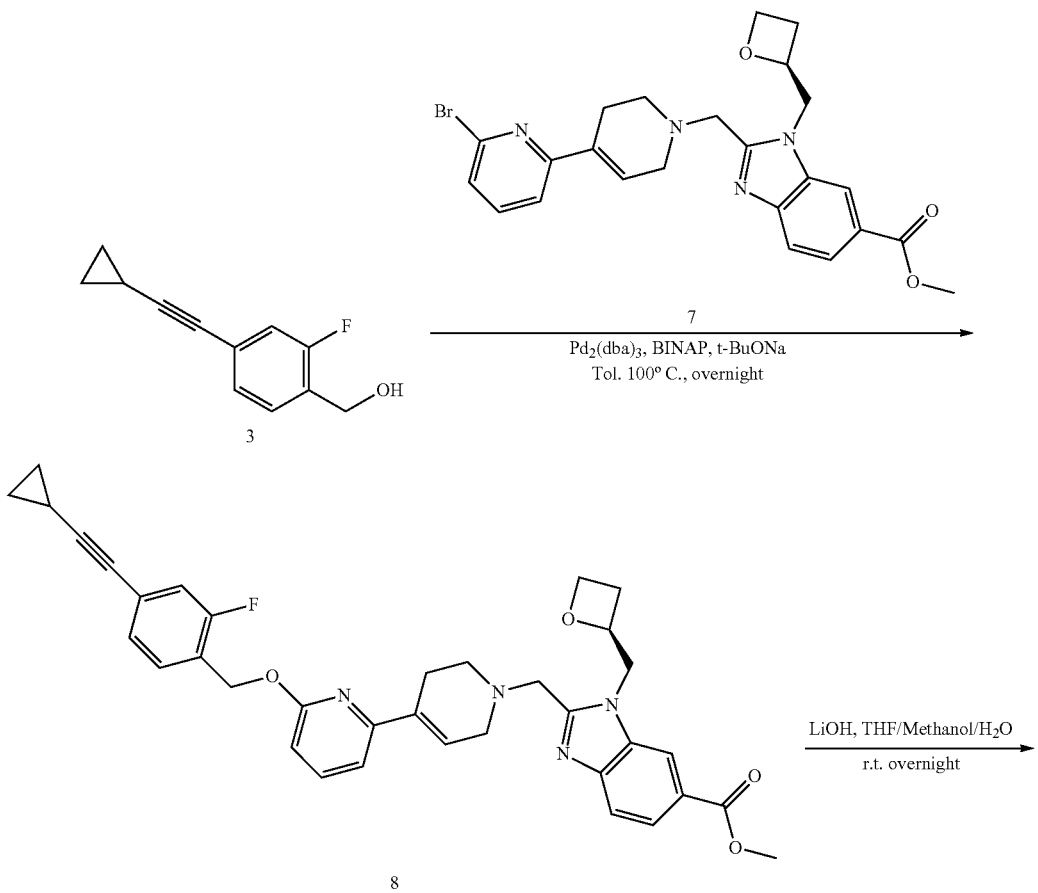
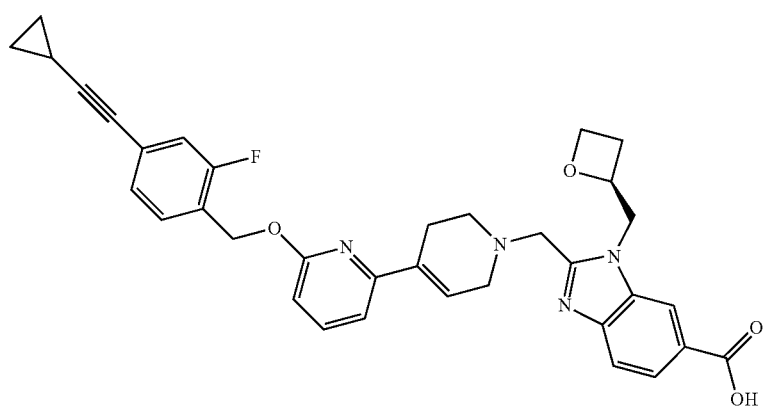
Compound 108

Step 1

To a solution of (4-bromo-2-fluorophenyl)methanol (1.03 g, 5.0 mmol) in 1,4-dioxnae (30 mL), ethynylcyclopropane (396 mg, 6.0 mmol), Pd(PPh$_3$)Cl$_2$ (180 mg, 0.25 mmol), CuI (50 mg, 0.25 mmol) and DIPEA (1.94 g, 15 mmol) was added under N$_2$, the reaction was stirred at 70° C. for 16 h. The mixture was diluted with water, and extracted with EA (30 mL×2), the organic layer was dried in Na$_2$SO$_4$, filtered with Buchner funnel and concentrated. The residue was purified by prep-HPLC to give (4-(cyclopropylethynyl)-2-fluorophenyl) methanol (770 mg, 80% yield) as a yellow solid. LCMS [M-OH]=173.1; Retention time (10 mM NH$_4$HCO$_3$)=1.71 min.

Step 2

To the solution of 2,6-dibromopyridine (1 g, 4.22 mmol, 1.0 eq) in 1,4-dioxane (25 mL) and H$_2$O (5 mL), tert-butyl 4-(4,4,5,5-tetramethyl-1,3,2-dioxaborolan-2-yl)-3,6-dihydropyridine-1(2H)-carboxylate (1.56 g, 5.06 mmol), Pd(PPh$_3$)$_4$ (500 mg, 0.42 mmol) and K$_2$CO$_3$ (1.46 g, 10.5 mmol) was added under N$_2$. The reaction mixture was stirred at 80° C. for 5 h. The reaction mixture was cooled to 30° C. and EA (100 mL) was added. The reaction mixture was filtered and the mixture was extracted with EA (50 mL×2). The combined organic phase was washed by sat. NaCl. The organic phase was dried by Na$_2$SO$_4$. The crude product was purified by chromatography (PE:EA=10:1) to give tert-butyl 6-bromo-3',6'-dihydro-[2,4'-bipyridine]-1'(2'H)-carboxylate (530 mg, 37% yield) as a pale yellow oil. LCMS [M+Na]$^+$=361.0; Retention time (0.01% TFA)=2.15 min.

Step 3

To the solution of tert-butyl 6-bromo-3',6'-dihydro-[2,4'-bipyridine]-1'(2'H)-carboxylate (750 mg, 2.21 mmol) in DCM (8 mL), TFA (3 mL) was added. The reaction mixture was stirred at 30° C. for 2 h. DCM was evaporated to give 6-bromo-1',2',3',6'-tetrahydro-2,4'-bipyridine (450 mg, 85% yield) as a pale yellow oil, which was used for next step without any purification. LCMS: [M+H]$^+$=240.9; Retention time (0.01% TFA)=1.11 min.

Step

To the solution of 6-bromo-1',2',3',6'-tetrahydro-2,4'-bipyridine (450 mg, 1.88 mmol, 1.0 eq) in 1,4-dioxane (5 mL), methyl (S)-2-(chloromethyl)-1-(oxetan-2-ylmethyl)-1H-benzo[d]imidazole-6-carboxylate (500 mg, 1.69 mmol) and DIPEA (3.5 g, 27.1 mmol) were added. The reaction mixture was stirred at 80° C. overnight. The solvent was evaporated. The residue was purified by prep-HPLC to give methyl (S)-2-((6-bromo-3',6'-dihydro-[2,4'-bipyridin]-1'(2'H)-yl)methyl)-1-(oxetan-2-ylmethyl)-1H-benzo[d]imidazole-6-carboxylate (240 mg, 26% yield) as a pale yellow solid. LCMS: [M+H]$^+$=497.0; Retention time (0.01% TFA)=1.48 min.

Step 5

To the solution of methyl (S)-2-((6-bromo-3',6'-dihydro-[2,4'-bipyridin]-1'(2'H)-yl)methyl)-1-(oxetan-2-ylmethyl)-1H-benzo[d]imidazole-6-carboxylate (30 mg, 0.06 mmol), (4-(cyclopropylethynyl)-2-fluorophenyl)methanol (15 mg, 0.08 mmol) in toluene (5 mL), Pd$_2$(dba)$_3$ (6 mg, 0.01 mmol), BINNP (6 mg, 0.01 mmol), and t-BuONa (15 mg, 0.16 mmol) were added under N$_2$. The reaction mixture was heated to 100° C. The reaction mixture was stirred at 100° C. overnight. The solvent was evaporated. The residue was purified by prep-HPLC to give methyl (S)-2-((6-((4-(cyclopropylethynyl)-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate (8 mg, 22% yield) as a yellow solid. LCMS: [M+H]$^+$=607.0, Retention time (10 mM NH$_4$HCO$_3$)=2.30 min.

Step 6

To the solution of (S)-2-((6-((4-(cyclopropylethynyl)-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (8 mg, 0.01 mmol) in THF (0.5 mL), Methanol (0.5 mL) and H$_2$O (0.5 mL), LiOH (8 mg, 0.33 mmol) was added. The reaction mixture was stirred at 30° C. for 72 h. The solvents were evaporated. The residue was purified by prep-HPLC to give (S)-2-((6-((4-(cyclopropylethynyl)-2-fluorobenzyl)oxy)-3',6'-dihydro-[2,4'-bipyridin]-1'(2'H)-yl)methyl)-1-(oxetan-2-ylmethyl)-1H-benzo[d] imidazole-6-carboxylic acid (5.5 mg, 70% yield) as a white solid. LCMS: [M+H]$^+$=593.1, Retention time (10 mM NH$_4$HCO$_3$)=1.685 min.

$^1$H NMR (400 MHz, DMSO) δ 8.26 (s, 1H), 7.82 (d, J=8.4 Hz, 1H), 7.70-7.65 (m, 2H), 7.46 (t, J=7.8 Hz, 1H), 7.25-7.18 (m, 2H), 7.08 (d, J=7.4 Hz, 1H), 6.75-6.72 (m, 2H), 5.39 (s, 2H), 5.06 (m, 1H), 4.84-4.78 (m, 1H), 4.68-4.63 (m, 1H), 4.50-4.44 (m, 1H), 4.39-4.34 (m, 1H), 3.99 (dd, J=63.5, 13.4 Hz, 2H), 3.27-3.18 (m, 4H), 2.76-2.72 (m, 2H), 2.68-2.64 (m, 1H), 2.44-2.36 (m, 1H), 1.59-1.49 (m, 1H), 0.97-0.82 (m, 2H), 0.75-0.72 (m, 2H).

(S)-2-((6-((4-chloro-2-fluorobenzyl)oxy)-4-phenyl-3',6'-dihydro-[2,4'-bipyridin]-1'(2'H)-yl)methyl)-1-(oxetan-2-ylmethyl)-1H-benzo[d]imidazole-6-carboxylic acid (Compound 109)

Compound 109

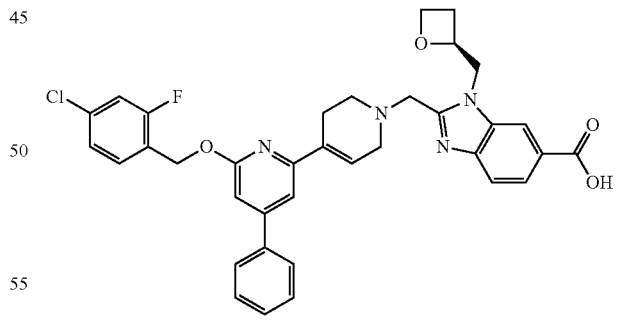

Prepared in analogous manner as for Compound 19

LCMS: [M+H]$^+$=639.0; Retention time (10 mM NH$_4$HCO$_3$)=1.77 min.

$^1$H NMR (400 MHz, MeOD) δ 8.23 (brs, 1H), 7.97 (dd, J=1.2, 7.6 Hz, 1H), 7.20-7.71 (m, 10H), 6.82-6.93 (m, 2H), 5.50 (s, 2H), 5.22-5.30 (m, 1H), 4.47-4.88 (m, 4H), 4.40-4.19 (m, 2H), 3.20-3.32 (m, 2H), 2.71-2.88 (m, 5H), 2.48-2.60 (m, 1H).

(S)-2-((4-(S)-2-((6-((4-chlorobenzyl)oxy)-3',6'-di-hydro-[2,4'-bipyridin]-1'(2'H)-yl)methyl)-7-methyl-1-(oxetan-2-ylmethyl)-1H-benzo[d]imidazole-6-carboxylic acid (Compound 110)
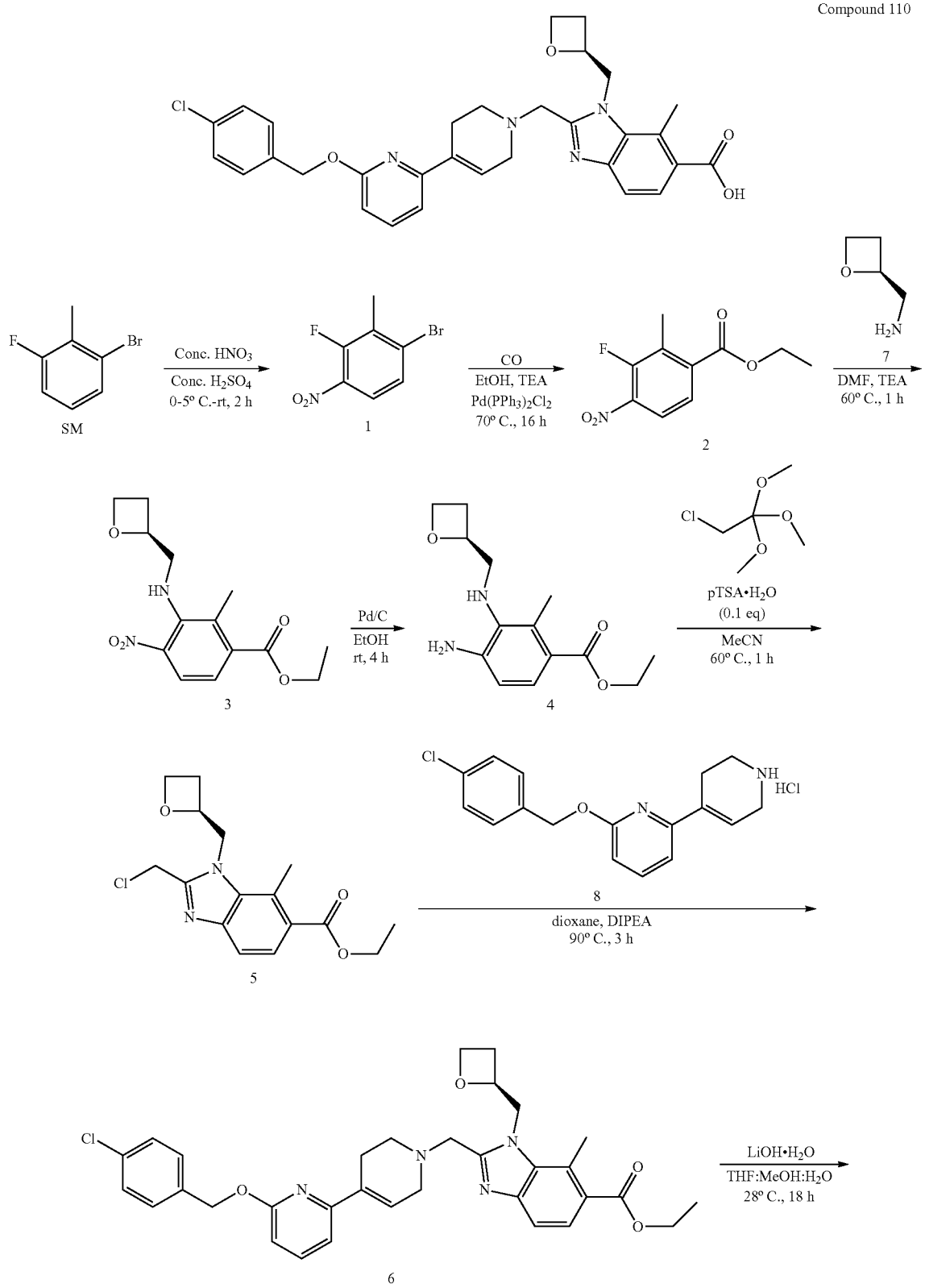

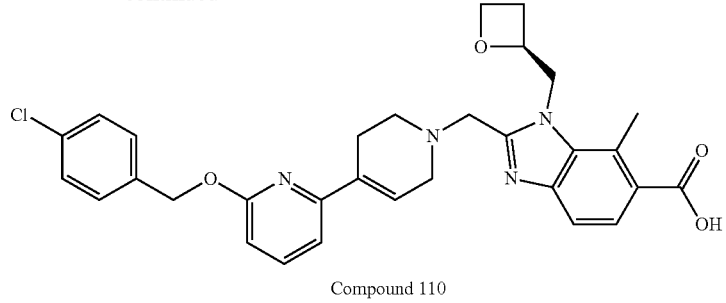 [SMILES: O=C(O)c1ccc2nc(CN3CC=C(c4cccc(CCc5ccc(Cl)cc5F)n4)CC3)n(C[C@@H]3CCO3)c2c1]

Compound 110

Step 1

In a 25 mL round-bottomed flask 1-bromo-3-fluoro-2-methylbenzene (2 g, 10.58 mmol, 1 eq) and concentrated sulfuric acid (7 mL) were cooled to −5-0° C. before adding concentrated nitric acid (1.03 g, 10.58 mmol, 65%) drop wise over 10 min. The reaction was stirred for 2 h at RT. The reaction was poured onto ice, extracted with EA (2×100 mL), washed with Sat. aq. $NH_4HCO_3$ (1×30 mL) and brine (1×30 mL), dried in $Na_2SO_4$, and filtered with Buchner funnel and concentrated. The crude solids were purified by Pre-TLC (PE:EA=30:1) to give 1-bromo-3-fluoro-2-methyl-4-nitrobenzene (1.67 g, 64% yield) as a pale yellowish solid.

Step 2

To a solution of 1-bromo-3-fluoro-2-methyl-4-nitro-benzene (1.3 g, 5.56 mmol) and 3-bromo-1-fluoro-2-methyl-4-nitro-benzene (1.30 g, 5.56 mmol) in EtOH:DMSO=4:3 (60 mL) was added $Pd(PPh_3)_2Cl_2$ (195 mg, 0.278 mmol) and N,N-diethylethanamine (1.12 g, 11.11 mmol, 1.55 mL). The mixture was cooled to 30° C., filtered with Buchner funnel through Celite and concentrated under reduced pressure, purified by Pre-TLC (PE:EA/2:1) to give ethyl 3-fluoro-2-methyl-4-nitro-benzoate (140 mg, 0.616 mmol, 100% purity) as a pale yellowish liquid. LCMS: $[M+H]^+$=228.1, Retention time (10 mM $NH_4HCO_3$)-1.61 min.

Step 3

A mixture of ethyl 3-fluoro-2-methyl-4-nitro-benzoate (140 mg, 0.616 mmol), ethyl 3-fluoro-2-methyl-6-nitro-benzoate (140 mg, 0.616 mmol) and TEA (125 mg, 1.23 mmol) in dioxane (5 mL) was stirred for 1 h at 90° C., until the reaction was complete as indicated by LCMS, the reaction mixture was concentrated in vacuo, purified by Pre-TLC (Hexanes/EtOAc=2:1) to give the desired product ethyl 2-methyl-4-nitro-3-[[(2S)-oxetan-2-yl] methylamino] benzoate (18 mg, 61 mmol, 9.9% yield) as a yellow solid. LCMS: $[M+H]^+$=295.1, Retention time (0.01% TFA)=1.83 min.

Step 4

A mixture of ethyl 2-methyl-4-nitro-3-[[(2S)-oxetan-2-yl] methylamino] benzoate (34 mg, 116 mmol) and Pd/C (10 mg, 0.082 mmol) in EtOH (6 mL) was stirred at 26° C. for 4 h in under $H_2$, until the reaction was complete as indicated by LCMS, the reaction mixture was filtered through a pad of Celite with EtOAc, and the combined organics were concentrated in vacuo, to give the desired product ethyl 4-amino-2-methyl-3-[[(2S)-oxetan-2-yl] methylamino] benzoate (21 mg, 0.044 mmol, 38.4% yield, 55.9% purity) as a pale yellow liquid. The crude was used directly next step without further purification.

LCMS: $[M+H]^+$=265.0; Retention time (0.01% TFA)=1.28 min.

Step 5

A mixture of ethyl 4-amino-2-methyl-3-[[(2S)-oxetan-2-yl] methylamino] benzoate (21 mg, 0.079 mmol), 2-chloro-1,1,1-trimethoxy-ethane (15 mg, 0.095 mmol), and pTSA·$H_2O$ (7.6 mg, 0.040 mmol) in MeCN (5 mL) was stirred for 1 h at 60° C., until the reaction was complete as indicated by LCMS, the reaction mixture was concentrated in vacuo, purified by Pre-HPLC (10 mM $NH_4HCO_3$) to give the desired product ethyl 2-(chloromethyl)-4-methyl-3-[[(2S)-oxetan-2-yl] methyl] benzimidazole-5-carboxylate (24 mg, 0.074 mmol, 93.6% yield) as a pale white solid.

LCMS: $[M+H]^+$=323.0; Retention time (10 mM $NH_4HCO_3$)=1.64 min.

Step 6

A mixture of ethyl 2-(chloromethyl)-4-methyl-3-[[(2S)-oxetan-2-yl] methyl] benzimidazole-5-carboxylate (24 mg, 0.074 mmol), 2-[(4-chlorophenyl) methoxy]-6-(1,2,3,6-tetrahydropyridin-4-yl) pyridine (15 mg, 0.031 mmol, HC), and DIPEA (6 mg, 0.050 mmol) in dioxane (3 mL) was stirred for 3 h at 90° C., until the reaction was complete as indicated by LCMS, the reaction mixture was concentrated in vacuo, purified by silica gel chromatography (Hexanes/EtOAc=20:1) to give the desired product ethyl 2-[[4-[6-[(4-chlorophenyl) methoxy]-2-pyridyl]-3,6-dihydro-2H-pyridin-1-yl] methyl]-4-methyl-3-[[(2S)-oxetan-2-yl] methyl] benzimidazole-5-carboxylate (23 mg, 0.027 mmol, 69.3% purity) as a pale yellowish liquid. The crude was used directly next step without further purification. LCMS: $[M+H]^+$=587.0; Retention time (10 mM $NH_4HCO_3$)=2.38 min.

Step 7

A mixture of ethyl 2-[[4-[6-[(4-chlorophenyl) methoxy]-2-pyridyl]-3,6-dihydro-2H-pyridin-1-yl]methyl]-4-methyl-3-[[(2S)-oxetan-2-yl] methyl] benzimidazole-5-carboxylate (23 mg, 0.039 mmol) in $H_2O$ (1.0 mL), MeOH (1.0 mL) and THF (1.0 mL) was stirred for 18 h at 28° C., until the reaction was complete as indicated by LCMS, the reaction mixture was concentrated, added water (1 mL), adjusted pH=6 with acetic acid, extracted with EA (2×20 mL), dried in $Na_2SO_4$, filtered with Buchner funnel and concentrated in vacuo, purified by Pre-HPLC (10 mM NH4HCO3) to give the desired product (S)-2-((6-((4-chlorobenzyl)oxy)-3',6'-dihydro-[2,4'-bipyridin]-1'(2'H)-yl)methyl)-7-methyl-1-(oxetan-2-ylmethyl)-1H-benzo[d]imidazole-6-carboxylic acid (5 mg, 0.010 mmol, 24.7% yield, 100% purity) as pale white solid. LCMS: $[M+H]^+$=559.0; Retention time (10 mM $NH_4HCO_3$)=1.64 min.

$^1$H NMR (400 MHz, DMSO-d6) δ 7.70 (t, J=8, 7.6 Hz, 1H), 7.56 (d, J=8.4 Hz, 1H), 7.47-7.40 (m, 5H), 7.08 (d, J=7.6 Hz, 1H), 6.74-6.72 (m, 2H), 5.36 (s, 2H), 5.08-5.02 (m, 2H), 4.83 (d, J=13.2 Hz, 1H), 4.51 (dd, J=8, 5.6 Hz, 1H), 4.37-4.31 (m, 1H), 4.10 (d, J=13.6 Hz, 1H), 3.90 (d, J=13.2

Hz, 1H), 3.23-3.15 (m, 2H), 2.80 (s, 3H), 2.74-2.66 (m, 3H), 2.54-2.51 (m, 2H), 2.40-2.32 (m, 1H).

(S)-2-((4-(6-(4-chlorobenzyloxy)pyridin-2-yl)-5,6-dihydropyridin-1(2H)-yl)methyl)-5-methyl-1-(oxetan-2-ylmethyl)-1H-benzo[d]imidazole-6-carboxylic acid (Compound 111)

Compound 111

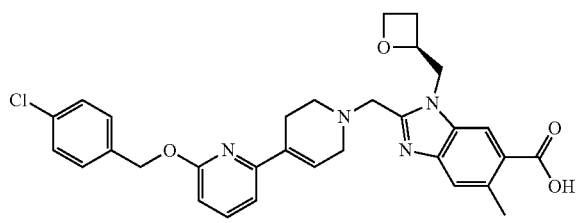

Prepared in analogous manner as for Compound 110

LCMS: [M+H]⁺=559.0; Retention time (10 mM NH₄HCO₃)=1.58 min.

¹H NMR (400 MHz, DMSO) δ 8.07-8.06 (brs, 1H), 7.68 (t, J=7.8 Hz, 1H), 7.44 (d, J=10.5 Hz, 4H), 7.36-7.31 (m, 1H), 7.07 (d, J=7.5 Hz, 1H), 6.73 (d, J=8.1 Hz, 2H), 5.39-5.30 (m, 2H), 5.04-5.03 (brs, 1H), 4.72 (dd, J=14.8, 6.3 Hz, 1H), 4.59 (d, J=13.1 Hz, 1H), 4.46-4.41 (m, 1H), 4.33 (d, J=9.0 Hz, 1H), 4.03 (d, J=13.5 Hz, 1H), 3.89 (d, J=13.4 Hz, 1H), 3.39 (dd, J=13.4, 6.7 Hz, 2H), 3.20 (s, 3H), 2.72-2.71 (brs, 2H), 2.59-2.58 (brs, 3H), 2.37-2.36 (brs, 1H).

2-((6-((4-chloro-2-fluorobenzyl)oxy)-3,6'-dihydro-[2,4'-bipyridin]-1'(2'H)-yl)methyl)-1-(1-(oxazol-2-yl)ethyl)-1H-benzo[d]imidazole-6-carboxylic acid (Compound 112)

Compound 112

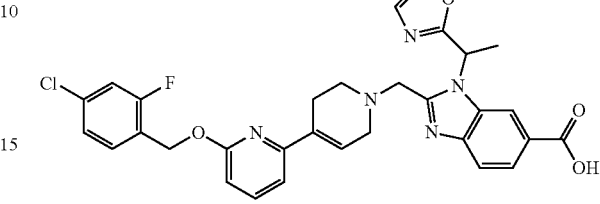

Prepared in analogous manner as for Compound 19

LCMS: [M+H]⁺=588.0; Retention time (10 mM NH₄HCO₃)= 1.62 min.

¹H NMR (400 MHz, DMSO) δ 8.03 (s, 1H), 7.76 (d, J=9.4 Hz, 1H), 7.66 (dd, J=16.9, 9.2 Hz, 2H), 7.54 (dd, J=14.9, 8.2 Hz, 2H), 7.47 (dd, J=10.0, 2.0 Hz, 1H), 7.34-7.22 (m, 2H), 7.07 (d, J=7.5 Hz, 1H), 6.79-6.66 (m, 2H), 6.44 (q, J=6.9 Hz, 1H), 5.39 (s, 2H), 4.09 (d, J=13.4 Hz, 1H), 3.95 (d, J=13.5 Hz, 1H), 3.24 (d, J=16.3 Hz, 2H), 2.76-2.59 (m, 2H), 2.47 (s, 2H), 1.93 (d, J=7.0 Hz, 3H).

(S)-2-((6-(4-chloro-2-fluorophenethyl)-3',6'-dihydro-[2,4'-bipyridin]-1'(2'H)-yl)methyl)-1-(oxetan-2-ylmethyl)-1H-benzo[d]imidazole-6-carboxylic acid (Compound 113)

Compound 113

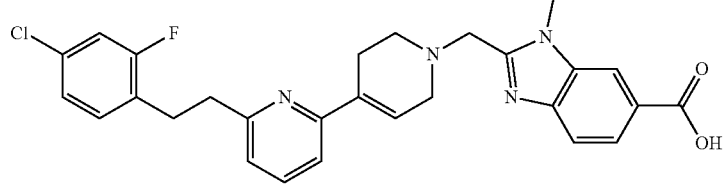

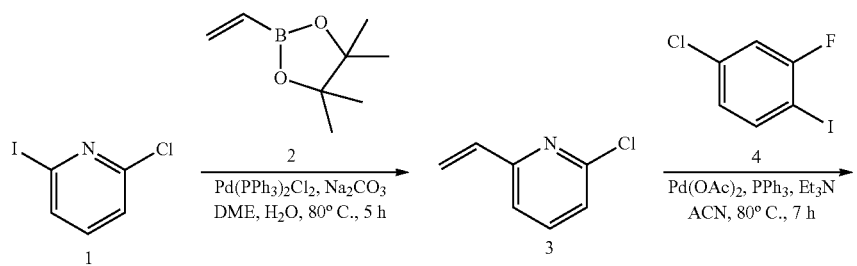

-continued
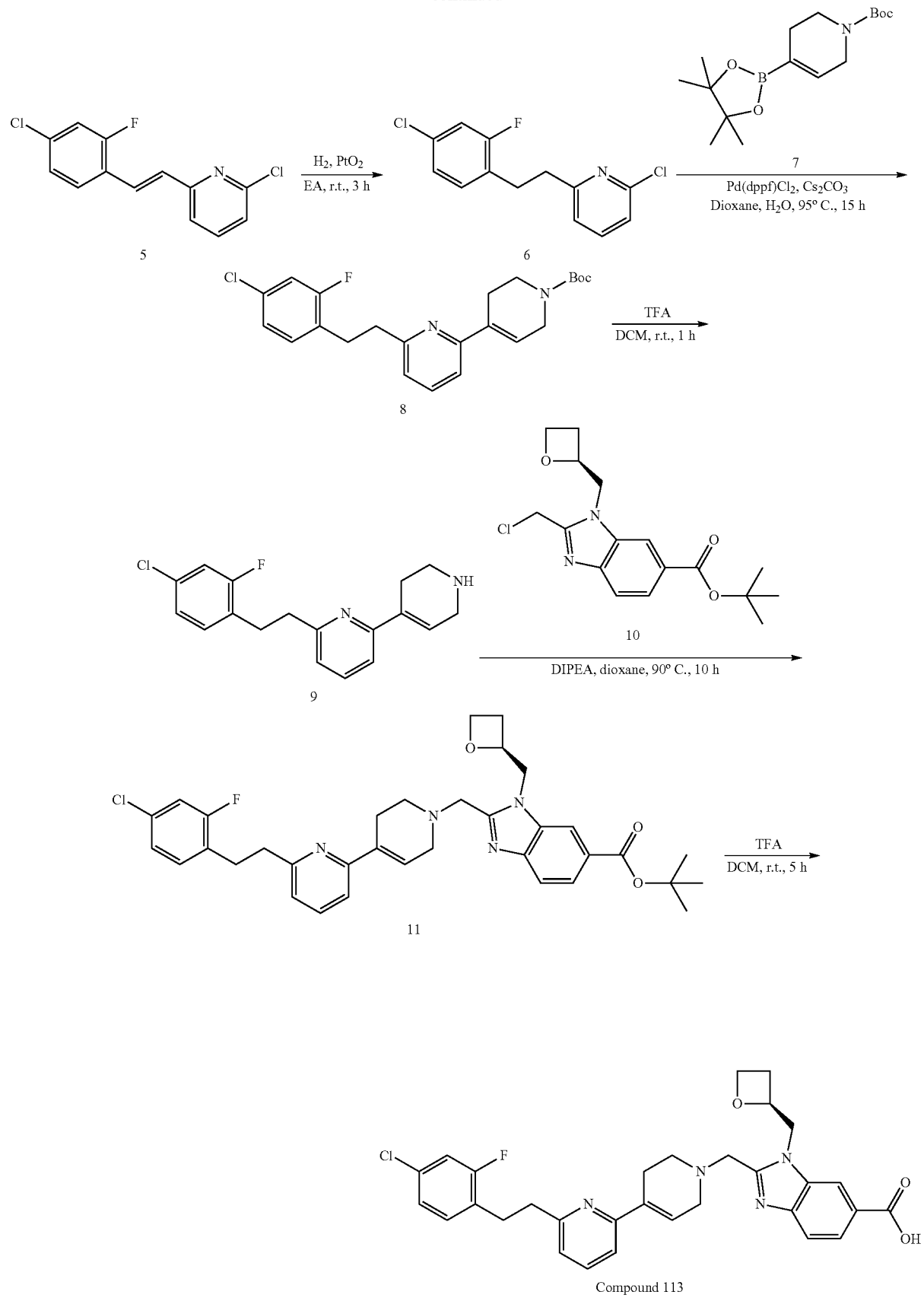
Compound 113

Step 1

A mixture of 4,4,5,5-tetramethyl-2-vinyl-1,3,2-dioxaborolane (354 mg, 2.30 mmol), 2-chloro-6-iodo-pyridine (500 mg, 2.09 mmol), $Na_2CO_3$ (332 mg, 3.13 mmol) and dichloropalladium triphenylphosphane (146 mg, 209 mmol) in 1,2-dimethoxyethane (2.5 mL) and $H_2O$ (0.5 mL) was stirred for 5 h at 80° C. in a round bottom flask under $N_2$. And upon completion of the reaction, as judged by LCMS, the reaction mixture was filtered and the filtrate was purified by silica gel column chromatography (PE:EA=50:1) to afford the crude product 2-chloro-6-vinyl-pyridine (400 mg, crude). LCMS: $[M+H]^+$=140.3; Retention time (0.01% TFA)=1.83 min;

Step 2

A mixture of 2-chloro-6-vinyl-pyridine (400 mg, 2.87 mmol), 4-chloro-2-fluoro-1-iodo-benzene (588 mg, 2.29 mmol), $Et_3N$ (580 mg, 5.73 mmol), $Pd(OAc)_2$ (64 mg, 0.287 mmol) and $PPh_3$ (90 mg, 0.344 mmol) in ACN (5 mL) was stirred for 7 h at 80° C. under N2, until the reaction was complete as indicated by LCMS, the reaction mixture was filtered through a pad of Celite with EtOAc, and the combined organics were concentrated in vacuo, purified by prep-HPLC to give the desired product 2-chloro-6-[(E)-2-(4-chloro-2-fluoro-phenyl)vinyl]pyridine (180 mg, 18.0% yield) as a pale yellow solid.

LCMS: $[M+H]^+$=268.0; Retention time (0.01% TFA)= 2.40 min;

Step 3

A mixture of 2-chloro-6-[(E)-2-(4-chloro-2-fluoro-phenyl)vinyl]pyridine (105 mg, 392 mmol) and $PtO_2$ (9 mg, 39 mmol) in EA (10 mL) was stirred for 3 h at rt in a RBF under $H_2$, until the reaction was complete as indicated by LCMS, the reaction mixture was filtered through a pad of Celite with EtOAc, and the combined organics were concentrated in vacuo, purified by prep-HPLC to give the desired product 2-chloro-6-[2-(4-chloro-2-fluoro-phenyl)ethyl]pyridine (35 mg, 33.1% yield) as a white solid.

LCMS: $[M+H]^+$=270.1; Retention time (0.01% TFA)= 2.017 min; Purity=100% (214 nm).

Step 4

A mixture of 2-chloro-6-[2-(4-chloro-2-fluoro-phenyl)ethyl]pyridine (25 mg, 0.093 mmol), tert-butyl 4-(4,4,5,5-tetramethyl-1,3,2-dioxaborolan-2-yl)-3,6-dihydro-2H-pyridine-1-carboxylate (57 mg, 0.185 mmol), $Pd(dppf)Cl_2$ (7 mg, 0.009 mmol) and $Cs_2CO_3$ (90 mg, 0.278 mmol) in dioxane (4 mL) and $H_2O$ (0.8 mL) was stirred for 15 h at 95° C. under $N_2$, until the reaction was completed as indicated by LCMS, the reaction mixture was filtered through a pad of Celite with EtOAc, and the combined organics were concentrated in vacuo, purified by silica gel chromatography (Hexanes:EtOAc=3:1) to give the desired product tert-butyl 4-[6-[2-(4-chloro-2-fluoro-phenyl)ethyl]-2-pyridyl]-3,6-dihydro-2H-pyridine-1-carboxylate (20 mg, 0.047 mmol, 51.8% yield) as a pale yellow solid.

LCMS: $[M+H]^+$=417.3; Retention time (0.01% TFA)= 1.99 min; purity=98.4% (254 nm).

Step 5

To a solution of tert-butyl 4-[6-[2-(4-chloro-2-fluoro-phenyl)ethyl]-2-pyridyl]-3,6-dihydro-2H-pyridine-1-carboxylate (20 mg, 0.048 mmol) in DCM (2 mL), TFA (0.4 mL) was added. The reaction mixture was stirred at r.t for 1 h, until the reaction was complete as indicated by TLC. The solvent was evaporate to give the crude product 2-[2-(4-chloro-2-fluoro-phenyl)ethyl]-6-(1,2,3,6-tetrahydropyridin-4-yl)pyridine (15 mg, crude).

LCMS: $[M+H]^+$=317.3; Retention time (0.01% TFA)= 1.57 min; purity=94.0% (254 nm).

Step 6

A mixture of 2-[2-(4-chloro-2-fluoro-phenyl)ethyl]-6-(1,2,3,6-tetrahydropyridin-4-yl)pyridine (15 mg, 0.047 mmol), tert-butyl 2-(chloromethyl)-3-[[(2S)-oxetan-2-yl]methyl]benzimidazole-5-carboxylate (15.95 mg, 0.047 mmol), and DIPEA (371 mg, 2.87 mmol, 0.5 mL) in dioxane (3.5 mL) was stirred for 10 h at 90° C. under $N_2$, until the reaction was complete as indicated by LCMS. The solvent was evaporated, and the residue was purified by silica gel chromatography (Hexanes:EtOAc=1:2) to give the desired product tert-butyl 2-[[4-[6-[2-(4-chloro-2-fluoro-phenyl)ethyl]-2-pyridyl]-3,6-dihydro-2H-pyridin-1-yl]methyl]-3-[[(2S)-oxetan-2-yl]methyl]benzimidazole-5-carboxylate (10 mg, 0.016 mmol, 34.2% yield) as a pale yellow solid. LCMS: $[M+H]^+$=617.0; Retention time (10 mM $NH_4HCO_3$)=2.33 min; Purity=88.6% (254 nm).

Step 7

To a solution of tert-butyl 2-[[4-[6-[2-(4-chloro-2-fluoro-phenyl)ethyl]-2-pyridyl]-3,6-dihydro-2H-pyridin-1-yl]methyl]-3-[[(2S)-oxetan-2-yl]methyl]benzimidazole-5-carboxylate (10 mg, 0.016 mmol) in DCM (3 mL) was added slowly TFA (740 mg, 6.49 mmol, 0.5 mL) at rt and stirred for 5 h under $N_2$. After completion of the reaction as judged by LCMS, TFA and DCM were evaporated. The residue was purified by prep-HPLC to afford 2-[[4-[6-[2-(4-chloro-2-fluoro-phenyl)ethyl]-2-pyridyl]-3,6-dihydro-2H-pyridin-1-yl]methyl]-3-[[(2S)-oxetan-2-yl]methyl]benzimidazole-5-carboxylic acid (3.7 mg, 0.007 mmol, 40.7% yield) as a colorless liquid. LCMS: $[M+H]^+$=561.0; Retention time (10 mM $NH_4HCO_3$)=1.58 min;

$^1$H NMR (400 MHz, DMSO) δ 8.22 (s, 1H), 7.84-7.79 (m, 1H), 7.66-7.59 (m, 2H), 7.36-7.25 (m, 3H), 7.17 (dd, J=8.3, 2.0 Hz, 1H), 7.07 (d, J=7.6 Hz, 1H), 6.68-6.63 (m, 1H), 5.11-5.03 (m, 1H), 4.84-4.76 (m, 1H), 4.70-4.62 (m, 1H), 4.51-4.44 (m, 1H), 4.41-4.33 (m, 1H), 3.99 (dd, J=62.1, 13.5 Hz, 2H), 3.25-3.20 (m, 4H), 3.03-2.98 (m, 4H), 2.78-2.72 (m, 2H), 2.71-2.62 (m, 1H), 2.45-2.38 (m, 1H).

(S)-2-((6-((2,4-dichlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 114)

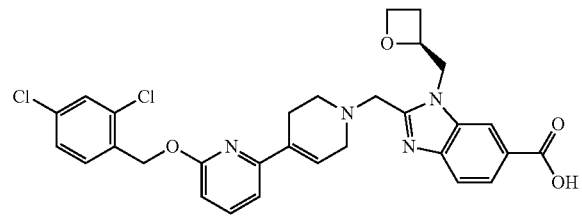

Compound 114

Prepared in analogous manner as for Compound 19

LCMS: $[M+H]^+$=579.1; Retention time (10 mM $NH_4HCO_3$)=1.50 min.

$^1$H NMR (400 MHz, MeOD) δ 8.32-8.29 (brs, 1H), 7.99 (dd, J=8.5, 1.4 Hz, 1H), 7.69-7.63 (m, 2H), 7.54-7.48 (m, 2H), 7.33 (dd, J=8.3, 2.1 Hz, 1H), 7.08 (d, J=7.4 Hz, 1H), 6.76-6.71 (m, 2H), 5.49 (s, 2H), 5.28-5.24 (m, 1H), 4.91-4.86 (m, 1H), 4.76-4.67 (m, 1H), 4.65-4.61 (m, 1H), 4.48 (dt, J=9.1, 5.9 Hz, 1H), 4.17 (d, J=13.7 Hz, 1H), 4.05 (d, J=13.6 Hz, 1H), 3.31-3.26 (m, 2H), 2.88-2.83 (m, 2H), 2.80-2.74 (m, 1H), 2.66-2.60 (m, 2H), 2.57-2.49 (m, 1H).

(S)-2-((6-((3,4-dichlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 115)

Compound 115

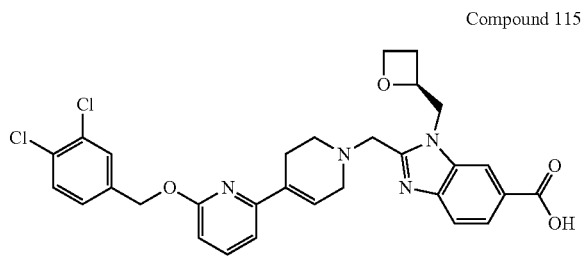 [SMILES: O=C(O)c1ccc2nc(CN3CC=C(c4cccc(OCc5ccc(Cl)c(Cl)c5)n4)CC3)n(C[C@@H]3CCO3)c2c1]

Prepared in analogous manner as for Compound 19

LCMS: [M+H]$^+$=579.2, Retention time (10 mM NH$_4$HCO$_3$)=1.50 min.

$^1$H NMR (400 MHz, MeOD) δ 8.26-8.23 (brs, 1H), 7.98 (dd, J=8.5, 1.4 Hz, 1H), 7.67-7.61 (m, 3H), 7.49 (d, J=8.3 Hz, 1H), 7.37 (dd, J=8.3, 1.9 Hz, 1H), 7.06 (d, J=7.4 Hz, 1H), 6.74-6.70 (m, 2H), 5.39 (s, 2H), 5.29-5.23 (m, 1H), 4.92-4.86 (m, 1H), 4.76-4.69 (m, 1H), 4.60-4.59 (m, 1H), 4.47 (dt, J=9.1, 6.0 Hz, 1H), 4.16 (d, J=13.6 Hz, 1H), 4.04 (d, J=13.6 Hz, 1H), 3.31-3.23 (m, 2H), 2.87-2.81 (m, 2H), 2.80-2.72 (m, 1H), 2.66-2.60 (m, 2H), 2.57-2.48 (m, 1H).

(S)-2-((6-((5-chloropyridin-2-yl)methoxy)-3',6'-dihydro-[2,4'-bipyridin]-1'(2'H)-yl)methyl)-1-(oxetan-2-ylmethyl)-1H-benzo[d]imidazole-6-carboxylic acid (Compound 116)

Compound 116

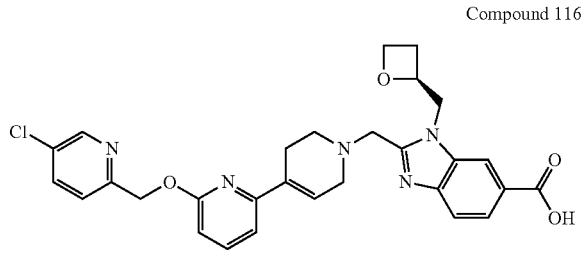 [SMILES: O=C(O)c1ccc2nc(CN3CC=C(c4cccc(OCc5ccc(Cl)cn5)n4)CC3)n(C[C@@H]3CCO3)c2c1]

Prepared in analogous manner as for Compound 19

LCMS: [M+H]$^+$=546.2; Retention time (10 mM NH$_4$HCO$_3$)=1.30 min.

$^1$H NMR (400 MHz, MeOD) δ 8.51 (d, J=2.2 Hz, 1H), 8.35-8.31 (brs, 1H), 7.99 (dd, J=8.5, 1.4 Hz, 1H), 7.84 (dd, J=8.4, 2.4 Hz, 1H), 7.72-7.62 (m, 2H), 7.51 (d, J=8.4 Hz, 1H), 7.07 (d, J=7.5 Hz, 1H), 6.78 (d, J=8.2 Hz, 1H), 6.68-6.63 (brs, 1H), 5.48 (s, 2H), 5.26-5.22 (m, 1H), 4.86-4.84 (m, 1H), 4.72 (dd, J=15.3, 2.4 Hz, 1H), 4.66-4.60 (m, 1H), 4.47 (dt, J=9.2, 6.0 Hz, 1H), 4.17 (d, J=13.8 Hz, 1H), 4.05 (d, J=13.8 Hz, 1H), 3.31-3.26 (m, 2H), 2.87-2.82 (m, 2H), 2.79-2.72 (m, 1H), 2.61-2.56 (m, 2H), 2.54-2.46 (m, 1H).

(S)-2-((6-((5-methoxypyridin-2-yl)methoxy)-3',6'-dihydro-[2,4'-bipyridin]-1'(2'H)-yl)methyl)-1-(oxetan-2-ylmethyl)-1H-benzo[d]imidazole-6-carboxylic acid (Compound 117)

Compound 117

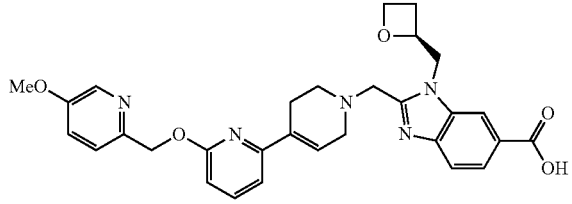

Prepared in analogous manner as for Compound 19

LCMS: [M+H]$^+$=542.1, Retention time (10 mM NH$_4$HCO$_3$)=1.40 min.

$^1$H NMR (400 MHz, DMSO) δ 8.25 (dd, J=2.8, 0.7 Hz, 1H), 8.24-8.21 (brs, 1H), 7.80 (dd, J=8.4, 1.5 Hz, 1H), 7.71-7.66 (m, 1H), 7.62 (d, J=8.4 Hz, 1H), 7.42 (d, J=8.0 Hz, 1H), 7.38 (dd, J=8.6, 2.8 Hz, 1H), 7.07 (d, J=7.4 Hz, 1H), 6.76-6.71 (m, 2H), 5.36 (s, 2H), 5.09-5.02 (m, 1H), 4.78 (dd, J=15.2, 7.2 Hz, 1H), 4.64 (dd, J=15.2, 2.7 Hz, 1H), 4.46 (dd, J=13.6, 7.7 Hz, 1H), 4.36 (dt, J=9.0, 5.9 Hz, 1H), 4.06 (d, J=13.5 Hz, 1H), 3.91 (d, J=13.5 Hz, 1H), 3.81 (s, 3H), 3.24-3.18 (m, 2H), 2.73 (s, 2H), 2.65 (dd, J=11.9, 5.2 Hz, 1H), 2.48-2.30 (m, 3H).

(S)-2-((6-((4-methoxybenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 118)

Compound 118

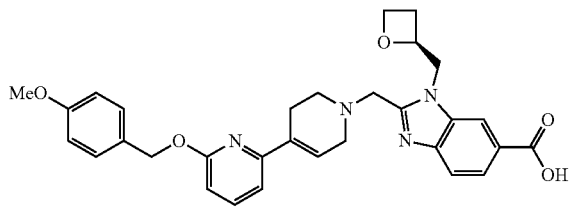

Prepared in analogous manner as for Compound 19

LCMS: [M+H]$^+$=540.0; Retention time (10 mM NH$_4$HCO$_3$)=1.45 min.

$^1$H NMR (400 MHz, MeOD) δ 8.31 (brs, 1H), 7.99 (dd, J=1.2, 6.8 Hz, 1H), 7.68 (d, J=8.4 Hz, 1H), 7.59 (t, J=7.6 Hz, 1H), 7.34-7.37 (m, 2H), 7.02 (d, J=7.6 Hz, 1H), 6.88-6.90 (m, 2H), 6.72-6.78 (m, 1H), 6.63 (d, J=8.0 Hz, 1H), 5.31 (s, 2H), 5.23-5.26 (m, 1H), 4.88 (t, J=7.2 Hz, 1H), 4.72 (dd, J=2.8 Hz, 12.4 Hz, H), 4.59-4.65 (m, 1H), 4.44-4.49 (m, 1H), 4.04-4.19 (m, 2H), 3.78 (s, 2H), 3.21-3.32 (m, 2H), 2.48-2.28 (m, 6H).

(S)-2-((6-((6-methoxypyridin-3-yl)methoxy)-3',6'-dihydro-[2,4'-bipyridin]-1'(2'H)-yl)methyl)-1-(oxetan-2-ylmethyl)-1H-benzo[d]imidazole-6-carboxylic acid (Compound 119)

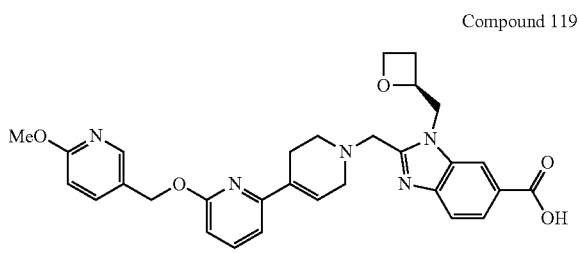 [SMILES: COc1ccc(COc2cccc(C3=CCN(Cc4nc5ccc(C(=O)O)cc5n4C[C@@H]4CCO4)CC3)n2)nc1]

Compound 119

Prepared in analogous manner as for Compound 19
LCMS: [M+H]⁺=542.1, Retention time (10 mM NH₄HCO₃)=1.43 min.
¹H NMR (400 MHz, DMSO) δ 8.27 (d, J=2.1 Hz, 1H), 8.24-8.21 (brs, 1H), 7.83-7.78 (m, 2H), 7.69-7.60 (m, 2H), 7.07 (d, J=7.4 Hz, 1H), 6.82 (d, J=8.5 Hz, 1H), 6.80-6.76 (brs, 1H), 6.69 (d, J=8.2 Hz, 1H), 5.32 (s, 2H), 5.10-5.03 (m, 1H), 4.79 (dd, J=15.2, 7.2 Hz, 1H), 4.65 (dd, J=15.1, 2.7 Hz, 1H), 4.50-4.44 (m, 1H), 4.36 (dt, J=9.0, 5.9 Hz, 1H), 4.07 (d, J=13.5 Hz, 1H), 3.92 (d, J=13.5 Hz, 1H), 3.83 (s, 3H), 3.27-3.22 (m, 2H), 2.80-2.72 (m, 2H), 2.70-2.64 (m, 1H), 2.57-2.52 (m, 2H), 2.44-2.37 (m, 1H).

(S)-1-(oxetan-2-ylmethyl)-2-((6-((4-(trifluoromethoxy)benzyl)oxy)-3,6'-dihydro-[2,4'-bipyridin]-1'(2'H)-yl)methyl)-1H-benzo[d]imidazole-6-carboxylic acid (Compound 120)

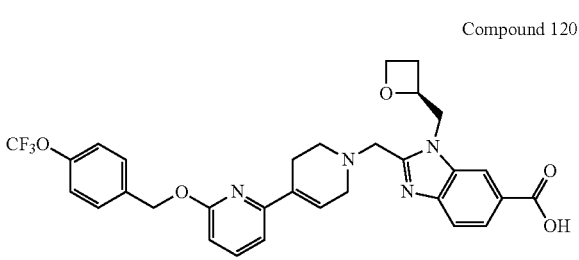

Compound 120

Prepared in analogous manner as for Compound 19
LCMS: [M+H]⁺=595.2, Retention time (10 mM NH₄HCO₃)=1.48 min.

(S)-1-(oxetan-2-ylmethyl)-2-((6-((6-(trifluoromethoxy)pyridin-3-yl)methoxy)-3',6'-dihydro-[2,4'-bipyridin]-1'(2'H)-yl)methyl)-1H-benzo[d]imidazole-6-carboxylic acid (Compound 121)

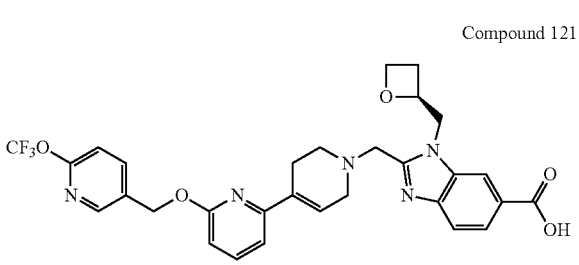

Compound 121

Prepared in analogous manner as for Compound 19
LCMS: [M+H]⁺=596.2; Retention time (10 mM NH₄HCO₃)=1.47 min.
¹H NMR (400 MHz, DMSO) δ 8.47 (d, J=2.2 Hz, 1H), 8.27 (s, 1H), 8.10 (dd, J=8.4, 2.4 Hz, 1H), 7.82 (dd, J=8.4, 1.3 Hz, 1H), 7.68 (dd, J=16.2, 8.2 Hz, 2H), 7.30 (d, J=8.4 Hz, 1H), 7.09 (d, J=7.5 Hz, 1H), 6.74 (d, J=8.1 Hz, 2H), 5.43 (brs, 2H), 5.07 (qd, J=7.2, 2.8 Hz, 1H), 4.80 (dd, J=15.2, 7.3 Hz, 1H), 4.65 (dd, J=15.1, 2.5 Hz, 1H), 4.47 (dd, J=13.6, 7.7 Hz, 1H), 4.36 (dt, J=8.9, 5.9 Hz, 1H), 4.08 (d, J=13.5 Hz, 1H), 3.92 (d, J=13.5 Hz, 1H), 3.21 (dd, J=24.1, 6.4 Hz, 4H), 2.80-2.71 (m, 2H), 2.65 (m, J=16.2, 8.7, 5.6 Hz, 1H), 2.40 (m, J=15.9, 11.1, 7.1 Hz, 1H).

(S)-2-((4-(4-(4-chloro-2-fluorobenzylamino)-5-fluoropyrimidin-2-yl)-5,6-dihydropyridin-1(2H)-yl)methyl)-1-(oxetan-2-ylmethyl)-1H-benzo[d]imidazole-6-carboxylic acid (Compound 122)

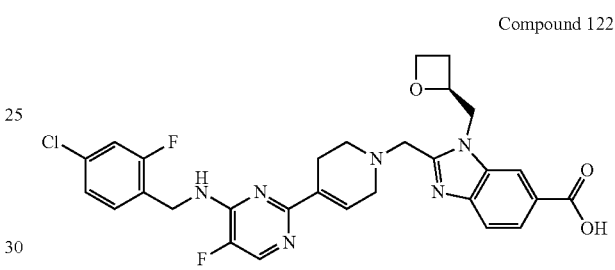

Compound 122

Prepared in analogous manner as for Compound 61
LCMS: [M+H]⁺=581.0; Retention time (10 mM NH₄HCO₃)=1.41 min.
¹H NMR (400 MHz, DMSO-d6) δ 8.26-8.25 (d, J=0.8 Hz, 1H), 8.22-8.19 (t, J=6.0 Hz, 1H), 8.14-8.13 (d, J=3.6 Hz, 1H), 7.82-7.79 (dd, J1=8.4 Hz, J2=1.6 Hz, 1H), 7.65-7.63 (d, J=8.4 Hz, 1H), 7.41-7.37 (m, 2H), 7.24-7.22 (dd, J1=8.0 Hz, J2=1.6 Hz, 1H), 6.86 (s, 1H), 5.05-5.01 (m, 1H), 4.81-4.75 (m, 1H), 4.65-4.59 (m, 3H), 4.48-4.42 (m, 1H), 4.38-4.33 (m, 1H), 4.06-4.03 (d, J=13.6 Hz, 1H), 3.89-3.86 (d, J=13.6 Hz, 1H), 3.24-3.12 (m, 2H), 2.66-2.61 (m, 3H), 2.46 (s, 2H), 2.42-2.36 (m, 1H).

(S)-2-((4-(4-(4-chloro-2-fluorobenzyloxy)-5-fluoropyrimidin-2-yl)-5,6-dihydropyridin-1(2H)-yl)methyl)-1-(oxetan-2-ylmethyl)-1H-benzo[d]imidazole-6-carboxylic acid (Compound 123)

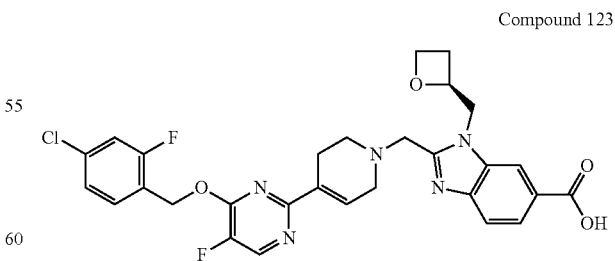

Compound 123

Prepared in analogous manner as for Compound 19
LCMS: [M+H]⁺=582.0; Retention time (10 mM NH₄HCO₃)=1.53 min.
¹H NMR (400 MHz, DMSO-d6) δ 8.59-8.58 (d, J=3.2 Hz, 1H), 8.26 (s, 1H), 7.82-7.80 (d, J=8.4 Hz, 1H), 7.66-7.60 (m, 2H), 7.53-7.50 (dd, J1=10.0 Hz, J2=2.0 Hz, 1H), 7.35-7.33 (dd, J1=8.4 Hz, J2=2.0 Hz, 1H), 7.08 (s, 1H), 5.57 (s, 2H), 5.09-5.03 (m, 1H), 4.82-4.77 (m, 1H), 4.67-4.62 (dd, J1=15.2 Hz, J2=2.4 Hz, 1H), 4.49-4.43 (m, 1H), 4.39-4.33 (m, 1H), 4.10-4.06 (d, J=13.6 Hz, 1H), 3.94-3.91 (d, J=13.2 Hz, 1H), 3.29-3.26 (m, 2H), 2.76-2.73 (t, J=6.0 Hz, 2H), 2.67-2.63 (m, 1H), 2.57 (s, 2H), 2.41-2.37 (m, 1H).

(S)-2-((4-(4-((4-chloro-2-fluorobenzyl)amino)pyrimidin-2-yl)-5,6-dihydropyridin-1(2H)-yl)methyl)-1-(oxetan-2-ylmethyl)-1H-benzo[d]imidazole-6-carboxylic acid (Compound 124)

Compound 124

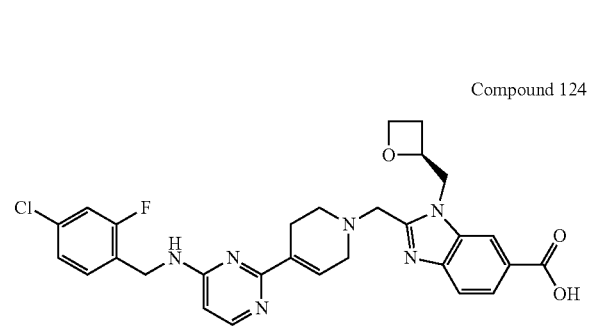

Prepared in analogous manner as for Compound 61

LCMS: [M+H]$^+$=563.0; Retention time (10 mM NH$_4$HCO$_3$)=1.37 min.

$^1$H NMR (400 MHz, MeOD) δ 8.23 (s, 1H), 7.88 (dd, J=8.5, 1.4 Hz, 2H), 7.59 (d, J=8.5 Hz, 1H), 7.27 (t, J=8.2 Hz, 1H), 7.11-6.99 (m, 2H), 6.86 (s, 1H), 6.29 (d, J=6.1 Hz, 1H), 5.13 (dt, J=7.0, 4.9 Hz, 1H), 4.79-4.70 (m, 3H), 4.64-4.47 (m, 4H), 4.36 (dt, J=9.1, 5.9 Hz, 1H), 4.07 (d, J=13.8 Hz, 1H), 3.94 (d, J=13.7 Hz, 1H), 3.33-3.30 (m, 1H), 2.76-2.58 (m, 3H), 2.53 (brs, 2H), 2.47-2.33 (m, 1H).

(S)-2-((4-(2-((4-chloro-2-fluorobenzyl)amino)pyrimidin-4-yl)-3,6-dihydropyridin-1(2H)-yl)methyl)-1-(oxetan-2-ylmethyl)-1H-benzo[d]imidazole-6-carboxylic acid (Compound 125)

Compound 125

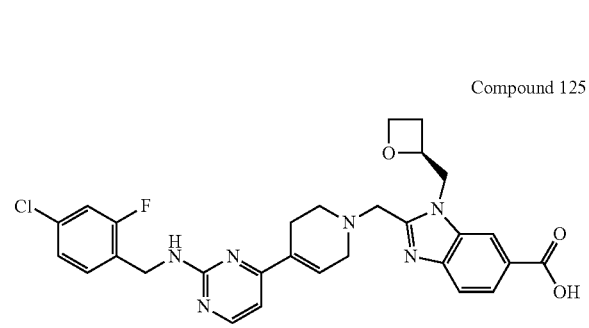 [SMILES: O=C(O)c1ccc2nc(CN3CC=C(c4ccnc(NCc5ccc(Cl)cc5F)n4)CC3)n(C[C@@H]3CCO3)c2c1]

Prepared in analogous manner as for Compound 61

LCMS: [M+H]$^+$=562.9; Retention time (10 mM NH$_4$HCO$_3$)=1.24 min.

$^1$H NMR (400 MHz, DMSO) δ 8.27-8.18 (m, 2H), 7.81 (d, J=8.4 Hz, 1H), 7.63 (d, J=8.4 Hz, 2H), 7.35 (t, J=8.2 Hz, 2H), 7.22 (d, J=8.3 Hz, 1H), 6.84-6.69 (m, 2H), 5.05 (d, J=5.9 Hz, 1H), 4.78 (dd, J=15.2, 7.2 Hz, 1H), 4.63 (d, J=14.9 Hz, 1H), 4.47 (dd, J=20.0, 6.6 Hz, 3H), 4.41-4.30 (m, 1H), 4.05 (d, J=13.4 Hz, 1H), 3.90 (d, J=13.5 Hz, 1H), 3.17 (brs, 2H), 2.77-2.59 (m, 3H), 2.46-2.33 (m, 3H).

(S)-2-((4-(2-(4-chloro-2-fluorobenzyloxy)-5-fluoropyrimidin-4-yl)-5,6-dihydropyridin-1(2H)-yl)methyl)-1-(oxetan-2-ylmethyl)-1H-benzo[d]imidazole-6-carboxylic acid (Compound 126)

Compound 126

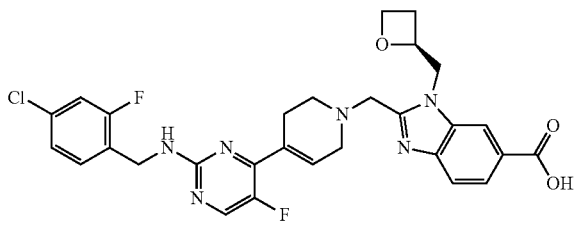

Prepared in analogous manner as for Compound 19

LCMS: [M+H]$^+$=582.0; Retention time (10 mM NH$_4$HCO$_3$)=1.52 min.

$^1$H NMR (400 MHz, DMSO-d6) δ 8.26 (s, 1H), 8.04-8.02 (t, J=4.4 Hz, 1H), 7.71-7.69 (d, J=7.2 Hz, 1H), 7.39-7.35 (t, J=8.0 Hz, 1H), 7.11-7.02 (m, 3H), 6.86 (s, 1H), 5.35 (s, 2H), 5.35-5.26 (m, 1H), 5.11-5.10 (d, J=5.2 Hz, 1H), 4.73-4.64 (m, 1H), 4.56-4.49 (m, 1H), 4.29-4.24 (d, J=18.8 Hz, 1H), 2.69-2.56 (m, 2H), 2.38-2.29 (m, 1H), 2.18-2.14 (t, J=7.6 Hz, 1H), 1.96-1.91 (t, J=9.2 Hz, 3H), 1.62-1.53 (m, 1H), 0.87-0.72 (m, 2H).

(S)-2-((4-(5-((4-chloro-2-fluorobenzyl)amino)-2-fluorophenyl)-3,6-dihydropyridin-1(2H)-yl)methyl)-1-(oxetan-2-ylmethyl)-1H-benzo[d]imidazole-6-carboxylic acid (Compound 127)

Compound 127

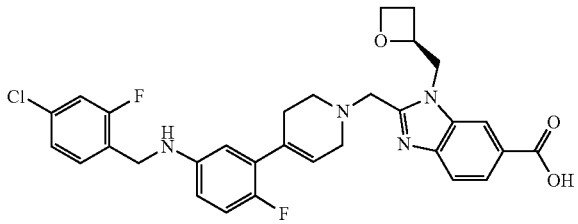

Prepared in analogous manner as for Compound 61

LCMS: [M+H]$^+$=579.0; Retention time (10 mM NH$_4$HCO$_3$)=1.56 min.

$^1$H NMR (400 MHz, DMSO) δ 8.25 (s, 1H), 7.81 (d, J=8.9 Hz, 1H), 7.63 (d, J=7.9 Hz, 1H), 7.44-7.34 (m, 2H), 7.25 (d, J=8.3 Hz, 1H), 6.87 (dd, J=11.0, 8.8 Hz, 1H), 6.46 (dd, J=28.8, 6.4 Hz, 2H), 6.13 (t, J=5.8 Hz, 1H), 5.86 (s, 1H), 5.07 (s, 1H), 4.78 (dd, J=15.1, 7.0 Hz, 1H), 4.65 (d, J=15.8 Hz, 1H), 4.51-4.42 (m, 1H), 4.41-4.32 (m, 1H), 4.25 (d, J=6.3 Hz, 2H), 4.04 (d, J=13.3 Hz, 1H), 3.88 (d, J=13.7 Hz, 1H), 3.14 (d, J=8.3 Hz, 2H), 2.69 (d, J=11.2 Hz, 3H), 2.37 (s, 3H).

(S)-2-((2'-((4-chloro-2-fluorobenzyl)oxy)-5'-fluoro-3,6-dihydro-[4,4'-bipyridin]-1(2H)-yl)methyl)-1-(oxetan-2-ylmethyl)-1H-benzo[d]imidazole-6-carboxylic acid (Compound 128)

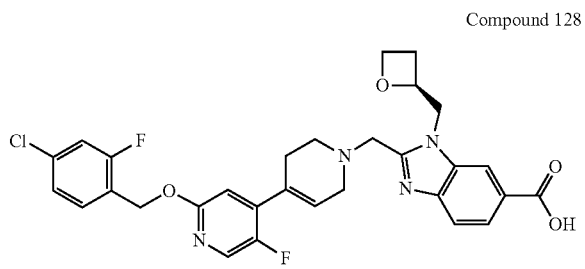 [SMILES: O=C(O)c1ccc2nc(CN3CC=C(c4cc(OCc5ccc(Cl)cc5F)ncc4F)CC3)n(C[C@@H]3CCO3)c2c1]

Compound 128

Prepared in analogous manner as for Compound 19

LCMS: [M+H]+=581.2; Retention time (10 mM NH₄HCO₃)=1.40 min.

¹H NMR (400 MHz, DMSO-d6) δ 8.26 (d, J=1.2 Hz, 1H), 8.12 (d, J=3.2 Hz, 1H), 7.82 (dd, J=1.6, 6.8 Hz, 1H), 7.66 (d, J=8.4 Hz, 1H), 7.58 (t, J=8.4, 8 Hz, 1H), 7.49 (dd, J=2, 7.6 Hz, 1H), 7.32 (dd, J=1.6, 6.4 Hz, 1H), 6.87 (d, J=5.6 Hz, 1H), 6.29 (brs, 1H), 5.33 (s, 2H), 5.09 (qd, J=2.8, 4.8 Hz, 1H), 4.81 (dd, J=7.2, 8.4 Hz, 1H), 4.66 (dd, J=2.4, 12.8 Hz, 1H), 4.49 (q, J=6.4, 7.2 Hz, 1H), 4.38-4.32 (m, 1H), 4.07 (d, J=13.6 Hz, 1H), 3.92 (d, J=13.6 Hz, 1H), 3.23-3.20 (m, 2H), 2.76-2.71 (m, 2H), 2.69-2.64 (m, 1H), 2.45 (brs, 2H), 2.42-2.37 (m, 1H).

(S)-2-((4-(3-((4-chloro-2-fluorobenzyl)amino)-4-fluorophenyl)-3,6-dihydropyridin-1(2H)-yl)methyl)-1-(oxetan-2-ylmethyl)-1H-benzo[d]imidazole-6-carboxylic acid (Compound 129)

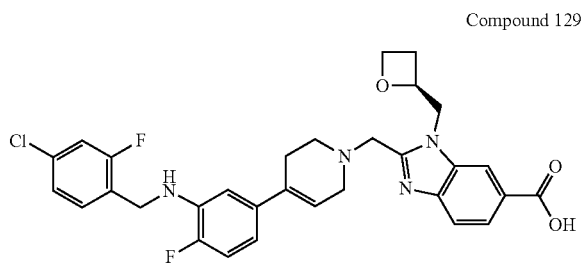 [SMILES: O=C(O)c1ccc2nc(CN3CC=C(c4ccc(F)c(NCc5ccc(Cl)cc5F)c4)CC3)n(C[C@@H]3CCO3)c2c1]

Compound 129

Prepared in analogous manner as for Compound 61

LCMS: [M+H]+=578.9; Retention time (10 mM NH₄HCO₃)=1.39 min.

¹H NMR (400 MHz, CD₃OD) δ 8.37 (s, 1H), 8.03 (dd, J=8.5, 1.4 Hz, 1H), 7.73 (d, J=8.5 Hz, 1H), 7.43 (t, J=8.2 Hz, 1H), 7.21 (dd, J=10.1, 9.1, 1.9 Hz, 2H), 6.95 (dd, J=11.6, 8.3 Hz, 1H), 6.69 (dd, J=16.1, 7.5, 2.0 Hz, 2H), 5.94 (s, 1H), 5.32-5.22 (m, 1H), 4.99 (brs, 2H), 4.94-4.85 (m, 1H), 4.74 (dd, J=15.4, 2.5 Hz, 1H), 4.66 (dd, J=13.9, 7.9 Hz, 1H), 4.54-4.48 (m, 2H), 4.19 (d, J=13.8 Hz, 1H), 4.07 (d, J=13.8 Hz, 1H), 3.22 (d, J=28.7 Hz, 2H), 2.87 (brs, 2H), 2.78 (dd, J=14.2, 9.8, 5.8 Hz, 1H), 2.61-2.53 (m, 1H), 2.50 (brs, 2H).

(S)-2-((2'-((4-chloro-2-fluorobenzyl)amino)-3,6-dihydro-[4,4'-bipyridin]-1(2H)-yl)methyl)-1-(oxetan-2-ylmethyl)-1H-benzo[d]imidazole-6-carboxylic acid (Compound 130)

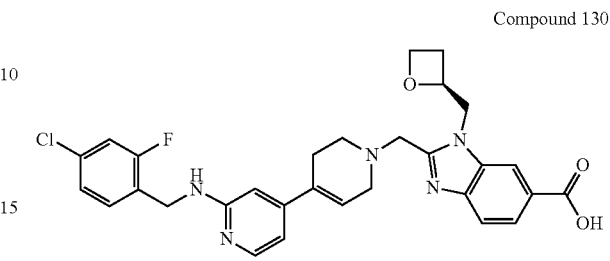

Compound 130

Prepared in analogous manner as for Compound 61

LCMS: [M+H]+=562.0; Retention time (10 mM NH₄HCO₃)=1.27 min.

¹H NMR (400 MHz, DMSO-d6) δ 8.26 (brs, 1H), 7.87 (d, J=5.2 Hz, 1H), 7.82 (d, J=8.4 Hz, 1H), 7.66 (d, J=8.4 Hz, 1H), 7.39-7.32 (m, 2H), 7.23 (dd, J=2, 6.4 Hz, 1H), 7.06 (t, J=6, 5.6 Hz, 1H), 6.61 (t, J=4, 1.2 Hz, 1H), 6.51 (brs, 1H), 6.29 (brs, 1H), 5.07-5.03 (m, 1H), 4.81 (dd, J=7, 2.8 Hz, 1H), 4.66 (dd, J=1.6, 13.2 Hz, 1H), 4.49-4.43 (m, 3H), 4.38-4.32 (m, 1H), 4.06 (d, J=13.6 Hz, 1H), 3.91 (d, J=13.6 Hz, 1H), 3.25-3.12 (m, 2H), 2.73-2.67 (m, 2H), 2.66 (dd, J=6.4, 4.8 Hz, 1H), 2.43-2.38 (m, 3H).

(S)-2-((4-(6-(4-chloro-2-fluorobenzyloxy)-3,5-difluoropyridin-2-yl)-5,6-dihydropyridin-1(2H)-yl)methyl)-1-(oxetan-2-ylmethyl)-1H-benzo[d]imidazole-6-carboxylic acid (Compound 131)

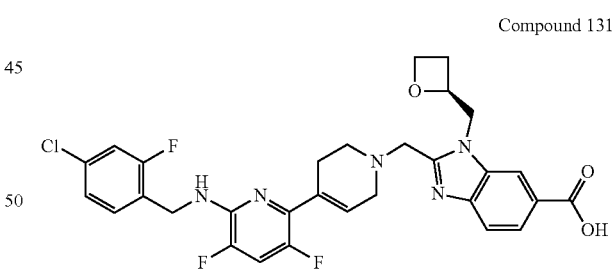

Compound 131

Prepared in analogous manner as for Compound 19

LCMS: [M+H]+=599.2; Retention time (10 mM NH₄HCO₃)=1.42 min.

¹H NMR (400 MHz, MeOD) δ 8.30 (s, 1H), 7.96-7.98 (m, 1H), 7.67 (d, J=8.8 Hz, 1H), 7.45-7.50 (m, 2H), 7.18-7.23 (m, 2H), 6.52 (brs, 1H), 5.45 (s, 2H), 5.21-5.27 (m, 1H), 4.85-4.89 (m, 1H), 4.70 (dd, J=2.4, 15.6 Hz, 1H), 4.61 (dd, J=8.0, 14.0 Hz, 1H), 4.43-4.48 (m, 1H), 4.01-4.16 (m, 2H), 3.23-3.29 (m, 2H), 2.71-2.84 (m, 3H), 2.66 (brs, 2H), 2.48-2.55 (m, 1H).

(S)-2-((4-(5-((4-chloro-2-fluorobenzyl)oxy)-2,4-difluorophenyl)-3,6-dihydropyridin-1(2H)-yl)methyl)-1-(oxetan-2-ylmethyl)-1H-benzo[d]imidazole-6-carboxylic acid (Compound 132)

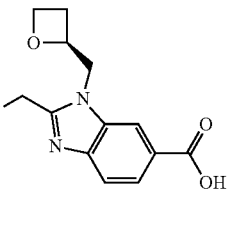

Compound 132

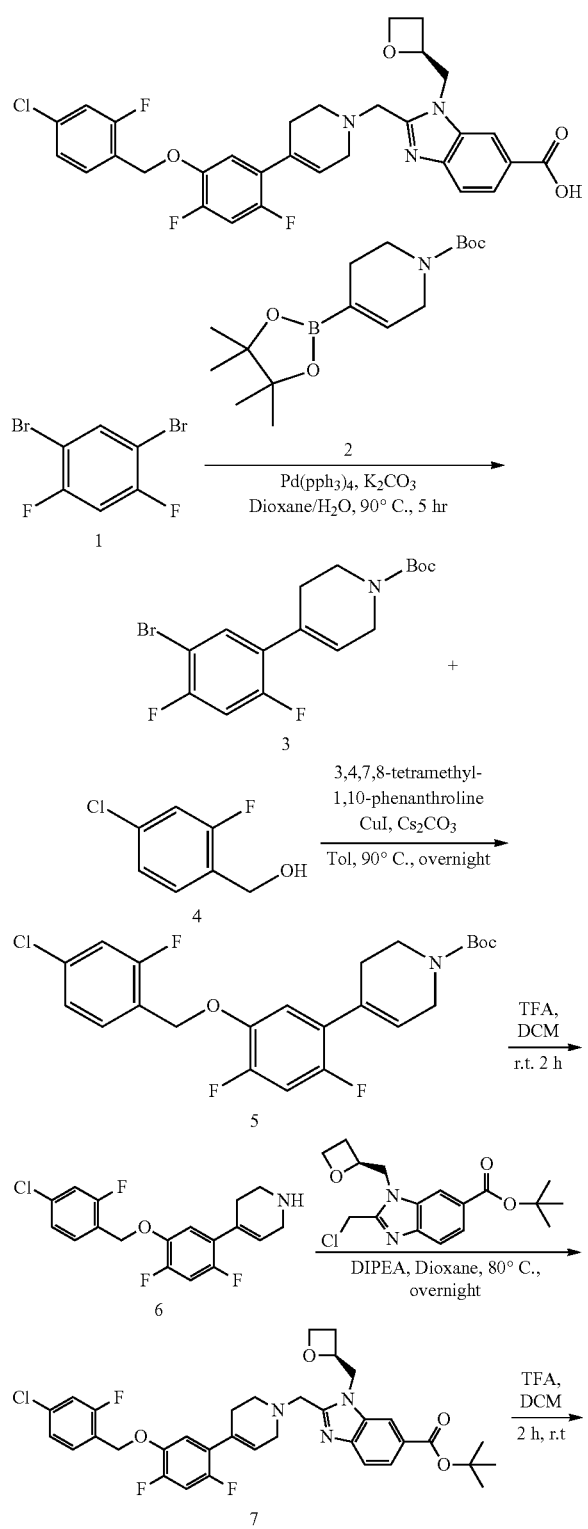

Step 1

A mixture of 1,5-dibromo-2,4-difluoro-benzene (300 mg, 1.10 mmol), tert-butyl 4-(4,4,5,5-tetramethyl-1,3,2-dioxaborolan-2-yl)-3,6-dihydro-2H-pyridine-1-carboxylate (409 mg, 1.32 mmol), palladium triphenylphosphane (128 mg, 0.110 mmol) and potassium carbonate (381 mg, 2.76 mmol) in 1,4-Dioxane (15 mL) and Water (3 mL) was stirred for 5 hr at 90° C. under $N_2$, until the reaction was complete as indicated by LCMS, the reaction mixture was filtered through a pad of Celite with EtOAc, and the combined organics were concentrated in vacuo, purified by silica gel chromatography (Hexanes:EtOAc=10:1) to give tert-butyl 4-(5-bromo-2,4-difluoro-phenyl)-3,6-dihydro-2H-pyridine-1-carboxylate (180 mg, 48% purity) as a pale yellow solid. Retention time (0.01% TFA)=2.39 min.

Step 2

A mixture of tert-butyl 4-(5-bromo-2,4-difluoro-phenyl)-3,6-dihydro-2H-pyridine-1-carboxylate (180 mg, 0.481 mmol), (4-chloro-2-fluoro-phenyl)methanol (77 mg, 0.481 mmol), 3,4,7,8-tetramethyl-1,10-phenanthroline (11 mg, 0.048 mmol), iodocopper (4 mg, 0.024 mmol) and dicesium carbonate (235 mg, 0.721 mmol) in Toluene (5 mL) was stirred for 16 h at 110° C. under $N_2$, until the reaction was complete as indicated by LCMS, the reaction mixture was filtered through a pad of Celite with EtOAc, and the combined organics were concentrated in vacuo, purified by prep-HPLC to give the desired product tert-butyl 4-[5-[(4-chloro-2-fluoro-phenyl)methoxy]-2,4-difluoro-phenyl]-3,6-dihydro-2H-pyridine-1-carboxylate (15 mg, 6.3% yield, 91% purity) as a pale yellow solid.

LCMS: [M+H-56]=398.0; Retention time (10 mM $NH_4HCO_3$)=2.10 min.

Step 3

A mixture of tert-butyl 4-[5-[(4-chloro-2-fluoro-phenyl)methoxy]-2,4-difluoro-phenyl]-3,6-dihydro-2H-pyridine-1-carboxylate (16 mg, 33 mmol) and 2,2,2-trifluoroacetic acid (740 mg, 6.49 mmol, 0.5 mL) in DCM (3 mL) was stirred for 2 h at 30° C. in a RBF, until the reaction was complete as indicated by LCMS, the combined organics were concentrated in vacuo to give the desired product 4-[5-[(4-chloro-2-fluoro-phenyl)methoxy]-2,4-difluoro-phenyl]-1,2,3,6-tetrahydropyridine (8 mg, 68.4% yield) as a yellow solid.

LCMS: [M+H]$^+$=354.0; Retention time (0.01% TFA)=1.59 min.

Step 4

A mixture of 4-[5-[(4-chloro-2-fluoro-phenyl)methoxy]-2,4-difluoro-phenyl]-1,2,3,6-tetrahydropyridine (10 mg, 28 mmol), tert-butyl 2-(chloromethyl)-3-[[(2S)-oxetan-2-yl]methyl]benzimidazole-5-carboxylate (14 mg, 42 mmol) and N-ethyl-N-isopropyl-propan-2-amine (9 mg, 71 mmol) in 1,4-Dioxane (2 mL) was stirred for 16 h at 80° C. in a RBF under N2, until the reaction was complete as indicated by LCMS, the reaction mixture was filtered through a pad of Celite with EtOAc, and the combined organics were concentrated in vacuo, purified by prep-HPLC to give the desired product tert-butyl 2-[[4-[5-[(4-chloro-2-fluoro-phenyl)methoxy]-2,4-difluoro-phenyl]-3,6-dihydro-2H-pyridin-1-yl]methyl]-3-[[(2S)-oxetan-2-yl]methyl]benzimidazole-5-carboxylate (3 mg, 16.2% yield) as a yellow solid. LCMS: [M+H]⁺=654.0; Retention time (10 mM NH₄HCO₃)= 2.46 min.

Step 5

A mixture of tert-butyl 2-[[4-[5-[(4-chloro-2-fluoro-phenyl)methoxy]-2,4-difluoro-phenyl]-3,6-dihydro-2H-pyridin-1-yl]methyl]-3-[[(2S)-oxetan-2-yl]methyl]benzimidazole-5-carboxylate (3 mg, 5 mmol) and 2,2,2-trifluoroacetic acid (3 mg, 26 mmol) in DCM (2 mL) was stirred for 2 h at 30° C. in a RBF, until the reaction was complete as indicated by LCMS and the combined organics were concentrated in vacuo, purified by prep-HPLC to give the desired product 2-[[4-[5-[(4-chloro-2-fluoro-phenyl)methoxy]-2,4-difluoro-phenyl]-3,6-dihydro-2H-pyridin-1-yl]methyl]-3-[[(2S)-oxetan-2-yl]methyl]benzimidazole-5-carboxylic acid (0.1 mg, 71% purity, 3% yield) as a yellow solid. LCMS: [M+H]⁺=598.0; Retention time (10 mM NH₄HCO₃)=1.62 min.

(S)-2-((4-(6-(4-chloro-2-fluorobenzylamino)-3,5-difluoropyridin-2-yl)-5,6-dihydropyridin-1(2H)-yl)methyl)-1-(oxetan-2-ylmethyl)-1H-benzo[d]imidazole-6-carboxylic acid (Compound 133)

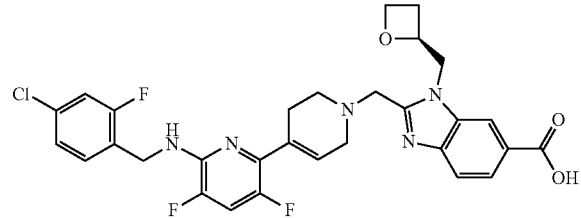

Compound 133

Prepared in analogous manner as for Compound 61
LCMS: [M+H]⁺=598.2; Retention time (10 mM NH₄HCO₃)=1.37 min.
¹H NMR (400 MHz, MeOD) δ 8.31 (s, 1H), 7.98 (d, J=8.8 Hz, 1H), 7.67 (d, J=8.4 Hz, 1H), 7.33-7.37 (d, J=8.4 Hz, 1H), 7.21-7.26 (d, J=10.0 Hz, 1H), 7.10-7.16 (m, 2H), 6.38 (brs, 1H), 5.22-5.27 (m, 1H), 4.85-4.90 (m, 1H), 4.60-4.73 (m, 4H), 4.45-4.50 (m, 1H), 4.00-4.16 (m, 2H), 3.19-3.25 (m, 2H), 2.73-2.81 (m, 3H), 2.48-2.54 (m, 3H).

(S)-1-(oxetan-2-ylmethyl)-2-((6-((3-(trifluoromethyl)benzyl)oxy)-3,6'-dihydro-[2,4'-bipyridin]-1'(2'H)-yl)methyl)-1H-benzo[d]imidazole-6-carboxylic acid (Compound 134)

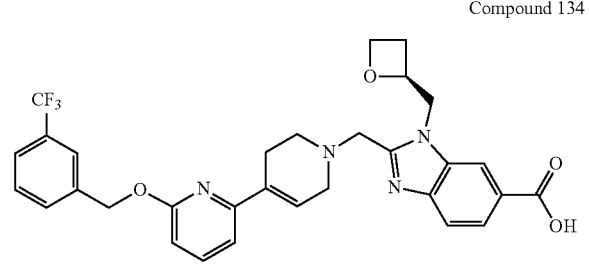 [SMILES: O=C(O)c1ccc2nc(CN3CC=C(c4cccc(OCc5cccc(C(F)(F)F)c5)n4)CC3)n(C[C@@H]3CCO3)c2c1]

Compound 134

Prepared in analogous manner as for Compound 19
LCMS: [M+H]⁺=579.2; Retention time (10 mM NH₄HCO₃)=1.48 min.
¹H NMR (400 MHz, DMSO) δ 8.26 (d, J=0.9 Hz, 1H), 7.85-7.78 (m, 2H), 7.75 (d, J=7.6 Hz, 1H), 7.68 (dd, J=14.6, 8.0 Hz, 3H), 7.60 (t, J=7.7 Hz, 1H), 7.08 (d, J=7.5 Hz, 1H), 6.79-6.70 (m, 2H), 5.46 (s, 2H), 5.06 (qd, J=7.3, 2.8 Hz, 1H), 4.80 (dd, J=15.2, 7.3 Hz, 1H), 4.65 (d, J=15.2, 2.6 Hz, 1H), 4.46 (dd, J=13.7, 7.7 Hz, 1H), 4.36 (m, J=9.0, 6.0 Hz, 1H), 4.06 (t, J=10.3 Hz, 1H), 3.92 (d, J=13.5 Hz, 1H), 3.25-3.13 (m, 2H), 2.79-2.71 (m, 2H), 2.65 (m, J=16.2, 8.6, 5.5 Hz, 1H), 2.50-2.45 (m, 2H), 2.39 (m, J=15.9, 11.2, 7.1 Hz, 1H).

(S)-1-(oxetan-2-ylmethyl)-2-((6-((2-(trifluoromethyl)benzyl)oxy)-3,6'-dihydro-[2,4'-bipyridin]-1'(2'H)-yl)methyl)-1H-benzo[d]imidazole-6-carboxylic acid (Compound 135)

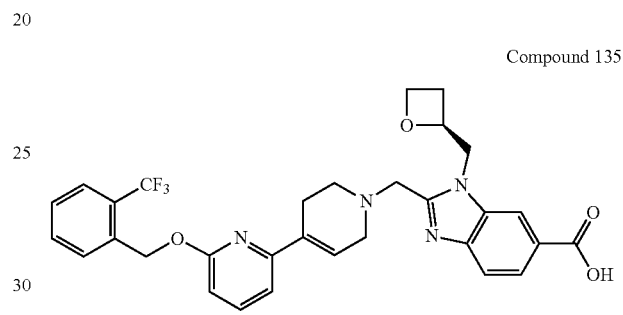

Compound 135

Prepared in analogous manner as for Compound 19
LCMS: [M+H]⁺=579.2; Retention time (10 mM NH₄HCO₃)=1.47 min.
¹H NMR (400 MHz, DMSO) δ 8.26 (d, J=0.9 Hz, 1H), 7.83-7.75 (m, 2H), 7.74-7.63 (m, 4H), 7.54 (t, J=7.3 Hz, 1H), 7.08 (t, J=9.4 Hz, 1H), 6.77 (d, J=8.2 Hz, 1H), 6.69 (s, 1H), 5.55 (s, 2H), 5.05 (qd, J=7.3, 2.8 Hz, 1H), 4.79 (dd, J=15.2, 7.3 Hz, 1H), 4.64 (dd, J=15.2, 2.6 Hz, 1H), 4.46 (dd, J=13.6, 7.7 Hz, 1H), 4.35 (dt, J=9.0, 5.9 Hz, 1H), 4.05 (t, J=11.3 Hz, 1H), 3.90 (d, J=13.5 Hz, 1H), 3.24-3.12 (m, 2H), 2.72 (m, J=9.4, 4.7 Hz, 2H), 2.64 (m, J=14.8, 8.0, 4.9 Hz, 1H), 2.48 (brs, 2H), 2.39 (m, J=15.9, 11.2, 7.1 Hz, 1H).

(S)-2-((6-((2-chlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 136)

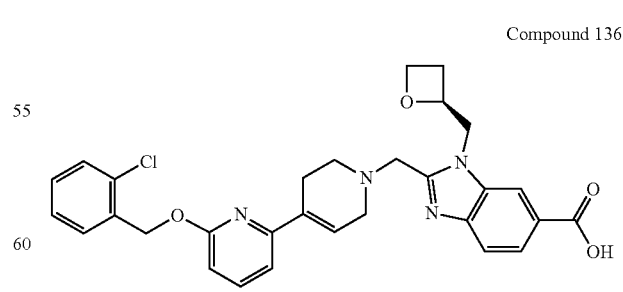

Compound 136

Prepared in analogous manner as for Compound 19
LCMS: [M+H]⁺=545.0; Retention time (10 mM NH₄HCO₃)=1.70 min.
¹H NMR (400 MHz, DMSO) δ 8.27-8.19 (brs, 1H), 7.81 (d, J=8.3 Hz, 1H), 7.70 (t, J=7.9 Hz, 1H), 7.67-7.62 (m, 1H), 7.58-7.54 (m, 1H), 7.51-7.47 (m, 1H), 7.38-7.33 (m, 2H), 7.09 (d, J=8.1 Hz, 1H), 6.78-6.72 (m, 2H), 5.45 (s, 2H), 5.10-5.03 (m, 1H), 4.84-4.73 (m, 1H), 4.68-4.60 (m, 1H), 4.50-4.41 (m, 1H), 4.39-4.28 (m, 1H), 4.06 (d, J=13.2 Hz, 1H), 3.91 (d, J=13.9 Hz, 1H), 3.25-3.20 (m, 2H), 2.77-2.70 (m, 2H), 2.68-2.66 (m, 1H), 2.42-2.36 (m, 2H), 2.34-2.31 (m, 1H).

(S)-2-((6-((3-chlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 137)

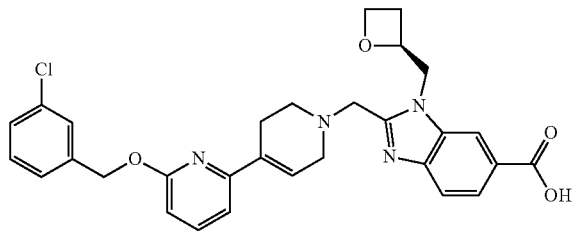

Compound 137

Prepared in analogous manner as for Compound 19

LCMS: [M+H]⁺=545.0; Retention time (10 mM NH₄HCO₃)=1.70 min.

¹H NMR (400 MHz, DMSO) δ 8.214-8.19 (brs, 1H), 7.81 (dd, J=8.4, 1.5 Hz, 1H), 7.71-7.66 (m, 1H), 7.61 (d, J=8.4 Hz, 1H), 7.53-7.49 (brs, 1H), 7.41-7.34 (m, 3H), 7.08 (d, J=7.4 Hz, 1H), 6.77-6.70 (m, 2H), 5.37 (s, 2H), 5.10-5.01 (m, 1H), 4.78 (dd, J=15.2, 7.2 Hz, 1H), 4.63 (dd, J=15.1, 2.7 Hz, 1H), 4.51-4.43 (m, 1H), 4.39-4.32 (m, 1H), 4.06 (d, J=13.4 Hz, 1H), 3.91 (d, J=13.5 Hz, 1H), 3.26-3.20 (m, 2H), 2.78-2.69 (m, 2H), 2.68-2.61 (m, 1H), 2.49-2.34 (m, 3H).

(S)-2-((6-((2,6-dichlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 138)

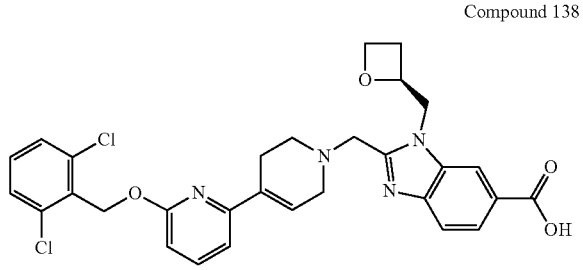 [SMILES: O=C(O)c1ccc2nc(CN3CC=C(c4cccc(OCc5c(Cl)cccc5Cl)n4)CC3)n(C[C@@H]3CCO3)c2c1]

Compound 138

Prepared in analogous manner as for Compound 19

LCMS: [M+H]⁺=579.0; Retention time (10 mM NH₄HCO₃)=1.60 min.

¹H NMR (400 MHz, DMSO) δ 8.28-8.23 (brs, 1H), 7.81 (dd, J=8.4, 1.5 Hz, 1H), 7.72-7.63 (m, 2H), 7.58-7.53 (m, 2H), 7.49-7.43 (m, 1H), 7.11 (d, J=7.4 Hz, 1H), 6.86-6.79 (brs, 1H), 6.71 (d, J=8.2 Hz, 1H), 5.52 (s, 2H), 5.11-5.03 (m, 1H), 4.81 (dd, J=15.2, 7.2 Hz, 1H), 4.66 (dd, J=15.2, 2.6 Hz, 1H), 4.51-4.44 (m, 1H), 4.37 (dt, J=9.0, 5.9 Hz, 1H), 4.08 (d, J=13.5 Hz, 1H), 3.93 (d, J=13.5 Hz, 1H), 3.29-3.23 (m, 2H), 2.82-2.72 (m, 2H), 2.70-2.63 (m, 1H), 2.61-2.53 (m, 2H), 2.44-2.38 (m, 1H).

(S)-2-((6-((3,5-dichlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 139)

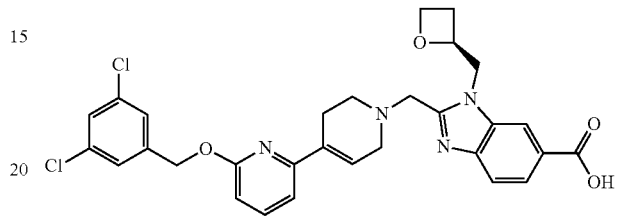

Compound 139

Prepared in analogous manner as for Compound 19

LCMS: [M+H]⁺=579.0; Retention time (10 mM NH₄HCO₃)=1.66 min.

¹H NMR (400 MHz, DMSO) δ 8.26-8.15 (brs, 1H), 7.81 (dd, J=8.4, 1.4 Hz, 1H), 7.69 (t, J=7.8 Hz, 1H), 7.63 (d, J=8.4 Hz, 1H), 7.56-7.45 (m, 3H), 7.08 (d, J=7.4 Hz, 1H), 6.77 (d, J=8.2 Hz, 1H), 6.74-6.67 (brs, 1H), 5.37 (s, 2H), 5.10-5.02 (m, 1H), 4.79 (dd, J=15.3, 7.2 Hz, 1H), 4.64 (dd, J=15.1, 2.4 Hz, 1H), 4.46 (dd, J=13.7, 7.6 Hz, 1H), 4.36 (dt, J=8.9, 5.9 Hz, 1H), 4.07 (d, J=13.5 Hz, 1H), 3.91 (d, J=13.5 Hz, 1H), 3.26-3.18 (m, 2H), 2.78-2.69 (m, 2H), 2.68-2.61 (m, 1H), 2.50-2.45 (m, 2H), 2.44-2.36 (m, 1H).

(S)-2-((6-((5-chloro-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 140)

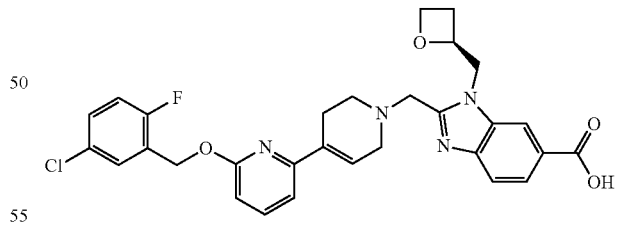

Compound 140

Prepared in analogous manner as for Compound 19

LCMS: [M+H]⁺=563.0; Retention time (0.01% TFA)=1.59 min.

¹H NMR (400 MHz, CD₃OD) δ 8.26 (s, 1H), 7.97-7.95 (m, 1H), 7.74-7.72 (m, 1H), 7.65-7.61 (m, 1H), 7.41 (s, 1H), 7.26-7.20 (m, 1H), 7.14-7.09 (m, 1H), 7.06-7.02 (m, 1H), 6.77-6.72 (m, 1H) 6.68 (s, 1H), 5.37 (s, 2H), 5.14-5.07 (m, 1H), 4.89-4.85 (m, 2H), 4.72-4.63 (m, 1H), 4.60-4.51 (m, 2H), 4.34-4.30 (m, 1H), 4.16 (s, 2H), 3.71 (s, 2H), 2.93 (s, 2H), 2.75-2.65 (m, 1H), 2.45-2.34 (m, 1H)

(S)-2-((6-((2,4-difluorobenzyl)oxy)-5',6'-dihydro-[2,4'-bipyridin]-1'(2'H)-yl)methyl)-1-(oxetan-2-ylmethyl)-1H-benzo[d]imidazole-6-carboxylic acid (Compound 141)

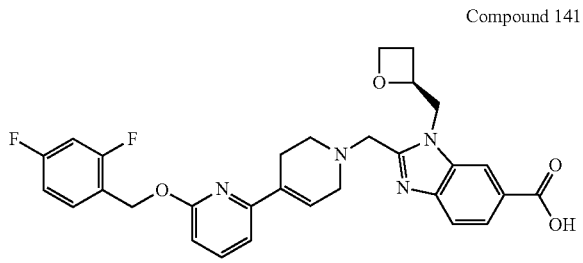 [SMILES: O=C(O)c1ccc2nc(CN3CC=C(c4cccc(OCc5ccc(F)cc5F)n4)CC3)n(C[C@@H]3CCO3)c2c1]

Compound 141

Prepared in analogous manner as for Compound 19

LCMS: [M+H]⁺=547.0; Retention time (10 mM NH₄HCO₃)=1.56 min.

¹H NMR (400 MHz, DMSO-d6) δ 8.25 (brs, 1H), 7.82 (dd, J=1.2, 7.2 Hz, 1H), 7.70-7.64 (m, 2H), 7.62 (dd, J=8.4, 7.2 Hz, 1H), 7.31-7.25 (m, 1H), 7.12-7.07 (m, 2H), 6.76 (brs, 1H), 6.72 (d, J=8.4 Hz, 1H), 5.38 (s, 2H), 5.07 (dd, J=4.8, 2.4 Hz, 1H), 4.83 (dd, J=7.2, 8 Hz, 1H), 4.67 (dd, J=2, 12.4 Hz, 1H), 4.49 (dd, J=7.2, 6.4 Hz, 1H), 4.38-4.33 (m, 1H), 4.09 (d, J=13.6 Hz, 1H), 3.93 (d, J=13.2 Hz, 1H), 3.25-3.18 (m, 2H), 2.75-2.70 (m, 2H), 2.68-2.63 (m, 1H), 2.51-2.50 (m, 2H), 2.44-2.37 (m, 1H).

(S)-2-((6-((3,5-difluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 142)

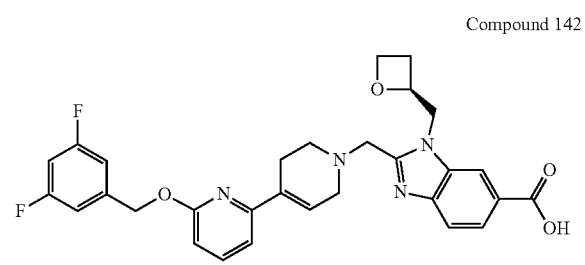 [SMILES: O=C(O)c1ccc2nc(CN3CC=C(c4cccc(OCc5cc(F)cc(F)c5)n4)CC3)n(C[C@@H]3CCO3)c2c1]

Compound 142

Prepared in analogous manner as for Compound 19

LCMS: [M+H]⁺=547.0; Retention time (10 mM NH₄HCO₃)=1.63 min. ¹H NMR (400 MHz, DMSO) δ 8.24 (s, 1H), 7.82-7.80 (m, 1H), 7.72-7.68 (m, 1H), 7.65-7.64 (m, 1H), 7.18-7.16 (m, 3H), 7.10-7.08 (m, 1H), 6.79-6.77 (m, 1H), 6.72 (s, 1H), 5.39 (s, 2H), 5.06-5.05 (m, 1H), 4.82-4.76 (m, 1H), 4.66-4.62 (m, 1H), 4.49-4.43 (m, 1H), 4.38-4.33 (m, 1H), 4.08-4.05 (m, 1H), 3.93-3.89 (m, 1H), 3.24-3.18 (m, 4H), 2.79-2.70 (m, 2H), 2.67-2.61 (m, 1H), 2.43-2.39 (m, 1H).

(S)-2-((6-((3-chloro-5-(trifluoromethyl)benzyl)oxy)-3,6'-dihydro-[2,4'-bipyridin]-1'(2'H)-yl)methyl)-1-(oxetan-2-ylmethyl)-1H-benzo[d]imidazole-6-carboxylic acid (Compound 143)

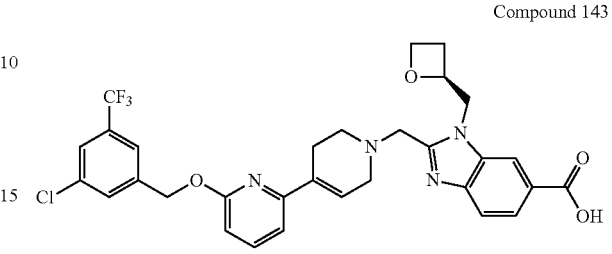

Compound 143

Prepared in analogous manner as for Compound 19

LCMS: [M+H]⁺=613.0; Retention time (10 mM NH₄HCO₃)= 1.70 min.

¹H NMR (400 MHz, DMSO) δ 8.24 (s, 1H), 7.86-7.78 (m, 4H), 7.74-7.61 (m, 2H), 7.09 (d, J=7.4 Hz, 1H), 6.79 (d, J=8.2 Hz, 1H), 6.72 (s, 1H), 5.45 (s, 2H), 5.06 (m, 1H), 4.79 (m, 1H), 4.64 (m, 1H), 4.46 (m, 1H), 4.36 (m, 1H), 4.11-3.88 (m, 2H), 3.23 (m, 4H), 2.73 (m, 2H), 2.64 (m, 1H), 2.40 (m, 1H).

(S)-2-((6-((2-chloro-4-fluorobenzyl)oxy)-3,6'-dihydro-[2,4'-bipyridin]-1'(2'H)-yl)methyl)-1-(oxetan-2-ylmethyl)-1H-benzo[d]imidazole-6-carboxylic acid (Compound 144)

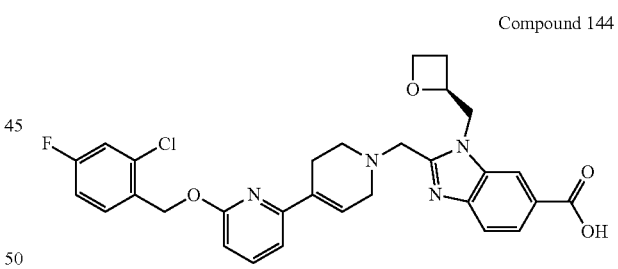

Compound 144

Prepared in analogous manner as for Compound 19

LCMS: [M+H]⁺=563.3; Retention time (0.01% TFA)=1.68 min.

¹H NMR (400 MHz, CD₃OD) δ 8.37 (s, 1H), 8.34 (s, 1H), 8.00 (d, J=8.4 Hz, 1H), 7.70 (d, J=8.4 Hz, 1H), 7.67-7.62 (m, 1H), 7.59-7.54 (m, 1H), 7.29-7.24 (m, 1H), 7.11-7.05 (m, 2H), 6.75-6.70 (m, 1H), 5.48 (s, 2H), 5.28-5.21 (m, 1H), 4.88-4.84 (m, 1H), 4.75-4.70 (m, 1H), 4.66-4.59 (m, 1H), 4.50-4.45 (m, 1H), 4.12 (dd, J=13.6 Hz, 2H), 3.31-3.25 (m, 2H), 2.91-2.85 (m, 2H), 2.82-2.72 (m, 1H), 2.68-2.63 (m, 2H), 2.55-2.46 (m, 1H).

(S)-2-((6-((3,4-difluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 145)

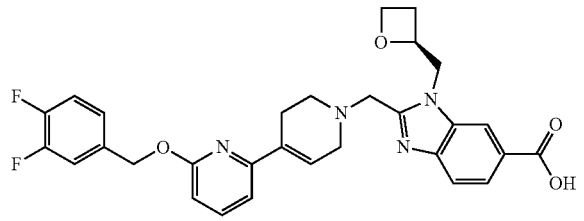

Compound 145

Prepared in analogous manner as for Compound 19

LCMS: [M+H]$^+$=546.9; Retention time (10 mM NH$_4$HCO$_3$)=1.36 min.

$^1$H NMR (400 MHz, DMSO) δ 8.26 (s, 1H), 7.83-7.80 (m, 1H), 7.71-7.64 (m, 2H), 7.56-7.49 (m, 1H), 7.47-7.37 (m, 1H), 7.32-7.29 (m, 1H), 7.08 (d, J=7.4 Hz, 1H), 6.75-6.73 (m, 2H), 5.35 (s, 2H), 5.07-5.03 (m, 1H), 4.82-4.77 (m, 1H), 4.67-4.63 (m, 1H), 4.49-4.46 (m, 1H), 4.38-4.33 (m, 1H), 4.12-3.99 (m, 1H), 3.93-3.89 (m, 1H), 3.25-3.20 (m, 4H), 2.77-2.72 (m, 2H), 2.67-2.63 (m, 1H), 2.44-2.38 (m, 1H).

(S)-2-((6-((4-methylbenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 146)

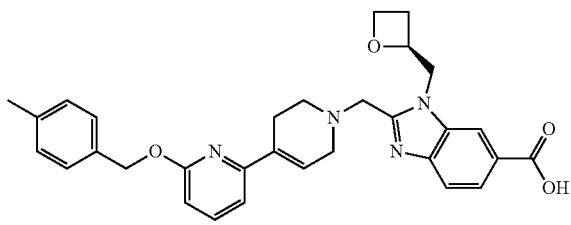

Compound 146

Prepared in analogous manner as for Compound 19

LCMS: [M+H]$^+$=525.1; Retention time (10 mM NH$_4$HCO$_3$)=1.57 min.

$^1$H NMR (400 MHz, DMSO) δ 8.06-8.03 (brs, 1H), 7.78 (d, J=8.3 Hz, 1H), 7.66 (t, J=7.8 Hz, 1H), 7.42 (d, J=8.3 Hz, 1H), 7.32 (d, J=8.0 Hz, 2H), 7.16 (d, J=7.8 Hz, 2H), 7.05 (d, J=7.5 Hz, 1H), 6.78-6.74 (brs, 1H), 6.69 (d, J=8.1 Hz, 1H), 5.31 (s, 2H), 5.09-5.03 (m, 1H), 4.71 (dd, J=15.2, 7.2 Hz, 1H), 4.61-4.55 (m, 1H), 4.47 (dd, J=13.5, 7.9 Hz, 1H), 4.36 (dt, J=11.9, 6.0 Hz, 1H), 4.03 (d, J=13.2 Hz, 1H), 3.88 (d, J=13.3 Hz, 1H), 3.25-3.13 (m, 3H), 2.76-2.70 (m, 2H), 2.67-2.63 (m, 1H), 2.46-2.36 (m, J=8.m, 2H), 2.28 (s, 3H).

(S)-2-((6-((4-(tert-butyl)benzyl)oxy)-5,6'-dihydro-[2,4'-bipyridin]-1'(2'H)-yl)methyl)-1-(oxetan-2-ylmethyl)-1H-benzo[d]imidazole-6-carboxylic acid (Compound 147)

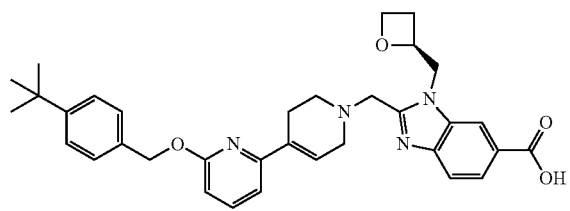

Compound 147

Prepared in analogous manner as for Compound 19

LCMS: [M+H]$^+$=567.2; Retention time (10 mM NH$_4$HCO$_3$)=1.70 min.

$^1$H NMR (400 MHz, DMSO) δ 8.25-8.21 (brs, 1H), 7.81 (dd, J=8.4, 1.5 Hz, 1H), 7.69-7.61 (m, 2H), 7.38-7.34 (brs, 4H), 7.06 (d, J=7.4 Hz, 1H), 6.78-6.74 (brs, 1H), 6.69 (d, J=8.1 Hz, 1H), 5.32 (s, 2H), 5.10-5.04 (m, 1H), 4.83-475 (m, 1H), 4.68-4.60 (m, 1H), 4.48-4.43 (m, 1H), 4.38-4.33 (m, 1H), 4.07 (d, J=13.5 Hz, 1H), 3.91 (d, J=13.4 Hz, 1H), 3.26-3.20 (m, 2H), 2.79-2.70 (m, 2H), 2.69-2.63 (m, J=16.4, 1H), 2.50-2.44 (m, 2H), 2.44-2.36 (m, 1H), 1.26 (s, 9H).

(S)-2-((6-((4-isopropylbenzyl)oxy)-5',6'-dihydro-[2,4'-bipyridin]-1'(2'H)-yl)methyl)-1-(oxetan-2-ylmethyl)-1H-benzo[d]imidazole-6-carboxylic acid (Compound 148)

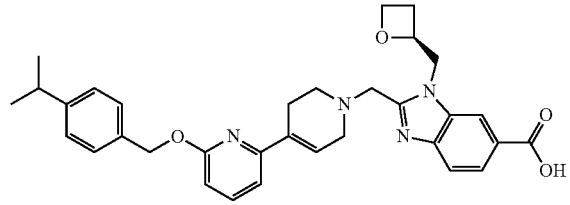

Compound 148

Prepared in analogous manner as for Compound 19

LCMS: [M+H]$^+$=553.3; Retention time (10 mM NH$_4$HCO$_3$)=1.56 min.

$^1$H NMR (400 MHz, DMSO) δ 8.23-8.18 (brs, 1H), 7.80 (d, J=8.4 Hz, 1H), 7.69-7.64 (m, 1H), 7.59 (d, J=7.9 Hz, 1H), 7.36 (d, J=8.1 Hz, 2H), 7.22 (d, J=8.0 Hz, 2H), 7.06 (d, J=7.5 Hz, 1H), 6.79-6.73 (brs, 1H), 6.69 (d, J=8.2 Hz, 1H), 5.32 (s, 2H), 5.10-5.03 (m, 1H), 4.78 (dd, J=15.1, 7.3 Hz, 1H), 4.63 (d, J=12.7 Hz, 1H), 4.47 (dd, J=13.7, 7.5 Hz, 1H), 4.39-4.34 (m, 1H), 4.06 (d, J=13.4 Hz, 1H), 3.91 (d, J=13.4 Hz, 1H), 3.26-3.22 (m, 2H), 2.90-2.83 (m, 1H), 2.78-2.70 (m, 2H), 2.69-2.64 (m, 1H), 2.55-2.52 (m, 1H), 2.44-2.37 (m, 2H), 1.18 (d, J=6.9 Hz, 6H).

(S)-2-((6-((3-fluoro-5-(trifluoromethyl)pyridin-2-yl)methoxy)-3,6'-dihydro-[2,4'-bipyridin]-1'(2'H)-yl)methyl)-1-(oxetan-2-ylmethyl)-1H-benzo[d]imidazole-6-carboxylic acid (Compound 149)

Compound 149

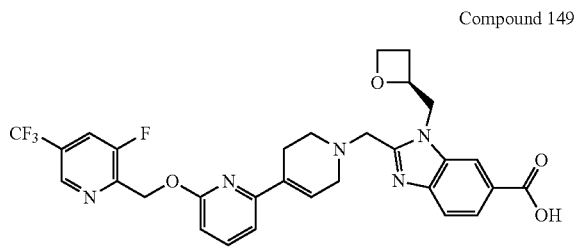 [SMILES: O=C(O)c1ccc2nc(CN3CC=C(c4cccc(OCc5ncc(C(F)(F)F)cc5F)n4)CC3)n(C[C@@H]3CCO3)c2c1]

Prepared in analogous manner as for Compound 19

LCMS: [M+H]+=598.3; Retention time (10 mM NH4HCO3)=1.51 min.

1H NMR (400 MHz, DMSO) δ 8.83-8.79 (brs, 1H), 8.35 (d, J=8.6 Hz, 1H), 8.28-8.24 (brs, 1H), 7.81 (dd, J=8.4, 1.5 Hz, 1H), 7.68 (dd, J=16.3, 8.3 Hz, 2H), 7.07 (d, J=7.4 Hz, 1H), 6.77 (d, J=8.2 Hz, 1H), 6.63-6.57 (brs, 1H), 5.58 (s, 2H), 5.08-5.00 (m, 1H), 4.79 (dd, J=15.3, 7.4 Hz, 1H), 4.68-4.60 (m, 1H), 4.46 (dd, J=13.6, 7.8 Hz, 1H), 4.35 (dt, J=9.1, 5.9 Hz, 1H), 4.05 (d, J=13.5 Hz, 1H), 3.90 (d, J=13.5 Hz, 1H), 3.22-3.08 (m, 2H), 2.74-2.64 (m, 3H), 2.44-2.34 (m, 3H).

(S)-1-(oxetan-2-ylmethyl)-2-((6-((4-(trifluoromethyl)pyridin-3-yl)methoxy)-3',6'-dihydro-[2,4'-bipyridin]-1'(2'H)-yl)methyl)-1H-benzo[d]imidazole-6-carboxylic acid (Compound 150)

Compound 150

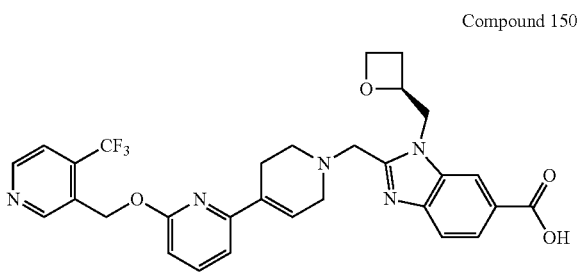 [SMILES: O=C(O)c1ccc2nc(CN3CC=C(c4cccc(OCc5cnccc5C(F)(F)F)n4)CC3)n(C[C@@H]3CCO3)c2c1]

Prepared in analogous manner as for Compound 19

LCMS: [M+H]+=580.0, Retention time (10 mM NH4HCO3)=1.43 min.

1H NMR (400 MHz, DMSO) δ 8.97-8.95 (brs, 1H), 8.82 (d, J=5.0 Hz, 1H), 8.26-8.23 (brs, 1H), 7.83-7.77 (m, 2H), 7.71 (t, J=7.8 Hz, 1H), 7.64 (d, J=8.4 Hz, 1H), 7.11 (d, J=7.5 Hz, 1H), 6.76 (d, J=8.2 Hz, 1H), 6.73-6.68 (brs, 1H), 5.58 (s, 2H), 5.09-5.02 (m, 1H), 4.79 (dd, J=15.3, 7.3 Hz, 1H), 4.68-4.61 (m, 1H), 4.46 (dd, J=13.6, 7.7 Hz, 1H), 4.36 (dt, J=9.0, 5.9 Hz, 1H), 4.06 (d, J=13.5 Hz, 1H), 3.91 (d, J=13.5 Hz, 1H), 3.25-3.16 (m, 2H), 2.77-2.71 (m, 2H), 2.68-2.63 (m, 1H), 2.48-2.32 (m, 3H).

(S)-2-((6-((2,3-dihydrobenzo[b][1,4]dioxin-6-yl)methoxy)-3,6'-dihydro-[2,4'-bipyridin]-1'(2'H)-yl)methyl)-1-(oxetan-2-ylmethyl)-1H-benzo[d]imidazole-6-carboxylic acid (Compound 151)

Compound 151

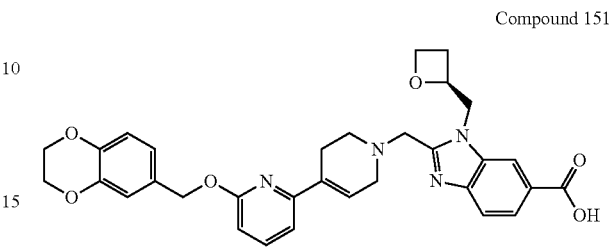

Prepared in analogous manner as for Compound 19

LCMS: [M+H]+=569.1; Retention time (10 mM NH4HCO3)=1.46 min.

1H NMR (400 MHz, DMSO) δ 8.25 (d, J=0.9 Hz, 1H), 7.81 (dd, J=8.4, 1.5 Hz, 1H), 7.66 (t, J=7.8 Hz, 2H), 7.05 (t, J=7.7 Hz, 1H), 6.93 (d, J=1.9 Hz, 1H), 6.90 (dd, J=8.2, 2.0 Hz, 1H), 6.85-6.79 (m, 1H), 6.76 (s, 1H), 6.68 (d, J=8.2 Hz, 1H), 5.25 (d, J=10.7 Hz, 2H), 5.07 (dt, J=7.0, 4.6 Hz, 1H), 4.80 (dd, J=15.2, 7.3 Hz, 1H), 4.65 (dd, J=15.1, 2.6 Hz, 1H), 4.47 (dd, J=13.6, 7.7 Hz, 1H), 4.36 (dt, J=8.8, 5.9 Hz, 1H), 4.28-4.16 (m, 4H), 4.07 (d, J=13.5 Hz, 1H), 3.92 (d, J=13.5 Hz, 1H), 3.24 (d, J=10.2 Hz, 2H), 2.73 (d, J=17.8 Hz, 2H), 2.70-2.61 (m, 1H), 2.52 (d, J=6.4 Hz, 2H), 2.45-2.37 (m, 1H).

(S)-2-((6-(benzo[d][1,3]dioxol-5-ylmethoxy)-3,6'-dihydro-[2,4'-bipyridin]-1'(2'H)-yl)methyl)-1-(oxetan-2-ylmethyl)-1H-benzo[d]imidazole-6-carboxylic acid (Compound 152)

Compound 152

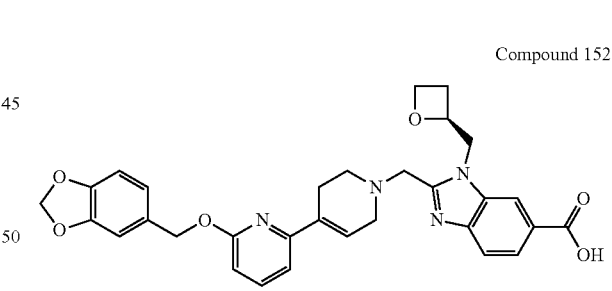

Prepared in analogous manner as for Compound 19

LCMS: [M+H]+=555.2; Retention time (10 mM NH4HCO3)=1.34 min.

1H NMR (400 MHz, DMSO) δ 8.26 (d, J=0.9 Hz, 1H), 7.81 (dd, J=8.4, 1.5 Hz, 1H), 7.70-7.62 (m, 2H), 7.06 (d, J=7.4 Hz, 1H), 7.01 (d, J=1.4 Hz, 1H), 6.94 (dd, J=7.9, 1.6 Hz, 1H), 6.88 (d, J=7.9 Hz, 1H), 6.76 (s, 1H), 6.69 (d, J=8.2 Hz, 1H), 6.00 (s, 2H), 5.25 (s, 2H), 5.07 (qd, J=7.3, 2.8 Hz, 1H), 4.81 (dd, J=15.2, 7.3 Hz, 1H), 4.66 (dd, J=15.2, 2.6 Hz, 1H), 4.47 (dd, J=14.2, 7.1 Hz, 1H), 4.36 (dt, J=8.9, 5.9 Hz, 1H), 4.12-3.99 (m, 1H), 3.92 (d, J=13.5 Hz, 1H), 3.24 (d, J=9.6 Hz, 2H), 2.79-2.60 (m, 3H), 2.53 (d, J=5.9 Hz, 2H), 2.39 (dd, J=21.7, 13.3, 7.5 Hz, 1H).

(S)-2-((6-((2,2-difluorobenzo[d][1,3]dioxol-5-yl)
methoxy)-3',6'-dihydro-[2,4'-bipyridin]-1'(2'H)-yl)
methyl)-1-(oxetan-2-ylmethyl)-1H-benzo[d]imida-
zole-6-carboxylic acid (Compound 153)

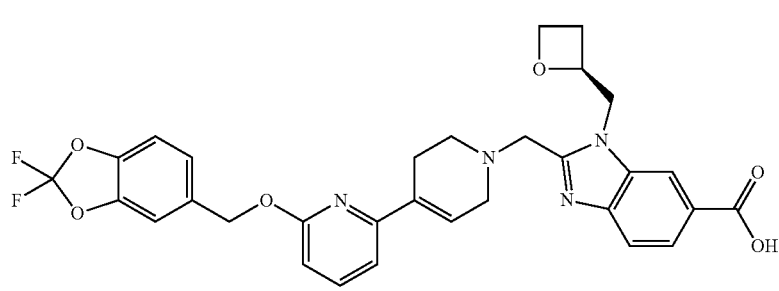

Compound 153

Prepared in analogous manner as for Compound 19

LCMS: [M+H]$^+$=591.0; Retention time (10 mM NH$_4$HCO$_3$)=1.62 min.

$^1$H NMR (400 MHz, DMSO) δ 8.25 (s, 1H), 7.80 (s, 1H), 7.72-7.62 (m, 2H), 7.51 (s, 1H), 7.39 (d, J=8.1 Hz, 1H), 7.31 (d, J=8.2 Hz, 1H), 7.08 (d, J=7.5 Hz, 1H), 6.80-6.68 (m, 2H), 5.36 (s, 2H), 5.06 (s, 1H), 4.79 (s, 1H), 4.65 (d, J=15.2 Hz, 1H), 4.45 (s, 1H), 4.36 (s, 1H), 4.07 (d, J=14.6 Hz, 1H), 3.91 (d, J=13.1 Hz, 1H), 3.24 (s, 2H), 2.75 (s, 2H), 2.60 (d, J=54.7 Hz, 2H), 2.40 (s, 2H).

(S)-2-((6-((4-(1H-imidazol-1-yl)benzyl)oxy)-3',6'-
dihydro-[2,4'-bipyridin]-1'(2'H)-yl)methyl)-1-
(oxetan-2-ylmethyl)-1H-benzo[d]imidazole-6-car-
boxylic acid (Compound 154)

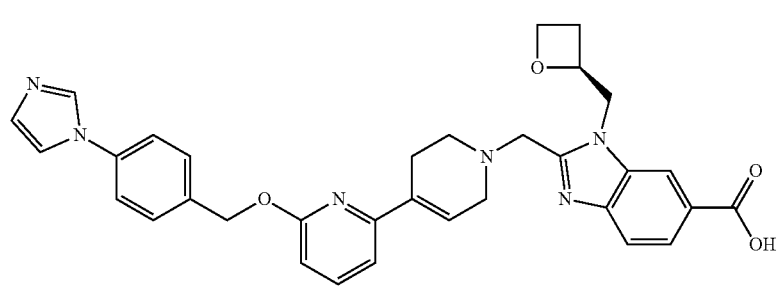

Compound 154

Prepared in analogous manner as for Compound 19

LCMS: [M+H]$^+$=577.0, Retention time (10 mM NH$_4$HCO$_3$)=1.57 min.

$^1$H NMR (400 MHz, DMSO) δ 8.29-8.22 (brs, 1H), 8.17-8.07 (brs, 1H), 7.80 (d, J=8.3 Hz, 1H), 7.76-7.72 (brs, 1H), 7.71-7.63 (m, 3H), 7.61-7.56 (m, 2H), 7.52 (d, J=8.3 Hz, 1H), 7.14-7.02 (m, 2H), 6.80-6.76 (brs, 1H), 6.74 (d, J=8.2 Hz, 1H), 5.41 (s, 2H), 5.10-5.02 (m, 1H), 4.75 (dd, J=15.2, 7.1 Hz, 1H), 4.61 (dd, J=15.1, 2.8 Hz, 1H), 4.49-4.42 (m, 1H), 4.35 (dt, J=8.9, 5.9 Hz, 1H), 4.05 (d, J=13.4 Hz, 1H), 3.90 (d, J=13.4 Hz, 1H), 3.26-3.21 (m, 2H), 2.78-2.70 (m, 2H), 2.68-2.62 (m, 1H), 2.57-2.52 (m, 2H), 2.44-2.37 (m, 1H).

(S)-2-((6-((2-fluorobenzyl)oxy)-3',6'-dihydro-[2,4'-
bipyridin]-1'(2'H)-yl)methyl)-1-(oxetan-2-ylmethyl)-
1H-benzo[d]imidazole-6-carboxylic acid (Com-
pound 155)

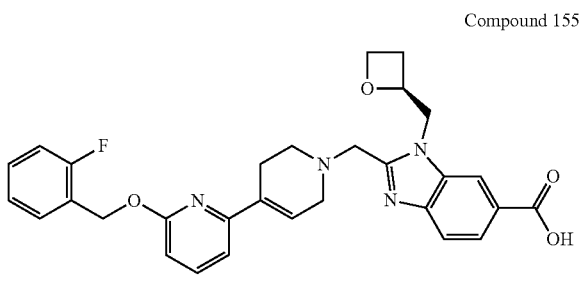 [SMILES: O=C(O)c1ccc2nc(CN3CC=C(c4cccc(OCc5ccccc5F)n4)CC3)n(C[C@@H]3CCO3)c2c1]

Compound 155

Prepared in analogous manner as for Compound 19
LCMS: [M+H]⁺=529.2; Retention time (10 mM NH₄HCO₃)= 1.47 min.
¹H NMR (400 MHz, DMSO) δ 8.25 (d, J=0.8 Hz, 1H), 7.81 (dd, J=8.4, 1.4 Hz, 1H), 7.72-7.62 (m, 2H), 7.53 (td, J=7.6, 1.6 Hz, 1H), 7.43-7.34 (m, 1H), 7.26-7.17 (m, 2H), 7.08 (d, J=7.4 Hz, 1H), 6.78-6.69 (m, 2H), 5.42 (s, 2H), 5.10-5.03 (m, 1H), 4.80 (dd, J=15.2, 7.3 Hz, 1H), 4.65 (dd, J=15.1, 2.6 Hz, 1H), 4.46 (dd, J=13.6, 7.7 Hz, 1H), 4.36 (dt, J=9.0, 5.9 Hz, 1H), 4.07 (d, J=13.5 Hz, 1H), 3.91 (d, J=13.5 Hz, 1H), 3.24 (dd, J=27.8, 17.7 Hz, 4H), 2.75 (brs, 2H), 2.69-2.61 (m, 1H), 2.39 (m, J=21.3, 8.7 Hz, 1H).

(S)-2-((6-((3-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 156)

Compound 156

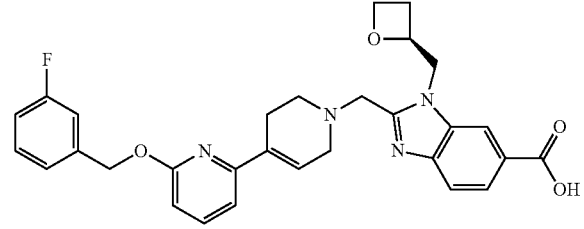

Prepared in analogous manner as for Compound 19
LCMS: [M+H]⁺=529.0; Retention time (10 mM NH₄HCO₃)=1.54 min.
¹H NMR (400 MHz, MeOD) δ 8.32-8.31 (brs, 1H), 7.98 (d, J=8.5 Hz, 1H), 7.74-7.55 (m, 2H), 7.34 (dd, J=13.8, 7.9 Hz, 1H), 7.20 (dd, J=27.8, 8.8 Hz, 2H), 7.08-6.93 (m, 2H), 6.70 (d, J=8.1 Hz, 2H), 5.40 (s, 2H), 5.24 (d, J=7.2 Hz, 1H), 4.85-4.84 (brs, 1H), 4.72 (d, J=15.3 Hz, 1H), 4.62 (dd, J=14.3, 7.2 Hz, 1H), 4.46 (dt, J=11.7, 5.9 Hz, 1H), 4.17 (d, J=13.7 Hz, 1H), 4.05 (d, J=13.8 Hz, 1H), 3.29-3.20 (m, 2H), 2.85 (d, J=5.2 Hz, 2H), 2.74 (dd, J=17.0, 8.5 Hz, 1H), 2.64-2.63 (brs, 2H), 2.51 (dd, J=17.6, 8.5 Hz, 1H).

(S)-2-((6-((4-fluorobenzyl)oxy)-3',6'-dihydro-[2,4'-bipyridin]-1'(2'H)-yl)methyl)-1-(oxetan-2-ylmethyl)-JH-benzo[d]imidazole-6-carboxylic acid (Compound 157)

Compound 157

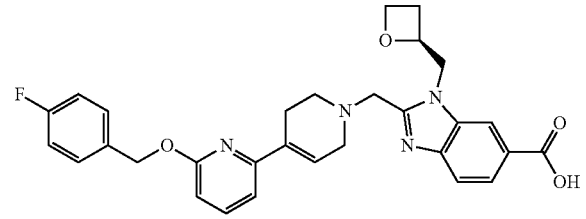

Prepared in analogous manner as for Compound 19
LCMS: [M+H]⁺=529.0; Retention time (10 mM NH₄HCO₃)=1.54 min.
¹H NMR (400 MHz, DMSO) δ 8.23-8.19 (brs, 1H), 7.80 (d, J=8.4 Hz, 1H), 7.67 (t, J=7.8 Hz, 1H), 7.61 (d, J=8.4 Hz, 1H), 7.49 (dd, J=8.6, 5.7 Hz, 2H), 7.18 (t, J=8.9 Hz, 2H), 7.07 (d, J=7.5 Hz, 1H), 6.77-6.73 (brs, 1H), 6.71 (d, J=8.2 Hz, 1H), 5.35 (s, 2H), 5.10-5.03 (m, 1H), 4.78 (dd, J=15.4, 7.1 Hz, 1H), 4.67-4.61 (m, 1H), 4.46 (dd, J=13.8, 7.6 Hz, 1H), 4.36 (dt, J=11.8, 5.9 Hz, 1H), 4.06 (d, J=13.4 Hz, 1H), 3.91 (d, J=13.5 Hz, 1H), 3.26-3.16 (m, 3H), 2.78-2.70 (m, 2H), 2.69-2.63 (m, 1H), 2.45-2.35 (m, 2H).

(S)-1-(oxetan-2-ylmethyl)-2-((6-(pyridin-3-ylmethoxy)-5',6'-dihydro-[2,4'-bipyridin]-1'(2'H)-yl)methyl)-1H-benzo[d]imidazole-6-carboxylic acid (Compound 158)

Compound 158

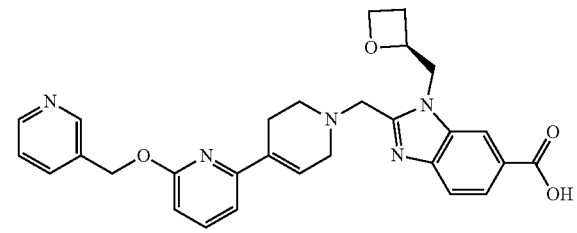

Prepared in analogous manner as for Compound 19
LCMS: [M+H]⁺=512.0; Retention time (10 mM NH₄HCO₃)=1.32 min.
¹H NMR (400 MHz, DMSO) δ 8.67 (d, J=1.6 Hz, 1H), 8.51-8.49 (m, 1H), 8.253 (brs, 1H), 7.86-7.79 (m, 2H), 7.70-7.63 (m, 2H), 7.40-7.37 (m, 1H), 7.08 (d, J=4 Hz 1H), 6.73 (d, J=8 Hz, 2H), 5.41 (s, 2H), 5.07-5.05 (m, 1H), 4.82-4.76 (m, 1H), 4.64 (dd, J=2.4, 2.4 Hz, 1H), 4.45 (t, J=6.4 Hz, 1H), 4.38-4.34 (m, 1H), 4.07 (d, J=13.6 Hz, 1H), 3.91 (d, J=13.6 Hz, 1H), 3.24-3.21 (m, 2H), 2.73 (d, J=5.6 Hz, 2H), 2.67-2.63 (m, 1H), 2.43-2.37 (m, 3H).

(S)-1-(oxetan-2-ylmethyl)-2-((6-(pyridin-2-ylmethoxy)-5',6'-dihydro-[2,4'-bipyridin]-1'(2'H)-yl)methyl)-1H-benzo[d]imidazole-6-carboxylic acid (Compound 159)

Compound 159

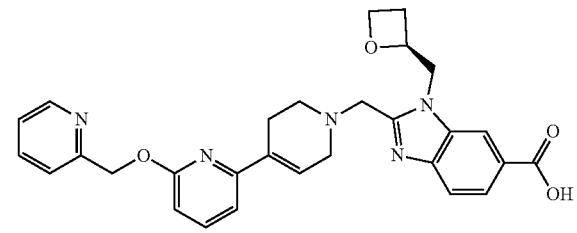

Prepared in analogous manner as for Compound 19
LCMS: [M+H]⁺=512.1; Retention time (10 mM NH₄HCO₃)=1.33 min.
¹H NMR (400 MHz, DMSO) δ 8.56-8.52 (m, 1H), 8.26-8.22 (brs, 1H), 7.82-7.76 (m, 2H), 7.70 (t, J=7.6 Hz, 1H), 7.63 (d, J=8 Hz, 1H), 7.43 (d, J=8 Hz, 1H), 7.31-7.28 (m, 1H), 7.08 (d, J=3.2 Hz, 1H), 6.79 (d, J=8.4 Hz, 1H), 6.67 (brs, 1H), 5.43 (s, 2H), 5.06-5.04 (m, 1H), 4.81-4.75 (m, 1H), 4.53 (dd, J=2.4, 2.4 Hz, 1H), 4.46-4.43 (m, 1H), 4.36-4.34 (m, 1H), 4.05 (d, J=13.2 Hz, 1H), 3.90 (d, J=13.6 Hz, 1H), 3.22-3.18 (m, 2H), 2.72-2.68 (m, 2H), 2.67-2.62 (m, 1H), 2.46 (s, 2H), 2.43-2.38 (m, 1H).

(S)-1-(oxetan-2-ylmethyl)-2-((6-(pyridin-4-yl-methoxy)-5',6'-dihydro-[2,4'-bipyridin]-1'(2'H)-yl)methyl)-JH-benzo[d]imidazole-6-carboxylic acid (Compound 160)

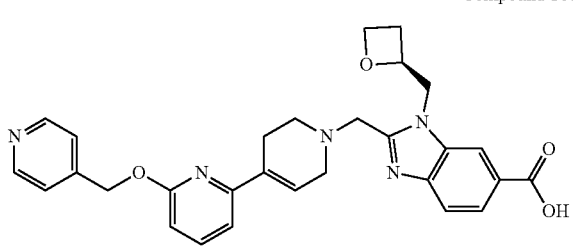

Compound 160

Prepared in analogous manner as for Compound 19
LCMS: [M+H]$^+$=512.1; Retention time (10 mM NH$_4$HCO$_3$)= 1.32 min.

$^1$H NMR (400 MHz, DMSO) δ 8.53 (dd, J=1.6, 1.6 Hz, 2H), 8. 22 (brs, 1H), 7.80 (dd, J=1.2, 1.2 Hz, 1H), 7.70 (t, J=7.6 Hz, 1H), 7.61 (d, J=4.4 Hz, 1H), 7.40 (d, J=2.4 Hz, 2H), 7.08 (d, J=7.6 Hz, 1H), 6.79 (d, J=8.4 Hz, 1H), 6.68 (brs, 1H), 5.42 (s, 2H), 5.06-5.03 (m, 1H), 4.80-4.74 (m, 1H), 4.62 (dd, J=2.8, 2.8 Hz, 1H), 4.48-4.42 (m, 1H), 4.37-4.32 (m, 1H), 4.05 (d, J=13.2 Hz, 1H), 3.89 (d, J=13.6 Hz, 1H), 3.27-3.18 (m, 2H), 2.71 (d, J=6 Hz, 2H), 2.67-2.61 (m, 1H), 2.47 (d, J=4.4 Hz, 2H), 2.38-2.36 (m, 1H).

(S)-2-((6-((2-methylpyridin-3-yl)methoxy)-3,6'-di-hydro-[2,4'-bipyridin]-1'(2'H)-yl)methyl)-1-(oxetan-2-ylmethyl)-1H-benzo[d]imidazole-6-carboxylic acid (Compound 161)

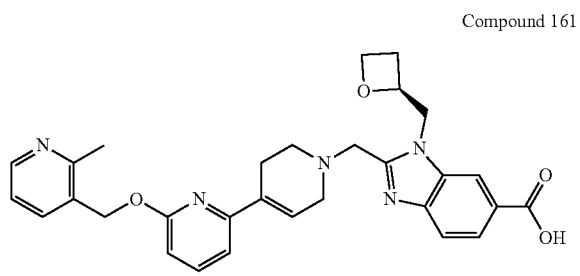 [SMILES: Cc1ncccc1COc1cccc(C2=CCN(Cc3nc4ccc(C(=O)O)cc4n3C[C@@H]3CCO3)CC2)n1]

Compound 161

Prepared in analogous manner as for Compound 19
LCMS: [M+H]$^+$=526.1; Retention time (10 mM NH$_4$HCO$_3$)=1.34 min.

$^1$H NMR (400 MHz, MeOD) δ 8.35 (d, J=5.0 Hz, 2H), 8.00 (d, J=8.5 Hz, 1H), 7.87 (d, J=7.7 Hz, 1H), 7.78-7.58 (m, 2H), 7.27 (dd, J=7.6, 5.1 Hz, 1H), 7.09 (d, J=7.4 Hz, 1H), 6.79-6.65 (m, 2H), 5.47 (s, 2H), 5.25 (dd, J=12.0, 6.9 Hz, 1H), 4.88 (d, J=7.2 Hz, 1H), 4.74 (dd, J=15.3, 2.4 Hz, 1H), 4.64 (d, J=13.9, 7.8 Hz, 1H), 4.48 (dt, J=9.0, 6.0 Hz, 1H), 4.20 (d, J=13.7 Hz, 1H), 4.08 (d, J=13.8 Hz, 1H), 3.32-3.30 (m, 2H), 2.88 (t, J=5.6 Hz, 2H), 2.82-2.71 (m, 1H), 2.66-2.65 (brs, 2H), 2.60 (s, 3H), 2.51 (dd, J=19.2, 8.2 Hz, 1H).

(S)-2-((6-((2-chloropyridin-4-yl)methoxy)-3,6'-di-hydro-[2,4'-bipyridin]-1'(2'H)-yl)methyl)-1-(oxetan-2-ylmethyl)-1H-benzo[d]imidazole-6-carboxylic acid (Compound 162)

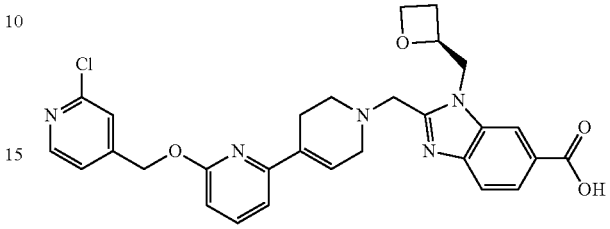

Compound 162

Prepared in analogous manner as for Compound 19
LCMS: [M+H]$^+$=546.0, Retention time (10 mM NH$_4$HCO$_3$)=1.43 min.

$^1$H NMR (400 MHz, DMSO) δ 8.37 (d, J=5.1 Hz, 1H), 8.26-8.23 (brs, 1H), 7.81 (dd, J=8.4, 1.4 Hz, 1H), 7.72 (t, J=7.8 Hz, 1H), 7.65 (d, J=8.5 Hz, 1H), 7.56-7.53 (brs, 1H), 7.43 (d, J=5.1 Hz, 1H), 7.10 (d, J=7.4 Hz, 1H), 6.82 (d, J=8.2 Hz, 1H), 6.70-6.65 (brs, 1H), 5.43 (s, 2H), 5.09-5.01 (m, 1H), 4.79 (dd, J=15.2, 7.4 Hz, 1H), 4.64 (dd, J=15.1, 2.6 Hz, 1H), 4.46 (dd, J=13.8, 7.6 Hz, 1H), 4.35 (dt, J=9.0, 5.9 Hz, 1H), 4.06 (d, J=13.5 Hz, 1H), 3.90 (d, J=13.5 Hz, 1H), 3.24-3.15 (m, 2H), 2.77-2.68 (m, 2H), 2.67-2.62 (m, 1H), 2.46-2.42 (m, 2H), 2.40-2.34 (m, 1H).

(S)-2-((6-((2-chloropyridin-3-yl)methoxy)-3,6'-di-hydro-[2,4'-bipyridin]-1'(2'H)-yl)methyl)-1-(oxetan-2-ylmethyl)-1H-benzo[d]imidazole-6-carboxylic acid (Compound 163)

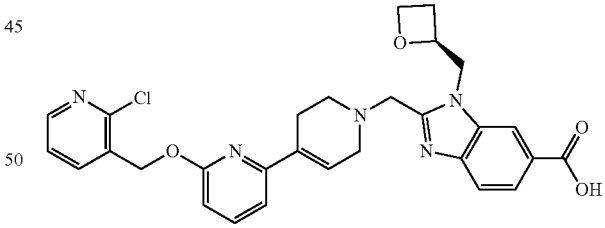

Compound 163

Prepared in analogous manner as for Compound 19
LCMS: [M+H]$^+$=545.8; Retention time (10 mM NH$_4$HCO$_3$)=1.23 min.

$^1$H NMR (400 MHz, CD$_3$OD) δ 8.34 (s, 1H), 8.32-8.28 (m, 1H), 8.02-7.98 (m, 1H), 7.97-7.94 (m, 1H), 7.72-7.64 (m, 2H), 7.39 (dd, J=7.6, 4.8 Hz, 1H), 7.10 (d, J=7.5 Hz, 1H), 6.78 (d, J=8.1 Hz, 1H), 6.72-6.67 (m, 1H), 5.52 (s, 2H), 5.28-5.20 (m, 1H), 4.88-4.85 (m, 1H), 4.77-4.69 (m, 1H), 4.61-4.59 (m, 1H), 4.51-4.42 (m, 1H), 4.11 (dd, J=13.7 Hz, 2H), 3.31-3.25 (m, 2H), 2.89-2.82 (m, 2H), 2.80-2.70 (m, 1H), 2.64-2.56 (m, 2H), 2.54-2.45 (m, 1H)

(S)-2-((6-((5-chloropyrimidin-2-yl)methoxy)-3,6'-dihydro-[2,4'-bipyridin]-1'(2'H)-yl)methyl)-1-(oxetan-2-ylmethyl)-1H-benzo[d]imidazole-6-carboxylic acid (Compound 164)

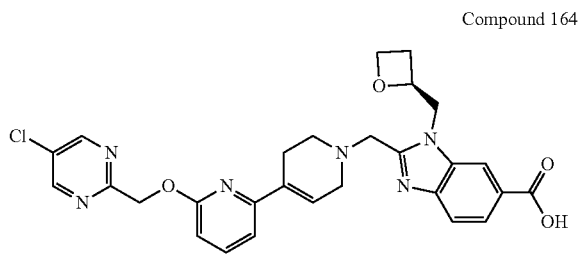 [SMILES: O=C(O)c1ccc2nc(CN3CC=C(c4cccc(OCc5ncc(Cl)cn5)n4)CC3)n(C[C@@H]3CCO3)c2c1]

Compound 164

Prepared in analogous manner as for Compound 19

LCMS: [M+H]+=547.0; Retention time (10 mM NH4HCO3)=1.31 min.

1H NMR (400 MHz, DMSO) δ 8.89 (s, 2H), 8.23 (s, 1H), 7.81 (d, J=8.5 Hz, 1H), 7.72-7.65 (m, 1H), 7.63 (d, J=8.4 Hz, 1H), 7.04 (d, J=7.4 Hz, 1H), 6.79 (d, J=8.2 Hz, 1H), 6.48 (s, 1H), 5.51 (s, 2H), 5.08-4.99 (m, 1H), 4.76 (dd, J=15.4, 7.3 Hz, 1H), 4.65-4.57 (m, 1H), 4.45 (dd, J=13.6, 7.7 Hz, 1H), 4.34 (dt, J=9.0, 5.9 Hz, 1H), 4.03 (d, J=13.6 Hz, 1H), 3.88 (t, J=13.2 Hz, 1H), 3.18-3.08 (m, 2H), 2.72-2.55 (m, 3H), 2.39 (dd, J=17.9, 9.3 Hz, 1H), 2.30 (s, 2H).

(S)-1-(oxetan-2-ylmethyl)-2-((6-(pyrazin-2-ylmethoxy)-3',6'-dihydro-[2,4'-bipyridin]-1'(2'H)-yl)methyl)-1H-benzo[d]imidazole-6-carboxylic acid (Compound 165)

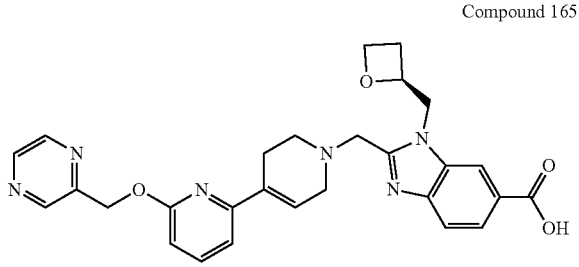 [SMILES: O=C(O)c1ccc2nc(CN3CC=C(c4cccc(OCc5cnccn5)n4)CC3)n(C[C@@H]3CCO3)c2c1]

Compound 165

Prepared in analogous manner as for Compound 19

LCMS: [M+H]+=513.3, Retention time (10 mM NH4HCO3)=1.30 min.

1H NMR (400 MHz, DMSO) δ 8.74 (d, J=1.3 Hz, 1H), 8.64-8.60 (m, 1H), 8.57 (d, J=2.5 Hz, 1H), 8.26-8.22 (brs, 1H), 7.81 (dd, J=8.4, 1.4 Hz, 1H), 7.71 (t, J=7.8 Hz, 1H), 7.64 (d, J=8.4 Hz, 1H), 7.09 (d, J=7.5 Hz, 1H), 6.80 (d, J=8.2 Hz, 1H), 6.68-6.64 (brs, 1H), 5.50 (s, 2H), 5.09-5.02 (m, 1H), 4.78 (dd, J=15.2, 7.3 Hz, 1H), 4.63 (dd, J=15.2, 2.7 Hz, 1H), 4.46 (dd, J=13.7, 7.7 Hz, 1H), 4.35 (dt, J=9.0, 6.0 Hz, 1H), 4.05 (d, J=13.6 Hz, 1H), 3.90 (d, J=13.5 Hz, 1H), 3.23-3.13 (m, 2H), 2.75-2.68 (m, 2H), 2.67-2.62 (m, 1H), 2.46-2.42 (m, 2H), 2.39-2.32 (m, 1H).

(S)-2-((6-((4-ethoxy-3-methoxybenzyl)oxy)-3,6'-dihydro-[2,4'-bipyridin]-1'(2'H)-yl)methyl)-1-(oxetan-2-ylmethyl)-1H-benzo[d]imidazole-6-carboxylic acid (Compound 166)

Compound 166

Prepared in analogous manner as for Compound 19

LCMS: [M+H]+=585.3; Retention time (10 mM NH4HCO3)=1.46 min.

1H NMR (400 MHz, DMSO) δ 8.23-8.18 (brs, 1H), 7.83-7.78 (m, 1H), 7.69-7.58 (m, 2H), 7.06 (dd, J=8.0, 4.6 Hz, 2H), 6.96 (dd, J=8.2, 1.7 Hz, 1H), 6.90 (d, J=8.2 Hz, 1H), 6.81-6.77 (brs, 1H), 6.69 (d, J=8.2 Hz, 1H), 5.27 (s, 2H), 5.10-5.03 (m, 1H), 4.78 (dd, J=15.2, 7.3 Hz, 1H), 4.64 (d, J=12.6 Hz, 1H), 4.47 (dd, J=13.6, 7.6 Hz, 1H), 4.36 (dt, J=8.7, 5.9 Hz, 1H), 4.07 (d, J=13.4 Hz, 1H), 4.01-3.89 (m, 3H), 3.72 (s, 3H), 3.26-3.21 (m, 2H), 2.79-2.71 (m, 2H), 2.69-2.63 (m, 1H), 2.58-2.52 (m, 2H), 2.45-2.38 (m, 1H), 1.30 (t, J=7.0 Hz, 3H).

(S)-2-((4-(4-((4-chloro-2-fluorobenzyl)oxy)-1,3,5-triazin-2-yl)piperazin-1-yl)methyl)-1-(oxetan-2-ylmethyl)-1H-benzo[d]imidazole-6-carboxylic acid (Compound 167)

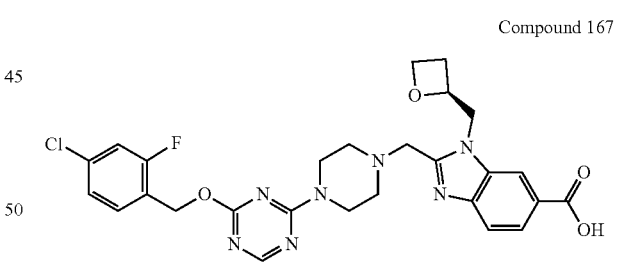

Compound 167

Prepared in analogous manner as for Compound 9

LCMS: [M+H]+=568.2, Retention time (10 mM NH4HCO3)=1.43 min.

1H NMR (400 MHz, DMSO) δ 8.39-8.37 (brs, 1H), 8.27-8.22 (brs, 1H), 7.82 (d, J=8.4 Hz, 1H), 7.63-7.54 (m, 2H), 7.50 (dd, J=10.0, 1.9 Hz, 1H), 7.33 (dd, J=8.3, 1.8 Hz, 1H), 5.38 (s, 2H), 5.13-5.07 (m, 1H), 4.78 (dd, J=15.2, 7.1 Hz, 1H), 4.64 (d, J=12.9 Hz, 1H), 4.49 (dd, J=14.0, 7.5 Hz, 1H), 4.37 (dt, J=8.7, 5.8 Hz, 1H), 3.97 (d, J=13.6 Hz, 1H), 3.84-3.74 (m, 5H), 2.71-2.69 (m, 1H), 2.59-2.52 (m, 3H), 2.47-2.32 (m, 2H).

257

(S)-2-((4-(6-(4-chloro-2-fluorobenzyloxy)pyridin-2-yl)-2,5-dioxopiperazin-1-yl)methyl)-1-(oxetan-2-ylmethyl)-1H-benzo[d]imidazole-6-carboxylic acid (Compound 168)

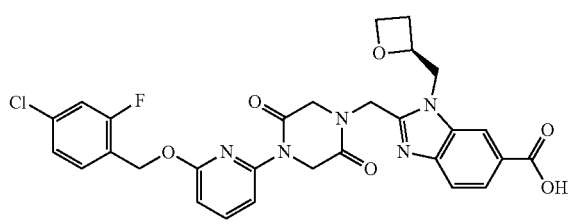

Compound 168

Prepared in analogous manner as for Compound 55

LCMS: [M+H]⁺=594.0; Retention time (10 mM NH₄HCO₃)=1.48 min.

¹H NMR (400 MHz, CDCL3) δ 8.12 (s, 1H), 8.05-8.03 (d, J=8.4 Hz, 1H), 7.87-7.85 (d, J=8.4 Hz, 1H), 7.68-7.62 (m, 2H), 7.43-7.39 (t, J=8.4 Hz, 1H), 7.17-7.13 (m, 2H), 6.67-6.65 (dd, J1=7.2 Hz, J2=0.8 Hz, 1H), 5.37 (s, 2H), 5.21 (s, 2H), 5.14-5.11 (d, J=15.6 Hz, 1H), 4.81-4.76 (m, 3H), 4.66-4.50 (m, 4H), 4.43-4.41 (m, 1H), 2.83-2.78 (t, J=9.6 Hz, 1H), 2.51-2.46 (t, J=8.4 Hz, 1H).

258

(S)-2-((6-((4-chloro-2-fluorobenzyl)oxy)-3,6'-dihydro-[2,4'-bipyridin]-1'(2'H)-yl)methyl)-3-(oxetan-2-ylmethyl)-3H-imidazo[4,5-b]pyridine-5-carboxylic acid (Compound 169)

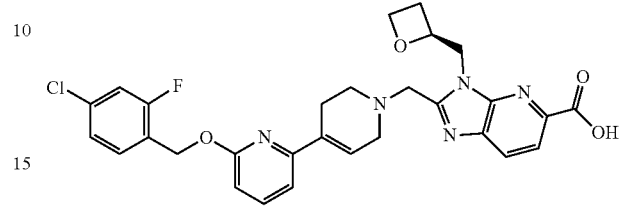

Compound 169

Prepared in analogous manner as for Compound 19.

LCMS: [M+H]⁺=565.1, Retention time (10 mM NH₄HCO₃)=1.80 min.

¹H NMR (400 MHz, DMSO) δ 8.13 (d, J=8.3 Hz, 1H), 7.99 (d, J=8.2 Hz, 1H), 7.68 (t, J=7.8 Hz, 1H), 7.55 (t, J=8.2 Hz, 1H), 7.47 (dd, J=10.0, 1.8 Hz, 1H), 7.30 (d, J=8.2 Hz, 1H), 7.08 (d, J=7.5 Hz, 1H), 6.81-6.68 (m, 2H), 5.39 (s, 2H), 5.21-5.07 (m, 1H), 4.83 (dd, J=14.6, 6.5 Hz, 1H), 4.70 (dd, J=14.7, 3.9 Hz, 1H), 4.47 (dd, J=14.5, 7.0 Hz, 1H), 4.35 (dd, J=14.8, 6.1 Hz, 1H), 4.08 (dd, J=37.5, 13.6 Hz, 2H), 3.27 (s, 2H), 2.75 (d, J=5.3 Hz, 2H), 2.72-2.61 (m, 1H), 2.53 (s, 2H), 2.43 (s, 1H).

(S)-2-((6-((4-chloro-2-fluorobenzyl)oxy)-3,6'-dihydro-[2,4'-bipyridin]-1'(2'H)-yl)methyl)-1-(oxetan-2-ylmethyl)-JH-imidazo[4,5-c]pyridine-6-carboxylic acid (Compound 170)

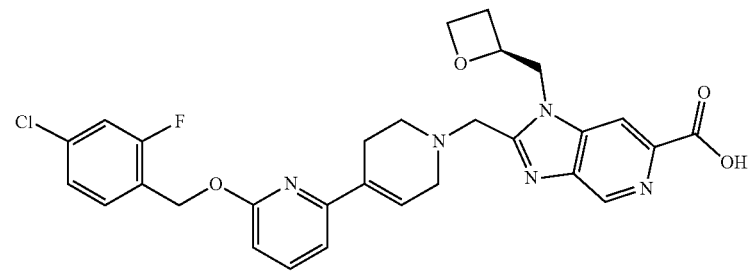

Compound 170

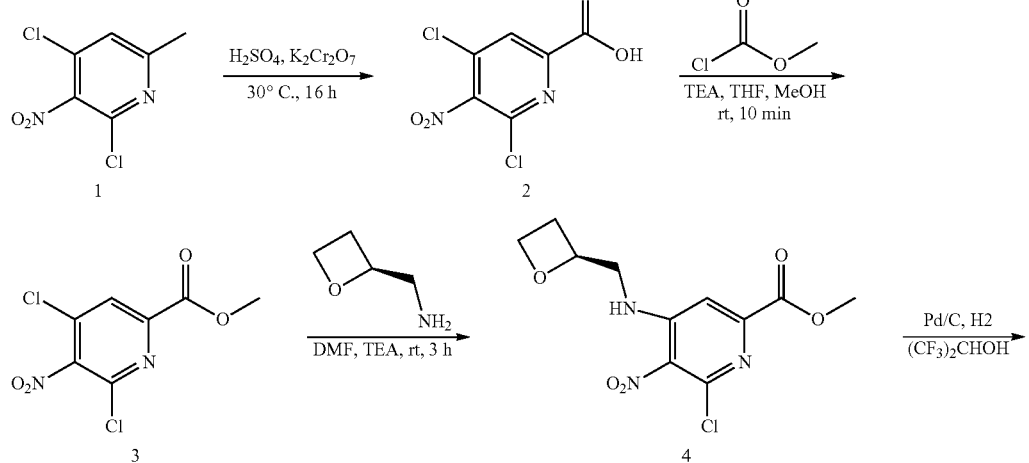

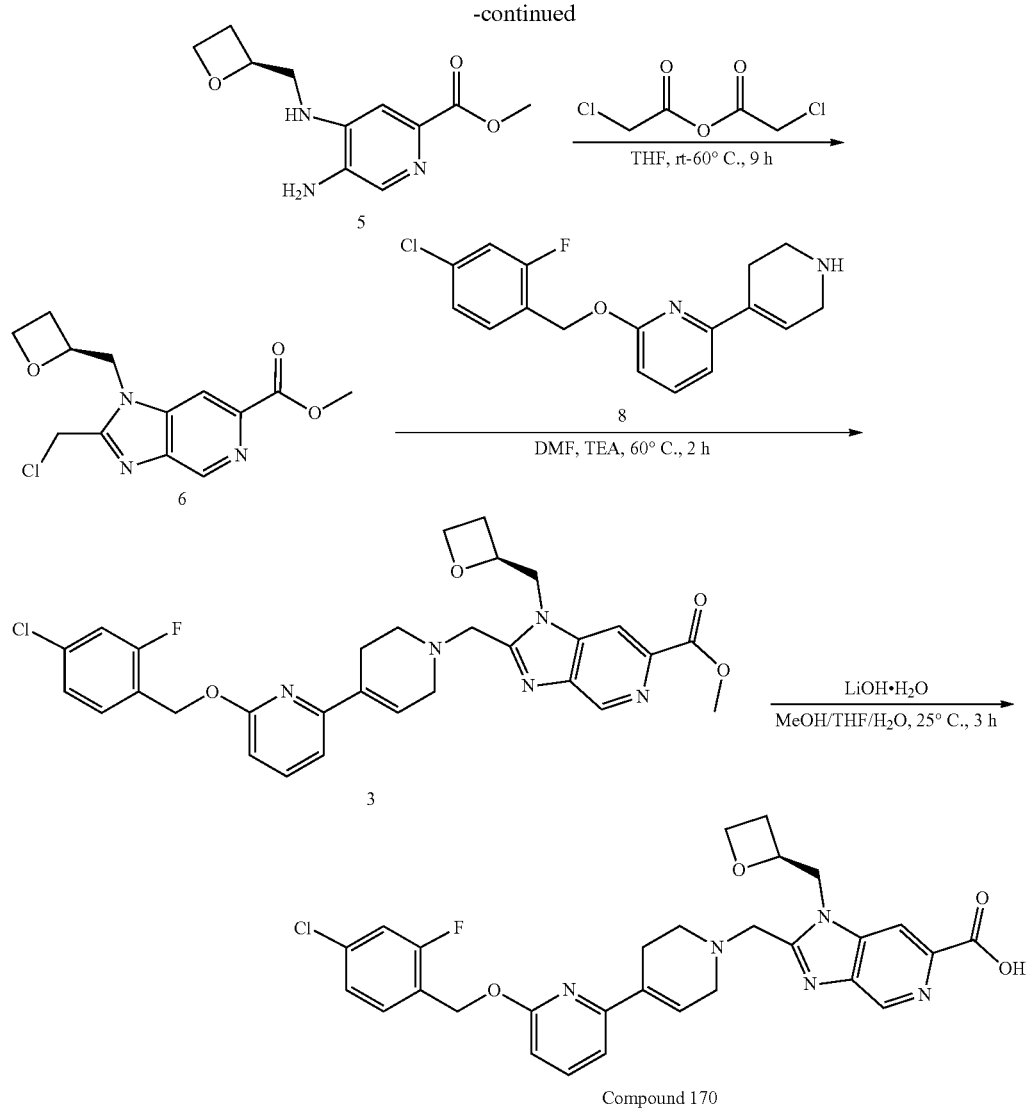

Compound 170

Step 1

Dipotassium oxido-(oxido(dioxo)chromio)oxy-dioxo-chromium (1.92 g, 6.52 mmol) was added to a mixture of 2,4-dichloro-6-methyl-3-nitro-pyridine (1.0 g, 4.83 mmol) in H2SO4 (3 mL) and stirred for 24 h at 30° C. Then the reaction was added to ice and stirred for 20 min and filtered, washed by water (10 ml), dried to give 4,6-dichloro-5-nitro-pyridine-2-carboxylic acid (1.0 g, 4.14 mmol, 83.0% yield) as a white solid which was used in the next step without further purification. LCMS: [M+H]⁺=237.0, Retention time (10 mM NH₄HCO₃)=1.75 min.

Step 2

4,6-dichloro-5-nitro-pyridine-2-carboxylic acid (900 mg, 3.72 mmol) was dissolved in Methanol/THF (10 mL/10 mL) was added N,N-diethylethanamine (3.77 g, 37.22 mmol, 5.19 mL) and methylcarbonochloridate (2.11 g, 22.33 mmol) under ice-cold conditions and the resultant mixture was stirred for 10 min. After completion of the reaction, water was added and the resultant mixture was extracted with ethyl acetate. The organic layer was washed with a saturated aqueous solution of ammonium chloride, dried over sodium sulfate and concentrated in vacuo. The obtained residue was purified using column chromatography (EA:PE=0-70% gradient) to afford methyl 4,6-dichloro-5-nitro-pyridine-2-carboxylate (900 mg, 3.51 mmol, 94.4% yield). LCMS: [M+H]⁺=250.9; Retention time (10 mM NH₄HCO₃)= 1.95 min.

Step 3

A mixture of [(2S)-oxetan-2-yl]methanamine (347 mg, 1.20 mmol), methyl 4,6-dichloro-5-nitro-pyridine-2-carboxylate (300 mg, 1.20 mmol) and N,N-diethylethanamine (363 mg, 3.59 mmol) in DMF (5 mL) was stirred for 2 hr at 15° C., until the reaction was complete as indicated by LCMS. Water (30 mL) was added the mixture and extracted with EtOAc (3×40 mL). The organic phase was washed with brine (20 mL) and dried over anhydrous Na₂SO₄, filtered and concentrated in vacuo. The crude product was purified by silica gel column (petroleum ether/ethyl acetate=1:1) to afford methyl 6-chloro-5-nitro-4-[[(2S)-oxetan-2-yl]methyl-amino]pyridine-2-carboxylate (145 mg, 0.336 mmol, 28.2% yield, 70% purity).

LCMS: [M+H]⁺=302.0; Retention time (10 mM NH₄HCO₃)=1.76 min.

¹H NMR (400 MHz, DMSO) δ 7.89 (dd, J=11.9, 6.2 Hz, 1H), 7.68 (s, 1H), 4.89 (t, J=11.5 Hz, 1H), 4.53-4.24 (m,

2H), 3.88 (d, J=7.6 Hz, 3H), 3.56 (dd, J=15.5, 10.7 Hz, 2H), 2.63 (dt, J=14.7, 8.0 Hz, 1H), 2.45 (dd, J=10.9, 6.9 Hz, 1H).
Step 4

A mixture of methyl 6-chloro-5-nitro-4-[[(2S)-oxetan-2-yl]methylamino]pyridine-2-carboxylate (130 mg, 302 mmol) and Palladium (64.20 mg, 603 mmol) in $(CF_3)_2$CHOH (10 mL) was stirred for 16 hr at 15° C. under $H_2$. The reaction mixture was filtered and concentrated to give the desired product methyl 5-amino-4-[[(2S)-oxetan-2-yl]methylamino]pyridine-2-carboxylate (100 mg, 0.295 mmoll). LCMS: [M+H]$^+$=238.1; Retention time (10 mM $NH_4HCO_3$)= 1.42 min.
Step 5

To a solution of methyl 5-amino-4-[[(2S)-oxetan-2-yl]methylamino]pyridine-2-carboxylate (100 mg, 0.295 mmol) in anhydrous THF (20 mL) was added a solution of (2-chloroacetyl) 2-chloroacetate (76 mg, 442 mmol) in anhydrous THF (2 mL) portion wise. The resultant solution was stirred at room temperature for 2 h and then heated at 60° C. for 24 h. The LCMS showed the SM was remained. A solution of (2-chloroacetyl) 2-chloroacetate (76 mg, 0.443 mmol) in anhydrous THF (2 mL) was added to the reaction mixture and stirred for 24 h at 80° C. Then the mixture was cooled to room temperature and the solvent was evaporated half under reduced pressure. The resulting solution was diluted with EtOAc (30 mL) and treated with aq. $NaHCO_3$ (10 mL). The biphasic mixture was stirred at room temperature for 30 min. The organic layer was separated and the aq. layer was extracted with EtOAc (30 mL×2). The combined organic layers were washed with brine (10 mL), dried over $Na_2SO_4$, filtered and concentrated under reduced pressure to afford methyl 2-(chloromethyl)-1-[[(2S)-oxetan-2-yl]methyl]imidazo[4,5-c]pyridine-6-carboxylate (80 mg, 0.189 mmol, 64.2% yield). LCMS: [M+H]$^+$=296.1, Retention time (0.01% TFA)=1.48 min.
Step 6

To a stirred solution of methyl 2-(chloromethyl)-1-[[(2S)-oxetan-2-yl]methyl]imidazo[4,5-c]pyridine-6-carboxylate (80 mg, 0.189 mmol) and 2-[(4-chloro-2-fluoro-phenyl)methoxy]-6-(1,2,3,6-tetrahydropyridin-4-yl)pyridine (60 mg, 0.189 mmol) in DMF (3 mL) was added N,N-diethylethanamine (57 mg, 0.568 mmol). The reaction mixture was stirred at 60° C. for 1 h and upon completion of the reaction, as judged by LCMS. The mixture was diluted with EtOAc (20 mL). The layers were separated, and the aqueous layer was extracted with EtOAc (2×20 mL). The combined organic phase was washed with brine (15 mL) and dried over anhydrous $Na_2SO_4$, filtered and concentrated in vacuo to afford crude methyl 2-[[4-[6-[(4-chloro-2-fluoro-phenyl)methoxy]-2-pyridyl]-3,6-dihydro-2H-pyridin-1-yl]methyl]-1-[[(2S)-oxetan-2-yl]methyl]imidazo[4,5-c]pyridine-6-carboxylate (100 mg, 0.107 mmol, 56.6% yield, 62% purity) as a yellow solid.

LCMS: [M+H]$^+$=578.1, Retention time (10 mM $NH_4HCO_3$)=2.17 min.
Step 7

To a stirred solution of methyl 2-[[4-[6-[(4-chloro-2-fluoro-phenyl)methoxy]-2-pyridyl]-3,6-dihydro-2H-pyridin-1-yl]methyl]-1-[[(2S)-oxetan-2-yl]methyl]imidazo[4,5-c]pyridine-6-carboxylate (100 mg, 0.107 mmol) in THF (1 mL), Methanol (1 mL), Water (1 mL) at 60° C. was added Lithium hydroxide monohydrate (17 mg, 0.405 mmol). The reaction mixture was stirred at 60° C. for 1 h and upon completion of the reaction, as judged by LCMS, the mixture was acidified with AcOH until pH ~6 and purified by Prep-HPLC to afford 2-[[4-[6-[(4-chloro-2-fluoro-phenyl)methoxy]-2-pyridyl]-3,6-dihydro-2H-pyridin-1-yl]methyl]-1-[[(2S)-oxetan-2-yl]methyl]imidazo[4,5-c]pyridine-6-carboxylic acid (10 mg, 0.018 mmol, 17.0% yield) as a white solid. LCMS: [M+H]$^+$=564.1; Retention time (10 mM $NH_4HCO_3$)=1.81 min.

$^1$H NMR (400 MHz, DMSO) δ 8.89 (s, 1H), 8.34 (s, 1H), 7.69 (t, J=7.8 Hz, 1H), 7.59-7.40 (m, 2H), 7.36-7.26 (m, 1H), 7.09 (d, J=7.4 Hz, 1H), 6.73 (d, J=8.3 Hz, 2H), 5.40 (s, 2H), 5.06 (d, J=5.0 Hz, 1H), 4.88-4.59 (m, 2H), 4.52-4.28 (m, 2H), 4.03 (dd, J=51.9, 13.6 Hz, 2H), 3.24 (s, 2H), 2.75 (d, J=3.5 Hz, 1H), 2.65 (d, J=16.0 Hz, 1H), 2.39 (dd, J=21.4, 12.7 Hz, 2H).

(S)-2-((6-((4-chloro-2-fluorobenzyl)oxy)-3,6'-dihydro-[2,4'-bipyridin]-1'(2'H)-yl)methyl)-7-fluoro-1-(oxetan-2-ylmethyl)-1H-benzo[d]imidazole-6-carboxylic acid (Compound 171)

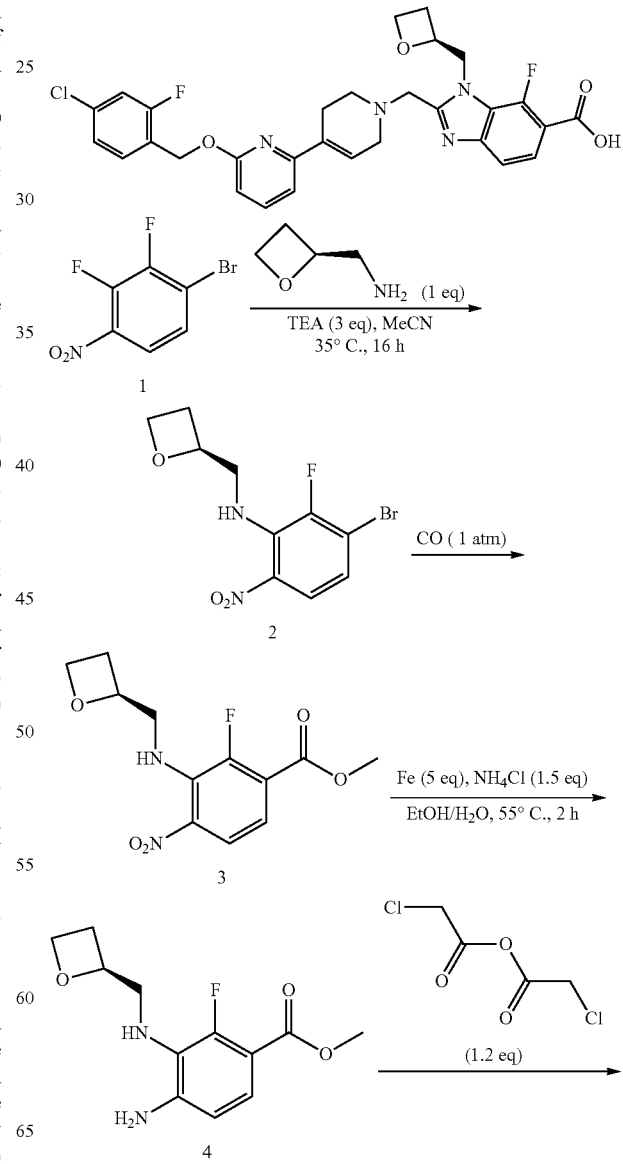

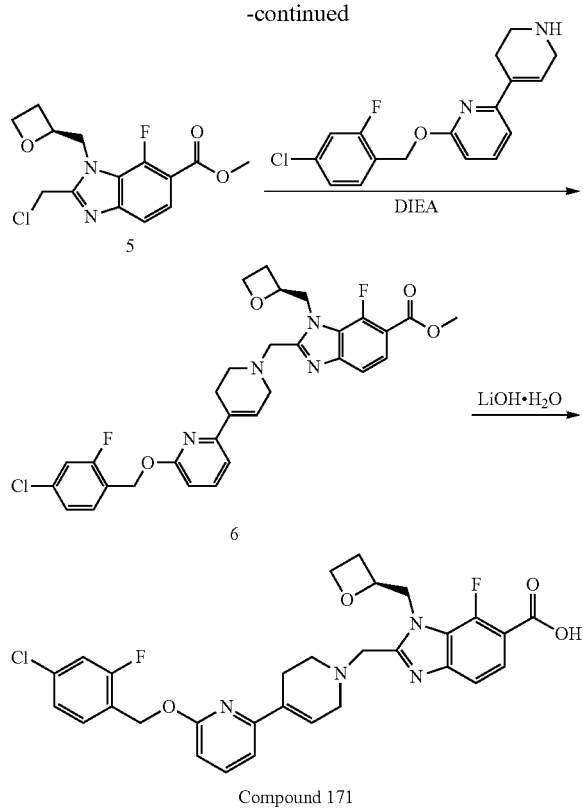

Compound 171

Step 1

A mixture of N,N-diethylethanamine (1.02 g, 10.08 mmol, 1.41 mL), [(2S)-oxetan-2-yl]methanamine (293 mg, 3.36 mmol) and 1-bromo-2,3-difluoro-4-nitro-benzene (800 mg, 3.36 mmol) in MeCN (8 mL) was stirred at 35° C. for 16 h. LCMS indicated the reaction was complete. Silica gel (2.0 g) was added into the reaction mixture, and the solvent was removed under reduced pressure. The dry powder was purified through chromatography column. 3-bromo-2-fluoro-6-nitro-N-[[(2S)-oxetan-2-yl]methyl]aniline (650 mg, 2.02 mmol, 60.2% yield, 95% purity) was obtained as yellow solid.

LCMS: [M+H]$^+$=305, Retention time (0.01% TFA)=2.02 min.

Step 2

A mixture of 3-bromo-2-fluoro-6-nitro-N-[[(2S)-oxetan-2-yl]methyl]aniline (200 mg, 0.655 mmol), [1,1'-Bis(diphenylphosphino)ferrocene]dichloropalladium(II) (48 mg, 0.066 mmol), N,N-diethylethanamine (166 mg, 1.64 mmol) and ethanol (302 mg, 6.56 mmol) in DMSO (2 mL) was exchanged with carbon monoxide three times and stirred under carbon monoxide atmosphere at 80° C. for 16 h. LCMS indicated 40% product, 60% SM. The reaction mixture was diluted with water (6 mL) and extracted with ethyl acetate (10 mL×3). The combined organic layers were dried over sodium sulfate and evaporated under reduced pressure. The residue was purified through silica gel. Methyl 2-fluoro-4-nitro-3-[[(2S)-oxetan-2-yl] methylamino]benzoate (52 mg, 0.157 mmol, 23.9% yield, 90% purity) was obtained as yellow solid.

LCMS: [M+H]$^+$=299, Retention time (10 mM NH$_4$HCO$_3$)=2.07 min.

Step 3

A mixture of ethyl 2-fluoro-4-nitro-3-[[(2S)-oxetan-2-yl] methylamino]benzoate (60 mg, 0.191 mmol), Iron (56 mg, 1.01 mmol), ammonium chloride (16 mg, 0.302 mmol) in Ethanol (1 mL) and Water (0.1 mL) was stirred at 50° C. for 2 h. LCMS indicated the reaction was complete. Silica gel (2 g) was added into the reaction mixture, and the solvent was removed under reduced pressure. The dry powder was purified through chromatography column (eluent: petroleum ether:ethyl acetate=2:1). Ethyl 4-amino-2-fluoro-3-[[(2S)-oxetan-2-yl] methylamino] benzoate (50 mg, 0.177 mmol, 95% purity) was obtained as light-yellow solid. LCMS: [M+H]$^+$=269, Retention time (10 mM NH$_4$HCO$_3$)=1.78 min.

Step 4

A solution of ethyl 4-amino-2-fluoro-3-[[(2S)-oxetan-2-yl]methylamino]benzoate (50 mg, 0.177 mmol), (2-chloroacetyl) 2-chloroacetate (36 mg, 0.212 mmol) in THF (1 mL) was stirred at 80° C. for 48 h.

LCMS indicated the reaction was complete. Sodium bicarbonate solution (2 mL) was added into this system and then stirred for 15 min. Silica gel (2 g) was added. The solvent was removed under reduced pressure and the dry powder was purified through chromatography column (eluent: petroleum ether/ethyl acetate=2:1). Ethyl 2-(chloromethyl)-4-fluoro-3-[[(2S)-oxetan-2-yl]methyl]benzimidazole-5-carboxylate (45 mg, 0.110 mmol, 62.2% yield, 80% purity) was obtained as brown gum. LCMS: [M+H]+=327, Retention time (10 mM NH$_4$HCO$_3$)=1.98 min.

Step 5

A solution of ethyl 2-(chloromethyl)-4-fluoro-3-[[(2S)-oxetan-2-yl]methyl]benzimidazole-5-carboxylate (45 mg, 0.110 mmol), 2-[(4-chloro-2-fluoro-phenyl)methoxy]-6-(1,2,3,6-tetrahydropyridin-4-yl)pyridine (35 mg, 0.110 mmol), N,N-diethylethanamine (33 mg, 0.330 mmol) in DMF (1 mL) was stirred at 60° C. for 3 h. LCMS indicated the reaction was complete. The reaction mixture was cooled to room temperature and diluted with brine (15 mL) and extracted with ethyl acetate (15 mL×3). The combined organic layers were washed with brine (15 mL×3), dried over sodium sulfate and evaporated to dryness. Ethyl 2-[[4-[6-[(4-chloro-2-fluoro-phenyl) methoxy]-2-pyridyl]-3,6-dihydro-2H-pyridin-1-yl]methyl]-4-fluoro-3-[[(2S)-oxetan-2-yl]methyl]benzimidazole-5-carboxylate (76 mg, 0.087 mmol, 79.3% yield, 70% purity) was obtained as brown oil. LCMS: [M+H]$^+$=609, Retention time (10 mM NH$_4$HCO$_3$)= 2.47 min.

Step 6

A solution of ethyl 2-[[4-[6-[(4-chloro-2-fluoro-phenyl) methoxy]-2-pyridyl]-3,6-dihydro-2H-pyridin-1-yl]methyl]-4-fluoro-3-[[(2S)-oxetan-2-yl]methyl]benzimidazole-5-carboxylate (76 mg, 0.087 mmol) in was added a solution of lithium hydroxide hydrate (15 mg, 357 mmol) in ice-bath. The reaction mixture was stirred at 25° C. for 2 h. LCMS indicated the reaction was complete. The reaction mixture was acidified with acetic acid solution until pH=5, and purified through prep-HPLC to provide the desired product (S)-2-((6-((4-chloro-2-fluorobenzyl)oxy)-3',6'-dihydro-[2,4'-bipyridin]-1'(2'H)-yl)methyl)-7-fluoro-1-(oxetan-2-ylmethyl)-1H-benzo[d]imidazole-6-carboxylic acid (17 mg, 0.029 mmol, 33.2% yield, 99% purity) was obtained as white solid.

LCMS: [M+H]$^+$=581, Retention time (10 mM NH$_4$HCO$_3$)=1.88 min.

$^1$H NMR (400 MHz, MeOD) δ 7.68-7.59 (m, 2H), 7.50 (t, J=8.0 Hz, 1H), 7.43 (d, J=8.4 Hz, 1H), 7.26-7.15 (m, 2H), 7.07 (d, J=7.5 Hz, 1H), 6.75 (s, 1H), 6.69 (d, J=8.2 Hz, 1H), 5.44 (s, 2H), 5.34-5.19 (m, 1H), 5.05 (dd, J=15.3, 7.2 Hz, 1H), 4.81 (dd, J=15.3, 2.6 Hz, 1H), 4.65 (dd, J=13.9, 7.7 Hz, 1H), 4.47 (dt, J=9.0, 6.0 Hz, 1H), 4.18 (d, J=13.7 Hz, 1H), 4.05 (d, J=13.7 Hz, 1H), 2.93-2.76 (m, 3H), 2.68 (d, J=16.6 Hz, 2H), 2.54 (dd, J=16.0, 11.4, 7.2 Hz, 1H).

(S)-2-((6-((4-chloro-2-fluorobenzyl)oxy)-3,6'-dihydro-[2,4'-bipyridin]-1'(2'H)-yl)methyl)-5-fluoro-1-(oxetan-2-ylmethyl)-1H-benzo[d]imidazole-6-carboxylic acid (Compound 172)

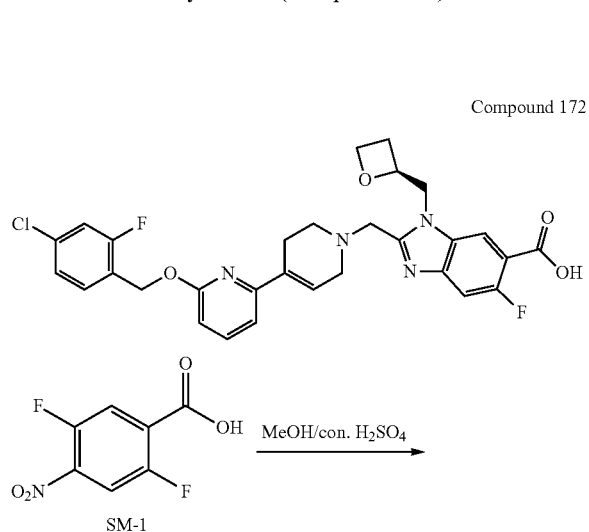

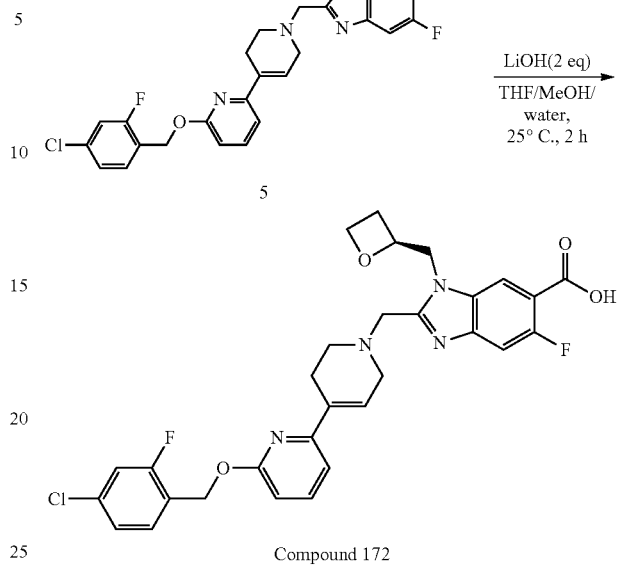

-continued

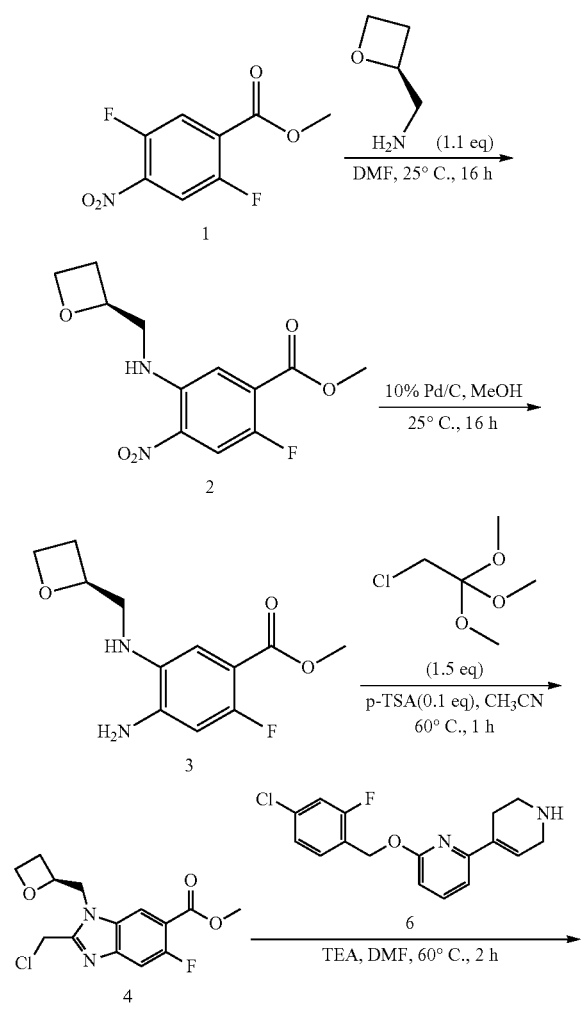

Step 1

A mixture of 2,5-difluoro-4-nitro-benzoic acid (1 g, 4.92 mmol), sulfuric acid (161 mg, 1.64 mmol, 0.1 mL) in MeOH (10 mL) was stirred at 65° C. overnight. LCMS monitored the results, the resulting mixture was cooled to rt and concentrated in vacuo, then the residue was dissolved in ethyl acetate and washed with saturated sodium bicarbonate solution and saturated salt water in turn, dried over anhydrous sodium sulfate and concentrated in vacuo to afford methyl 2,5-difluoro-4-nitro-benzoate (910 mg, 4.19 mmol, 85.1% yield) as a yellow solid.

Step 2

A mixture of methyl 2,5-difluoro-4-nitro-benzoate (481 mg, 2.22 mmol), [(2S)-oxetan-2-yl]methanamine (213 mg, 2.44 mmol) in DMF (3 mL) was stirred at 25° C. overnight, LCMS monitored the results, the resulting mixture was poured into water and extracted with ethyl acetate (3×20 mL). The combined organic layers were washed with brine (2×30 mL), dried over anhydrous sodium sulfate, concentrated and purified by silica gel chromatography (eluting with ethyl acetate/petroleum ether, v/v, 4/1) to afford methyl 2-fluoro-4-nitro-5-[[(2S)-oxetan-2-yl]methylamino]benzoate (185 mg, 651 mmol, 29.32% yield) as a yellow solid. LCMS: [M+H]$^+$=285.1; Retention time (0.01% TFA)=1.72 min.

Step 3

A mixture of methyl 2-fluoro-4-nitro-5-[[(2S)-oxetan-2-yl]methylamino]benzoate (185 mg, 0.651 mmol) and Palladium (69 mg, 0.065 mmol) in Hexafluoroisopropanol (10 mL) was flushed with hydrogen atmosphere and stirred at room temperature overnight. The resulting mixture was filtered through celite.

The filtrate was concentrated in vacuo to afford methyl 4-amino-2-fluoro-5-[[(2S)-oxetan-2-yl]methylamino]benzoate (159 mg, 0.625 mmol, 96.1% yield) as a white solid. LCMS: [M+H]$^+$=255.2; Retention time (0.01% TFA)=1.61 min.

Step 4

A mixture of methyl 4-amino-2-fluoro-5-[[(2S)-oxetan-2-yl]methylamino]benzoate (159 mg, 0.625 mmol), 2-chloro- 1,1,1-trimethoxy-ethane (145 mg, 0.938 mmol) and 4-methylbenzenesulfonic acid hydrate (12 mg, 0.062 mmol) in MeCN (2 mL) was stirred at 60° C. for 1 h. The resulting mixture was concentrated and purified by silica gel chromatography (eluting with petroleum ether/ethyl acetate, v/v, 1/4) to afford methyl 2-(chloromethyl)-6-fluoro-3-[[(2S)-oxetan-2-yl]methyl]benzimidazole-5-carboxylate (82 mg, 0.262 mmol, 41.9% yield) as a white solid. LCMS: [M+H]$^+$= 313.1; Retention time (0.01% TFA)=1.73 min.

Step 5

A mixture of methyl 2-(chloromethyl)-6-fluoro-3-[[(2S)-oxetan-2-yl]methyl]benzimidazole-5-carboxylate (82 mg, 0.262 mmol), 2-[(4-chloro-2-fluoro-phenyl)methoxy]-6-(1,2,3,6-tetrahydropyridin-4-yl)pyridine (84 mg, 0.262 mmol), N,N-diethylethanamine (80 mg, 0.787 mmol) in DMF (2 mL) was stirred at 60° C. for 2 h. The resulting mixture was poured into water and extracted with ethyl acetate (3×10 mL). The combined organic layers were washed with brine (2×20 mL), dried over anhydrous sodium sulfate, concentrated to afford methyl 2-[[4-[6-[(4-chloro-2-fluoro-phenyl)methoxy]-2-pyridyl]-3,6-dihydro-2H-pyridin-1-yl]methyl]-6-fluoro-3-[[(2S)-oxetan-2-yl]methyl]benzimidazole-5-carboxylate (150 mg, 0.201 mmol, 76.9% yield) as a white solid. LCMS: [M+H]$^+$=595.3; Retention time (0.01% TFA)= 1.79 min.

Step 6

A solution of methyl 2-[[4-[6-[(4-chloro-2-fluoro-phenyl)methoxy]-2-pyridyl]-3,6-dihydro-2H-pyridin-1-yl]methyl]-6-fluoro-3-[[(2S)-oxetan-2-yl]methyl]benzimidazole-5-carboxylate (82 mg, 0.113 mmol), LiOH (5 mg, 0.226 mmol) in THF (1 mL), Methanol (1 mL) and Water (1 mL) was stirred at 25° C. for 2 hr. LCMS indicated complete reaction. After removal of partial solvent, the mixture was neutralized with acetic acid to pH=5 and the crude was purified by Prep-HPLC (Column:Xtimate C18 21.2×250 mm, 10 μm; Mobile Phase: A:water (10 mM NH$_4$HCO$_3$ & 0.025% NH$_3$.H$_2$O), B: ACN; Gradient: 34% B for 1 min, then 49% B in 7 min, stop at 15 min; Flow Rate (mL/min): 30.00; Detective Wavelength (nm): 214 nm & 254 nm) to give 2-[[4-[6-[(4-chloro-2-fluoro-phenyl)methoxy]-2-pyridyl]-3,6-dihydro-2H-pyridin-1-yl]methyl]-6-fluoro-3-[[(2S)-oxetan-2-yl]methyl]benzimidazole-5-carboxylic acid (7 mg, 0.013 mmol, 11.9% yield, 100% purity) as a white solid. LCMS: [M+H]$^+$=581.2; Retention time (0.01% TFA)=1.71 min.

1H NMR (400 MHz, DMSO) δ 8.98 (d, J=1.3 Hz, 1H), 8.26 (dd, J=8.2, 2.1 Hz, 1H), 7.90-7.71 (m, 1H), 7.57 (t, J=7.9 Hz, 2H), 7.48 (t, J=8.0 Hz, 1H), 7.35 (d, J=8.4 Hz, 1H), 6.27 (d, J=8.2 Hz, 1H), 6.16 (d, J=7.7 Hz, 1H), 5.51 (s, 1H), 5.43 (s, 2H), 5.00 (s, 1H), 4.62 (dd, J=15.5, 7.4 Hz, 1H), 4.54-4.39 (m, 2H), 4.34 (dt, J=8.8, 6.0 Hz, 1H), 3.73 (dd, J=25.8, 15.9 Hz, 3H), 2.68 (d, J=6.8 Hz, 2H), 2.39 (dd, J=22.8, 14.1 Hz, 2H), 2.1 (br s, 2H).

(S)-2-((6-((4-chloro-2-fluorobenzyl)oxy)-3,6'-dihydro-[2,4'-bipyridin]-1'(2'H)-yl)methyl)-1-(oxetan-2-ylmethyl)-N-((trifluoromethyl)sulfonyl)-1H-benzo[d]imidazole-6-carboxamide (Compound 173)

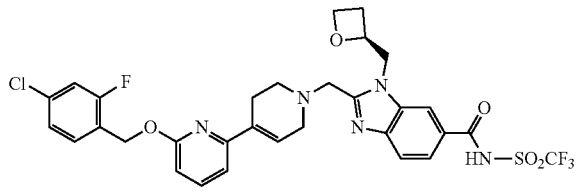

Compound 173

Prepared in analogous manner as for Compound 19

LCMS: [M+H]$^+$=693.9; Retention time (10 mM NH$_4$HCO$_3$)=1.84 min.

$^1$H NMR (400 MHz, DMSO) δ 8.16-8.15 (brs, 1H), 7.84 (dd, J=8.4, 1.4 Hz, 1H), 7.68 (t, J=7.8 Hz, 1H), 7.61-7.45 (m, 3H), 7.30 (dd, J=8.2, 1.7 Hz, 1H), 7.09 (d, J=7.5 Hz, 1H), 6.78-6.68 (m, 2H), 6.09-6.08 (brs, 1H), 5.40 (s, 2H), 5.07 (d, J=4.2 Hz, 1H), 4.75 (dd, J=15.2, 7.0 Hz, 1H), 4.67-4.57 (m, 1H), 4.46 (dd, J=13.8, 7.6 Hz, 1H), 4.35 (dt, J=9.1, 6.0 Hz, 1H), 4.05 (d, J=13.4 Hz, 1H), 3.90 (d, J=13.4 Hz, 1H), 3.25-3.24 (brs, 2H), 2.73 (d, J=5.4 Hz, 2H), 2.67-2.66 (brs, 1H), 2.49-2.46 (m, 2H), 2.40 (d, J=10.6 Hz, 1H).

(S)-2-((6-((4-chloro-2-fluorobenzyl)oxy)-5,6'-dihydro-[2,4'-bipyridin]-1'(2'H)-yl)methyl)-N-hydroxy-1-(oxetan-2-ylmethyl)-1H-benzo[d]imidazole-6-carboxamide (Compound 174)

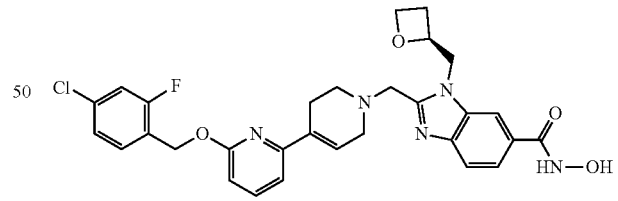

Compound 174

Prepared in analogous manner as for Compound 19

LCMS: [M+H]$^+$=578.7; Retention time (10 mM NH$_4$HCO$_3$)=1.60 min.

$^1$H NMR (400 MHz, DMSO) δ 8.99 (s, 1H), 8.06 (s, 1H), 7.71-7.53 (m, 5H), 7.30 (d, J=6.3 Hz, 1H), 7.09 (dd, J=7.4 Hz, 1H), 6.77-6.71 (m, 2H), 5.40 (s, 2H), 5.13-5.04 (m, 1H), 4.86-4.67 (m, 1H), 4.66-4.54 (m, 1H), 4.50-4.38 (m, 2H), 4.07 (d, J=13.5 Hz, 1H), 3.90 (d, J=13.4 Hz, 1H), 3.26-3.17 (m, 2H), 2.79-2.65 (m, 3H), 2.46-2.32 (m, 3H).

(S)-2-((4-(3-((4-cyano-2-fluorobenzyl)oxy)phenyl)-3,6-dihydropyridin-1(2H)-yl)methyl)-1-(oxetan-2-ylmethyl)-1H-benzo[d]imidazole-6-carboxylic acid (Compound 175)

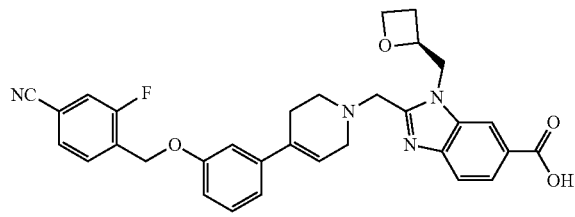

Compound 175

Prepared in analogous manner as for Compound 28

LCMS: [M+H]+=553.0; Retention time (10 mM NH4HCO3)=1.51 min.

1H NMR (400 MHz, DMSO) δ 8.27 (s, 1H), 7.92 (d, J=10.2 Hz, 1H), 7.82-7.74 (m, 3H), 7.68 (s, 1H), 7.26 (d, J=7.4 Hz, 1H), 7.08 (s, 2H), 6.95-6.92 (m, 1H), 6.19 (s, 1H), 5.25 (s, 2H), 5.05 (s, 1H), 4.80 (dd, J=14.9, 6.7 Hz, 1H), 4.65 (d, J=14.3 Hz, 1H), 4.47 (d, J=5.8 Hz, 1H), 4.35 (d, J=8.6 Hz, 1H), 4.10-3.85 (m, 2H), 3.17 (s, 2H), 2.79-2.64 (m, 3H), 2.44-2.23 (m, 3H).

(S)-2-((4-(4-((4-cyano-2-fluorobenzyl)oxy)pyrimidin-2-yl)-3,6-dihydropyridin-1(2H)-yl)methyl)-1-(oxetan-2-ylmethyl)-1H-benzo[d]imidazole-6-carboxylic acid (Compound 176)

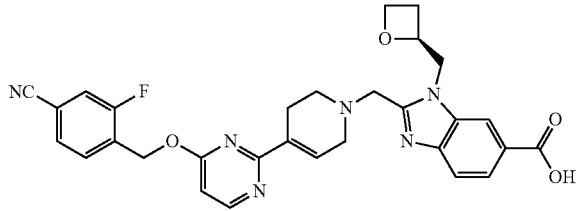

Compound 176

Prepared in analogous manner as for Compound 33

LCMS: [M+H]+=555.3; Retention time (10 mM NH4HCO3)=1.22 min.

1H NMR (400 MHz, DMSO) δ 8.52 (d, J=5.7 Hz, 1H), 8.26 (s, 1H), 7.92 (d, J=10.1 Hz, 1H), 7.82 (d, J=8.3 Hz, 1H), 7.75-7.71 (m, 2H), 7.65 (d, J=8.4 Hz, 1H), 7.14 (s, 1H), 6.86 (d, J=5.7 Hz, 1H), 5.57 (s, 2H), 5.10-5.04 (brs, 1H), 4.80 (dd, J=15.3, 7.3 Hz, 1H), 4.64 (d, J=12.8 Hz, 1H), 4.49-4.43 (m, 1H), 4.39-4.34 (m, 1H), 4.08 (d, J=13.5 Hz, 1H), 3.92 (d, J=13.4 Hz, 1H), 3.29-3.22 (m, 2H), 2.78-2.69 (m, 2H), 2.69-2.62 (m, J=6.4 Hz, 1H), 2.56 (s, 2H), 2.43-2.38 (m, 1H).

(S)-2-((4-(2-((4-cyano-2-fluorobenzyl)oxy)pyrimidin-4-yl)-5,6-dihydropyridin-1(2H)-yl)methyl)-1-(oxetan-2-ylmethyl)-1H-benzo[d]imidazole-6-carboxylic acid (Compound 177)

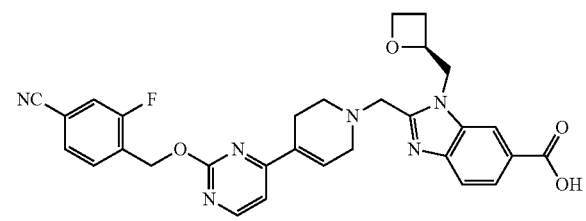

Compound 177

Prepared in analogous manner as for Compound 19

LCMS: [M+H]+=555.0; Retention time (10 mM NH4HCO3)=1.35 min.

1H NMR (400 MHz, DMSO) δ 8.54 (d, J=5.2 Hz, 1H), 8.24 (s, 1H), 7.91 (d, J=9.6 Hz, 1H), 7.81 (d, J=8.4 Hz, 1H), 7.74-7.70 (m, 2H), 7.63 (d, J=8.4 Hz, 1H), 7.28 (d, J=5.2 Hz, 1H), 7.00 (s, 1H), 5.51 (s, 2H), 5.06-5.03 (m, 1H), 4.80-4.74 (m, 1H), 4.65-4.61 (m, 1H), 4.46-4.43 (m, 1H), 4.37-4.34 (m, 1H), 4.07 (d, J=13.6 Hz, 1H), 3.92 (d, J=13.2 Hz, 1H), 3.27 (d, J=8.4 Hz, 2H), 2.74-2.64 (m, 3H), 2.43-2.32 (m, 3H).

(S)-2-((4-(3-((4-chloro-2-fluorobenzyl)oxy)phenyl)piperazin-1-yl)methyl)-1-(oxetan-2-ylmethyl)-1H-benzo[d]imidazole-6-carboxylic acid (Compound 178)

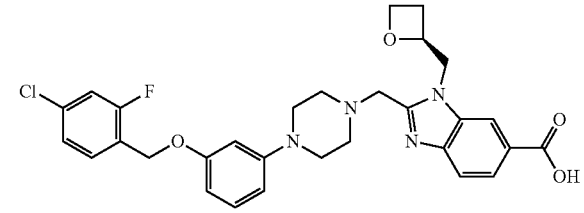

Compound 178

Prepared in analogous manner as for Compound 9

LCMS: [M+H]+=565.0; Retention time (10 mM NH4HCO3)=1.57 min.

1H NMR (400 MHz, DMSO) δ 8.25-8.24 (brs, 1H), 7.80 (dd, J=8.4, 1.4 Hz, 1H), 7.66-7.53 (m, 2H), 7.49 (dd, J=10.0, 2.0 Hz, 1H), 7.33 (dd, J=8.3, 1.8 Hz, 1H), 7.11 (t, J=8.2 Hz, 1H), 6.54 (d, J=8.0 Hz, 2H), 6.48-6.38 (m, 1H), 5.09 (d, J=8.4 Hz, 3H), 4.78 (dd, J=15.1, 7.1 Hz, 1H), 4.68-4.58 (m, 1H), 4.48 (dd, J=13.5, 7.8 Hz, 1H), 4.37 (dt, J=9.0, 5.9 Hz, 1H), 3.98 (d, J=13.5 Hz, 1H), 3.80 (d, J=13.5 Hz, 1H), 3.13-3.12 (brs, 4H), 2.74-2.66 (m, 1H), 2.59 (td, J=11.4, 6.2 Hz, 4H), 2.45-2.39 (m, 1H).

(S)-2-((4-(2-(4-chloro-2-fluorobenzyloxy)-5-fluoro-pyrimidin-4-yl)piperazin-1-yl)methyl)-1-(oxetan-2-ylmethyl)-JH-benzo[d]imidazole-6-arboxylic acid (Compound 179)

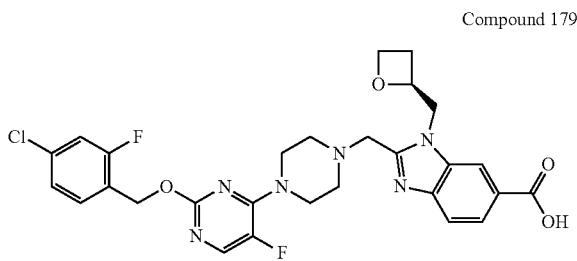 [SMILES: O=C(O)c1ccc2nc(CN3CCN(c4nc(OCc5ccc(Cl)cc5F)ncc4F)CC3)n(C[C@@H]3CCO3)c2c1]

Compound 179

Prepared in analogous manner as for Compound 9
LCMS: [M+H]⁺=585.0; Retention time (10 mM NH4HCO3)=1.47 min.
¹H NMR (400 MHz, CDCL3) δ 8.06 (s, 1H), 7.94-7.85 (m, 2H), 7.76-7.74 (d, J=8.4 Hz, 1H), 7.44-7.40 (t, J=7.6 Hz, 1H), 7.12-7.07 (m, 2H), 5.32 (s, 2H), 5.19-5.18 (d, J=5.2 Hz, 1H), 4.86-4.78 (t, J=15.2 Hz, 2H), 4.63-4.58 (m, 1H), 4.39-4.30 (m, 3H), 4.01 (s, 4H), 3.06-2.70 (m, 5H), 2.43-2.39 (t, J=8.4 Hz, 1H).

(S)-2-((4-(4-(4-chloro-2-fluorobenzyloxy)-5-fluoro-pyrimidin-2-yl)piperazin-1-yl)methyl)-1-(oxetan-2-ylmethyl)-1H-benzo[d]imidazole-6-carboxylic acid (Compound 180)

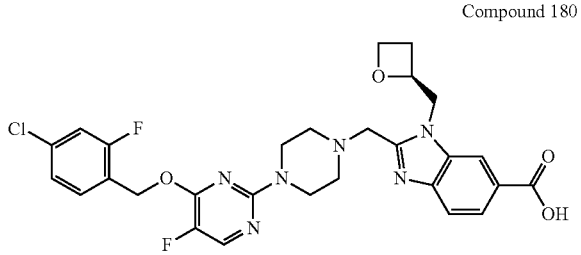 [SMILES: O=C(O)c1ccc2nc(CN3CCN(c4ncc(F)c(OCc5ccc(Cl)cc5F)n4)CC3)n(C[C@@H]3CCO3)c2c1]

Compound 180

Prepared in analogous manner as for Compound 33
LCMS: [M+H]⁺=585.0; Retention time (10 mM NH4HCO3)= 1.54 min.
¹H NMR (400 MHz, CDCL3) δ 8.24 (s, 1H), 8.09-8.06 (dd, J1=8.4 Hz, J2=1.2 Hz, 1H), 8.01-8.00 (d, J=2.8 Hz, 1H), 7.86-7.84 (d, J=8.4 Hz, 1H), 7.44-7.40 (t, J=8.0 Hz, 1H), 7.18-7.15 (dd, J1=8.0 Hz, J2=1.6 Hz, 1H), 7.14-7.11 (dd, J1=9.6 Hz, J2=2.0 Hz, 1H), 5.43 (s, 2H), 5.28-5.25 (m, 1H), 4.79-4.72 (m, 2H), 4.69-4.63 (m, 1H), 4.45-4.40 (m, 1H), 4.11 (s, 2H), 3.78 (s, 4H), 2.80-2.69 (m, 5H), 2.51-2.46 (m, 1H).

(S)-2-((4-(4-((4-chloro-2-fluorobenzyl)oxy)pyrimidin-2-yl)piperazin-1-yl)methyl)-1-(oxetan-2-ylmethyl)-1H-benzo[d]imidazole-6-carboxylic acid (Compound 181)

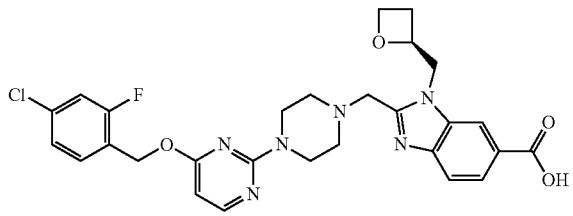

Compound 181

Prepared in analogous manner as for Compound 33
LCMS: [M+H]⁺=567.0; Retention time (10 mM NH4HCO3)=1.53 min.
¹H NMR (400 MHz, DMSO) δ 8.23 (s, 1H), 8.10 (d, J=5.6 Hz, 1H), 7.80 (dd, J=1.2, 1.2 Hz, 1H), 7.61-7.53 (m, 2H), 7.47 (dd, J=2 Hz, J=2 Hz, 1H), 7.31 (dd, J=1.6 Hz, J=1.6 Hz, 1H), 6.10 (d, J=5.2 Hz, 1H), 5.36 (s, 2H), 5.11-5.09 (m, 1H), 4.81-4.76 (m, 1H), 4.67-4.62 (m, 1H), 4.49-4.46 (m, 1H), 4.40-4.36 (m, 1H), 3.96 (d, J=13.6 Hz, 1H), 3.80 (d, J=13.2 Hz, 1H), 3.71 (s, 4H), 2.73-2.67 (m, 1H), 2.47-2.40 (m, 2H).

2-((6-((4-cyano-2-fluorobenzyl)oxy)-3',6'-dihydro-[2,4'-bipyridin]-1'(2'H)-yl)methyl)-1-((1-ethyl-1H-imidazol-5-yl)methyl)-1H-benzo[d]imidazole-6-carboxylic acid (Compound 182)

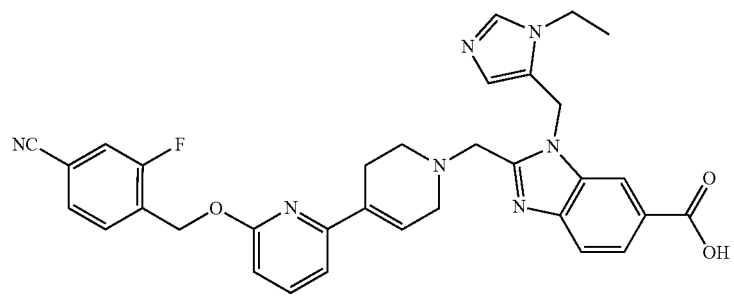

Compound 182

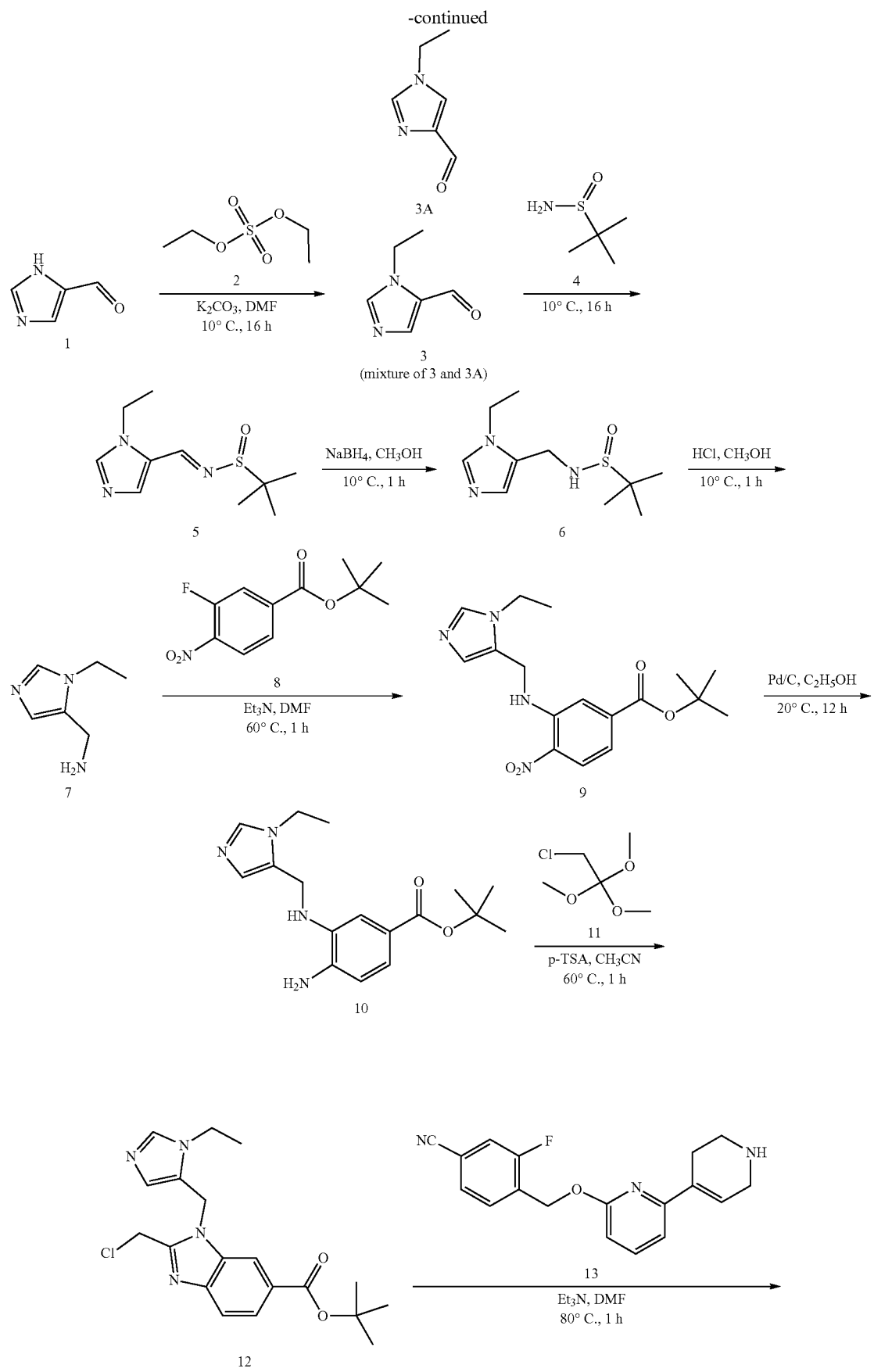

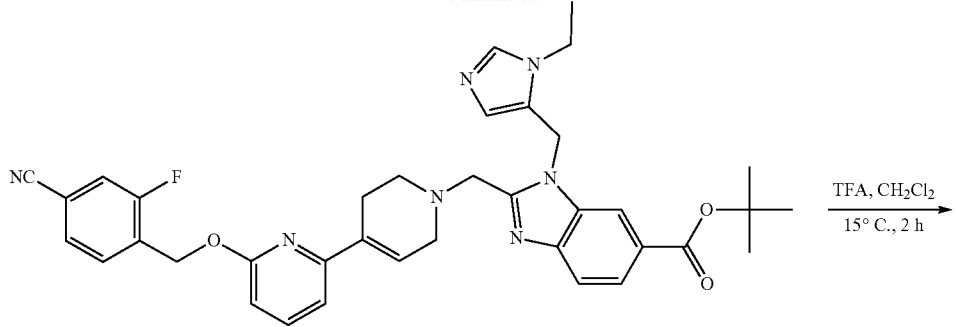

14

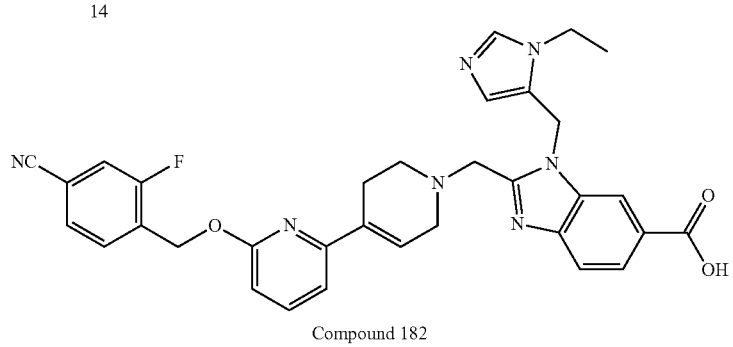

Compound 182

Step 1

A mixture of diethyl sulfate (3.21 g, 20.81 mmol, 2.72 mL), 1H-imidazole-5-carbaldehyde (2.0 g, 20.81 mmol), and potassium carbonate (3.45 g, 24.98 mmol, 1.51 mL) in DMF (20 mL) was stirred for 16 h at 10° C. in a RBF under $N_2$, until the reaction was complete as indicated by LCMS, the reaction mixture was filtered through a pad of Celite with EtOAc, and the combined organics were concentrated in vacuo, purified by silica gel chromatography (DCM/MeOH=20:1) to give the desired product 3-ethylimidazole-4-carbaldehyde (1.2 g, 9.67 mmol, 46.4% yield) as pale yellow oil. LCMS: $[M+H]^+$=125; Retention time ($NH_4HCO_3$)=0.90 min.

Step 2

A mixture of tetraisopropoxytitanium (703 mg, 2.48 mmol), 2-methylpropane-2-sulfinamide (300 mg, 2.48 mmol) and 3-ethylimidazole-4-carbaldehyde (307 mg, 2.48 mmol) in THF (20 mL) was stirred for 16 h at 10° C. in a round bottom flask (RBF) under $N_2$, until the reaction was complete as indicated by LCMS, the reaction mixture was filtered through a pad of Celite with EtOAc, and the combined organics were concentrated in vacuo, purified by silica gel chromatography (Hexanes:EtOAc=20:1) to give the desired product (NE)-N-[(3-ethylimidazol-4-yl)methylene]-2-methyl-propane-2-sulfinamide (100 mg, 0.440 mmol, 17.8% yield, 100% purity) as pale yellow solid. LCMS: $[M+H]^+$=228; Retention time ($NH_4HCO_3$)=1.15 min.

Step 3

A mixture of (NE)-N-[(3-ethylimidazol-4-yl)methylene]-2-methyl-propane-2-sulfinamide (2.0 g, 8.80 mmol), sodium borohydride (333 mg, 8.80 mmol) in MeOH (20 mL) was stirred for 16 h at 10° C. in a RBF under $N_2$, until the reaction was complete as indicated by LCMS, the reaction mixture was filtered through a pad of Celite with EtOAc, and the combined organics were concentrated in vacuum, purified by silica gel chromatography (Hexanes:EtOAc=20:1) to give the desired product N-[(3-ethylimidazol-4-yl)methyl]-2-methyl-propane-2-sulfinamide (0.9 g, 3.92 mmol, 44.6% yield, 100% purity) as pale yellow solid. LCMS: $[M+H]^+$=230; Retention time ($NH_4HCO_3$)=1.20 min.

Step 4

A mixture of N-[(3-ethylimidazol-4-yl)methyl]-2-methyl-propane-2-sulfinamide (101 mg, 0.440 mmol) hydrochloric acid (16 mg, 0.440 mmol) in Methanol (20 mL) was stirred for 1 h at 10° C. under $N_2$, until the reaction was complete as indicated by LCMS, the reaction mixture was filtered through a pad of Celite with EtOAc, and the combined organics were concentrated in vacuum to give the desired product (3-ethylimidazol-4-yl)methanamine (20 mg, 0.160 mmol, 36.3% yield) as pale yellow solid.

LCMS: $[M+H]^+$=126; Retention time (10 mM $NH_4HCO_3$)=0.70 min.

Step 5

A mixture of tert-butyl 3-fluoro-4-nitro-benzoate (100 mg, 0.415 mmol), (3-ethylimidazol-4-yl)methanamine (52 mg, 0.415 mmol) and N,N-diethylethanamine (126 mg, 1.24 mmol) in DMF (2 mL) was stirred for 12 h at 25° C. in a RBF under $N_2$, until the reaction was complete as indicated by LCMS, the reaction mixture was filtered through a pad of celite with EtOAc, and the combined organics were concentrated in vacuum, purified by silica gel chromatography (Hexanes/EtOAc=2:1) to give the desired product as pale yellow solid. LCMS: $[M+H]^+$=347.0; Retention time (10 mM $NH_4HCO_3$)=1.61 min.

Step 6

A mixture of tert-butyl 3-[(3-ethylimidazol-4-yl)methylamino]-4-nitro-benzoate (500 mg, 1.44 mmol) and Pa/C (154 mg) in Ethanol (10 mL) was stirred for 12 h at 25° C. under $N_2$, until the reaction was complete as indicated by LCMS, the reaction mixture was filtered through a pad of Celite with EtOAc, and the combined organics were concentrated in vacuum, purified by silica gel chromatography (Hexanes:EtOAc=20:1) to give the desired product tert-butyl 4-amino-3-[(3-ethylimidazol-4-yl)methylamino]benzoate (430 mg, 1.36 mmol, 94.2% yield) as pale yellow solid. LCMS: [M+H]⁺=347.0; Retention time (10 mM NH₄HCO₃)=1.60 min.

Step 7

A mixture of 2-chloro-1,1,1-trimethoxy-ethane (5.6 mg, 0.036 mmol), tert-butyl 4-amino-3-[(3-ethylimidazol-4-yl)methylamino]benzoate (12 mg, 0.036 mmol), in CH₃CN (10 mL) was stirred for 1 hr at 60° C. in a RBF under H₂, until the reaction was complete as indicated by LCMS, the reaction mixture was filtered through a pad of Celite with EtOAc, and the combined organics were concentrated in vacuum, purified by silica gel chromatography (Hexanes: EtOAc=2:1) to give the desired product tert-butyl 2-(chloromethyl)-3-[(3-ethylimidazol-4-yl)methyl]benzimidazole-5-carboxylate (10 mg, 0.021 mmol, 58.5% yield, 80% purity) as pale yellow solid. LCMS: [M+H]⁺=375; Retention time (0.01% TFA)=1.48 min.

Step 8

A mixture of tert-butyl 2-(chloromethyl)-3-[(3-ethylimidazol-4-yl)methyl]benzimidazole-5-carboxylate (120 mg, 0.320 mmol), 3-fluoro-4-[[6-(1,2,3,6-tetrahydropyridin-4-yl)-2-pyridyl]oxymethyl]benzonitrile (99 mg, 0.320 mmol), and N,N-diethylethanamine (32 mg, 0.320 mmol) in DMF (5 mL) was stirred for 2 h at 60° C. in a RBF under N₂, until the reaction was complete as indicated by LCMS, the reaction mixture was filtered through a pad of Celite with EtOAc, and the combined organics were concentrated in vacuum, purified by silica gel chromatography (Hexanes: EtOAc=1:1) to give the desired product tert-butyl 2-[[4-[6-[(4-cyano-2-fluoro-phenyl)methoxy]-2-pyridyl]-3,6-dihydro-2H-pyridin-1-yl]methyl]-3-[(3-ethylimidazol-4-yl)methyl]benzimidazole-5-carboxylate (60 mg, 0.093 mmol, 28.9% yield) as pale yellow solid. LCMS: [M+H]⁺=648; Retention time (0.01% TFA)=1.67 min.

Step 9

A mixture of tert-butyl 2-[[4-[6-[(4-cyano-2-fluoro-phenyl)methoxy]-2-pyridyl]-3,6-dihydro-2H-pyridin-1-yl]methyl]-3-[(3-ethylimidazol-4-yl)methyl]benzimidazole-5-carboxylate (50 mg, 0.077 mmol) and 2,2,2-trifluoroacetic acid (9 mg, 0.077 mmol) in DCM (5 mL) was stirred for 2 h at 30° C. in a RBF under N₂, until the reaction was complete as indicated by LCMS, the reaction mixture was concentrated in vacuum, purified by prep-HPLC to give the desired product 2-[[4-[6-[(4-cyano-2-fluoro-phenyl)methoxy]-2-pyridyl]-3,6-dihydro-2H-pyridin-1-yl]methyl]-3-[(3-ethylimidazol-4-yl)methyl]benzimidazole-5-carboxylic acid (20 mg, 0.033 mmol, 43.1% yield) as pale yellow solid.

LCMS: [M+H]⁺=592; Retention time (0.01% NH₄HCO₃)= 1.31 min.

¹H NMR (400 MHz, CDCl3) δ 8.68 (s, 1H), 8.05 (d, J=8.6 Hz, 1H), 7.75 (d, J=9.1 Hz, 2H), 7.61 (dd, J=14.8, 7.2 Hz, 2H), 7.51-7.41 (m, 1H), 7.38 (dd, J=9.3, 1.2 Hz, 1H), 7.09 (s, 1H), 6.99 (d, J=7.4 Hz, 1H), 6.80-6.67 (m, 2H), 5.60 (s, 2H), 5.53 (s, 2H), 4.11 (s, 2H), 3.78 (d, J=7.4 Hz, 2H), 3.33 (s, 2H), 2.93 (d, J=5.3 Hz, 2H), 2.66 (s, 2H), 1.23 (t, J=7.3 Hz, 3H).

2-((6-((4-cyano-2-fluorobenzyl)oxy)-3',6'-dihydro-[2,4'-bipyridin]-1'(2'H)-yl)methyl)-1-((1-ethyl-1H-imidazol-4-yl)methyl)-1H-benzo[d]imidazole-6-carboxylic acid (Compound 183)

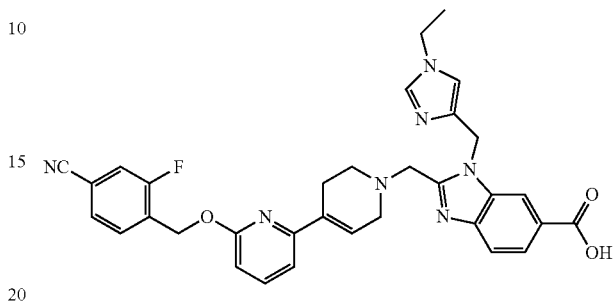

Compound 183

Prepared in analogous manner as for Compound 182

LCMS: [M+H]⁺=592; Retention time (0.01% TFA)=1.29 min.

¹H NMR (400 MHz, CDCl3) δ 8.05 (s, 2H), 7.71 (d, J=77.3 Hz, 4H), 7.41 (d, J=38.1 Hz, 2H), 6.97 (s, 2H), 6.69 (d, J=16.3 Hz, 2H), 5.69 (s, 2H), 5.53 (s, 2H), 3.96 (d, J=61.0 Hz, 4H), 3.33 (s, 2H), 2.85 (s, 2H), 2.52 (s, 2H), 1.24 (d, J=23.4 Hz, 3H).

(S)-2-((4-(3-((4-chloro-2-fluorobenzyl)oxy)-4-fluorophenyl)piperazin-1-yl)methyl)-1-(oxetan-2-ylmethyl)-1H-benzo[d]imidazole-6-carboxylic acid (Compound 184)

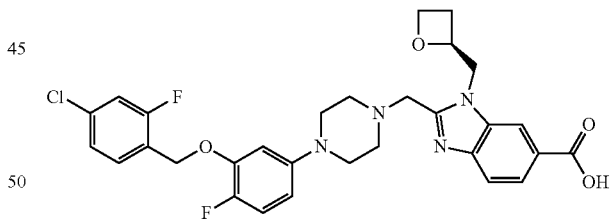

Compound 184

Prepared in analogous manner as for Compound 9

LCMS: [M+H]⁺=584.0; Retention time (10 mM NH₄HCO₃)=1.58 min.

¹H NMR (400 MHz, DMSO) δ 8.28 (s, 1H), 7.85-7.79 (m, 1.4 Hz, 1H), 7.69-7.64 (m, 1H), 7.63-7.56 (m, 1H), 7.54-7.48 (dd, J=10.0, 1.8 Hz, 1H), 7.38-7.33 (m, 1H), 7.09-7.00 (m, 1H), 6.88-6.82 (dd, J=7.5, 2.7 Hz, 1H), 6.50-6.44 (m, 1H), 5.22-5.16 (s, 2H), 5.15-5.06 (m, 1H), 4.84-4.76 (m, 1H), 4.70-4.62 (m, 1H), 4.53-4.45 (m, 1H), 4.42-4.34 (m, 1H), 4.05-3.78 (dd, J=70.5, 13.5 Hz, 2H), 3.14-3.04 (m, 4H), 2.75-2.56 (m, 5H), 2.48-2.38 (m, 1H).

(S)-2-((4-(3-((4-chloro-2-fluorobenzyl)oxy)-5-fluorophenyl)piperazin-1-yl)methyl)-1-(oxetan-2-ylmethyl)-1H-benzo[d]imidazole-6-carboxylic acid (Compound 185)

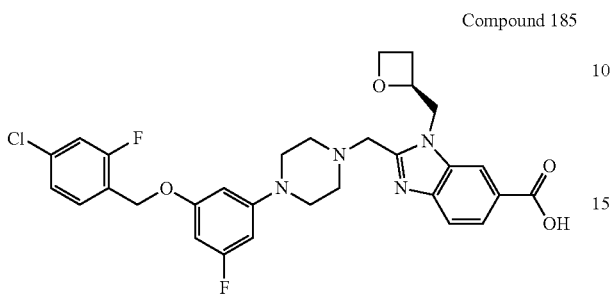

Compound 185

Prepared in analogous manner as for Compound 9

LCMS: [M+H]$^+$=583.2; Retention time (10 mM NH$_4$HCO$_3$)=1.37 min.

$^1$H NMR (400 MHz, CD$_3$OD) δ 8.33 (s, 1H), 7.99-7.95 (m, 1H), 7.68-7.66 (m, 1H), 7.53-7.49 (m, 1H), 7.25-7.21 (m, 2H), 6.37-6.32 (m, 2H), 6.25-6.20 (m, 1H), 5.33-5.25 (m, 1H), 5.08 (s, 2H), 4.76-4.72 (m, 1H), 4.68-4.61 (m, 1H), 4.51-4.43 (m, 1H), 4.01 (dd, J=13.8 Hz, 2H), 3.26-3.15 (m, 5H), 2.85-2.76 (m, 1H), 2.73-2.26 (m, 4H), 2.57-2.48 (m, 1H).

(S)-2-((4-(5-(4-chloro-2-fluorobenzyloxy)-2-fluorophenyl)piperazin-1-yl)methyl)-1-(oxetan-2-ylmethyl)-JH-benzo[d]imidazole-6-carboxylic acid (Compound 186)

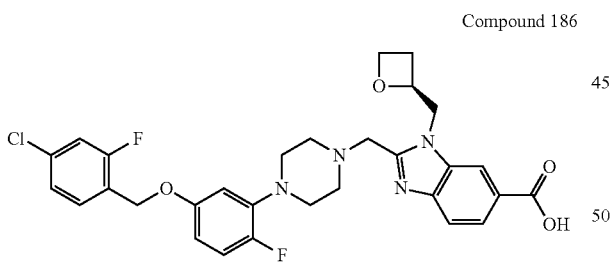

Compound 186

Prepared in analogous manner as for Compound 9

LCMS: [M+H]$^+$=583.2; Retention time (10 mM NH$_4$HCO$_3$)=1.47 min.

$^1$H NMR (400 MHz, DMSO) δ 8.27 (d, J=0.8 Hz, 1H), 7.81 (dd, J=1.2 Hz, 8.4 Hz, 1H), 7.65 (d, J=8.4 Hz, 1H), 7.58 (d, J=8.4 Hz, 1H), 7.49 (dd, J=1.6 Hz, 9.6 Hz, 1H), 7.33 (dd, J=1.6 Hz, 8.4 Hz, 1H), 7.02-7.08 (m, 1H), 6.58-6.62 (m, 2H), 5.08-5.11 (m, 3H), 4.79 (dd, J=7.2 Hz, 15.2 Hz, 1H), 4.63-4.68 (m, 1H), 4.47-4.52 (m, 1H), 4.36-4.41 (m, 1H), 3.99 (d, J=13.2 Hz, 1H), 3.83 (d, J=13.6 Hz, 1H), 3.01 (m, 4H), 2.59-2.720 (m, 5H), 2.38-2.47 (m, 1H).

(S)-2-((4-(3-(4-chloro-2-fluorobenzyloxy)-4,5-difluorophenyl)piperazin-1-yl)methyl)-1-(oxetan-2-ylmethyl)-1H-benzo[d]imidazole-6-carboxylic acid (Compound 187)

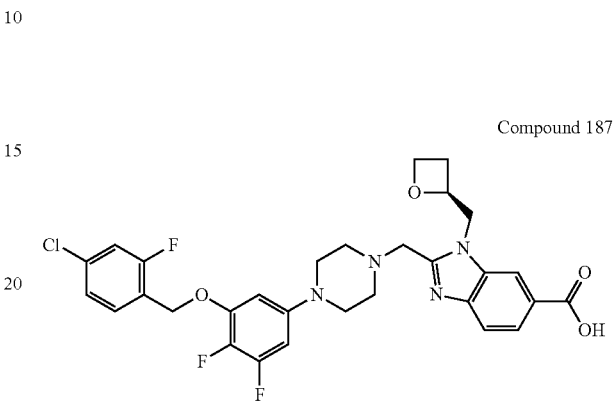

Compound 187

Prepared in analogous manner as for Compound 9

LCMS: [M+H]$^+$=601.1; Retention time (0.01% TFA)=1.59 min.

$^1$H NMR (400 MHz, DMSO) δ 8.27 (s, 1H), 7.81 (dd, J=1.2 Hz, 8.4 Hz, 1H), 7.58-7.65 (m, 2H), 7.50-7.53 (m, 1H), 7.35-7.38 (m, 1H), 7.66-7.67 (m, 1H), 6.52-6.57 (m, 1H), 5.22 (s, 2H), 5.07-5.12 (m, 1H), 4.76-4.82 (m, 1H), 4.65 (dd, J=2.8 Hz, 15.2 Hz, 1H), 4.46-4.52 (m, 1H), 4.36-4.41 (m, 1H), 3.80-4.01 (m, 2H), 3.13-3.16 (m, 4H), 2.56-2.72 (m, 5H), 2.40-2.47 (m, 1H)

(S)-2-((4-(5-((4-chloro-2-fluorobenzyl)oxy)-2,4-difluorophenyl)piperazin-1-yl)methyl)-1-(oxetan-2-ylmethyl)-JH-benzo[d]imidazole-6-carboxylic acid) (Compound 188)

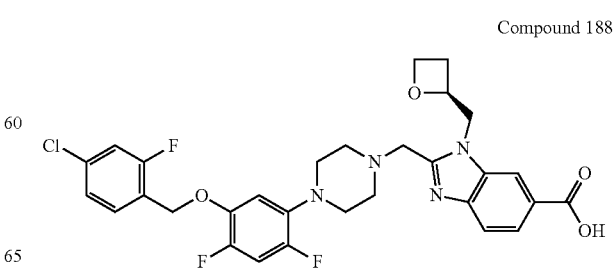

Compound 188

Prepared in analogous manner as for Compound 9

LCMS: [M+H]$^+$=601.0; Retention time (10 mM NH$_4$HCO$_3$)=1.59 min.

$^1$H NMR (400 MHz, MeOD) δ 8.34 (s, 1H), 7.99 (dd, J=8.5, 1.4 Hz, 1H), 7.68 (d, J=8.5 Hz, 1H), 7.52 (t, J=8.2 Hz, 1H), 7.27 (dd, J=7.0, 4.7 Hz, 2H), 7.00-6.94 (m, 1H), 6.82 (t, J=8.4 Hz, 1H), 5.29 (dd, J=9.6, 4.6 Hz, 1H), 5.16 (s, 2H), 4.92 (d, J=9.1 Hz, 2H), 4.75 (dd, J=15.3, 2.6 Hz, 1H), 4.66 (dd, J=13.8, 7.9 Hz, 1H), 4.49 (dt, J=9.0, 5.9 Hz, 1H), 4.08 (d, J=13.7 Hz, 1H), 3.97 (d, J=13.7 Hz, 1H), 3.06 (s, 4H), 2.86-2.80 (m, 1H), 2.72 (d, J=4.6 Hz, 4H), 2.57-2.52 (m, 1H)

(S)-1-(oxetan-2-ylmethyl)-2-((4-(3-((4-(trifluoromethyl)benzyl)oxy)phenyl)piperazin-1-yl)methyl)-1H-benzo[d]imidazole-6-carboxylic acid (Compound 189)

Compound 189

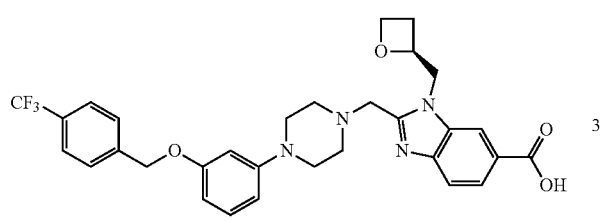

Prepared in analogous manner as for Compound 9 LCMS: [M+H]$^+$=581.1; Retention time (10 mM NH$_4$HCO$_3$)=1.59 min.

$^1$H NMR (400 MHz, DMSO) δ 8.27 (s, 1H), 7.84-7.80 (m, 1H), 7.78-7.74 (m, 2H), 7.70-7.62 (m, 3H), 7.15-7.08 (m, 1H), 6.58-6.52 (m, 2H), 6.47-6.42 (m, 1H), 5.19 (s, 2H), 5.14-5.08 (m, 1H), 4.83-4.75 (m, 1H), 4.68-4.62 (m, 1H), 4.52-4.45 (m, 1H), 4.41-4.35 (m, 1H), 4.01-3.79 (dd, J=70.7, 13.5 Hz, 2H), 3.16-3.11 (m, 4H), 2.73-2.67 (m, 1H), 2.66-2.55 (m, 4H), 2.46-2.40 (m, 1H).

(S)-2-((4-(3-((4-(cyclopropylethynyl)-2-fluorobenzyl)oxy)phenyl)piperazin-1-yl)methyl)-1-(oxetan-2-ylmethyl)-1H-benzo[d]imidazole-6-carboxylic acid (Compound 190)

Prepared in analogous manner as for Compound 9 LCMS: [M+H]$^+$=595.3; Retention time (10 mM NH$_4$HCO$_3$)=1.65 min.

$^1$H NMR (400 MHz, CD3OD) δ 8.34 (s, 1H), 7.99 (dd, J=8.5, 1.4 Hz, 1H), 7.68 (d, J=8.5 Hz, 1H), 7.43 (t, J=7.8 Hz, 1H), 7.18-7.06 (m, 3H), 6.63-6.56 (m, 2H), 6.50 (dd, J=8.1, 1.9 Hz, 1H), 5.28 (dt, J=7.0, 4.6 Hz, 1H), 5.08 (brs, 2H), 4.87-4.83 (m, 1H), 4.74 (dd, J=15.3, 2.5 Hz, 1H), 4.69-4.63 (m, 1H), 4.48 (m, J=9.1, 5.9 Hz, 1H), 4.07 (d, J=13.7 Hz, 1H), 3.96 (d, J=13.6 Hz, 1H), 3.20 (t, J=4.7 Hz, 4H), 2.81 (m, J=16.1, 12.8, 8.2 Hz, 1H), 2.74-2.66 (m, 4H), 2.59-2.48 (m, 1H), 1.53-1.43 (m, 1H), 0.94-0.88 (m, 2H), 0.79-0.72 (m, 2H).

(S)-2-((4-(3-((4-cyano-2-fluorobenzyl)oxy)phenyl)piperidin-1-yl)methyl)-1-(oxetan-2-ylmethyl)-1H-benzo[d]imidazole-6-carboxylic acid (Compound 191)

Compound 191

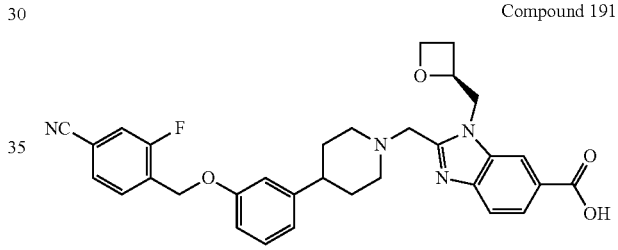

Prepared in analogous manner as for Compound 239 LCMS: [M+H]$^+$=577.2; Retention time (10 mM NH$_4$HCO$_3$)= 1.33 min.

$^1$H NMR (400 MHz, DMSO-d6) δ 8.17 (s, 1H), 7.93-7.90 (d, J=10.0 z, 1H), 7.79-7.75 (m, 3H), 7.55-7.53 (d, J=8.0 Hz, 1H), 7.24-7.20 (m, 1H), 6.91-6.84 (m, 3H), 5.21 (s, 2H), 5.01 (m, 1H), 4.76-4.36 (m, 4H), 3.94-3.76 (m, 2H), 2.38-2.4 (m, 2H), 2.44 (m, 1H), 2.21-2.15 (m, 2H), 1.74-1.56 (m, 4H), 0.86-0.83 (m, 2H).

Compound 190

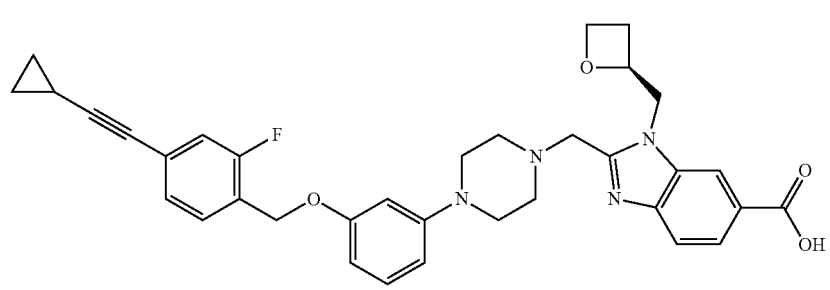

(S)-2-((4-(3-((4-(cyclopropylethynyl)-2-fluorobenzyl)oxy)phenyl)piperidin-1-yl)methyl)-1-(oxetan-2-ylmethyl)-1H-benzo[d]imidazole-6-carboxylic acid (Compound 192)

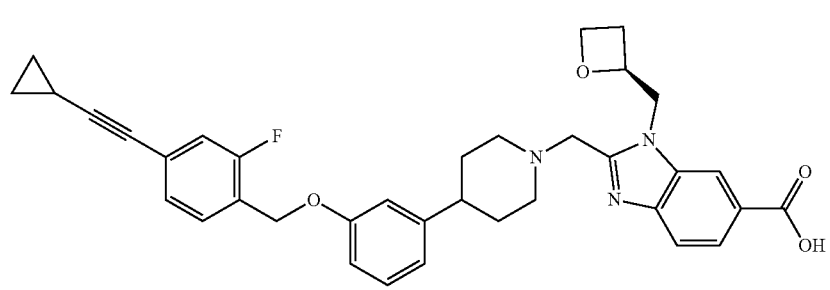

Compound 192

Prepared in analogous manner as for Compound 28 LCMS: [M+H]$^+$=594.0; Retention time (10 mM NH$_4$HCO$_3$)=1.71 min.

$^1$H NMR (400 MHz, DMSO) δ 8.26 (s, 1H), 7.80 (dd, J=8.4, 1.4 Hz, 1H), 7.63 (d, J=8.4 Hz, 1H), 7.49 (t, J=7.9 Hz, 1H), 7.28-7.19 (m, 3H), 6.89-6.82 (m, 3H), 5.10 (s, 3H), 4.81 (dd, J=15.1, 7.1 Hz, 1H), 4.66 (d, J=12.6 Hz, 1H), 4.50 (dd, J=13.5, 7.7 Hz, 1H), 4.38 (dt, J=9.0, 5.9 Hz, 1H), 3.95 (d, J=13.5 Hz, 1H), 3.79 (d, J=13.5 Hz, 1H), 3.00 (d, J=10.8 Hz, 1H), 2.87 (d, J=10.8 Hz, 1H), 2.71 (dd, J=15.3, 9.4 Hz, 1H), 2.45 (d, J=9.2 Hz, 2H), 2.25-2.16 (m, 2H), 1.77-1.54 (m, 6H), 0.89 (dd, J=15.1, 9.4, 5.7 Hz, 2H), 0.78-0.73 (m, 2H).

(S)-2-((4-(3-(4-cyano-2-fluorobenzyloxy)phenyl)piperazin-1-yl)methyl)-1-(oxetan-2-ylmethyl)-1H-benzo[d]imidazole-6-carboxylic acid (Compound 193)

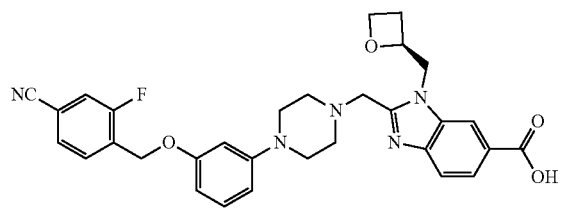

Compound 193

Prepared in analogous manner as for Compound 9 LCMS: [M+H]$^+$=556.0; Retention time (10 mM NH$_4$HCO$_3$)=1.44 min.

$^1$H NMR (400 MHz, CDCL3) δ 8.23 (s, 1H), 8.08-8.06 (t, J=8.8 Hz, 1H), 7.85-7.83 (d, J=8.4 Hz, 1H), 7.69-7.65 (t, J=7.2 Hz, 1H), 7.48-7.45 (dd, J1=8.0 Hz, J2=0.8 Hz, 1H), 7.38-7.35 (dd, J1=9.6 Hz, J2=1.6 Hz, 1H), 7.18-7.14 (d, J=8.0 Hz, 1H), 6.58-6.55 (dd, J1=8.0 Hz, J2=1.6 Hz, 1H), 6.52-6.51 (t, J=2.0 Hz, 1H), 6.45-6.42 (dd, J1=8.4 Hz, J2=2.0 Hz, 1H), 5.25-5.21 (m, 1H), 5.14 (s, 2H), 4.77-4.60 (m, 3H), 4.42-4.37 (m, 1H), 4.11-4.04 (m, 2H), 3.20 (s, 4H), 2.77-2.69 (t, J=14.0 Hz, 5H), 2.48-2.43 (m, 1H).

(S)-2-((4-(2-((4-(cyclopropylethynyl)-2-fluorobenzyl)oxy)pyrimidin-4-yl)piperazin-1-yl)methyl)-1-(oxetan-2-ylmethyl)-1H-benzo[d]imidazole-6-carboxylic acid (Compound 194)

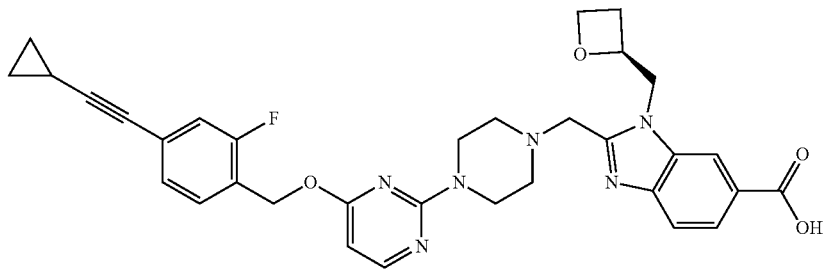

Compound 194

Prepared in analogous manner as for Compound 33

LCMS: [M+H]⁺=597.0; Retention time (10 mM NH₄HCO₃)=1.51 min.

¹H NMR (400 MHz, DMSO) δ 8.24 (s, 1H), 8.01 (d, J=6 Hz, 1H), 7.80 (dd, J=1.6 Hz, J=8.4 Hz, 1H), 7.61 (d, J=8.4 Hz, 1H), 7.43 (t, J=7.6 Hz, 1H), 7.24-7.18 (m, 2H), 6.49 (d, J=6.4 Hz, 1H), 5.29 (s, 1H), 5.10-5.08 (m, 1H), 4.80-4.75 (m, 1H), 4.64 (dd, J=2.4 Hz, J=15.2 Hz, 1H), 4.51-4.45 (m, 1H), 4.39-4.34 (m, 1H), 3.95 (d, J=13.2 Hz, 1H), 3.80 (d, J=13.6 Hz, 1H), 3.58 (s, 4H), 2.73-2.66 (m, 1H), 2.55-2.50 (m, 2H), 2.49-2.39 (m, 2H), 1.57-1.51 (m, 1H), 0.92-0.87 (m, 2H), 0.76-0.72 (m, 2H).

(S)-2-((4-(3-((4-cyano-2-fluorobenzyl)oxy)-4-fluorophenyl)piperazin-1-yl)methyl)-1-(oxetan-2-ylmethyl)-1H-benzo[d]imidazole-6-carboxylic acid (Compound 195)

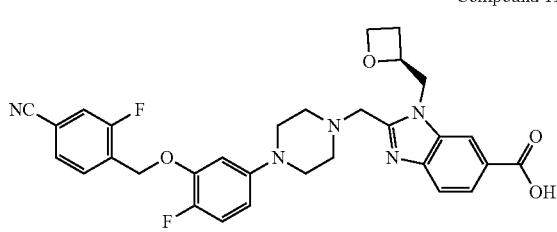

Compound 195

Prepared in analogous manner as for Compound 9

LCMS: [M+H]⁺=574.3; Retention time (10 mM NH₄HCO₃)=1.47 min.

¹H NMR (400 MHz, DMSO) δ 8.27 (s, 1H), 7.93 (d, J=10.3 Hz, 1H), 7.85-7.74 (m, 3H), 7.64 (d, J=8.4 Hz, 1H), 7.06 (dd, J=11.1, 9.0 Hz, 1H), 6.85 (dd, J=7.5, 2.6 Hz, 1H), 6.47 (dt, J=8.9, 3.2 Hz, 1H), 5.29 (brs, 2H), 5.10 (dd, J=9.6, 4.8 Hz, 1H), 4.79 (dd, J=15.3, 7.2 Hz, 1H), 4.65 (dd, J=15.2, 2.6 Hz, 1H), 4.48 (dd, J=13.7, 7.7 Hz, 1H), 4.38 (dt, J=9.0, 5.9 Hz, 1H), 3.99 (d, J=13.5 Hz, 1H), 3.82 (d, J=13.5 Hz, 1H), 3.09 (brs, 4H), 2.70 (m, J=11.8, 5.8 Hz, 1H), 2.60 (m, J=11.4, 5.3 Hz, 4H), 2.41 (m, J=19.1, 8.2 Hz, 1H).

(S)-2-((4-(3-((4-(cyclopropylethynyl)-2-fluorobenzyl)oxy)-4-fluorophenyl)piperazin-1-yl)methyl)-1-(oxetan-2-ylmethyl)-1H-benzo[d]imidazole-6-carboxylic acid (Compound 196)

Prepared in analogous manner as for Compound 9

LCMS: [M+H]⁺=613.4; Retention time (10 mM NH₄HCO₃)=1.63 min.

¹H NMR (400 MHz, CD3OD) δ 8.23 (s, 1H), 7.97 (d, J=8.4 Hz, 1H), 7.62 (d, J=8.4 Hz, 1H), 7.44 (t, J=7.8 Hz, 1H), 7.17 (d, J=7.9 Hz, 1H), 7.10 (d, J=10.7 Hz, 1H), 6.98 (dd, J=11.0, 9.0 Hz, 1H), 6.74 (dd, J=7.3, 2.7 Hz, 1H), 6.58-6.51 (m, 1H), 5.29 (d, J=4.5 Hz, 1H), 5.16 (brs, 2H), 4.87 (s, 1H), 4.73 (dd, J=15.2, 2.7 Hz, 1H), 4.68-4.64 (m, 1H), 4.48 (dt, J=9.3, 6.0 Hz, 1H), 4.06 (d, J=13.6 Hz, 1H), 3.96 (d, J=13.6 Hz, 1H), 3.13 (d, J=4.5 Hz, 4H), 2.83-2.78 (m, 1H), 2.71 (brs, 4H), 2.56 (dd, J=18.2, 9.3 Hz, 1H), 1.52-1.43 (m, 1H), 0.91 (m, J=6.7, 4.0 Hz, 2H), 0.80-0.72 (m, 2H).

(S)-2-((4-(5-((4-cyano-2-fluorobenzyl)oxy)-2-fluorophenyl)piperazin-1-yl)methyl)-1-(oxetan-2-ylmethyl)-1H-benzo[d]imidazole-6-carboxylic acid (Compound 197)

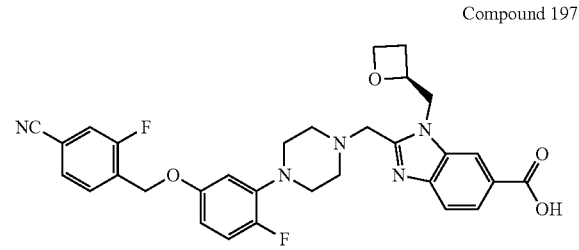 [SMILES: N#Cc1ccc(COc2ccc(F)c(N3CCN(Cc4nc5ccc(C(=O)O)cc5n4C[C@@H]4CCO4)CC3)c2)c(F)c1]

Compound 197

Prepared in analogous manner as for Compound 9

LCMS: [M+H]⁺=574.0; Retention time (10 mM NH₄HCO₃)=1.48 min.

¹H NMR (400 MHz, MeOD) δ 8.21-8.20 (brs, 1H), 7.95 (d, J=8.5 Hz, 1H), 7.73 (t, J=7.5 Hz, 1H), 7.60 (d, J=10.6 Hz, 3H), 6.95 (dd, J=12.3, 8.9 Hz, 1H), 6.66 (dd, J=7.2, 2.6 Hz, 1H), 6.57 (dd, J=8.8, 3.0 Hz, 1H), 5.27 (d, J=7.0 Hz, 1H), 5.17 (s, 2H), 4.85-4.84 (brs, 1H), 4.72 (dd, J=15.2, 2.4 Hz, 1H), 4.63 (dd, J=13.9, 7.6 Hz, 1H), 4.46 (dt, J=8.9, 5.9 Hz, 1H), 4.05 (d, J=13.6 Hz, 1H), 3.96 (d, J=13.6 Hz, 1H), 3.10-3.09 (brs, 4H), 2.82-2.77 (m, 1H), 2.72 (d, J=21.8 Hz, 4H), 2.57-2.47 (m, 1H).

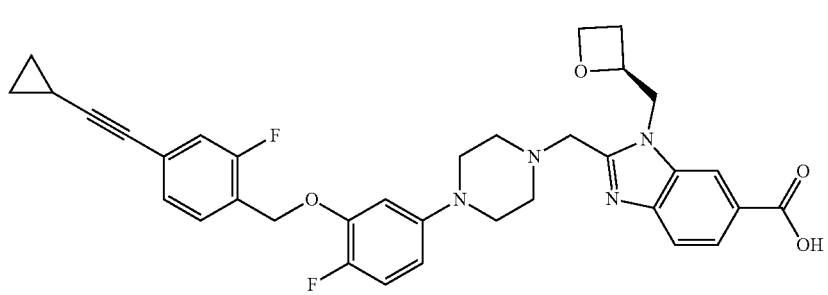

Compound 196

(S)-2-((4-(5-((4-(cyclopropylethynyl)-2-fluorobenzyl)oxy)-2-fluorophenyl)piperazin-1-yl)methyl)-1-(oxetan-2-ylmethyl)-1H-benzo[d]imidazole-6-carboxylic acid (Compound 198)

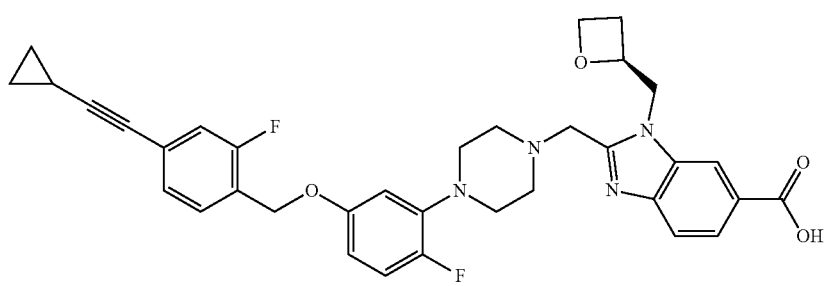

Compound 198

Prepared in analogous manner as for Compound 9

LCMS: [M+H]$^+$=613.0; Retention time (10 mM NH$_4$HCO$_3$)=1.69 min.

$^1$H NMR (400 MHz, DMSO) δ 8.28-8.27 (brs, 1H), 7.80 (dd, J=8.5, 1.5 Hz, 1H), 7.65 (d, J=8.4 Hz, 1H), 7.48 (t, J=7.8 Hz, 1H), 7.28-7.16 (m, 2H), 7.04 (dd, J=12.5, 8.6 Hz, 1H), 6.64-6.51 (m, 2H), 5.13-5.00 (m, 3H), 4.79 (dd, J=15.2, 7.2 Hz, 1H), 4.68-4.59 (m, 1H), 4.51-4.43 (m, 1H), 4.38 (dt, J=9.0, 5.9 Hz, 1H), 3.99 (d, J=13.6 Hz, 1H), 3.82 (d, J=13.4 Hz, 1H), 3.00-2.99 (brs, 4H), 2.76-2.54 (m, 5H), 2.43-2.37 (m, 1H), 1.56 (dd, J=9.3, 4.1 Hz, 1H), 0.89 (dd, J=12.8, 8.3, 4.6 Hz, 2H), 0.77-0.70 (m, 2H).

(S)-2-((4-(3-((4-(cyclopropylethynyl)-2-fluorobenzyl)oxy)phenyl)-3,6-dihydropyridin-1(2H)-yl)methyl)-1-(oxetan-2-ylmethyl)-1H-benzo[d]imidazole-6-carboxylicacid (Compound 199)

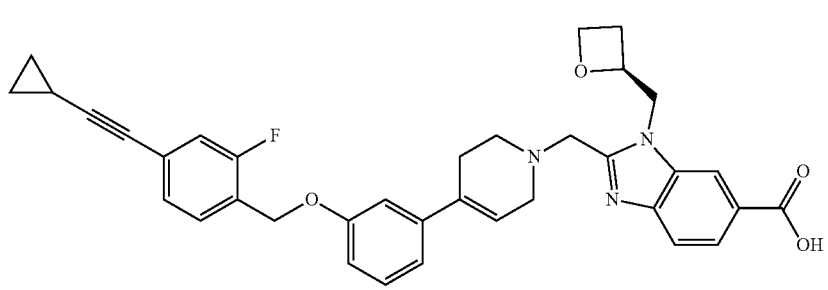

Compound 199

Prepared in analogous manner as for Compound 28

LCMS: [M+H]$^+$=592.3; Retention time (10 mM NH$_4$HCO$_3$)=1.47 min.

$^1$H NMR (400 MHz, CD$_3$OD) δ 8.31 (s, 1H), 8.01 (d, J=8.4 Hz, 1H), 7.68 (d, J=8.4 Hz, 1H), 7.45-7.42 (m, 1H), 7.26-7.22 (m, 1H), 7.17-7.15 (m, 1H), 7.11-7.08 (m, 1H), 7.06-7.03 (m, 2H), 6.90-6.87 (m, 1H), 6.12 (s, 1H), 5.27-5.23 (m, 1H), 5.12 (s, 2H), 4.76-4.73 (m, 1H), 4.66-4.60 (m, 1H), 4.50-4.44 (m, 1H), 4.12 (dd, J=13.6 Hz, 2H), 3.32-3.25 (m, 3H), 2.87-2.84 (m, 2H), 2.78-2.75 (m, 1H), 2.55-2.53 (m, 2H), 2.51-2.47 (m, 1H), 1.50-1.44 (m, 1H), 0.93-0.88 (m, 2H), 0.78-0.74 (m, 2H).

(S)-2-((4-(4-((4-(cyclopropylethynyl)-2-fluorobenzyl)oxy)pyrimidin-2-yl)-3,6-dihydropyridin-1(2H)-yl)methyl)-1-(oxetan-2-ylmethyl)-1H-benzo[d]imidazole-6-carboxylic acid (Compound 200)

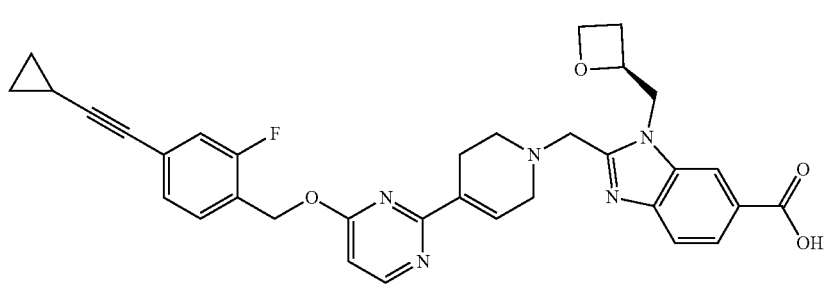

Compound 200

Prepared in analogous manner as for Compound 33

LCMS: [M+H]$^+$=594.3; Retention time (10 mM NH$_4$HCO$_3$)=1.40 min.

$^1$H NMR (400 MHz, CD$_3$OD) δ 8.42-8.40 (m, 1H), 8.34 (s, 1H), 8.01-7.99 (m, 1H), 7.71-7.69 (m, 1H), 7.44-7.40 (m, 1H), 7.20-7.17 (m, 1H), 7.15-7.08 (m, 2H), 6.73-6.70 (m, 1H), 5.51 (s, 2H), 5.27-5.23 (m, 1H), 4.87-4.85 (m, 1H), 4.76-4.73 (m, 1H), 4.66-4.60 (m, 1H), 4.50-4.45 (m, 1H), 4.12 (dd, J=13.6 Hz, 2H), 3.41-3.34 (m, 2H), 2.87-2.83 (m, 2H), 2.84-2.81 (m, 1H), 2.75-2.69 (m, 2H), 2.54-2.50 (m, 1H), 1.49-1.44 (m, 1H), 0.93-0.88 (m, 2H), 0.77-0.75 (m, 2H).

(S)-2-((4-(2-((4-(cyclopropylethynyl)-2-fluorobenzyl)oxy)pyrimidin-4-yl)-3,6-dihydropyridin-1(2H)-yl)methyl)-1-(oxetan-2-ylmethyl)-1H-benzo[d]imidazole-6-carboxylic acid (Compound 201)

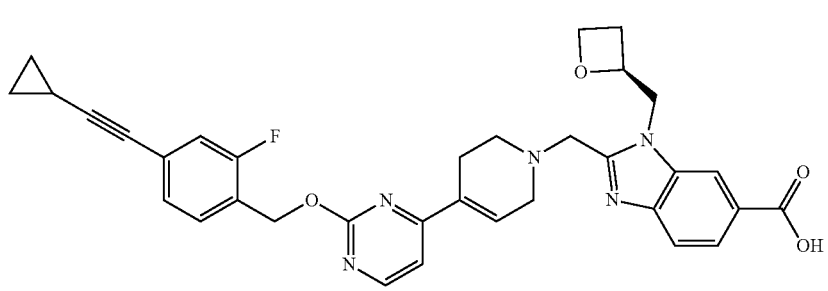

Compound 201

Prepared in analogous manner as for Compound 18

LCMS: [M+H]$^+$=594.3; Retention time (10 mM NH$_4$HCO$_3$)=1.36 min.

$^1$H NMR (400 MHz, CD$_3$OD) δ 8.48-8.46 (m, 1H), 8.31 (s, 1H), 8.00-7.98 (m, 1H), 7.69-7.67 (m, 1H), 7.47-7.43 (m, 1H), 7.22-7.19 (m, 1H), 7.16-7.08 (m, 2H), 7.05-7.02 (m, 1H), 5.49 (s, 2H), 5.26-5.23 (m, 1H), 4.87-4.85 (m, 1H), 4.74-4.70 (m, 1H), 4.65-4.60 (m, 1H), 4.49-4.44 (m, 1H), 4.12 (dd, J=13.6 Hz, 2H), 3.40-3.35 (m, 2H), 2.87-2.84 (m, 2H), 2.78-2.75 (m, 1H), 2.67-2.63 (m, 2H), 2.54-2.49 (m, 1H), 1.48-1.44 (m, 1H), 0.93-0.88 (m, 2H), 0.78-0.73 (m, 2H).

(S)-2-((4-(3-((4-(cyclopropylethynyl)-2-fluorobenzyl)oxy)-4-fluorophenyl)-3,6-dihydropyridin-1(2H)-yl)methyl)-1-(oxetan-2-ylmethyl)-1H-benzo[d]imidazole-6-carboxylic acid (Compound 202)

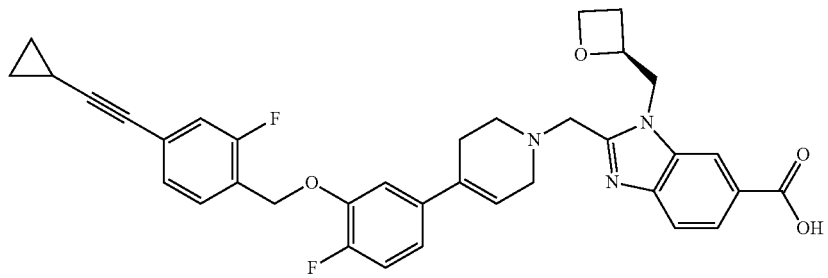

Compound 202

Prepared in analogous manner as for Compound 28

LCMS: [M+H]$^+$=610.0; Retention time (10 mM NH$_4$HCO$_3$)=1.69 min.

$^1$H NMR (400 MHz, DMSO) δ 8.19 (s, 1H), 7.90-7.70 (m, 1H), 7.68-7.55 (m, 1H), 7.50-7.40 (m, 1H), 7.33-7.21 (m, 3H), 7.19-7.10 (m, 1H), 7.08-7.00 (m, 1H), 6.19-6.12 (m, 1H), 5.24 (s, 2H), 5.12-5.05 (m, 1H), 4.81-4.74 (m, 1H), 4.65-4.60 (m, 1H), 4.50-4.45 (m, 1H), 4.39-4.33 (m, 1H), 4.06-3.88 (dd, J=58.7, 13.4 Hz, 2H), 3.20-3.15 (m, 2H), 2.79-2.61 (m, 4H), 2.38-2.30 (m, 2H), 1.59-1.50 (m, 1H), 0.95-0.89 (m, 2H), 0.79-0.71 (m, 2H).

(S)-2-((4-(3-(4-(cyclopropylethynyl)-2-fluorobenzyloxy)-4,5-difluorophenyl)-5,6-dihydropyridin-1(2H)-yl)methyl)-1-(oxetan-2-ylmethyl)-1H-benzo[d]imidazole-6-carboxylic acid (Compound 203)

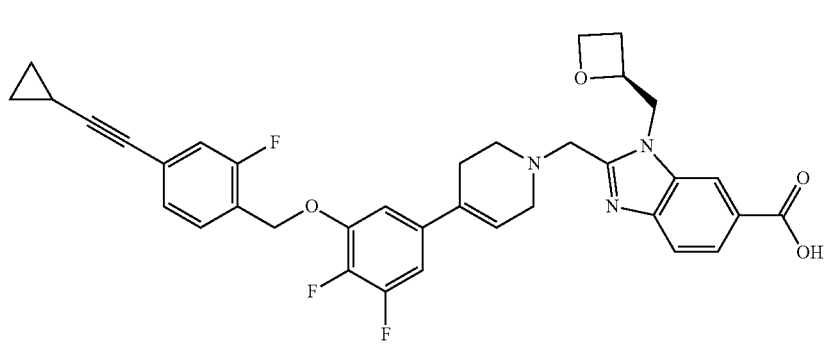

Compound 203

Prepared in analogous manner as for Compound 28

LCMS: [M+H]$^+$=628.2; Retention time (10 mM NH$_4$HCO$_3$)=1.57 min.

$^1$H NMR (400 MHz, DMSO) δ 8.26 (s, 1H), 7.80-7.83 (m, 1H), 7.64 (d, J=8.4 Hz, 1H), 7.51 (t, J=7.6 Hz, 1H), 7.23-7.29 (m, 2H), 7.17 (d, J=6.8 Hz, 1H), 7.07-7.12 (m, 1H), 6.25 (s, 1H), 5.28 (s, 2H), 5.04-5.10 (m, 1H), 4.71-4.82 (m, 1H), 4.63-4.67 (m, 1H), 4.45-4.50 (m, 1H), 4.34-4.39 (m, 1H), 3.90-4.08 (m, 2H), 3.13-3.20 (m, 2H), 2.65-2.75 (m, 3H), 2.37-2.46 (m, 3H), 1.53-1.58 (m, 1H), 0.88-0.93 (m, 2H), 0.74-0.77 (m, 2H).

(S)-2-((4-(3-((4-cyano-2-fluorobenzyl)oxy)-4-fluorophenyl)-3,6-dihydropyridin-1(2H)-yl)methyl)-1-(oxetan-2-ylmethyl)-1H-benzo[d]imidazole-6-carboxylic acid (Compound 204)

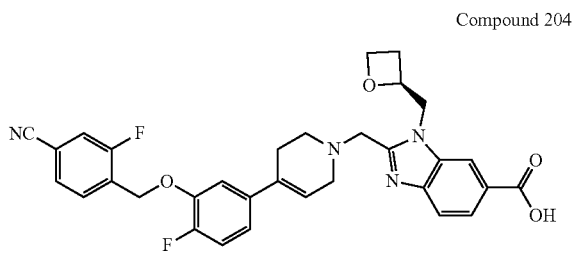 [SMILES: N#Cc1ccc(COc2cc(C3=CCN(Cc4nc5ccc(C(=O)O)cc5n4C[C@@H]4CCO4)CC3)ccc2F)c(F)c1]

Compound 204

Prepared in analogous manner as for Compound 28

LCMS: [M+H]⁺=571.0; Retention time (10 mM NH₄HCO₃)=1.50 min.

$^1$H NMR (400 MHz, DMSO) δ 8.26 (s, 1H), 7.95-7.93 (d, J=9.8 Hz, 1H), 7.86-7.74 (m, 3H), 7.66-7.64 (d, J=8.2 Hz, 1H), 7.35-7.33 (m, 1H), 7.23-7.15 (m, 1H), 7.05-7.04 (m, 1H), 6.19-6.16 (m, 1H), 5.36 (s, 2H), 5.08-5.06 (m, 1H), 4.85-4.75 (m, 1H), 4.67-4.64 (m, 1H), 4.50-4.43 (m, 1H), 4.37-4.35 (m, 1H), 4.08-3.89 (dd, J=59.2, 13.3 Hz, 2H), 3.19-3.13 (m, 4H), 2.76-2.72 (m, 2H), 2.70-2.62 (m, 2H).

(S)-2-((4-(3-(4-cyano-2-fluorobenzyloxy)-4,5-difluorophenyl)-5,6-dihydropyridin-1(2H)-yl)methyl)-1-(oxetan-2-ylmethyl)-1H-benzo[d]imidazole-6-carboxylic acid (Compound 205)

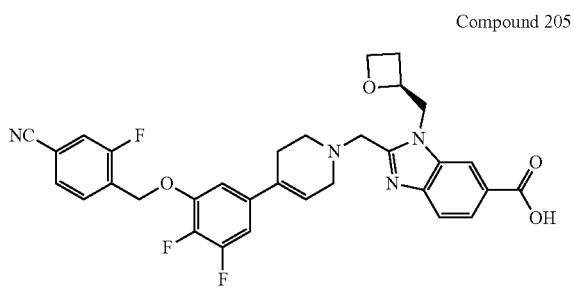 [SMILES: N#Cc1ccc(COc2cc(C3=CCN(Cc4nc5ccc(C(=O)O)cc5n4C[C@@H]4CCO4)CC3)cc(F)c2F)c(F)c1]

Compound 205

Prepared in analogous manner as for Compound 28

LCMS: [M+H]⁺=589.2; Retention time (10 mM NH₄HCO₃)=1.44 min.

$^1$H NMR (400 MHz, MeOD) δ 8.34 (s, 1H), 7.99 (dd, J=1.2 Hz, 8.4 Hz, 1H), 7.78 (t, J=7.6 Hz, 1H), 7.63-7.71 (m, 3H), 7.06-7.08 (m, 1H), 6.97-7.02 (m, 1H), 6.16 (s, 1H), 5.35 (s, 2H), 5.24-5.26 (m, 1H), 4.71-4.75 (m, 1H), 4.61-4.67 (m, 2H), 4.46-4.48 (m, 1H), 4.03-4.18 (m, 2H), 3.15-3.26 (m, 2H), 2.76-2.87 (m, 3H), 2.49-2.54 (m, 3H).

(S)-2-((4-(5-((4-cyano-2-fluorobenzyl)oxy)-2-fluorophenyl)-3,6-dihydropyridin-1(2H)-yl)methyl)-1-(oxetan-2-ylmethyl)-1H-benzo[d]imidazole-6-carboxylic acid (Compound 206)

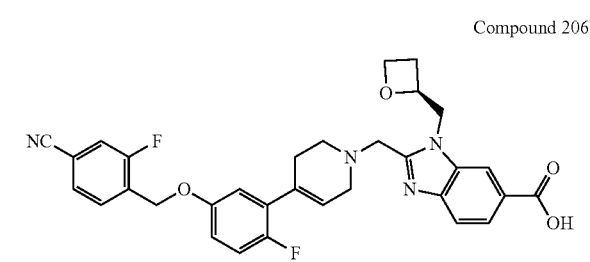 [SMILES: N#Cc1ccc(COc2ccc(F)c(C3=CCN(Cc4nc5ccc(C(=O)O)cc5n4C[C@@H]4CCO4)CC3)c2)c(F)c1]

Compound 206

Prepared in analogous manner as for Compound 28

LCMS: [M+H]⁺=571.2; Retention time (10 mM NH₄HCO₃)=1.41 min.

(S)-2-((4-(4-((4-cyano-2-fluorobenzyl)oxy)-5-fluoropyrimidin-2-yl)-5,6-dihydropyridin-1(2H)-yl)methyl)-1-(oxetan-2-ylmethyl)-1H-benzo[d]imidazole-6-carboxylic acid (Compound 207)

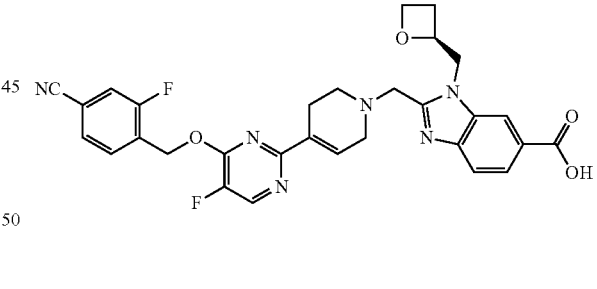

Compound 207

Prepared in analogous manner as for Compound 33

LCMS: [M+H]⁺=573.3; Retention time (10 mM NH₄HCO₃)=1.24 min.

$^1$H NMR (400 MHz, DMSO) δ 8.61 (d, J=2.8 Hz, 1H), 8.24 (brs, 1H), 7.92-7.95 (m, 1H), 7.73-7.82 (m, 3H), 7.63 (d, J=8.8 Hz, 1H), 7.05 (brs, 1H), 5.65 (s, 2H), 5.04-5.06 (m, 1H), 4.75-4.81 (m, 1H), 4.61-4.65 (m, 1H), 4.34-4.47 (m, 2H), 4.07 (d, J=13.6 Hz, 1H), 3.92 (d, J=13.6 Hz, 1H), 3.25-3.28 (m, 2H), 2.62-2.72 (m, 3H), 2.50-2.52 (m, 2H), 2.39-2.41 (m, 1H).

(S)-2-((4-(5-((4-(cyclopropylethynyl)-2-fluorobenzyl)oxy)-2-fluorophenyl)-3,6-dihydropyridin-1(2H)-yl)methyl)-1-(oxetan-2-ylmethyl)-1H-benzo[d]imidazole-6-carboxylic acid (Compound 208)

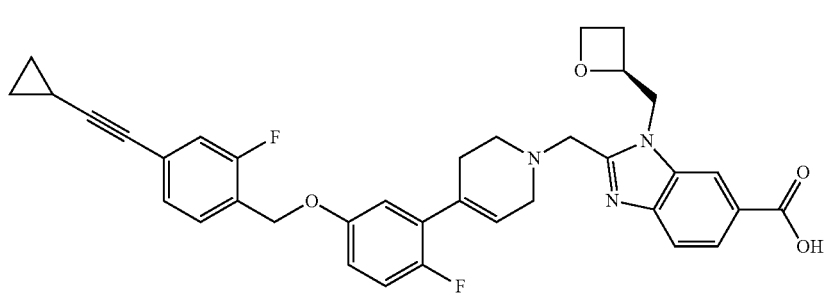

Compound 208

Prepared in analogous manner as for Compound 28

LCMS: [M+H]$^+$=569.0; Retention time (10 mM NH$_4$HCO$_3$)=1.59 min.

$^1$H NMR (400 MHz, CD$_3$OD) δ 8.31 (s, 1H), 8.00-7.97 (m, 1H), 7.69-7.67 (m, 1H), 7.64-7.62 (m, 1H), 7.31-7.29 (m, 1H), 7.15-7.10 (m, 1H), 6.67 (s, 1H), 6.55-6.52 (m, 1H), 5.54 (s, 2H), 5.28-5.22 (m, 1H), 4.88-4.86 (m, 1H), 4.74-4.70 (m, 1H), 4.66-4.60 (m, 1H), 4.50-4.45 (m, 1H), 4.12 (dd, J=13.6 Hz, 2H), 3.28-3.22 (m, 2H), 2.84-2.79 (m, 2H), 2.77-2.73 (m, 1H), 2.56-2.48 (m, 3H).

(S)-2-((4-(4-((4-(cyclopropylethynyl)-2-fluorobenzyl)oxy)-5-fluoropyrimidin-2-yl)-3,6-dihydropyridin-1(2H)-yl)methyl)-1-(oxetan-2-ylmethyl)-1H-benzo[d]imidazole-6-carboxylic acid (Compound 209)

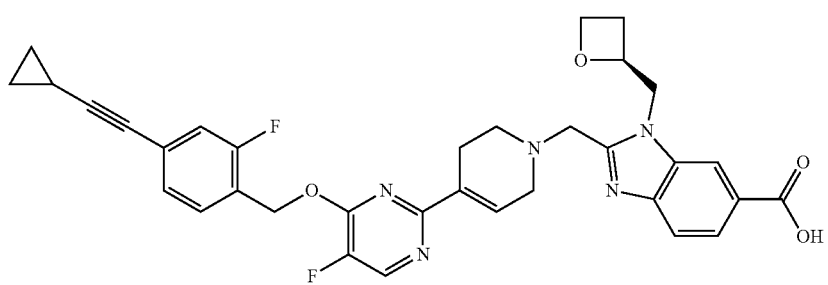

Compound 209

Prepared in analogous manner as for Compound 33

LCMS: [M+H]$^+$=612.0; Retention time (10 mM NH$_4$HCO$_3$)=1.65 min.

$^1$H NMR (400 MHz, DMSO) δ 8.58 (d, J=2.8 Hz, 1H), 8.25 (s, 1H), 7.81 (d, J=8.9 Hz, 1H), 7.65 (d, J=8.2 Hz, 1H), 7.52 (t, J=7.8 Hz, 1H), 7.25 (dd, J=18.2, 9.5 Hz, 2H), 7.08 (s, 1H), 5.56 (s, 2H), 5.06 (s, 1H), 4.78 (s, 1H), 4.65 (d, J=14.9 Hz, 1H), 4.47 (d, J=7.0 Hz, 1H), 4.36 (d, J=8.4 Hz, 1H), 4.08 (d, J=13.5 Hz, 1H), 3.92 (d, J=13.4 Hz, 1H), 3.30-3.14 (m, 3H), 2.70 (d, J=23.6 Hz, 3H), 2.56 (s, 2H), 1.55 (t, J=6.5 Hz, 1H), 0.92-0.87 (m, 2H), 0.74 (dd, J=4.9, 2.6 Hz, 2H).

(S)-2-((4-(2-(4-cyano-2-fluorobenzyloxy)-5-fluoro-pyrimidin-4-yl)-5,6-dihydropyridin-1(2H)-yl)methyl)-1-(oxetan-2-ylmethyl)-1H-benzo[d]imidazole-6-carboxylic acid (Compound 210)

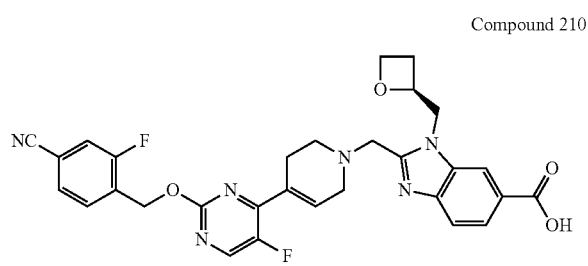 [SMILES: N#Cc1ccc(COc2ncc(F)c(C3=CCN(Cc4nc5ccc(C(=O)O)cc5n4C[C@@H]4CCO4)CC3)n2)c(F)c1]

Compound 210

Prepared in analogous manner as for Compound 18

LCMS: [M+H]⁺=573.0; Retention time (10 mM NH₄HCO₃)=1.39 min.

¹H NMR (400 MHz, CDCL3) δ 8.30-8.29 (d, J=3.2 Hz, 1H), 8.22 (s, 1H), 8.06 (s, 1H), 7.84-7.83 (d, J=7.2 Hz, 1H), 7.67-7.64 (t, J=7.6 Hz, 1H), 7.46-7.44 (d, J=8.0 Hz, 1H), 7.38-7.35 (dd, J1=9.2 Hz, J2=0.8 Hz, 1H), 6.91 (s, 1H), 5.50 (s, 2H), 5.22-5.21 (d, J=4.0 Hz, 1H), 4.78-4.60 (m, 3H), 4.42-4.36 (m, 1H), 4.16 (s, 2H), 3.37 (s, 2H), 2.86-2.83 (t, J=5.2 Hz, 2H), 2.75-2.67 (m, 3H), 2.46-2.44 (d, J=8.4 Hz, 1H).

(S)-2-((4-(2-(4-(cyclopropylethynyl)-2-fluorobenzyloxy)-5-fluoropyrimidin-4-yl)-5,6-dihydropyridin-1(2H)-yl)methyl)-1-(oxetan-2-ylmethyl)-1H-benzo[d]imidazole-6-carboxylic acid (Compound 211)

Prepared in analogous manner as for Compound 18

LCMS: [M+H]⁺=612.3; Retention time (10 mM NH₄HCO₃)=1.40 min.

¹H NMR (400 MHz, CDCL3) δ 8.29-8.28 (d, J=3.6 Hz, 1H), 8.21 (s, 1H), 8.06-8.04 (d, J=7.6 Hz, 1H), 7.83-7.80 (d, J=8.4 Hz, 1H), 7.39-7.36 (t, J=7.6 Hz, 1H), 7.12-7.10 (dd, J1=8.0 Hz, J2=1.2 Hz, 1H), 7.06-7.04 (d, J=10.4 Hz, 1H), 6.89 (s, 1H), 5.41 (s, 2H), 5.21-5.20 (d, J=4.8 Hz, 1H), 4.75-4.73 (d, J=5.6 Hz, 1H), 4.67-4.61 (m, 2H), 4.40-4.38 (d, J=8.8 Hz, 1H), 4.15 (s, 2H), 3.36 (s, 2H), 2.85-2.83 (t, J=4.8 Hz, 2H), 2.69 (s, 3H), 2.43 (s, 1H), 1.44-1.40 (m, 1H), 0.89-0.85 (m, 2H), 0.81-0.77 (m, 2H).

(S)-2-((6-((4-cyano-2-fluorobenzyl)oxy)-3,5-difluoro-3',6'-dihydro-[2,4'-bipyridin]-1'(2'H)-yl)methyl)-1-(oxetan-2-ylmethyl)-1H-benzo[d]imidazole-6-carboxylic acid (Compound 212)

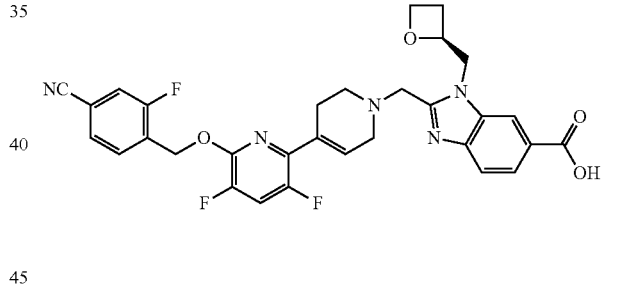

Compound 212

Prepared in analogous manner as for Compound 19

LCMS: [M+H]⁺=590.2; Retention time (0.01% TFA)=1.45 min.

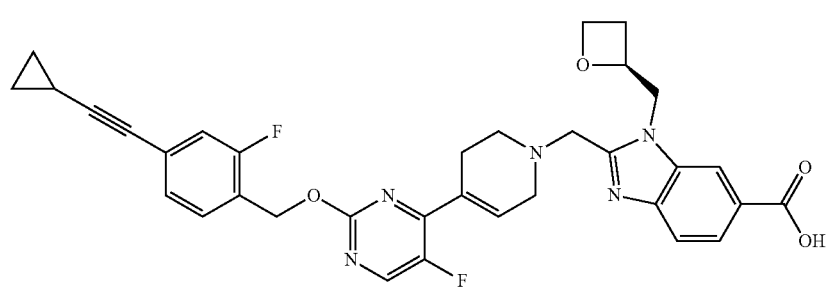

Compound 211

(S)-2-((4-(6-(4-(cyclopropylethynyl)-2-fluorobenzyloxy)-3,5-difluoropyridin-2-yl)-5,6-dihydropyridin-1(2H)-yl)methyl)-3-(oxetan-2-ylmethyl)-3H-benzo[d]imidazole-5-carboxylic acid (Compound 213)

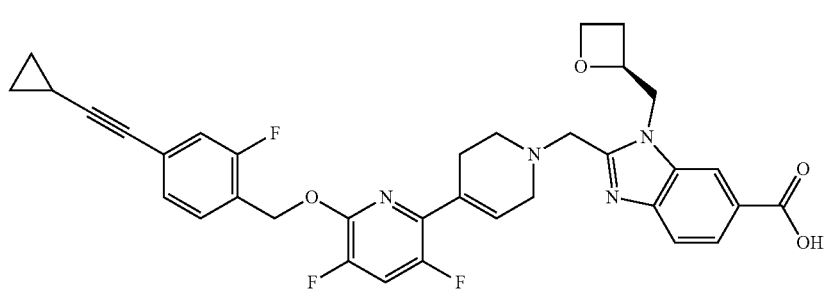

Compound 213

Prepared in analogous manner as for Compound 19

LCMS: [M+H]⁺=629.2; Retention time (0.01% TFA)=1.65 min.

¹H NMR (400 MHz, MeOD) δ 8.34 (s, 1H), 8.28 (s, 1H), 7.98 (d, J=8.4 Hz, 1H), 7.69 (d, J=8.5 Hz, 1H), 7.49 (t, J=9.8 Hz, 1H), 7.39 (t, J=7.9 Hz, 1H), 7.10 (dd, J=22.5, 9.3 Hz, 2H), 6.52 (s, 1H), 5.46 (s, 2H), 5.24 (dd, J=12.1, 6.8 Hz, 1H), 4.85 (s, 1H), 4.77-4.68 (m, 1H), 4.62 (dd, J=14.0, 7.6 Hz, 1H), 4.46 (dt, J=9.1, 6.0 Hz, 1H), 4.18 (d, J=13.8 Hz, 1H), 4.05 (d, J=13.8 Hz, 1H), 2.86 (s, 2H), 2.75 (dd, J=15.9, 9.7 Hz, 1H), 2.67 (s, 2H), 2.56-2.45 (m, 1H), 1.46 (dd, J=13.1, 8.4, 5.0 Hz, 1H), 0.89 (dt, J=6.4, 4.0 Hz, 2H), 0.78-0.69 (m, 2H).

(S)-2-((4-(4-((2,4-difluorobenzyl)oxy)pyrimidin-2-yl)-3,6-dihydropyridin-1(2H)-yl)methyl)-1-(oxetan-2-ylmethyl)-1H-benzo[d]imidazole-6-carboxylic acid (Compound 214)

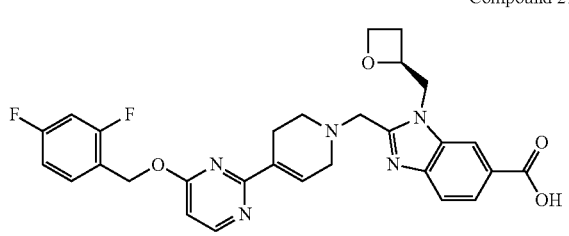

Compound 214

Prepared in analogous manner as for Compound 33

LCMS: [M+H]⁺=548.0; Retention time (0.01% TFA)=1.44 min.

¹H NMR (400 MHz, DMSO) δ 8.50 (d, J=5.7 Hz, 1H), 8.27 (s, 1H), 7.82 (dd, J=8.4, 1.4 Hz, 1H), 7.69-7.60 (m, 2H), 7.35-7.28 (m, 1H), 7.21-7.09 (m, 2H), 6.81 (d, J=5.7 Hz, 1H), 5.47 (s, 2H), 5.06 (dt, J=7.4, 4.9 Hz, 1H), 4.81 (dd, J=15.2, 7.3 Hz, 1H), 4.71-4.63 (m, 1H), 4.47 (dd, J=14.3, 7.1 Hz, 1H), 4.37 (dt, J=9.0, 6.0 Hz, 1H), 4.10 (d, J=13.5 Hz, 1H), 3.94 (d, J=13.5 Hz, 1H), 3.33-3.20 (m, 3H), 2.80-2.57 (m, 5H), 2.40 (dd, J=13.4, 6.4 Hz, 1H).

(S)-2-((4-(2-((2,4-difluorobenzyl)oxy)pyrimidin-4-yl)-3,6-dihydropyridin-1(2H)-yl)methyl)-1-(oxetan-2-ylmethyl)-1H-benzo[d]imidazole-6-carboxylic acid (Compound 215)

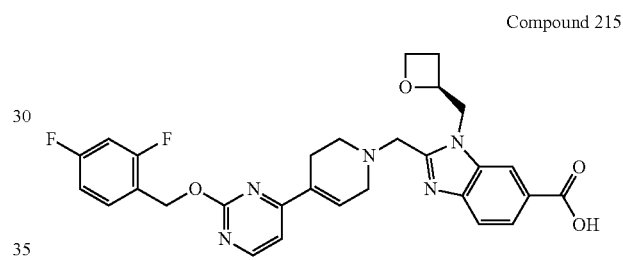

Compound 215

Prepared in analogous manner as for Compound 18

LCMS: [M+H]⁺=548.0; Retention time (10 mM NH₄HCO₃)=1.40 min.

¹H NMR (400 MHz, MeOD) δ 8.49 (t, J=5.0 Hz, 1H), 8.35 (s, 1H), 8.00 (dd, J=8.5, 1.4 Hz, 1H), 7.70 (d, J=8.5 Hz, 1H), 7.60 (dd, J=15.1, 8.6 Hz, 1H), 7.23 (d, J=5.3 Hz, 1H), 7.08-6.96 (m, 3H), 5.50 (s, 2H), 5.29-5.22 (m, 1H), 4.91 (d, J=4.0 Hz, 1H), 4.86 (s, 2H), 4.73 (dd, J=15.3, 2.5 Hz, 1H), 4.64 (dd, J=13.9, 7.9 Hz, 1H), 4.47 (dt, J=9.1, 5.9 Hz, 1H), 4.18 (d, J=13.7 Hz, 1H), 4.07 (d, J=13.7 Hz, 1H), 3.36 (d, J=3.2 Hz, 1H), 2.87 (t, J=5.4 Hz, 2H), 2.81-2.74 (m, 1H), 2.66 (s, 2H), 2.51 (dd, J=13.8, 6.6 Hz, 1H).

(S)-2-((4-(6-(2,4-difluorobenzyloxy)-3,5-difluoropyridin-2-yl)-5,6-dihydropyridin-1(2H)-yl)methyl)-1-(oxetan-2-ylmethyl)-1H-benzo[d]imidazole-6-carboxylic acid (Compound 216)

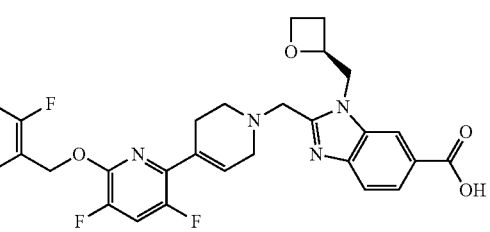

Compound 216

Prepared in analogous manner as for Compound 19
LCMS: [M+H]⁺=583.2; Retention time (10 mM NH₄HCO₃)=1.45 min.
¹H NMR (400 MHz, DMSO) δ 8.24 (d, J=0.8 Hz, 1H), 7.94 (t, J=10.0 Hz, 1H), 7.81 (dd, J=1.6 Hz, 8.4 Hz, 1H), 7.58-7.64 (m, 2H), 7.28-7.33 (m, 1H), 7.10-7.14 (m, 1H), 6.51 (brs, 1H), 5.43 (s, 2H), 5.04-5.10 (m, 1H), 4.77-4.83 (m, 1H), 4.65 (dd, J=2.8 Hz, 15.2 Hz, 1H), 4.44-4.50 (m, 1H), 4.34-4.39 (m, 1H), 3.90-4.09 (m, 2H), 3.18-3.30 (m, 2H), 2.63-2.78 (m, 3H), 2.58 (brs, 2H), 2.38-2.45 (m, 1H).

(S)-2-((6-((4-cyano-2-fluorobenzyl)amino)-3,5-difluoro-3',6'-dihydro-[2,4'-bipyridin]-1'(2'H)-yl)methyl)-1-(oxetan-2-ylmethyl)-1H-benzo[d]imidazole-6-carboxylic acid (Compound 217)

Compound 217

Prepared in analogous manner as for Compound 19
LCMS: [M+H]⁺=589.0; Retention time (10 mM NH₄HCO₃)=1.46 min.
¹H NMR (400 MHz, DMSO) δ 8.25 (s, 1H), 7.83-7.78 (m, 1H), 7.66-7.58 (m, 3H), 7.53-7.47 (m, 1H), 7.41-7.36 (m, 1H), 6.29 (s, 1H), 5.10-5.01 (m, 1H), 4.82-4.74 (m, 1H), 4.67-4.57 (m, 3H), 4.49-4.42 (m, 1H), 4.39-4.33 (m, 1H), 4.06-3.84 (dd, J=64.4, 13.5 Hz, 2H), 3.18-3.11 (m, 2H), 2.71-2.59 (m, 4H), 2.35-2.31 (m, 3H).

(S)-2-((4-(3-((4-cyano-2-fluorobenzyl)oxy)-5-fluorophenyl)-5,6-dihydropyridin-1(2H)-yl)methyl)-1-(oxetan-2-ylmethyl)-1H-benzo[d]imidazole-6-carboxylic acid (Compound 218)

Compound 218

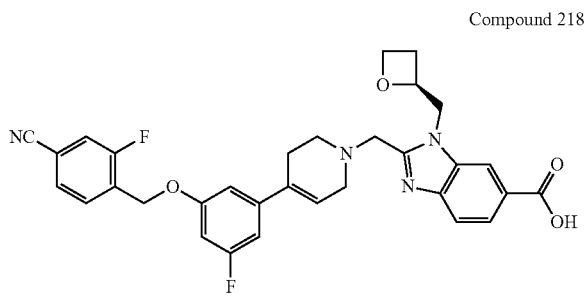 [SMILES: N#Cc1ccc(COc2cc(F)cc(C3=CCN(Cc4nc5ccc(C(=O)O)cc5n4C[C@@H]4CCO4)CC3)c2)c(F)c1]

Prepared in analogous manner as for Compound 28
LCMS: [M+H]⁺=567.0; Retention time (10 mM NH₄HCO₃)=1.63 min.
¹H NMR (400 MHz, DMSO) δ 8.26 (s, 1H), 7.93 (d, J=10.3 Hz, 1H), 7.84-7.74 (m, 3H), 7.65 (d, J=8.5 Hz, 1H), 6.89 (dd, J=23.4, 12.3 Hz, 3H), 6.28 (s, 1H), 5.27 (s, 2H), 5.06 (d, J=4.7 Hz, 1H), 4.79 (dd, J=15.2, 7.4 Hz, 1H), 4.71-4.58 (m, 1H), 4.47 (dd, J=13.6, 7.5 Hz, 1H), 4.35 (dt, J=9.0, 6.0 Hz, 1H), 4.05 (d, J=13.5 Hz, 1H), 3.90 (d, J=13.5 Hz, 1H), 3.25-3.08 (m, 2H), 2.82-2.58 (m, 3H), 2.40 (dd, J=29.1, 20.5 Hz, 4H).

(S)-1-(oxetan-2-ylmethyl)-2-((4-(2-((6-(trifluoromethyl)pyridin-3-yl)methoxy) pyrimidin-4-yl)-5,6-dihydropyridin-1(2H)-yl)methyl)-1H-benzo[d]imidazole-6-carboxylic acid (Compound 219)

Compound 219

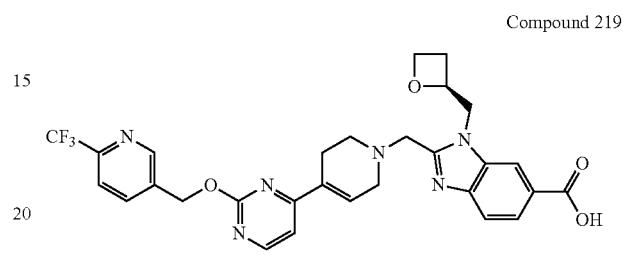

Prepared in analogous manner as for Compound 18
LCMS: [M+H]⁺=567.0; Retention time (10 mM NH₄HCO₃)=1.63 min.
¹H NMR (400 MHz, DMSO) δ 8.87 (s, 1H), 8.56 (d, J=5.3 Hz, 1H), 8.26 (s, 1H), 8.16 (d, J=7.7 Hz, 1H), 7.93 (d, J=8.0 Hz, 1H), 7.81 (dd, J=8.4, 1.5 Hz, 1H), 7.65 (d, J=8.5 Hz, 1H), 7.28 (d, J=5.3 Hz, 1H), 7.02 (s, 1H), 5.55 (s, 2H), 5.05 (d, J=4.9 Hz, 1H), 4.78 (dd, J=15.2, 7.3 Hz, 1H), 4.63 (d, J=12.5 Hz, 1H), 4.46 (dd, J=13.8, 7.7 Hz, 1H), 4.35 (dt, J=12.0, 6.0 Hz, 1H), 4.08 (d, J=13.7 Hz, 1H), 3.93 (d, J=13.5 Hz, 1H), 3.29 (s, 4H), 2.75 (s, 2H), 2.66 (d, J=11.3 Hz, 1H), 2.45-2.31 (m, 2H).

(S)-2-((3,5-difluoro-6-((6-(trifluoromethyl)pyridin-3-yl)methoxy)-5',6'-dihydro-[2,4'-bipyridin]-1'(2'H)-yl)methyl)-1-(oxetan-2-ylmethyl)-1H-benzo[d]imidazole-6-carboxylic acid (Compound 220)

Compound 220

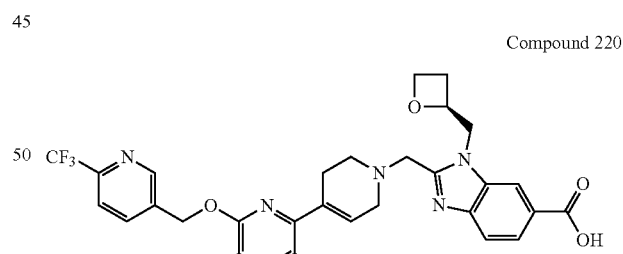

Prepared in analogous manner as for Compound 19
LCMS: [M+H]⁺=616.2; Retention time (10 mM NH₄HCO₃)=1.42 min.
¹H NMR (400 MHz, DMSO) δ 8.86 (s, 1H), 8.25 (d, J=0.8 Hz, 1H), 8.14-8.16 (m, 1H), 7.93-8.00 (m, 2H), 7.80-7.83 (m, 1H), 7.64 (d, J=8.4 Hz, 1H), 6.50 (brs, 1H), 5.58 (s, 2H), 5.04-5.10 (m, 1H), 4.76-4.82 (m, 1H), 4.64 (dd, J=2.4 Hz, 15.2 Hz, 1H), 4.44-4.48 (m, 1H), 4.33-4.39 (m, 1H), 3.90-4.08 (m, 2H), 3.22-3.24 (m, 2H), 2.64-2.75 (m, 3H), 2.54 (brs, 2H), 2.36-2.44 (m, 1H).

301

(S)-2-((6-((4-chloro-2-fluorobenzyl)oxy)-3,6'-di-hydro-[2,4'-bipyridin]-1'(2'H)-yl)methyl)-1-(oxetan-2-ylmethyl)-1H-benzo[d]imidazole-6-carboxylic acid (Compound 221)

Compound 221

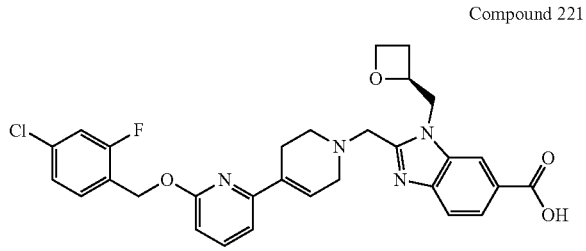 [SMILES: O=C(O)c1ccc2nc(CN3CC=C(c4cccc(OCc5ccc(Cl)cc5F)n4)CC3)n(C[C@@H]3CCO3)c2c1]

Prepared in analogous manner as for Compound 19

LCMS: [M+H]$^+$=564.0; Retention time (10 mM NH$_4$HCO$_3$)=1.60 min.

$^1$H NMR (400 MHz, DMSO) δ 8.26 (s, 1H), 7.84-7.80 (m, 1H), 7.72-7.63 (m, 2H), 7.59-7.53 (m, 1H), 7.50-7.46 (dd, J=10.0, 2.0 Hz, 1H), 7.33-7.28 (m, 1H), 7.11-7.07 (m, 1H), 6.78-6.71 (m, 2H), 5.40 (s, 2H), 5.11-5.03 (m, 1H), 4.85-4.76 (m, 1H), 4.69-4.62 (m, 1H), 4.51-4.43 (m, 1H), 4.40-4.33 (m, 1H), 4.11-3.88 (dd, J=62.7, 13.5 Hz, 2H), 3.27-3.18 (m, 3H), 2.80-2.71 (m, 2H), 2.70-2.60 (m, 1H), 2.45-2.32 (m, 2H).

(S)-2-((6-((4-cyano-2-fluorobenzyl)oxy)-5-fluoro-3',6'-dihydro-[2,4'-bipyridin]-1'(2'H)-yl)methyl)-1-(oxetan-2-ylmethyl)-1H-benzo[d]imidazole-6-carboxylic acid (Compound 222)

Compound 222

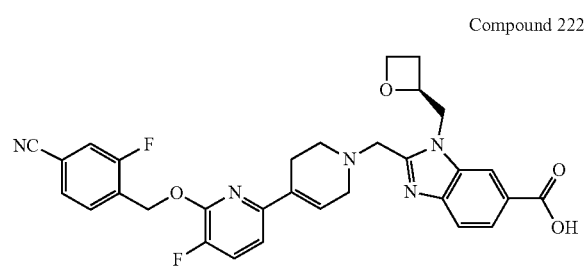 [SMILES: N#Cc1ccc(COc2nc(C3=CCN(Cc4nc5ccc(C(=O)O)cc5n4C[C@@H]4CCO4)CC3)ccc2F)c(F)c1]

Prepared in analogous manner as for Compound 19

LCMS: [M+H]$^+$=572.2; Retention time (10 mM NH$_4$HCO$_3$)=1.30 min.

$^1$H NMR (400 MHz, Methanol-d4) δ 8.33 (s, 1H), 7.99 (dd, J=8.5, 1.4 Hz, 1H), 7.71 (dd, J=14.8, 7.9 Hz, 2H), 7.61 (dd, J=15.5, 4.7 Hz, 2H), 7.47 (dd, J=10.0, 8.2 Hz, 1H), 7.09 (dd, J=8.2, 2.7 Hz, 1H), 6.63 (s, 1H), 5.62 (s, 2H), 5.25 (d, J=5.0 Hz, 1H), 4.87 (d, J=7.2 Hz, 1H), 4.72 (dd, J=15.3, 2.6 Hz, 1H), 4.63 (dd, J=13.9, 7.8 Hz, 1H), 4.47 (dt, J=9.1, 6.0 Hz, 1H), 4.16 (d, J=13.7 Hz, 1H), 4.05 (d, J=13.7 Hz, 1H), 3.27 (t, J=10.6 Hz, 2H), 2.79 (dd, J=22.2, 12.7, 6.8 Hz, 3H), 2.67-2.48 (m, 3H).

302

(S)-2-((6-((4-cyano-2-fluorobenzyl)oxy)-3-fluoro-3',6'-dihydro-[2,4'-bipyridin]-1'(2'H)-yl)methyl)-1-(oxetan-2-ylmethyl)-1H-benzo[d]imidazole-6-carboxylic acid (Compound 223)

Compound 223

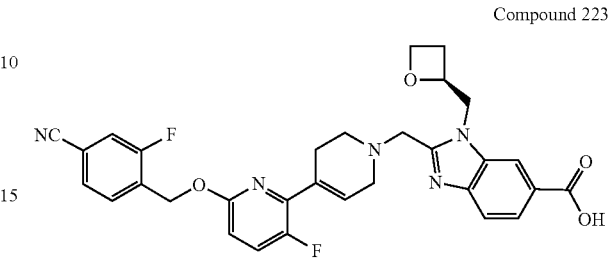

Prepared in analogous manner as for Compound 19

LCMS: [M+H]$^+$=572.2; Retention time (10 mM NH$_4$HCO$_3$)=1.31 min.

$^1$H NMR (400 MHz, Methanol-d4) δ 8.34 (s, 1H), 8.00-7.98 (m, 1H), 7.70-7.61 (m, 2H), 7.58-7.48 (m, 3H), 6.78-6.75 (m, 1H), 6.75 (s, 1H), 5.50 (s, 2H), 5.26 (d, J=7.1 Hz, 1H), 4.72 (dd, J=27.6, 14.6 Hz, 1H), 4.54 (dd, J=15.1, 12.6, 5.5 Hz, 2H), 4.11 (dd, J=49.6, 13.7 Hz, 2H), 2.90-2.71 (m, 3H), 2.70-2.45 (m, 3H), 1.52 (d, J=17.0 Hz, 2H).

(S)-2-((4-(3-((4-chloro-2-fluorobenzyl)oxy)phenyl)-3,6-dihydropyridin-1(2H)-yl)methyl)-3-(oxetan-2-ylmethyl)-3H-imidazo[4,5-b]pyridine-5-carboxylic acid (Compound 224)

Compound 224

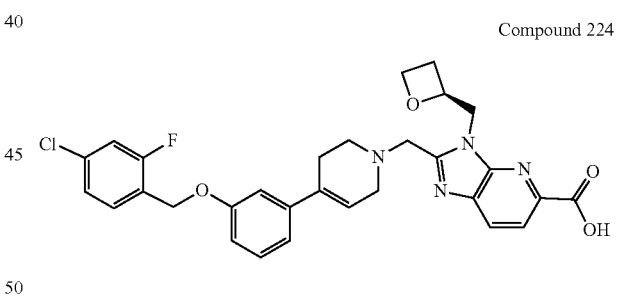

Prepared in analogous manner as for Compound 28

LCMS: [M+H]$^+$=563.0; Retention time (10 mM NH$_4$HCO$_3$)=1.59 min.

$^1$H NMR (400 MHz, DMSO) δ 8.12 (d, J=8.2 Hz, 1H), 7.98 (d, J=8.2 Hz, 1H), 7.59 (t, J=8.2 Hz, 1H), 7.49 (dd, J=10.0, 2.0 Hz, 1H), 7.33 (dd, J=8.2, 1.8 Hz, 1H), 7.25 (t, J=7.9 Hz, 1H), 7.04 (d, J=7.5 Hz, 2H), 6.98-6.83 (m, 1H), 6.19-6.18 (brs, 1H), 5.20-5.09 (m, 3H), 4.83 (dd, J=14.6, 6.5 Hz, 1H), 4.70 (dd, J=14.6, 4.1 Hz, 1H), 4.47 (dd, J=13.7, 7.6 Hz, 1H), 4.36 (dt, J=8.9, 6.1 Hz, 1H), 4.11 (d, J=13.6 Hz, 1H), 4.02 (d, J=13.6 Hz, 1H), 3.22-3.21 (brs, 2H), 2.76 (t, J=5.5 Hz, 2H), 2.67 (dt, J=22.7, 8.2 Hz, 1H), 2.49-2.45 (m, 3H).

(S)-2-((6-((4-cyano-2-fluorobenzyl)oxy)-3',6'-di-hydro-[2,4'-bipyridin]-1'(2'H)-yl)methyl)-3-(oxetan-2-ylmethyl)-3H-imidazo[4,5-b]pyridine-5-carboxylic acid (Compound 225)

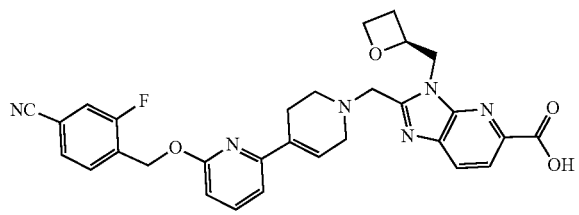

Compound 225

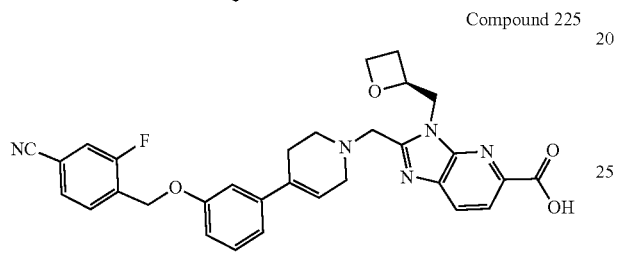

Compound 225

Prepared in analogous manner as for Compound 19

LCMS: [M+H]⁺=555, Retention time (10 mM NH₄HCO₃)=1.59 min.

¹H NMR (400 MHz, DMSO) δ 8.08 (d, J=8.2 Hz, 1H), 7.96 (d, J=8.2 Hz, 1H), 7.90 (d, J=10.3 Hz, 1H), 7.70 (dd, J=9.6, 6.1 Hz, 3H), 7.10 (d, J=7.4 Hz, 1H), 6.78 (d, J=8.2 Hz, 1H), 6.72 (s, 1H), 5.49 (s, 2H), 5.25-5.00 (m, 1H), 4.82 (dd, J=14.7, 6.5 Hz, 1H), 4.74-4.62 (m, 1H), 4.47 (dd, J=13.8, 7.6 Hz, 1H), 4.35 (dt, J=12.0, 6.1 Hz, 1H), 4.11 (d, J=13.6 Hz, 1H), 4.01 (d, J=13.6 Hz, 1H), 3.26 (s, 3H), 2.74 (d, J=5.4 Hz, 2H), 2.65 (d, J=8.4 Hz, 1H).

(S)-2-((1-(6-((4-cyano-2-fluorobenzyl)oxy)pyridin-2-yl)piperidin-4-yl)methyl)-1-(oxetan-2-ylmethyl)-1H-benzo[d]imidazole-6-carboxylic acid (Compound 226)

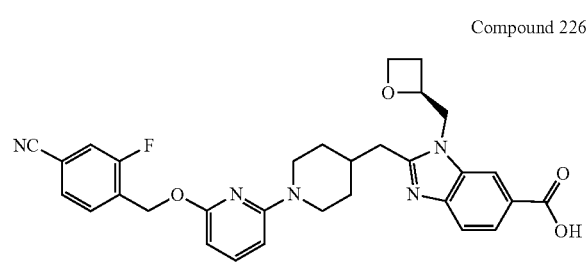 [SMILES: N#Cc1ccc(COc2cccc(N3CCC(Cc4nc5ccc(C(=O)O)cc5n4C[C@@H]4CCO4)CC3)n2)c(F)c1]

Compound 226

Prepared in analogous manner as for Compound 228.

LCMS: [M+H]⁺=556.0; Retention time (10 mM NH₄HCO₃)=1.53 min.

¹H NMR (400 MHz, CDCl₃) δ 8.22 (brs, 1H), 8.10 (d, J=7.7 Hz, 1H), 7.99 (brs, 1H), 7.60 (t, J=7.4 Hz, 1H), 7.42 (t, J=8.0 Hz, 2H), 7.36-7.27 (m, 1H), 6.25 (s, 1H), 6.16 (d, J=7.8 Hz, 1H), 5.43 (s, 2H), 5.22 (s, 1H), 4.63 (m, 1H), 4.40 (s, 1H), 4.20 (d, J=11.8 Hz, 2H), 3.17 (m, 2H), 2.88 (m, 4H), 2.48 (m, 4H), 1.86 (m, 3H).

(S)-2-((1-(6-((4-cyano-2-fluorobenzyl)oxy)pyridin-2-yl)piperidin-4-yl)methyl)-3-(oxetan-2-ylmethyl)-3H-imidazo[4,5-b]pyridine-5-carboxylic acid (Compound 227)

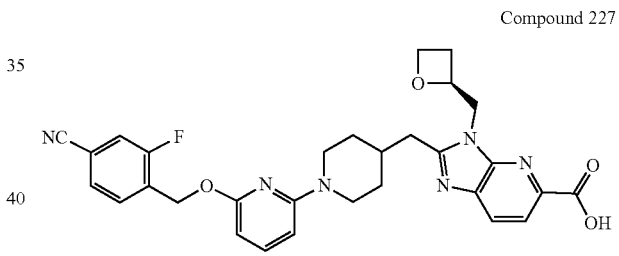

Compound 227

Prepared in analogous manner as for Compound 228.

LCMS: [M+H]⁺=557.1; Retention time (10 mM NH₄HCO₃)=1.51 min.

¹H NMR (400 MHz, MeOD) δ 8.15 (d, J=8.2 Hz, 1H), 8.08 (d, J=8.2 Hz, 1H), 7.63 (t, J=7.6 Hz, 1H), 7.54 (t, J=7.8 Hz, 2H), 7.43 (t, J=8.0 Hz, 1H), 6.28 (d, J=8.1 Hz, 1H), 6.10 (d, J=7.8 Hz, 1H), 5.44 (s, 2H), 5.24 (d, J=5.2 Hz, 1H), 4.76 (dd, J=15.1, 6.8 Hz, 1H), 4.63 (dd, J=21.8, 14.5, 5.1 Hz, 2H), 4.41 (dt, J=12.2, 6.1 Hz, 1H), 4.24 (d, J=13.0 Hz, 2H), 3.13-3.00 (m, 2H), 2.78 (dd, J=23.9, 10.6 Hz, 3H), 2.57-2.45 (m, 1H), 2.33-2.32 (brs, 1H), 1.77 (d, J=12.6 Hz, 2H), 1.29 (t, J=12.0 Hz, 2H).

(S)-2-((1-(6-((4-cyano-2-fluorobenzyl)oxy)pyridin-2-yl)piperidin-4-yl)methyl)-7-fluoro-1-(oxetan-2-ylmethyl)-1H-benzo[d]imidazole-6-carboxylic acid (Compound 228)
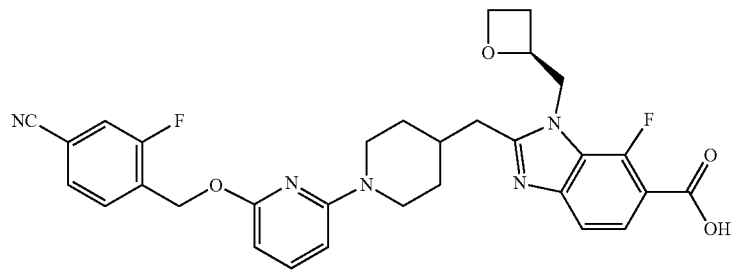
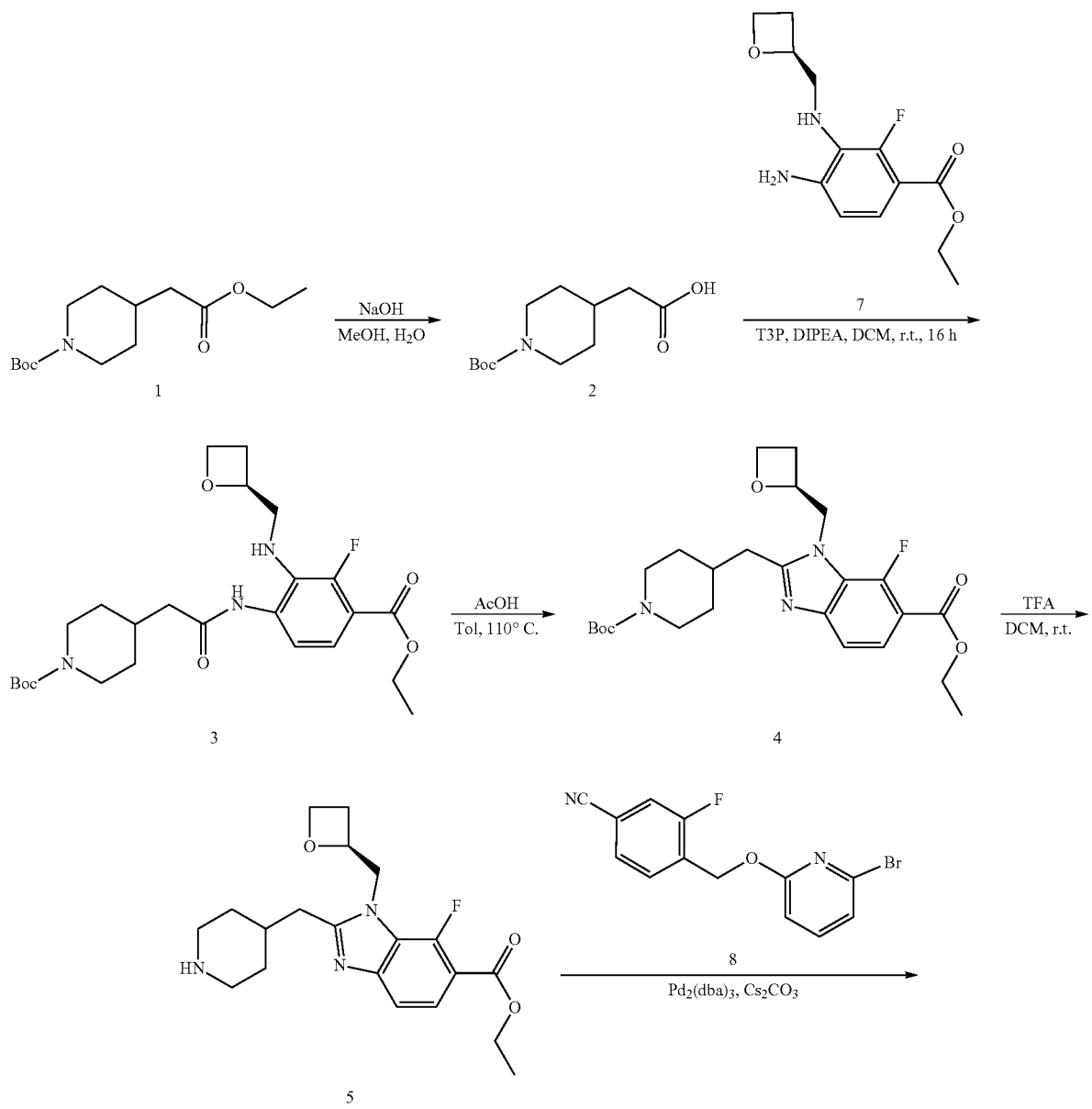

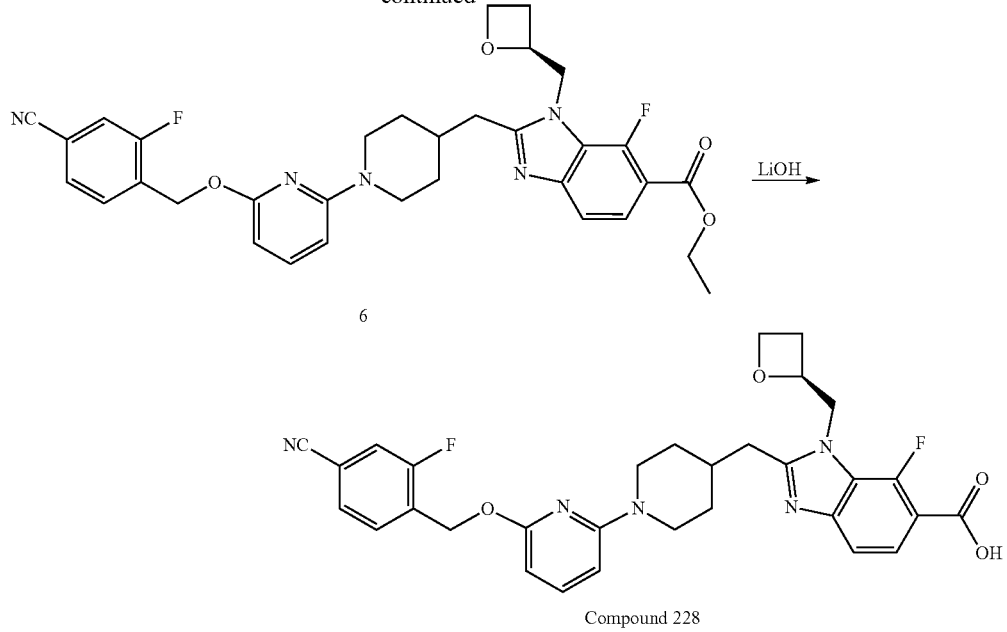

Compound 228

Step 1

To a suspension of tert-butyl 4-(2-ethoxy-2-oxo-ethyl)piperidine-1-carboxylate (500 mg, 1.84 mmol) in methanol (3 mL) was added sodium hydroxide (147 mg, 3.69 mmol) and water (1 mL) at rt. The mixture was stirred for 1 h. After completion of the reaction as judged by LCMS, reaction mixture was quenched with ice-cold water (10 mL) and extracted with EtOAc (3×10 mL). The organic phase was washed with brine (20 mL) and dried over anhydrous $Na_2SO_4$, filtered and concentrated in vacuo to afford 2-(1-tert-butoxycarbonyl-4-piperidyl)acetic acid (440 mg, crude) as a colorless oil.

LCMS: [M−56+H]=188.1; Retention time (0.01% TFA)= 1.68 min.

Step 2

To a suspension of 2-(1-tert-butoxycarbonyl-4-piperidyl)acetic acid (272 mg, 1.12 mmol) in DCM (5 mL) was added ethyl 4-amino-2-fluoro-3-[[(2S)-oxetan-2-yl]methylamino]benzoate (200 mg, 0.745 mmol), 2,4,6-tripropyl-1,3,5,2,4,6trioxatriphosphinane 2,4,6-trioxide (18.98 g, 59.64 mmol) and N-ethyl-N-isopropyl-propan-2-amine (289 mg, 2.24 mmol). The mixture was stirred at rt for 16 h. The mixture was concentrated to give the crude material. The crude material was purified by flash chromatography ($SiO_2$, hexane/ethyl acetate 2:1) to afford tert-butyl 4-[2-[4-ethoxycarbonyl-3-fluoro-2-[[(2S)-oxetan-2-yl]methylamino]anilino]-2-oxo-ethyl]piperidine-1-carboxylate (150 mg, 0.176 mmol, 23.6% yield, 57.8% purity) as a yellow oil. LCMS: $[M+H]^+=494.0$; Retention time (10 mM $NH_4HCO_3$)=1.95 min.

Step 3

To a suspension of tert-butyl 4-[2-[4-ethoxycarbonyl-3-fluoro-2-[[(2S)-oxetan-2-yl]methylamino]anilino]-2-oxo-ethyl]piperidine-1-carboxylate (150 mg, 0.304 mmol) in Toluene (1 mL) was added acetic acid (2 mg, 40 mmol). The mixture was stirred at 110° C. for 2 h. After completion of the reaction as judged by LCMS, reaction mixture was quenched with ice-cold water (10 mL) and extracted with EtOAc (3×10 mL). The organic phase was washed with brine (10 mL) and dried over anhydrous $Na_2SO_4$, filtered and concentrated in vacuo to afford ethyl 2-[(1-tert-butoxycarbonyl-4-piperidyl)methyl]-4-fluoro-3-[[(2S)-oxetan-2-yl]methyl]benzimidazole-5-carboxylate (100 mg, 0.207 mmol, 68.2% yield, 98.5% purity) as a yellow oil.

LCMS: $[M+H]^+=476.1$; Retention time (0.01% TFA)= 1.91 min.

Step 4

To a suspension of ethyl 2-[(1-tert-butoxycarbonyl-4-piperidyl)methyl]-4-fluoro-3-[[(2S)-oxetan-2-yl]methyl]benzimidazole-5-carboxylate (100 mg, 0.210 mmol) in DCM (3 mL) was added 2,2,2-trifluoroacetic acid (23 mg, 210 mmol). The mixture was stirred at r.t for 2 h. After completion of the reaction as judged by LCMS, reaction mixture was quenched with ice-cold water (10 mL) and extracted with EtOAc (3 10 mL). The organic phase was washed with brine (20 mL) and dried over anhydrous $Na_2SO_4$, filtered and concentrated in vacuo to afford ethyl 4-fluoro-3-[[(2S)-oxetan-2-yl]methyl]-2-(4-piperidylmethyl)benzimidazole-5-carboxylate (55 mg, 0.123 mmol, 58.5% yield) as a yellow oil. LCMS: $[M+H]^+=376.1$; Retention time (0.01% TFA)=1.44 min.

Step 5

To a suspension of 4-[(6-bromo-2-pyridyl)oxymethyl]-3-fluoro-benzonitrile (54 mg, 176 mmol) and ethyl 4-fluoro-3-[[(2S)-oxetan-2-yl]methyl]-2-(4-piperidylmethyl)benzimidazole-5-carboxylate (55 mg, 146 mmol) in toluene (4 mL) was added (1E,4E)-1,5-diphenylpenta-1,4-dien-3-one; palladium (27 mg, 0.029 mmol), benzyl-[1-[2-[benzyl(phenyl)phosphanyl]-1-naphthyl]-2-naphthyl]-phenyl-phosphane (19 mg, 0.029 mmol) and cesium carbonate (143 mg, 0.439 mmol). The mixture was stirred at 110° C. for 3 h under $N_2$. After completion of the reaction as judged by LCMS, reaction mixture was quenched with ice-cold water (10 mL) and extracted with EtOAc (3×10 mL). The organic phase was washed with brine (20 mL) and dried over anhydrous $Na_2SO_4$, filtered and concentrated in vacuo. The crude product was purified by prep-HPLC to afford ethyl 2-[[1-[6-[(4-cyano-2-fluoro-phenyl)methoxy]-2-pyridyl]-4- piperidyl]methyl]-4-fluoro-3-[[(2S)-oxetan-2-yl]methyl]benzimidazole-5-carboxylate (40 mg, 0.041 mmol, 28.3% yield, 62.3% purity) as a yellow solid. LCMS: [M+H]$^+$=602.1; Retention time (10 mM NH$_4$HCO$_3$)=2.13 min.

Step 6

To a suspension of ethyl 2-[[1-[6-[(4-cyano-2-fluorophenyl)methoxy]-2-pyridyl]-4-piperidyl]methyl]-4-fluoro-3-[[(2S)-oxetan-2-yl]methyl]benzimidazole-5-carboxylate (40 mg, 0.066 mmol) in THF (1 mL) was added sodium hydroxide (13 mg, 0.332 mmol) in water (1 mL). The mixture was stirred at r.t for 4 h. After completion of the reaction as judged by LCMS, reaction mixture was quenched with ice-cold water (10 mL) and extracted with EtOAc (3×10 mL). The organic phase was washed with brine (20 mL) and dried over anhydrous Na$_2$SO$_4$, filtered and concentrated in vacuo. The crude product was purified by prep-HPLC to afford (S)-2-((1-(6-((4-cyano-2-fluorobenzyl)oxy)pyridin-2-yl)piperidin-4-yl)methyl)-7-fluoro-1-(oxetan-2-ylmethyl)-1H-benzo[d]imidazole-6-carboxylic acid (7 mg, 0.012 mmol, 18.1% yield) as a white solid. LCMS: [M+H]$^+$=574.0; Retention time (10 mM NH$_4$HCO$_3$) =1.53 min.

$^1$H NMR (400 MHz, DMSO) δ 7.91-7.85 (m, 1H), 7.74-7.57 (m, 3H), 7.51-7.32 (m, 2H), 6.34 (d, J=8.2 Hz, 1H), 6.08 (d, J=7.8 Hz, 1H), 5.40 (s, 2H), 5.00 (d, J=4.4 Hz, 1H), 4.68 (dd, J=15.5, 7.4 Hz, 1H), 4.58-4.42 (m, 2H), 4.34 (dt, J=8.9, 6.0 Hz, 1H), 4.18 (d, J=12.9 Hz, 2H), 2.96-2.85 (m, 2H), 2.82-2.68 (m, 3H), 2.43-2.33 (m, 1H), 2.26 (s, 1H), 1.76 (d, J=12.1 Hz, 2H), 1.20 (dd, J=22.7, 10.3 Hz, 2H).

(S)-2-((1-(6-((2,4-difluorobenzyl)oxy)pyridin-2-yl)piperidin-4-yl)methyl)-3-(oxetan-2-ylmethyl)-3H-imidazo[4,5-b]pyridine-5-carboxylic acid (Compound 229)

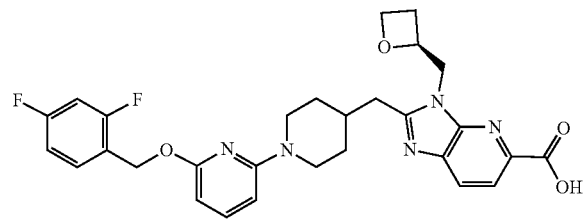

Compound 229

Prepared in analogous manner as for Compound 228.

LCMS: [M+H]$^+$=550.2; Retention time (10 mM NH$_4$HCO$_3$)=1.66 min.

$^1$H NMR (400 MHz, MeOD) δ 8.17 (d, J=8.1 Hz, 1H), 8.11 (d, J=8.3 Hz, 1H), 7.51 (dd, J=15.2, 8.7 Hz, 1H), 7.43 (t, J=8.0 Hz, 1H), 7.02-6.87 (m, 2H), 6.30 (d, J=8.1 Hz, 1H), 6.07 (d, J=7.8 Hz, 1H), 5.34 (s, 2H), 5.27 (d, J=4.2 Hz, 1H), 4.79 (dd, J=15.3, 6.7 Hz, 1H), 4.70 (d, J=12.8 Hz, 1H), 4.61 (d, J=6.1 Hz, 1H), 4.42 (d, J=8.8 Hz, 1H), 4.33 (d, J=13.1 Hz, 2H), 3.14-3.02 (m, 2H), 2.83 (dd, J=27.1, 15.2 Hz, 3H), 2.53-2.52 (brs, 1H), 2.37-2.36 (brs, 1H), 1.83 (d, J=11.8 Hz, 2H), 1.40 (dd, J=21.2, 11.7 Hz, 2H).

(S)-2-((1-(6-((5-chloropyridin-2-yl)methoxy)pyridin-2-yl)piperidin-4-yl)methyl)-3-(oxetan-2-ylmethyl)-3H-imidazo[4,5-b]pyridine-5-carboxylic acid (Compound 230)

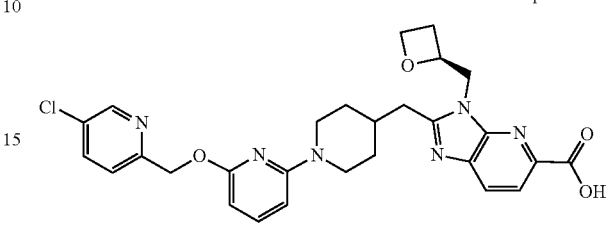

Compound 230

Prepared in analogous manner as for Compound 228.

LCMS: [M+H]$^+$=549.0; Retention time (10 mM NH$_4$HCO$_3$)=1.45 min.

$^1$H NMR (400 MHz, DMSO) δ 8.56 (d, J=2.4 Hz, 1H), 8.06 (d, J=8.2 Hz, 1H), 7.95 (d, J=8.2 Hz, 1H), 7.91-7.88 (dd, J=8.4, 2.5 Hz, 1H), 7.47-7.41 (dd, J=15.9, 8.1 Hz, 2H), 6.31 (d, J=8.2 Hz, 1H), 6.10 (d, J=7.8 Hz, 1H), 5.33 (s, 2H), 5.11-5.05 (m, 1H), 4.66-4.60 (m, 1H), 4.53-4.22 (m, 2H), 4.33-4.28 (m, 1H), 4.14 (d, J=13.0 Hz, 2H), 2.99-2.91 (m, 2H), 2.77-2.65 (m, 3H), 2.45-2.40 (m, 1H), 2.33-2.26 (m, 1H), 1.73 (d, J=12.8 Hz, 2H), 1.21-1.12 (m, 2H).

(S)-2-((1-(6-((5-cyanopyridin-2-yl)methoxy)pyridin-2-yl)piperidin-4-yl)methyl)-3-(oxetan-2-ylmethyl)-3H-imidazo[4,5-b]pyridine-5-carboxylic acid (Compound 231)

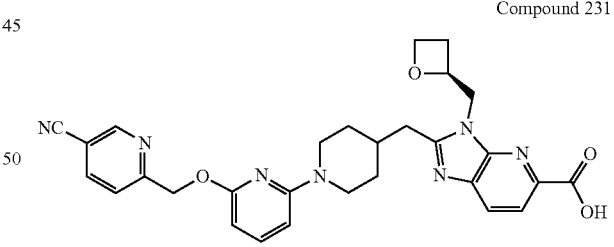

Compound 231

Prepared in analogous manner as for Compound 228.

LCMS: [M+H]$^+$=540.3; Retention time (0.01% TFA) =1.70 min.

$^1$H NMR (400 MHz, CD$_3$OD) δ 8.92-8.90 (m, 1H), 8.24-8.15 (m, 3H), 7.67-7.64 (m, 1H), 7.54-7.50 (m, 1H), 6.36 (d, J=8.0 Hz, 1H), 6.24 (d, J=8.0 Hz, 1H), 5.52 (s, 2H), 5.32-5.30 (m, 1H), 4.86-4.82 (m, 1H), 4.75-4.65 (m, 2H), 4.51-4.47 (m, 1H), 4.23-4.20 (m, 2H), 3.12-3.10 (m, 2H), 2.88-2.77 (m, 3H), 2.60-2.56 (m, 1H), 2.38-2.36 (m, 1H), 1.81-1.78 (m, 2H), 1.31-1.29 (m, 2H).

311

(S)-2-((1-(6-((5-chloropyridin-2-yl)methoxy)pyridin-2-yl)piperidin-4-yl)methyl)-7-fluoro-1-(oxetan-2-ylmethyl)-1H-benzo[d]imidazole-6-carboxylic acid (Compound 232)

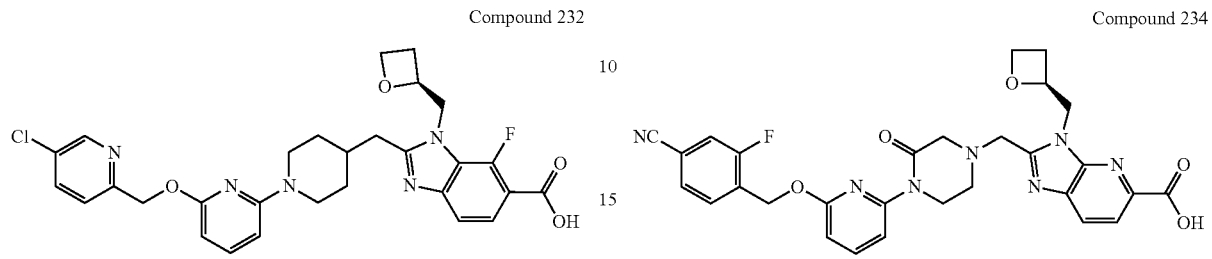

Compound 232

Prepared in analogous manner as for Compound 228.

LCMS: [M+H]$^+$=566.2; Retention time (10 mM NH$_4$HCO$_3$)=1.53 min.

$^1$H NMR (400 MHz, DMSO-d$_6$) δ 8.56 (d, J=2.1 Hz, 1H), 7.90 (dd, J=8.4, 2.5 Hz, 1H), 7.62 (dd, J=8.4, 6.8 Hz, 1H), 7.43 (dd, J=15.2, 8.2 Hz, 3H), 6.32 (d, J=8.2 Hz, 1H), 6.09 (d, J=7.8 Hz, 1H), 5.32 (s, 2H), 4.99 (d, J=4.6 Hz, 1H), 4.67 (dd, J=15.5, 7.4 Hz, 1H), 4.58-4.40 (m, 2H), 4.33 (dt, J=9.0, 6.0 Hz, 1H), 4.12 (d, J=13.4 Hz, 2H), 2.96-2.78 (m, 2H), 2.80-2.62 (m, 3H), 2.39 (dd, J=17.7, 9.1 Hz, 1H), 2.23 (s, 1H), 1.71 (d, J=11.9 Hz, 2H), 1.29-1.05 (m, 2H).

(S)-2-((1-(6-((5-cyanopyridin-2-yl)methoxy)pyridin-2-yl)piperidin-4-yl)methyl)-7-fluoro-1-(oxetan-2-ylmethyl)-1H-benzo[d]imidazole-6-carboxylic acid (Compound 233)

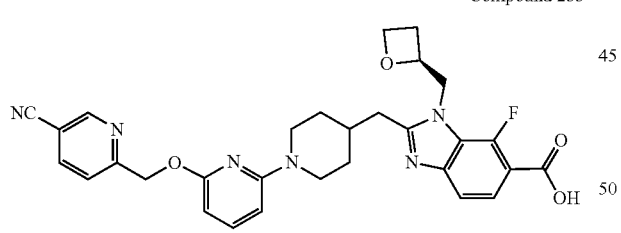

Compound 233

Prepared in analogous manner as for Compound 228.

LCMS: [M+H]$^+$=557.3; Retention time (10 mM NH$_4$HCO$_3$)=1.39 min.

$^1$H NMR (400 MHz, DMSO) δ 8.97 (d, J=1.4 Hz, 1H), 8.27 (dd, J=8.2, 2.1 Hz, 1H), 7.69-7.51 (m, 2H), 7.50-7.33 (m, 2H), 6.32 (d, J=8.2 Hz, 1H), 6.13 (d, J=7.7 Hz, 1H), 5.41 (s, 2H), 4.99 (d, J=5.5 Hz, 1H), 4.66 (dd, J=15.3, 7.3 Hz, 1H), 4.47 (dd, J=14.3, 10.0 Hz, 2H), 4.33 (dt, J=9.0, 5.9 Hz, 1H), 4.06 (d, J=13.2 Hz, 2H), 2.94-2.77 (m, 2H), 2.70 (t, J=11.0 Hz, 3H), 2.40 (d, J=8.9 Hz, 1H), 2.21 (s, 1H), 1.69 (d, J=11.8 Hz, 2H), 1.11 (d, J=12.5 Hz, 2H).

312

(S)-2-((4-(6-(4-cyano-2-fluorobenzyloxy)pyridin-2-yl)-3-oxopiperazin-1-yl)methyl)-3-(oxetan-2-ylmethyl)-3H-imidazo[4,5-b]pyridine-5-carboxylic acid (Compound 234)

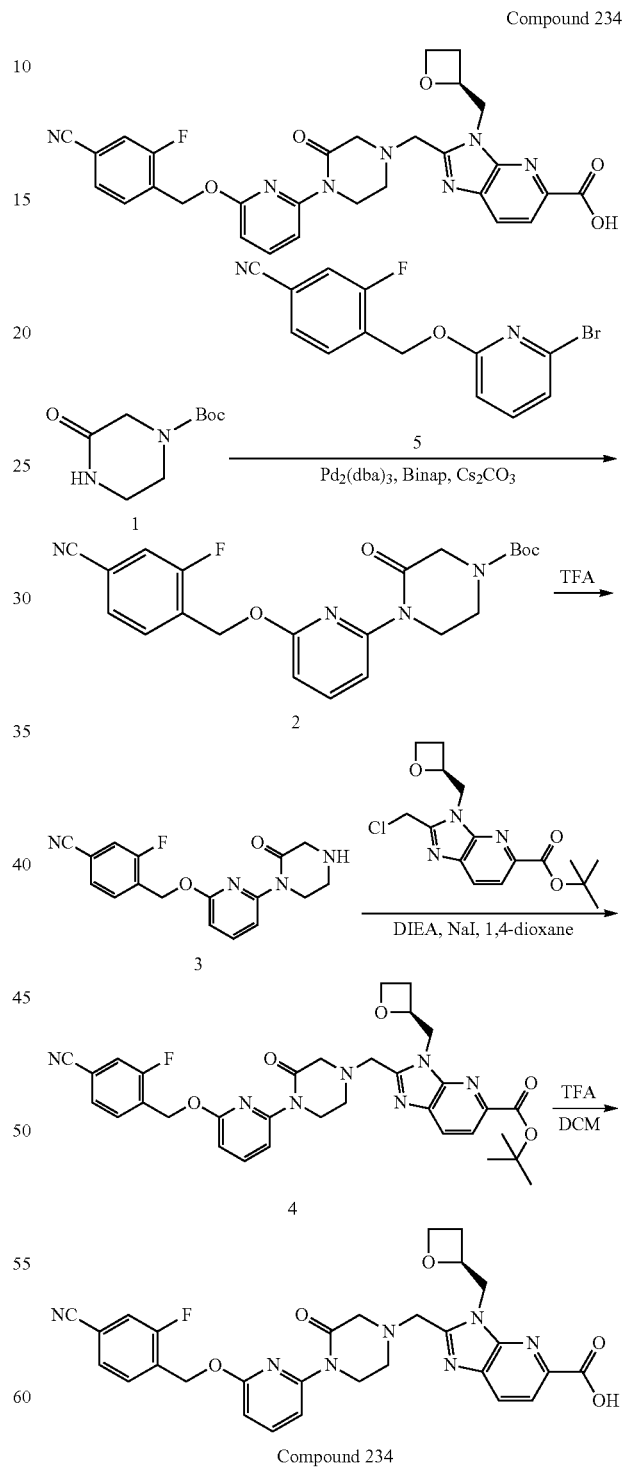

Step 1

A mixture of tert-butyl 3-oxopiperazine-1-carboxylate (0.5 g, 2.50 mmol), 4-[(6-bromo-2-pyridyl)oxymethyl]-3- fluoro-benzonitrile (767 mg, 2.50 mmol), (1E,4E)-1,5-diphenylpenta-1,4-dien-3-one palladium (229 mg, 0.249 mmol), benzyl-[1-[2-[benzyl(phenyl)phosphanyl]-1-naphthyl]-2-naphthyl]-phenyl-phosphane (325 mg, 0.499 mmol), cesium carbonate (2.44 g, 7.49 mmol) in Toluene (30 mL) was stirred for 1 h at 100° C. under N₂, until the reaction was complete as indicated by LCMS, the reaction mixture was filtered through a pad of Celite with EtOAc, and the combined organics were concentrated in vacuo, purified by silica gel chromatography (Hexanes:EtOAc=4:1) to give the desired product tert-butyl 4-[6-[(4-cyano-2-fluoro-phenyl)methoxy]-2-pyridyl]-3-oxo-piperazine-1-carboxylate (1.5 g, crude) as yellow solid. LCMS: [M+H]⁺=427.0; Retention time (10 mM NH₄HCO₃)=1.95 min.

Step 2

A mixture of tert-butyl 4-[6-[(4-cyano-2-fluoro-phenyl)methoxy]-2-pyridyl]-3-oxo-piperazine-1-carboxylate (400 mg, 0.938 mmol) in Dichloromethane (10 mL) was added 2,2,2-trifluoroacetic acid (7.40 g, 64.90 mmol, 5 mL) stirred for 0.5 h at rt in a RBF under N₂, until the reaction was complete as indicated by LCMS, the reaction mixture was concentrated in vacuo to give the desired product 3-fluoro-4-[[6-(2-oxopiperazin-1-yl)-2-pyridyl]oxymethyl]benzonitrile (300 mg, crude) as yellow solid. LCMS: [M+H]⁺= 327.1; Retention time (10 mM NH₄HCO₃)=1.31 min.

Step 3

A mixture of 3-fluoro-4-[[6-(2-oxopiperazin-1-yl)-2-pyridyl]oxymethyl]benzonitrile (300 mg, 0.919 mmol), tert-butyl 2-(chloromethyl)-3-[[(2S)-oxetan-2-yl]methyl]imidazo[4,5-b]pyridine-5-carboxylate (311 mg, 0.919 mmol), N-ethyl-N-isopropyl-propan-2-amine (475 mg, 3.68 mmol), iodosodium (14 mg, 0.092 mmol) in Dioxane (20 mL) was stirred for 2 h at 80° C. in a RBF under N₂, until the reaction was complete as indicated by LCMS, the reaction mixture was concentrated in vacuo, purified by Prep-HPLC to give the desired product tert-butyl 2-[[4-[6-[(4-cyano-2-fluoro-phenyl)methoxy]-2-pyridyl]-3-oxo-piperazin-1-yl]methyl]-3-[[(2S)-oxetan-2-yl]methyl]imidazo[4,5-b]pyridine-5-carboxylate (210 mg, 0.334 mmol, 36.4% yield) as pale yellow solid. LCMS: [M+H]⁺=628.3; Retention time (10 mM NH₄HCO₃)=1.85 min.

Step 4

A mixture of tert-butyl 2-[[4-[6-[(4-cyano-2-fluoro-phenyl)methoxy]-2-pyridyl]-3-oxo-piperazin-1-yl]methyl]-3-[[(2S)-oxetan-2-yl]methyl]imidazo[4,5-b]pyridine-5-carboxylate (114 mg, 0.182 mmol) in dichloromethane (10 mL) was added 2,2,2-trifluoroacetic acid (7.40 g, 65 mmol, 5 mL) was stirred for 0.5 h at rt in a RBF under N₂, until the reaction was complete as indicated by LCMS, the reaction mixture was concentrated in vacuo, purified by Prep-HPLC to give the desired product 2-[[4-[6-[(4-cyano-2-fluoro-phenyl)methoxy]-2-pyridyl]-3-oxo-piperazin-1-yl]methyl]-3-[[(2S)-oxetan-2-yl]methyl]imidazo[4,5-b]pyridine-5-carboxylic acid (33 mg, 0.057 mmol, 31.3% yield) as white solid.

LCMS: [M+H]⁺=572.0; Retention time (10 mM NH4HCO3)=1.36 min.

¹H NMR (400 MHz, DMSO-D6) δ 8.12-8.10 (d, J=8.4 Hz, 1H), 7.99-7.97 (d, J=8.0 Hz, 1H), 7.90-7.88 (d, J=10.0 Hz, 1H), 7.78-7.70 (m, 3H), 7.59-7.57 (d, J=8.0 Hz, 1H), 6.74-6.72 (d, J=8.0 Hz, 1H), 5.45 (s, 2H), 5.16-5.13 (m, 1H), 4.83-4.78 (m, 1H), 4.69-4.65 (m, 1H), 4.49-4.44 (m, 1H), 4.38-4.33 (m, 1H), 4.15-4.03 (m, 2H), 3.85-3.82 (t, J=4.8 Hz, 2H), 3.50-3.40 (m, 2H), 2.95-2.92 (t, J=5.2 Hz, 2H), 2.70-2.65 (m, 1H), 2.47-2.44 (m, 1H).

(S)-2-((6-((4-cyano-2-fluorobenzyl)oxy)-3',3'-dimethyl-3',6'-dihydro-[2,4'-bipyridin]-1'(2'H)-yl)methyl)-1-(oxetan-2-ylmethyl)-1H-benzo[d]imidazole-6-carboxylic acid (Compound 235)

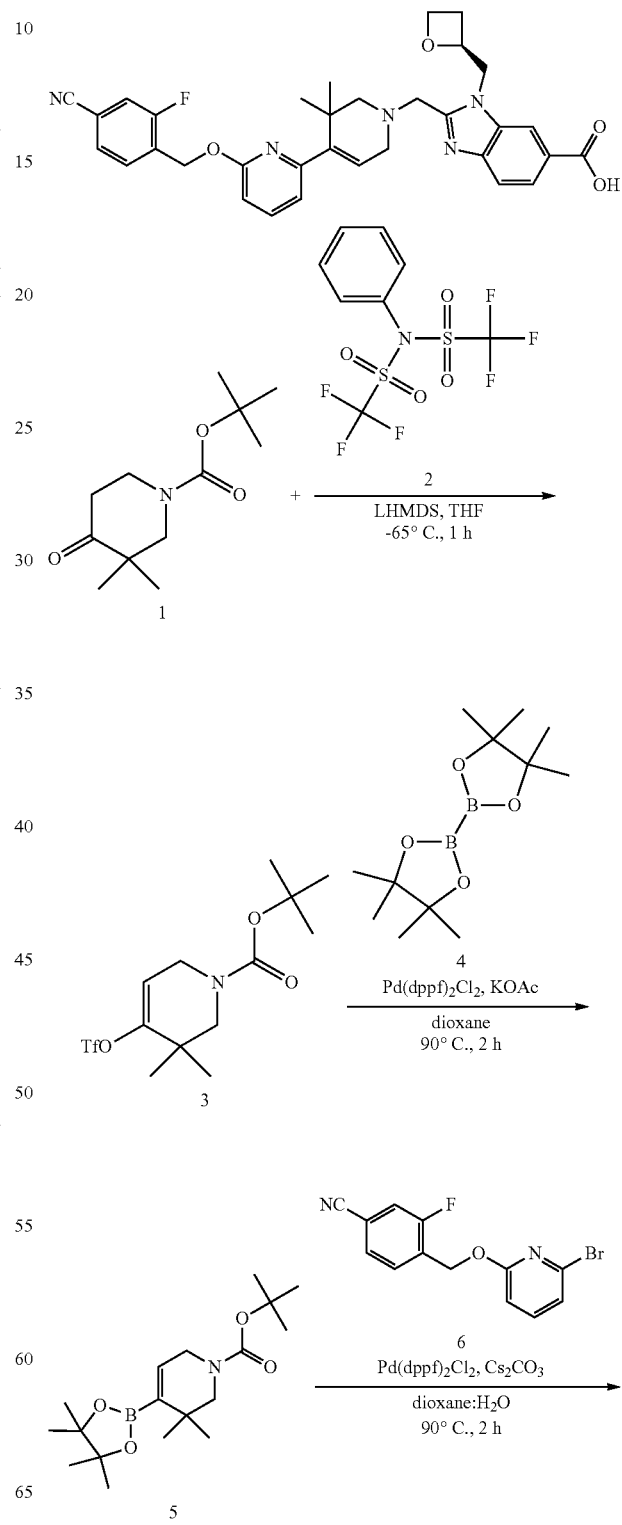

Compound 235

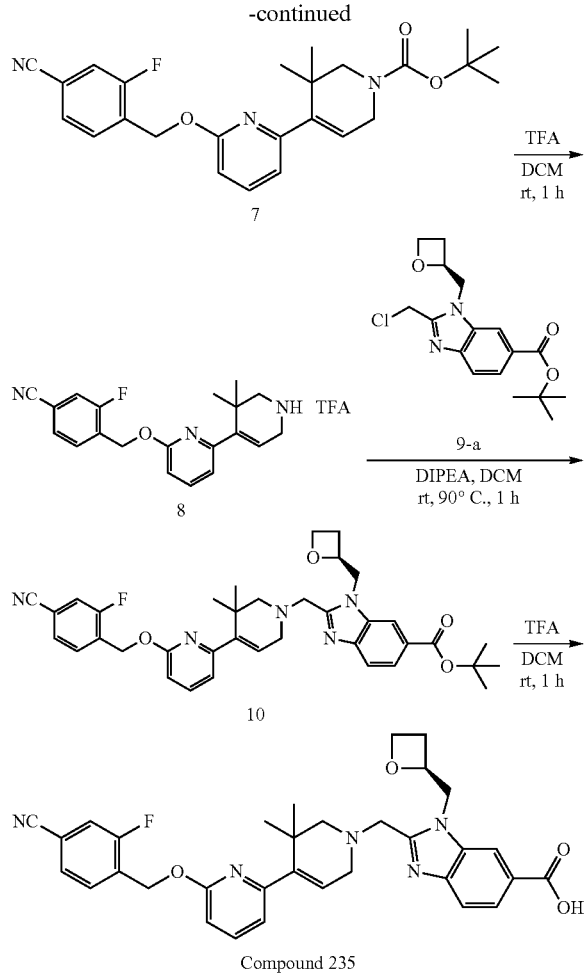

Compound 235

Step 1

A mixture of lithium bis (trimethylsilyl) amide (1 M, 14.25 mL) was added drop-wise to a solution of tert-butyl 3,3-dimethyl-4-oxo-piperidine-1-carboxylate (3 g, 13.20 mmol) in THF (30 mL), maintaining the reaction temperature below −60° C. After the addition was complete, the reaction mixture was stirred at −65° C. for 1.5 h, and then a solution of 1,1,1-trifluoro-N-phenyl-N-(trifluoromethylsulfonyl) methanesulfonamide (5.09 g, 14.25 mmol) in 5 mL of tetrahydrofuran was added drop-wise over 10 min. The mixture reaction was showed deep-brown. The solution was allowed to warm to 0° C. and r.t, and was stirred overnight. The reaction mixture was quenched with Sat. aqueous $NH_4Cl$, extracted with EA (3×60 mL), washed with brine (1×50 mL), dried and concentrated under reduced pressure and the residue was subjected to neutral alumina chromatography, eluting with hexanes:ethyl acetate (5:1) to give the desired product tert-butyl 3,3-dimethyl-4-(trifluoromethylsulfonyloxy)-2,6-dihydropyridine-1-carboxylate (2.55 g, 7.10 mmol, 53.8% yield) as a pale yellow oil. LCMS: $[M+H]^+$=304.1; Retention time (0.01% TFA)=2.26 min.

Step 2

A mixture of tert-butyl 3,3-dimethyl-4-(trifluoromethylsulfonyloxy)-2,6-dihydropyridine-1-carboxylate (500 mg, 1.39 mmol), 4,4,5,5-tetramethyl-2-(4,4,5,5-tetramethyl-1,3,2-dioxaborolan-2-yl)-1,3,2-dioxaborolane (530 mg, 2.09 mmol), $Pd(dppf)_2Cl_2$ (101 mg, 0.139 mmol) and KOAc (273 mg, 2.78 mmol) in dioxane (9 mL) was stirred for 2 h at 90° C. in a RBF under N2, until the reaction was complete as indicated by LCMS, the reaction mixture was directly used next step without further purification.

Step 3

A mixture of tert-butyl 3,3-dimethyl-4-(4,4,5,5-tetramethyl-1,3,2-dioxaborolan-2-yl)-2,6-dihydropyridine-1-carboxylate (70 mg, 0.208 mmol), 4-[(6-bromo-2-pyridyl)oxymethyl]-3-fluoro-benzonitrile (70 mg, 0.228 mmol), $Cs_2CO_3$ (6 mg, 0.090 mmol) and $Pd(dppf)_2Cl_2$ (15 mg, 0.021 mmol) in dioxane (6 mL) was stirred for 2 h at 90° C. under Argon, until the reaction was complete as indicated by LCMS, the reaction mixture was filtered through a pad of Celite with EtOAc, and the combined organics were concentrated in vacuo, purified by silica gel chromatography (Hexanes:EtOAc=10:1) to give the desired product tert-butyl 4-[6-[(4-cyano-2-fluoro-phenyl) methoxy]-2-pyridyl]-3,3-dimethyl-2,6-dihydropyridine-1-carboxylate (20 mg, 0.046 mmol, 22% yield) as a brown oil. LCMS: $[M+H]^+$=438.2; Retention time (0.01% TFA)=2.37 min.

Step 4

A mixture of tert-butyl 4-[6-[(4-cyano-2-fluoro-phenyl) methoxy]-2-pyridyl]-3,3-dimethyl-2,6-dihydropyridine-1-carboxylate (20 mg, 0.046 mmol) in DCM (4 mL) was added drop-wise TFA (1.48 g, 12.98 mmol, 1 mL) at rt, and stirred for 1 hr at rt in a RBF, until the reaction was complete as indicated by LCMS, the reaction mixture was filtered through a pad of Celite with EtOAc, and the combined organics were concentrated in vacuo, purified by silica gel chromatography (Hexanes:EtOAc=20:1) to give the desired product 4-[[6-(3,3-dimethyl-2,6-dihydro-1H-pyridin-4-yl)-2-pyridyl]oxymethyl]-3-fluoro-benzonitrile (16 mg, 0.036 mmol, 77.7% yield, TF) as a pale yellow oil. LCMS: $[M+H]^+$=338.3; Retention time (0.01% TFA)=1.40 min.

Step 5

A mixture of 4-[[6-(3,3-dimethyl-2,6-dihydro-1H-pyridin-4-yl)-2-pyridyl] oxymethyl]-3-fluoro-benzonitrile (16 mg, 0.035 mmol, TF), tert-butyl 2-(chloromethyl)-3-[[(2S)-oxetan-2-yl] methyl]benzimidazole-5-carboxylate (12 mg, 0.035 mmol) and DIPEA (23 mg, 0.177 mmol) in Dioxane (3 mL) was stirred for 1 h at 90° C., until the reaction was complete as indicated by LCMS, the reaction mixture was filtered through a pad of Celite with EtOAc, and the combined organics were concentrated in vacuo, purified by silica gel chromatography (Hexanes:EtOAc=20:1) to give the desired product tert-butyl 2-[[4-[6-[(4-cyano-2-fluoro-phenyl) methoxy]-2-pyridyl]-3,3-dimethyl-2,6-dihydropyridin-1-yl]methyl]-3-[[(2S)-oxetan-2-yl] methyl] benzimidazole-5-carboxylate (7 mg, 0.011 mmol, 29.9% yield, 96.6% purity) as a pale yellow solid.

LCMS: $[M+H]^+$=638.3; Retention time (10 mM $NH_4HCO_3$)=1.92 min.

Step 6

A mixture of tert-butyl 2-[[4-[6-[(4-cyano-2-fluoro-phenyl) methoxy]-2-pyridyl]-3,3-dimethyl-2,6-dihydropyridin-1-yl] methyl]-3-[[(2S)-oxetan-2-yl] methyl] benzimidazole-5-carboxylate (7 mg, 0.011 mmol) in DCM (4 mL) was added drop-wise TFA (1.18 g, 10.38 mmol, 0.8 mL) at rt, and was stirred for 1 hr at rt, until the reaction was complete as indicated by LCMS, the reaction mixture was concentrated in vacuo, purified by pre-HPLC (10 mM $NH_4HCO_3$) to give the desired product (S)-2-((6-((4-cyano-2-fluorobenzyl) oxy)-3',3'-dimethyl-3',6'-dihydro-[2,4'-bipyridin]-1'(2'H)-yl) methyl)-1-(oxetan-2-ylmethyl)-1H-benzo[d]imidazole-6-carboxylic acid (1.5 mg, 0.003 mmol, 23.2% yield, 98.9% purity) as a pale white solid. LCMS: $[M+H]^+$=582.3; Retention time (10 mM $NH_4HCO_3$)=1.37 min.

$^1$H NMR (400 MHz, DMSO-d6) δ 8.26 (br s, 1H), 7.89 (d, J=10 Hz, 1H), 7.81 (d, J=9.6 Hz, 1H), 7.71-7.63 (m, 3H), 7.60 (t, J=7.6 Hz, 1H), 7.01 (d, J=7.6 Hz, 1H), 6.82 (d, J=8 Hz, 1H), 5.93-5.91 (m, 1H), 5.48 (s, 2H), 5.07-5.04 (m, 1H), 4.89-4.86 (m, 1H), 4.72-4.69 (m, 1H), 4.49-4.45 (m, 1H), 4.40-4.36 (m, 1H), 4.07 (d, J=13.6 Hz, 1H), 3.89 (d, J=13.2

Hz, 1H), 3.10-3.02 (m, 2H), 2.69-2.65 (m, 1H), 2.35-2.32 (m, 1H), 2.02-1.95 (m, 2H), 1.06 (s, 3H), 0.99 (s, 3H).

(S)-2-((4-(3-((4-chloro-2-fluorobenzyl)oxy)-4-fluorophenyl)-5,6-dihydropyridin-1(2H)-yl)methyl)-3-(oxetan-2-ylmethyl)-3H-imidazo[4,5-b]pyridine-5-carboxylic acid (Compound 236)

Compound 236

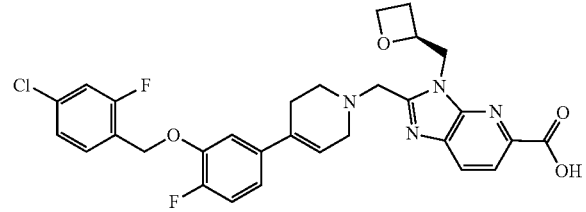

Prepared in analogous manner as or Compound
LCMS: [M+H]⁺=581.0; Retention time (10 mM NH₄HCO₃)=1.57 min.

¹H NMR (400 MHz, DMSO) δ 8.08 (d, J=8 Hz, 1H), 7.96 (d, J=8 Hz, 1H), 7.59 (t, J=8.4 Hz, 1H), 7.49 (dd, J=2, 10 Hz, 1H), 7.36-7.31 (m, 2H), 7.19-7.14 (m, 1H), 7.03-6.99 (m, 1H), 6.17 (s, 1H), 5.23 (s, 2H), 5.15-5.13 (m, 1H), 4.84-4.79 (m, 1H), 4.72-4.68 (m, 1H), 4.48-4.44 (m, 1H), 4.36-4.33 (m, 1H), 4.12-43.99 (m, 2H), 3.22-3.16 (m, 3H), 2.77-2.74 (m, 2H), 2.67-2.66 (m, 1H), 2.49-2.43 (m, 2H).

(S)-2-((4-(3-((4-chloro-2-fluorobenzyl)oxy)phenyl)-3,6-dihydropyridin-1(2H)-yl)methyl)-7-fluoro-1-(oxetan-2-ylmethyl)-1H-benzo[d]imidazole-6-carboxylic acid (Compound 237)

Compound 237

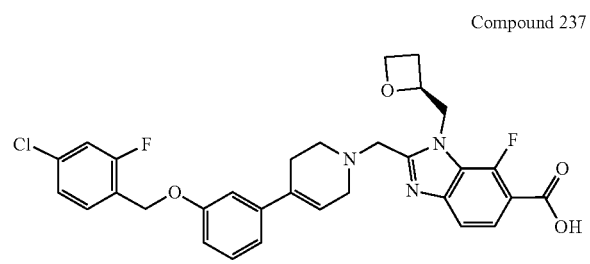 [SMILES: O=C(O)c1ccc2nc(CN3CC=C(c4cccc(OCc5ccc(Cl)cc5F)c4)CC3)n(C[C@@H]3CCO3)c2c1F]

Prepared in analogous manner as for Compound 28.
LCMS: [M+H]⁺=580.0; Retention time (10 mM NH₄HCO₃)=1.62 min H NMR (400 MHz, DMSO) δ 7.61 (dt, J=16.2, 8.3 Hz, 2H), 7.50 (dd, J=10.0, 2.0 Hz, 1H), 7.44 (d, J=8.5 Hz, 1H), 7.34 (dd, J=8.3, 1.8 Hz, 1H), 7.26 (t, J=8.0 Hz, 1H), 7.04 (d, J=7.3 Hz, 2H), 6.93-6.89 (m, 1H), 6.19 (s, 1H), 5.14 (s, 2H), 5.07 (d, J=7.3 Hz, 1H), 4.87 (dd, J=15.2, 7.4 Hz, 1H), 4.72-4.64 (m, 1H), 4.48 (dd, J=14.6, 6.6 Hz, 1H), 4.37 (dt, J=8.9, 6.0 Hz, 1H), 4.05 (d, J=13.5 Hz, 1H), 3.91 (d, J=13.5 Hz, 1H), 3.24-3.10 (m, 3H), 2.78-2.68 (m, 3H), 2.45-2.68 (m, 2H).

(S)-2-((4-(3-((4-chloro-2-fluorobenzyl)oxy)-4-fluorophenyl)-3,6-dihydropyridin-1(2H)-yl)methyl)-7-fluoro-1-(oxetan-2-ylmethyl)-1H-benzo[d]imidazole-6-carboxylic acid (Compound 238)

Compound 238

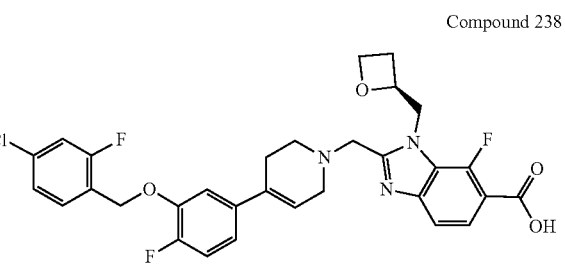

Prepared in analogous manner as for Compound 28
LCMS: [M+H]⁺=599.2; Retention time (10 mM NH₄HCO₃)=1.53 min.

¹H NMR (400 MHz, DMSO) δ 7.61 (dt, J=11.6, 7.6 Hz, 2H), 7.51 (dd, J=10.0, 2.0 Hz, 1H), 7.45 (d, J=8.5 Hz, 1H), 7.37-7.31 (m, 2H), 7.17 (dd, J=11.2, 8.5 Hz, 1H), 7.02 (d, J=2.3 Hz, 1H), 6.17 (s, 1H), 5.24 (s, 2H), 5.08 (d, J=7.6 Hz, 1H), 4.87 (dd, J=15.0, 7.4 Hz, 1H), 4.69 (d, J=12.5 Hz, 1H), 4.49 (dd, J=14.2, 7.2 Hz, 1H), 4.37 (dt, J=12.0, 6.0 Hz, 1H), 4.06 (d, J=13.6 Hz, 1H), 3.92 (d, J=13.5 Hz, 1H), 3.21 (s, 3H), 2.72 (dd, J=18.0, 6.3 Hz, 3H), 2.38 (d, J=36.7 Hz, 2H).

(S)-2-((4-(3-((4-chloro-2-fluorobenzyl)oxy)phenyl)piperidin-1-yl)methyl)-1-(oxetan-2-ylmethyl)-1H-benzo[d]imidazole-6-carboxylic acid (Compound 239)

Compound 239

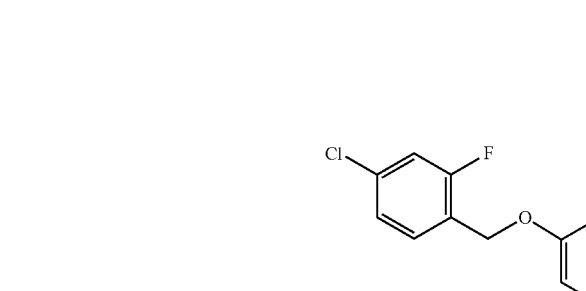

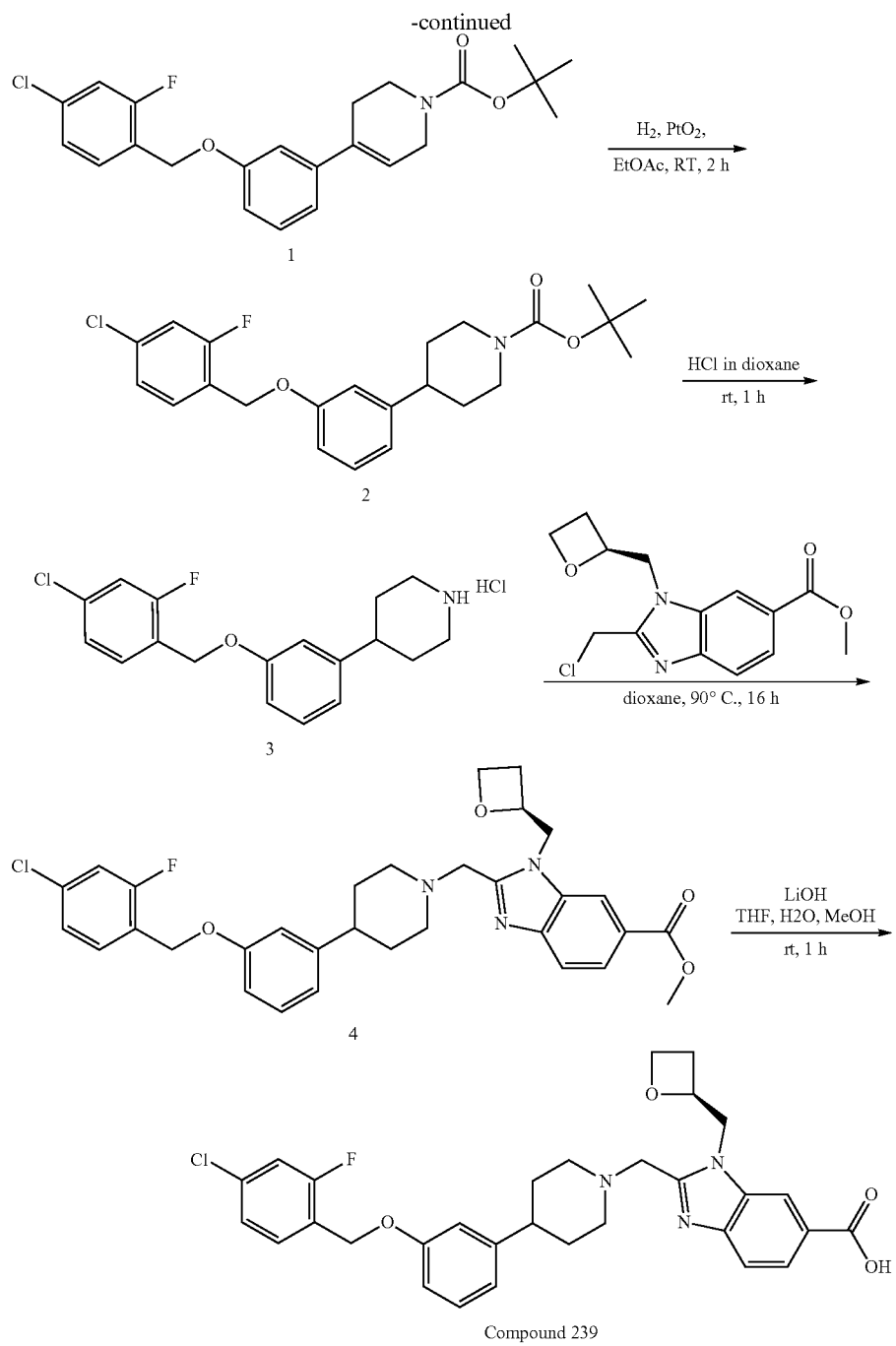

Compound 239

Step 1

A mixture of tert-butyl 4-[3-[(4-chloro-2-fluoro-phenyl)methoxy]phenyl]-3,6-dihydro-2H-pyridine-1-carboxylate (160 mg, 0.383 mmol) in ethyl acetate (2.5 mL) and then PtO$_2$ (16 mg) was added into the mixture was stirred at rt for 2 h under H$_2$ protection. LC-MS showed the starting material was consumed and desired product was detected. Then the mixture was filtered, and the filtrate was concentrated. The residue was dissolved with EtOAc and extracted with water, washed by brine, then dried and evaporated to give the product tert-butyl 4-[3-[(4-chloro-2-fluoro-phenyl)methoxy]phenyl]piperidine-1-carboxylate (155 mg, 0.369 mmol, 96.4% yield). LCMS: [M+H]$^+$=366.1; Retention time (0.01% TFA)=2.51 min.

Step 2

A mixture of tert-butyl 4-[3-[(4-chloro-2-fluoro-phenyl)methoxy]phenyl]piperidine-1-carboxylate (220 mg, 0.524 mmol) in Chlorine (20 mL), dioxane (10 mL) was stirred at rt for 1 h under N$_2$ protection. LC-MS showed the starting material was consumed and desired product was detected. Then the solvent was removed under reduced pressure to give 4-[3-[(4-chloro-2-fluoro-phenyl)methoxy]phenyl]piperidine (167 mg, 0.433 mmol, 82.7% yield). LCMS: [M+H]$^+$= 320.0; Retention time (0.01% TFA)=1.78 min.

Step 3

A mixture of 4-[3-[(4-chloro-2-fluoro-phenyl)methoxy]phenyl]piperidine (167 mg, 0.522 mmol), methyl 2-(chloromethyl)-3-[[(2S)-oxetan-2-yl]methyl]benzimidazole-5- carboxylate (154 mg, 0.522 mmol), N-ethyl-N-isopropyl-propan-2-amine (675 mg, 5.22 mmol), iodosodium (8 mg, 0.052 mmol) in dioxane (10 mL) was stirred at 90° C. for 16 h under N₂ protection. LC-MS showed the starting material was consumed and desired product was detected. Then the residue was dissolved with EtOAc and washed with saturated aq. NH₄Cl and brine, dried and evaporated to give methyl 2-[[4-[3-[(4-chloro-2-fluoro-phenyl)methoxy]phenyl]-1-piperidyl]methyl]-3-[[(2S)-oxetan-2-yl]methyl]benzimidazole-5-carboxylate (200 mg, 0.301 mmol, 57.6% yield). LCMS: [M+H]⁺=578.1; Retention time (0.01% TFA)= 1.88 min.

Step 4

A mixture of methyl 2-[[4-[3-[(4-chloro-2-fluoro-phenyl)methoxy]phenyl]-1-piperidyl]methyl]-3-[[(2S)-oxetan-2-yl]methyl]benzimidazole-5-carboxylate (383 mg, 0.576 mmol), lithium hydroxide hydrate (121 mg, 2.88 mmol) in methanol (1 mL), THF (1 mL), Water (1 mL) was stirred at rt for 1 h under N₂ protection. LC-MS showed the starting material was consumed and desired product was detected. Then the residue was purified by perp-HPLC to give 2-[[4-[3-[(4-chloro-2-fluoro-phenyl)methoxy]phenyl]-1-piperidyl]methyl]-3-[[(2S)-oxetan-2-yl]methyl]benzimidazole-5-carboxylic acid (50 mg, 0.089 mmol, 15. 5% yield). LCMS: [M+H]⁺=564.0; Retention time (10 mM NH₄HCO₃)= 1.63 min.

¹H NMR (400 MHz, DMSO) δ 8.26 (d, J=0.8 Hz, 1H), 7.79 (dd, J=8.4, 6.8 Hz, 1H), 7.64-7.56 (m, 2H), 7.49 (dd, J=10.8 Hz, 1H), 7.33 (dd, J=8, 6.4 Hz, 1H), 7.21 (t, J=8 Hz, 1H), 6.88-6.82 (m, 3H), 5.10-5.08 (m, 3H), 4.83-4.78 (m, 1H), 4.65 (dd, J=15.6, 12.4 Hz, 1H), 4.52-4.47 (m, 1H), 4.40-4.35 (m, 1H), 3.94 (d, J=13.6 Hz, 1H), 3.78 (d, J=13.6 Hz, 1H), 3.00 (d, J=10.4 Hz, 1H), 2.86 (d, J=5.2 Hz, 1H), 2.73-2.67 (m, 1H), 2.49-2.40 (m, 2H), 2.25-2.13 (m, 2H), 1.77-1.57 (m, 4H).

(S)-2-((6'-((4-cyano-2-fluorobenzyl)oxy)-3,6-dihydro-2H-[1,2'-bipyridin]-4-yl)methyl)-1-(oxetan-2-ylmethyl)-1H-benzo[d]imidazole-6-carboxylic acid (Compound 240)

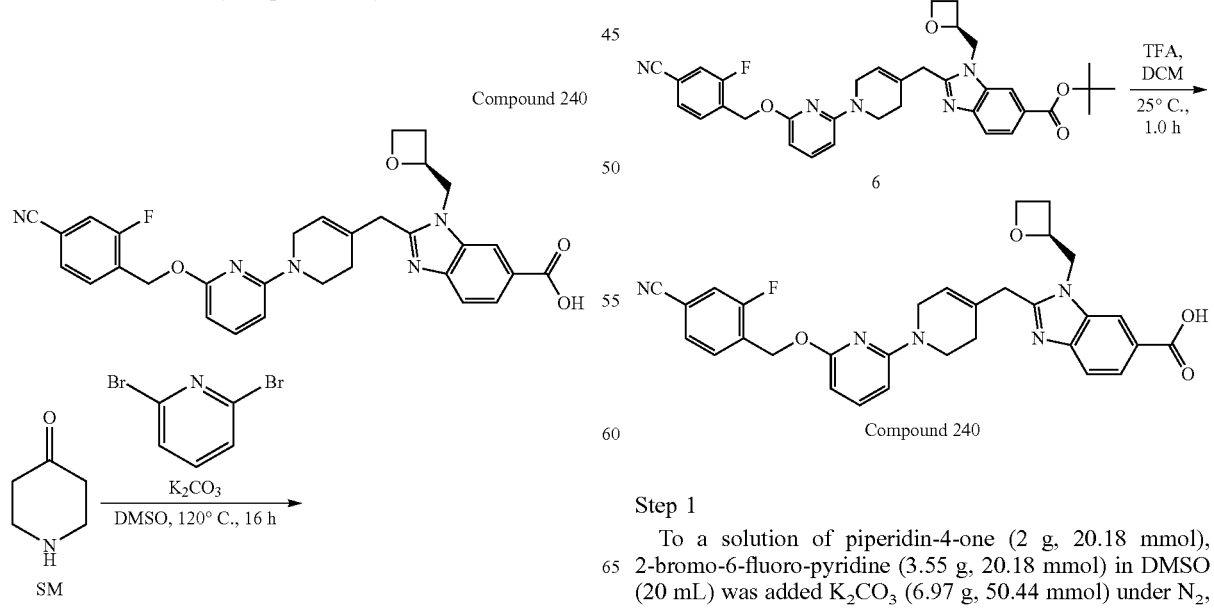

Step 1

To a solution of piperidin-4-one (2 g, 20.18 mmol), 2-bromo-6-fluoro-pyridine (3.55 g, 20.18 mmol) in DMSO (20 mL) was added K₂CO₃ (6.97 g, 50.44 mmol) under N₂, the mixture was stirred at 120° C. for 16 h. The reaction mixture was diluted with water (50 mL) and extracted with ethyl acetate (20 mL×3). The combined organics were washed with brine (20 mL×3), dried over $Na_2SO_4$ and concentrated to give crude product, which was purified by chromatography column on silica gel (eluting with PE:EA=10:1) to give 1-(6-bromo-2-pyridyl)piperidin-4-one (1.5 g, 26.1% yield) as yellow solid.

LCMS: $[M+H]^+$=255.0; Retention time (0.01% TFA)=1.62 min.

Step 2

To a solution of 1-(6-bromo-2-pyridyl)piperidin-4-one (1.5 g, 5.88 mmol) in toluene (20 mL) was added 2-cyanoacetic acid (500 mg, 5.88 mmol). The mixture was stirred at 125° C. for 16 h under $N_2$. The solution was diluted with water (20 mL) and extracted with ethyl acetate (20 mL×3). The combined organics were washed with brine (20 mL×3), dried over $Na_2SO_4$ and concentrated to give crude product, which was purified by chromatography column on silica gel (eluting with PE:EA=10:1) to give 2-[1-(6-bromo-2-pyridyl)-3,6-dihydro-2H-pyridin-4-yl]acetonitrile (0.8 g, 36.8% yield) as yellow oil.

LCMS: $[M+H]^+$=278.0, 280.0; Retention time (0.01% TFA)=1.76 min.

Step 3

A mixture of 2-[1-(6-bromo-2-pyridyl)-3,6-dihydro-2H-pyridin-4-yl]acetonitrile (800 mg, 2.88 mmol) in HCl (10 mL) was stirred at 100° C. for 2 h under $N_2$. LCMS showed the reaction was completed, the mixture was cooled to 25° C., the mixture was diluted with saturated aq. $NaHCO_3$ until pH was adjusted to 5, and extracted with DCM (50 mL×3). The combined organics were washed with brine (20 mL×3), dried over $Na_2SO_4$ and concentrated to give crude product, which was purified by chromatography column on silica gel (eluting with PE:EA=8:1) to give 2-[1-(6-bromo-2-pyridyl)-3,6-dihydro-2H-pyridin-4-yl]acetic acid (230 mg, 26.9% yield) as yellow oil. LCMS: $[M+H]^+$=297.0; Retention time (0.01% TFA)=1.64 min.

Step 4

To the solution of 2-[1-(6-bromo-2-pyridyl)-3,6-dihydro-2H-pyridin-4-yl]acetic acid (229 mg, 0.771 mmol, 1.0 eq) in DCM (10 mL) was added tert-butyl 4-amino-3-[[(2S)-oxetan-2-yl]methylamino]benzoate (215 mg, 0.771 mmol, the synthesis is disclosed in international application WO/2018/109607, which is incorporated herein by reference), HATU (589 mg, 1.54 mmol) and DIPEA (299 mg, 2.31 mmol) at 0° C., the reaction mixture was stirred at 25° C. for 2 h. The solution was diluted with Saturated ammonium chloride solution (20 mL) and extracted with DCM (20 mL×3). The combined organics were washed with brine (20 mL×3), dried over $Na_2SO_4$ and concentrated to give crude product, which was purified by chromatography column on silica gel (eluting with PE:EA=2:1) to give tert-butyl 4-[[2-[1-(6-bromo-2-pyridyl)-3,6-dihydro-2H-pyridin-4-yl]acetyl]amino]-3-[[(2S)-oxetan-2-yl]methylamino]benzoate (220 mg, 46.5% yield) as yellow oil. LCMS: $[M+H]^+$=557.2; Retention time (0.01% TFA)=2.16 min.

Step 5

A mixture of tert-butyl 4-[[2-[1-(6-bromo-2-pyridyl)-3,6-dihydro-2H-pyridin-4-yl]acetyl]amino]-3-[[(2S)-oxetan-2-yl]methylamino]benzoate (220 mg, 0.395 mmol) in acetic acid (10 mL) under $N_2$ was stirred at 60° C. for 1 h. LCMS showed the reaction was completed. The mixture was cooled to 25° C., diluted with water (20 mL) and extracted with ethyl acetate (20 mL×3). The combined organics were washed with brine (20 mL×3), dried over $Na_2SO_4$ and concentrated to give tert-butyl 2-[[1-(6-bromo-2-pyridyl)-3,6-dihydro-2H-pyridin-4-yl]methyl]-3-[[(2S)-oxetan-2-yl]methyl]benzimidazole-5-carboxylate (200 mg, 93.9% yield) as yellow oil. LCMS: $[M+H]^+$=539.2; Retention time (0.01% TFA)=1.67 min.

Step 6

A mixture of tert-butyl 2-[[1-(6-bromo-2-pyridyl)-3,6-dihydro-2H-pyridin-4-yl]methyl]-3-[[(2S)-oxetan-2-yl]methyl]benzimidazole-5-carboxylate (80 mg, 148 mmol), 3-fluoro-4-(hydroxymethyl)benzonitrile (27 mg, 0.178 mmol), $Pd_2(dba)_3$ (14 mg, 15 mmol), JohnPhos (9 mg, 0.030 mmol, 0.2 eq) and $Cs_2CO_3$ (77 mg, 0.237 mmol) in Dioxane (6 mL) were stirred at 90° C. for 16 h under $N_2$, LCMS showed the reaction was completed, the mixture was cooled to 25° C., the mixture was diluted with ethyl acetate (20 mL), filtered through a pad of celite, the filtrate was concentrated to give the crude product, which was purified by Prep-HPLC to give the desired product tert-butyl 2-[[1-[6-[(4-cyano-2-fluoro-phenyl)methoxy]-2-pyridyl]-3,6-dihydro-2H-pyridin-4-yl]methyl]-3-[[(2S)-oxetan-2-yl]methyl]benzimidazole-5-carboxylate (110 mg, crude) as pale yellow solid. LCMS: $[M+H]^+$=610.2; Retention time (0.01% TFA)=1.75 min.

Step 7

To a solution of tert-butyl 2-[[1-[6-[(4-cyano-2-fluorophenyl)methoxy]-2-pyridyl]-3,6-dihydro-2H-pyridin-4-yl]methyl]-3-[[(2S)-oxetan-2-yl]methyl]benzimidazole-5-carboxylate (110 mg, 0.180 mmol) in DCM (3 mL) was added TFA (1 mL), the mixture was stirred at 90° C. for 1 hr. The reaction mixture was diluted with water (50 mL) and extracted with ethyl acetate (20 mL×3). The combined organics were washed with brine (20 mL×3), dried over $Na_2SO_4$ and concentrated to give crude product, which was purified by Prep-HPLC to give the desired product (S)-2-((6'-((4-cyano-2-fluorobenzyl)oxy)-3,6-dihydro-2H-[1,2'-bipyridin]-4-yl)methyl)-1-(oxetan-2-ylmethyl)-1H-benzo[d]imidazole-6-carboxylic acid (5.6 mg, 5.6% yield) as white solid.

LCMS: $[M+H]^+$=554.0; Retention time (10 mM NH4HCO3)=1.56 min.

$^1$H NMR (400 MHz, DMSO) δ 8.22-8.20 (brs, 1H), 7.91 (d, J=8.7 Hz, 1H), 7.80 (dd, J=8.5, 1.5 Hz, 1H), 7.73-7.70 (m, 1H), 7.69-7.64 (m, 2H), 7.50 (t, J=8.0 Hz, 1H), 6.65-6.59 (m, 1H), 6.44 (d, J=8.2 Hz, 1H), 6.12 (d, J=7.6 Hz, 1H), 5.45 (s, 2H), 5.04-4.97 (m, 1H), 4.69 (dd, J=15.5, 6.8 Hz, 1H), 4.60-4.53 (m, 1H), 4.48-4.42 (m, 1H), 4.30 (dt, J=9.1, 6.0 Hz, 1H), 3.68-3.58 (m, 4H), 3.31-3.29 (m, 2H), 3.17-3.08 (m, 2H), 2.70-2.65 (m, 1H), 2.35-2.31 (m, 1H).

(S)-2-((6-((1-methyl-1H-benzo[d]imidazol-6-yl)methoxy)-3,6'-dihydro-[2,4'-bipyridin]-1'(2'H)-yl)methyl)-1-(oxetan-2-ylmethyl)-1H-benzo[d]imidazole-6-carboxylic acid (Compound 241)

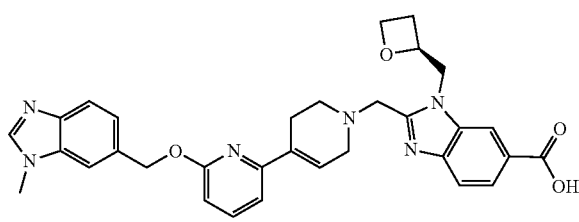

Compound 241

Prepared in analogous manner as for Compound 19

LCMS: [M+H]$^+$=566.2; Retention time (10 mM NH$_4$HCO$_3$)=1.32 min.

$^1$H NMR (400 MHz, DMSO) δ 8.28 (s, 1H), 8.18 (s, 1H), 7.82 (d, J=7.8 Hz, 1H), 7.68 (s, 3H), 7.62 (d, J=8.2 Hz, 1H), 7.31 (d, J=8.3 Hz, 1H), 7.08 (d, J=7.5 Hz, 1H), 6.80 (s, 1H), 6.73 (d, J=8.1 Hz, 1H), 5.49 (s, 2H), 5.07 (d, J=5.1 Hz, 1H), 4.84-4.77 (m, 1H), 4.66 (d, J=12.7 Hz, 1H), 4.49-4.43 (m, 1H), 4.36 (d, J=9.1 Hz, 1H), 4.20-3.95 (m, 2H), 3.81 (s, 3H), 2.75-2.65 (m, 2H), 2.63-2.55 (m, 2H), 2.46-2.30 (m, 4H).

(S)-1-(oxetan-2-ylmethyl)-2-((6-((4-(pyridin-3-yl) benzyl)oxy)-3',6'-dihydro-[2,4'-bipyridin]-1'(2'H)-yl) methyl)-1H-benzo[d]imidazole-6-carboxylic acid (Compound 242)

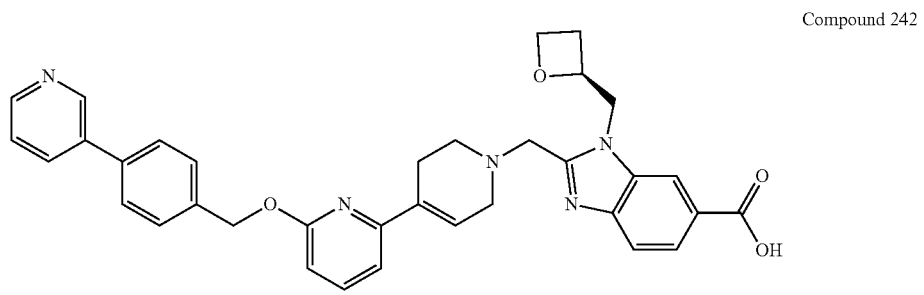 [SMILES: O=C(O)c1ccc2nc(CN3CC=C(c4cccc(OCc5ccc(-c6cccnc6)cc5)n4)CC3)n(C[C@@H]3CCO3)c2c1]

Compound 242

Prepared in analogous manner as for Compound 19

LCMS: [M+H]$^+$=598.2; Retention time (10 mM NH$_4$HCO$_3$)=1.39 min.

$^1$H NMR (400 MHz, MeOD) δ 8.95 (d, J=1.7 Hz, 1H), 8.64 (d, J=4.2 Hz, 1H), 8.43 (d, J=8.1 Hz, 1H), 8.34 (s, 1H), 8.04 (dd, J=8.5, 1.4 Hz, 1H), 7.83-7.71 (m, 5H), 7.65-7.59 (m, 2H), 7.17 (d, J=14.4 Hz, 1H), 6.82 (d, J=6.9 Hz, 1H), 6.77 (s, 1H), 5.50 (s, 2H), 5.22-5.17 (m, 1H), 4.94 (s, 2H), 4.76 (d, J=6.9 Hz, 1H), 4.69-4.59 (m, 2H), 4.44-4.33 (m, 1H), 4.22 (s, 2H), 3.79 (d, J=4.8 Hz, 2H), 3.02 (s, 2H), 2.85-2.70 (m, 1H), 2.52-2.39 (m, 1H).

(S)-2-((6-((4-(2H-1,2,3-triazol-2-yl)benzyl)oxy)-3', 6'-dihydro-[2,4'-bipyridin]-1'(2'H)-yl)methyl)-1-(oxetan-2-ylmethyl)-1H-benzo[d]imidazole-6-carboxylic acid (Compound 243)

Compound 243

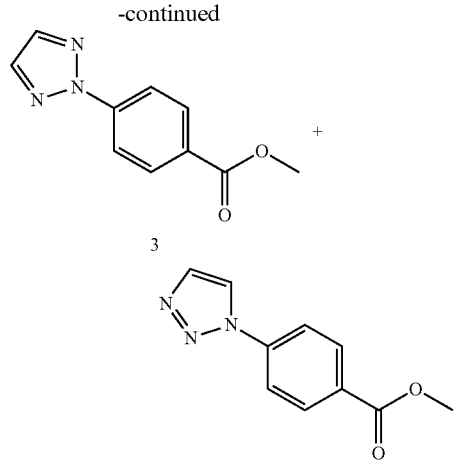

-continued

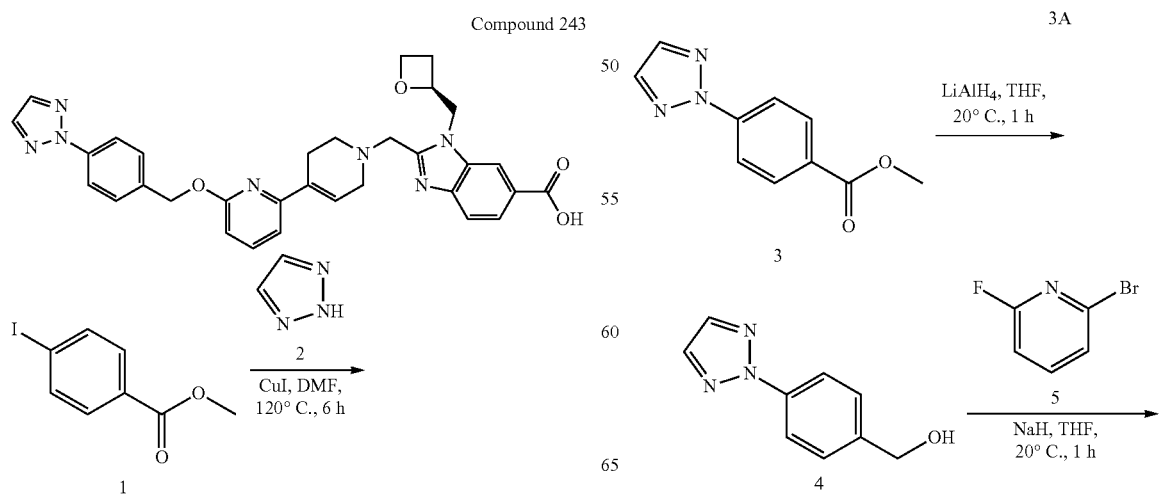

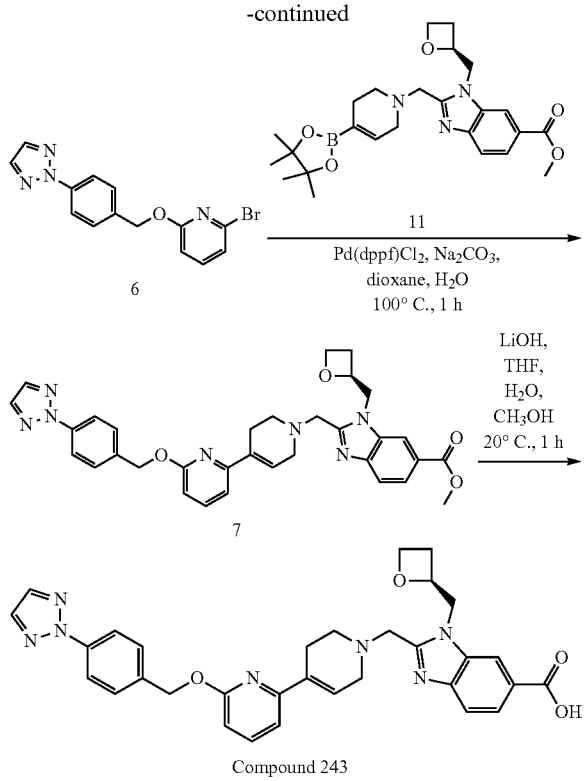

Compound 243

Step 1

A mixture of N1,N2-dimethylcyclohexane-1,2-diamine (163 mg, 1.14 mmol), methyl 4-iodobenzoate (3.0 g, 11.45 mmol), 2H-triazole (1.19 g, 17.17 mmol), iodocopper (218 mg, 1.14 mmol), cesium carbonate (5.60 g, 17.17 mmol) in DMF (30 mL) was stirred for 16 h at 120° C. under $N_2$, until the reaction was complete as indicated by TLC, the reaction mixture was filtered through a pad of Celite with EtOAc, and the combined organics were concentrated in vacuum and purified by silica gel chromatography (Hexanes:EtOAc=10:1) to give the desired product methyl 4-(triazol-2-yl)benzoate (720 mg, 3.54 mmol, 31.0% yield) and side product methyl 4-(triazol-1-yl)benzoate (430 mg, 2.12 mmol, 18.5% yield) as pale yellow solid.

Step 2

A mixture of methyl 4-(triazol-2-yl)benzoate (200 mg, 0.984 mmol), lithium aluminium hydride (37 mg, 0.984 mmol) in THF (10 mL) was stirred for 2 h at 30° C. under $N_2$, until the reaction was complete as indicated by TLC, the reaction mixture was filtered through a pad of Celite with EtOAc, and the combined organics were concentrated in vacuo and purified by silica gel chromatography (Hexanes:EtOAc=10:1) to give the desired product [4-(triazol-2-yl)phenyl]methanol (150 mg, 0.856 mmol, 87.0% yield) as pale yellow solid. LCMS: [M+H]$^+$=176; Retention time (0.01% $NH_4HCO_3$)=1.15 min.

Step 3

A mixture of 2-bromo-6-fluoro-pyridine (151 mg, 0.856 mmol), [4-(triazol-2-yl)phenyl]methanol (150 mg, 0.856 mmol) and Sodium hydride (20 mg, 0.856 mmol) in THF (10 mL) was stirred for 2 h at 30° C. in a RBF under $N_2$, until the reaction was complete as indicated by LCMS, the reaction mixture was filtered through a pad of Celite with EtOAc, and the combined organics were concentrated in vacuum, purified by silica gel chromatography (Hexanes:EtOAc=20:1) to give the desired product 2-bromo-6-[[4-(triazol-2-yl)phenyl]methoxy]pyridine (170 mg, 0.513 mmol, 60.0% yield) as pale yellow solid.

LCMS: [M+H]$^+$=176.0; Retention time (0.01% TFA)= 1.40 min.

Step 4

A mixture of methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (148 mg, 0.317 mmol), 2-bromo-6-[[4-(triazol-2-yl)phenyl]methoxy]pyridine (105 mg, 0.317 mmol) and sodium carbonate (101 mg, 0.951 mmol) in water (4 mL) and dioxane (15 mL) was stirred for 2 h at 100° C. under $N_2$, until the reaction was complete as indicated by LCMS, the reaction mixture was filtered through a pad of Celite with EtOAc, and the combined organics were concentrated in vacuo, purified by silica gel chromatography (DCM:MeOH=20:1) to give the desired product methyl 3-[[(2S)-oxetan-2-yl]methyl]-2-[[4-[6-[[4-(triazol-2-yl)phenyl]methoxy]-2-pyridyl]-3,6-dihydro-2H-pyridin-1-yl]methyl]benzimidazole-5-carboxylate (160 mg, 0.270 mmol, 85.3% yield) as pale yellow solid.

LCMS: [M+H]$^+$=592.0; Retention time (0.01% $NH_4HCO_3$)= 1.77 min.

Step 5

A mixture of methyl 3-[[(2S)-oxetan-2-yl]methyl]-2-[[4-[6-[[4-(triazol-2-yl)phenyl]methoxy]-2-pyridyl]-3,6-dihydro-2H-pyridin-1-yl]methyl]benzimidazole-5-carboxylate (160 mg, 0.270 mmol), lithium hydroxide hydrate (11 mg, 0.270 mmol) in Methanol (1 mL) and Water (1 mL) was stirred for 2 h at 20° C. in a RBF under $N_2$ until the reaction was complete as indicated by LCMS, the reaction mixture was adjusted to pH=2 with aq. HCl, purified by Prep-HPLC to give the desired product 3-[[(2S)-oxetan-2-yl]methyl]-2-[[4-[6-[[4-(triazol-2-yl)phenyl]methoxy]-2-pyridyl]-3,6-dihydro-2H-pyridin-1-yl]methyl]benzimidazole-5-carboxylic acid (68 mg, 0.118 mmol, 43.5% yield) as pale yellow solid.

LCMS: [M+H]$^+$=578.0; Retention time (0.01% TFA)= 1.54 min.

$^1$H NMR (400 MHz, DMSO) δ 8.25 (s, 1H), 8.11 (s, 2H), 8.01 (d, J=8.4 Hz, 2H), 7.82 (d, J=8.4 Hz, 1H), 7.74-7.57 (m, 4H), 7.08 (d, J=7.5 Hz, 1H), 6.76 (d, J=7.9 Hz, 2H), 5.44 (s, 2H), 5.06 (d, J=4.9 Hz, 1H), 4.71 (dd, J=51.6, 10.1 Hz, 3H), 4.40 (dd, J=42.7, 7.6 Hz, 3H), 3.99 (dd, J=60.9, 13.5 Hz, 4H), 3.25 (s, 7H), 2.75 (s, 2H), 2.70-2.58 (m, 2H), 2.40 (d, J=7.8 Hz, 2H).

(S)-2-((6-((4-(1H-1,2,3-triazol-1-yl)benzyl)oxy)-3,
6'-dihydro-[2,4'-bipyridin]-1'(2'H)-yl)methyl)-1-
(oxetan-2-ylmethyl)-1H-benzo[d]imidazole-6-car-
boxylic acid (Compound 244)

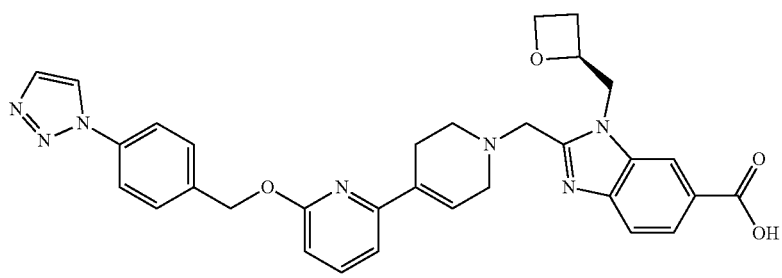

Compound 244

Prepared in analogous manner as for Compound 19

LCMS: [M+H]$^+$=578.0; Retention time (0.01% TFA) =1.29 min.

$^1$H NMR (400 MHz, DMSO) δ 8.81 (s, 1H), 8.25 (s, 1H), 8.01-7.86 (m, 4H), 7.81 (d, J=8.3 Hz, 1H), 7.73-7.58 (m, 5H), 7.08 (d, J=7.5 Hz, 1H), 6.76 (d, J=8.0 Hz, 2H), 5.46 (s, 2H), 5.06 (d, J=6.9 Hz, 1H), 4.79 (dd, J=15.1, 7.4 Hz, 1H), 4.65 (d, J=13.2 Hz, 1H), 4.45 (s, 2H), 4.05 (s, 1H), 3.94 (s, 1H), 2.71 (d, J=32.8 Hz, 4H), 2.40 (d, J=8.5 Hz, 3H).

(S)-2-((4-(6-(4-(1H-imidazol-1-yl)benzyloxy)pyri-
din-2-yl)-5,6-dihydropyridin-1(2H)-yl)methyl)-3-
(oxetan-2-ylmethyl)-3H-imidazo[4,5-b]pyridine-5-
carboxylic acid (Compound 245)

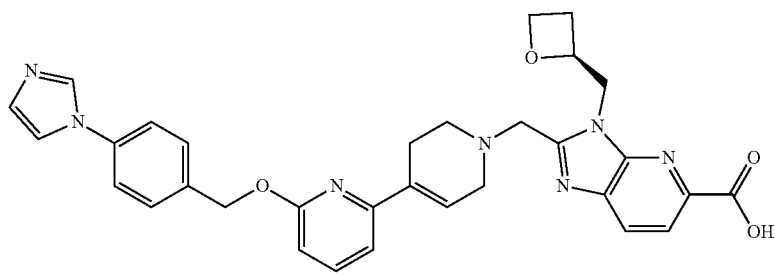

Compound 245

Prepared in analogous manner as for Compound 19

LCMS: [M+H]$^+$=579.0, Retention time (10 mM NH$_4$HCO$_3$)=1.40 min.

$^1$H NMR (400 MHz, DMSO) δ 8.26-8.23 (brs, 1H), 8.12 (d, J=8.2 Hz, 1H), 7.99 (d, J=8.2 Hz, 1H), 7.75-7.73 (m, 1H), 7.71-7.63 (m, 3H), 7.60-7.56 (m, 2H), 7.11-7.07 (m, 2H), 6.80-6.76 (m, 1H), 6.74 (d, J=8.2 Hz, 1H), 5.42 (s, 2H), 5.16-5.10 (m, 1H), 4.83 (dd, J=14.7, 6.6 Hz, 1H), 4.70 (dd, J=14.6, 4.0 Hz, 1H), 4.46 (dd, J=14.1, 7.1 Hz, 1H), 4.35 (dt, J=8.9, 6.0 Hz, 1H), 4.13 (d, J=13.6 Hz, 1H), 4.03 (d, J=13.6 Hz, 1H), 3.30-3.25 (m, 4H), 2.79-2.73 (m, 2H), 2.69-2.62 (m, 1H), 2.57-2.54 (m, 1H).

What is claimed is:

1. A compound represented by structural formula (I):

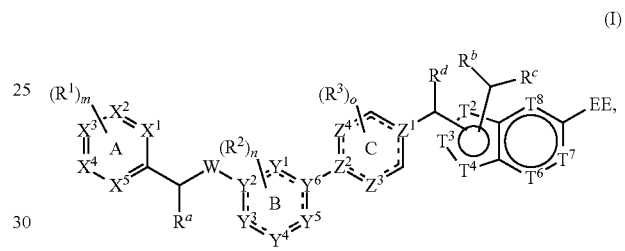

(I)

or a pharmaceutically acceptable salt, stereoisomer, solvate, or hydrate thereof, wherein:

- - - - - indicates a single bond or a double bond;

$X^1$, $X^2$, $X^3$, $X^4$, and $X^5$ are each independently selected from N and CH; wherein no more than three of $X^1$, $X^2$, $X^3$, $X^4$, and $X^5$ are N and wherein ring A does not contain 3 nitrogen ring atoms at 3 contiguous positions;

W is selected from O, S, CR$^5$R$^6$, and NR$^{5'}$;

$Y^1$, $Y^3$, $Y^4$, and $Y^5$ are each independently selected from N, NH, CH, and CH$_2$;

$Y^2$ and $Y^6$ are each independently selected from N, C, or CH;

wherein there is no more than 3 nitrogen ring atoms in ring B and wherein ring B does not contain 3 nitrogen ring atoms at 3 contiguous positions;

wherein

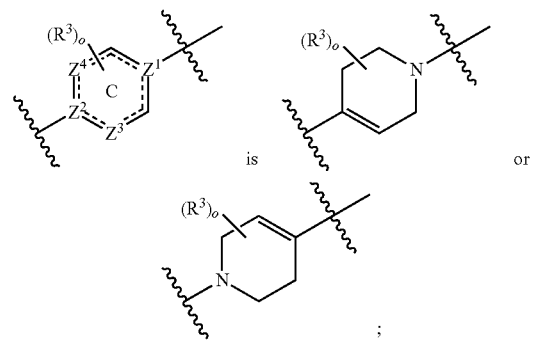

is or

;

wherein:
T², T³, and T⁴ are each independently selected from N, NR⁴, O, S, C, and CR⁴;
T⁶, T⁷, and T⁸ are each independently selected from N and CR⁴;
wherein no more than 4 of T², T³, T⁴, T⁶, T⁷, and T⁸ are selected from N, O, and S;
EE is —COOH,

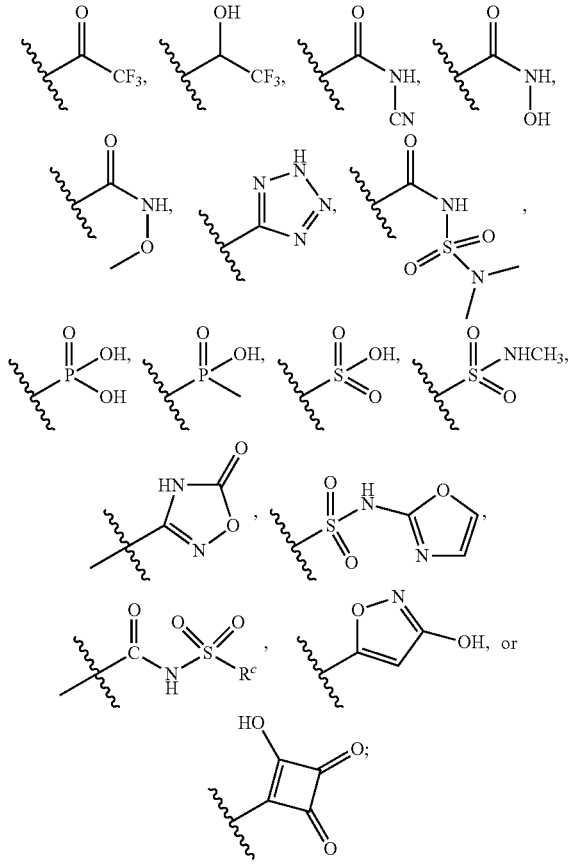

R$^a$ is selected from hydrogen, deuterium, halogen, —CN, C$_1$-C$_6$ alkyl, C$_1$-C$_6$ alkoxy, NR$^5$R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl or C$_1$-C$_6$ alkoxy represented by R$^a$ is optionally substituted with one or more groups selected from halogen, oxo, CN, OH, and C$_3$-C$_6$ saturated or partially saturated cycloalkyl; and wherein the aryl, heteroaryl, saturated or partially saturated cycloalkyl, or saturated or partially saturated heterocyclyl represented by R$^a$ or in the group represented by R$^a$ is optionally substituted with one or more groups selected from halogen, oxo, CN, OH, C$_1$-C$_3$ alkyl (optionally substituted with 1 to 3 groups selected from F, OH, and OCH$_3$), and C$_1$-C$_3$ alkoxy (optionally substituted with 1 to 3 groups selected from F, OH, and OCH$_3$), and NR$^5$R$^{6'}$;

R$^b$ is selected from hydrogen, deuterium, halogen, —CN, C$_1$-C$_6$ alkyl, C$_1$-C$_6$ alkoxy, NR$^5$R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl or C$_1$-C$_6$ alkoxy represented by R$^b$ is optionally substituted with one or more groups selected from halogen, oxo, CN, OH, and C$_3$-C$_6$ saturated or partially saturated cycloalkyl; and wherein the aryl, heteroaryl, saturated or partially saturated cycloalkyl, or saturated or partially saturated heterocyclyl represented by R$^b$ or in the group represented by R$^b$ is optionally substituted with one or more groups selected from halogen, oxo, CN, OH, C$_1$-C$_3$ alkyl (optionally substituted with 1 to 3 groups selected from F, OH, and OCH$_3$), and C$_1$-C$_3$ alkoxy (optionally substituted with 1 to 3 groups selected from F, OH, and OCH$_3$), and NR$^5$R$^{6'}$;

R$^c$ is selected from hydrogen, deuterium, halogen, —CN, C$_1$-C$_6$ alkyl, C$_1$-C$_6$ alkoxy, NR$^5$'R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl or C$_1$-C$_6$ alkoxy represented by R$^c$ is optionally substituted with one or more groups selected from halogen, oxo, CN, OH, and C$_3$-C$_6$ saturated or partially saturated cycloalkyl; and wherein the aryl, heteroaryl, saturated or partially saturated cycloalkyl, or saturated or partially saturated heterocyclyl represented by R$^c$ or in the group represented by R$^c$ is optionally substituted with one or more groups selected from halogen, oxo, CN, and NR$^5$R$^{6'}$;

R$^d$ is selected from hydrogen, deuterium, halogen, —CN, C$_1$-C$_6$ alkyl, C$_1$-C$_6$ alkoxy, NR$^5$R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl or C$_1$-C$_6$ alkoxy represented by R$^d$ is optionally substituted with one or more groups selected from halogen, oxo, CN, and saturated or partially saturated C$_3$-C$_6$ cycloalkyl; and wherein the aryl, heteroaryl, saturated or partially saturated cycloalkyl, or saturated or partially saturated heterocyclyl represented by R$^d$ or in the group represented by R$^d$ is optionally substituted with one or more groups selected from halogen, oxo, CN, and NR$^5$R$^{6'}$;

each R$^1$ is independently selected from halogen, —CN, OH, C$_1$-C$_6$ alkyl, C$_1$-C$_6$ alkoxy, C$_1$-C$_6$ alkenyl, C$_1$-C$_6$ alkynyl, NR$^5$R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl, C$_1$-C$_6$ alkoxy, C$_1$-C$_6$ alkenyl, or C1-C6 alkynyl represented by R$^1$ is optionally substituted with one or more groups selected from halogen, oxo, CN, CF$_3$, OH, OCH₃, OCH₂CH₃, and saturated or partially saturated C₃-C₆ cycloalkyl (optionally substituted with one or more groups selected from halogen, oxo, CN, CF₃, OH, OCH₃, OCH₂CH₃); and wherein the aryl, heteroaryl, saturated or partially saturated cycloalkyl, or saturated or partially saturated heterocyclyl represented by R¹ or in the group represented by R¹ is optionally substituted with one or more groups selected from halogen, oxo, CN, OH, C₁-C₃ alkyl (optionally substituted with 1 to 3 groups selected from F, OH, and OCH₃), and C₁-C₃ alkoxy (optionally substituted with 1 to 3 groups selected from F, OH, and OCH₃), and NR⁵'R⁶';

each R² is independently selected from halogen, —CN, OH, oxo, C₁-C₆ alkyl, C₁-C₆ alkoxy, NR⁵'R⁶', 6-10 membered aryl, 5-8 membered heteroaryl, 3-8 membered saturated or partially saturated cycloalkyl and 3-8 membered saturated or partially saturated heterocyclyl, wherein the C₁-C₆ alkyl or C₁-C₆ alkoxy represented by R² is optionally substituted with one or more groups selected from halogen, oxo, CN, CF₃, OH, OCH₃, OCH₂CH₃, and saturated or partially saturated C₃-C₆ cycloalkyl (optionally substituted with one or more groups selected from halogen, oxo, CN, CF₃, OH, OCH₃, OCH₂CH₃); and wherein the aryl, heteroaryl, saturated or partially saturated cycloalkyl, or saturated or partially saturated heterocyclyl represented by R² or in the group represented by R² is optionally substituted with one or more groups selected from halogen, oxo, CN, OH, C₁-C₃ alkyl (optionally substituted with 1 to 3 groups selected from F, OH, and OCH₃), and C₁-C₃ alkoxy (optionally substituted with 1 to 3 groups selected from F, OH, and OCH₃), and NR⁵'R⁶';

each R³ is independently selected from halogen, —CN, OH, oxo, C₁-C₆ alkyl, C₁-C₆ alkoxy, NR⁵'R⁶', 6-10 membered aryl, 5-8 membered heteroaryl, 3-8 membered saturated or partially saturated cycloalkyl and 3-8 membered saturated or partially saturated heterocyclyl, wherein the C₁-C₆ alkyl or C₁-C₆ alkoxy represented by R³ is optionally substituted with one or more groups selected from halogen, oxo, CN, CF₃, OH, OCH₃, OCH₂CH₃, and saturated or partially saturated C₃-C₆ cycloalkyl (optionally substituted with one or more groups selected from halogen, oxo, CN, CF₃, OH, OCH₃, OCH₂CH₃); and wherein the aryl, heteroaryl, saturated or partially saturated cycloalkyl, or saturated or partially saturated heterocyclyl represented by R³ or in the group represented by R³ is optionally substituted with one or more groups selected from halogen, oxo, CN, OH, C₁-C₃ alkyl (optionally substituted with 1 to 3 groups selected from F, OH, and OCH₃), and C₁-C₃ alkoxy (optionally substituted with 1 to 3 groups selected from F, OH, and OCH₃), and NR⁵'R⁶';

each R⁴ is H, deuterium, halogen, OH, —CN, C₁-C₆ alkyl, C₁-C₆ alkoxy, or NR⁵'R⁶', wherein the C₁-C₆ alkyl and C₁-C₆ alkoxy represented by R⁴ is optionally substituted with one or more groups selected from halogen, oxo, CN, CF₃, and saturated or partially saturated C₃-C₆ cycloalkyl (optionally substituted with one or more groups selected from halogen, oxo, CN, CF₃, OH, OCH₃, OCH₂CH₃);

R⁵ and R⁶ are each independently selected from hydrogen, deuterium, halogen, CN, OH, oxo, C₁-C₆ alkyl, C₁-C₆ alkoxy, NR⁵'R⁶', 6-10 membered aryl, 5-8 membered heteroaryl, 3-8 membered saturated or partially saturated cycloalkyl and 3-8 membered saturated or partially saturated heterocyclyl, wherein the C₁-C₆ alkyl, C₁-C₆ alkoxy, C₁-C₆ alkenyl, or C₁-C₆ alkynyl represented by R⁵ or Rᶜ is optionally substituted with one or more groups selected from halogen, oxo, CN, CF₃, OH, OCH₃, OCH₂CH₃, and saturated or partially saturated C₃-C₆ cycloalkyl (optionally substituted with one or more groups selected from halogen, oxo, CN, CF₃, OH, OCH₃, OCH₂CH₃); and wherein the aryl, heteroaryl, saturated or partially saturated cycloalkyl, or saturated or partially saturated heterocyclyl represented by R⁵ or R⁶ or in the group represented by R⁵ or R⁶ is optionally substituted with one or more groups selected from halogen, oxo, CN, OH, C₁-C₃ alkyl (optionally substituted with 1 to 3 groups selected from F, OH, and OCH₃), and C₁-C₃ alkoxy (optionally substituted with 1 to 3 groups selected from F, OH, and OCH₃), and NR⁵'R⁶';

R⁵' and R⁶' are each independently selected from hydrogen, deuterium, and C₁-C₆ alkyl;

wherein optionally two R¹; two R²; two R³; two R⁴; R¹ and R²; R² and R³; Rᵃ and R¹; Rᵃ and R²; R¹ and any of R⁵, R⁵' (in the group represented by W), or R⁶; Rᵃ and any of R⁵, R⁵ (in the group represented by W), or R⁶; R² and any of R⁵, R⁵ (in the group represented by W), or R⁶; R⁵ and R⁶; any of two groups selected from Rᶜ, Rᵈ, Rᵉ, and Rᶠ; or R⁴ and any one of Rᶜ, Rᵈ, Rᵉ, and Rᶠ; taken together with their respective intervening carbon or hetero atom(s), form phenyl, 5-6 membered heteroaryl, 4-8 membered saturated or partially saturated cycloalkyl or 4-8 membered saturated or partially saturated heterocyclyl, each of which is optionally substituted with one or more groups selected from halogen, —CN, —OH, CF₃, C₁-C₆ alkyl, C₁-C₆ alkoxy, —NH₂, —NHC₁-C₆ alkyl, —N(C₁-C₆ alkyl) 2, oxo, and saturated or partially saturated C₃-C₆ cycloalkyl, wherein the C₁-C₆ alkyl and C₁-C₆ alkoxy is optionally substituted with one or more groups selected from halogen, oxo, CN, CF₃, OH, OCH₃, OCH₂CH₃, and saturated or partially saturated C₃-C₆ cycloalkyl, wherein the cycloalkyl is optionally substituted with one or more groups selected from halogen, oxo, CN, CF₃, OH, OCH₃, OCH₂CH₃;

m is an integer selected from 0, 1, 2, 3, and 4, n is an integer selected from 0, 1, 2, 3, 4, and 5, and is an integer selected from 0, 1, 2, 3, 4, and 5.

2. The compound according to claim 1, wherein the compound is represented by the structural formula (II-A):

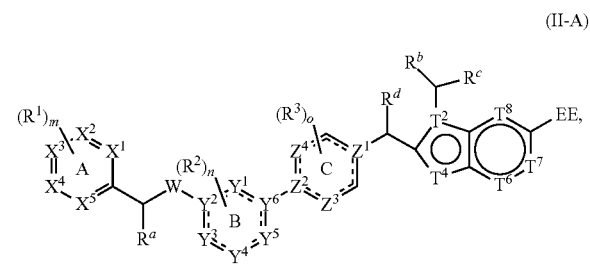

(II-A)

or a pharmaceutically acceptable salt, stereoisomer, solvate, or hydrate thereof, wherein Rᵈ is H, F, CH₃, or CF₃; or wherein the compound is represented by structural formula (III-A):

(III-A)

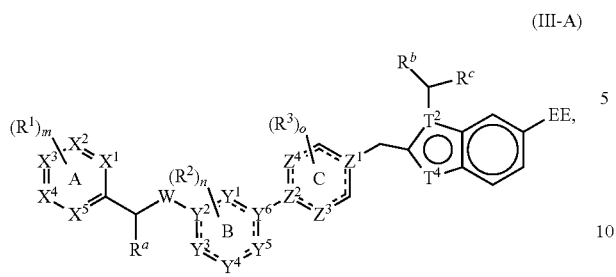

or a pharmaceutically acceptable salt, stereoisomer, solvate, or hydrate thereof, wherein T² is N, and T⁴ is N or CR⁴, wherein R⁴ is H, halogen, OH, CN, $C_1$-$C_3$ alkyl, $C_1$-$C_3$ haloalkyl, or $C_1$-$C_3$ alkoxy; or T² is C, and T⁴ is NR⁴, wherein R⁴ is H, $C_1$-$C_3$ alkyl, $C_1$-$C_3$ haloalkyl; or wherein the compound is represented by structural formula (IV-A):

(IV-A)

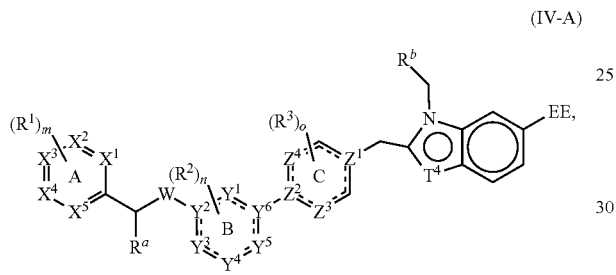

or a pharmaceutically acceptable salt, stereoisomer, solvate, or hydrate thereof, wherein T⁴ is N or CH; and R$^a$ is H, CH₃, or CF₃; or R$^a$, R¹ and X⁵, taken together with their respective intervening carbons, form 5-7 membered cycloalkenyl or 5-7 membered partially saturated monoheterocyclyl.

3. The compound according to claim 2, or a pharmaceutically acceptable salt, stereoisomer, solvate, or hydrate thereof, wherein R$^b$ is

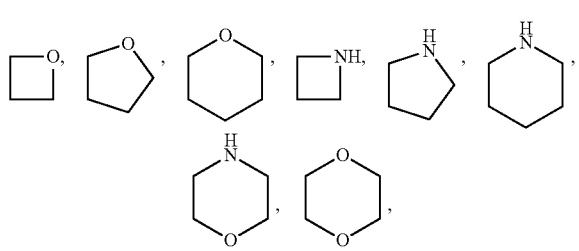

wherein R$^b$ is optionally substituted with 1 or 2 groups selected from oxo, CN, F, Cl, $C_1$-$C_3$ alkyl, and $C_1$-$C_3$ alkoxy, wherein the $C_1$-$C_3$ alkyl or $C_1$-$C_3$ alkoxy in the group represented by R$^b$ is optionally substituted with 1 or 2 groups selected from F, OH, and OCH₃, or wherein R$^b$ is

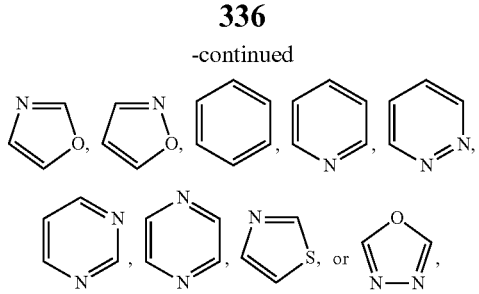

wherein R$^b$ is optionally substituted with 1 or 2 groups selected from halogen, OH, NR⁵R⁶', $C_1$-$C_3$ alkyl, and $C_1$-$C_3$ alkoxy, wherein the $C_1$-$C_3$ alkyl or $C_1$-$C_3$ alkoxy in the group represented by R$^b$ is optionally substituted with 1 or 2 groups selected from F, OH, and OCH₃.

4. The compound according to claim 2, or a pharmaceutically acceptable salt, stereoisomer, solvate, or hydrate thereof, wherein

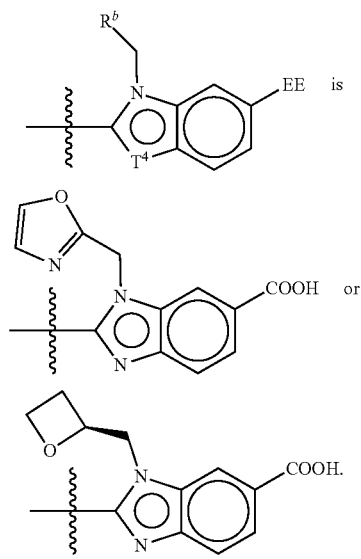

5. The compound according to claim 3, or a pharmaceutically acceptable salt, stereoisomer, solvate, or hydrate thereof, wherein

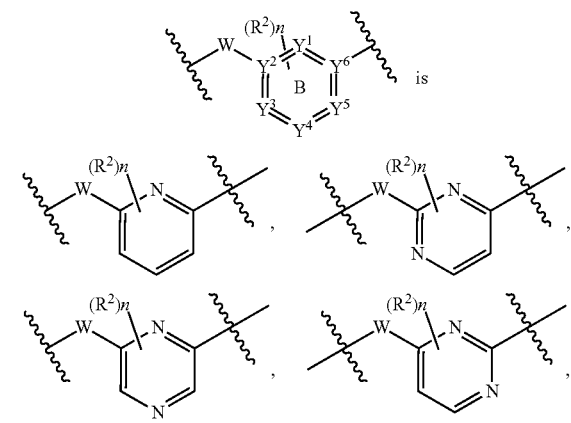

-continued

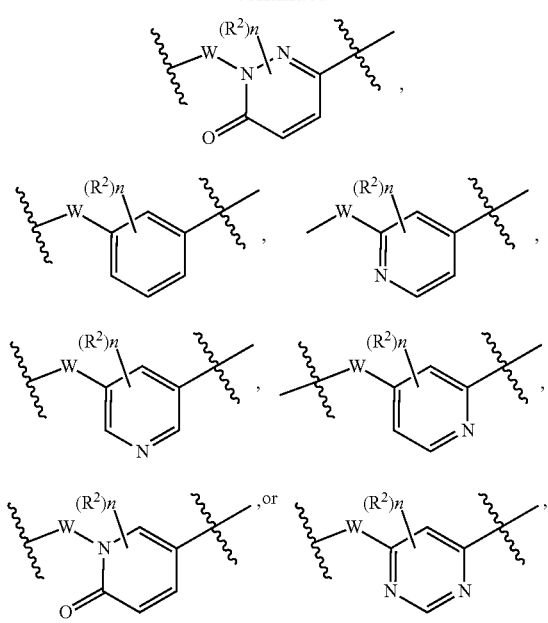

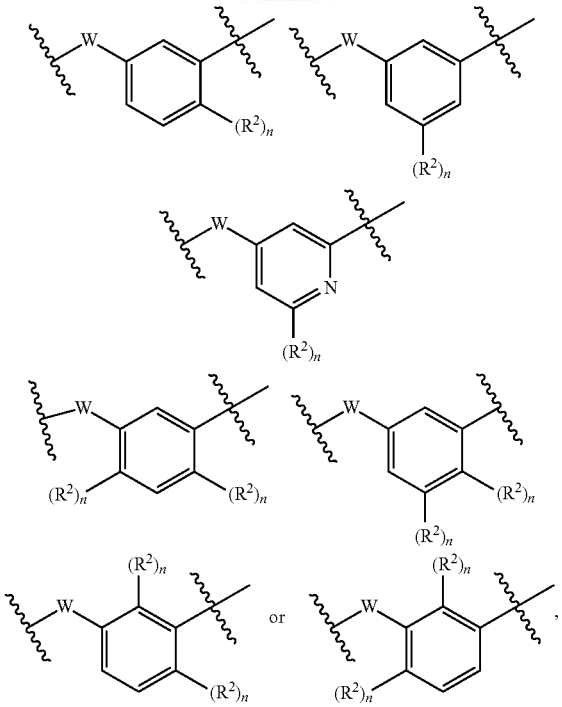

wherein each $R^2$ is independently selected from halogen, —CN, OH, oxo, $C_1$-$C_2$ alkyl, C1-C2 haloalkyl, and C1-C2 alkoxy; and n is an integer selected from 0, 1, 2, and 3.

6. The compound according to claim 4, or a pharmaceutically acceptable salt, stereoisomer, solvate, or hydrate thereof, wherein

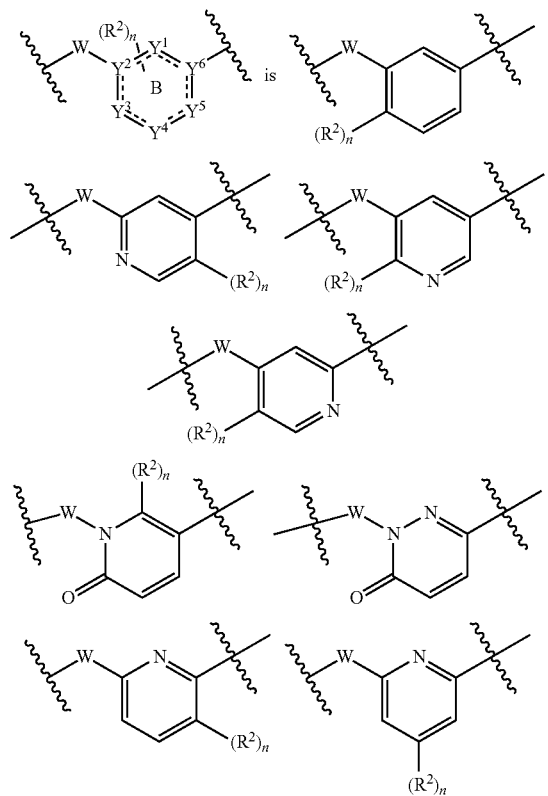

wherein $R^2$ is halogen, —CN, OH, oxo, $C_1$-$C_2$ alkyl, C1-C2 haloalkyl, or C1-C2 alkoxy, n is 0 or 1, and no more than two $R^2$ are attached to ring B.

7. The compound according to claim 5, or a pharmaceutically acceptable salt, stereoisomer, solvate, or hydrate thereof, wherein two $R^2$ groups together with ring B form a bicyclic structure:

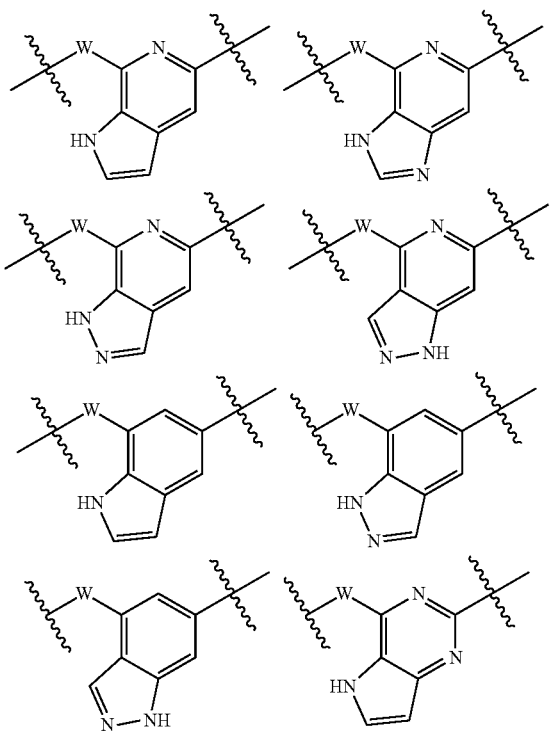

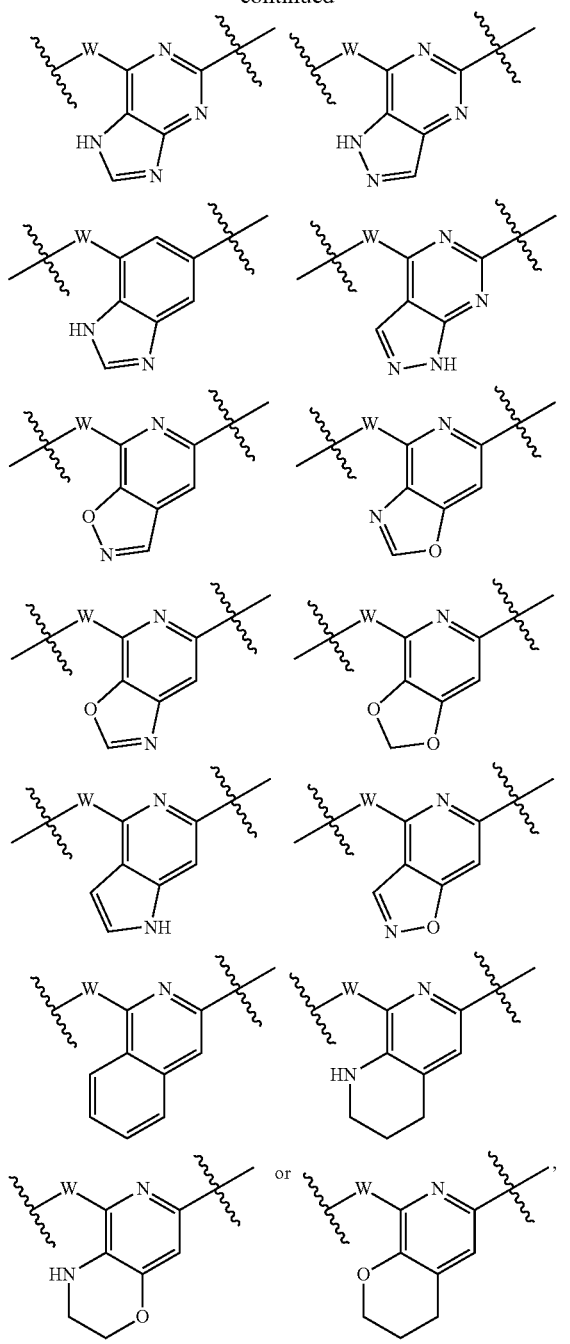

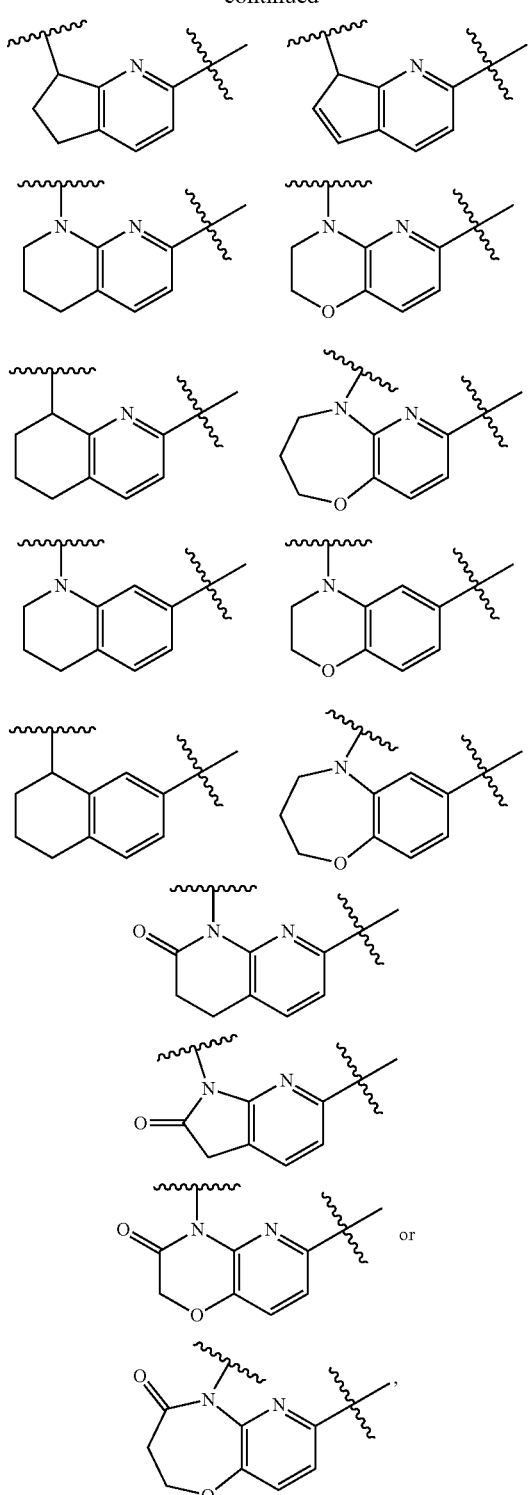

each of which is optionally substituted with 1 or 2 groups selected from halogen, oxo, CN, $CF_3$, $C_1$-$C_2$ alkyl, $C_1$-$C_2$ haloalkyl, $C_1$-$C_2$ alkoxy, —NH2, —NH$C_1$-$C_2$ alkyl, and —N($C_1$-$C_2$ alkyl)$_2$; or wherein W and ring B form a bicyclic structure:

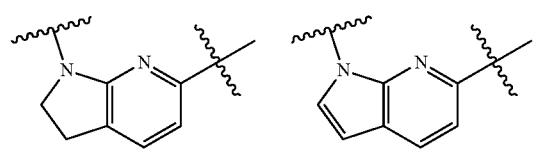

each of which is optionally substituted with 1 or 2 groups selected from halogen, oxo, CN, $CF_3$, —NH2, —NH$C_1$-$C_2$ alkyl, and —N($C_1$-$C_2$ alkyl)$_2$.

8. The compound according to claim 7, or a pharmaceutically acceptable salt, stereoisomer, solvate, or hydrate thereof, wherein two $R^2$ groups together with ring B form a bicyclic structure:

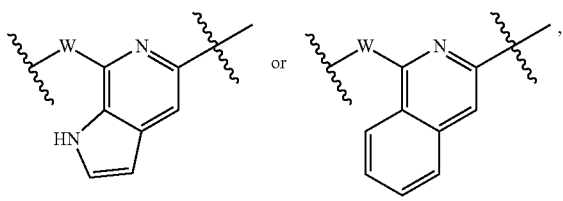

each of which is optionally substituted with halogen.

9. The compound according to claim 7, or a pharmaceutically acceptable salt, stereoisomer, solvate, or hydrate thereof, wherein ring A is

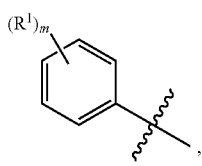

each $R^1$ is independently selected from halogen, OH, CN, $CF_3$, $C_1$-$C_2$ alkyl, $C_1$-$C_2$ haloalkyl, $C_1$-$C_2$ alkoxy, —$NH_2$, —$NHC_1$-$C_2$ alkyl, —$N(C_1$-$C_2$ alkyl$)_2$, and $C_2$-$C_4$alkynyl optionally substituted with cyclopropane; and m is an integer selected from 0, 1, 2, and 3; or
wherein ring A is

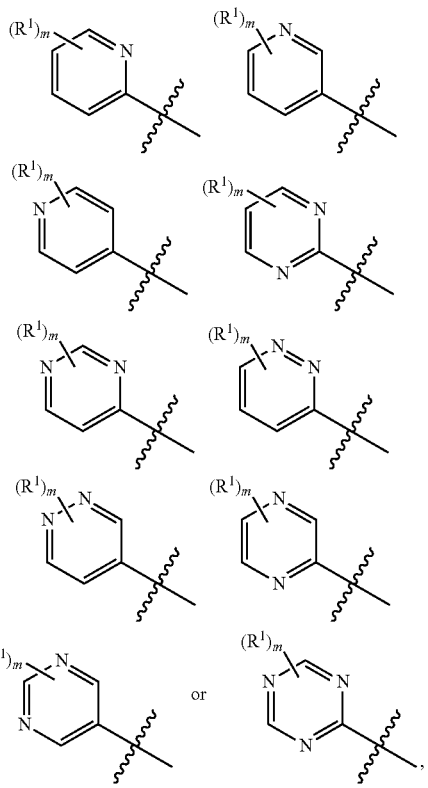

each $R^1$ is independently selected from halogen, OH, CN, $CF_3$, $C_1$-$C_2$ alkyl, $C_1$-$C_2$ haloalkyl, $C_1$-$C_2$ alkoxy, —NH2, —$NHC_1$-$C_2$ alkyl, —$N(C_1$-$C_2$ alkyl) 2, and $C_2$-$C_4$alkynyl optionally substituted with cyclopropane; and m is an integer selected from 0, 1, and 2.

10. The compound according to claim 6, or a pharmaceutically acceptable salt, stereoisomer, solvate, or hydrate thereof, wherein ring A is

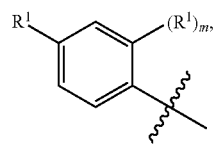

and m is 0 or 1, and $R^1$ is halogen, CN, $CH_3$, $CF_3$, OH, or $C_2$-$C_4$alkynyl optionally substituted with cyclopropane.

11. The compound according to claim 9, or a pharmaceutically acceptable salt, stereoisomer, solvate, or hydrate thereof, wherein ring A is

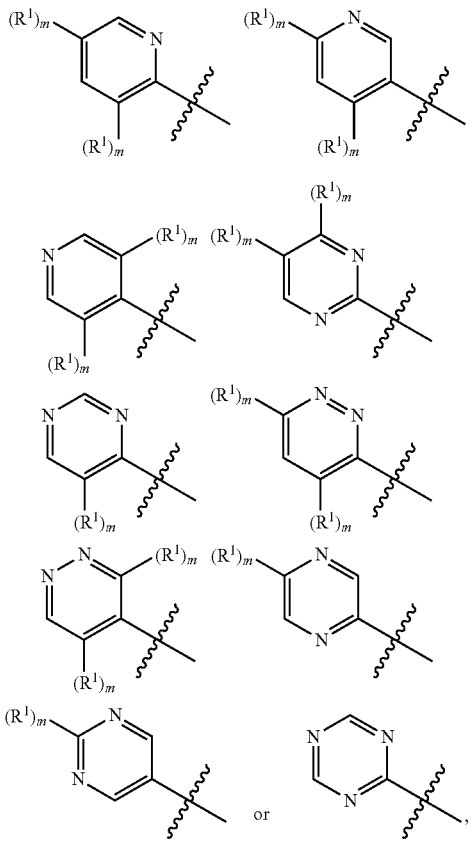

each of which is optionally substituted with halogen, OH, CN, C≡CH, $CH_3$, or $CF_3$, m is 0 or 1.

12. The compound according to claim 10 or a pharmaceutically acceptable salt, stereoisomer, solvate, or hydrate thereof, wherein W is O, NH or $CH_2$.

13. The compound according to claim 11, or a pharmaceutically acceptable salt, stereoisomer, solvate, or hydrate thereof, wherein $R^1$ is selected from halogen, CN, $CH_3$, $CF_3$, and C≡CH.

14. The compound according to claim 1, wherein the compound is represented by the structural formula (I'):

(I')

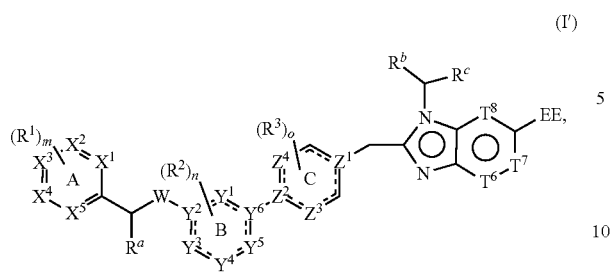

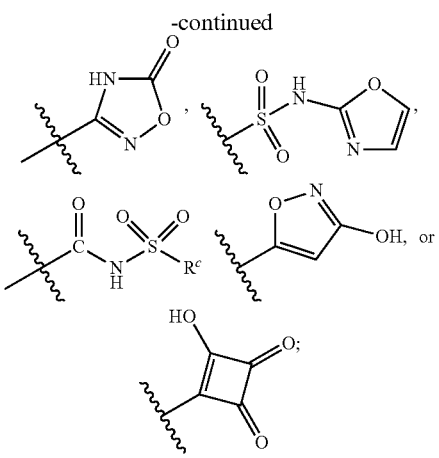

or a pharmaceutically acceptable salt, stereoisomer, solvate, or hydrate thereof, wherein

- ---- indicates a single bond or a double bond;
- $X^1$, $X^2$, $X^3$, $X^4$, and $X^5$ are each independently selected from N and CH; wherein no more than three of $X^1$, $X^2$, $X^3$, $X^4$, and $X^5$ are N and ring A does not contain 3 nitrogen ring atoms at 3 contiguous positions;
- W is selected from O, $CR^{5'}R^{6'}$, and $NR^{5'}$;
- $Y^1$, $Y^3$, $Y^4$, and $Y^5$ are each independently selected from N, NH, CH, and $CH_2$;
- $Y^2$ and $Y^6$ are each independently selected from N, C, or CH;
- wherein there is no more than 3 nitrogen ring atoms in ring B and wherein ring B does not contain 3 nitrogen ring atoms at 3 contiguous positions;

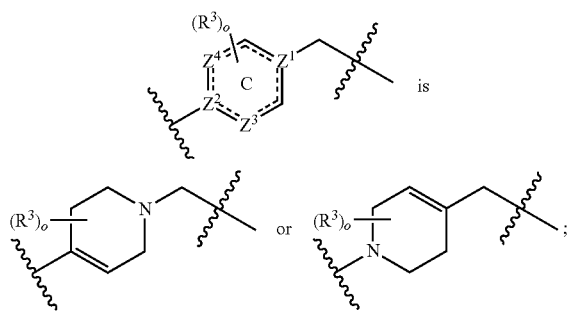

$T^6$, $T^7$, and $T^8$ are each independently selected from N and $CR^4$; and no more than 2 of $T^6$, $T^7$, and $T^8$ are selected from N;

EE is —COOH,

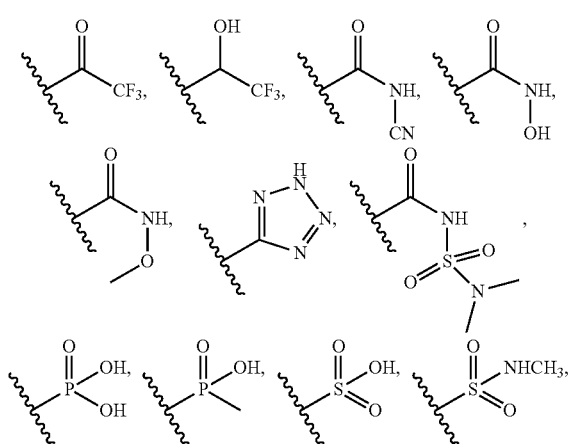

- $R^a$ is selected from hydrogen, halogen, $C_1$-$C_6$ alkyl, $C_1$-$C_6$ alkoxy, $NR^{5'}R^{6'}$, wherein the $C_1$-$C_6$ alkyl or $C_1$-$C_6$ alkoxy represented by $R^a$ is optionally substituted with one or more groups selected from halogen, oxo, CN, and OH;
- $R^b$ is 5-6 membered heteroaryl or 4-7 membered saturated or partially saturated heterocyclyl, wherein the heteroaryl or saturated or partially saturated heterocyclyl represented by $R^b$ is optionally substituted with one or more groups selected from halogen, $C_1$-$C_3$ alkyl, $C_1$-$C_3$ haloalkyl, $C_1$-$C_3$ hydroxyalkyl, $C_1$-$C_3$ alkoxy, and $C_1$-$C_3$ haloalkoxy;
- $R^c$ is hydrogen, $C_1$-$C_6$ alkyl, or $C_1$-$C_6$ haloalkyl;
- each $R^1$ is independently halogen, —CN, OH, $C_1$-$C_6$ alkyl, $C_1$-$C_6$ alkoxy, $C_2$-$C_6$ alkenyl, $C_2$-$C_6$ alkynyl, $NR^{5'}R^{6'}$, phenyl, 5-6 membered heteroaryl, 4-6 membered saturated or partially saturated cycloalkyl and 3-7 membered saturated or partially saturated heterocyclyl, wherein the $C_1$-$C_6$ alkyl, $C_1$-$C_6$ alkoxy, $C_2$-$C_6$ alkenyl, or $C_2$-$C_6$ alkynyl represented by $R^1$ is optionally substituted with one or more groups selected from halogen, CN, OH, and $C_3$-$C_6$ cycloalkyl; and wherein the aryl, heteroaryl, saturated or partially saturated cycloalkyl, or saturated or partially saturated heterocyclyl represented by $R^1$ or in the group represented by $R^1$ is optionally substituted with one or more groups selected from halogen, oxo, CN, OH, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_1$-$C_3$ hydroxyalkoxy, and $NR^{5'}R^{6'}$;
- each $R^2$ is independently selected from halogen, oxo, $C_1$-$C_6$ alkyl, $C_1$-$C_6$ haloalkyl, $C_1$-$C_6$ alkoxy, $C_1$-$C_6$ haloalkoxy, and $NR^{5'}R^{6'}$;
- each $R^3$ is independently halogen, —CN, oxo, $C_1$-$C_6$ alkyl, $C_1$-$C_6$ haloalkyl, $C_1$-$C_6$ alkoxy, or $C_1$-$C_6$ haloalkoxy; and/or
- two $R^3$ taken together with Ring C, form 6-10 membered bridged heterocyclyl optionally substituted with one or more groups selected from halogen, $C_1$-$C_6$ alkyl, $C_1$-$C_6$ haloalkyl, $C_1$-$C_6$ alkoxy, or $C_1$-$C_6$ haloalkoxy;
- each $R^4$ is independently H, halogen, or $C_1$-$C_6$ alkyl optionally substituted with one or more groups selected from halogen;
- $R^{5'}$ and $R^{6'}$ are each independently hydrogen or $C_1$-$C_6$ alkyl;
- wherein optionally two $R^1$; two $R^2$; two $R^3$; $R^a$ and $R^1$; $R^a$ and $R^2$; $R^1$ and $R^{5'}$; $R^2$ and $R^{5'}$; taken together with their respective intervening carbon or hetero atom(s), form phenyl, 5-6 membered heteroaryl, 4-6 membered saturated or partially saturated cycloalkyl or 4-7 membered saturated or partially saturated heterocyclyl, each of which is optionally substituted with one or more groups selected from halogen, —CN, —OH, $C_1$-$C_6$ alkyl, $C_1$-$C_6$ haloalkyl, $C_1$-$C_6$ alkoxy, $C_1$-$C_6$ haloalkoxy, and $NR^{5'}R^{6'}$;

m is 0, 1, 2, 3, or 4;

n is 0, 1, 2, 3, or 4; and o is 0, 1, 2, 3, or 4.

15. The compound according to claim 14, or a pharmaceutically acceptable salt, stereoisomer, solvate, or hydrate thereof, wherein

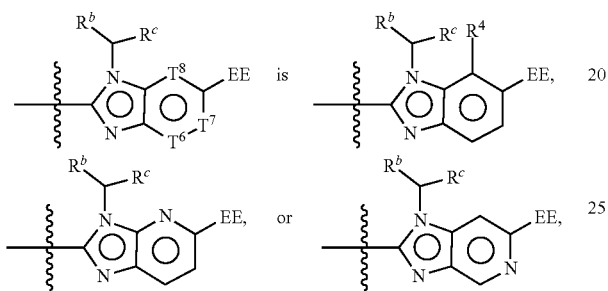

wherein $R^4$ is H or halogen; or wherein EE is —COOH, —C(O)NHOH, —C(O)NHSO$_2$CH$_3$, —C(O)NHSO$_2$CF$_3$,

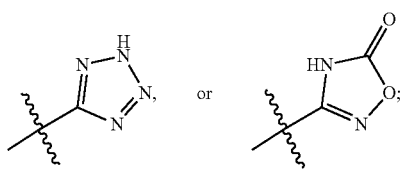 [SMILES: *c1nn[nH]n1 ; *c1noc(=O)[nH]1]

or

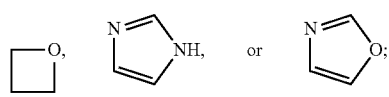

wherein $R^b$ is each of which is optionally substituted with one or more groups selected from $C_1$-$C_3$ alkyl; and $R^c$ is H or $C_1$-$C_3$ alkyl; or wherein W is O, NH or CH$_2$, and $R^a$ is H.

16. The compound according to claim 14, or a pharmaceutically acceptable salt, stereoisomer, solvate, or hydrate thereof, wherein

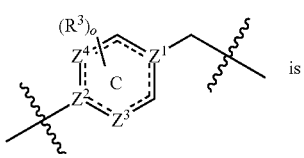 is

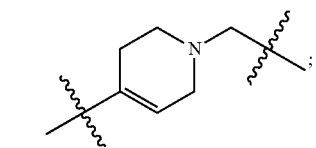

wherein 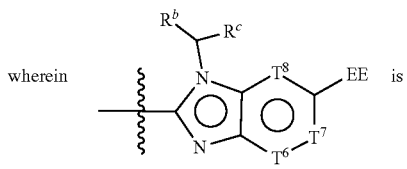 is

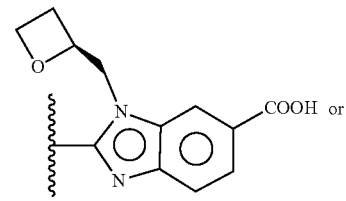

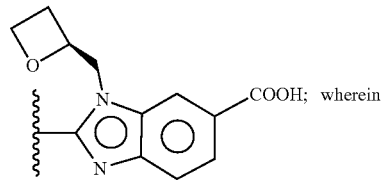

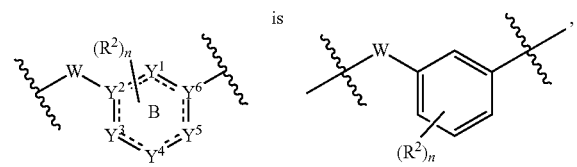

or

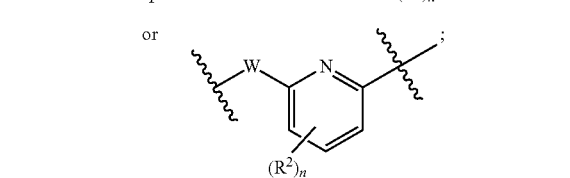

$R^2$ is F; and n is 0, 1, or 2.

17. The compound according to claim 15, or a pharmaceutically acceptable salt, stereoisomer, solvate, or hydrate thereof, wherein is

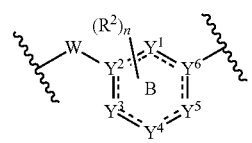

is

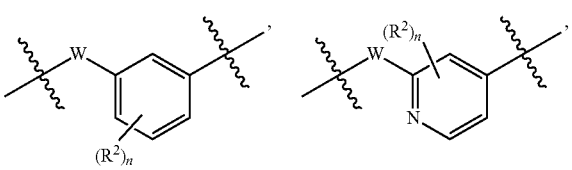

-continued

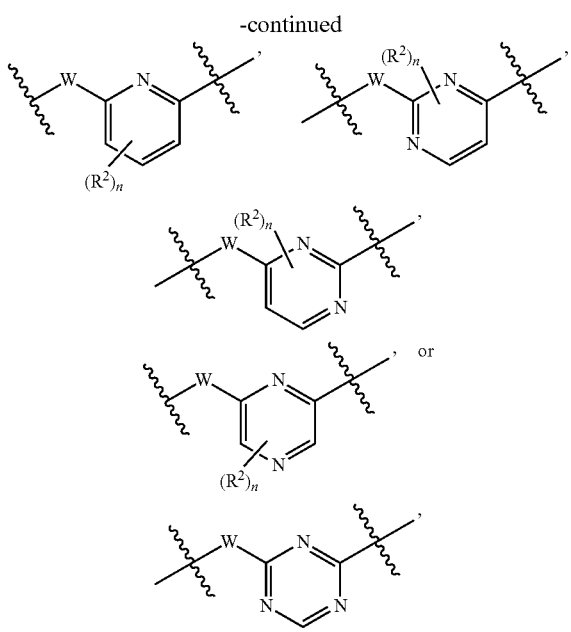

wherein R² is halogen; n is 0, 1, or 2.

18. The compound according to claim 17, or a pharmaceutically acceptable salt, stereoisomer, solvate, or hydrate thereof, wherein
ring A is

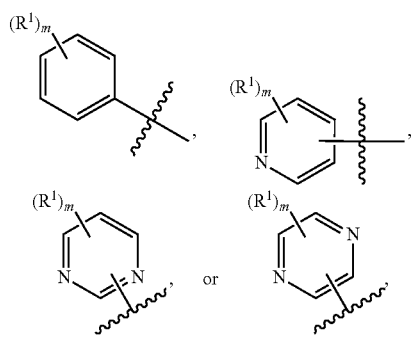

each R¹ is independently selected from halogen, CN, $C_1$-$C_4$ alkyl, $C_1$-$C_4$ haloalkyl, $C_1$-$C_4$ alkoxy, $C_1$-$C_4$ haloalkoxy, $C_2$-$C_4$alkynyl optionally substituted with cyclopropyl, and 5-6 membered heteroaryl (wherein the hetero ring atom is nitrogen) optionally substituted with $C_1$-$C_4$ alkyl; and/or two R¹, taken together with and their respective intervening carbon atoms, form 4-7 membered heterocyclyl (wherein the hetero ring atom is nitrogen and/or oxygen) optionally substituted with $C_1$-$C_4$ alkyl; and m is 0, 1, 2, or 3.

19. The compound according to claim 16, or a pharmaceutically acceptable salt, stereoisomer, solvate, or hydrate thereof, wherein W is O.

20. The compound according to claim 19, or a pharmaceutically acceptable salt, stereoisomer, solvate, or hydrate thereof, wherein ring A is

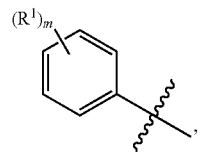

each R¹ is independently selected from halogen, CN, $C_1$-$C_4$ alkyl, $C_1$-$C_4$ haloalkyl, $C_1$-$C_4$ alkoxy, imidazolyl, triazolyl, pyridyl, and $C_2$-$C_4$alkynyl optionally substituted with cyclopropyl; and m is 0, 1, or 2.

21. The compound according to claim 20, or a pharmaceutically acceptable salt, stereoisomer, solvate, or hydrate thereof, wherein R¹ is selected from halogen and CN.

22. The compound according to claim 1, or a pharmaceutically acceptable salt, stereoisomer, solvate, or hydrate thereof, wherein the compound is a compound selected from the group consisting of Compound 19

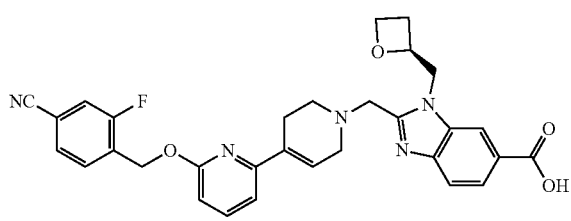

Compound 139

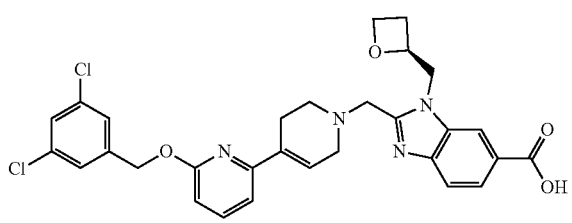

Compound 20

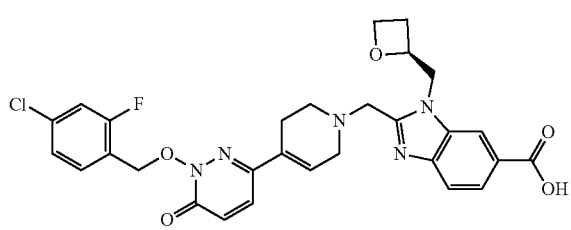

Compound 140

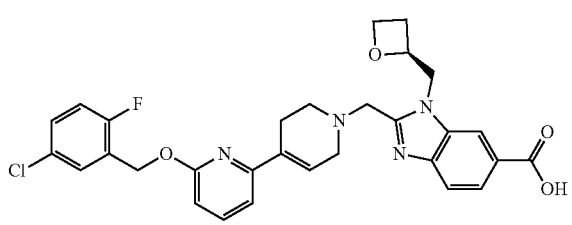

-continued
Compound 23
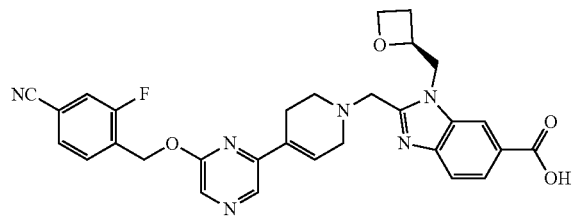
Compound 141
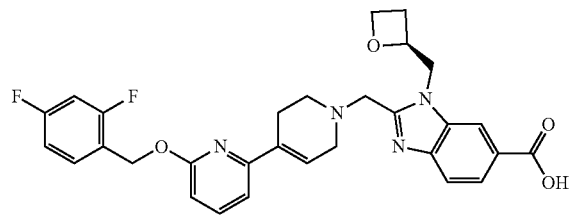
Compound 25
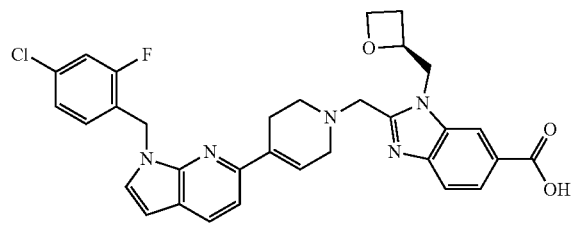
Compound 142
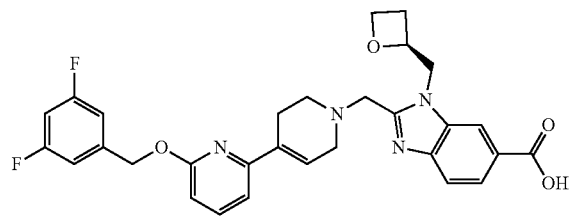
Compound 27
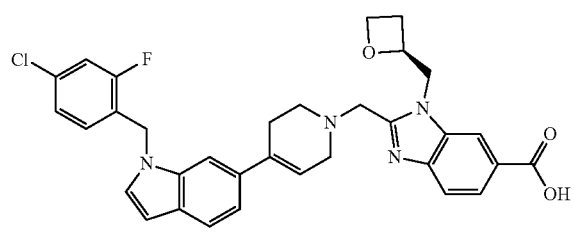
Compound 143
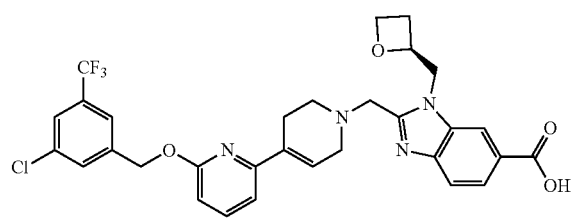
Compound 28
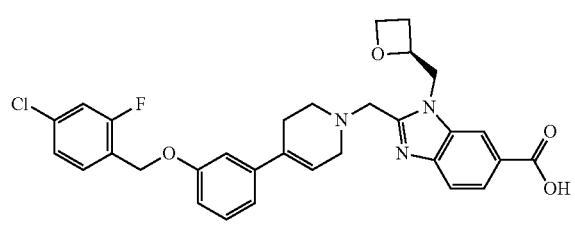
Compound 144
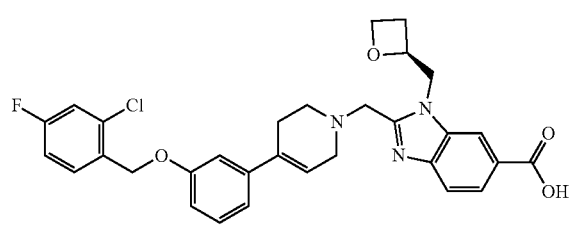
Compound 29
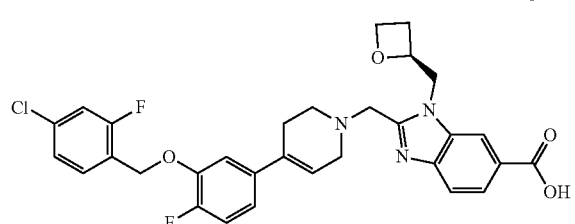
Compound 145
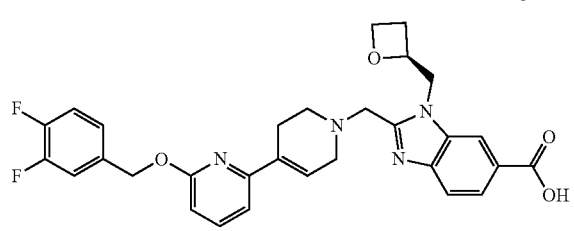
Compound 30
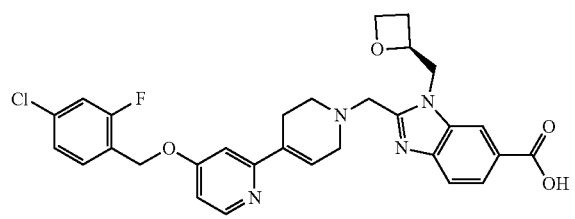
Compound 146
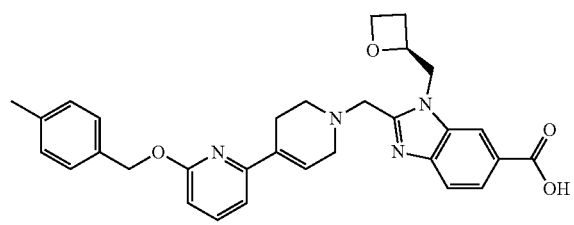

-continued
Compound 31
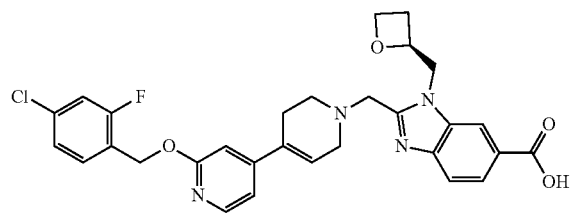
Compound 147
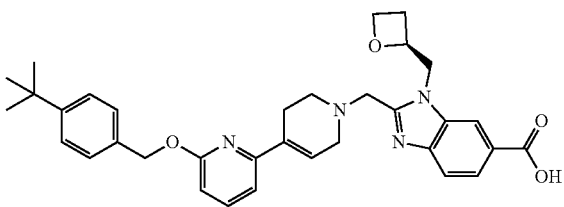
Compound 32
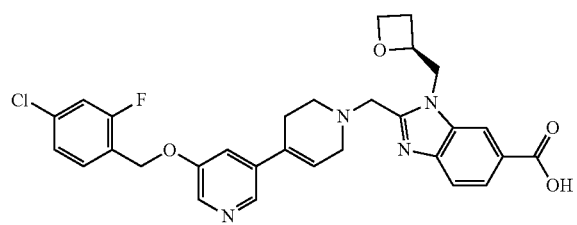
Compound 148
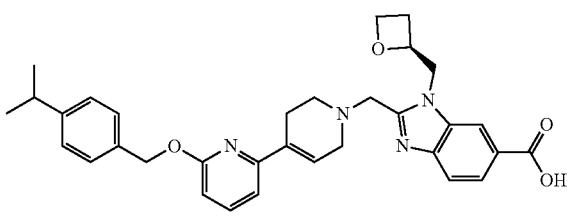
Compound 33
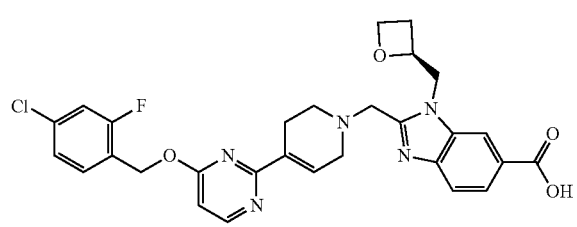
Compound 149
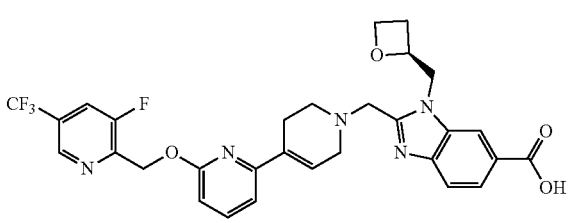
Compound 34
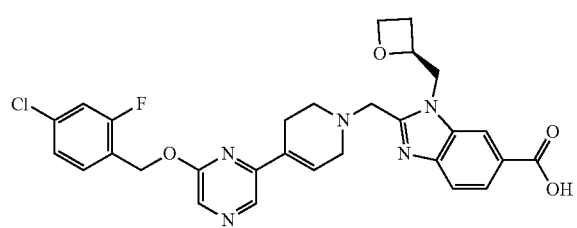
Compound 150
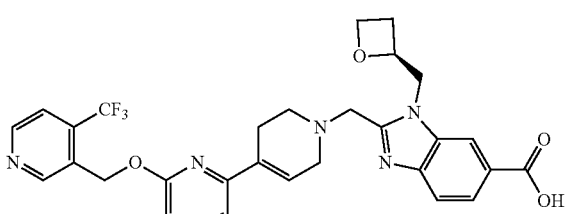
Compound 35
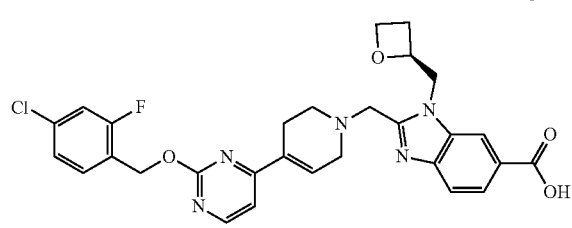
Compound 151
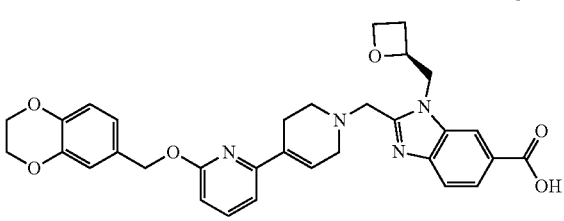
Compound 152
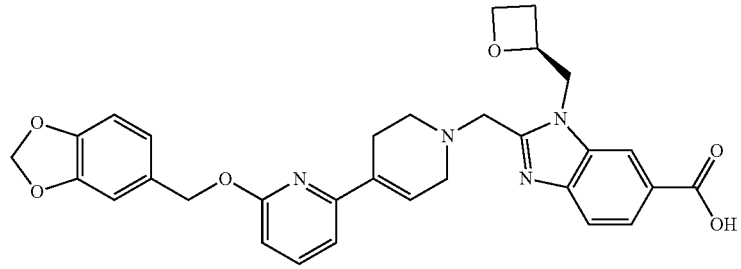

-continued
Compound 153
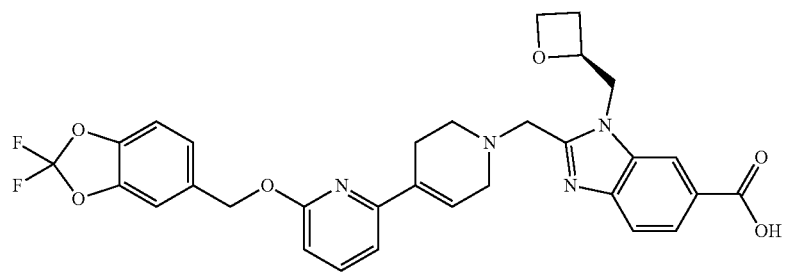
Compound 39
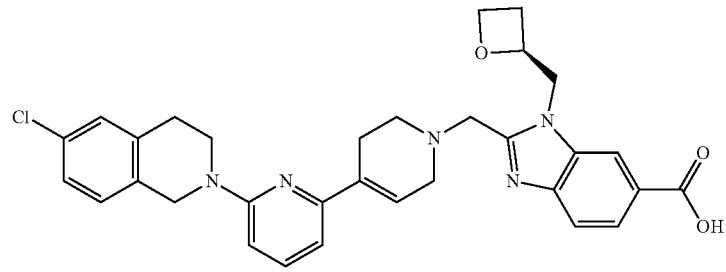
Compound 154
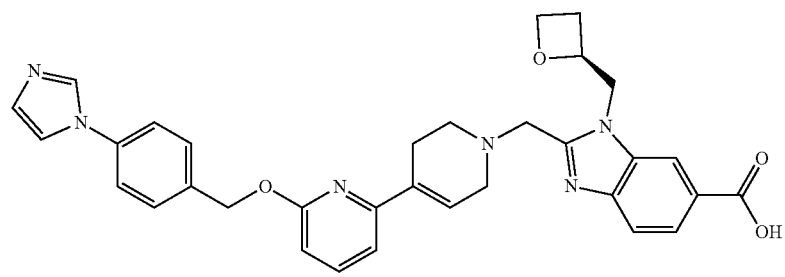
Compound 40
Compound 155
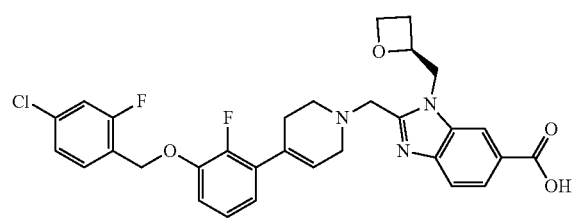
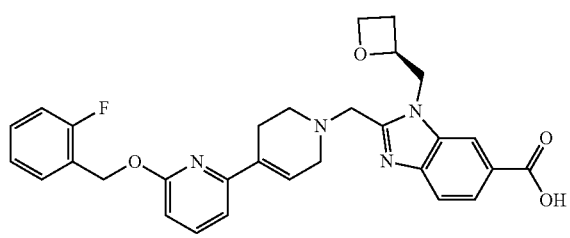
Compound 41
Compound 156
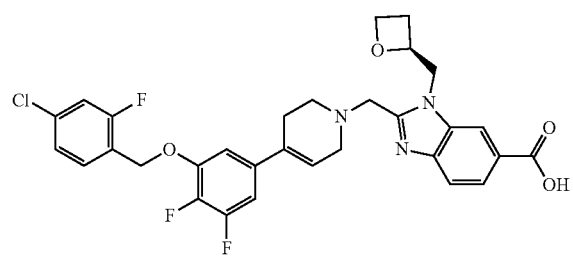
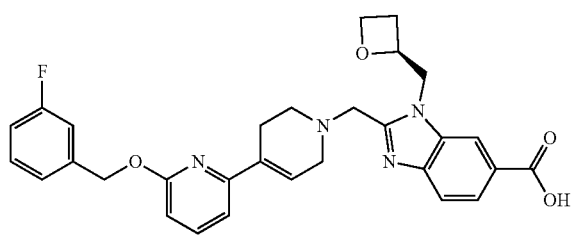
Compound 42
Compound 157
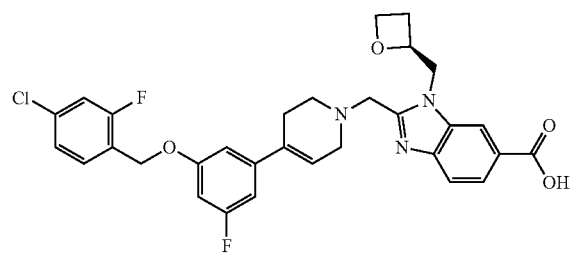
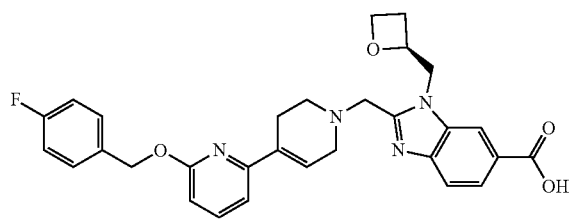

-continued
Compound 43
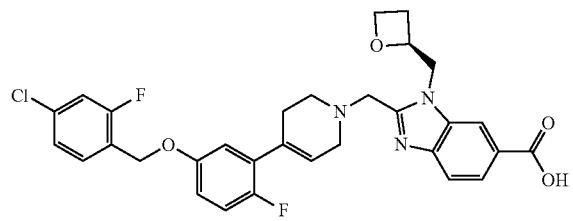
Compound 158
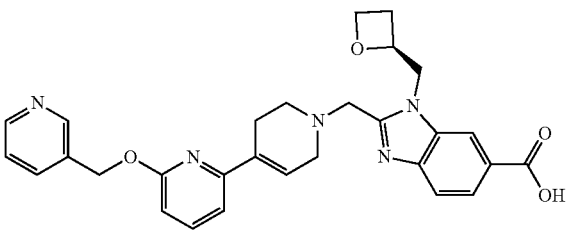
Compound 44
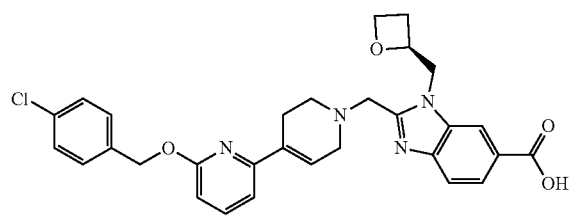
Compound 159
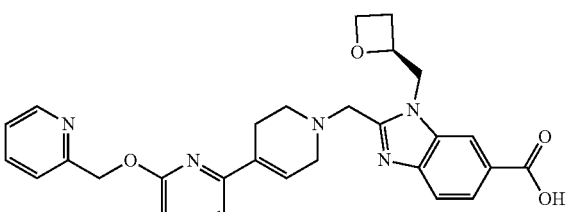
Compound 45
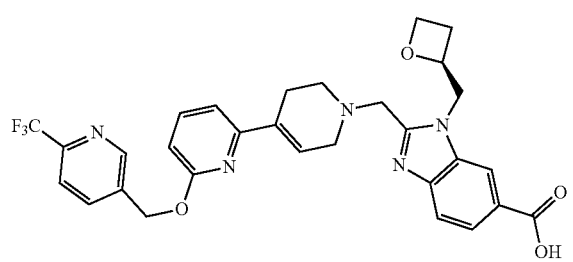
Compound 160
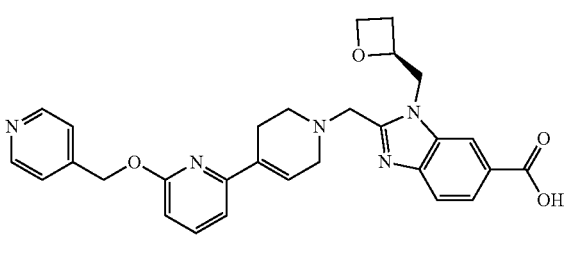
Compound 46
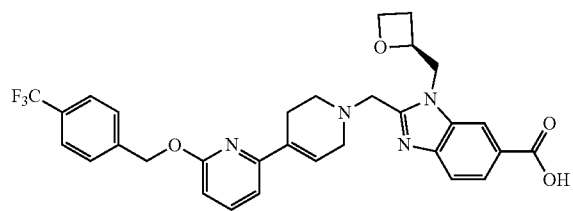
Compound 161
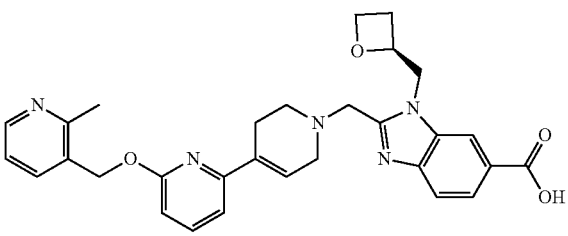
Compound 47
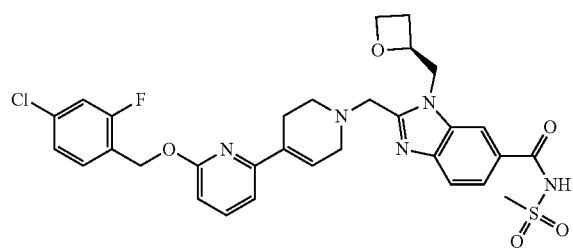
Compound 162
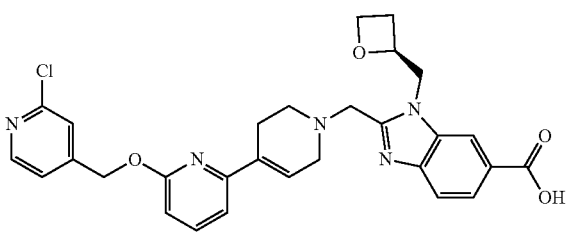
Compound 48
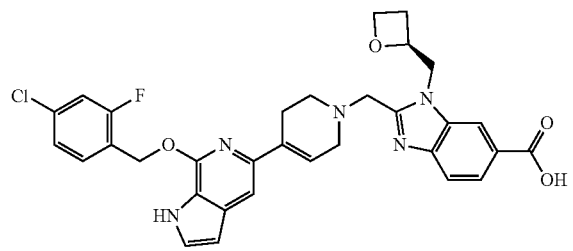
Compound 163
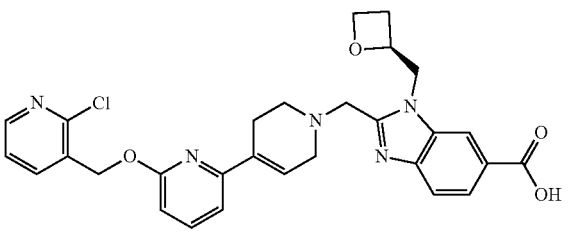

-continued
Compound 51
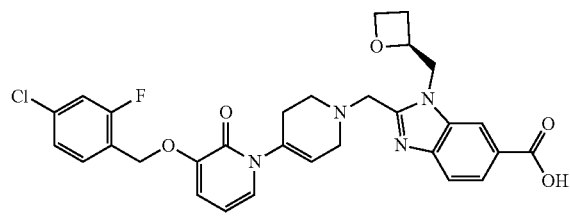
Compound 164
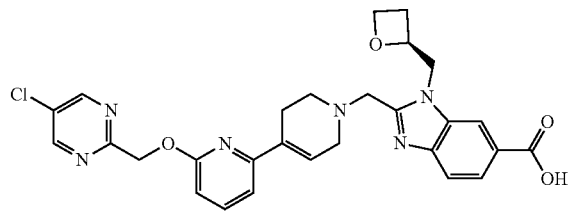
Compound 58
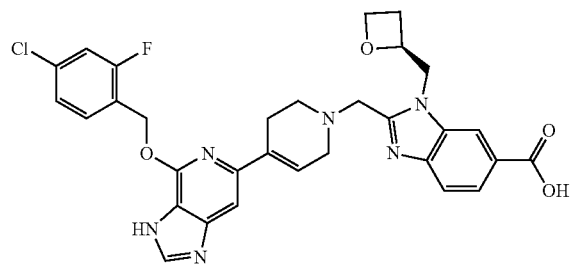
Compound 165
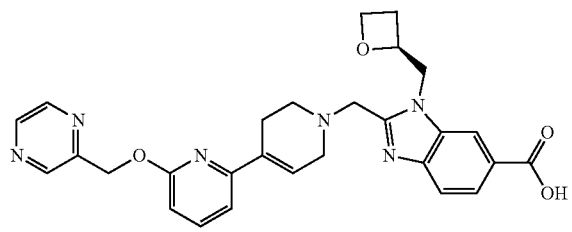
Compound 59
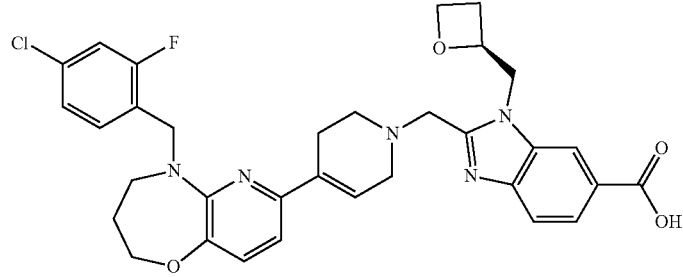
Compound 166
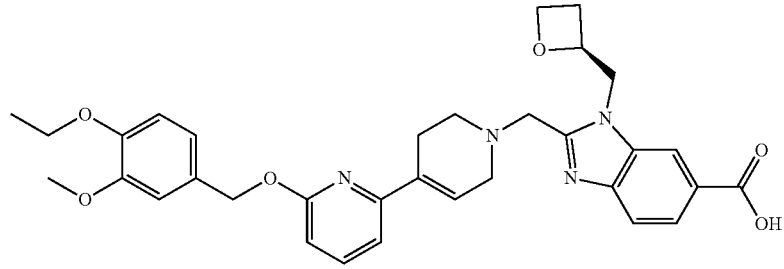
Compound 60
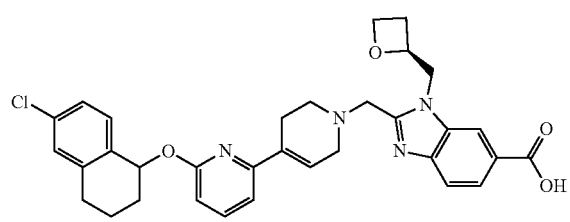
Compound 169
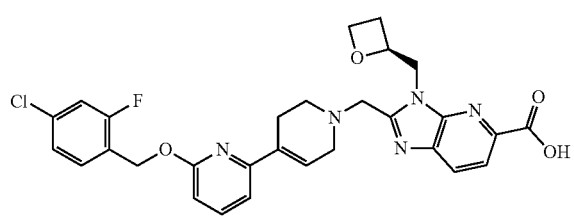
Compound 61
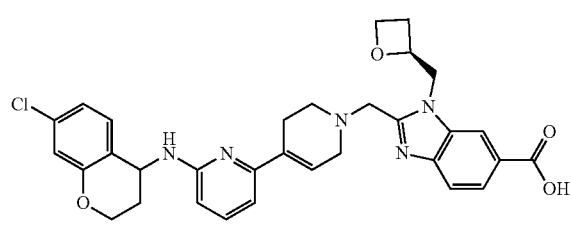
Compound 170

-continued
Compound 62
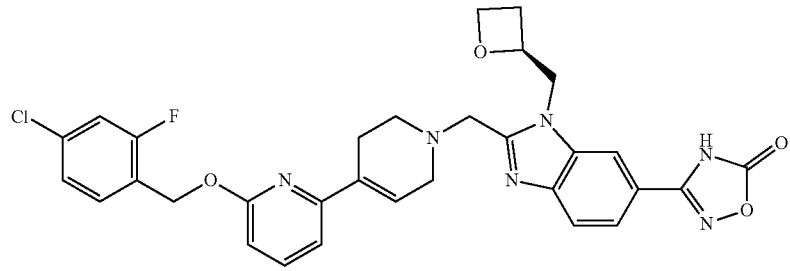
Compound 171
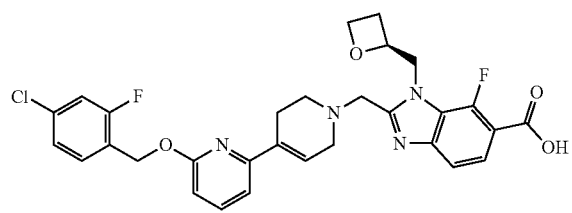
Compound 63
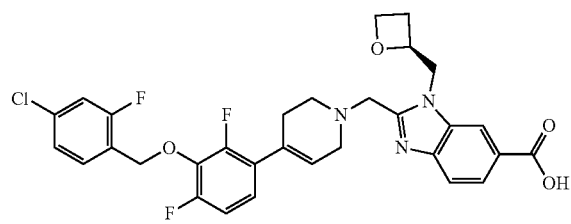
Compound 172
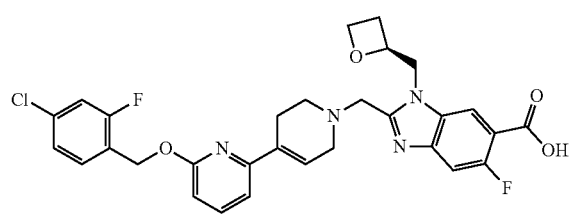
Compound 64
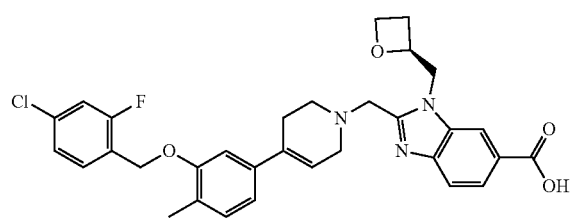
Compound 173
Compound 68
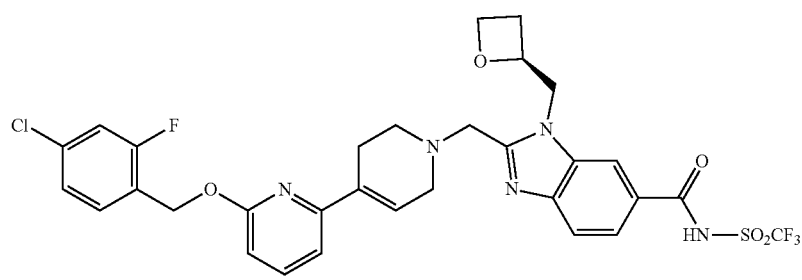
Compound 174
Compound 69
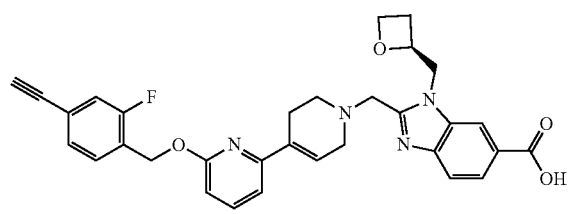
Compound 175
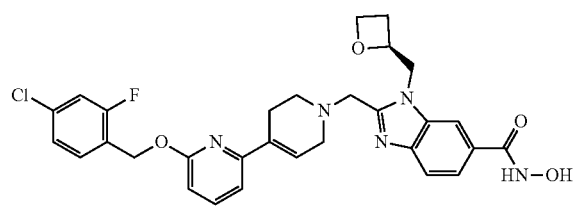
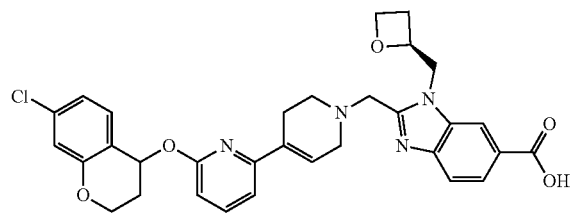
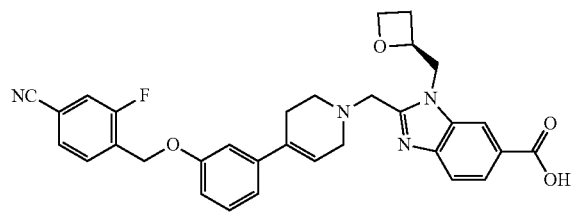

361 362
Compound 70
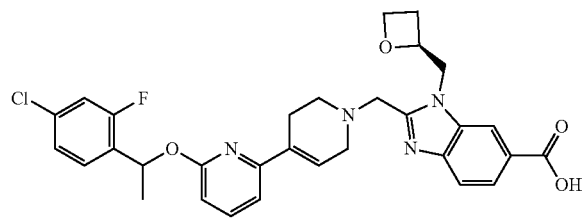
Compound 176
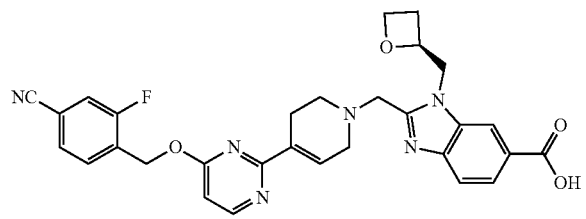
Compound 71
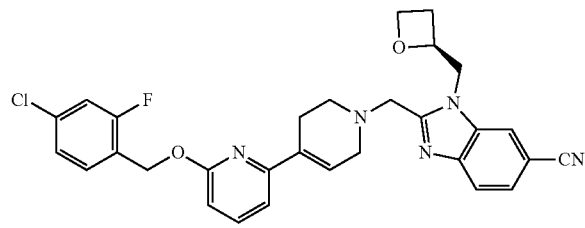
Compound 177
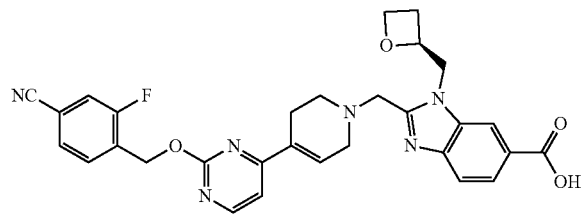
Compound 72
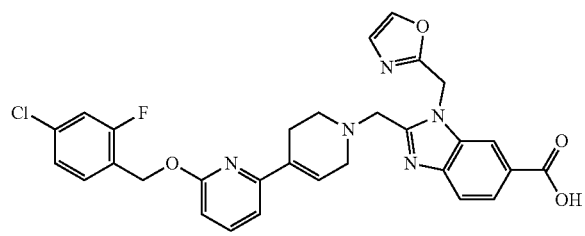
Compound 182
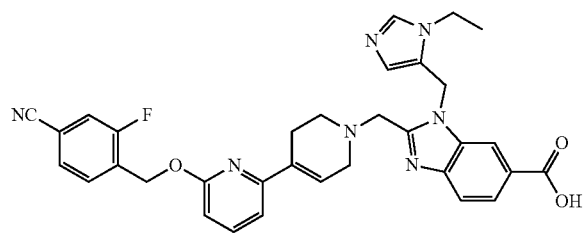
Compound 73
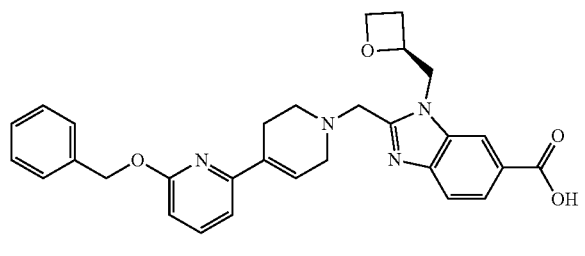
Compound 183
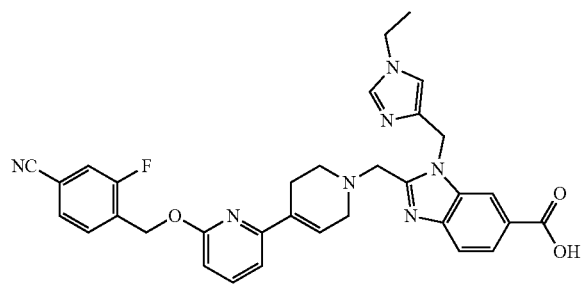
Compound 103
Compound 199
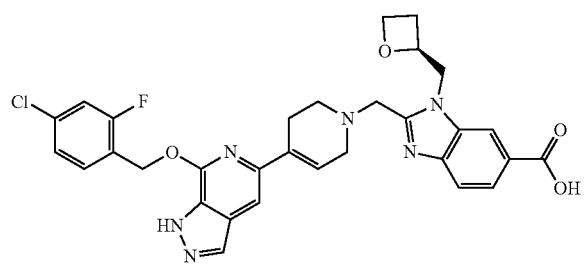
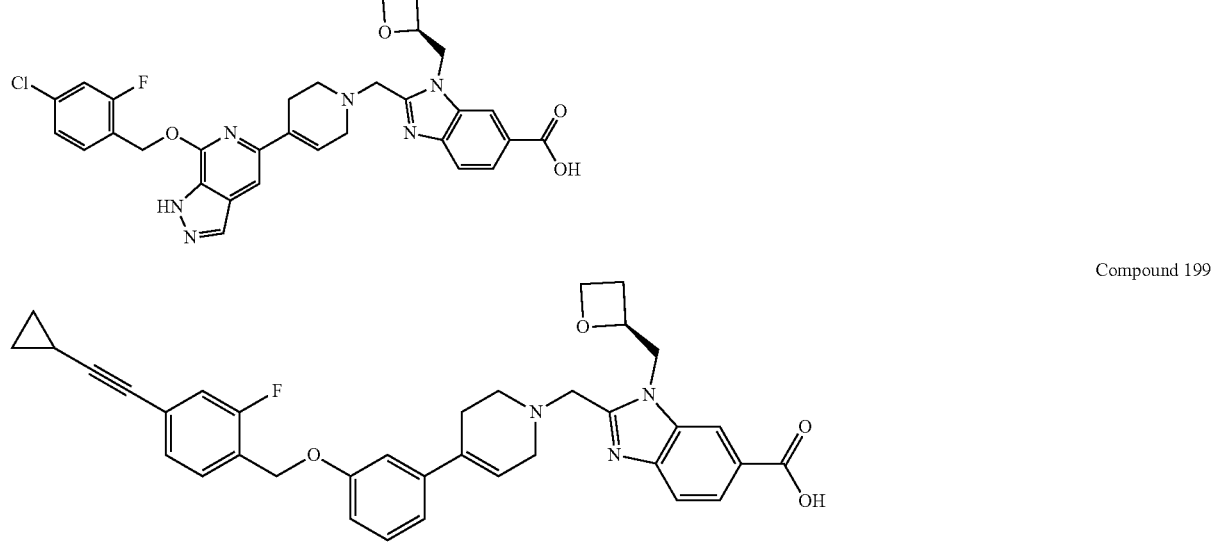

-continued
Compound 104
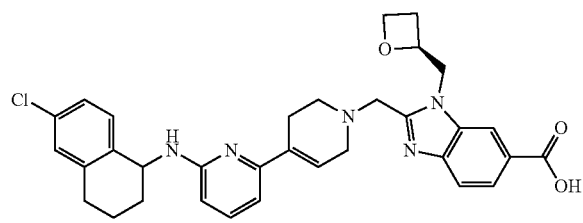
Compound 200
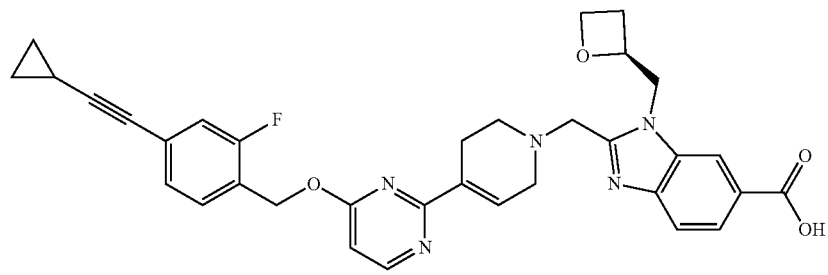
Compound 105
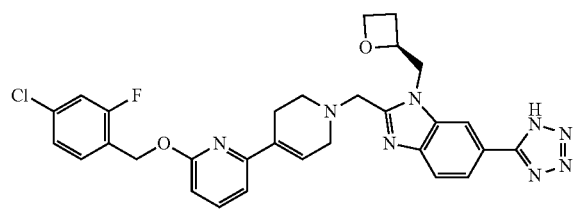
Compound 201
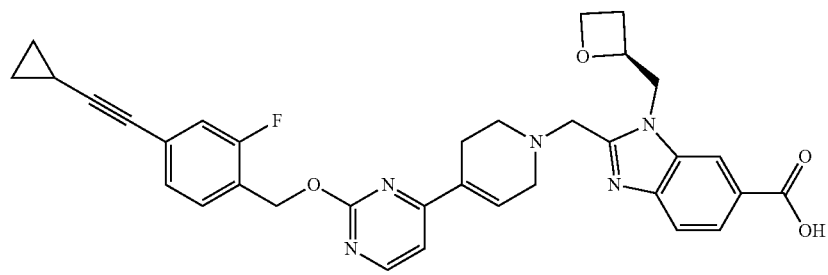
Compound 107
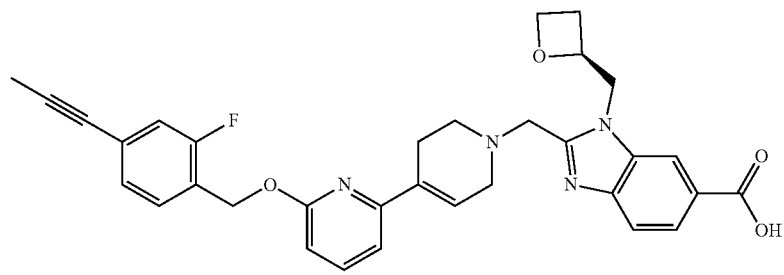
Compound 202
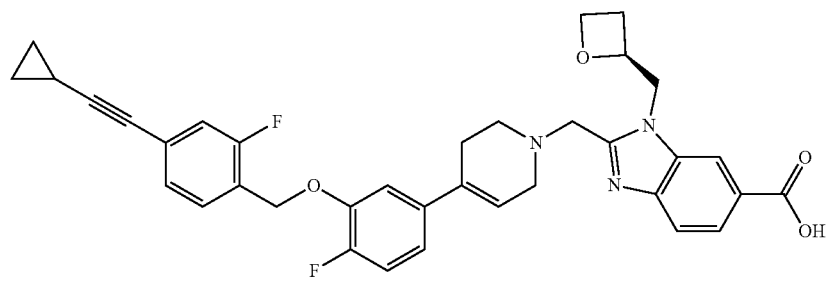

-continued
Compound 108
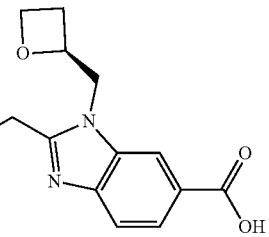
Compound 203
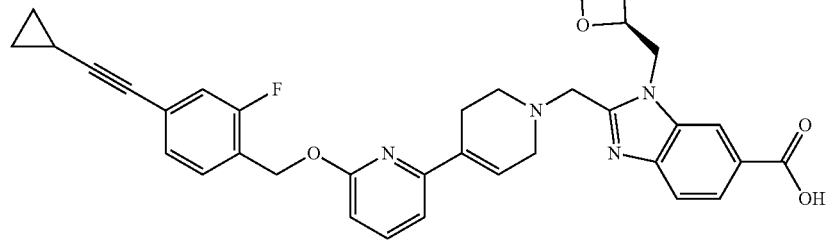
Compound 109
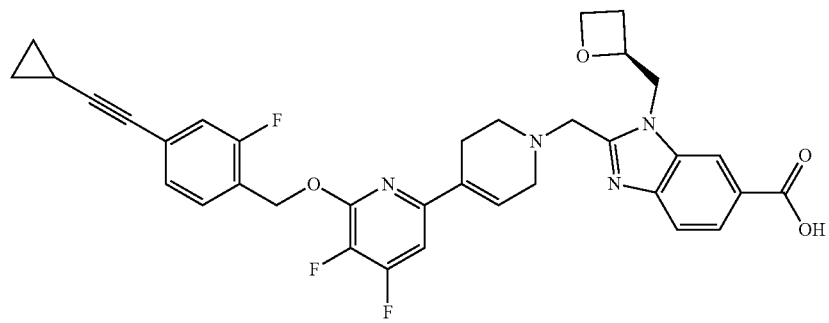
Compound 204
Compound 110
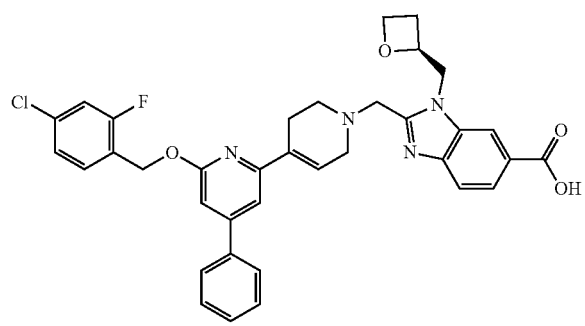
Compound 205
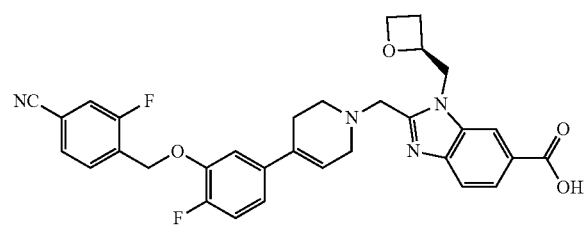
Compound 111
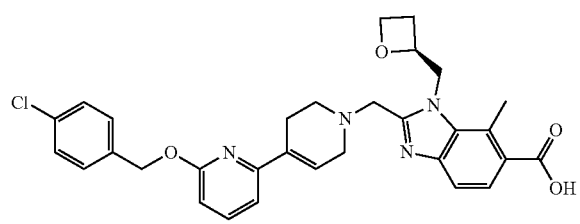
Compound 206
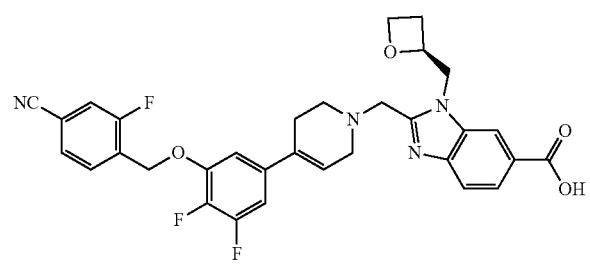
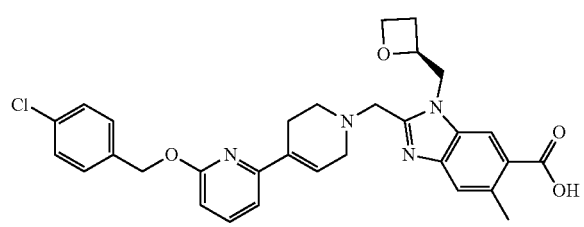
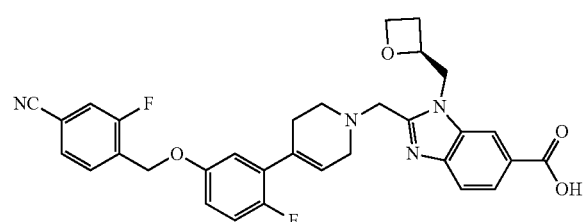

-continued
Compound 112
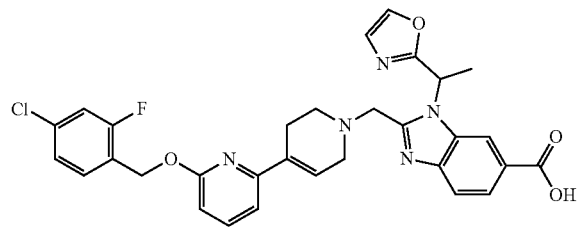
Compound 207
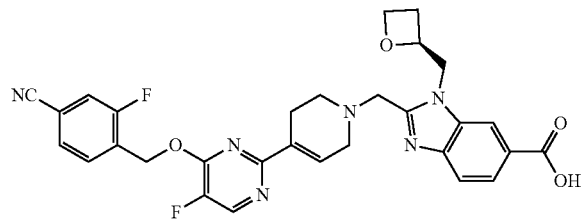
Compound 113
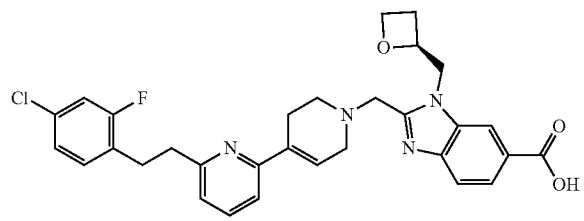
Compound 208
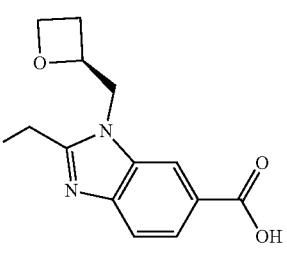
Compound 114
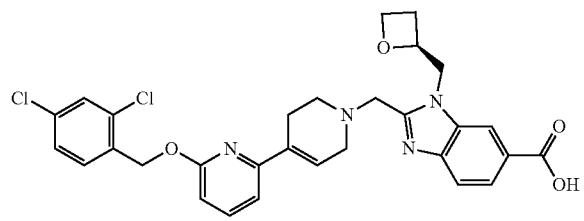
Compound 209
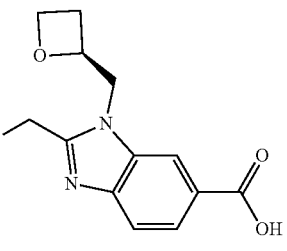
Compound 115
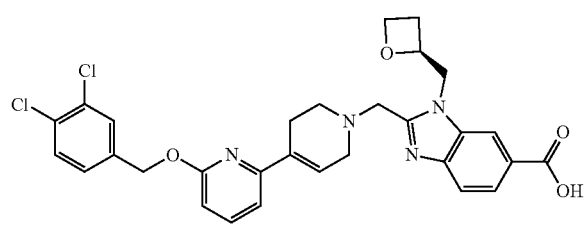
Compound 210
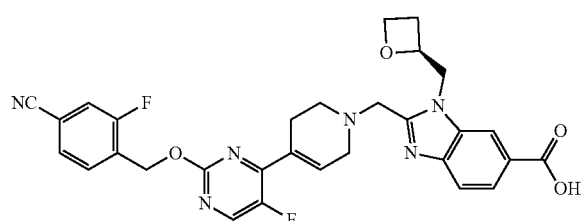

-continued
Compound 116
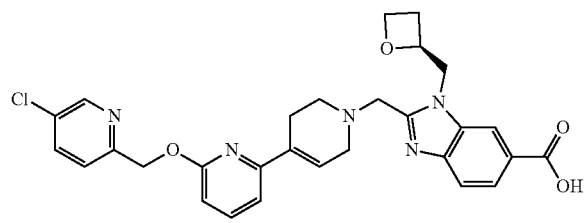
Compound 117
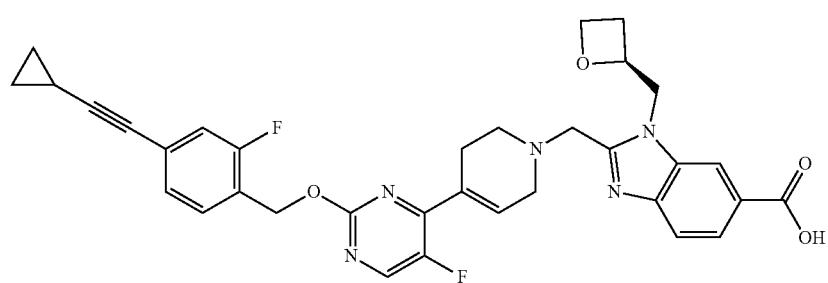
Compound 118
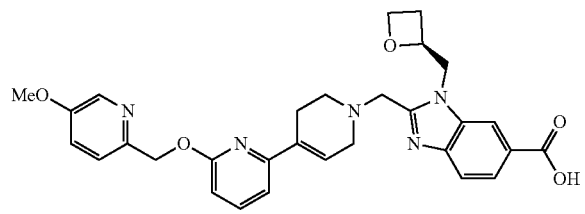
Compound 211
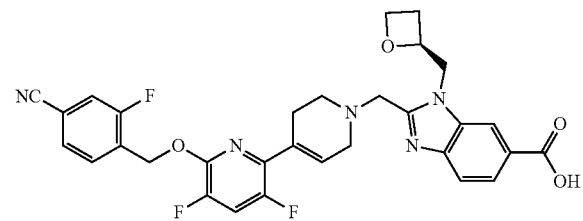
Compound 212
Compound 119
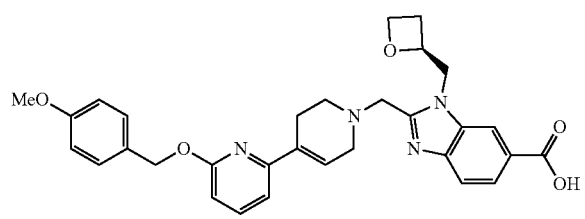
Compound 213
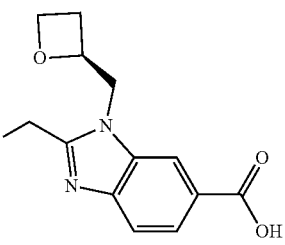
Compound 214
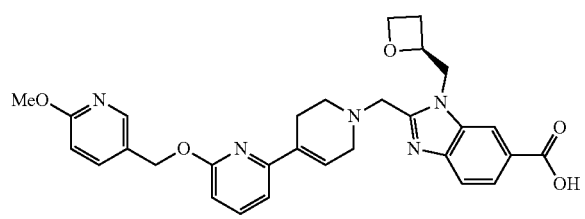
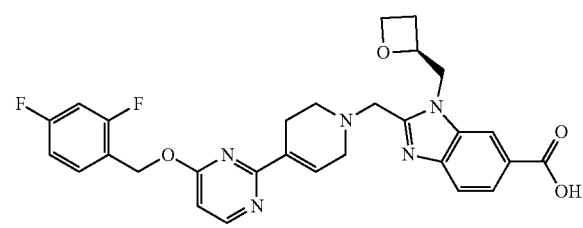

-continued
Compound 120
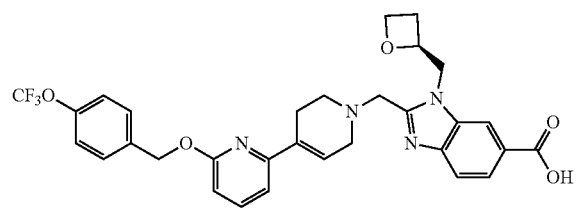
Compound 215
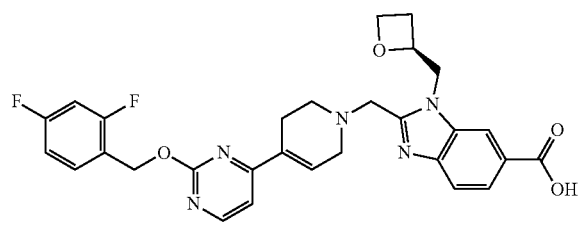
Compound 121
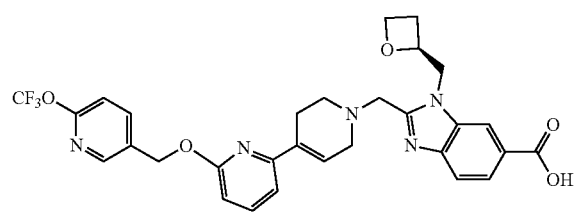
Compound 216
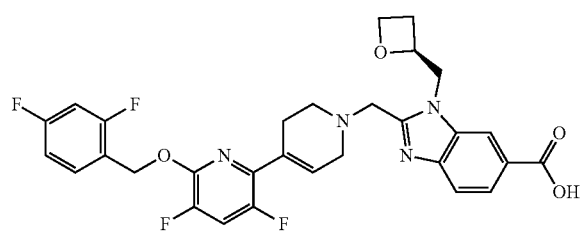
Compound 122
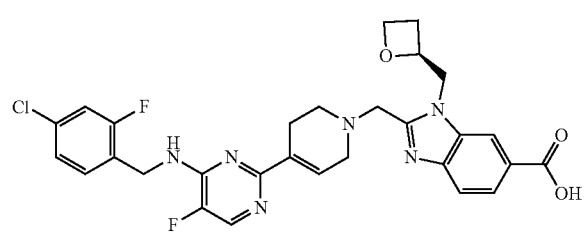
Compound 217
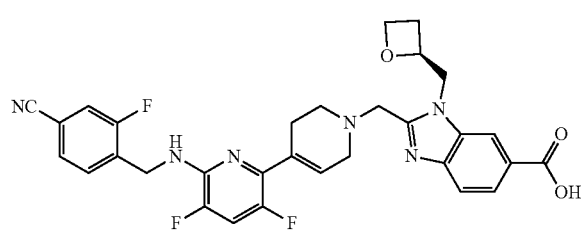
Compound 123
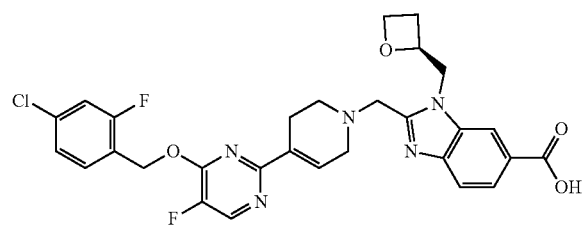
Compound 218
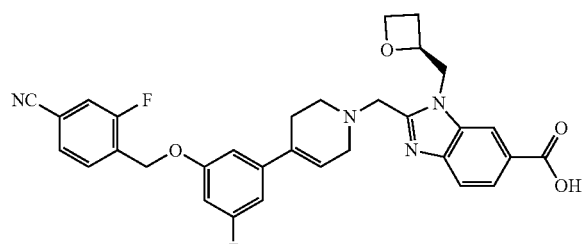
Compound 124
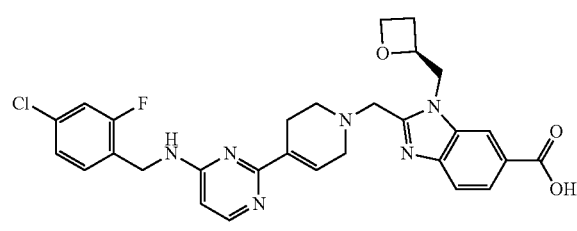
Compound 219
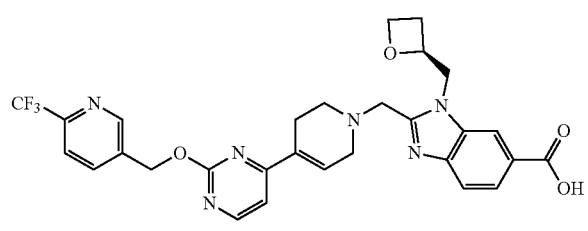
Compound 125
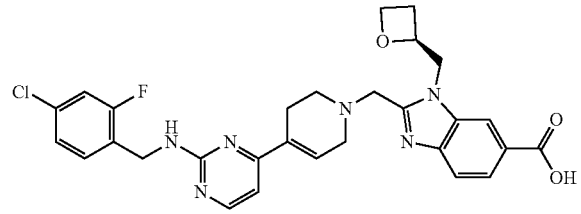
Compound 220
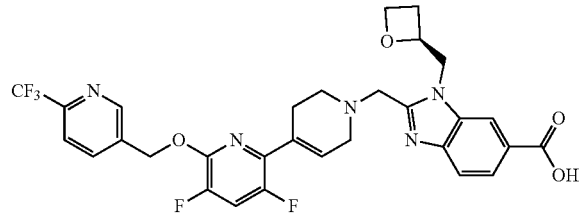

-continued
Compound 126
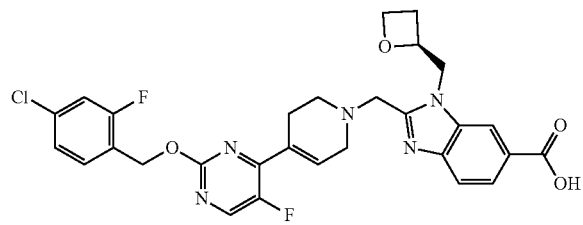
Compound 221
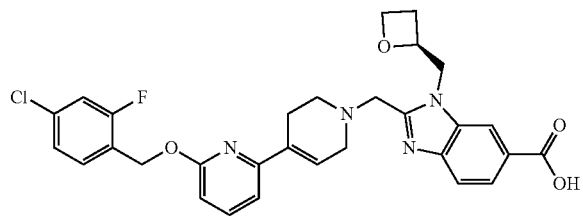
Compound 127
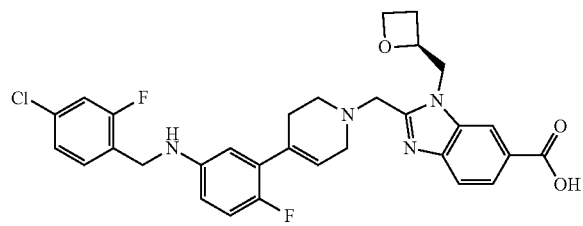
Compound 222
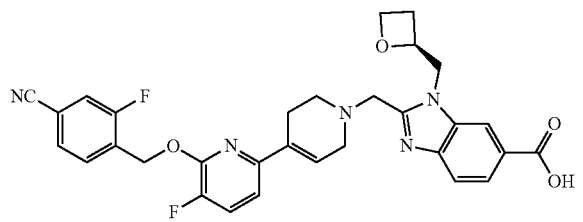
Compound 128
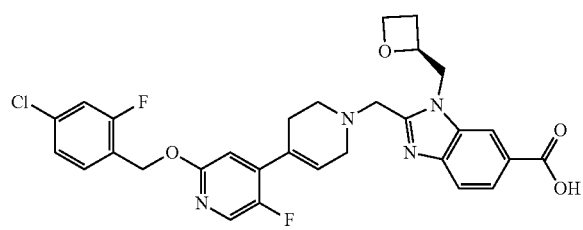
Compound 223
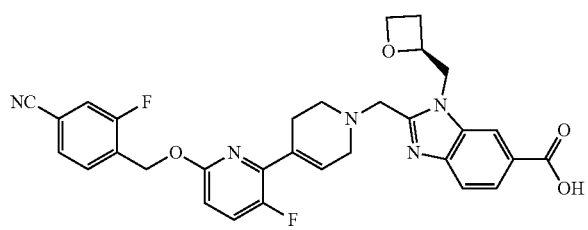
Compound 129
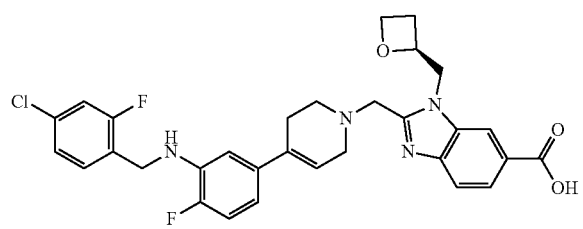
Compound 224
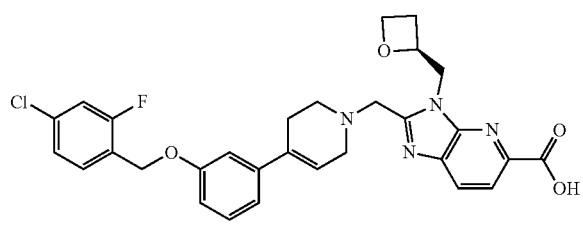
Compound 130
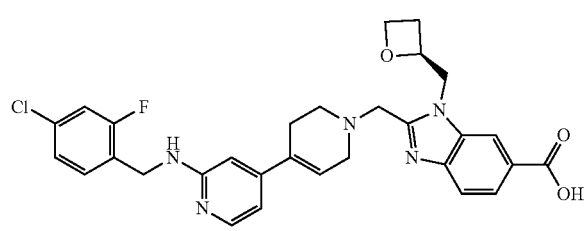
Compound 225
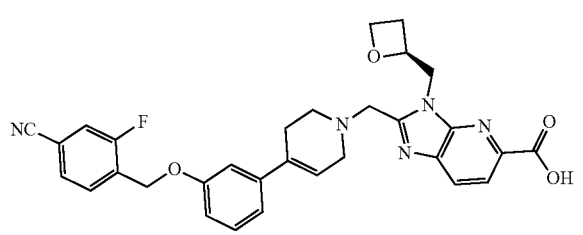
Compound 131
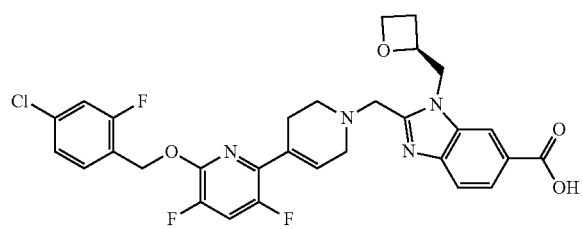
Compound 235
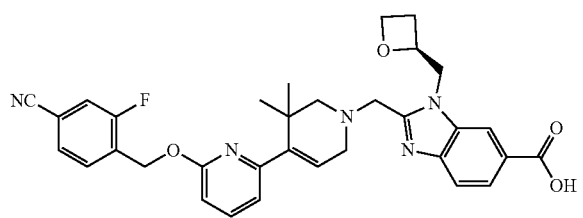

-continued
Compound 132
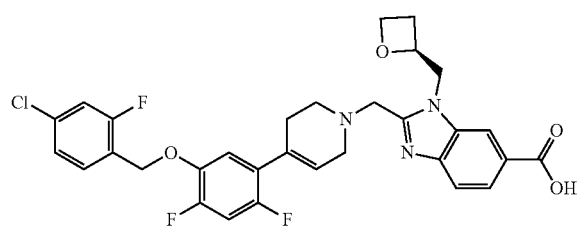
Compound 236
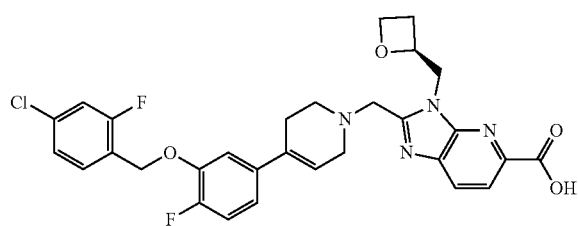
Compound 133
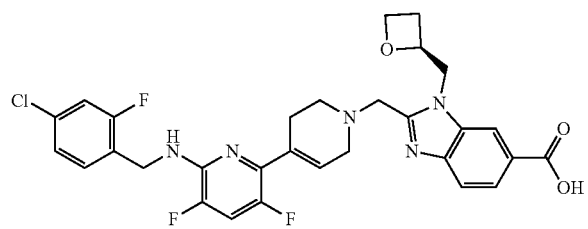
Compound 237
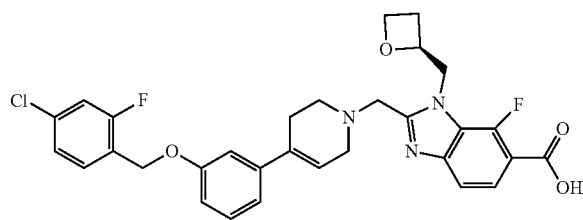
Compound 134
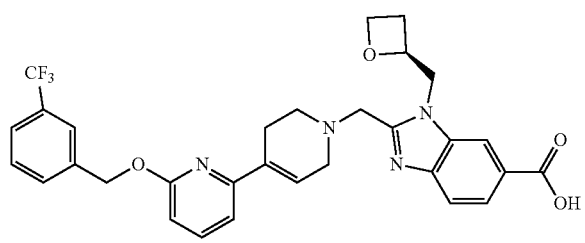
Compound 238
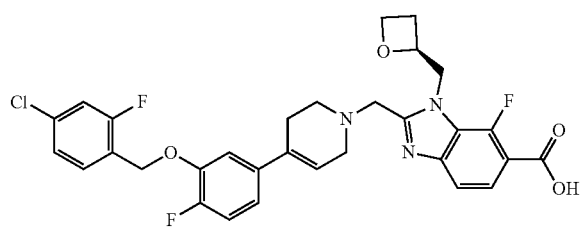
Compound 135
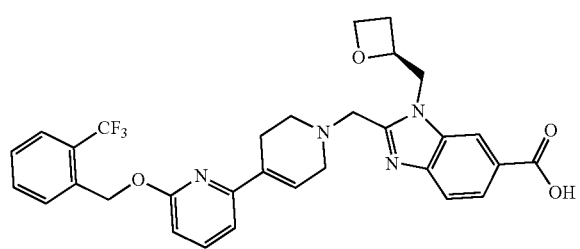
Compound 240
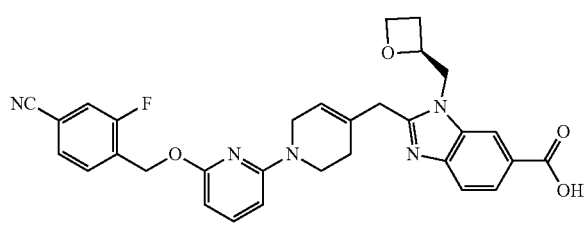
Compound 136
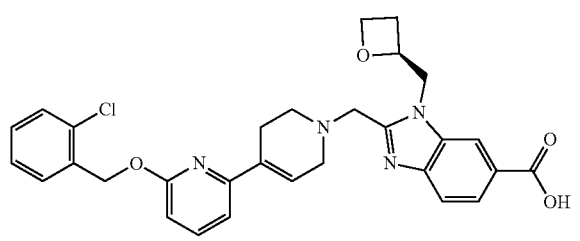
Compound 241
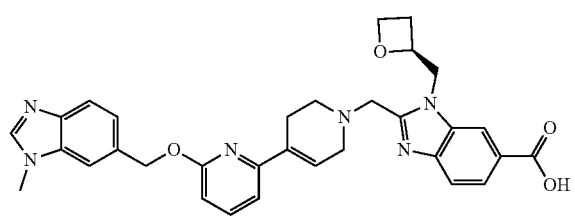

-continued

Compound 137

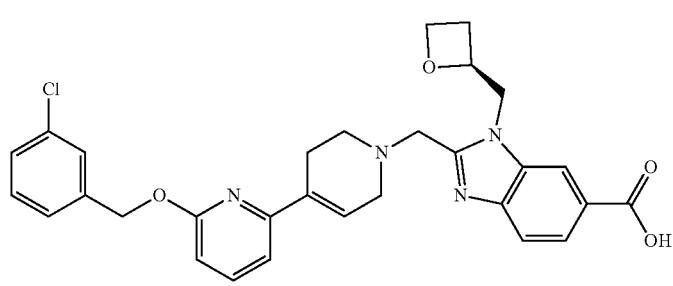

Compound 138

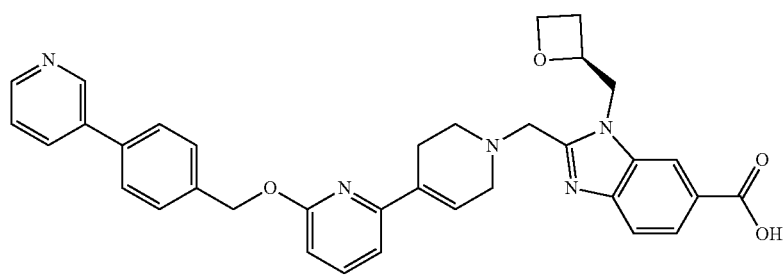

Compound 242

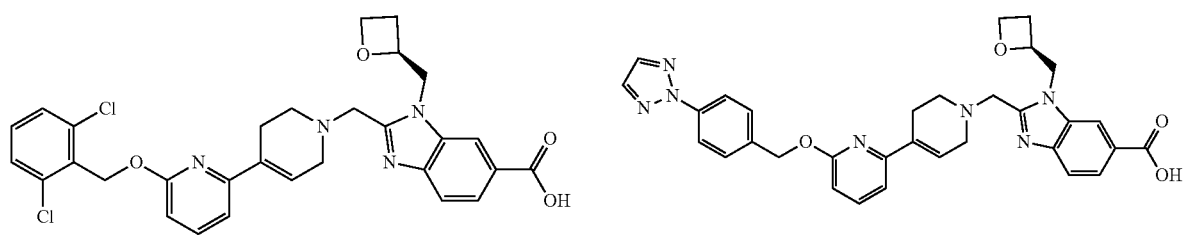

Compound 243

Compound 244

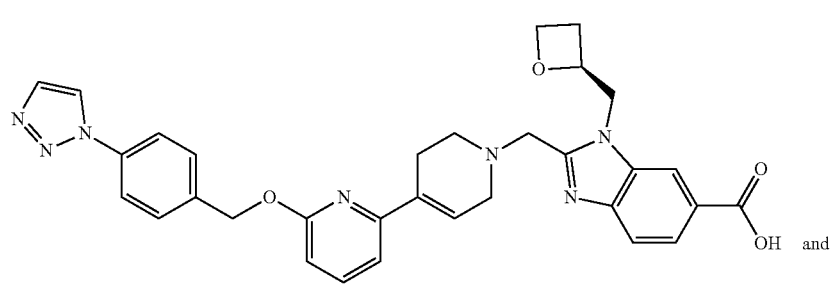

Compound 245

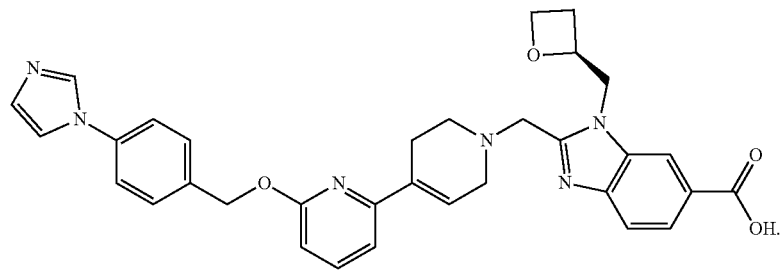

23. A pharmaceutical composition comprising the compound of claim 1, or a pharmaceutically acceptable salt, stereoisomer, solvate, or hydrate thereof, and a pharmaceutically acceptable excipient.

24. A method of treating cardiometabolic and associated diseases comprising administering to a subject in need of such treatment a therapeutically effective amount of a compound of claim 1 or a pharmaceutically acceptable salt, stereoisomer, solvate, or hydrate thereof, wherein the disease is T1D, T2DM, pre-diabetes, idiopathic T1D, LADA, EOD, YOAD, MODY, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity, eating disorders, weight gain from use of other agents, excessive sugar craving, dyslipidemia, hyperinsulinemia, NAFLD, NASH, fibrosis, cirrhosis, hepatocellular carcinoma, cardiovascular disease, coronary artery disease, peripheral vascular disease, hypertension, endothelial dysfunction, impaired vascular compliance, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome Crohn's disease, colitis, irritable bowel syndrome, prevention or treatment of Polycystic Ovary Syndrome and treatment of addiction.

25. The method of claim 24, wherein the disease is Alzheimer's Disease, Type 1 diabetes (TID), Type 2 diabetes mellitus, hyperglycemia, non-alcoholic steatohepatitis, obesity, nonalcoholic fatty liver disease (NAFLD), or Parkinson's Disease.

\* \* \* \* \*